US011820775B2

(12) United States Patent
Jacobsen et al.

(10) Patent No.: US 11,820,775 B2
(45) Date of Patent: *Nov. 21, 2023

(54) PYRROLOPYRIMIDINE ITK INHIBITORS

(71) Applicant: ACLARIS THERAPEUTICS, INC., Wayne, PA (US)

(72) Inventors: Eric Jon Jacobsen, Chesterfield, MO (US); David Randolph Anderson, Salem, CT (US); James Robert Blinn, O'Fallon, MO (US); Susan Landis Hockerman, Kirkwood, MO (US); Richard Heier, Columbia, IL (US); Paramita Mukherjee, Carbondale, IL (US)

(73) Assignee: Aclaris Therapeutics, Inc., Wayne, PA (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/236,531

(22) Filed: Apr. 21, 2021

(65) Prior Publication Data

US 2022/0348579 A1 Nov. 3, 2022

Related U.S. Application Data

(63) Continuation of application No. 16/538,354, filed on Aug. 12, 2019, now Pat. No. 11,021,482.

(60) Provisional application No. 62/717,400, filed on Aug. 10, 2018.

(51) Int. Cl.
*C07D 487/04* (2006.01)
*C07D 471/04* (2006.01)
*A61K 45/06* (2006.01)

(52) U.S. Cl.
CPC ......... *C07D 487/04* (2013.01); *C07D 471/04* (2013.01); *A61K 45/06* (2013.01)

(58) Field of Classification Search
CPC .................................................. C07D 487/04
See application file for complete search history.

(56) References Cited

U.S. PATENT DOCUMENTS

| 5,760,068 A | 6/1998 | Talley et al. |
| 7,799,782 B2 | 9/2010 | Munson et al. |
| 7,879,844 B2 | 2/2011 | Inoue et al. |

(Continued)

FOREIGN PATENT DOCUMENTS

| EP | 2924026 A1 | 9/2015 |
| GB | 2515785 A1 | 1/2015 |

(Continued)

OTHER PUBLICATIONS

Pinedo et al. (2000).*
McMahon et al. (2000).*

(Continued)

*Primary Examiner* — Paul V Ward
(74) *Attorney, Agent, or Firm* — DLA Piper LLP

(57) ABSTRACT

Disclosed herein are arylpyridinone compounds and compositions useful in the treatment of ITK mediated diseases, such as inflammation, having the structures of Formulas (I)-(IV):

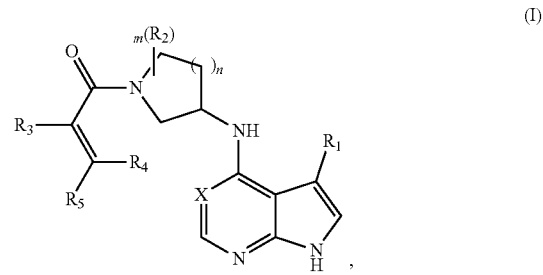

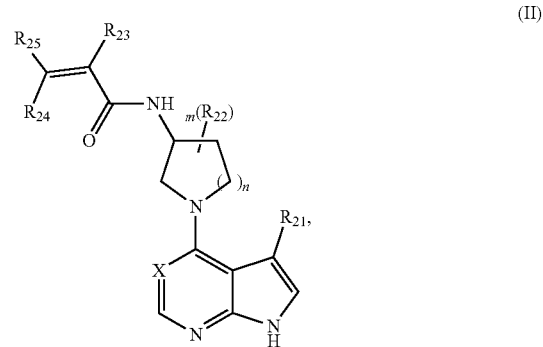

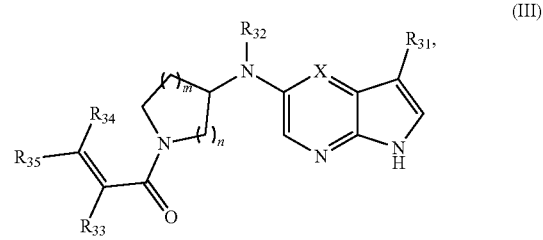

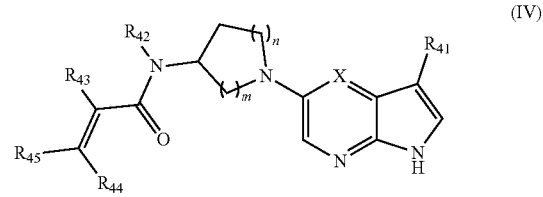

wherein the R groups, m, n, and X are as defined in the detailed description. Methods of inhibition of ITK activity in a human or animal subject are also provided.

34 Claims, No Drawings

(56) References Cited

U.S. PATENT DOCUMENTS

| | | | |
|---|---|---|---|
| 8,163,767 B2 | 4/2012 | Inoue et al. |
| 8,722,693 B2 | 5/2014 | Rodgers et al. |
| 8,921,376 B2 | 12/2014 | Ledeboer et al. |
| 9,556,187 B2 | 1/2017 | Hayashi et al. |
| 10,800,775 B2 | 10/2020 | Anderson et al. |
| 10,981,906 B2 | 4/2021 | Anderson et al. |
| 2007/0135461 A1 | 6/2007 | Rodgers et al. |
| 2007/0135466 A1 | 6/2007 | Ledeboer et al. |
| 2009/0264399 A1 | 10/2009 | Inoue et al. |
| 2010/0105661 A1 | 4/2010 | Shirakami et al. |
| 2010/0113416 A1 | 5/2010 | Friedman et al. |
| 2010/0298355 A1 | 11/2010 | Li et al. |
| 2011/0039822 A1 | 2/2011 | Inoue et al. |
| 2012/0149681 A1 | 6/2012 | Rodgers et al. |
| 2014/0221379 A1 | 8/2014 | Rodgers et al. |
| 2015/0158864 A1 | 6/2015 | Thorarensen et al. |
| 2015/0329542 A1 | 11/2015 | Coe et al. |
| 2016/0272648 A1 | 9/2016 | Rodgers et al. |
| 2017/0333557 A1 | 11/2017 | Ardeleanu et al. |
| 2017/0349579 A1 | 12/2017 | Rodgers et al. |
| 2018/0055846 A1 | 3/2018 | Bates et al. |
| 2019/0135813 A1 | 5/2019 | Rodgers et al. |
| 2020/0405627 A1 | 12/2020 | Butler et al. |

FOREIGN PATENT DOCUMENTS

| | | |
|---|---|---|
| WO | 1999065909 A1 | 12/1999 |
| WO | 2000000202 A1 | 1/2000 |
| WO | 2004099205 A1 | 11/2004 |
| WO | 2006069080 A2 | 6/2006 |
| WO | 2007007919 A2 | 1/2007 |
| WO | 2007077949 A1 | 7/2007 |
| WO | 2008077057 A2 | 6/2008 |
| WO | 2012058645 A1 | 5/2012 |
| WO | 2015083028 A1 | 6/2015 |
| WO | 2015144773 A1 | 10/2015 |
| WO | 2016000615 A1 | 1/2016 |
| WO | 2016118951 A2 | 7/2016 |
| WO | 2016178110 A1 | 11/2016 |
| WO | 2017097224 A1 | 6/2017 |
| WO | 2018004306 A1 | 1/2018 |
| WO | 2019090143 A1 | 5/2019 |
| WO | 2019090158 A1 | 5/2019 |
| WO | 2020033955 A1 | 2/2020 |

OTHER PUBLICATIONS

Bundgaard "Design of Prodrugs" 1985, Elsevier (cover and TOC).
Eliel et al. "Stereochemistry of Organic Compounds" Sep. 1994, Wiley, New York, NY (cover and TOC).
Grimstein et al. "Alpha-1 Antitrypsin Protein and Gene Therapies Decrease Autoimmunity and Delay Arthritis Development in Mouse Model" 2011, J. Translational Med. 9:1-13.
Higuchi et al. "Pro-drugs as Novel Delivery Systems" ACS Symposium Series, 14:1-115.
International Search Report and Written Opinion for PCT/US2018/059050 dated Feb. 25, 2019.
International Search Report and Written Opinion for PCT/US2018/059071 dated Feb. 25, 2019.
International Search Report and Written Opinion for PCT/US2019/046182 dated Dec. 17, 2019.
McMahon "VEGF Receptor Signaling in Tumor Angiogenesis" 2000, The Oncologist 5(supp 1):3-10.
Mozaffari et al. "New Biologic Therapeutics for Ulcerative Colitis and Crohn's Disease" 2014, Expert Opin. Biol. Ther. 14(5):583-600.
Notification, International Search Report and Written Opinion for PCT/US2020/031332 dated Jul. 16, 2020.
Notification, International Search Report and Written Opinion for PCT/US2020/044542 dated Oct. 29, 2020.
Papp et al. "Phase 2 Trial of Selective Tyrosine Kinase 2 Inhibition in Psoriasis" 2018, New England Journal of Medicine 379(14):1313-1321.
Pineda et al. "Translation Research: The Role of VEGF in Tumor Angiogenesis" 2000, The Oncologist 5(supp 1):1-2.
PubChem CID 118115746, https://pubchem.ncbi.nlm.nih.gov/compound/118115746 (downloaded Oct. 7, 2019).
PubChem CID 118115872, pp. 1-9, Feb. 23, 2016.
PubChem CID 59291875, pp. 1-10, Aug. 20, 2012.
Roche "Bioreversible Carriers in Drug Design" 1987, American Pharmaceutical Association, Pergamon Press (Cover and TOC only).
Stahl "Pharmaceutical Salts: Properties, Selection, and Use" 2002, Wiley-VCHA, Zurich, Switzerland (abstract only).
Testa et al. "Hydrolysis in Drug and Prodrug Metabolism: Chemistry, Biochemistry and Enzymology" 2003, Wiley-VHCA, Zurich, Switzerland (Cover and TOC only).
Jin et al., "Topical Application of JAK1/JAK2 Inhibitor Momelotinib Exhibits Significant Anty-Inflammatory Responses in DNCB-Induced Atopic Dermatitis Model Mice", Dec. 10, 2018, Int. J. Molec. Sci. 19(12)(3973):1-14.
Musumeci et al., "Pyrrolo{2, 3- d]pyrimidines active as BTK inhibitors", Jul. 20, 2017, Ex. Opn. Therapeutic Patents 27(12):1305-1318.
Extended European Search Report and Written Opinion for Application No. EP 20798983.1 dated Nov. 10, 2022.
Mark Zak et al., "Identification of C-2 Hydroxyethyl Imidazopyrrolopyridines as Potent JAK1 Inhibitors with Favorable Physiochemical Properties and High Selectivity over JAK2", Journal of Medicinal Chemistry, May 9, 2013, pp. 4764-4785, vol. 56, No. 11.

* cited by examiner

PYRROLOPYRIMIDINE ITK INHIBITORS

CROSS-REFERENCE TO RELATED APPLICATIONS

This application is a continuation of U.S. patent application Ser. No. 16/538,354 filed Aug. 12, 2019, which claims the benefit of U.S. Provisional Application No. 62/717,400 filed Aug. 10, 2018, which is hereby incorporated by reference in its entirety for all purposes.

SUMMARY

Embodiments are directed to compounds disclosed herein, pharmaceutical compositions of such compounds, methods of manufacture and methods of use of such compounds, as described herein.

Some embodiments disclosed herein are directed to a compound of Formula (I):

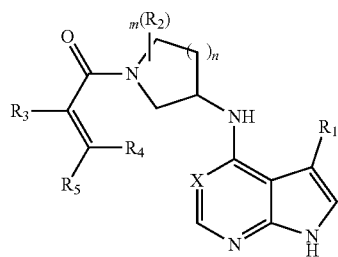

(I)

wherein:
X is N or $CR_3$;
n is 0, 1 or 2;
m is 0, 1, or 2;
$R_1$ is selected from $COOR_6$, $C_1$-$C_5$ alkyl-$COOR_6$, bicycloalkyl, $C_1$-$C_5$-alkyl-heterocyclyl, $C_1$-$C_5$-alkyl-$C_3$-$C_6$-cyclcoalkyl, $C_3$-$C_6$ cycloalkyl, $C(O)C_1$-$C_5$ alkyl, $C(O)C_3$-$C_6$ cycloalkyl, $C(O)C_3$-$C_6$ heterocyclyl, where cycloalkyl, bicycloalkyl, heterocyclyl, and alkyl are optionally substituted with one or more groups selected from $C_1$-$C_5$ alkyl, $C_1$-$C_5$ alkoxy, $C_1$-$C_5$ alkyl-$C_1$-$C_5$ alkoxy, CN, halogen, $COOR_6$, or $C_1$-$C_5$-alkyl-$COOR_6$;
$R_2$ is selected from H, $C_1$-$C_5$ alkyl, $C_3$-$C_6$ cycloalkyl, $C_1$-$C_5$-alkyl-$C_3$-$C_6$-cyclcoalkyl, CN, OH, $C_1$-$C_5$ alkoxy, and halogen where two $R_2$ groups on the same carbon may be joined with or without a heteroatom to make a spirocyclic ring system;
$R_3$ is selected from H, CN, $C_1$-$C_6$ alkyl, $C_3$-$C_6$ cycloalkyl;
$R_4$ is selected from H, $C_1$-$C_6$ alkyl;
$R_5$ is selected from H, $C_1$-$C_6$ alkyl, $C_3$-$C_6$ cycloalkyl, $C_1$-$C_6$-alkyl-$NH_2$, $C_1$-$C_6$ alkyl $NH(C_1$-$C_6$ alkyl), $C_1$-$C_6$ alkyl-$N(C_1$-$C_6$ alkyl)($C_1$-$C_6$ alkyl), $C_1$-$C_5$ alkyl-$C_1$-$C_5$ alkoxy or $C_1$-$C_6$ alkyl-heterocyclyl;
$R_6$ is selected from H, $C_1$-$C_5$ alkyl, $C_3$-$C_6$ cycloalkyl, $C_1$-$C_5$-alkyl-$C_3$-$C_6$-cyclcoalkyl, $C_1$-$C_5$ alkyl-$C_1$-$C_5$ alkoxy, $C_1$-$C_5$ alkyl-OH, $C_1$-$C_5$ alkyl-$NH_2$, $C_1$-$C_5$ alkyl-NH—$C_1$-$C_5$ alkyl, and $C_1$-$C_5$ alkyl-N—($C_1$-$C_5$ alkyl)($C_1$-$C_5$ alkyl); and a derivative thereof.

Some embodiments disclosed herein are directed to a compound of Formula (II):

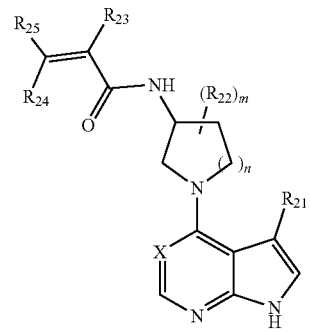

(II)

wherein:
X is N or $CR_{23}$;
n is 0, 1 or 2;
m is 0, 1, or 2;
$R_{21}$ is selected from $COOR_{26}$, $C_1$-$C_5$ alkyl-$COOR_{26}$, bicycloalkyl, $C_1$-$C_5$-alkyl-heterocyclyl, $C_1$-$C_5$-alkyl-$C_3$-$C_6$-cyclcoalkyl, $C_3$-$C_6$ cycloalkyl, $C(O)C_1$-$C_5$ alkyl, $C(O)C_3$-$C_6$ cycloalkyl, $C(O)C_3$-$C_6$ heterocyclyl, where cycloalkyl, bicycloalkyl, heterocyclyl, and alkyl are optionally substituted with one or more groups selected from $C_1$-$C_5$ alkyl, $C_1$-$C_5$ alkoxy, $C_1$-$C_5$ alkyl-$C_1$-$C_5$ alkoxy, CN, halogen, $COOR_{26}$, or $C_1$-$C_5$-alkyl-$COOR_{26}$;
$R_{22}$ is selected from H, $C_1$-$C_5$ alkyl, $C_3$-$C_6$ cycloalkyl, $C_1$-$C_5$-alkyl-$C_3$-$C_6$-cyclcoalkyl, CN, OH, $C_1$-$C_5$ alkoxy, halogen and where two $R_2$ groups on the same carbon may be joined with or without a heteroatom to make a spirocyclic ring system;
$R_{23}$ is selected from H, CN, $C_1$-$C_6$ alkyl, $C_3$-$C_6$ cycloalkyl;
$R_{24}$ is selected from H, $C_1$-$C_6$ alkyl;
$R_{25}$ is selected from H, $C_1$-$C_6$ alkyl, $C_3$-$C_6$ cycloalkyl, $C_1$-$C_6$-alkyl-$NH_2$, $C_1$-$C_6$ alkyl $NH(C_1$-$C_6$ alkyl), $C_1$-$C_6$ alkyl-$N(C_1$-$C_6$ alkyl)($C_1$-$C_6$ alkyl), $C_1$-$C_5$ alkyl-$C_1$-$C_5$ alkoxy or $C_1$-$C_6$ alkyl-heterocyclyl;
$R_{26}$ is selected from H, $C_1$-$C_5$ alkyl, $C_3$-$C_6$ cycloalkyl, $C_1$-$C_5$-alkyl-$C_3$-$C_6$-cyclcoalkyl, $C_1$-$C_5$ alkyl-$C_1$-$C_5$ alkoxy, $C_1$-$C_5$ alkyl-OH, $C_1$-$C_5$ alkyl-$NH_2$, $C_1$-$C_5$ alkyl-NH—$C_1$-$C_5$ alkyl, and $C_1$-$C_5$ alkyl-N—($C_1$-$C_5$ alkyl)($C_1$-$C_5$ alkyl); and a derivative thereof.

Some embodiments disclosed herein are directed to a compound of Formula (III):

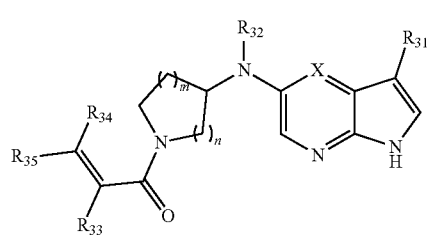

(III)

wherein:
X is $CR_{33}$ or N;
n is 1 or 2;
m is 0, 1 or 2 when n is 1, m is 1 when n is 2;
$R_{31}$ is selected from $COOR_{36}$, $C_1$-$C_5$ alkyl-$COOR_{36}$, bicycloalkyl, $C_1$-$C_5$-alkyl-heterocyclyl, $C_1$-$C_5$-alkyl- $C_3$-$C_6$-cyclcoalkyl, $C_3$-$C_6$ cycloalkyl, C(O)$C_1$-$C_5$ alkyl, C(O)$C_3$-$C_6$ cycloalkyl, C(O)$C_3$-$C_6$ heterocyclyl, where cycloalkyl, bicycloalkyl, heterocyclyl, and alkyl are optionally substituted with one or more groups selected from $C_1$-$C_5$ alkyl, $C_1$-$C_5$ alkoxy, $C_1$-$C_5$ alkyl-$C_1$-$C_5$ alkoxy, CN, halogen, COOR$_{36}$, or $C_1$-$C_5$-alkyl-COOR$_{36}$;

$R_{32}$ is selected from H, $C_1$-$C_5$ alkyl, $C_3$-$C_6$ cycloalkyl, $C_1$-$C_5$-alkyl-$C_3$-$C_6$-cyclcoalkyl;

$R_{33}$ is selected from H, CN, $C_1$-$C_6$ alkyl, $C_3$-$C_6$ cycloalkyl;

$R_{34}$ is selected from H, $C_1$-$C_6$ alkyl;

$R_{35}$ is selected from H, $C_1$-$C_6$ alkyl, $C_3$-$C_6$ cycloalkyl, $C_1$-$C_6$-alkyl-NH$_2$, $C_1$-$C_6$ alkyl NH($C_1$-$C_6$ alkyl), $C_1$-$C_6$ alkyl-N($C_1$-$C_6$ alkyl)($C_1$-$C_6$ alkyl), $C_1$-$C_5$ alkyl-$C_1$-$C_5$ alkoxy;

$R_{36}$ is selected from H, $C_1$-$C_5$ alkyl, $C_3$-$C_6$ cycloalkyl, $C_1$-$C_5$-alkyl-$C_3$-$C_6$-cyclcoalkyl, $C_1$-$C_5$ alkyl-$C_1$-$C_5$ alkoxy, $C_1$-$C_5$ alkyl-OH, $C_1$-$C_5$ alkyl-NH$_2$, $C_1$-$C_5$ alkyl-NH—$C_1$-$C_5$ alkyl, and $C_1$-$C_5$ alkyl-N—($C_1$-$C_5$ alkyl)($C_1$-$C_5$ alkyl); and a derivative thereof.

Some embodiments disclosed herein are directed to a compound of Formula (IV):

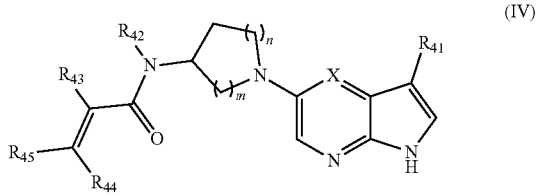

(IV)

wherein:
X is CR$_{43}$ or N;
n is 1 or 2;
m is 0, 1 or 2 when n is 1, m is 1 when n is 2;
$R_{41}$ is selected from COOR$_{46}$, $C_1$-$C_5$ alkyl-COOR$_{46}$, bicycloalkyl, $C_1$-$C_5$-alkyl-heterocyclyl, $C_1$-$C_5$-alkyl-$C_3$-$C_6$-cyclcoalkyl, $C_3$-$C_6$ cycloalkyl, C(O)$C_1$-$C_5$ alkyl, C(O)$C_3$-$C_6$ cycloalkyl, C(O)$C_3$-$C_6$ heterocyclyl, where cycloalkyl, bicycloalkyl, heterocyclyl, and alkyl are optionally substituted with one or more groups selected from $C_1$-$C_5$ alkyl, $C_1$-$C_5$ alkoxy, $C_1$-$C_5$ alkyl-$C_1$-$C_5$ alkoxy, CN, halogen, COOR$_{46}$, or $C_1$-$C_5$-alkyl-COOR$_{46}$;

$R_{42}$ is selected from H, $C_1$-$C_5$ alkyl, $C_3$-$C_6$ cycloalkyl, $C_1$-$C_5$-alkyl-$C_3$-$C_6$-cyclcoalkyl;

$R_{43}$ is selected from H, CN, $C_1$-$C_6$ alkyl, $C_3$-$C_6$ cycloalkyl;

$R_{44}$ is selected from H, $C_1$-$C_6$ alkyl;

$R_{45}$ is selected from H, $C_1$-$C_6$ alkyl, $C_3$-$C_6$ cycloalkyl, $C_1$-$C_6$-alkyl-NH$_2$, $C_1$-$C_6$ alkyl NH($C_1$-$C_6$ alkyl), $C_1$-$C_6$ alkyl-N($C_1$-$C_6$ alkyl)($C_1$-$C_6$ alkyl), $C_1$-$C_5$ alkyl-$C_1$-$C_5$ alkoxy;

$R_{46}$ is selected from H, $C_1$-$C_5$ alkyl, $C_3$-$C_6$ cycloalkyl, $C_1$-$C_5$-alkyl-$C_3$-$C_6$-cyclcoalkyl, $C_1$-$C_5$ alkyl-$C_1$-$C_5$ alkoxy, $C_1$-$C_5$ alkyl-OH, $C_1$-$C_5$ alkyl-NH$_2$, $C_1$-$C_5$ alkyl-NH—$C_1$-$C_5$ alkyl, and $C_1$-$C_5$ alkyl-N—($C_1$-$C_5$ alkyl)($C_1$-$C_5$ alkyl); and a derivative thereof.

In some embodiments, the compounds disclosed herein may possess useful ITK inhibiting activity. Some embodiments herein are directed to treatment or prophylaxis of a disease or condition in which ITK plays an active role using the compounds disclosed herein. In some embodiments, a method of treating an ITK mediated disease or disorder in a subject comprises administering to the subject a compound of embodiments herein.

Some embodiments provide methods for treating an ITK-mediated disorder in a subject in need of such treatment comprising administering to the subject a therapeutically effective amount of a compound or composition according to the present disclosure. Also provided is the use of compounds disclosed herein in the manufacture of a medicament for the treatment of a disease or condition ameliorated by the inhibition of ITK.

DEFINITIONS

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must also be noted that as used herein and in the appended claims, the singular forms "a," "an," and "the" include plural reference unless the context clearly dictates otherwise. Thus, for example, reference to an "ITK inhibitor" is a reference to one or more ITK inhibitor and equivalents thereof known to those skilled in the art, and so forth.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the pharmaceutical composition, composition or the method includes only the elements, steps, or ingredients specifically recited in the particular claimed embodiment or claim.

As used herein, the term "consisting essentially of" or "consists essentially of" means that the pharmaceutical composition, or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the composition or method that treats the specified condition (e.g., nutrient depletion) is the specifically recited therapeutic(s) in the particular embodiment or claim.

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is CH2 is mutually exclusive with an embodiment wherein the same group is NH.

The term "inhibit" means to limit, prevent or block the action or function of a target enzyme and/or, to prevent, alleviate or eliminate the onset of one or more symptoms associated with a disease, condition or disorder, or to prevent, alleviate or eliminate a disease, condition or disorder.

Unless otherwise indicated, the term "skin" means that outer integument or covering of the body, consisting of the dermis and the epidermis and resting upon subcutaneous tissue.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein.

Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—).

Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)NH(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C6H4= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a-OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term, "compound," as used herein is meant to include all stereoisomers, geometric isomers, tautomers, and isotopes (e.g., tritium, deuterium) of the structures depicted.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "halocycloalkyl" as used herein, alone or in combination, refers to an cycloalkyl radical having the meaning as defined above wherein one or more hydrogens are replaced with a halogen. Specifically embraced are monohalocycloalkyl, dihalocycloalkyl and polyhalochaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluorocyclopropyl, difluorocyclopropyl, fluorocyclobutyl, chlorocyclobutyl, and chlorocyclopentyl.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower alkyl," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between four and six ring members, of which between one and four may be heteroatoms chosen from N, O, and S (i.e., $C_3$-$C_6$ heterocycloalkyl). Examples of lower heterocycloalkyls include oxetane, azetidiene, pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

As used herein, an "N-oxide" is formed from the tertiary basic amines or imines present in the molecule, using a convenient oxidizing agent.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "substantially free" as used herein, alone or in combination, refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS).

The terms "sulfonate," "sulfonic acid," and "sulfonic," as used herein, alone or in combination, refer the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to a ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Stereogenic centers exist in the compounds disclosed herein. These centers are designated by the symbols "R" or "S," depending on the configuration of substituents around the stereogenic center. It should be understood that the invention encompasses all stereoisomeric forms, including diastereomeric, enantiomeric, and epimeric forms, as well as d-isomers and l-isomers, and mixtures thereof. Individual stereoisomers of compounds can be prepared synthetically from commercially available starting materials which contain defined stereochemical configurations or by separation of mixtures of stereoisomeric products by conversion to a mixture of diastereomers followed by separation or recrystallization, chromatographic techniques, direct separation of stereoisomers by chiral chromatographic columns, or any other appropriate method known in the art. Starting compounds of particular configurations are either commercially available or can be made and resolved by techniques known in the art. Additionally, the compounds disclosed herein may exist as geometric isomers. The present invention includes all cis, trans, syn, anti, endo, exo entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

Compounds described herein may contain one or more stereogenic centers and may thus exists as stereoisomers. Embodiments herein includes all such possible stereoisomers as substantially pure resolved stereoisomers, racemic mixtures thereof, as well as mixtures of diastereomers. In some embodiments, the formulas are shown without a definitive stereochemistry at certain positions. In other embodiments, the compounds are isolated as single stereoisomers, but the absolute configurations of the stereogenic centers are unknown or only the relative stereochemical configuration (i.e., cis or trans isomerism) is known. In such embodiments, the formulas are shown with provisionally assigned absolute assignments to denote that they are single stereoisomers and relative stereochemical configuration is likewise described. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any stereoisomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, stereoisomers and stereoisomer-enriched mixtures.

Conventional techniques for the preparation/isolation of individual enantiomers include chiral synthesis from a suitable enantioenriched or optically pure precursors or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of embodiments herein (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g., "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of its corresponding enantiomer) and stereoisomer-enriched mixtures, i.e. mixtures of atropisomers. Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

As used herein, the term "a derivative thereof" refers to a salt thereof, a pharmaceutically acceptable salt thereof, an ester thereof, a free acid form thereof, a free base form thereof, a solvate thereof, a co-crystal thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

By "pharmaceutically acceptable", it is meant the carrier, diluent or excipient must be compatible with the other ingredients of the pharmaceutical composition and not deleterious to the recipient thereof.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

Suitable pharmaceutically acceptable acid addition salts of the compounds of embodiments herein may be prepared from an inorganic acid or an organic acid. All of these salts may be prepared by conventional means from the corresponding compound of embodiments herein by treating, for example, the compound with the appropriate acid or base.

Pharmaceutically acceptable acids include both inorganic acids, for example hydrochloric, hydrobromic, hydroiodic, nitric, carbonic, sulfuric, phosphoric and diphosphoric acid; and organic acids, for example formic, acetic, trifluoroacetic, propionic, succinic, glycolic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, O-hydroxybutyric, malonic, galactic, galacturonic, citric, fumaric, gluconic, glutamic, lactic, maleic, malic, mandelic, mucic, ascorbic, oxalic, pantothenic, succinic, tartaric, benzoic, acetic, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, chloroprocaine, diethanolamine, N-methylglucamine, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to embodiments herein are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

In some embodiments, the salt is a hydrochloride salt. In some embodiments, the salt is besylate salt. In some embodiments, the salt is a trifluoroacetate salt.

The compounds of embodiments herein may exist in both unsolvated and solvated forms. The term solvate is used herein to describe a molecular complex comprising a compound of embodiments herein and an amount of one or more pharmaceutically acceptable solvent molecules. The term hydrate is employed when said solvent is water. Examples of solvate forms include, but are not limited to, compounds of embodiments herein in association with water, acetone, dichloromethane, 2-propanol, ethanol, methanol, dimethylsulfoxide (DMSO), ethyl acetate, acetic acid, ethanolamine, or mixtures thereof. It is specifically contemplated that in embodiments herein one solvent molecule can be associated with one molecule of the compounds of embodiments herein, such as a hydrate.

Furthermore, it is specifically contemplated that in embodiments herein, more than one solvent molecule may be associated with one molecule of the compounds of embodiments herein, such as a dihydrate. Additionally, it is specifically contemplated that in embodiments herein less than one solvent molecule may be associated with one molecule of the compounds of embodiments herein, such as a hemihydrate. Furthermore, solvates of embodiments herein are contemplated as solvates of compounds of embodiments herein that retain the biological effectiveness of the non-solvate form of the compounds.

Embodiments herein also include isotopically-labeled compounds of embodiments herein, wherein one or more atoms is replaced by an atom having the same atomic number, but an atomic mass or mass number different from the atomic mass or mass number usually found in nature. Examples of isotopes suitable for inclusion in the compounds of embodiments herein include isotopes of hydrogen, such as $^2H$ and $^3H$, carbon, such as $^{11}C$, $^{13}C$ and $^{14}C$, chlorine, such as $^{31}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{15}S$. Certain isotopically-labeled compounds of embodiments herein, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of embodiments herein can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of embodiments herein. As used herein, the term deuterated derivative embraces compounds of embodiments herein where in a particular position at least one hydrogen atom is replaced by deuterium. Deuterium (D or $^2H$) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of embodiments herein has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In some embodiments, the isotopic enrichment factor is at least 5000 (75% deuterium). In some embodiments, the isotopic enrichment factor is at least 6333.3 (95% deuterium incorporation). In some embodiments, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known to one of ordinary skilled in the art, including mass spectrometry (MS) and nuclear magnetic resonance (NMR).

The term "prodrug" refers to a compound that is made more active in vivo. Prodrugs of the compounds described herein are also within the scope of embodiments herein. Thus, certain derivatives of the compounds of embodiments herein, which derivatives may have little or no pharmacological activity themselves, when administered into or onto the body may be converted into compounds of embodiments herein having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association) or Hydrolysis in Drug and Prodrug Metabolism: Chemistry, Biochemistry, and Enzymology (Testa, Bernard and Mayer, Joachim M. Wiley-VHCA, Zurich, Switzerland 2003).

Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. Prodrugs in accordance with embodiments herein can, for example, be produced by replacing appropriate functionalities present in the compounds of embodiments herein with certain moieties known to those skilled in the art as 'pro-moieties' as described, for example, in Design of Prodrugs by H. Bundgaard (Elsevier, 1985).

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent."

In the case of compounds of embodiments herein that are solids, it is understood by those skilled in the art that the inventive compounds and salts may exist in different crystalline or polymorphic forms, or in an amorphous form, all of which are intended to be within the scope of embodiments herein.

The compounds disclosed herein can exist as and therefore include all stereoisomers, conformational isomers and mixtures thereof in all proportions as well as isotopic forms such as deuterated compounds.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "ITK inhibitor" is used herein to refer to a compound that exhibits an $IC_{50}$ with respect to ITK activity of no more than about 100 µM and more typically not more than about 50 µM, as measured in the ITK enzyme assay described generally herein. $IC_{50}$ is that concentration of inhibitor that reduces the activity of an enzyme (e.g., ITK) to half-maximal level. Certain compounds disclosed herein have been discovered to exhibit inhibition against ITK. In certain embodiments, compounds will exhibit an $IC_{50}$ with respect to ITK of no more than about M; in further embodiments, compounds will exhibit an $IC_{50}$ with respect to ITK of no more than about 5 µM; in yet further embodiments, compounds will exhibit an $IC_{50}$ with respect to ITK of not more than about 1 µM; in yet further embodiments, compounds will exhibit an $IC_{50}$ with respect to ITK of not more than about 200 nM, as measured in the ITK binding assay described herein.

The term "immune checkpoint inhibitor" means a compound or pharmaceutical composition that inhibit immune checkpoint molecules.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound of embodiments herein, can include, but is not limited to, providing the compound into or onto the target tissue; providing the compound systemically to a patient by, e.g., intravenous injection whereby the therapeutic reaches the target tissue; providing the compound in the form of the encoding sequence thereof to the target tissue (e.g., by so-called gene-therapy techniques). "Administering" a composition may be accomplished by injection, topically, orally, or by any of these methods in combination with other known techniques.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The phrase "therapeutically effective" is intended to qualify the amount of active ingredients used in the treatment of a disease or disorder or on the effecting of a clinical endpoint.

As used herein, the term "therapeutic" or "therapeutic agent" or "pharmaceutically active agent" means an agent utilized to treat, combat, ameliorate, prevent or improve an unwanted condition or disease of a patient. In part, embodiments of the present invention are directed to the treatment of ITK-mediated diseases.

A "therapeutically effective amount" or "effective amount" of a composition is a predetermined amount calculated to achieve the desired effect, e.g., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The term "therapeutically acceptable" refers to those compounds, or a derivative thereof, which are suitable for use in contact with the tissues of patients without undue toxicity, irritation, and allergic response, are commensurate with a reasonable benefit/risk ratio, and are effective for their intended use.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

Also provided is a compound chosen from the Examples disclosed herein. The compounds of embodiments herein may also refer to a salt thereof, an ester thereof, a free acid form thereof, a free base form thereof, a solvate thereof, a co-crystal thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination of the foregoing of the compounds of embodiments herein.

The present disclosure relates to new pyrrolopyrimidine compounds and compositions, and their application as pharmaceuticals for the treatment of disease. Methods of inhibition of ITK activity in a human or animal subject are also provided for the treatment diseases such as those caused by inflammation.

The Tec (tyrosine kinase expressed in hepatocellular carcinoma) family of tyrosine kinases (TFTK) consists of five family members: Tec, BTK (Bruton's tyrosine kinase), BMX (bone marrow kinase on the X chromosome also known as ETK), RLK (resting lymphocyte kinase also known as TXK) and ITK (interleukin-2 inducible T cell kinase, also known as EMT and TSK). These kinases are central to the regulation of hematopoietic cell biology and more specifically the development and activity of lymphocytes and myeloid cells. The TFTK have structural similarities to other non-receptor tyrosine kinases while exhibiting some family specific motifs resulting in a diversity of domain structures associated with complex localization, scaffolding and activation mechanisms. Generally, TFTK contain an amino terminal plekstrin homology domain (PH domain) involved in lipid interactions and membrane targeting followed by a BTK homology domain (BH) that binds $Zn^{2+}$ and an SH3 domain generally involved in proline rich domain binding. A phosphotyrosine binding SH2 domain and a carboxy terminal ATP binding kinase domain complete the TFTK structure. TFTK expression is generally limited to hematopoietic lineage cells with the exception of ETK and TEC that are expressed in the liver and endothelial cells, respectively. BMX is expressed in monocytes, granulocytes and cardiac endothelium while BTK is expressed in B cells and mast cells but not plasma cells and T cells. TEC, RLK and ITK are all expressed in T cells. To date the TFTK with the most clear biological role in T cells is ITK.

Antigen/MHC dependent activation of the T cell receptor (TCR) has been shown to transduce its signal through ITK. TCR stimulation results in the activation of the kinase LCK and subsequent phosphorylation of the immunoreceptor tyrosine-based activation motifs (ITAMs) on CD3 inducing the binding and activation of the kinase ZAP70. In turn, ZAP70 phosphorylates the adaptor proteins LAT and SLP-76, which together with LCK and other proteins forms a hetermultimeric signaling complex that activates PI3K and generates $PIP_3$ on the plasma membrane. ITK binds to this signaling complex via SH2 and SH3 domains and to $PIP_3$ through its PH domain, resulting in LCK dependent phosphorylation of ITK Y511 and subsequent ITK autophosphorylation of Y180. Activated ITK phosphorylates PLCγ1 that, once activated, hydrolyzes $PIP_2$ to the second messengers IP3 and DAG. The cellular consequences of these sequelae of events include calcium mobilization and flux, PKC and MEK/ERK pathway activation, and transcriptional activation via APi, NFκactiv NFAT. As a critical enzyme in the TCR activation pathway ITK impacts T cell function in a number of ways including positive and negative selection, cellular differentiation, and cytokine production and release.

The role of ITK in T cell function has been delineated through genetic knockdown/kinase inactivation of the ITK gene in rodents and through characterizing human ITK mutant individuals. Mice with a null mutation of the itk gene expressed a decreased number of mature T cells and a block in thymocyte development as well as a decreased TCR driven T cell proliferative response. Interestingly IL2 and CD28 signaling as well as PMA/ionomycin driven responses remained unchanged, suggesting that the ITK response is membrane proximal and stimuli specific. It appears that ITK is responsible for amplification of TCR signaling versus an 'on/off' switch, as dual knockdown of the T cell expressing TFTK, ITK and RLK in mice produce a more complete TCR inactivation phenotype compared with ITK genetic deletion alone. In contrast to the modulatory effect that ITK appears to have on naïve T cell activation, it plays a more significant role in T helper cell differentiation. Several studies in ITK deficient mice have demonstrated a reduction in the Th2 protective response to parasitic infection. This reduced Th2 response was linked to a decrease in concentrations of Th2 cytokines IL4, IL5, IL13 and IL10 and to a reduction in RLK expression. In contrast to the ITK requirement for mounting Th2 driven responses, its impact on Th1 responses is modest. For example, IFNg production in ITK knockout cells is partially inhibited while the double ITK/RLK knockout has a more severe phenotype. Evaluation of Th17 T helper cells in ITK knockout in vivo and in vitro studies demonstrated a reduction of IL17A mRNA and protein while having little impact on IL17F. The role of ITK in cytotoxic CD8+ T cells was investigated using ITK knockout mice. Stimulation of CD8+ T cells deficient in ITK results in a reduction in activation of PLCg1, ERK and p38 MAPK and loss of $Ca^{2+}$ response resulting in decreased proliferative response and effector cytokine production (IL2, IL4 and IFNg) while not impacting cytolytic capacity of these cells. In addition to the defects observed in CD4+ and CD8+ T cells, natural killer T cell development and TCR stimulated response is reduced in ITK knockout cells and animals.

Rodent genetic knockout studies reflect the impact of enzyme expression, not necessarily its catalytic activity, on biological responses. As ITK, through its multiple domain structure, has a role in scaffolding, in addition to its catalytic role. It is important to delineate the impact of blocking each of these functions on cellular biology. Kinase activity-independent ITK activities include recruitment of the guanine nucleotide exchange factor VAV to the cell membrane associated with actin polymerization (PH and SH2 domain dependent), antigen receptor stimulation, and receptor activation of SRF. However, ITK knockout mice expressing an ITK kinase domain deleted transgene demonstrated that the kinase domain is essential for induction of a normal Th2 response.

The relationship between ITK expression and activity and human disease has recently been documented in studies characterizing individuals exhibiting mutations in the gene encoding this protein and or correlation between expression and disease. The ITK gene was found to be elevated in peripheral blood T cells from patients with moderate to severe atopic dermatitis, a Th2 driven chronic inflammatory skin disease. An investigation of disease-associated single nucleotide polymorphisms (SNP) in seasonal allergic rhinitis identified ITK as a significant risk factor. A human primary immunodeficiency was uncovered in siblings that died from immune dysregulation resulting in lymphoproliferation following Epstein Barr Virus (EBV) infection. This disorder was linked to a missense (R335W) mutation in the SH2 domain of ITK resulting in structural instability and reduced steady state levels of the enzyme. The finding was confirmed and extended in studies that identified three patients harboring a C1764G nonsense mutation in ITK resulting in a premature stop codon and reduced expression and/or activity of the protein. These patients presented with EBV-positive Hodgkins Lymphoma. These two reports suggest that mutational disruption of the ITK gene in humans results in an autosomal recessive lymphoproliferative disorder and identifies this kinase as a critical modulator in T cell biology.

In addition to the human genetic data summarized above, animal models support ITK as a therapeutic target for autoimmune and inflammatory disease. ITK knockout mice demonstrate reduced airway hypersensitivity and inflammation in models of allergic asthma. In a murine model of atopic dermatitis, ITK deficient mice do not develop inflammation while ITK inhibition reduces the response in wild type mice. The ITK dependent regulation of TCR dependent $Ca^{2+}$ mobilization and transcription factor induction makes it a critical factor in protecting against Influenza A and HIV infection and viral replication. ITK inhibitors have been shown to alter HIV replication at multiple stages and have the potential as effective HIV therapeutics.

From an oncology perspective, studies have demonstrated that ITK inhibitors selectively target the killing of acute lymphblastic T-cell leukemia and cutaneous T-cell lymphoma while normal T cells are minimally impacted. ITK is highly expressed in transformed T-cell lines relative to normal T cells and other cancer cell lines. The impact of ITK inhibition on T cell tumors was confirmed in mouse xenograph models. Cancer evasion of the immune system as a result of tumor antigen tolerance induction versus priming is critical for tumor survival. Tumors that develop a microenvironment that induces T cell unresponsiveness demonstrate altered T cell gene expression suggesting skewing to the Th2 phenotype. ITK inhibition will favor Th1 differentiation and could be used to enhance cancer immunotherapy.

The utility of simultaneously inhibiting signals downstream of both the T cell receptor and cytokines receptors is best exemplified by the field of organ transplantation (Halloran). Standard-of-care in the immediate post-transplant setting is to prevent immunological graft rejection by dosing with a cocktail of inhibitors that impinge on lymphocyte activation at different points. The most common drugs used in both the initial post-transplant period, as well as the discharge setting—are a calcineurin inhibitor such as Prograf or Neoral, which block TCR signaling, and an antimetabolite, such mycophenolate mofetil or rapamycin, which block the proliferation induced downstream of cytokines such as IL-2 or IL-15. These drugs cannot be used as monotherapy, as it would require higher doses resulting in drug-specific toxicity. By using these drugs at sub-optimal doses simultaneously, synergistic immunosuppression is achieved with reduced toxicity. ITK is downstream of TCR and JAK3 is downstream of the common g chain of cytokine receptors. By virtue of covalently modifying the cysteine in the catalytic domain of both kinases, it is possible to inhibit both enzymes with a single drug and thereby synergistically inhibit the activation of T cells.

The detailed description set-forth herein is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

Compounds

In some embodiments, said compound has structural Formula (I):

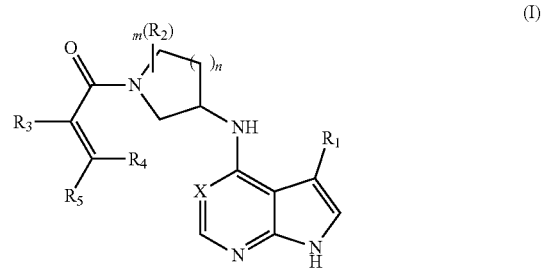

(I)

wherein:

X is N or CR$_3$;

n is 0, 1 or 2;

m is 0, 1, or 2;

R$_1$ is selected from COOR$_6$, C$_1$-C$_5$ alkyl-COOR$_6$, bicycloalkyl, C$_1$-C$_5$-alkyl-heterocyclyl, C$_1$-C$_5$-alkyl-C$_3$-C$_6$-cyclcoalkyl, C$_3$-C$_6$ cycloalkyl, C(O)C$_1$-C$_5$ alkyl, C(O)C$_3$-C$_6$ cycloalkyl, C(O)C$_3$-C$_6$ heterocyclyl, where cycloalkyl, bicycloalkyl, heterocyclyl, and alkyl are optionally substituted with one or more groups selected from C$_1$-C$_5$ alkyl, C$_1$-C$_5$ alkoxy, C$_1$-C$_5$ alkyl-C$_1$-C$_5$ alkoxy, CN, halogen, COOR$_6$, or C$_1$-C$_5$-alkyl-COOR$_6$;

R$_2$ is selected from H, C$_1$-C$_5$ alkyl, C$_3$-C$_6$ cycloalkyl, C$_1$-C$_5$-alkyl-C$_3$-C$_6$-cyclcoalkyl, CN, OH, C$_1$-C$_5$ alkoxy, and halogen where two R$_2$ groups on the same carbon may be joined with or without a heteroatom to make a spirocyclic ring system;

R$_3$ is selected from H, CN, C$_1$-C$_6$ alkyl, C$_3$-C$_6$ cycloalkyl;

R$_4$ is selected from H, C$_1$-C$_6$ alkyl;

R$_5$ is selected from H, C$_1$-C$_6$ alkyl, C$_3$-C$_6$ cycloalkyl, C$_1$-C$_6$-alkyl-NH$_2$, C$_1$-C$_6$ alkyl NH(C$_1$-C$_6$ alkyl), C$_1$-C$_6$ alkyl-N(C$_1$-C$_6$ alkyl)(C$_1$-C$_6$ alkyl), C$_1$-C$_5$ alkyl-C$_1$-C$_5$ alkoxy or C$_1$-C$_6$ alkyl-heterocyclyl;

R$_6$ is selected from H, C$_1$-C$_5$ alkyl, C$_3$-C$_6$ cycloalkyl, C$_1$-C$_5$-alkyl-C$_3$-C$_6$-cyclcoalkyl, C$_1$-C$_5$ alkyl-C$_1$-C$_5$ alkoxy, C$_1$-C$_5$ alkyl-OH, C$_1$-C$_5$ alkyl-NH$_2$, C$_1$-C$_5$ alkyl-NH—C$_1$-C$_5$ alkyl, and C$_1$-C$_5$ alkyl-N—(C$_1$-C$_5$ alkyl)(C$_1$-C$_5$ alkyl); and a derivative thereof.

In an embodiment of said compound of structural Formula (I), a compound of the present disclosure is administered with a pharmaceutically acceptable carrier, adjuvant, or vehicle.

Embodiments of the present disclosure are directed to a compound of structural Formula (II):

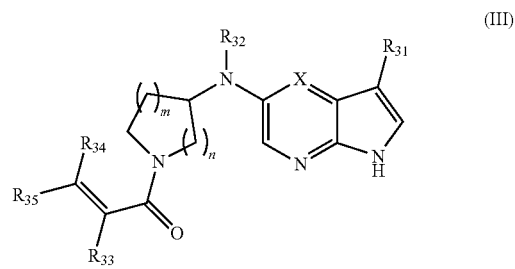

(II)

wherein:

X is N or CR$_{23}$;

n is 0, 1 or 2;

m is 0, 1, or 2;

R$_{21}$ is selected from COOR$_{26}$, C$_1$-C$_5$ alkyl-COOR$_{26}$, bicycloalkyl, C$_1$-C$_5$-alkyl-heterocyclyl, C$_1$-C$_5$-alkyl-C$_3$-C$_6$-cyclcoalkyl, C$_3$-C$_6$ cycloalkyl, C(O)C$_1$-C$_5$ alkyl, C(O)C$_3$-C$_6$ cycloalkyl, C(O)C$_3$-C$_6$ heterocyclyl, where cycloalkyl, bicycloalkyl, heterocyclyl, and alkyl are optionally substituted with one or more groups selected from C$_1$-C$_5$ alkyl, C$_1$-C$_5$ alkoxy, C$_1$-C$_5$ alkyl-C$_1$-C$_5$ alkoxy, CN, halogen, COOR$_{26}$, or C$_1$-C$_5$-alkyl-COOR$_{26}$;

R$_{22}$ is selected from H, C$_1$-C$_5$ alkyl, C$_3$-C$_6$ cycloalkyl, C$_1$-C$_5$-alkyl-C$_3$-C$_6$-cyclcoalkyl, CN, OH, C$_1$-C$_5$ alkoxy, halogen and where two R$_2$ groups on the same carbon may be joined with or without a heteroatom to make a spirocyclic ring system;

R$_{23}$ is selected from H, CN, C$_1$-C$_6$ alkyl, C$_3$-C$_6$ cycloalkyl;

R$_{24}$ is selected from H, C$_1$-C$_6$ alkyl;

R$_{25}$ is selected from H, C$_1$-C$_6$ alkyl, C$_3$-C$_6$ cycloalkyl, C$_1$-C$_6$-alkyl-NH$_2$, C$_1$-C$_6$ alkyl NH(C$_1$-C$_6$ alkyl), C$_1$-C$_6$ alkyl-N(C$_1$-C$_6$ alkyl)(C$_1$-C$_6$ alkyl), C$_1$-C$_5$ alkyl-C$_1$-C$_5$ alkoxy or C$_1$-C$_6$ alkyl-heterocyclyl; R$_{26}$ is selected from H, C$_1$-C$_5$ alkyl, C$_3$-C$_6$ cycloalkyl, C$_1$-C$_5$-alkyl-C$_3$-C$_6$-cyclcoalkyl, C$_1$-C$_5$ alkyl-C$_1$-C$_5$ alkoxy, C$_1$-C$_5$ alkyl-OH, C$_1$-C$_5$ alkyl-NH$_2$, C$_1$-C$_5$ alkyl-NH—C$_1$-C$_5$ alkyl, and C$_1$-C$_5$ alkyl-N—(C$_1$-C$_5$ alkyl)(C$_1$-C$_5$ alkyl); and a derivative thereof.

In an embodiment of said compound of structural Formula (II), a compound of the present disclosure is administered with a pharmaceutically acceptable carrier, adjuvant, or vehicle.

Embodiments of the present disclosure are directed to a compound of structural Formula (III):

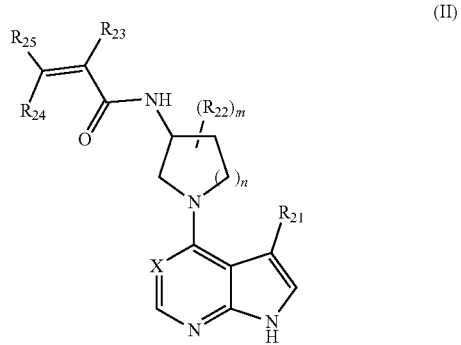

(III)

wherein:

X is CR$_{33}$ or N;

n is 1 or 2;

m is 0, 1 or 2 when n is 1, m is 1 when n is 2;

R$_{31}$ is selected from COOR$_{36}$, C$_1$-C$_5$ alkyl-COOR$_{36}$, bicycloalkyl, C$_1$-C$_5$-alkyl-heterocyclyl, C$_1$-C$_5$-alkyl-C$_3$-C$_6$-cyclcoalkyl, C$_3$-C$_6$ cycloalkyl, C(O)C$_1$-C$_5$ alkyl, C(O)C$_3$-C$_6$ cycloalkyl, C(O)C$_3$-C$_6$ heterocyclyl, where cycloalkyl, bicycloalkyl, heterocyclyl, and alkyl are optionally substituted with one or more groups selected from C$_1$-C$_5$ alkyl, C$_1$-C$_5$ alkoxy, C$_1$-C$_5$ alkyl-C$_1$-C$_5$ alkoxy, CN, halogen, COOR$_{36}$, or C$_1$-C$_5$-alkyl-COOR$_{36}$;

R$_{32}$ is selected from H, C$_1$-C$_5$ alkyl, C$_3$-C$_6$ cycloalkyl, C$_1$-C$_5$-alkyl-C$_3$-C$_6$-cyclcoalkyl;

R$_{33}$ is selected from H, CN, C$_1$-C$_6$ alkyl, C$_3$-C$_6$ cycloalkyl;

R$_{34}$ is selected from H, C$_1$-C$_6$ alkyl;

R$_{35}$ is selected from H, C$_1$-C$_6$ alkyl, C$_3$-C$_6$ cycloalkyl, C$_1$-C$_6$-alkyl-NH$_2$, C$_1$-C$_6$ alkyl NH(C$_1$-C$_6$ alkyl), C$_1$-C$_6$ alkyl-N(C$_1$-C$_6$ alkyl)(C$_1$-C$_6$ alkyl), C$_1$-C$_5$ alkyl-C$_1$-C$_5$ alkoxy;

R$_{36}$ is selected from H, C$_1$-C$_5$ alkyl, C$_3$-C$_6$ cycloalkyl, C$_1$-C$_5$-alkyl-C$_3$-C$_6$-cyclcoalkyl, C$_1$-C$_5$ alkyl-C$_1$-C$_5$ alkoxy, C$_1$-C$_5$ alkyl-OH, C$_1$-C$_5$ alkyl-NH$_2$, C$_1$-C$_5$ alkyl-NH—C$_1$-C$_5$ alkyl, and C$_1$-C$_5$ alkyl-N—(C$_1$-C$_5$ alkyl)(C$_1$-C$_5$ alkyl); and a derivative thereof.

In an embodiment of said compound of structural Formula (III), a compound of the present disclosure is administered with a pharmaceutically acceptable carrier, adjuvant, or vehicle.

Embodiments of the present disclosure are directed to a compound of structural Formula (IV):

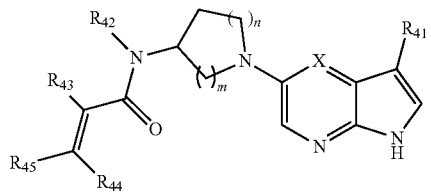

(IV)

wherein:
X is $CR_{43}$ or N;
n is 1 or 2;
m is 0, 1 or 2 when n is 1, m is 1 when n is 2;
$R_{41}$ is selected from $COOR_{46}$, $C_1$-$C_5$ alkyl-$COOR_{46}$, bicycloalkyl, $C_1$-$C_5$-alkyl-heterocyclyl, $C_1$-$C_5$-alkyl-$C_3$-$C_6$-cyclcoalkyl, $C_3$-$C_6$ cycloalkyl, $C(O)C_1$-$C_5$ alkyl, $C(O)C_3$-$C_6$ cycloalkyl, $C(O)C_3$-$C_6$ heterocyclyl, where cycloalkyl, bicycloalkyl, heterocyclyl, and alkyl are optionally substituted with one or more groups selected from $C_1$-$C_5$ alkyl, $C_1$-$C_5$ alkoxy, $C_1$-$C_5$ alkyl-$C_1$-$C_5$ alkoxy, CN, halogen, $COOR_{46}$, or $C_1$-$C_5$-alkyl-$COOR_{46}$;
$R_{42}$ is selected from H, $C_1$-$C_5$ alkyl, $C_3$-$C_6$ cycloalkyl, $C_1$-$C_5$-alkyl-$C_3$-$C_6$-cyclcoalkyl;
$R_{43}$ is selected from H, CN, $C_1$-$C_6$ alkyl, $C_3$-$C_6$ cycloalkyl;
$R_{44}$ is selected from H, $C_1$-$C_6$ alkyl;
$R_{45}$ is selected from H, $C_1$-$C_6$ alkyl, $C_3$-$C_6$ cycloalkyl, $C_1$-$C_6$-alkyl-$NH_2$, $C_1$-$C_6$ alkyl $NH(C_1$-$C_6$ alkyl), $C_1$-$C_6$ alkyl-$N(C_1$-$C_6$ alkyl)($C_1$-$C_6$ alkyl), $C_1$-$C_5$ alkyl-$C_1$-$C_5$ alkoxy;
$R_{46}$ is selected from H, $C_1$-$C_5$ alkyl, $C_3$-$C_6$ cycloalkyl, $C_1$-$C_5$-alkyl-$C_3$-$C_6$-cyclcoalkyl, $C_1$-$C_5$ alkyl-$C_1$-$C_5$ alkoxy, $C_1$-$C_5$ alkyl-OH, $C_1$-$C_5$ alkyl-$NH_2$, $C_1$-$C_5$ alkyl-NH—$C_1$-$C_5$ alkyl, and $C_1$-$C_5$ alkyl-N—($C_1$-$C_5$ alkyl)($C_1$-$C_5$ alkyl); and a derivative thereof.

In an embodiment of said compound of structural Formula (IV), a compound of the present disclosure is administered with a pharmaceutically acceptable carrier, adjuvant, or vehicle.

In some embodiments, the compound of Formula (I), or a derivative thereof, may be selected from:

| Example # | Structure | Name |
|---|---|---|
| 1 | 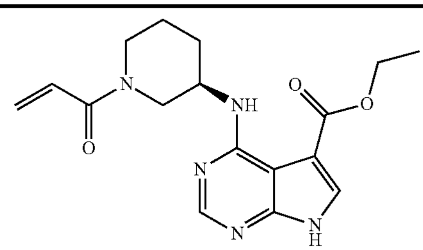 | ethyl (R)-4-((1-acryloylpiperidin-3-yl)amino)-7H-pyrrolo[2,3-d]pyrimidine-5-carboxylate |
| 2 | 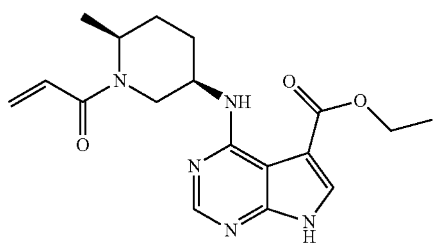 [SMILES: C=CC(=O)N1C[C@H](Nc2ncnc3[nH]cc(C(=O)OCC)c23)CC[C@@H]1C] | ethyl 4-(((3R,6S)-1-acryloyl-6-methylpiperidin-3-yl)amino)-7H-pyrrolo[2,3-d]pyrimidine-5-carboxylate |
| 3 | 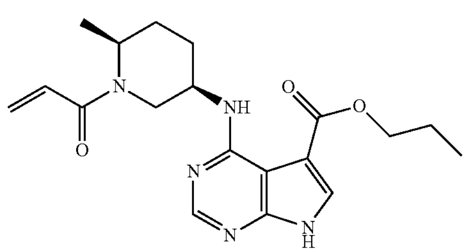 [SMILES: C=CC(=O)N1C[C@H](Nc2ncnc3[nH]cc(C(=O)OCCC)c23)CC[C@@H]1C] | propyl 4-(((3R,6S)-1-acryloyl-6-methylpiperidin-3-yl)amino)-7H-pyrrolo[2,3-d]pyrimidine-5-carboxylate |
| 4 | 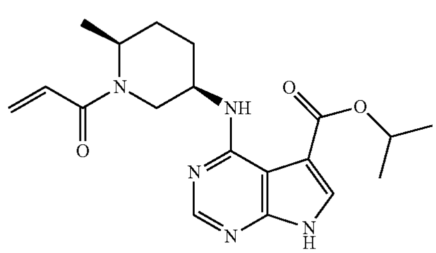 [SMILES: C=CC(=O)N1C[C@H](Nc2ncnc3[nH]cc(C(=O)OC(C)C)c23)CC[C@@H]1C] | isopropyl 4-(((3R,6S)-1-acryloyl-6-methylpiperidin-3-yl)amino)-7H-pyrrolo[2,3-d]pyrimidine-5-carboxylate |

-continued

| Example # | Structure | Name |
|---|---|---|
| 5 | 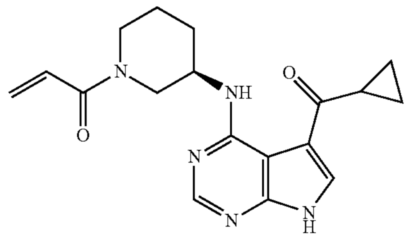 [SMILES: C=CC(=O)N1CCC[C@@H](Nc2ncnc3[nH]cc(C(=O)C4CC4)c23)C1] | (R)-1-(3-((5-(cyclopropanecarbonyl)-7H-pyrrolo[2,3-d]pyrimidin-4-yl)amino)piperidin-1-yl)prop-2-en-1-one |
| 6 | 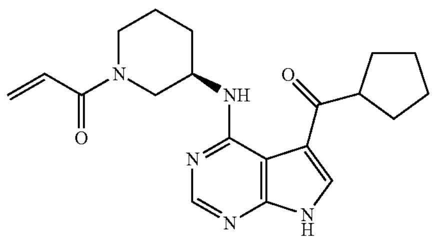 [SMILES: C=CC(=O)N1CCC[C@@H](Nc2ncnc3[nH]cc(C(=O)C4CCCC4)c23)C1] | (R)-1-(3-((5-(cyclopentanecarbonyl)-7H-pyrrolo[2,3-d]pyrimidin-4-yl)amino)piperidin-1-yl)prop-2-en-1-one |
| 7 | 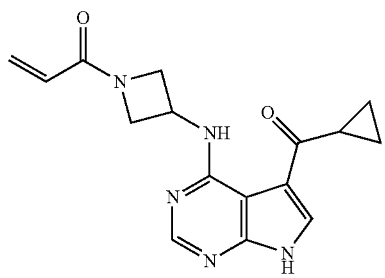 [SMILES: C=CC(=O)N1CC(Nc2ncnc3[nH]cc(C(=O)C4CC4)c23)C1] | 1-(3-((5-(cyclopropanecarbonyl)-7H-pyrrolo[2,3-d]pyrimidin-4-yl)amino)azetidin-1-yl)prop-2-en-1-one |
| 8 | 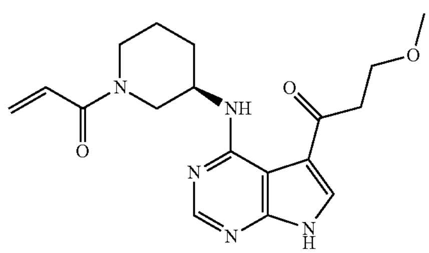 [SMILES: C=CC(=O)N1CCC[C@@H](Nc2ncnc3[nH]cc(C(=O)CCOC)c23)C1] | (R)-1-(3-((3-(3-methoxypropanoyl)-1H-pyrrolo[2,3-b]pyridin-4-yl)amino)piperidin-1-yl)prop-2-en-1-one |
| 9 | 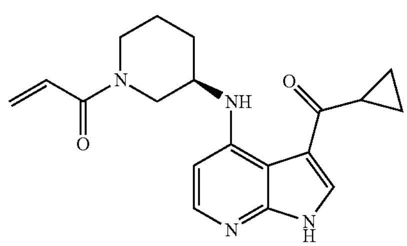 [SMILES: C=CC(=O)N1CCC[C@@H](Nc2ccnc3[nH]cc(C(=O)C4CC4)c23)C1] | (R)-1-(3-((3-(cyclopropanecarbonyl)-1H-pyrrolo[2,3-b]pyridin-4-yl)amino)piperidin-1-yl)prop-2-en-1-one |
| 10 | 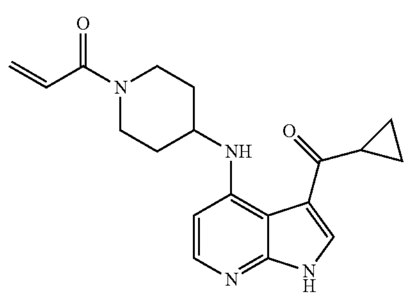 [SMILES: C=CC(=O)N1CCC(Nc2ccnc3[nH]cc(C(=O)C4CC4)c23)CC1] | 1-(4-((3-(cyclopropanecarbonyl)-1H-pyrrolo[2,3-b]pyridin-4-yl)amino)piperidin-1-yl)prop-2-en-1-one |

-continued

| Example # | Structure | Name |
| --- | --- | --- |
| 11 | 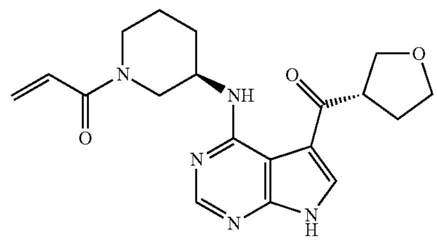 [SMILES: C=CC(=O)N1CCC[C@@H](Nc2ncnc3[nH]cc(C(=O)[C@H]4CCOC4)c23)C1] | 1-((R)-3-((5-((S)-tetrahydrofuran-3-carbonyl)-7H-pyrrolo[2,3-d]pyrimidin-4-yl)amino)piperidin-1-yl)prop-2-en-1-one |
| 12 | 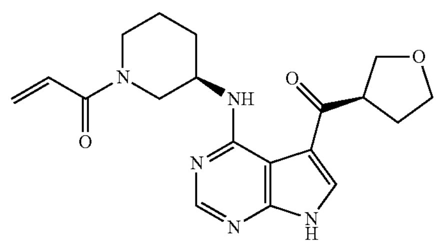 [SMILES: C=CC(=O)N1CCC[C@@H](Nc2ncnc3[nH]cc(C(=O)[C@@H]4CCOC4)c23)C1] | 1-((R)-3-((5-((R)-tetrahydrofuran-3-carbonyl)-7H-pyrrolo[2,3-d]pyrimidin-4-yl)amino)piperidin-1-yl)prop-2-en-1-one |
| 13 | 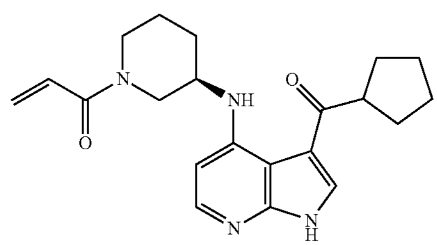 [SMILES: C=CC(=O)N1CCC[C@@H](Nc2ccnc3[nH]cc(C(=O)C4CCCC4)c23)C1] | (R)-1-(3-((3-(cyclopentanecarbonyl)-1H-pyrrolo[2,3-b]pyridin-4-yl)amino)piperidin-1-yl)prop-2-en-1-one |
| 14 | 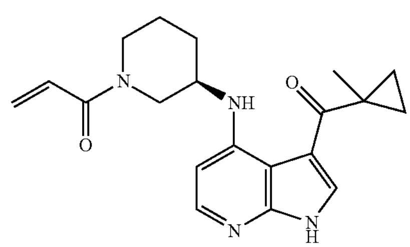 [SMILES: C=CC(=O)N1CCC[C@@H](Nc2ccnc3[nH]cc(C(=O)C4(C)CC4)c23)C1] | (R)-1-(3-((3-(1-methylcyclopropane-1-carbonyl)-1H-pyrrolo[2,3-b]pyridin-4-yl)amino)piperidin-1-yl)prop-2-en-1-one |
| 15 | 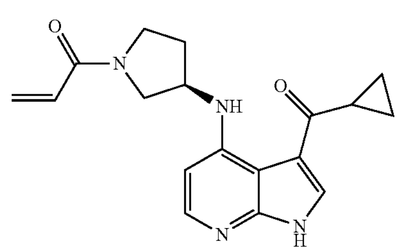 [SMILES: C=CC(=O)N1CC[C@@H](Nc2ccnc3[nH]cc(C(=O)C4CC4)c23)C1] | (R)-1-(3-((3-(cyclopropanecarbonyl)-1H-pyrrolo[2,3-b]pyridin-4-yl)amino)pyrrolidin-1-yl)prop-2-en-1-one |
| 16 | 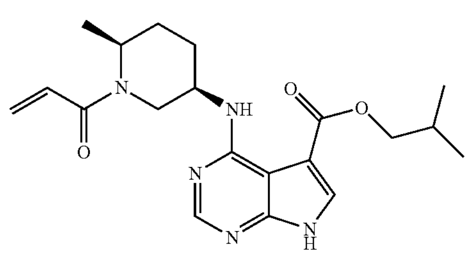 [SMILES: C=CC(=O)N1C[C@H](Nc2ncnc3[nH]cc(C(=O)OCC(C)C)c23)CC[C@@H]1C] | isobutyl 4-(((3R,6S)-1-acryloyl-6-methylpiperidin-3-yl)amino)-7H-pyrrolo[2,3-d]pyrimidine-5-carboxylate |

-continued

| Example # | Structure | Name |
|---|---|---|
| 17 | 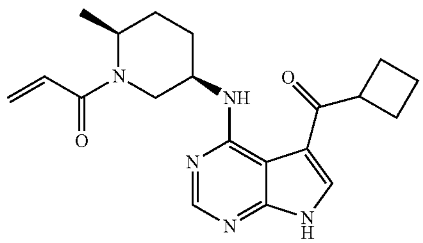 [SMILES: C=CC(=O)N1C[C@H](Nc2ncnc3[nH]cc(C(=O)C4CCC4)c23)CC[C@@H]1C] | 1-((2S,5R)-5-((5-(cyclobutanecarbonyl)-7H-pyrrolo[2,3-d]pyrimidin-4-yl)amino)-2-methylpiperidin-1-yl)prop-2-en-1-one |
| 18 | 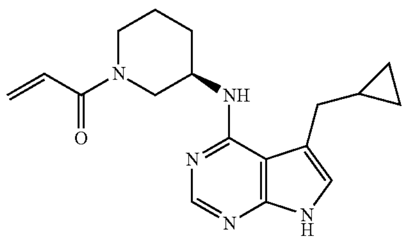 [SMILES: C=CC(=O)N1CCC[C@@H](Nc2ncnc3[nH]cc(CC4CC4)c23)C1] | (R)-1-(3-((5-(cyclopropylmethyl)-7H-pyrrolo[2,3-d]pyrimidin-4-yl)amino)piperidin-1-yl)prop-2-en-1-one |
| 19 | 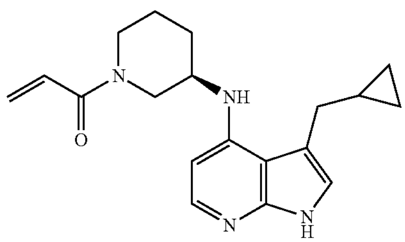 [SMILES: C=CC(=O)N1CCC[C@@H](Nc2ccnc3[nH]cc(CC4CC4)c23)C1] | (R)-1-(3-((3-(cyclopropylmethyl)-1H-pyrrolo[2,3-b]pyridin-4-yl)amino)piperidin-1-yl)prop-2-en-1-one |
| 20 | 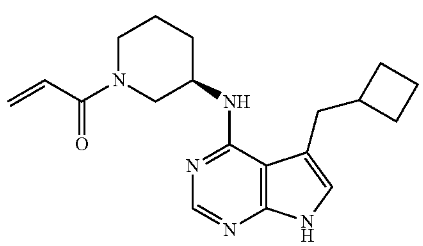 [SMILES: C=CC(=O)N1CCC[C@@H](Nc2ncnc3[nH]cc(CC4CCC4)c23)C1] | (R)-1-(3-((5-(cyclobutylmethyl)-7H-pyrrolo[2,3-d]pyrimidin-4-yl)amino)piperidin-1-yl)prop-2-en-1-one |
| 21 | 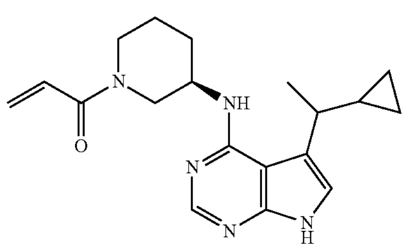 [SMILES: C=CC(=O)N1CCC[C@@H](Nc2ncnc3[nH]cc(C(C)C4CC4)c23)C1] | 1-((3R)-3-((5-(1-cyclopropylethyl)-7H-pyrrolo[2,3-d]pyrimidin-4-yl)amino)piperidin-1-yl)prop-2-en-1-one |
| 22 | 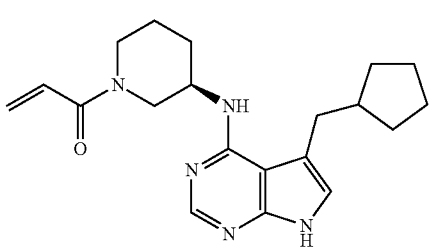 [SMILES: C=CC(=O)N1CCC[C@@H](Nc2ncnc3[nH]cc(CC4CCCC4)c23)C1] | (R)-1-(3-((3-(cyclopentylmethyl)-1H-pyrrolo[2,3-b]pyridin-4-yl)amino)piperidin-1-yl)prop-2-en-1-one |

-continued

| Example # | Structure | Name |
|---|---|---|
| 23 | 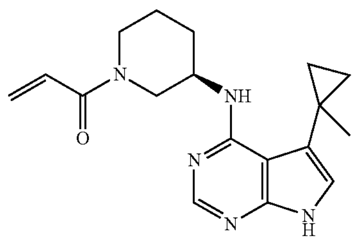 [SMILES: C=CC(=O)N1CCC[C@@H](Nc2ncnc3[nH]cc(C4(C)CC4)c23)C1] | (R)-1-(3-((5-(1-methylcyclopropyl)-7H-pyrrolo[2,3-d]pyrimidin-4-yl)amino)piperidin-1-yl)prop-2-en-1-one |
| 24 | 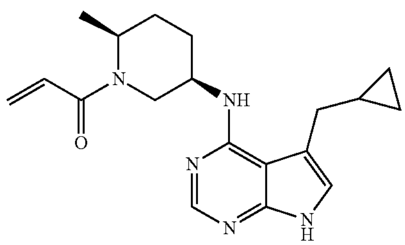 [SMILES: C=CC(=O)N1C[C@H](Nc2ncnc3[nH]cc(CC4CC4)c23)CC[C@@H]1C] | 1-((2S,5R)-5-((5-(cyclopropylmethyl)-7H-pyrrolo[2,3-d]pyrimidin-4-yl)amino)-2-methylpiperidin-1-yl)prop-2-en-1-one |
| 25 | 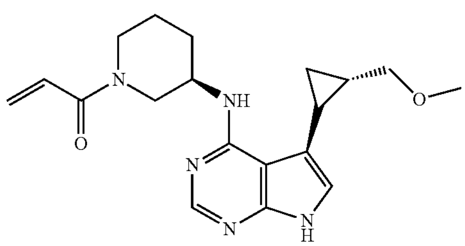 | 1-((R)-3-((5-((1S,2S)-2-(methoxymethyl)cyclopropyl)-7H-pyrrolo[2,3-d]pyrimidin-4-yl)amino)piperidin-1-yl)prop-2-en-1-one |
| 26 | 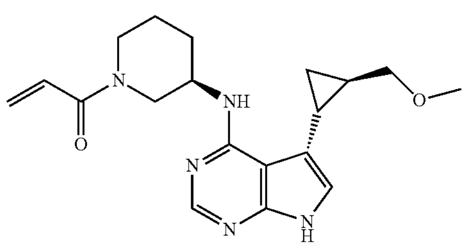 | 1-((R)-3-((5-((1R,2R)-2-(methoxymethyl)cyclopropyl)-7H-pyrrolo[2,3-d]pyrimidin-4-yl)amino)piperidin-1-yl)prop-2-en-1-one |
| 27 | 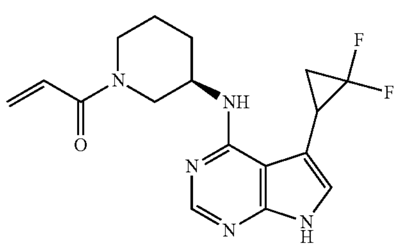 [SMILES: C=CC(=O)N1CCC[C@@H](Nc2ncnc3[nH]cc(C4CC4(F)F)c23)C1] | 1-((3R)-3-((5-(2,2-difluorocyclopropyl)-7H-pyrrolo[2,3-d]pyrimidin-4-yl)amino)piperidin-1-yl)prop-2-en-1-one |
| 28 | 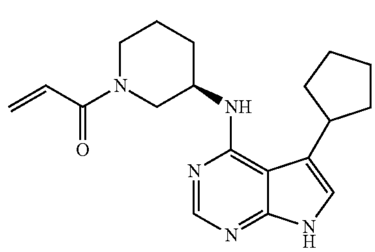 [SMILES: C=CC(=O)N1CCC[C@@H](Nc2ncnc3[nH]cc(C4CCCC4)c23)C1] | (R)-1-(3-((3-cyclopentyl-1H-pyrrolo[2,3-b]pyridin-4-yl)amino)piperidin-1-yl)prop-2-en-1-one |

-continued

| Example # | Structure | Name |
|---|---|---|
| 29 | 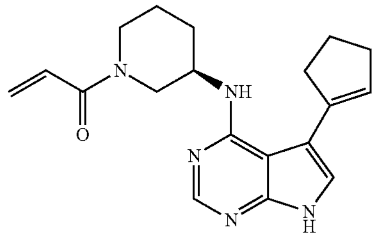 [SMILES: C=CC(=O)N1CCC[C@@H](Nc2ncnc3[nH]cc(C4=CCCC4)c23)C1] | (R)-1-(3-((3-(cyclopent-1-en-1-yl)-1H-pyrrolo[2,3-b]pyridin-4-yl)amino)piperidin-1-yl)prop-2-en-1-one |
| 30 | 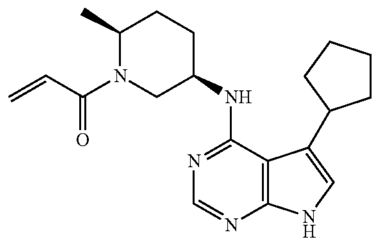 [SMILES: C=CC(=O)N1C[C@H](Nc2ncnc3[nH]cc(C4CCCC4)c23)CC[C@@H]1C] | 1-((2S,5R)-5-((5-cyclopentyl-7H-pyrrolo[2,3-d]pyrimidin-4-yl)amino)-2-methylpiperidin-1-yl)prop-2-en-1-one |
| 31 | 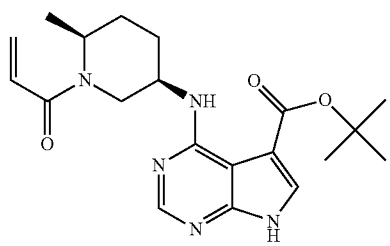 [SMILES: C=CC(=O)N1C[C@H](Nc2ncnc3[nH]cc(C(=O)OC(C)(C)C)c23)CC[C@@H]1C] | tert-butyl 4-(((3R,6S)-1-acryloyl-6-methylpiperidin-3-yl)amino)-7H-pyrrolo[2,3-d]pyrimidine-5-carboxylate |
| 32 | 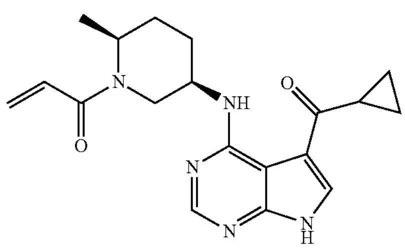 [SMILES: C=CC(=O)N1C[C@H](Nc2ncnc3[nH]cc(C(=O)C4CC4)c23)CC[C@@H]1C] | 1-((2S,5R)-5-((5-(cyclopropanecarbonyl)-7H-pyrrolo[2,3-d]pyrimidin-4-yl)amino)-2-methylpiperidin-1-yl)prop-2-en-1-one |
| 33 | 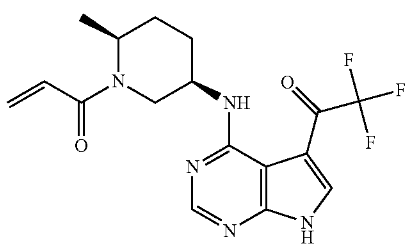 [SMILES: C=CC(=O)N1C[C@H](Nc2ncnc3[nH]cc(C(=O)C(F)(F)F)c23)CC[C@@H]1C] | 1-((2S,5R)-2-methyl-5-((5-(2,2,2-trifluoroacetyl)-7H-pyrrolo[2,3-d]pyrimidin-4-yl)amino)piperidin-1-yl)prop-2-en-1-one |
| 34 | 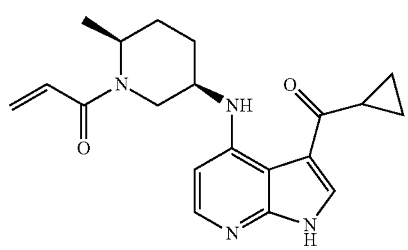 | 1-((2S,5R)-5-((3-(cyclopropanecarbonyl)-1H-pyrrolo[2,3-b]pyridin-4-yl)amino)-2-methylpiperidin-1-yl)prop-2-en-1-one |

-continued

| Example # | Structure | Name |
|---|---|---|
| 35 | 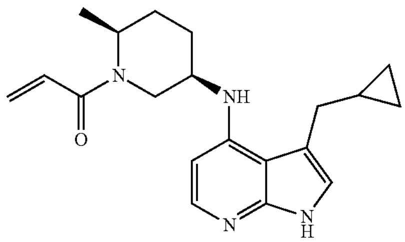 [SMILES: C=CC(=O)N1C[C@H](Nc2ccnc3[nH]cc(CC4CC4)c23)CC[C@@H]1C] | 1-((2S,5R)-5-((3-(cyclopropylmethyl)-1H-pyrrolo[2,3-b]pyridin-4-yl)amino)-2-methylpiperidin-1-yl)prop-2-en-1-one |
| 36 | 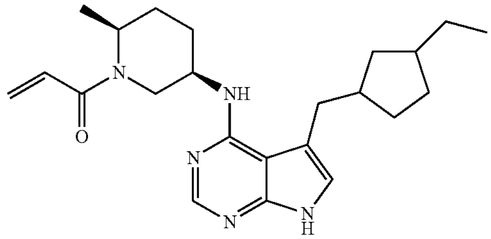 [SMILES: C=CC(=O)N1C[C@H](Nc2ncnc3[nH]cc(CC4CCC(CC)C4)c23)CC[C@@H]1C] | 1-((2S,5R)-5-((5-((3-ethylcyclopentyl)methyl)-7H-pyrrolo[2,3-d]pyrimidin-4-yl)amino)-2-methylpiperidin-1-yl)prop-2-en-1-one |
| 37 | 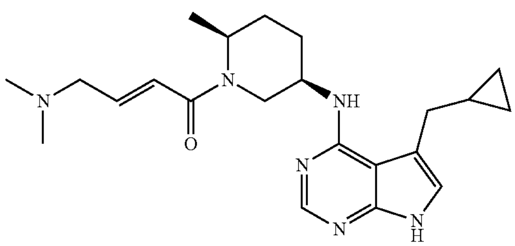 [SMILES: C[C@H]1CC[C@@H](Nc2ncnc3[nH]cc(CC4CC4)c23)CN1C(=O)/C=C/CN(C)C] | (E)-1-((2S,5R)-5-((5-(cyclopropylmethyl)-7H-pyrrolo[2,3-d]pyrimidin-4-yl)amino)-2-methylpiperidin-1-yl)-4-(dimethylamino)but-2-en-1-one |
| 38 | 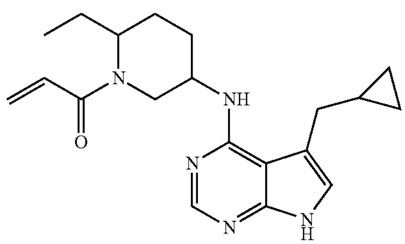 [SMILES: C=CC(=O)N1CC(Nc2ncnc3[nH]cc(CC4CC4)c23)CCC1CC] | 1-(5-((5-(cyclopropylmethyl)-7H-pyrrolo[2,3-d]pyrimidin-4-yl)amino)-2-ethylpiperidin-1-yl)prop-2-en-1-one |
| 39 | 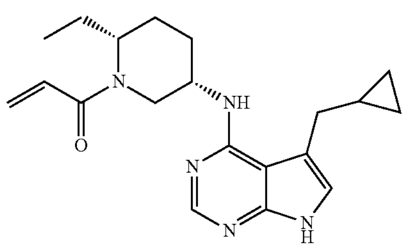 [SMILES: C=CC(=O)N1C[C@@H](Nc2ncnc3[nH]cc(CC4CC4)c23)CC[C@H]1CC] | 1-((2R,5S)-5-((5-(cyclopropylmethyl)-7H-pyrrolo[2,3-d]pyrimidin-4-yl)amino)-2-ethylpiperidin-1-yl)prop-2-en-1-one |
| 40 | 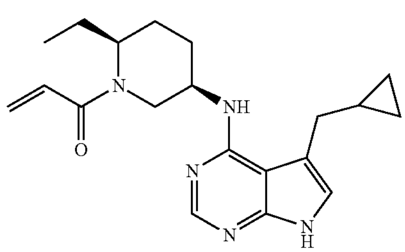 [SMILES: C=CC(=O)N1C[C@H](Nc2ncnc3[nH]cc(CC4CC4)c23)CC[C@@H]1CC] | 1-((2S,5R)-5-((5-(cyclopropylmethyl)-7H-pyrrolo[2,3-d]pyrimidin-4-yl)amino)-2-ethylpiperidin-1-yl)prop-2-en-1-one |

-continued

| Example # | Structure | Name |
|---|---|---|
| 41 | 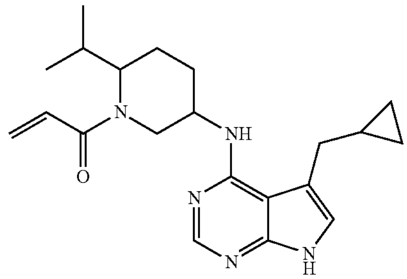 [SMILES: C=CC(=O)N1CC(Nc2ncnc3[nH]cc(CC4CC4)c23)CCC1C(C)C] | 1-(5-((5-(cyclopropylmethyl)-7H-pyrrolo[2,3-d]pyrimidin-4-yl)amino)-2-isopropylpiperidin-1-yl)prop-2-en-1-one |
| 42 | 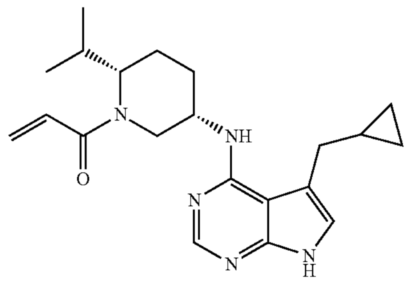 [SMILES: C=CC(=O)N1C[C@@H](Nc2ncnc3[nH]cc(CC4CC4)c23)CC[C@H]1C(C)C] | 1-((2S,5S)-5-((5-(cyclopropylmethyl)-7H-pyrrolo[2,3-d]pyrimidin-4-yl)amino)-2-isopropylpiperidin-1-yl)prop-2-en-1-one |
| 43 | 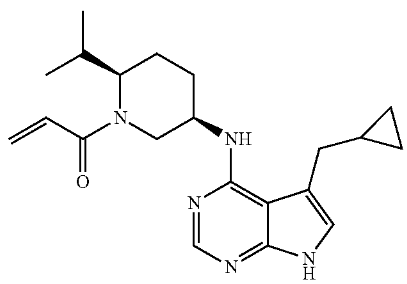 [SMILES: C=CC(=O)N1C[C@H](Nc2ncnc3[nH]cc(CC4CC4)c23)CC[C@@H]1C(C)C] | 1-((2R,5R)-5-((5-(cyclopropylmethyl)-7H-pyrrolo[2,3-d]pyrimidin-4-yl)amino)-2-isopropylpiperidin-1-yl)prop-2-en-1-one |
| 44 | 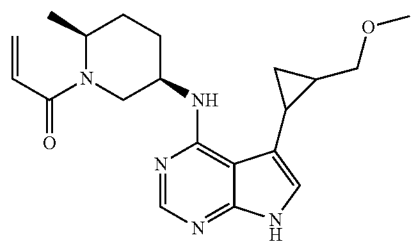 [SMILES: C=CC(=O)N1C[C@H](Nc2ncnc3[nH]cc(C4CC4COC)c23)CC[C@@H]1C] | 1-((2S,5R)-5-((5-(2-(methoxymethyl)cyclopropyl)-7H-pyrrolo[2,3-d]pyrimidin-4-yl)amino)-2-methylpiperidin-1-yl)prop-2-en-1-one |
| 45 | 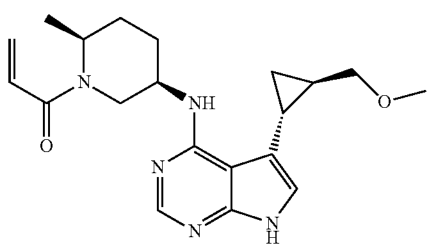 [SMILES: C=CC(=O)N1C[C@H](Nc2ncnc3[nH]cc([C@@H]4C[C@H]4COC)c23)CC[C@@H]1C] | 1-((2S,5R)-5-((5-((1R,2R)-2-(methoxymethyl)cyclopropyl)-7H-pyrrolo[2,3-d]pyrimidin-4-yl)amino)-2-methylpiperidin-1-yl)prop-2-en-1-one |
| 46 | 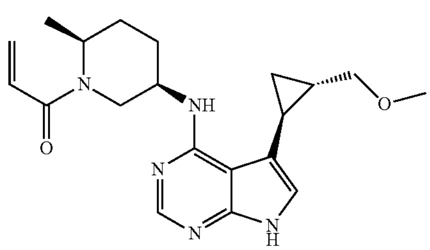 [SMILES: C=CC(=O)N1C[C@H](Nc2ncnc3[nH]cc([C@H]4C[C@@H]4COC)c23)CC[C@@H]1C] | 1-((2S,5R)-5-((5-((1S,2S)-2-(methoxymethyl)cyclopropyl)-7H-pyrrolo[2,3-d]pyrimidin-4-yl)amino)-2-methylpiperidin-1-yl)prop-2-en-1-one |

-continued

| Example # | Structure | Name |
|---|---|---|
| 47 | 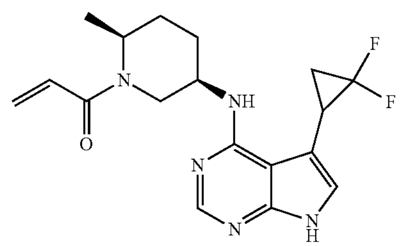 | 1-((2S,5R)-5-((5-(2,2-difluorocyclopropyl)-7H-pyrrolo[2,3-d]pyrimidin-4-yl)amino)-2-methylpiperidin-1-yl)prop-2-en-1-one |
| 48 | 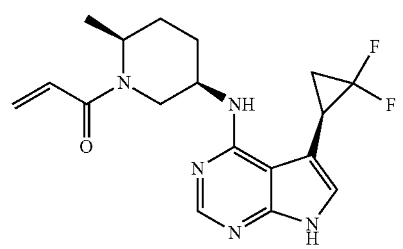 | 1-((2S,5R)-5-((5-((R)-2,2-difluorocyclopropyl)-7H-pyrrolo[2,3-d]pyrimidin-4-yl)amino)-2-methylpiperidin-1-yl)prop-2-en-1-one |
| 49 | 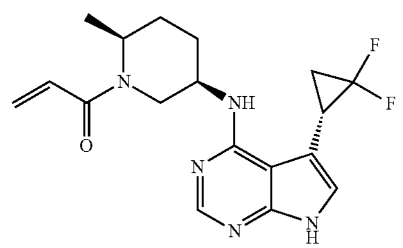 | 1-((2S,5R)-5-((5-((S)-2,2-difluorocyclopropyl)-7H-pyrrolo[2,3-d]pyrimidin-4-yl)amino)-2-methylpiperidin-1-yl)prop-2-en-1-one |
| 50 | 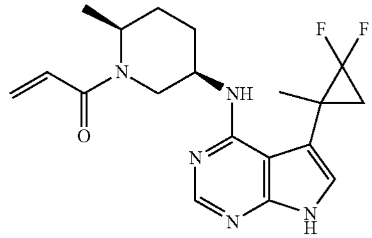 [SMILES: C=CC(=O)N1C[C@H](Nc2ncnc3[nH]cc(C4(C)CC4(F)F)c23)CC[C@@H]1C] | 1-((2S,5R)-5-((5-(2,2-difluoro-1-methylcyclopropyl)-7H-pyrrolo[2,3-d]pyrimidin-4-yl)amino)-2-methylpiperidin-1-yl)prop-2-en-1-one |
| 51 | 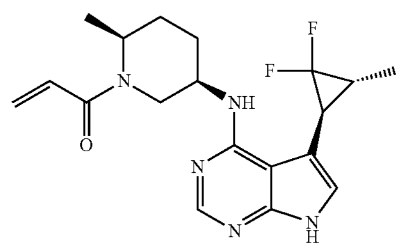 [SMILES: C=CC(=O)N1C[C@H](Nc2ncnc3[nH]cc([C@@H]4[C@@H](C)C4(F)F)c23)CC[C@@H]1C] | 1-((2S,5R)-5-((5-((1S,3R)-2,2-difluoro-3-methylcyclopropyl)-7H-pyrrolo[2,3-d]pyrimidin-4-yl)amino)-2-methylpiperidin-1-yl)prop-2-en-1-one |
| 52 | 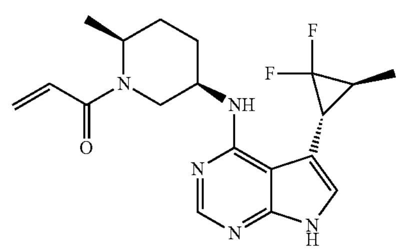 [SMILES: C=CC(=O)N1C[C@H](Nc2ncnc3[nH]cc([C@H]4[C@H](C)C4(F)F)c23)CC[C@@H]1C] | 1-((2S,5R)-5-((5-((1R,3S)-2,2-difluoro-3-methylcyclopropyl)-7H-pyrrolo[2,3-d]pyrimidin-4-yl)amino)-2-methylpiperidin-1-yl)prop-2-en-1-one |

-continued

| Example # | Structure | Name |
|---|---|---|
| 53 | 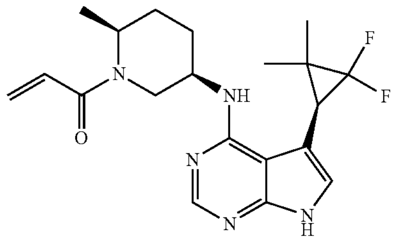 [SMILES: C=CC(=O)N1C[C@H](Nc2ncnc3[nH]cc([C@H]4C(C)(C)C4(F)F)c23)CC[C@@H]1C] | 1-((2S,5R)-5-((5-((S)-2,2-difluoro-3,3-dimethylcyclopropyl)-7H-pyrrolo[2,3-d]pyrimidin-4-yl)amino)-2-methylpiperidin-1-yl)prop-2-en-1-one |
| 54 | 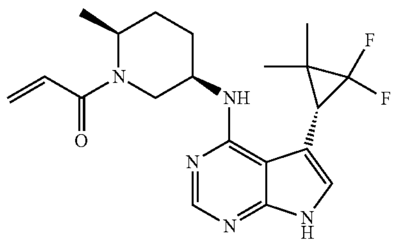 [SMILES: C=CC(=O)N1C[C@H](Nc2ncnc3[nH]cc([C@@H]4C(C)(C)C4(F)F)c23)CC[C@@H]1C] | 1-((2S,5R)-5-((5-((R)-2,2-difluoro-3,3-dimethylcyclopropyl)-7H-pyrrolo[2,3-d]pyrimidin-4-yl)amino)-2-methylpiperidin-1-yl)prop-2-en-1-one |
| 55 | 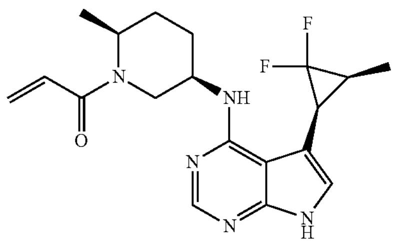 [SMILES: C=CC(=O)N1C[C@H](Nc2ncnc3[nH]cc([C@@H]4[C@H](C)C4(F)F)c23)CC[C@@H]1C] | 1-((2S,5R)-5-((5-((1S,3S)-2,2-difluoro-3-methylcyclopropyl)-7H-pyrrolo[2,3-d]pyrimidin-4-yl)amino)-2-methylpiperidin-1-yl)prop-2-en-1-one |
| 56 | 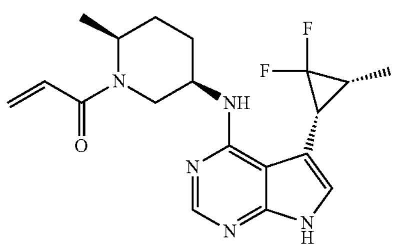 [SMILES: C=CC(=O)N1C[C@H](Nc2ncnc3[nH]cc([C@H]4[C@@H](C)C4(F)F)c23)CC[C@@H]1C] | 1-((2S,5R)-5-((5-((1R,3R)-2,2-difluoro-3-methylcyclopropyl)-7H-pyrrolo[2,3-d]pyrimidin-4-yl)amino)-2-methylpiperidin-1-yl)prop-2-en-1-one |
| 57 | 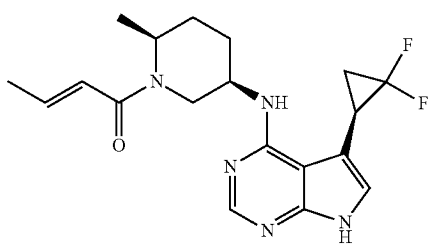 [SMILES: C/C=C/C(=O)N1C[C@H](Nc2ncnc3[nH]cc([C@H]4CC4(F)F)c23)CC[C@@H]1C] | (E)-1-((2S,5R)-5-((5-((R)-2,2-difluorocyclopropyl)-7H-pyrrolo[2,3-d]pyrimidin-4-yl)amino)-2-methylpiperidin-1-yl)but-2-en-1-one |
| 58 | 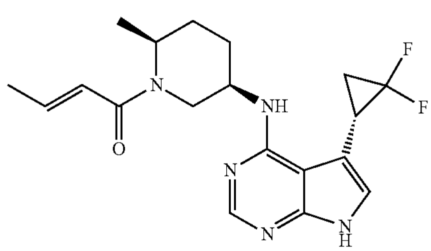 [SMILES: C/C=C/C(=O)N1C[C@H](Nc2ncnc3[nH]cc([C@@H]4CC4(F)F)c23)CC[C@@H]1C] | (E)-1-((2S,5R)-5-((5-((S)-2,2-difluorocyclopropyl)-7H-pyrrolo[2,3-d]pyrimidin-4-yl)amino)-2-methylpiperidin-1-yl)but-2-en-1-one |

-continued

| Example # | Structure | Name |
|---|---|---|
| 59 | 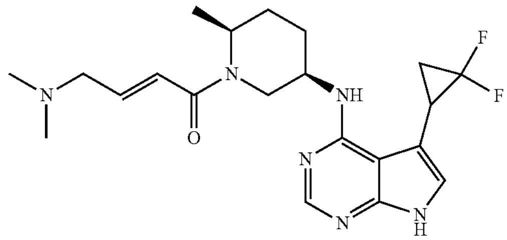 [SMILES: C[C@H]1CC[C@@H](Nc2ncnc3[nH]cc(C4CC4(F)F)c23)CN1C(=O)/C=C/CN(C)C] | (E)-1-((2S,5R)-5-((5-(2,2-difluorocyclopropyl)-7H-pyrrolo[2,3-d]pyrimidin-4-yl)amino)-2-methylpiperidin-1-yl)-4-(dimethylamino)but-2-en-1-one |
| 60 | 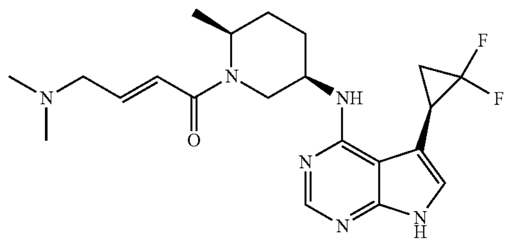 [SMILES: C[C@H]1CC[C@@H](Nc2ncnc3[nH]cc([C@H]4CC4(F)F)c23)CN1C(=O)/C=C/CN(C)C] | (E)-1-((2S,5R)-5-((5-((R)-2,2-difluorocyclopropyl)-7H-pyrrolo[2,3-d]pyrimidin-4-yl)amino)-2-methylpiperidin-1-yl)-4-(dimethylamino)but-2-en-1-one |
| 61 | 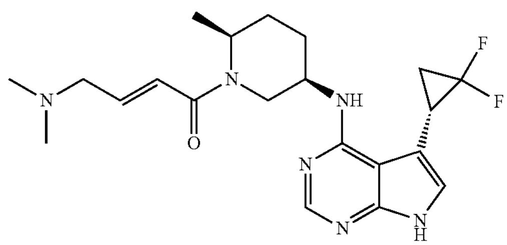 | (E)-1-((2S,5R)-5-((5-((S)-2,2-difluorocyclopropyl)-7H-pyrrolo[2,3-d]pyrimidin-4-yl)amino)-2-methylpiperidin-1-yl)-4-(dimethylamino)but-2-en-1-one |
| 62 | 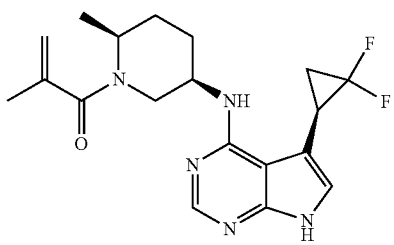 [SMILES: C=C(C)C(=O)N1C[C@H](Nc2ncnc3[nH]cc([C@H]4CC4(F)F)c23)CC[C@@H]1C] | 1-((2S,5R)-5-((5-((R)-2,2-difluorocyclopropyl)-7H-pyrrolo[2,3-d]pyrimidin-4-yl)amino)-2-methylpiperidin-1-yl)-2-methylprop-2-en-1-one |
| 63 | 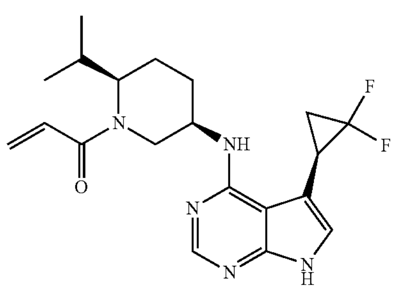 [SMILES: C=CC(=O)N1C[C@H](Nc2ncnc3[nH]cc([C@H]4CC4(F)F)c23)CC[C@@H]1C(C)C] | 1-((2R,5R)-5-((5-((R)-2,2-difluorocyclopropyl)-7H-pyrrolo[2,3-d]pyrimidin-4-yl)amino)-2-isopropylpiperidin-1-yl)prop-2-en-1-one |
| 64 | 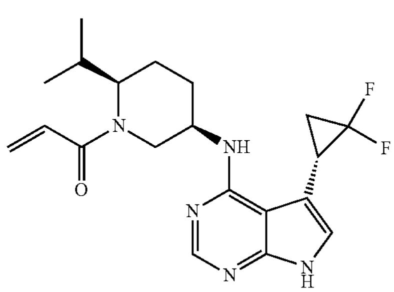 [SMILES: C=CC(=O)N1C[C@H](Nc2ncnc3[nH]cc([C@@H]4CC4(F)F)c23)CC[C@@H]1C(C)C] | 1-((2R,5R)-5-((5-((S)-2,2-difluorocyclopropyl)-7H-pyrrolo[2,3-d]pyrimidin-4-yl)amino)-2-isopropylpiperidin-1-yl)prop-2-en-1-one |

-continued

| Example # | Structure | Name |
|---|---|---|
| 65 | 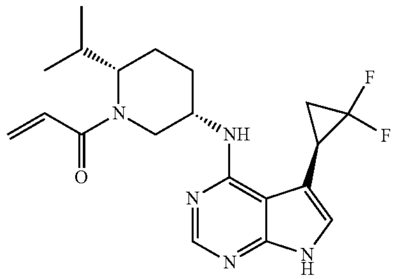 [SMILES: C=CC(=O)N1C[C@@H](Nc2ncnc3[nH]cc([C@H]4CC4(F)F)c23)CC[C@H]1C(C)C] | 1-((2S,5S)-5-((5-((R)-2,2-difluorocyclopropyl)-7H-pyrrolo[2,3-d]pyrimidin-4-yl)amino)-2-isopropylpiperidin-1-yl)prop-2-en-1-one |
| 66 | 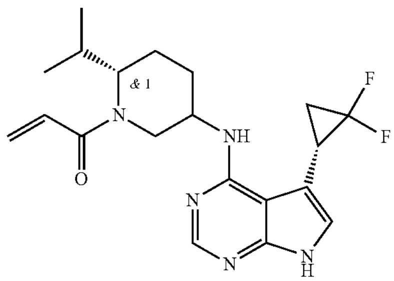 [SMILES: C=CC(=O)N1CC(Nc2ncnc3[nH]cc([C@@H]4CC4(F)F)c23)CC[C@H]1C(C)C] | 1-((2S)-5-((5-((S)-2,2-difluorocyclopropyl)-7H-pyrrolo[2,3-d]pyrimidin-4-yl)amino)-2-isopropylpiperidin-1-yl)prop-2-en-1-one |
| 67 | 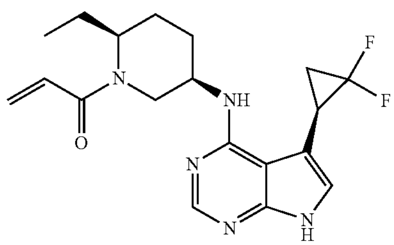 [SMILES: C=CC(=O)N1C[C@H](Nc2ncnc3[nH]cc([C@H]4CC4(F)F)c23)CC[C@@H]1CC] | 1-((2S,5R)-5-((5-((R)-2,2-difluorocyclopropyl)-7H-pyrrolo[2,3-d]pyrimidin-4-yl)amino)-2-ethylpiperidin-1-yl)prop-2-en-1-one |
| 68 | 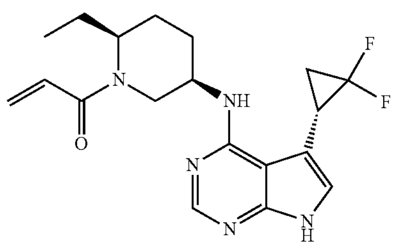 [SMILES: C=CC(=O)N1C[C@H](Nc2ncnc3[nH]cc([C@@H]4CC4(F)F)c23)CC[C@@H]1CC] | 1-((2S,5R)-5-((5-((S)-2,2-difluorocyclopropyl)-7H-pyrrolo[2,3-d]pyrimidin-4-yl)amino)-2-ethylpiperidin-1-yl)prop-2-en-1-one |
| 69 | 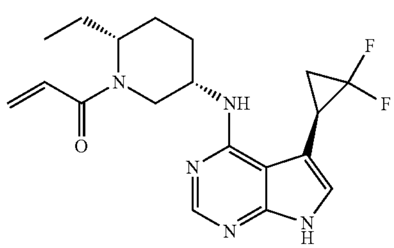 [SMILES: C=CC(=O)N1C[C@@H](Nc2ncnc3[nH]cc([C@H]4CC4(F)F)c23)CC[C@H]1CC] | 1-((2R,5S)-5-((5-((R)-2,2-difluorocyclopropyl)-7H-pyrrolo[2,3-d]pyrimidin-4-yl)amino)-2-ethylpiperidin-1-yl)prop-2-en-1-one |
| 70 | 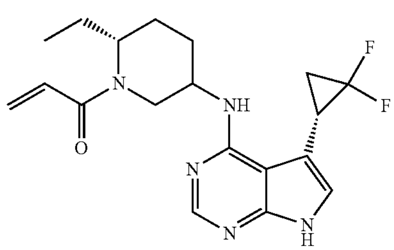 [SMILES: C=CC(=O)N1CC(Nc2ncnc3[nH]cc([C@@H]4CC4(F)F)c23)CC[C@H]1CC] | 1-((2R)-5-((5-((S)-2,2-difluorocyclopropyl)-7H-pyrrolo[2,3-d]pyrimidin-4-yl)amino)-2-ethylpiperidin-1-yl)prop-2-en-1-one |

-continued

| Example # | Structure | Name |
|---|---|---|
| 71 | 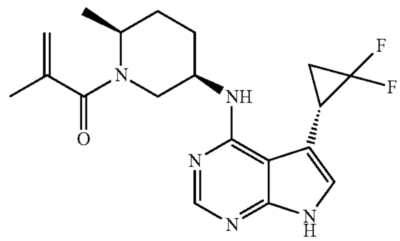 [SMILES: C=C(C)C(=O)N1C[C@H](Nc2ncnc3[nH]cc([C@@H]4CC4(F)F)c23)CC[C@@H]1C] | 1-((2S,5R)-5-((5-((S)-2,2-difluorocyclopropyl)-7H-pyrrolo[2,3-d]pyrimidin-4-yl)amino)-2-methylpiperidin-1-yl)-2-methylprop-2-en-1-one |
| 72 | 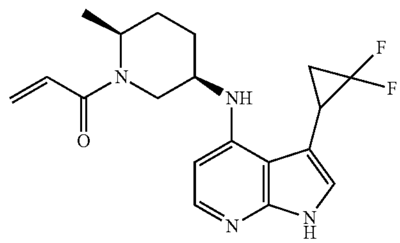 [SMILES: C=CC(=O)N1C[C@H](Nc2ccnc3[nH]cc(C4CC4(F)F)c23)CC[C@@H]1C] | 1-((2S,5R)-5-((3-(2,2-difluorocyclopropyl)-1H-pyrrolo[2,3-b]pyridin-4-yl)amino)-2-methylpiperidin-1-yl)prop-2-en-1-one |
| 73 | 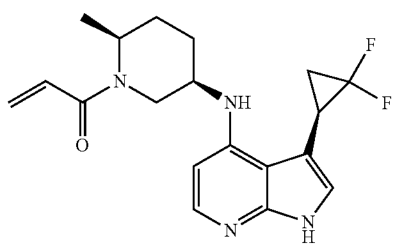 [SMILES: C=CC(=O)N1C[C@H](Nc2ccnc3[nH]cc([C@H]4CC4(F)F)c23)CC[C@@H]1C] | 1-((2S,5R)-5-((3-((R)-2,2-difluorocyclopropyl)-1H-pyrrolo[2,3-b]pyridin-4-yl)amino)-2-methylpiperidin-1-yl)prop-2-en-1-one |
| 74 | 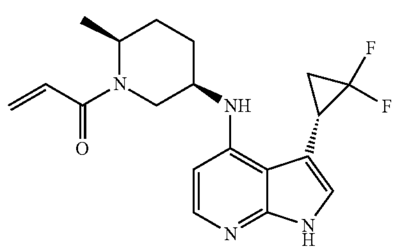 [SMILES: C=CC(=O)N1C[C@H](Nc2ccnc3[nH]cc([C@@H]4CC4(F)F)c23)CC[C@@H]1C] | 1-((2S,5R)-5-((3-((S)-2,2-difluorocyclopropyl)-1H-pyrrolo[2,3-b]pyridin-4-yl)amino)-2-methylpiperidin-1-yl)prop-2-en-1-one |
| 75 | 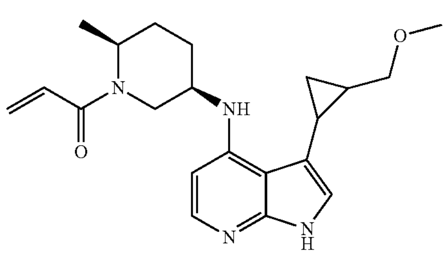 [SMILES: C=CC(=O)N1C[C@H](Nc2ccnc3[nH]cc(C4CC4COC)c23)CC[C@@H]1C] | 1-((2S,5R)-5-((3-(2-(methoxymethyl)cyclopropyl)-1H-pyrrolo[2,3-b]pyridin-4-yl)amino)-2-methylpiperidin-1-yl)prop-2-en-1-one |
| 76 | 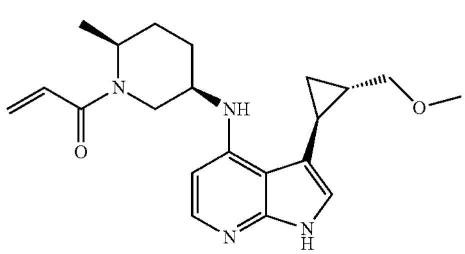 [SMILES: C=CC(=O)N1C[C@H](Nc2ccnc3[nH]cc([C@H]4C[C@@H]4COC)c23)CC[C@@H]1C] | 1-((2S,5R)-5-((3-((1S,2S)-2-(methoxymethyl)cyclopropyl)-1H-pyrrolo[2,3-b]pyridin-4-yl)amino)-2-methylpiperidin-1-yl)prop-2-en-1-one |

-continued

| Example # | Structure | Name |
|---|---|---|
| 77 | 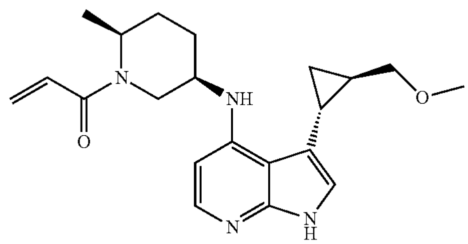 [SMILES: C=CC(=O)N1C[C@H](Nc2ccnc3[nH]cc([C@@H]4C[C@H]4COC)c23)CC[C@@H]1C] | 1-((2S,5R)-5-((3-((1R,2R)-2-(methoxymethyl)cyclopropyl)-1H-pyrrolo[2,3-b]pyridin-4-yl)amino)-2-methylpiperidin-1-yl)prop-2-en-1-one |
| 78 | 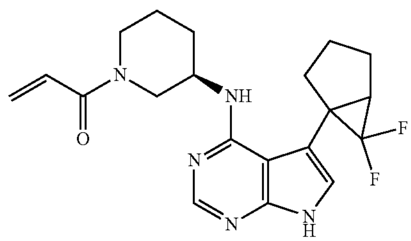 [SMILES: C=CC(=O)N1CCC[C@@H](Nc2ncnc3[nH]cc(C45CCCC4C5(F)F)c23)C1] | 1-((3R)-3-((5-(6,6-difluorobicyclo[3.1.0]hexan-1-yl)-7H-pyrrolo[2,3-d]pyrimidin-4-yl)amino)piperidin-1-yl)prop-2-en-1-one |
| 79 | 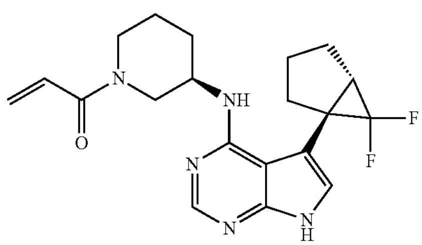 [SMILES: C=CC(=O)N1CCC[C@@H](Nc2ncnc3[nH]cc([C@@]45CCC[C@@H]4C5(F)F)c23)C1] | 1-((R)-3-((5-((1R,5S)-6,6-difluorobicyclo[3.1.0]hexan-1-yl)-7H-pyrrolo[2,3-d]pyrimidin-4-yl)amino)piperidin-1-yl)prop-2-en-1-one |
| 80 | 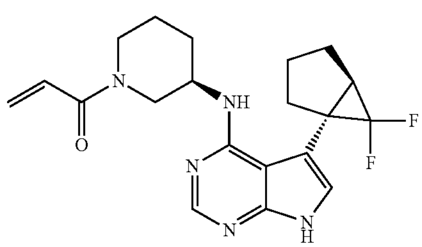 [SMILES: C=CC(=O)N1CCC[C@@H](Nc2ncnc3[nH]cc([C@]45CCC[C@H]4C5(F)F)c23)C1] | 1-((R)-3-((5-((1S,5R)-6,6-difluorobicyclo[3.1.0]hexan-1-yl)-7H-pyrrolo[2,3-d]pyrimidin-4-yl)amino)piperidin-1-yl)prop-2-en-1-one |
| 81 | 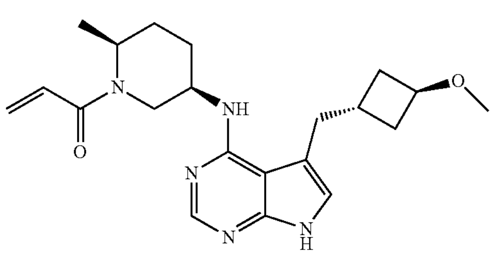 [SMILES: C=CC(=O)N1C[C@H](Nc2ncnc3[nH]cc(C[C@H]4C[C@H](OC)C4)c23)CC[C@@H]1C] | 1-((2S,5R)-5-((5-(((1r,3S)-3-methoxycyclobutyl)methyl)-7H-pyrrolo[2,3-d]pyrimidin-4-yl)amino)-2-methylpiperidin-1-yl)prop-2-en-1-one |
| 82 | 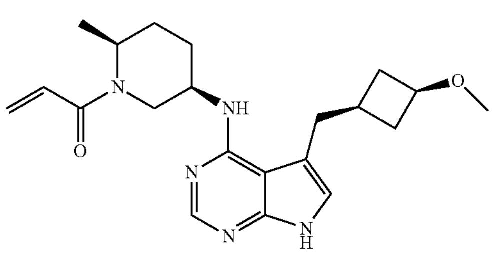 [SMILES: C=CC(=O)N1C[C@H](Nc2ncnc3[nH]cc(C[C@H]4C[C@@H](OC)C4)c23)CC[C@@H]1C] | 1-((2S,5R)-5-((5-(((1s,3R)-3-methoxycyclobutyl)methyl)-7H-pyrrolo[2,3-d]pyrimidin-4-yl)amino)-2-methylpiperidin-1-yl)prop-2-en-1-one |

-continued

| Example # | Structure | Name |
|---|---|---|
| 83 | 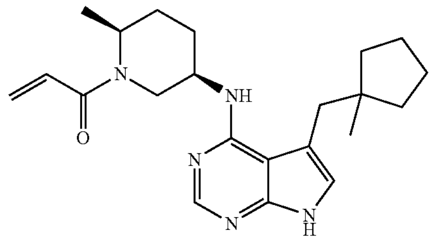 [SMILES: C=CC(=O)N1C[C@H](Nc2ncnc3[nH]cc(CC4(C)CCCC4)c23)CC[C@@H]1C] | 1-((2S,5R)-2-methyl-5-((5-((1-methylcyclopentyl)methyl)-7H-pyrrolo[2,3-d]pyrimidin-4-yl)amino)piperidin-1-yl)prop-2-en-1-one |
| 84 | 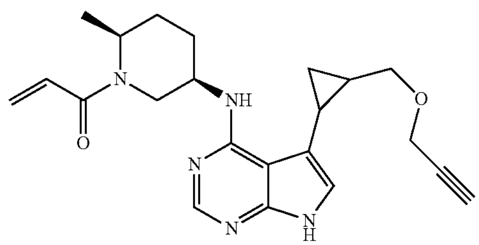 [SMILES: C#CCOCC1CC1c1c[nH]c2ncnc(N[C@@H]3CC[C@H](C)N(C(=O)C=C)C3)c12] | 1-((2S,5R)-2-methyl-5-((5-(2-((prop-2-yn-1-yloxy)methyl)cyclopropyl)-7H-pyrrolo[2,3-d]pyrimidin-4-yl)amino)piperidin-1-yl)prop-2-en-1-one |
| 85 | 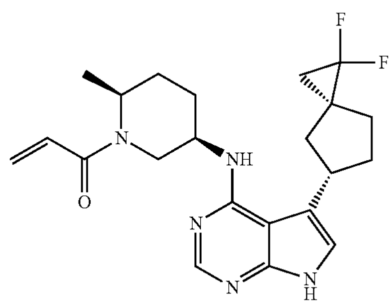 [SMILES: C=CC(=O)N1C[C@H](Nc2ncnc3[nH]cc([C@H]4CC[C@]5(C4)CC5(F)F)c23)CC[C@@H]1C] | 1-((2S,5R)-5-((5-((3S,5S)-1,1-difluorospiro[2.4]heptan-5-yl)-7H-pyrrolo[2,3-d]pyrimidin-4-yl)amino)-2-methylpiperidin-1-yl)prop-2-en-1-one |
| 86 | 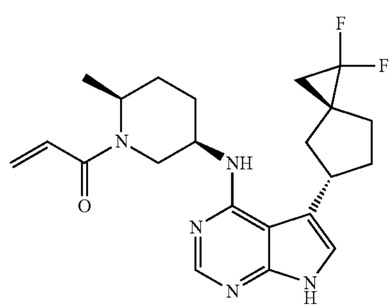 [SMILES: C=CC(=O)N1C[C@H](Nc2ncnc3[nH]cc([C@H]4CC[C@@]5(C4)CC5(F)F)c23)CC[C@@H]1C] | 1-((2S,5R)-5-((5-((3R,5S)-1,1-difluorospiro[2.4]heptan-5-yl)-7H-pyrrolo[2,3-d]pyrimidin-4-yl)amino)-2-methylpiperidin-1-yl)prop-2-en-1-one |
| 87 | 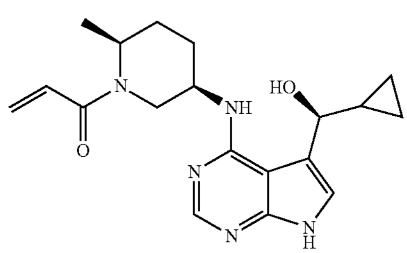 [SMILES: C=CC(=O)N1C[C@H](Nc2ncnc3[nH]cc([C@@H](O)C4CC4)c23)CC[C@@H]1C] | 1-((2S,5R)-5-((5-((S)-cyclopropyl(hydroxy)methyl)-7H-pyrrolo[2,3-d]pyrimidin-4-yl)amino)-2-methylpiperidin-1-yl)prop-2-en-1-one |
| 88 | 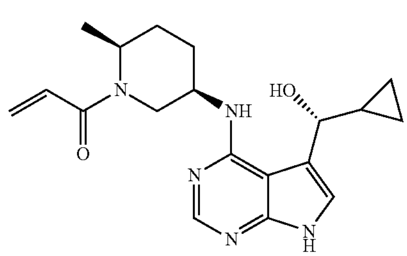 [SMILES: C=CC(=O)N1C[C@H](Nc2ncnc3[nH]cc([C@H](O)C4CC4)c23)CC[C@@H]1C] | 1-((2S,5R)-5-((5-((R)-cyclopropyl(hydroxy)methyl)-7H-pyrrolo[2,3-d]pyrimidin-4-yl)amino)-2-methylpiperidin-1-yl)prop-2-en-1-one |

| Example # | Structure | Name |
|---|---|---|
| 89 | 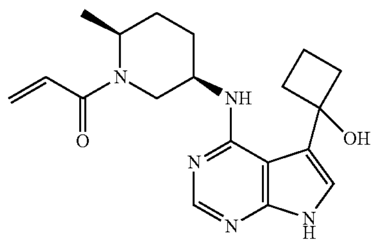 [SMILES: C=CC(=O)N1C[C@H](Nc2ncnc3[nH]cc(C4(O)CCC4)c23)CC[C@@H]1C] | 1-((2S,5R)-5-((5-(1-hydroxycyclobutyl)-7H-pyrrolo[2,3-d]pyrimidin-4-yl)amino)-2-methylpiperidin-1-yl)prop-2-en-1-one |
| 90 | 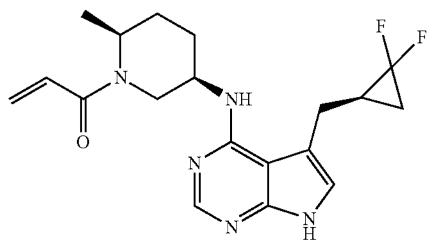 [SMILES: C=CC(=O)N1C[C@H](Nc2ncnc3[nH]cc(C[C@@H]4CC4(F)F)c23)CC[C@@H]1C] | 1-((2S,5R)-5-((5-(((R)-2,2-difluorocyclopropyl)methyl)-7H-pyrrolo[2,3-d]pyrimidin-4-yl)amino)-2-methylpiperidin-1-yl)prop-2-en-1-one |
| 91 | 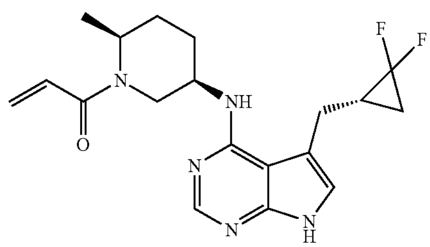 [SMILES: C=CC(=O)N1C[C@H](Nc2ncnc3[nH]cc(C[C@H]4CC4(F)F)c23)CC[C@@H]1C] | 1-((2S,5R)-5-((5-(((S)-2,2-difluorocyclopropyl)methyl)-7H-pyrrolo[2,3-d]pyrimidin-4-yl)amino)-2-methylpiperidin-1-yl)prop-2-en-1-one |
| 92 | 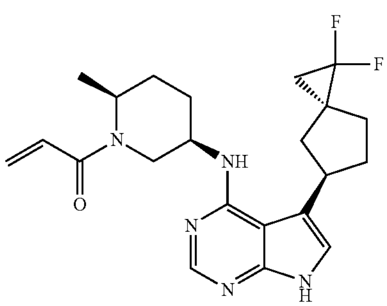 [SMILES: C=CC(=O)N1C[C@H](Nc2ncnc3[nH]cc([C@@H]4CC[C@]5(C4)CC5(F)F)c23)CC[C@@H]1C] | 1-((2S,5R)-5-((5-((3S,5R)-1,1-difluorospiro[2.4]heptan-5-yl)-7H-pyrrolo[2,3-d]pyrimidin-4-yl)amino)-2-methylpiperidin-1-yl)prop-2-en-1-one |
| 93 | 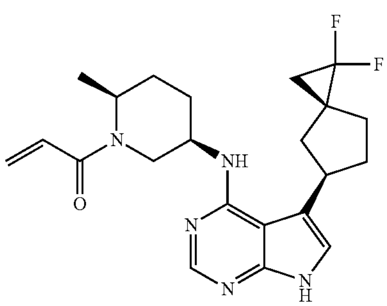 [SMILES: C=CC(=O)N1C[C@H](Nc2ncnc3[nH]cc([C@@H]4CC[C@@]5(C4)CC5(F)F)c23)CC[C@@H]1C] | 1-((2S,5R)-5-((5-((3R,5R)-1,1-difluorospiro[2.4]heptan-5-yl)-7H-pyrrolo[2,3-d]pyrimidin-4-yl)amino)-2-methylpiperidin-1-yl)prop-2-en-1-one |

| Example # | Structure | Name |
|---|---|---|
| 94 | 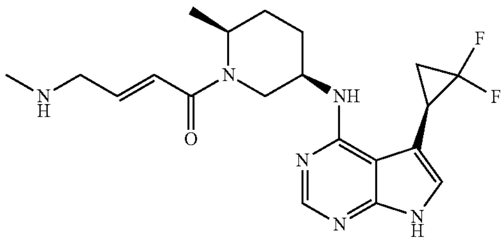 [SMILES: CNC/C=C/C(=O)N1C[C@H](Nc2ncnc3[nH]cc([C@H]4CC4(F)F)c23)CC[C@@H]1C] | (E)-1-((2S,5R)-5-((5-((R)-2,2-difluorocyclopropyl)-7H-pyrrolo[2,3-d]pyrimidin-4-yl)amino)-2-methylpiperidin-1-yl)-4-(methylamino)but-2-en-1-one |
| 95 | 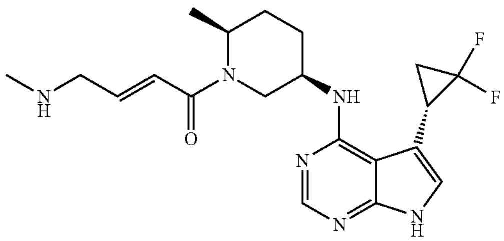 [SMILES: CNC/C=C/C(=O)N1C[C@H](Nc2ncnc3[nH]cc([C@@H]4CC4(F)F)c23)CC[C@@H]1C] | (E)-1-((2S,5R)-5-((5-((S)-2,2-difluorocyclopropyl)-7H-pyrrolo[2,3-d]pyrimidin-4-yl)amino)-2-methylpiperidin-1-yl)-4-(methylamino)but-2-en-1-one |

In some embodiments, the compound of Formula (III), or a derivative thereof, may be selected from:

| Example # | Structure | Name |
|---|---|---|
| 96 | 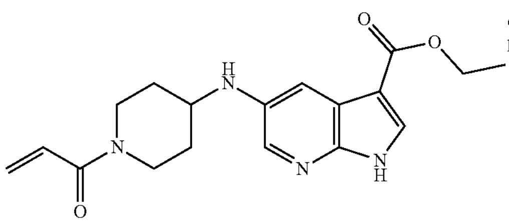 | ethyl 5-((1-acryloylpiperidin-4-yl)amino)-1H-pyrrolo[2,3-b]pyridine-3-carboxylate |
| 97 | 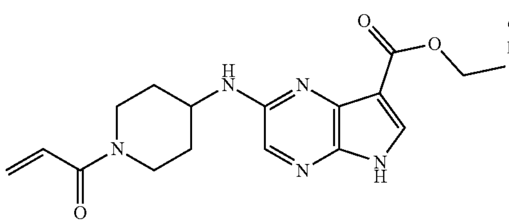 | ethyl 2-((1-acryloylpiperidin-4--yl)amino)-5H-pyrrolo[2,3-b]pyrazine-7-carboxylate |
| 98 | 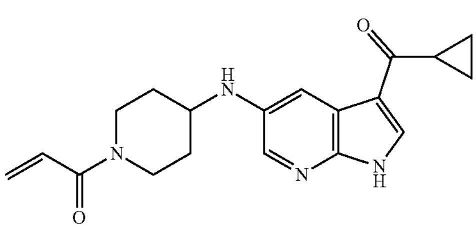 [SMILES: C=CC(=O)N1CCC(Nc2cnc3[nH]cc(C(=O)C4CC4)c3c2)CC1] | 1-(4-((3-(cyclopropanecarbonyl)-1H-pyrrolo[2,3-b]pyridin-5-yl)amino)piperidin-1-yl)prop-2-en-1-one |
| 99 | 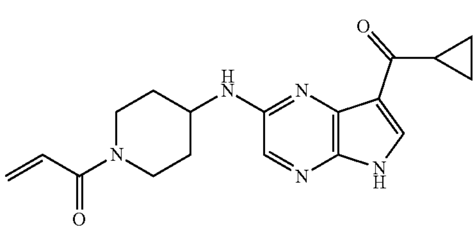 [SMILES: C=CC(=O)N1CCC(Nc2cnc3[nH]cc(C(=O)C4CC4)c3n2)CC1] | 1-(4-((7-(cyclopropanecarbonyl)-5H-pyrrolo[2,3-b]pyrazin-2-yl)amino)piperidin-1-yl)prop-2-en-1-one |

| Example # | Structure | Name |
|---|---|---|
| 100 | 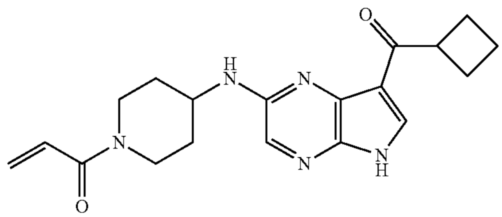 [SMILES: C=CC(=O)N1CCC(Nc2cnc3[nH]cc(C(=O)C4CCC4)c3n2)CC1] | 1-(4-((7-(cyclobutanecarbonyl)-5H-pyrrolo[2,3-b]pyrazin-2-yl)amino)piperidin-1-yl)prop-2-en-1-one |
| 101 | 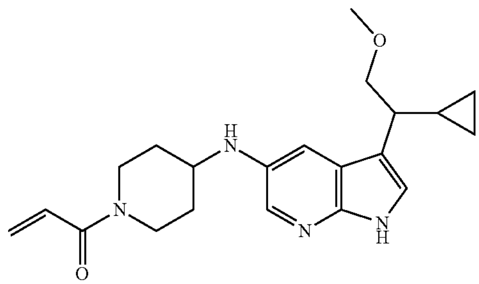 [SMILES: C=CC(=O)N1CCC(Nc2cnc3[nH]cc(C(COC)C4CC4)c3c2)CC1] | 1-(4-((3-(1-cyclopropyl-2-methoxyethyl)-1H-pyrrolo[2,3-b]pyridin-5-yl)amino)piperidin-1-yl)prop-2-en-1-one |
| 102 | 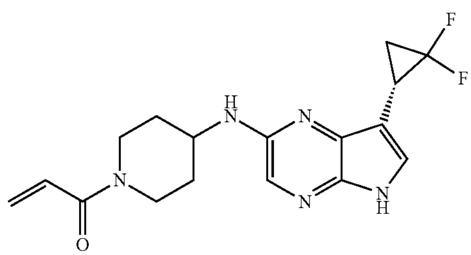 [SMILES: C=CC(=O)N1CCC(Nc2cnc3[nH]cc([C@@H]4CC4(F)F)c3n2)CC1] | (S)-1-(4-((7-(2,2-difluorocyclopropyl)-5H-pyrrolo[2,3-b]pyrazin-2-yl)amino)piperidin-1-yl)prop-2-en-1-one |
| 103 | 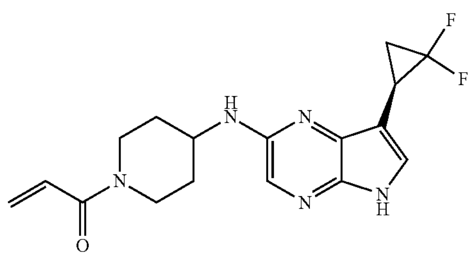 [SMILES: C=CC(=O)N1CCC(Nc2cnc3[nH]cc([C@H]4CC4(F)F)c3n2)CC1] | (R)-1-(4-((7-(2,2-difluorocyclopropyl)-5H-pyrrolo[2,3-b]pyrazin-2-yl)amino)piperidin-1-yl)prop-2-en-1-one |
| 104 | 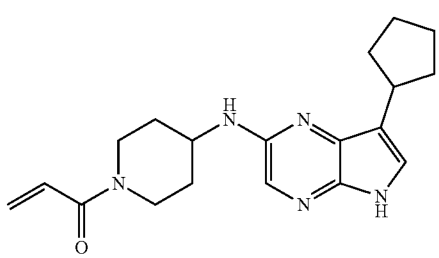 [SMILES: C=CC(=O)N1CCC(Nc2cnc3[nH]cc(C4CCCC4)c3n2)CC1] | 1-(4-((7-cyclopentyl-5H-pyrrolo[2,3-b]pyrazin-2-yl)amino)piperidin-1-yl)prop-2-en-1-one |

Pharmaceutical Compositions

Also provided is a pharmaceutical composition comprising a compound as disclosed herein, together with a pharmaceutically acceptable excipient.

In certain embodiments, the pharmaceutical composition may comprise about 0.01% to about 50% of one or more compounds disclosed herein. In some embodiments, the one or more compounds is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition.

In some embodiments, the compound is in a therapeutically effective amount. In some embodiments, the therapeutically effective amount may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

While it may be possible for the compounds described herein to be administered as the raw chemical, it is also possible to present them as a pharmaceutical composition. Accordingly, provided herein are pharmaceutical compositions which comprise one or more of certain compounds disclosed herein, or a derivative thereof, together with one or more pharmaceutically acceptable excipients thereof and optionally one or more other therapeutic ingredients. The excipient(s) must be "acceptable" in the sense of being compatible with the other ingredients of the formulation and not deleterious to the recipient thereof. Proper formulation of the pharmaceutical composition is dependent upon the route of administration chosen. Any of the well-known techniques and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In some embodiments, the pharmaceutical compositions for use in accordance with embodiments herein can be formulated in conventional manner using one or more physiologically acceptable excipients.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be oral, parenteral (including subcutaneous, intradermal, intramuscular, intravenous, intraarticular, and intramedullary), pulmonary (e.g., by inhalation or insufflation of powders or aerosols, including by nebulizer; intratracheal or intranasal), intraperitoneal, intrathecal, intradural, transmucosal, transdermal, rectal, topical (including dermal, buccal, sublingual and intraocular), or intravaginal administration. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the compounds can be contained in such formulations pharmaceutical compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, Modern Pharmaceutics, 5th Edition, Banker & Rhodes, CRC Press (2009); and Goodman & Gilman's The Pharmaceutical Basis of Therapeutics, 13th Edition, McGraw Hill, New York (2018) can be consulted.

In some embodiments, a method of treating an ITK mediated disease comprises administering a compound or a pharmaceutical composition of embodiments disclosed herein. In some embodiments, the compound is in a therapeutically effective amount. In some embodiments, the therapeutically effective amount is an amount disclosed herein.

Some embodiments disclosed herein also include pharmaceutical compositions which contain, as the active ingredient, one or more of the compounds disclosed herein in combination with one or more pharmaceutically acceptable carriers (excipients).

In some embodiments, a method of making a pharmaceutical composition comprises mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The pharmaceutical compositions can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The pharmaceutical compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The compositions include those suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example, dermal, buccal, sublingual and intraocular), intravitreal, or intravaginal administration although the most suitable route may depend upon for example the condition and disorder of the recipient. The composition could include those suitable for administration by depot injections or by implants. The composition could include those suitable for administration by inhalation, such as, for example, a gas, vapor, or powder. The composition could include those suitable for administration, e.g., as an aerosol via a nebulizer, humidifier, inhaler and vaporizer or the like. The compositions may conveniently be presented in unit dosage form and may be prepared by any of the methods well known in the art of pharmacy. Typically, these methods include the step of bringing into association a compound disclosed herein or a derivative thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

Compositions of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the pharmaceutical composition so that the pharmaceutical composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The compounds may be formulated for parenteral administration by injection, e.g., by bolus injection or continuous infusion. Compositions for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the composition isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the pharmaceutical compositions described previously, the compounds may also be formulated as a depot preparation. Such long acting compositions may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the pharmaceutical compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

In some embodiments, the pharmaceutical composition is suitable for topical administration. In some embodiments, the pharmaceutical composition is suitable for oral administration. In some embodiments, the composition is suitable for oral, parenteral (including subcutaneous, intradermal, intramuscular, intravenous, intraarticular, and intramedullary), intraperitoneal, intrathecal, intradural, transmucosal, transdermal, rectal, intranasal, topical (including, for example. dermal, buccal, sublingual and intraocular), intravitreal, or intravaginal administration.

In some embodiments, the compounds disclosed herein may be administered ophthalmically. In some embodiments, the compounds disclosed herein may be administered as an ophthalmic composition. The compounds of embodiments herein may be administered as, for example, liquid preparations, including eye lotions, spray, or eye drops for topical administration. In some embodiments, the compounds disclosed herein may be administered as semi-solid preparations, for example, applied to the eyelid, such as cream, lotion, gel, ointment, or paste. In some embodiments, the compounds disclosed herein may be administered as solid dosage forms, for example, applied to the eye surface to produce modified release, such as a powder. In some embodiments, the compounds of embodiments herein are administered through devices for surgical implantation, parenteral products, (e.g., intracorneal or intravitreous products), liquids for irrigation, or the like. In some embodiments, the pharmaceutical composition comprising the compounds disclosed herein are sterile and free from particulate matters. In some embodiments, the compounds disclosed herein may be administered by intraocular injection, intraorbital injection, or an intravitreal injection. In some embodiments, the intraocular injection may be to the anterior chamber of the eye, posterior chamber of the eye, or a combination thereof. For example, the compounds disclosed herein may be administered to the posterior intraorbital region of the eye.

In some embodiments, pharmaceutical compositions suitable for topical administration include liquid or semi-liquid preparations suitable for penetration through the skin to the site of inflammation such as a solution, powder, fluid, emulsion, fluid suspension, semi-solid, gels, liniments, lotions, creams, ointment, paste, jelly, foam, and drops suitable for administration to the eye, ear or nose. The active ingredient for topical administration may comprise, for example, from 0.001% to 10% w/w (by weight) of the composition. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the composition.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid pharmaceutical compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The pharmaceutical composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Pharmaceutical compositions for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the pharmaceutical compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the composition in an appropriate manner.

In some embodiments, the pharmaceutical compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

Preferred unit dosage pharmaceutical compositions are those containing an effective dose, as herein below recited, or an appropriate fraction thereof, of the active ingredient.

It should be understood that in addition to the ingredients particularly mentioned above, the pharmaceutical compositions described above may include other agents conventional in the art having regard to the type of pharmaceutical composition in question, for example those suitable for oral administration may include flavoring agents.

In some embodiments, the therapeutically effective amount can vary according to, for example, the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, composition of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. In addition, the route of administration may vary depending on the condition and its severity.

The compositions can further include one or more additional pharmaceutical agents such as a chemotherapeutic, steroid, anti-inflammatory compound, or immunosuppressant.

Methods of Treatment

Some embodiments herein are directed to a method of modulation of an ITK-mediated function in a subject comprising the administration of a therapeutically effective amount of a compound as disclosed herein. In some embodiments, a method of inhibiting ITK in a subject comprises administering to the subject a compound of embodiments herein.

The present invention also relates to a method of inhibiting at least one ITK function comprising the step of contacting ITK with a compound as described herein. The cell phenotype, cell proliferation, activity of ITK, change in biochemical output produced by active ITK, expression of ITK, or binding of ITK with a natural binding partner may be monitored. Such methods may be modes of treatment of disease, biological assays, cellular assays, biochemical assays, or the like.

The compounds of the present invention may be useful as JAK3 kinase inhibitors as well as inhibitors of ITK. This dual use of a single compound inhibiting either ITK or JAK3 pathways individually or both pathways simultaneously may lead to a beneficial effect. As a result, the compounds of the present invention may find utility in treating a broad range of diseases or conditions mediated by ITK activity, JAK3 activity, or both. Accordingly, some embodiments herein are directed to treatment or prophylaxis of a disease or condition in which JAK, particularly JAK3, plays an active role using the compounds disclosed herein. In some embodiments, a method of treating a JAK3 mediated disease or disorder in a subject comprises administering to the subject a compound of embodiments herein. Some embodiments provide methods for treating a JAK3-mediated disorder in a subject in need of such treatment comprising administering to the subject a therapeutically effective amount of a compound or composition according to the present disclosure. Also provided is the use of compounds disclosed herein for use in the manufacture of a medicament for the treatment of a disease or condition ameliorated by the inhibition of JAK3, ITK, or a combination thereof. Embodiments discussed herein which are directed to methods of treatment of ITK-mediated conditions or diseases may also apply to methods of treatment for JAK3 mediated conditions or diseases.

Also provided herein is a method of treating an ITK-mediated or JAK3 mediated disease comprising administering to a patient in need thereof a therapeutically effective amount of a compound as disclosed herein, a derivative thereof, or a combination thereof. In certain embodiments, the therapeutically effective amount of a compound as disclosed herein, a derivative thereof, or a combination thereof, may be in the form of a pharmaceutical composition. In embodiments, the pharmaceutical composition may include a pharmaceutically acceptable excipient.

Also provided herein is a method of inhibiting ITK or JAK3 activity in a population of cells, said method comprising: administering, to a population of cells, one or more compound as disclosed herein, a derivative thereof, or a combination thereof, in an amount effective to inhibit ITK or JAK3 activity in the population of cells. In some embodiments the population of cells is a population of human cells.

In some embodiments, the present invention provides a method for treating a ITK mediated or JAK3 mediated disease or disorder in a patient in need thereof, wherein said method comprises administering to said patient a therapeutically effective amount of a compound of embodiments herein, or composition thereof. Such ITK-mediated diseases or disorders include, but are not limited to, those described herein.

In some embodiments, diseases or disorders associated with a ITK kinase or a JAK3 kinase that are treated by compounds of the present invention include autoimmune disorders, chronic inflammatory disorders, acute inflammatory disorders, auto-inflammatory disorders, fibrotic disorders, metabolic disorders, neoplasias, cardiovascular or cerebrovascular disorders, respiratory diseases, allergy and allergic diseases and allergic hypersensitivity disorders, immunological disorders, proliferative disorders, transplant rejection, graft versus host disease, HIV, aplastic anemia, pain including inflammatory pain and other diseases and disorders associated with ITK.

In some embodiments, said ITK-mediated or JAK3 mediated disease or disorder is chosen from a skin disorder, pruritus, a hair loss disorder, a cancer, a neoplasm, Alzheimer's disease, an inflammatory condition, connective tissue diseases, an autoimmune condition, asthma, rheumatoid arthritis, juvenile idiopathic arthritis, psoriatic arthritis, ankylosing spondylitis, contact hypersensitivity and inflammatory bowel disease.

In some embodiments, the compounds and pharmaceutical compositions of the present disclosure may be administered in therapeutically effective amounts to prevent or treat HIV.

In certain embodiments, said ITK-mediated or JAK3 mediated disease or disorder is a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, leukemias, childhood leukemias, acute leukemias, acute lymphoblastic T-cell leukemia, acute and chronic leukemias, lymphomas, including systemic lymphomas, T-cell lymphomas, B-cell lymphomas, Hodgkins lymphoma, non-Hodgkins lymphomas, cutaneous lymphomas including but not limited to cutaneous T-cell lymphoma (CTCL), mucosis fungoides, and cutaneous B-cell lymphoma, other myeloid malignancies, and myelodysplastic syndrome. In certain embodiments the ITK-mediated or JAK3 mediated disease or disorder is resistant to prior therapy (e.g. a cancer that is resistant to or has failed chemotherapy).

In some embodiments, the ITK-mediated or JAK3 mediated disease or disorder is an autoimmune disorder, a chronic and/or acute inflammatory disorder, and/or auto-inflammatory disorder. Exemplary autoimmune and/or inflammatory and/or autoinflammatory disorders include: arthritis, rheumatoid arthritis, juvenile rheumatoid arthritis, systemic-onset juvenile rheumatoid arthritis, systemic onset juvenile idiopathic arthritis, Still's disease, adult-onset Still's disease, seronegative spondyloarthropathies, osteoarthritis, enthesitis, enthesopathy, infectious arthritis, Lyme disease, inflammatory arthritis, inflammatory bowel disease-associated arthritis, myositis, autoimmune myositis, carditis, myocarditis, dermatomyositis, juvenile dermatomyositis, idiopathic arthritis, juvenile idiopathic arthritis, systemic juvenile idiopathic arthritis, ankylosing spondylitis, gout, scleroderma, juvenile scleroderma, Reiter's syndrome, spondylitis, spondyloarthritis, spondyloarthropathy, lupus, systemic lupus erythematosus (SLE), pediatric systemic lupus erythematosus, cutaneous lupus, subacute cutaneous lupus, chronic cutaneous lupus, discoid lupus, psoriatic arthritis, reactive arthritis, Sjogren's syndrome, polymyositis, polymyalgia rheumatica, mixed connective tissue disease, vasculitis, large vessel vasculitis, small vessel vasculitis, vasculitis syndromes including Takayasu's arteritis, Wegener's granulomatosis, giant-cell arteritis, polyarteritis nodosa, sarcoidosis, familial Mediterranean fever, a Cryopyrin associated periodic syndrome (e.g.), Muckle-Wells syndrome, familial cold auto-inflammatory syndrome, neonatal-onset multisystem inflammatory disease, TNF receptor associated periodic syndrome; gastrointestinal disorders (e.g.) inflammatory bowel disease, irritable bowel syndrome, spastic colon, Crohn's disease, ulcerative colitis, acute and chronic pancreatitis, celiac disease, primary biliary cirrhosis, primary sclerosing cholangitis, periodontitis, gingivitis, esophagitis, gastritis, eosinophilic gastritis, gastric and duodenal ulcers, peritonitis, periodontitis, enteritis, colitis; pulmonary-respiratory disorders (e.g.) pulmonary inflammation, sinusitis, rhinitis, pneumonia, bronchitis, pulmonary fibrosis, idiopathic pulmonary fibrosis, asthma, allergic asthma, eosinophilic asthma, bronchial asthma, Churg-Strauss syndrome, bronchiolitis, bronchiolitis obliterans, chronic obstructive pulmonary disease (COPD), interstitial lung disease; endocrinologic disorders (e.g.) diabetes, Type I diabetes, Hashimoto's thyroiditis, Graves' disease, Addison's disease; autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia; neurological/neuromuscular disorders (e.g.), neurodegenerative disorders, multiple sclerosis Parkinson's disease, Huntington's disease, amyotrophic lateral sclerosis (ALS), familial ALS, Alzheimer's disease, myasthenia gravis (Lambert-Eaton myasthenic syndrome (LEMS)), Guillain-Barret syndrome, meningitis, encephalitis, traumatic brain injury; nephropathies including (e.g.) immunologically mediated glomerulonephropathy, autoimmune nephropathy, membranous glomerulopathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease, diabetic kidney disease; ocular disorders including, (e.g.), dry eye, uveitis, keratoconjunctivitis sicca, scleritis, episcleritis, keratitis, keratopathy, chorditis, retinal vasculitis, optic neuritis, retinopathy, diabetic retinopathy, immune mediated retinopathy, macular degeneration, wet macular degeneration, dry (age related) macular degeneration, and ocular malignancies; allergy and allergic reactions including hypersensitivity reactions such as Type I hypersensitivity reactions, (e.g. including anaphylaxis), Type II hypersensitivity reactions (e.g. Goodpasture's Disease, autoimmune hemolytic anemia), Type III hypersensitivity reaction diseases (e.g. the Arthus reaction, serum sickness), and Type IV hypersensitivity reactions (e.g. contact dermatitis, allograft rejection); disorders of fibrosis and scarring (e.g.), hepatic fibrosis, pulmonary fibrosis, idiopathic pulmonary fibrosis, low grade scarring such as, scleroderma, increased fibrosis, keloids, post-surgical scars; dermatologic disorders (e.g.), psoriasis, atopy, atopic dermatitis, acne, acne vulgaris, comedonal acne, inflammatory acne, nodulo-cystic acne, scarring acne, acne keloidalis nuchae, hidradenitis suppurativa, neutrophilic dermatoses, pyoderma gangrenosum, acute febrile neutrophilic dermatosis (Sweet's syndrome), erythema elevatinum diutinum (EED), neutrophilic eccrine hidradenitis, histiocytoid neutrophilic dermatosis, bowel-bypass syndrome dermatosis, Behcet's disease, palisading neutrophilic granulomatous dermatitis neutrophilic urticarial dermatosis, alopecia, non-scarring alopecia, alopecia areata (AA), including patchy AA, alopecia totalis (AT), alopecia universalis (AU), androgenetic alopecia (AGA), male and female pattern AGA, ophiasis pattern alopecia areata, sisaihpo pattern alopecia areata, telogen effluvium, tinea capitis, hypotrichosis, hereditary hypotrichosis simplex, scarring alopecia, lichen planopilaris, central centrifugal cicatricial alopecia, frontal fibrosing alopecia, eyebrow alopecia, intranasal hair alopecia; vitiligo including segmental vitiligo, unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (non-segmental associated with segmental vitiligo), focal vitiligo, solitary mucosal vitiligo or vitiligo with or without leukotricia (involvement of body hair); immunobullous diseases such as (e.g.), bullous pemphigoid, cicatricial pemphigoid, pemphigus vulgaris, linear IgA disease; dermatologic drug reactions, and pruritus (itch) including (e.g.), atopic pruritus, xerotic pruritus, pruritus associated with psoriasis ("psoriatic itch"), acute pruritus, chronic pruritus, idiopathic pruritus, chronic idiopathic itch, hepatobiliary-associated itch, renal associated itch, lichen simplex chronicus associated pruritus, prurigo nodularis, Type II diabetes, hypophysitis, idiopathic thrombocytopenic purpura, metal-induced autoimmunity, autoimmune deafness (including, for example, Meniere's disease), interstitial cystitis, enterocolitis, ocular inflammation, non-small cell lung carcinoma, small cell lung carcinoma, skin cancer, organ transplant rejection, bone marrow transplant rejection, graft vs. host reaction (for example, graft vs. host disease), allograft rejections (for example, acute allograft rejection or chronic allograft rejection), early transplantation, diabetes, a myeloproliferative disorder, a rejection (for example, acute allograft rejection); bone resorption diseases, asthma (e.g., bronchial asthma), atopy, autoimmune thyroid disorders, chronic atypical neutrophilic dermatosis with lipodystrophy and elevated temperature syndrome (CANDLE Syndrome), SAVI (stimulator of interferon genes (STING) associated vasculopathy with onset in infancy), nephropathies, myocarditis, secondary hematologic manifestations of autoimmune diseases (for example, anemias), autoimmune hemolytic syndromes, autoimmune and inflammatory hepatitis, autoimmune ovarian failure, autoimmune orchitis, autoimmune thrombocytopenia, silicone implant associated autoimmune disease, drug-induced autoimmunity, HIV-related autoimmune syndromes; acute and chronic infection, sepsis syndromes (e.g.) sepsis, septic shock, endotoxic shock, exotoxin-induced toxic shock, gram negative sepsis, gram positive sepsis, fungal sepsis, toxic shock syndrome; hyperoxia induced inflammations, reperfusion injury, post-surgical trauma, tissue injury, pain (e.g.) acute pain, chronic pain, neuropathic pain, or fibromyalgia, autoimmune disorders, chronic inflammatory disorders, acute inflammatory disorders, autoinflammatory disorders, fibrotic disorders, metabolic disorders, neoplasias, or cardiovascular or cerebrovascular disorders, a skin disorder, pruritus, a hair loss disorder, a cancer, a neoplasm, an inflammatory condition, connective tissue diseases and an autoimmune condition, a neoplasm, a malignancy, a myeloproliferative disorder, a hematopoietic neoplasm, a myeloid neoplasm, a lymphoid neoplasm, including myelofibrosis, primary myelofibrosis, polycythemia vera, essential thrombocythemia, acute and chronic leukemias, lymphomas, cutaneous lymphomas including mycosis fungoides, other myeloid malignancies, and myelodysplastic syndrome, atopic dermatitis, psoriasis, psoriasis vulgaris, skin sensitization, skin irritation, skin rash, contact dermatitis, allergic contact sensitization, allergic dermatitis, inflammatory dermatoses, neutrophilic dermatoses, pruritus, atopic itch, atopic dermatitis-associated itch, autoimmune responses, autoimmune connective tissue disease, bacterial infection, biliary itch, broad activation of the immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, pyoderma gangrenosum, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, popular uritcariaurticaria, pediculosis, peripheral neuropathy, photodermatitis, polycythemia vera, psychiatric disease, psychogenic itch, pruritic popular eruption of HIV, pruritic urticarial papules and plaques of pregnancy (PUPP), psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uremia, uremic itch, urticaria, urticarial itch, varicella, viral infection, wound or scab healing, xerosis, chilblain lupus erythematosus, polychondritis, relapsing polychondritis, an immunologically mediated nephropathy, prostate cancer, renal cancer, hepatic cancer, breast cancer, thyroid cancer, Kaposi's sarcoma, Castleman's disease, pancreatic cancer, lymphoma, leukemia, multiple myeloma, polycythemia vera (PV), essential thrombocythemia (ET), myeloid metaplasia with myelofibrosis (MMM), primary myelofibrosis (PMF), chronic myelogenous leukemia (CML), chronic myelomonocytic leukemia (CMML), hypereosinophilic syndrome (HES), idiopathic myelofibrosis (IMF), systemic mast cell disease (SMCD), systemic sclerosis/scleroderma, lupus nephritis, wound healing, surgical scarring, spinal cord injury, CNS scarring, acute lung injury, cystic fibrosis, adult respiratory distress syndrome, acute lung injury, drug-induced lung injury, glomerulonephritis, chronic kidney disease (for example, diabetic nephropathy), hypertension induced nephropathy, alimentary track or gastrointestinal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, mediastinal fibrosis, myelofibrosis, retroperitoneal fibrosis, progressive massive fibrosis, nephrogenic systemic fibrosis, obesity, steroid-resistance, glucose intolerance, metabolic syndrome, angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xeroderma pigmentosum, keratoacanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, liver, nerve, brain (for example, glioma or glioblastoma multiforme), head and neck, throat, ovary, uterus, testis, bladder, kidney, gall bladder, cervix, atherosclerosis, restenosis of an atherosclerotic coronary artery, acute coronary syndrome, myocardial infarction, cardiac-allograft vasculopathy, stroke, spinal cord injury, neuronal ischemia, and peripheral neuropathy.

In some embodiments, additional exemplary disorders include, but are not limited to: complications from organ transplants (including xenotransplantation) such as graft vs. host reaction (for example, graft vs. host disease), allograft rejections (for example, acute allograft rejection or chronic allograft rejection), early transplantation, diabetes, a myeloproliferative disorder, a rejection (for example, acute allograft rejection); bone resorption diseases, asthma (e.g., bronchial asthma), atopy, autoimmune thyroid disorders, chronic atypical neutrophilic dermatosis with lipodystrophy and elevated temperature syndrome (CANDLE Syndrome), SAVI (stimulator of interferon genes (STING) associated vasculopathy with onset in infancy), ulcerative colitis, inflammatory bowel disease, Crohn's disease, celiac disease, ulcerative colitis, Behcet's disease, myasthenia gravis, nephropathies, and myocarditis, secondary hematologic manifestations of autoimmune diseases (for example, anemias), autoimmune hemolytic syndromes, autoimmune and inflammatory hepatitis, autoimmune ovarian failure, autoimmune orchitis, autoimmune thrombocytopenia, silicone implant associated autoimmune disease, drug-induced autoimmunity, HIV-related autoimmune syndromes; acute and chronic infection, sepsis syndromes (e.g.) sepsis, septic shock, endotoxic shock, exotoxin-induced toxic shock, gram negative sepsis, gram positive sepsis, fungal sepsis, toxic shock syndrome; hyperoxia induced inflammations, reperfusion injury, post-surgical trauma, tissue injury, pain (e.g.) acute pain, chronic pain, neuropathic pain, or fibromyalgia.

In some embodiments, the ITK-mediated or JAK3 mediated disease or disorder is asthma. In an embodiment, said asthma is allergic asthma, non-allergic asthma, allergic bronchopulmonary mycosis, aspirin-induced asthma, adult-onset asthma, asthma with fixed airflow obstruction, exercise-induced asthma, cough-variant asthma, work-related asthma, nighttime (nocturnal) asthma, asthma with obesity, eosinophilic asthma, steroid-resistant asthma/severe asthma, extrinsic asthma, or intrinsic/cryptogenic asthma.

In some embodiments, the ITK-mediated or JAK3 mediated disease or disorder is vitiligo. In an embodiment, said vitiligo is segmental vitiligo including unisegmental, bisegmental or multisegmental vitiligo, non-segmental vitiligo including acral, facial, or acrofacial vitiligo, centrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, generalized vitiligo, universal vitiligo, mixed vitiligo (nonsegmental associated with segmental vitiligo), focal vitiligo, solitary mucosal vitiligo or vitiligo with or without leukotricia (involvement of body hair) or any type of vitiligo set forth in Table 1 below:

TABLE 1

Classification of vitiligo.

| NOMENCLATURE | SUBSET | NOTES |
| --- | --- | --- |
| Non-segmental vitiligo | Acrofacial | Usually limited to face, head, hands, and feet |
| | Generalized | Symmetrical macules, mainly hands, fingers, face, and trauma-exposed areas |
| | Mucosal (at least two sites involved) | Involvement of the oral and/or genital mucosae with other sites of skin involvement |
| | Universal | Depigmentation affects 80%-90% of body surface. |
| Segmental vitiligo | Unisegmental | One or more depigmented macules distributed on one side of the body |
| | Bisegmental | Two segmental lesions distributed either unilaterally or bilaterally |
| | Plurisegmental | Multiple segmental lesions distributed either unilaterally or bi-laterally |
| Mixed vitiligo | Occurrence of SV and NSV | SV followed by NSV with a delay of at least 6 months. At least 20% of a dermatomal segment affected by SV. |
| Unclassified vitiligo | Focal vitiligo | Isolated macules that do not have a segmental distribution. No evolution into NSV after at least 2 years |
| | Mucosal vitiligo (only one site involved) | Exclusive involvement of the oral or genital mucosae |

In some embodiments, the ITK-mediated or JAK3 mediated disease or disorder is a skin disorder. In an embodiment, said skin disorder is atopic dermatitis, psoriasis, psoriasis vulgaris, skin sensitization, skin irritation, skin rash, contact dermatitis, allergic contact sensitization, allergic dermatitis, inflammatory dermatoses, or neutrophilic dermatoses.

In some embodiments, the ITK-mediated or JAK3 mediated disease or disorder is pruritus. "Pruritus", as used herein, is interchangeable with "itch." In some embodiments, pruritus includes chronic idiopathic pruritus, as well as pruritic components of other pruritic disorders. In some embodiments, pruritus may be a symptom of a disease or condition selected from the group consisting of: allergic reaction, arthropod bites, athlete's foot, atopic dermatitis (AD), atopic itch, atopic dermatitis-associated itch, autoimmune responses, autoimmune connective tissue disease, bacterial infection, biliary itch, broad activation of the immune responses, body louse, bullous diseases, brachioradial pruritus, brain tumors, chronic idiopathic pruritus, contact dermatitis, cholestasis, cutaneous larva migrans, cutaneous T-cell lymphoma, nervous system damage, dandruff, delusional parasitosis, dermatomyositis, dermatosis of pregnancy, diabetes mellitus, drug eruptions, dysregulation of neuronal processes and sensory perception, eczema, eosinophilic folliculitis, foreign objects or devices on skin, fungal infection, gestational pemphigoid, head lice, herpes, hidradenitis suppurativa, hives, Hodgkin's disease, hyperparathyroidism, idiopathic chronic itch, inflammation, insect infestation, insect bites, insect stings, intrahepatic cholestasis of pregnancy, iron deficiency anemia, increased accumulation of exogenous opioids or synthetic opioids, internal cancer, jaundice, lichen planus, lichen sclerosus, lupus erythematosus, lymphoma, lymphoma-associated itch, leukemia-associated itch, malignancy, mastocytosis, menopause, multiple sclerosis, neoplasm, nerve irritation, neurogenic itch, neuropathic itch, notalgia paresthetica, notalgia obsessive-compulsive disorders, paresthetica, parasitic infection, popular urticaria, pediculosis, peripheral neuropathy, photodermatitis, polycythemia vera, psychiatric disease, psychogenic itch, pruritic popular eruption of HIV, pruritic urticarial papules and plaques of pregnancy (PUPPP), psoriasis, psoriasis-associated itch, psoriatic itch, pubic lice, punctate palmoplantar keratoderma, renal itch, rheumatoid arthritis, scabies, scar growth, shaving, seborrheic dermatitis, stasis dermatitis, sunburn, swimmer's itch, systemic immune senescence, tactile hallucinations, Th17-associated inflammation, thyroid illness, uremia, pruritus or uremic itch, urticaria, urticarial itch, varicella, viral infection, wound or scab healing, and xerosis.

In some embodiments, the ITK-mediated or JAK3 mediated disease or disorder is a hair loss disorder. In an embodiment, the hair loss disorder is selected from alopecia, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, tinea capitis, hypotrichosis, hereditary hypotrichosis simplex, scarring alopecia, lichen planopilaris, central centrifugal cicatricial alopecia, frontal fibrosing alopecia, eyebrow alopecia, folliculitis decalvans, or intranasal hair alopecia.

In some embodiments, the ITK-mediated or JAK3 mediated disease or disorder is a connective tissue disease. In an embodiment, the connective tissue disease is selected from SLE (systemic lupus erythematosus), cutaneous lupus (e.g. SCLE, discoid lupus), chilblain lupus erythematosus, myositis, polymyositis, dermatomyositis, scleroderma, Sjogren's syndrome, polychondritis (relapsing polychondritis), vasculitis, or large vessel vasculitis.

In some embodiments, the ITK-mediated or JAK3 mediated disease or disorder is a nephropathy. In an embodiment, the nephropathy is selected from an immunologically mediated nephropathy, autoimmune nephropathy, chronic progressive nephropathies, diabetic nephropathy, renal fibrosis, ischemic/reperfusion injury associated, HIV associated nephropathy, ureteral obstructive nephropathy, glomerulosclerosis, proteinuria, nephrotic syndrome, polycystic kidney disease, autosomal dominant polycystic kidney disease or diabetic kidney disease.

In some embodiments, the ITK-mediated or JAK3 mediated disease or disorder is a cancer. In an embodiment, said cancer is a solid tumor.

In an embodiment, said cancer is prostate cancer, a genitourinary cancer, renal cancer, hepatic cancer, breast cancer, lung cancer, thyroid cancer, Kaposi's sarcoma, Castleman's disease, pancreatic cancer, skin cancer, bone cancer, ovarian cancer, liver cancer, non-small cell lung cancer, brain cancer, cancer of the larynx, gall bladder, pancreas, rectum, parathyroid, adrenal, neural tissue, head and neck, colon, stomach, bronchi, kidney cancer, basal cell carcinoma, squamous cell carcinoma, metastatic skin carcinoma, osteo sarcoma, Ewing's sarcoma, myeloma, giant cell tumor, small-cell lung tumor, islet cell tumor, primary brain tumor, lymphocytic and granulocytic tumors, hairy-cell tumor, adenoma, hyperplasia, medullary carcinoma, pheochromocytoma, mucosal neuromas, intestinal ganglioneuromas, ovarian tumor, cervical dysplasia, neuroblastoma, retinoblastoma, soft tissue sarcoma, malignant carcinoid, topical skin lesion, rhabdomyosarcoma, Kaposi's sarcoma, osteogenic sarcoma, malignant hypercalcemia, adenocarcinoma, glioblastoma multiforma, leukemias, lymphomas, malignant melanomas, and epidermoid carcinomas.

In an embodiment, said cancer is lymphoma, leukemia, or multiple myeloma.

In some embodiments, the ITK-mediated or JAK3 mediated disease or disorder is a myeloproliferative disorder (MPD). In an embodiment, said MPD is polycythemia vera (PV), essential thrombocythemia (ET), myeloid metaplasia with myelofibrosis (MMM), primary myelofibrosis (PMF), chronic myelogenous leukemia (CML), chronic myelomonocytic leukemia (CMML), hypereosinophilic syndrome (HES), idiopathic myelofibrosis (IMF), or systemic mast cell disease (SMCD).

In an embodiment, said myeloproliferative disorder is myelofibrosis.

In an embodiment, said myeloproliferative disorder is primary myelofibrosis (PMF).

In some embodiments, the ITK-mediated or JAK3 mediated disease or disorder is a bone resorption disease. In an embodiment, said bone resorption disease is osteoporosis, osteoarthritis, bone resorption associated with hormonal imbalance, bone resorption associated with hormonal therapy, bone resorption associated with autoimmune disease, or bone resorption associated with cancer.

In some embodiments, the ITK-mediated or JAK3 mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and non-alcoholic steatosis)), radiation induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the ITK-mediated or JAK3 mediated disease or disorder is a metabolic disorder. Exemplary metabolic disorders include obesity, steroid-resistance, glucose intolerance, and metabolic syndrome. In some embodiments, the ITK-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xeroderma pigmentosum, keratoacanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the ITK-mediated or JAK3 mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

Also provided herein is a compound as disclosed herein for use as a medicament. Also provided herein is a compound as disclosed herein for use as a medicament for the treatment of a ITK-mediated or JAK3 mediated disease. Also provided is the use of a compound as disclosed herein as a medicament. Also provided is the use of a compound as disclosed herein as a medicament for the treatment of a ITK-mediated or JAK3 mediated disease. Also provided is a compound as disclosed herein for use in the manufacture of a medicament for the treatment of a ITK-mediated or JAK3 mediated disease. Also provided is the use of a compound as disclosed herein for the treatment of a ITK-mediated or JAK3 mediated disease. Also provided herein is a method of inhibiting ITK comprising contacting ITK with a compound as disclosed herein. Also provided herein is a method of inhibiting JAK3 comprising contacting JAK3 with a compound as disclosed herein.

Also provided herein is a method for achieving an effect in a patient comprising the administration of a therapeutically effective amount of a compound as disclosed herein to a patient, wherein the effect is chosen from cognition enhancement.

In certain embodiments, the ITK-mediated or JAK3 mediated disease is chosen from pruritus, alopecia, alopecia areata, vitiligo, male pattern androgenetic alopecia, female pattern androgenetic alopecia, atopic dermatitis, and psoriasis.

In certain embodiments, the ITK-mediated or JAK3 mediated disease is chosen from arthritis, psoriatic arthritis, rheumatoid arthritis, juvenile rheumatoid arthritis, adult-onset Still's disease, and seronegative spondyloarthropathies.

In certain embodiments, the ITK-mediated or JAK3 mediated disease is chosen from inflammatory bowel disease, Crohn's disease, ulcerative colitis, celiac disease, enteritis, colitis, gastritis, and eosinophilic gastritis.

In certain embodiments, the ITK-mediated or JAK3 mediated disease is chosen from asthma, allergic asthma, eosinophilic asthma, sinusitis, and rhinitis.

In certain embodiments, the ITK-mediated or JAK3 mediated disease is chosen from lymphoma, T-cell lymphoma, cutaneous T-cell lymphoma, and leukemia.

In certain embodiments, the ITK-mediated or JAK3 mediated disease is chosen from organ or bone marrow transplant rejection, and graft vs. host disease (GVHD).

Some embodiments are directed to a method of inhibiting ITK or JAK3 activity in a biological sample comprising contacting the biological sample with a compound or pharmaceutical composition as described herein.

Besides being useful for human treatment, the compounds and compositions disclosed herein may also be useful for veterinary treatment of companion animals, exotic animals and farm animals, including mammals, rodents, and the like. More preferred animals include horses, dogs, and cats.

Combination Therapy

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In an embodiment, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, an agent for treating immunodeficiency disorders, and immune checkpoint inhibitors. Compounds and pharmaceutically acceptable compositions of the present disclosure can be employed in combination therapies, that is, the compounds and pharmaceutically acceptable compositions may have potential utility in combination with other therapies for the treatment of immune, inflammatory, proliferative, and allergic disorders. Examples include, but not limited, to co-administration with steroids, leukotriene antagonists, anti-histamines, anti-cancer agents, protein kinase inhibitors, cyclosporine, rapamycin, or immune checkpoint inhibitors.

Cancer cells often use immune checkpoint molecules to evade or suppress attack by the immune system. Thus, expression of immune checkpoint molecules on the surface of cancers cells prevents immune cells such as T cells from recognizing them as "foreign" or "abnormal." Consequently, immune checkpoint inhibitors are compounds which block inhibitory immune checkpoint molecules leading to the activation of the immune system via T cell recognition.

Inhibitory checkpoint molecules have been increasingly considered as new targets for cancer immunotherapies due to the effectiveness of two checkpoint inhibitor drugs that were initially indicated for advanced melanoma—ipilimumab (e.g. YERVOY™; a monoclonal antibody that works to activate the immune system by targeting CTLA-4), and pembrolizumab (e.g. KEYTRUDA™; a humanized antibody that targets the programmed cell death 1 (PD-1) receptor). Another checkpoint inhibitor known as nivolumab (e.g. OPDIVO™) blocks the interaction between PD-1 and programmed cell death ligand 1 (PD-L1) which prevents inhibition of an immune.

Any molecule capable of inhibiting one or more immune checkpoint molecules can be used in the methods disclosed herein as an additional pharmaceutical agent. Such immune checkpoint inhibitors include, without limitation, antibodies or functional fragments thereof, inhibitory polypeptides, small molecule chemical compounds, and/or inhibitory nucleic acids (such as, but not limited to, antisense oligonucleotides, small inhibitory RNAs (siRNAs), small hairpin RNAs (shRNAs), and/or catalytic nucleic acids such as ribozymes). Immune checkpoint molecules suitable for targeting by checkpoint inhibitors for use in any of the methods disclosed herein include, without limitation, one or more of the adenosine $A_{2A}$ receptor (A2AR), B7-H3 (a.k.a. CD276; e.g., MGA271), cytotoxic T-lymphocyte-associated protein 4 (CTLA4; a.k.a. CD152; e.g., ipilimumab; AGEN-1884 (Agenus), programmed cell death ligand 1 (PD-L1; a.k.a. CD274; e.g., MDX-1105 (Bristol Myers Squibb), WBP-3155 (C-stone), LY3300054 (Eli Lilly)), programmed cell death protein 1 (PD-1; a.k.a. CD279; e.g., pembrolizumab, SHR-1210 (Incyte), STI-A1110 (Sorrento), REGN2810 (Regeneron), CT-011 (pidilizumab; Curetech), PDR-001 (Novartis), BGB-A317 (BeiGene), TSR-042 (Tesaro), ENUMC-8 (Enumeral), MGD-013 (Macrogenics; bispecific antibody for PD1 and Lag3), B7-H4 (a.k.a. VTCN1), T-cell immunoglobulin and mucin-domain containing-3 (TIM3; a.k.a. HAVCR2), B and T Lymphocyte Attenuator (BTLA; a.k.a. CD272), indoleamine-pyrrole 2,3-dioxygenase (IDO), killer-cell immunoglobulin-like receptors (KIRs; e.g., lirilumab), lymphocyte-activation gene 3 (LAG-3; e.g., BMS-986016), T cell immunoreceptor with Ig and ITIM domains (TIGIT; a.k.a. WUCAM and Vstm3), ILT-3, ILT-4, and/or V-domain Ig suppressor of T cell activation (VISTA).

In some embodiments, the immune checkpoint inhibitor is an antagonistic antibody, such as, but not limited to, one or more of ipilimumab (Bristol-Myers Squibb), nivolumab (Bristol-Myers Squibb), Pembrolizumab (Merck) durvalumab (Medimmune), atezolizumab (Genentech/Roche), tremelimumab (Medimmune), and/or avelumab (Pfizer).

The compounds and pharmaceutical composition of the present disclosure may be used to prevent or treat an ITK-mediated disorder by the sequential or co-administration of another pharmaceutical agent.

In certain instances, it may be appropriate to administer at least one of the compounds described herein, or a derivative thereof, in combination with another pharmaceutical agent. By way of example only, if one of the side effects experienced by a patient upon receiving one of the compounds herein is hypertension, then it may be appropriate to administer an anti-hypertensive agent in combination with the initial pharmaceutical agent. Or, by way of example only, the therapeutic effectiveness of one of the compounds described herein may be enhanced by administration of an adjuvant (i.e., by itself the adjuvant may only have minimal therapeutic benefit, but in combination with another pharmaceutical agent, the overall therapeutic benefit to the patient is enhanced). Or, by way of example only, the benefit of experienced by a patient may be increased by administering one of the compounds described herein with another pharmaceutical agent (which also includes a therapeutic regimen) that also has therapeutic benefit. By way of example only, in a treatment for diabetes involving administration of one of the compounds described herein, increased therapeutic benefit may result by also providing the patient with another pharmaceutical agent for diabetes. In any case, regardless of the disease, disorder or condition being treated, the overall benefit experienced by the patient may simply be additive of the two pharmaceutical agents or the patient may experience a synergistic benefit.

Specific, non-limiting examples of possible combination therapies include use of compounds of embodiments herein with: chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

Specific, non-limiting examples of possible combination therapies for inflammation include use of certain compounds of the disclosure with: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON™), flurbiprofen (ANSAID™), ketoprofen, oxaprozin (DAYPRO™) diclofenac sodium (VOLTAREN™), diclofenac potassium (CATAFLAM™), etodolac (LODINE™), indomethacin (INDOCIN™), ketorolac (TORADOL™), sulindac (CLINORIL™) tolmetin (TOLECTIN™), meclofenamate (MECLOMEN™), mefenamic acid (PONSTEL™) nabumetone (RELAFEN™) and piroxicam (FELDENE™); (3) immunosuppressants, including but not limited to methotrexate (RHEUMATREX™), leflunomide (ARAVA™), azathioprine (IMIURAN™), cyclosporine (NEORAL™, SANDIMMUNE™), tacrolimus and cyclophosphamide (CYTOXAN™); (4) CD20 blockers, including but not limited to rituximab (RITUXAN™); (5) Tumor Necrosis Factor (TNF) blockers, including but not limited to etanercept (ENBREL™), infliximab (REMICADE™) and adalimumab (HUMIRA™); (6) interleukin-1 receptor antagonists, including but not limited to anakinra (KINERET™); (7) interleukin-6 inhibitors, including but not limited to tocilizumab (ACTEMRA™); (8) interleukin-17 inhibitors, including but not limited to AIN457; (9) Janus kinase inhibitors, including but not limited to tasocitinib; and (10) syk inhibitors, including but not limited to fostamatinib.

Specific, non-limiting examples of possible combination therapies for the treatment of cancer include use of certain compounds of the disclosure with: (1) alkylating agents, including but not limited to cisplatin (PLATIN™), carboplatin (PARAPLATIN™), oxaliplatin (ELOXATIN™), streptozocin (ZANOSAR™), busulfan (MYLERAN™) and cyclophosphamide (ENDOXAN™); (2) anti-metabolites, including but not limited to mercaptopurine (PURINETHOL™), thioguanine, pentostatin (NIPENT™), cytosine arabinoside (ARA-C™), gemcitabine (GEMZAR™), fluorouracil (CARAC™), leucovorin (FUSILEV™) and methotrexate (RHEUMATREX™); (3) plant alkaloids and terpenoids, including but not limited to vincristine (ONCOVIN™), vinblastine and paclitaxel (TAXOL™); (4) topoisomerase inhibitors, including but not limited to irinotecan (CAMPTOSAR™), topotecan (HYCAMTIN™) and etoposide (EPOSIN™); (5) cytotoxic antibiotics, including but not limited to actinomycin D (COSMEGEN™), doxorubicin (ADRIAMYCIN™), bleomycin (BLENOXANE™) and mitomycin (MITOSOL™); (6) angiogenesis inhibitors, including but not limited to sunitinib (SUTENT™) and bevacizumab (AVASTIN™); (7) tyrosine kinase inhibitors, including but not limited to imatinib (GLEEVEC™), erlotinib (TARCEVA™), lapatininb (TYKERB™) and axitinib (INLYTA™); and (8) immune checkpoint inhibitors, including but not limited to atezolizumab (TECENTRIQ™), avelumab (BAVENCIO™), durvalumab (IMFINZI™) ipilimumab (YERVOY™), pembrolizumab (KEYTRUDA™), nivolumab (OPDIVO™), and tremelimumab.

In some embodiments, the compounds disclosed in embodiments herein can also be co-administered (concurrently or sequentially) with a variety of other pharmaceutical agents or treatments, for example, pharmaceutical agents or treatments that are administered systemically, such as orally or parenterally. Examples of such systemic treatments include topical or systemic corticosteroids (such as prednisone), antibiotics (such as erythromycin, tetracycline, and dicloxacillin), antifungal agents (such as ketoconazole and fluconazole sold under the tradename Diflucan™), antiviral agents (such as valacyclovir sold under the tradename Valtrex™, acyclovir, and famciclovir sold under the tradename Famvir™), corticosteroids, immunosuppressants (such as cyclophosphamide sold under the tradename Cytoxan™, azathioprine, methotrexate, mycophenolate), biologics (such as rituximab sold under the tradename Rituxan™, etanercept sold under the tradename Enbrel™, adalimumab sold under the tradename Humira™, infliximab sold under the tradename Remicade™, ustenkinumab sold under the tradename Stelara™, and alefacept sold under the tradename Amevive™), and/or thyroid hormone replacement.

In some embodiments, other therapies that can be used in combination with the compounds disclosed herein include, for example, mercaptopurine, topical or systemic corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil, azathioprine, various antibodies, for example, anti-lymphocyte globulin (ALG), antithymocyte globulin (ATG), monoclonal anti-T-cell antibodies (OKT3), and irradiation. These various agents can be used in accordance with their standard or common dosages, as specified in the prescribing information accompanying commercially available forms of the drugs (see also, the prescribing information in the 2006 Edition of The Physician's Desk Reference). In some embodiments, standard dosages of these agents may be reduced when used in combination with the compounds of embodiments herein. Without limiting the scope of this disclosure, it is believed the such combination may result in synergistic results with better efficacy, less toxicity, longer duration of action, or quicker response to therapy. In some embodiments, the combination therapies in embodiments herein may be administered in sub-therapeutic amounts of either the compounds of embodiments herein or the additional pharmaceutical agents, or both. Azathioprine is currently available from Salix Pharmaceuticals, Inc. under the brand name Azasan™; mercaptopurine is currently available from Gate Pharmaceuticals, Inc. under the brand name Purinethol™; prednisone and prednisolone are currently available from Roxane Laboratories, Inc.; methyl prednisolone is currently available from Pfizer; sirolimus (rapamycin) is currently available from Wyeth-Ayerst under the brand name Rapamune™; tacrolimus is currently available from Fujisawa under the brand name Prograf™; cyclosporine is current available from Novartis under the brand name Sandimmune™ and Abbott under the brand name Gengraf™; IMPDH inhibitors such as mycophenolate mofetil and mycophenolic acid are currently available from Roche under the brand name Cellcept™ and Novartis under the brand name Myfortic™; azathioprine is currently available from Glaxo Smith Kline under the brand name Imuran™; and antibodies are currently available from Ortho Biotech under the brand name Orthoclone™, Novartis under the brand name Simulect™ (basiliximab) and Roche under the brand name Zenapax™ (daclizumab).

In some embodiments, the compounds of embodiments herein are administered in conjunction, concomitantly or adjunctively, with the pharmaceutical agents or therapies above and/or with a pharmaceutical agent or therapy for another disease. For example, the compounds of embodiments herein may be combined with thyroid hormone replacement therapy or with anti-inflammatory or immunomodulatory therapies.

In any case, the multiple pharmaceutical agents (at least one of which is a compound disclosed herein) may be administered in any order or even simultaneously. If simultaneously, the multiple pharmaceutical agents may be provided in a single, unified form, or in multiple forms (by way of example only, either as a single pill or as two separate pills). One of the pharmaceutical agents may be given in multiple doses, or both may be given as multiple doses. If not simultaneously, the timing between the multiple doses may be any duration of time ranging from a few minutes to eight weeks or at any interval appropriate to maintain the desired therapeutic efficacy. In some embodiments, the timing between the multiple doses may be a minute, an hour, six hours, a day, two days, three days, four days, five days, six days, a week, two weeks, three weeks, four weeks, five weeks, six weeks, seven weeks or eight weeks.

Thus, in another aspect, certain embodiments provide methods for treating ITK-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of ITK-mediated disorders.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

In another embodiment, the pharmaceutical compositions can further include one or more additional pharmaceutical agents such as a chemotherapeutic, steroid, anti-inflammatory compound, or immunosuppressant.

ITK inhibitor compositions described herein are also optionally used in combination with other therapeutic reagents that are selected for their therapeutic value for the condition to be treated. In general, the pharmaceutical compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified. In certain instances, it is appropriate to administer a ITK inhibitor composition as described herein in combination with another therapeutic agent. By way of example only, if one of the side effects experienced by a patient upon receiving a ITK inhibitor composition as described herein is rash, then it is appropriate to administer an anti-histamine agent in combination with the initial therapeutic agent. Or, by way of example only, the therapeutic effectiveness of a ITK inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a ITK inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses.

If not simultaneous, the timing between the multiple doses optionally varies from more than zero weeks to less than twelve weeks.

In addition, the combination methods and compositions are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a ITK inhibitor is optionally used in combination with procedures that provide additional or synergistic benefit to the patient. A ITK inhibitor and the additional therapy(ies) are optionally administered before, during or after the occurrence of a disease or condition, and the timing of administering the pharmaceutical composition containing a ITK inhibitor varies in some embodiments. Thus, for example, a ITK inhibitor is used as a prophylactic and is administered continuously to subjects with a propensity to develop conditions or diseases in order to prevent the occurrence of the disease or condition. A ITK inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A ITK inhibitor may be used in combination with drugs from the following classes: NSAIDs, immunosuppressive drugs, immunomodulatory drugs, cytostatic drugs, anti-proliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a ITK inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.)

Where a subject is suffering from or at risk of suffering from an inflammatory condition, a ITK inhibitor composition described herein is optionally used together with one or more agents or methods for treating an inflammatory condition in any combination.

One or more additional pharmaceutical agents such as, for example, anti-inflammatory agents, steroids, immunosuppressants, as well as one or more other ITK kinase inhibitors and/or other kinase inhibitors, such as JAK3 kinase, JAK1 kinase, JAK1/2 kinase, or JAK2 kinase inhibitors, such as, for example, those described in WO 99/65909, WO 00/00202, and/or WO/2004/099205, or other agents can be used in combination with the compounds of the present invention for treatment of ITK-associated diseases, disorders or conditions.

In certain embodiments, the additional pharmaceutical agent is selected from taxanes, inhibitors of bcr-abl, inhibitors of EGFR, DNA damaging agents, antimetabolites, paclitaxel, imatinib, dasatinib, nilotinib, erlotinib, gefitinib, cisplatin, oxaliplatin, carboplatin, anthracyclines, AraC, 5-FU, camptothecin, doxorubicin, idarubicin, paclitaxel, docetaxel, vincristine, a MEK inhibitor, U0126, a KSP inhibitor, vorinostat, pembrolizumab, nivolumab, atezolizumab, avelumab, tremelimumab, and durvalumab.

In some embodiments, said composition further comprises an additional pharmaceutical agent selected from a chemotherapeutic or anti-proliferative agent, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, and an agent for treating immunodeficiency disorders.

In some embodiments, one or more compounds of the embodiments herein can be used in combination with one or more other therapeutics used in the treatment of ITK-mediated disorders, and may improve the treatment response as compared to the response to the other therapeutics alone, without exacerbation of its toxic effects. In some embodiments, compounds of embodiments herein can be used in combination with one or more other ITK inhibitors, and/or JAK1 and/or JAK2 and/or JAK3 inhibitors and/or TYK2 inhibitors for the treatment of ITK-mediated disorders. Additive or synergistic effects are desirable outcomes of such combinations. The additional agents can be combined with the present compounds in a single or continuous dosage form, or the agents can be administered simultaneously or sequentially as separate dosage forms. In some embodiments, one or more additional agents can be administered to a patient in combination with at least one ITK inhibitor described herein where the additional agents are administered intermittently as opposed to continuously.

For example, in certain embodiments, a topically or orally administered ITK inhibitor/antagonist described herein can be used for the treatment of alopecia areata (e.g. patchy alopecia areata, alopecia totalis, alopecia universalis) alone or in combination with topical or intralesional corticosteroids, topical minoxidil, oral finasteride, oral dutasteride, contact sensitization therapy such as with squaric acid dibutyl ester, dinitrochlorobenzene, diphencyprone, topical or oral methoxalen and ultraviolet a (PUVA), topical anthralin, hair transplantation procedures, or other therapies known to have beneficial effects in the condition.

For example, in certain embodiments, a topically or orally administered ITK inhibitor/antagonist disclosed herein can be used for the treatment of male or female-pattern baldness (androgenetic alopecia) alone or in combination with topical minoxidil, oral finasteride (in male), oral dutasteride (in male), topical antiandrogens, hair transplantation procedures, or other therapies known to have beneficial effects in the condition.

For example, in certain embodiments, the compounds can be used for the treatment of vitiligo (e.g. localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin mini-grafting, transplantation of autologous epidermal suspension, camouflage such as with make-up or dihydroxyacetone and such, or other therapies known to have beneficial effects in the condition.

In certain embodiments the compounds of the disclosure may be used in combination with one or more agents which act by the same mechanism or by different mechanisms to effect treatment of gastrointestinal disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin Cv37 antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the presently disclosed compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNF□ antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $\square_4\square_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, Gut, 2012, 61, 918-932; Lam et al., *Immunotherapy,* 2014, 6, 963-971.)

Other compounds that may be used in combination with the presently disclosed compounds include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, *Trichuris suis* ova, K(D)PT, midismase, DNVX-078, vatelizumab, alequel, low molecular weight heparin, metenkefalin, tridecactide, HMPL-004, SB-012, olsalazine, balsalazide, propionyl-L-camitine, *Clostridium butyricum*, beclomethasone and acemannan.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1 and 2 below. Solvents and reagents, whose synthetic preparations are not described below, can be purchased at Sigma-Aldrich or Fisher Scientific.

Scheme 1 highlights the general synthesis of the 3,4-disubstituted pyrrolopyrimidines and pyrrolopyridines. Protection of 1a as a 2-(trimethylsilyl)ethoxymethyl (SEM) amine is carried out with SEM chloride and a strong base such as sodium hydride in a solvent such as DMF or THE which provides 1b. Suzuki or related transition metal mediated coupling of 1b with the desired $R^3$ group as the boronate ester or other coupling partner using a transition metal catalyst such as [1,1'-bis(diphenylphosphino)ferrocene]dichloroplalladium (II) (Pd(dppf)Cl$_2$) in the presence of a weak base such as potassium carbonate in dioxane/water as the solvent mixture provides 1c. In some cases, the $R^3$ group may be further modified after the coupling reaction by methods known to those skilled in the art. Further illustration of incorporating the desired $R^3$ groups into the heterocyclic core are shown in Schemes 6-8. An amino-heterocycle may be added to 1c via nucleophilic aromatic substitution under thermal conditions in the presence of potassium hydroxide in dioxane/water to give 1d. Deprotection of the carbamate and SEM ether may be accomplished by treating 1d with an acid such as trifluoroacetic acid (TFA) in methylene chloride to give 1e. Treating 1e with acrylic acid and a peptide coupling agent such as 1-ethyl-3-(3-dimethylaminopropyl)carbodiimide (EDC) in the presence of a weak base such as diisopropylethylamine (DIEA) in DMF or reaction with acryloyl chloride in the presence of a tertiary amine base such as triethyl amine in a solvent such as tetrahydrofuran provides acrylamide 1f.

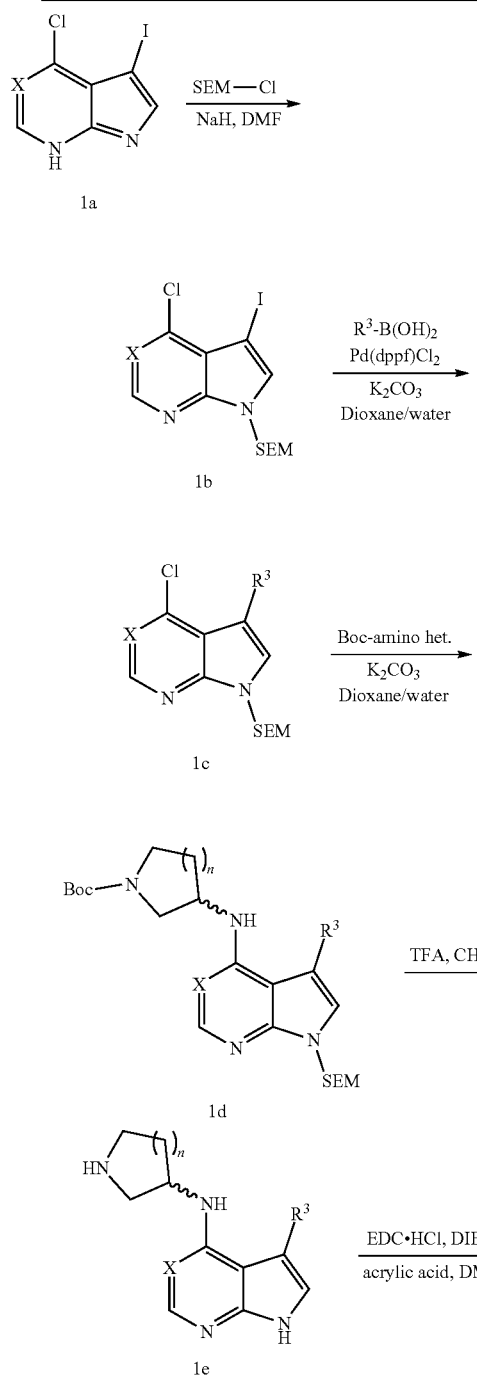

Scheme 1. Preparation of 3,4-disubstituted pyrrolopyrimidines and pyrrolidines

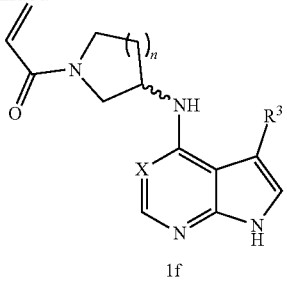

1f

Scheme 2 highlights the general synthesis of 3,4-disubstituted pyrrolopyrimidines and pyrrolopyridines. Protection of 1a as a 2-(trimethylsilyl)ethoxymethyl (SEM) amine is carried out with SEM chloride and a strong base such as sodium hydride in a solvent such as DMF or THF which provides 2a. Suzuki or related coupling of 1b with the desired $R^3$ group as the boronate ester using as palladium catalyst such as [1,1'-bis(diphenylphosphino)ferrocene]dichloropalladium (II) (Pd(dppf)Cl$_2$) in the presence of a weak base such as potassium carbonate in dioxane/water as the solvent mixture provides 2b. In some cases, the $R^3$ group may be further modified after the coupling reaction by methods know to those skilled in the art. An amino-heterocycle is added to 2b by nucleophilic aromatic substitution via thermal conditions in the presence of potassium hydroxide in dioxane/water to give 2c. Deprotection of the carbamate and SEM ether is accomplished by treating 2c with an acid such as trifluoroacetic acid (TFA) in methylene chloride to give 2d. Treating 2d with acrylic acid and a peptide coupling agent such as 1-ethyl-3-(3-dimethylaminopropyl)carbodiimide (EDC) in the presence of a weak base such as diisopropylethylamine (DIEA) in DMF or reaction with acryloyl chloride in the presence of a tertiary amine base such as triethyl amine in a solvent such as tetrahydrofuran provides acrylamide 2e.

Scheme 2. Preparation of 3,4-disubstituted pyrrolopyrimidines and pyrrolidines

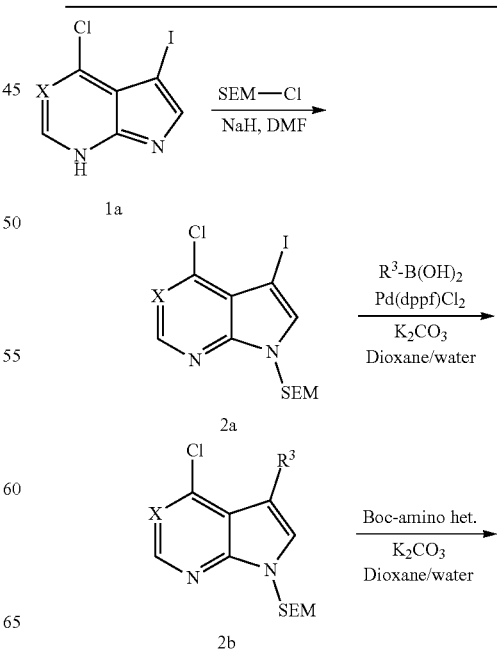

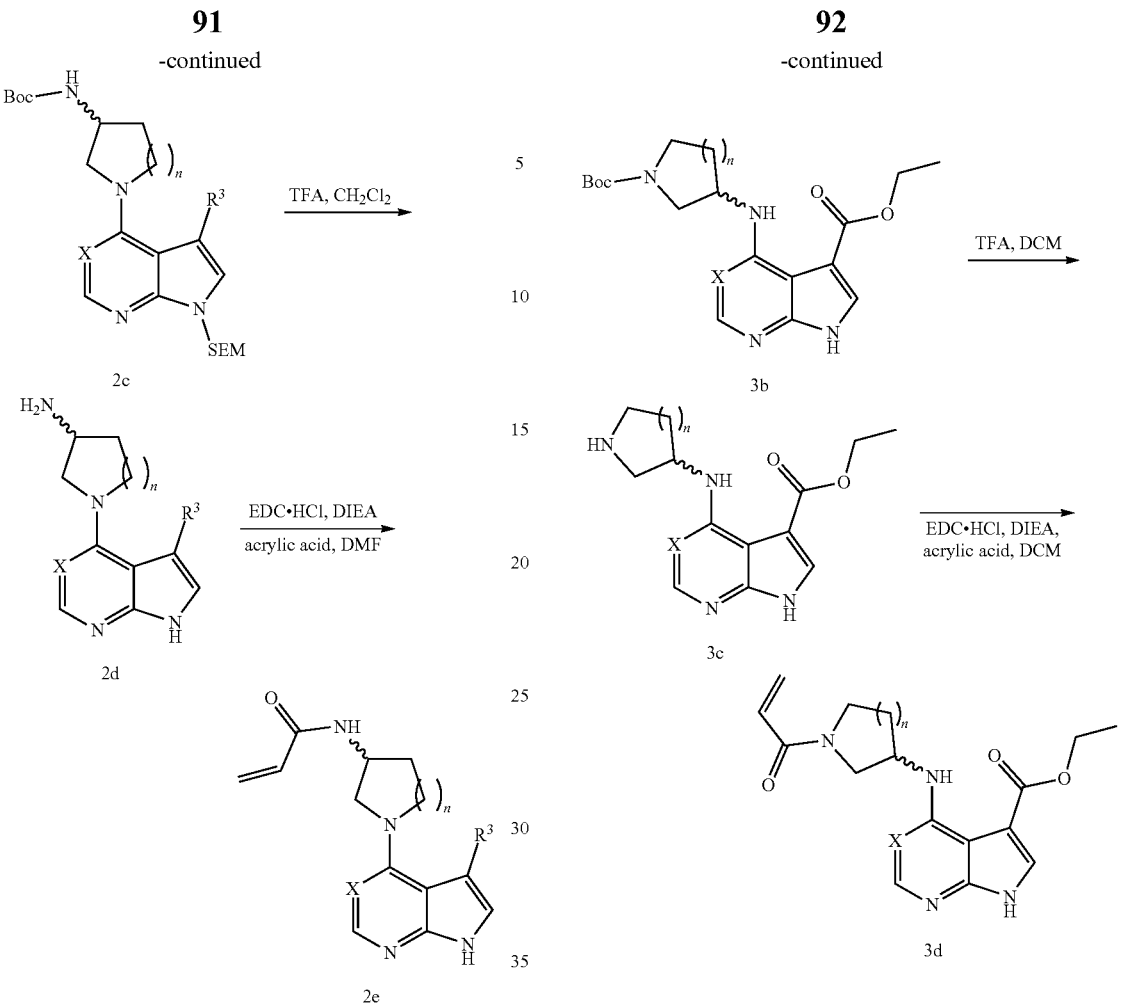

Scheme 3 highlights the general synthesis the 3-ester 4-substituted pyrrolopyrimidines and pyrrolopyridines. The amino-heterocycle is added to 3a using thermal conditions in the presence of potassium carbonate in dioxane/water to give 3b. Deprotection of the carbamate is accomplished by treating 3b with an acid such as trifluoroacetic acid (TFA) in methylene chloride to give 3c. Treating 3c with acrylic acid and a peptide coupling agent such as 1-ethyl-3-(3-dimethylaminopropyl)carbodiimide (EDC) in the presence of a weak base such as diisopropylethylamine (DIEA) in DMF provides acrylamide 3d. Alternatively, 3c may be acylated using acryloyl chloride in the presence of a weak base such as triethylamine in dichloromethane to give 3d.

Scheme 4 highlights the general synthesis the 3-ester 4-substituted pyrrolopyrimidines and pyrrolopyridines. The amino-heterocycle is added to 3a via nucleophilic aromatic substitution under thermal conditions in the presence of potassium carbonate in dioxane/water to give 4a. Deprotection of the carbamate is accomplished by treating 4a with an acid such as trifluoroacetic acid (TFA) in methylene chloride to give 4b. Treating 4b with acrylic acid and a peptide coupling agent such as 1-ethyl-3-(3-dimethylaminopropyl) carbodiimide (EDC) in the presence of a weak base such as diisopropylethylamine (DIEA) in DMF provides acrylamide 4c. Alternatively, 4b may be acylated using acryloyl chloride in the presence of a weak base such as triethylamine in dichloromethane to give 4c.

Scheme 3. Preparation of 3-ester 4-substituted pyrrolopyrimidines and pyrrolopyridines.

Scheme 4. Preparation of 3-ester 4-substituted pyrrolopyrimidines and pyrrolopyridines.

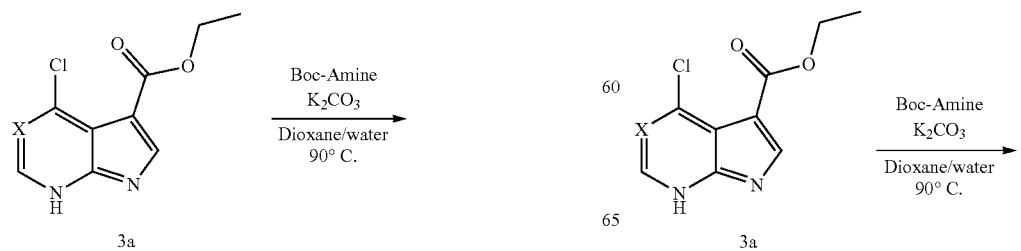

93                                                                                       94

-continued

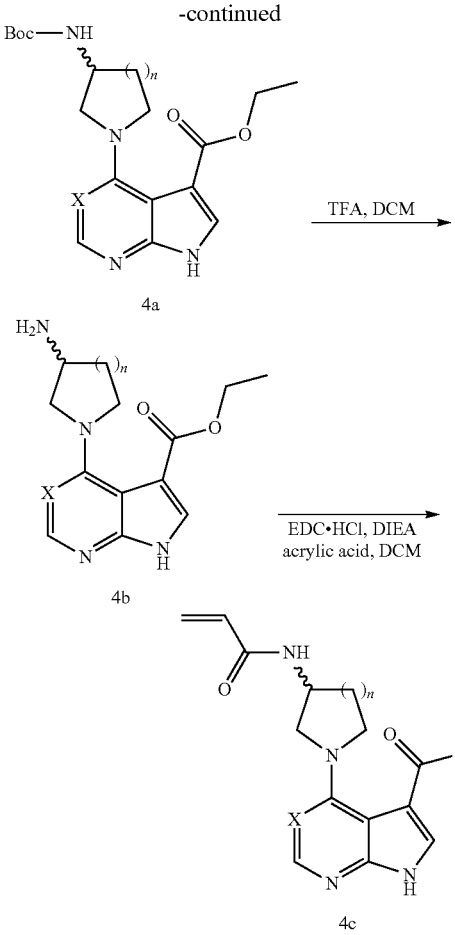

(II) (Pd(dppf)Cl$_2$) in the presence of a weak base such as potassium carbonate in dioxane/water as the solvent mixture provides 5c.

Scheme 5. Preparation of 3,5-disubstituted pyrrolopyrimidines and pyrrolopyrazines.

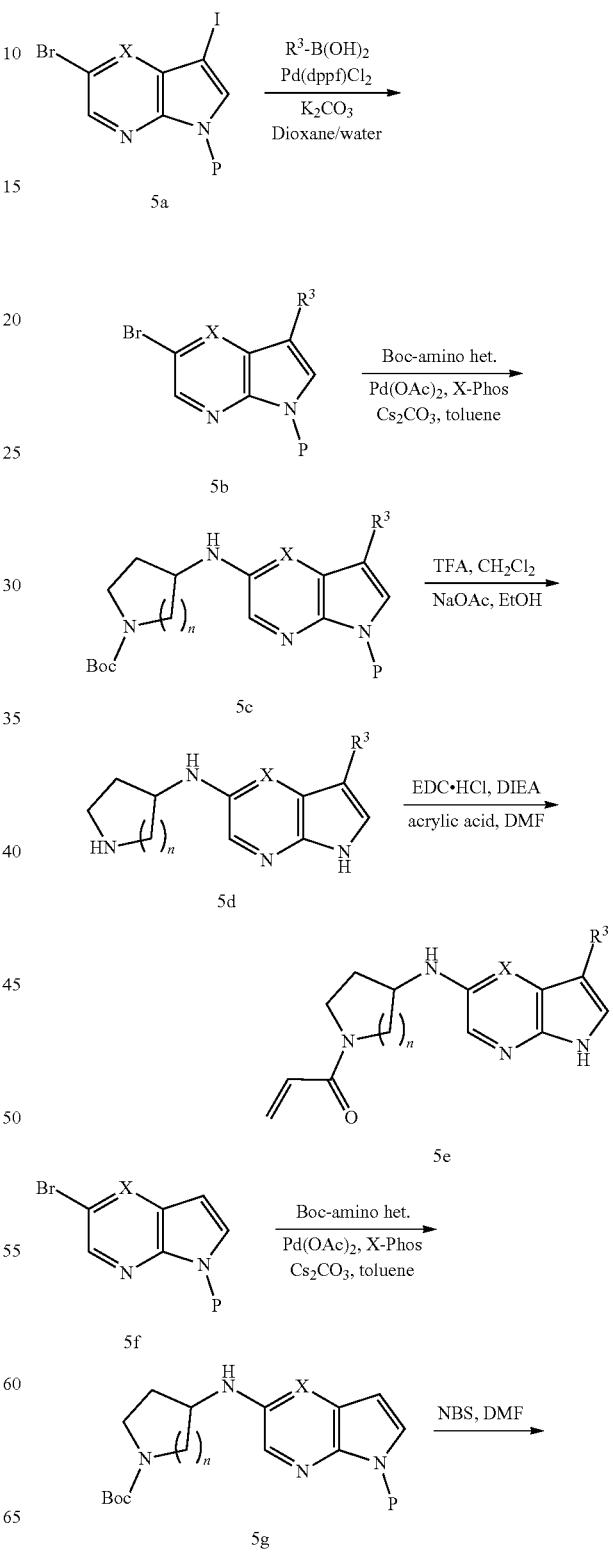

Scheme 5 highlights the general synthesis of the 3,5-disubstituted pyrrolopyrimidines and pyrrolopyrazines. Protected 5a is synthesized as in Scheme 1. Suzuki or related coupling of 5a with the desired R$^3$ group as the boronate ester using as palladium catalyst such as [1,1'-bis(diphenylphosphino)ferrocene]dichloroplalladium (II) (Pd(dppf)Cl$_2$) in the presence of a weak base such as potassium carbonate in dioxane/water as the solvent mixture provides 5b. In some cases, the R$^3$ group may be further modified after the coupling reaction by methods know to those skilled in the art. The amino-heterocycle is added to 5b using Buchwald or Hartwig conditions in the presence palladium acetate as a catalyst, a ligand such as Xantphos, a base such as cesium carbonate in toluene to give 5c. Deprotection of the carbamate and SEM protecting groups\ is accomplished by treating 5c with an acid such as trifluoroacetic acid (TFA) in methylene chloride followed by sodium acetate in ethanol to give 5d. Treating 5d with acrylic acid and a peptide coupling agent such as 1-ethyl-3-(3-dimethylaminopropyl) carbodiimide (EDC) in the presence of a weak base such as diisopropylethylamine (DIEA) in DMF provides acrylamide 5e. The sequence of adding the R$^3$ and R$^5$ substituents may be reversed. In this case, the amino-heterocycle is added to 5f using Buchwald or Hartwig conditions in the presence palladium acetate as a catalyst, a ligand such as Xantphos, and a base such as cesium carbonate in toluene to give 5g. Halogenation of 5g with NBS in DMF provides bromo 5h. Suzuki or related coupling of 5h with the desired R$^3$ group as the boronate ester using as palladium catalyst such as [1,1'-bis(diphenylphosphino)ferrocene]dichloroplalladium

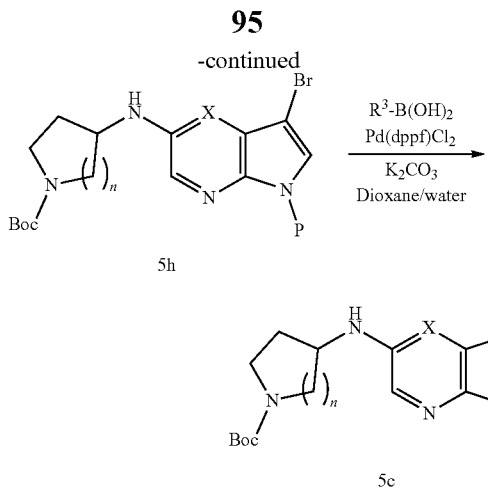

Scheme 6 highlights the synthesis of selected R³ keto and alkyl groups attached to the heteroaromatic core. In this sequence, metal halogen exchange of iodo-substituted 5a (or Br) is carried out and the intermediate anion treated with the Weinreb amide of the desired R³ substituent. Following this general procedure 6a is treated with n-butyl lithium in ether at –78° C. followed by the appropriate Weinreb amide to give ketone 6b, keto-cycloalkyl 6f or keto-heterocycle 6d. If so desired these ketone products may be further manipulated. For instance, ketone 6f may be treated with methyl magnesium bromide in THE to give an intermediate alcohol which is further reduced using triethylsilane in a mixture of TFA/DCM to give alkyl 6g. Alternatively, the anion of 6a may be reacted with an aldehyde instead of a Weinreb amide to give an alcohol directly. In this case, the anion of 6a may be reacted with various aldehydes such as 6i to give alcohol 6j. The alcohol may be removed if desired using triethylsilane in a mixture of TFA/DCM to give 6k. In all cases the protecting group of 6a can be selected as desired by one skilled in the art. Often a (SEM) or besylate protecting group is preferred. The chemistry outlined in scheme 6 is meant to be representative with many more options are available to those skilled in the art.

Scheme 6. Elaboration of the R³ position in the heterocaromatic core.

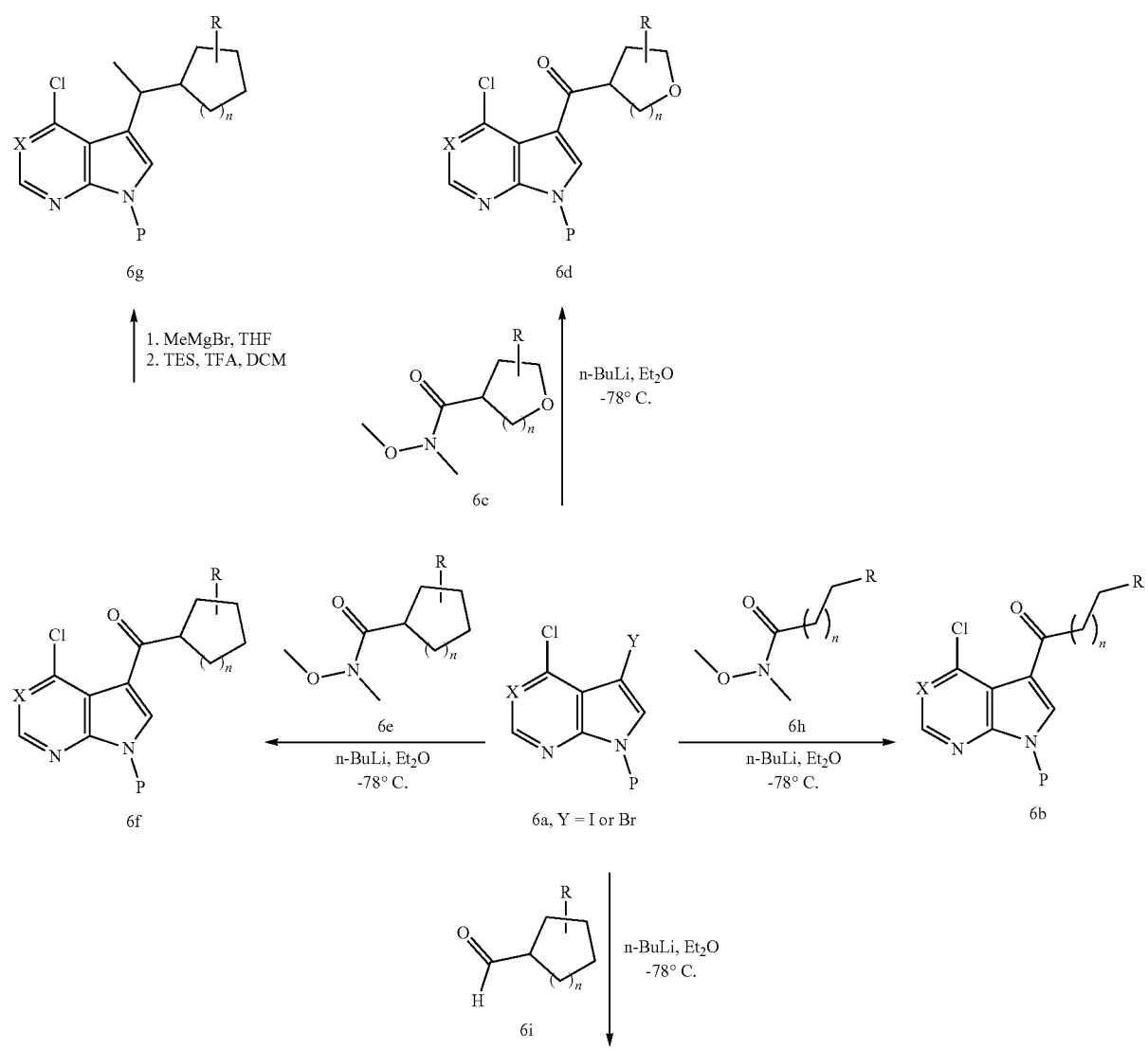

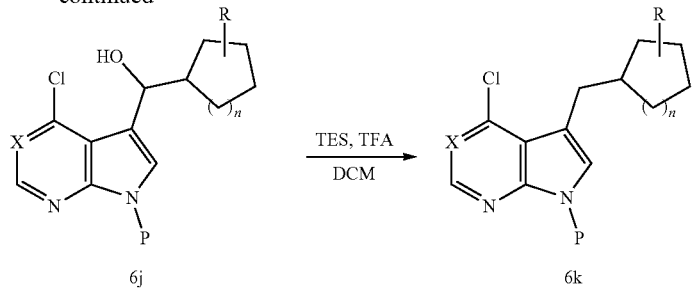

Scheme 7 highlights the synthesis where $R^3$ is a substituted cyclopropyl group attached to the heterocyclic core. Suzuki or a related coupling of 7a (X=Cl or OMe) with the desired $R^3$ group as the boronate ester (7b) using as palladium catalyst such as [1,1'-bis(diphenylphosphino)ferrocene]dichloroplalladium (II) (Pd(dppf)Cl$_2$) in the presence of a weak base such as potassium carbonate in dioxane/water as the solvent mixture provides 7c. Cyclopropanation of 7c can be accomplished via a variety of methods, including CH$_2$I$_2$ and Et$_2$Zn, TMSCF$_3$ with NaI, and NMU KOH and Pd(OAc)$_2$ to give the desired substituted cyclopropyl 7d. In many cases the R or $R^{3-1}$ substituent may be modified by conventional procedures as those known in the art.

Scheme 7. Elaboration of the $R^3$ position to substituted cyclopropyl analogs.

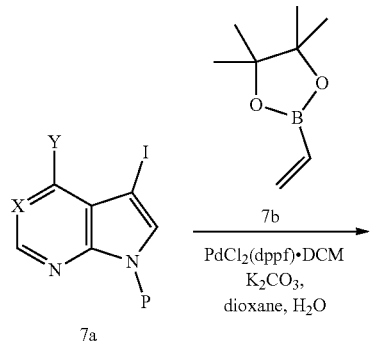

Y = Cl or OMe

Scheme 8 highlights the synthesis where $R^3$ is a substituted cycloalkyl group off the heteroaromatic core. Suzuki or a related coupling of 6a with the desired $R^3$ group as the boronate ester (8a) using as palladium catalyst such as [1,1'-bis(diphenylphosphino)ferrocene]dichloroplalladium (II) (Pd(dppf)Cl$_2$) in the presence of a weak base such as potassium carbonate in dioxane/water as the solvent mixture provides 8b. Hydrogenation of 8b using hydrogen, Pd/C in a solvent such as ethanol provides 8c. Alternatively, 8b may be treated with CH$_2$I$_2$ and Et$_2$Zn under Simmons-Smith conditions to form the bicyclic analog 8d.

Scheme 8. Elaboration of the $R^3$ position to substituted cycloalkyl analogs.

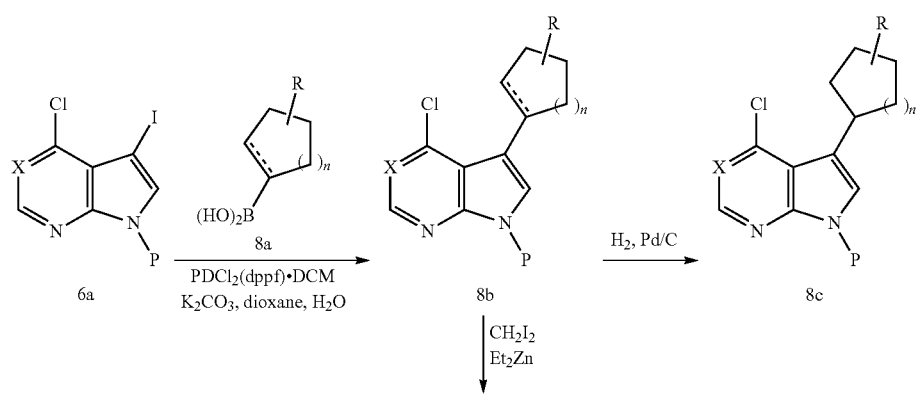

-continued

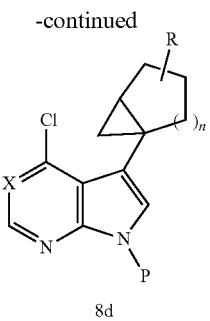

8d

The disclosure is further illustrated by the following examples.

EXAMPLE 1

Preparation of Ethyl (R)-4-((1-acryloylpiperidin-3-yl)amino)-7H-pyrrolo[2,3-d]pyrimidine-5-carboxylate

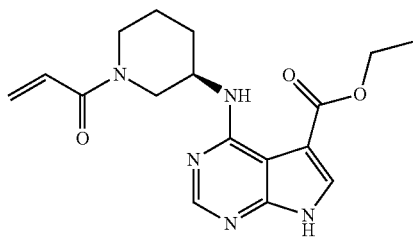 [SMILES: C=CC(=O)N1CCC[C@@H](Nc2ncnc3[nH]cc(C(=O)OCC)c23)C1]

Step 1: Preparation of Ethyl (R)-4-((1-(tert-butoxylcarbonyl)piperidin-3-yl)amino)-7H-pyrrolo[2,3-d]pyrimidine carboxylate

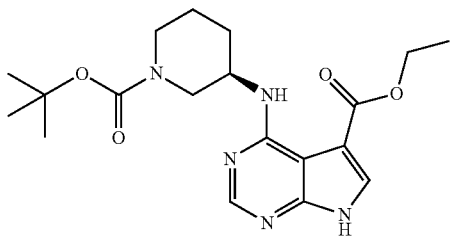 [SMILES: CCOC(=O)c1c[nH]c2ncnc(N[C@@H]3CCCN(C(=O)OC(C)(C)C)C3)c12]

A mixture of ethyl 4-chloro-7-H-pyrrolo[2,3-d]pyrimidine-5-carboxylate (0.150 g, 0.665 mmol), tert-butyl (3R)-3-aminopiperidine-1-carboxylate (0.146 g, 0.731 mmol), and N,N-diisopropylethylamine (0.346 mL, 1.99 mmol) in N-butanol (2 mL) was heated at 135° C. in a sealed vessel for 1 hour. At this time, the reaction was cooled and partitioned between ethyl acetate and water. The ethyl acetate layer was washed with brine, dried over sodium sulfate, filtered and concentrated in vacuo. The resulting oil was chromatographed on silica gel, eluting with methanol and ethyl acetate. Pure fractions were pooled and concentrated to give ethyl (R)-4-((1-(tert-butoxylcarbonyl)piperidin-3-yl)amino)-7H-pyrrolo[2,3-d]pyrimidine carboxylate as a clear oil (0.256 g, 99% yield): MS (ES) m/z 390.3 (M+H).

Step 2: Preparation of Ethyl (R)-4-(piperidin-3-ylamino)-7H-pyrrolo[2,3-d]pyrimidine-5-carboxylate

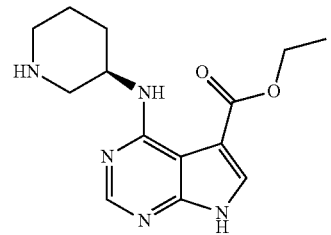 [SMILES: CCOC(=O)c1c[nH]c2ncnc(N[C@@H]3CCCNC3)c12]

To a solution of ethyl (R)-4-((1-(tert-butoxylcarbonyl)piperidin-3-yl)amino)-7H-pyrrolo[2,3-d]pyrimidine carboxylate (0.256 g, 0.657 mmol) in dichloromethane (3 mL) at 0° C. was added trifluoroacetic acid (1 mL, 13.1 mmol). The solution was stirred at ambient temperature for 1 hour. The reaction was concentrated in vacuo to give ethyl (R)-4-(piperidin-3-ylamino)-7H-pyrrolo[2,3-d]pyrimidine-5-carboxylate as an oil in quantitative yield. The material was carried forward without further purification: (MS (ES) m/z 290.2 (M+H).

Step 3: Preparation of Ethyl (R)-4-((1-acryloylpiperidin-3-yl)amino)-7H-pyrrolo[2,3-d]pyrimidine-5-carboxylate

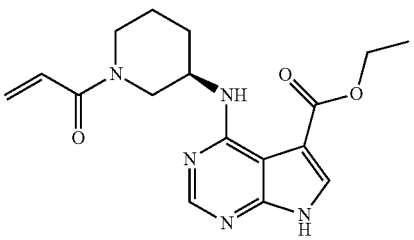 [SMILES: C=CC(=O)N1CCC[C@@H](Nc2ncnc3[nH]cc(C(=O)OCC)c23)C1]

To a solution of ethyl (R)-4-(piperidin-3-ylamino)-7H-pyrrolo[2,3-d]pyrimidine-5-carboxylate (0.190 g, 0.657 mmol) in dichloromethane (2 mL) was added N,N-diisopropylethylamine (0.340 mL, 1.96 mmol). Separately, a solution of prop-2-enoic acid (0.066 mg, 0.919 mmol) in dichloromethane (2 mL) was treated with 1-ethyl-3-(3-dimethylaminopropyl)carbodiimide hydrochloride (0.190 g, 0.985 mmol) and N,N-diisopropylethylamine (0.340 mL, 1.96 mmol). After 15 minutes at ambient temperature, the solution of activated acid was added to the amine solution and the mixture stirred at ambient temperature for 1.5 hours. The reaction was then taken up in ethyl acetate and washed with water then brine. The ethyl acetate layer was then dried over sodium sulfate, filtered and concentrated in vacuo. The resulting material was chromatographed on silica gel, eluting with methanol and ethyl acetate. Pure fractions were pooled and concentrated to give ethyl (R)-4-((1-acryloylpiperidin-3-yl)amino)-7H-pyrrolo[2,3-d]pyrimidine-5-carboxylate (90 mg, 40% yield): $^1$H-NMR (400 MHz, DMSO-$d_6$) δ 12.48 (br s, 1H), 8.58 (br d, J=7.04 Hz, 1H), 8.21 (br d, J=11.35 Hz, 1H), 7.92 (s, 1H), 6.49-6.89 (m, 1H), 5.91-6.12 (m, 1H), 5.42-5.72 (m, 1H), 4.11-4.35 (m, 3H), 3.83-4.08 (m, 1H), 3.38-3.72 (m, 3H), 1.87-2.10 (m, 1H), 1.63-1.86 (m, 2H), 1.47-1.62 (m, 1H), 1.30 (t, J=7.04 Hz, 3H); MS (ES) m/z 344.3 (M+H).

EXAMPLE 2

Preparation of Ethyl 4-(((3R,6S)-1-acryloyl-6-methylpiperidin-3-yl)amino)-7H-pyrrolo[2,3-d]pyrimidine-5-carboxylate

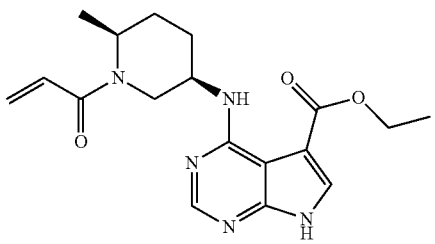 [SMILES: C=CC(=O)N1C[C@H](Nc2ncnc3[nH]cc(C(=O)OCC)c23)CC[C@@H]1C]

Step 1: Preparation of Ethyl 4-chloro-7-(phenylsulfonyl)-7H-pyrrolo[2,3-d]pyrimidine-5-carboxylate

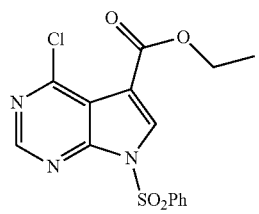

To a stirred solution of ethyl 4-chloro-7H-pyrrolo[2,3-d]pyrimidine-5-carboxylate (4.00 g, 17.7 mmol) in DCM (40 mL) was added triethylamine (7.48 mL, 53.3 mmol) and N,N-dimethylaminopyridine (0.210 g, 1.77 mmol) at room temperature. Benzene sulfonyl chloride (4.00 g, 22.9 mmol) was then added dropwise over 10 min. The resulting reaction mixture was stirred at room temperature for another 30 min. After completion of reaction, the reaction mixture was diluted with DCM (50 mL) and washed with water. The organic layer was then washed with brine and dried over anhydrous sodium sulfate. The organic layer was filtered and concentrated under vacuum to provide crude material which was then purified by Combi-flash purifier with 20% ethyl acetate in hexane as an eluent to afford ethyl 4-chloro-7-(phenylsulfonyl)-7H-pyrrolo[2,3-d]pyrimidine-5-carboxylate as a light yellow solid: (5.3 g, 82% yield): MS (ES) m/z 366.3 (M+H)$^{+1}$.

Step 2: Preparation of Ethyl 4-(((3R,6S)-1-((benzyloxy)carbonyl)-6-methylpiperidin-3-yl)amino)-7-(phenylsulfonyl)-7H-pyrrolo[2,3-d]pyrimidine-5-carboxylate

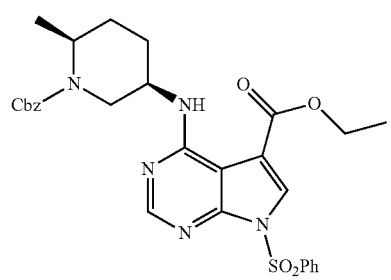

To a stirred solution of 4-chloro-7-(phenylsulfonyl)-7H-pyrrolo[2,3-d]pyrimidine-5-carboxylate (5.30 g, 14.5 mmol) in n-butanol (50 mL) was added benzyl (2S,5R)-5-amino-2-methylpiperidine-1-carboxylate (4.53 g, 15.9 mmol) and N,N diisopropylethylamine. The reaction mixture was heated to 130° C. in sealed tube for 16 h. After completion of reaction, the reaction mixture was allowed to cool and was concentrated under reduced pressure. The crude residue was then dissolved in ethyl acetate and washed with water and brine solution. The organic layer was dried over anhydrous sodium sulfate and concentrated under vacuum. The crude material was purified by Combi-flash purifier with 50% ethyl acetate in hexane as an eluent to afford benzyl ethyl 4-(((3R,6S)-1-((benzyloxy)carbonyl)-6-methylpiperidin-3-yl)amino)-7-(phenylsulfonyl)-7H-pyrrolo[2,3-d]pyrimidine-5-carboxylate as a pale brown solid. (6.5 g, 78% yield): MS (ES) m/z 578.1 (M+H)$^{+1}$ Step-3: Preparation of Ethyl 4-(((3R,6S)-1-((benzyloxy)carbonyl)-6-methylpiperidin-3-yl)amino)-7H-pyrrolo[2,3-d]pyrimidine-5-carboxylate

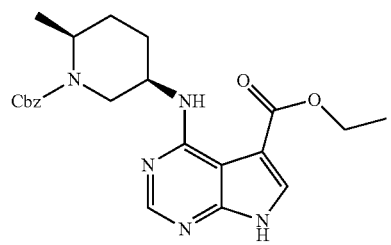 [SMILES: CCOC(=O)c1c[nH]c2ncnc(N[C@@H]3CC[C@H](C)N(C(=O)OCc4ccccc4)C3)c12]

To a stirred solution benzyl ethyl 4-(((3R,6S)-1-((benzyloxy)carbonyl)-6-methylpiperidin-3-yl)amino)-7-(phenylsulfonyl)-7H-pyrrolo[2,3-d]pyrimidine-5-carboxylate (6.50 g, 11.7 mmol) in tetrahydrofuran (100 mL) was added potassium tert-butoxide (3.9 g, 35 mmol) at room temperature. The reaction mixture was stirred at room temperature for 2 hours. After completion of reaction, the reaction mixture was quenched with water and extracted with ethyl acetate. The organic layer was washed with brine solution, dried over anhydrous sodium sulfate, filtered, and concentrated under reduced pressure to obtain ethyl 4-(((3R,6S)-1-((benzyloxy)carbonyl)-6-methylpiperidin-3-yl)amino)-7H-pyrrolo[2,3-d]pyrimidine-5-carboxylate as a light yellow solid (3.4 g, 69% yield): MS (ES) m/z 438.1 (M+H)$^{+1}$.

Step-4: Preparation of Ethyl 4-(((3R,6S)-6-methylpiperidin-3-yl)amino)-7H-pyrrolo[2,3-d]pyrimidine-5-carboxylate

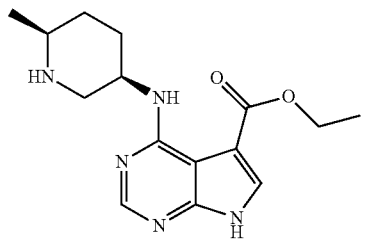 [SMILES: CCOC(=O)c1c[nH]c2ncnc(N[C@@H]3CC[C@H](C)NC3)c12]

To a nitrogen purged solution of ethyl 4-(((3R,6S)-1-((benzyloxy)carbonyl)-6-methylpiperidin-3-yl)amino)-7H-pyrrolo[2,3-d]pyrimidine-5-carboxylate (3.4 g, 7.8 mmol) in tetrahydrofuran (100 mL) was added 10% Pd/C (3 g). The reaction mixture was stirred under a hydrogen atmosphere for 16 h at room temperature. After completion of the reaction, the mixture was filtered through celite and filtrate was concentrated under reduced pressure to give the desired crude compound. The obtained crude was used for the next step without any purification (2.35 g, 100% yield): MS (ES) m/z 304.1 (M+H)$^{+1}$.

Step 5: Preparation of tert-butyl 4-((3-(1-cyclopropyl-2-methoxyethyl)-1-((2-(trimethylsilyl)ethoxy)methyl)-1H-pyrrolo[2,3-b]pyridine-5-yl)amino)piperidine-1-carboxylate

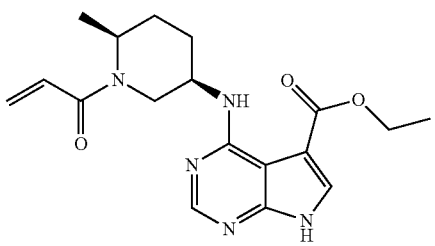 [SMILES: C=CC(=O)N1C[C@H](Nc2ncnc3[nH]cc(C(=O)OCC)c23)CC[C@@H]1C]

To a stirred solution of ethyl 4-(((3R,6S)-6-methylpiperidin-3-yl)amino)-7H-pyrrolo[2,3-d]pyrimidine-5-carboxylate (2.4 g, 7.92 mmol) in THF/water (60/40 mL) at 0° C. was added triethylamine (3.3 mL, 23.7 mmol). Acryloyl chloride (0.76 mL, 9.5 mmol) was then added slowly at 0° C. The resulting reaction mixture was stirred at the same temperature for 20 min. After completion of reaction, the mixture was quenched with saturated NaHCO$_3$ solution and extracted with ethyl acetate. The organic layer was washed with water, brine and dried over anhydrous sodium sulfate. The organic layer concentrated under vacuum to provide crude material which was purified by silica gel chromatography (20% MeOH in DCM) to afford the pure title compound as a white solid (1.14 g, 40% yield): $^1$H NMR (400 MHz, DMSO-d$_6$) δ 12.43 (s, 1H), 8.42 (d, J=6.8 Hz, 1H), 8.19 (s, 1H), 7.9 (s, 1H), 6.81-6.74 (m, 1H), 6.1-6.05 (dd, J$_1$=2 Hz, J$_2$=16.8 Hz, 1H), 5.67-5.64 (m, 1H), 4.51 (bs, 2H), 4.29 (q, J$_1$=6.8 Hz, 2H), 3.93 (bs, 1H), 2.64 (bs, 1H), 1.92 (bs, 1H), 1.71-1.64 (m, 3H), 1.30 (t, J=7.2 Hz, 3H), 1.17 (d, J=6.4 Hz, 3H); MS (ES) m/z 358.0 (M+H).

EXAMPLE 3

Preparation of Isopropyl 4-(((3R,6S)-1-acryloyl-6-methylpiperidin-3-yl)amino)-7H-pyrrolo[2,3-d]pyrimidine-5-carboxylate

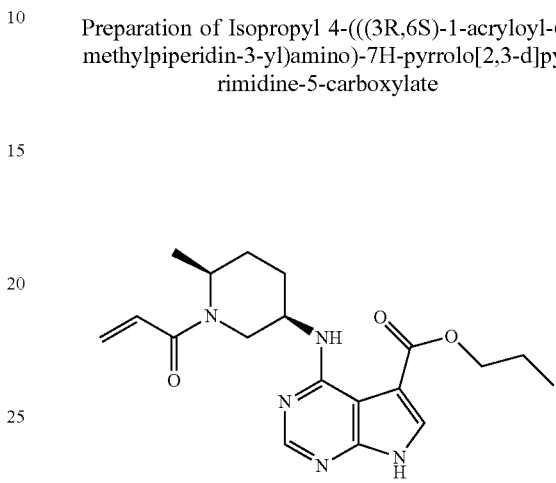

The title compound was prepared by the method described in Scheme 9.

Scheme 9.
Preparation of isopropyl 4-(((3R,6S)-1-acryloyl-6-methylpiperidin-3-yl)amino)-7H-pyrrolo[2,3-d]pyrimidine-5-carboxylate

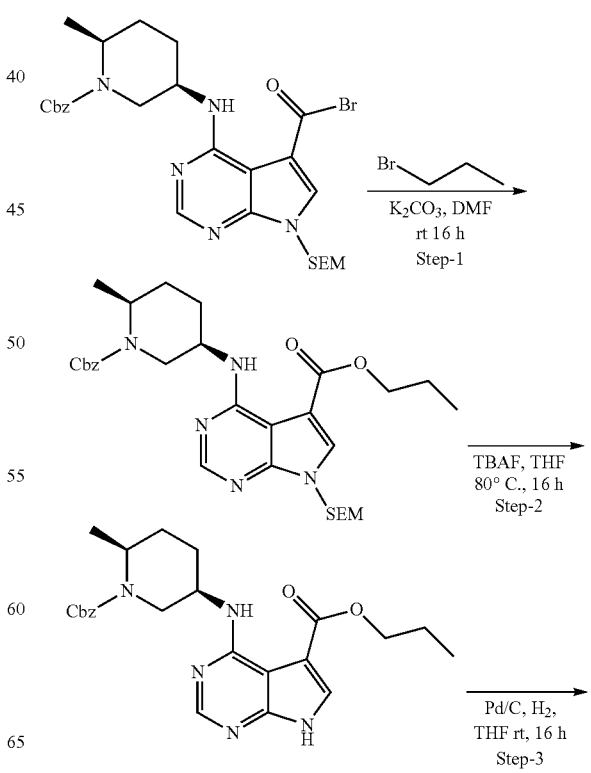

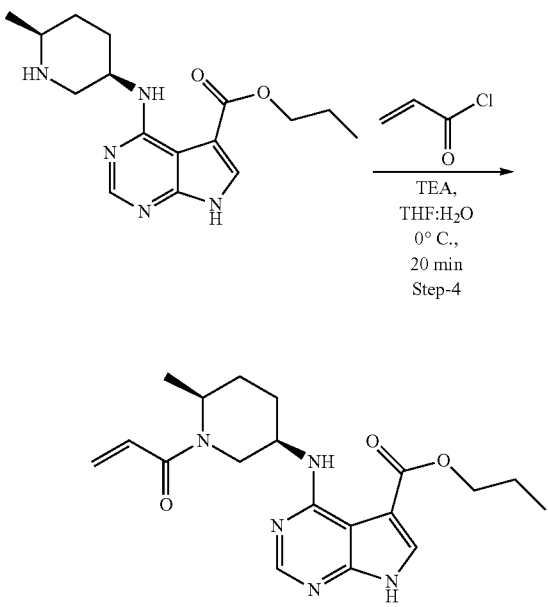

Step 1: Preparation of Propyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate

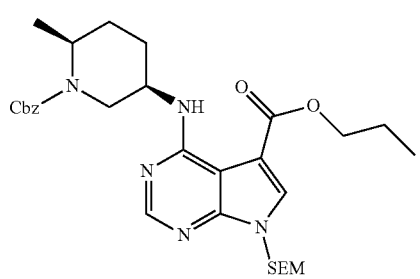 [SMILES: CCCOC(=O)c1cn(COCC[Si](C)(C)C)c2ncnc(N[C@@H]3CC[C@H](C)N(C(=O)OCc4ccccc4)C3)c12]

To a suspension of potassium carbonate (0.153 g, 1.1 mmol) in N,N-dimethylformamide (10 mL) were added benzyl ethyl-4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylic acid (Prepared by the method described in Example 4, Step 5, 0.2 g, 0.37 mmol), n-propyl bromide (0.22 g, 1.85 mmol) and the mixture was stirred at ambient temperature for 16 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (30% ethyl acetate/hexane) to provide propyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate as a yellow solid (0.2 g, 93% yield): MS (ES) m/z 582.5 (M+H).

Step 2: Preparation of Propyl 4-(((3R,6S)-1-((benzyloxy)carbonyl)-6-methylpiperidin-3-yl)amino)-7H-pyrrolo[2,3-d]pyrimidine-5-carboxylate

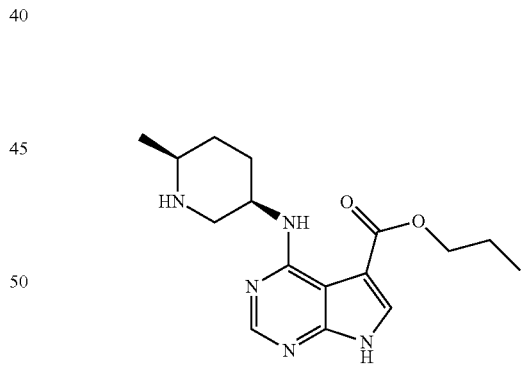

To a solution of propyl 4-(((3R,6S)-1-((benzyloxy)carbonyl)-6-methylpiperidin-3-yl)amino)-7-((2-(trimethylsilyl)ethoxy)-methyl)-7H-pyrrolo[2,3-d]pyrimidine-5-carboxylate (0.2 g, 0.34 mmol) in tetrahydrofuran (5 mL) was added tetrabutylammonium fluoride (5 mL, 1M in tetrahydrofuran) and the solution was heated to 80° C. for 16 hours. The reaction was poured into ice water and extracted with ethyl acetate. The organic layer was washed with water, brine, dried over anhydrous sodium sulfate, filtered and concentrated in vacuo. The crude material was purified using flash chromatography (70% ethyl acetate/hexane) to provide propyl 4-(((3R,6S)-1-((benzyloxy)carbonyl)-6-methylpiperidin-3-yl)amino)-7H-pyrrolo[2,3-d]pyrimidine-5-carboxylate as a white solid (0.09 g, 58% yield): MS (ES) m/z 452.4 (M+H).

Step 3: Propyl 4-(((3R,6S)-6-methylpiperidin-3-yl)amino)-7H-pyrrolo[2,3-d]pyrimidine-5-carboxylate To a solution of isopropyl 4-(((3R,6S)-1-((benzyloxy)carbonyl)-6-methylpiperidin-3-yl)amino)-7H-pyrrolo[2,3-d]pyrimidine-5-carboxylate (0.09 g, 0.2 mmol) in tetrahydrofuran (10 mL) was added palladium on carbon (0.05 g, 10 wet w/w) under nitrogen atmosphere. The reaction mixture was stirred under hydrogen atmosphere at room temperature for 16 hours. The reaction mixture was filtered through celite and filtrate was concentrated in vacuo to provide propyl 4-(((3R,6S)-6-methylpiperidin-3-yl)amino)-7H-pyrrolo[2,3-d]pyrimidine-5-carboxylate as a white solid (0.06 g, crude): MS (ES) m/z 318.1 (M+H).

Step 4: Preparation of Propyl 4-(((3R,6S)-1-acryloyl-6-methylpiperidin-3-yl)amino)-7H-pyrrolo[2,3-d]pyrimidine-5-carboxylate

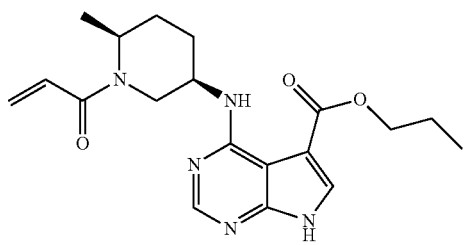 [SMILES: C=CC(=O)N1C[C@H](Nc2ncnc3[nH]cc(C(=O)OCCC)c23)CC[C@@H]1C]

To a stirred solution of propyl 4-(((3R,6S)-6-methylpiperidin-3-yl)amino)-7H-pyrrolo[2,3-d]pyrimidine-5-carboxylate (0.06 g, 0.188 mmol) in tetrahydrofuran:water (3:2 mL) was added triethylamine (0.08 mL, 0.56 mmol) followed by a solution of acryloyl chloride (0.02 mL, 0.22 mmol) in tetrahydrofuran (0.5 mL) at 0° C. and stirred for 20 minutes. The reaction mixture was quenched with sodium bicarbonate solution and extracted with ethyl acetate. The organic layer was washed with brine, dried over anhydrous sodium sulfate, filtered and concentrated in vacuo. The crude material was purified using flash chromatography (20% methanol/dichloromethane) to provide propyl 4-(((3R,6S)-1-acryloyl-6-methylpiperidin-3-yl)amino)-7H-pyrrolo[2,3-d]pyrimidine-5-carboxylate as a white solid (0.02 g, 20% yield): $^1$H NMR (400 MHz, DMSO-$d_6$) δ 12.44 (s, 1H), 8.42 (d, J=6.8 Hz, 1H), 8.18 (s, 1H), 7.91 (s, 1H), 6.74-6.81 (m, 1H), 6.07 (d, J=16.8 Hz, 1H), 5.65 (d, J=10 Hz, 1H), 4.5 (br s, 3H), 4.2 (t, J=6.4 Hz, 2H), 3.93 (bs, 1H), 1.91 (br s, 1H), 1.67-1.78 (m, 4H), 1.14-1.46 (m, J=7.2 Hz, 5H), 0.95 (t, J=7.2 Hz, 2H); MS (ES) m/z 371.1.0 (M+H).

EXAMPLE 4

Preparation of Isopropyl 4-(((3R,6S)-1-acryloyl-6-methylpiperidin-3-yl)amino)-7H-pyrrolo[2,3-d]pyrimidine-5-carboxylate

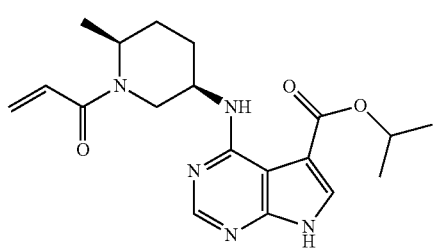 [SMILES: C=CC(=O)N1C[C@H](Nc2ncnc3[nH]cc(C(=O)OC(C)C)c23)CC[C@@H]1C]

The title compound was prepared by the method described in Scheme 10.

Scheme 10.
Preparation of isopropyl 4-(((3R,6S)-1-acryloyl-6-methylpiperidin-3-yl)amino)-7H-pyrrolo[2,3-d]pyrimidine-5-carboxylate

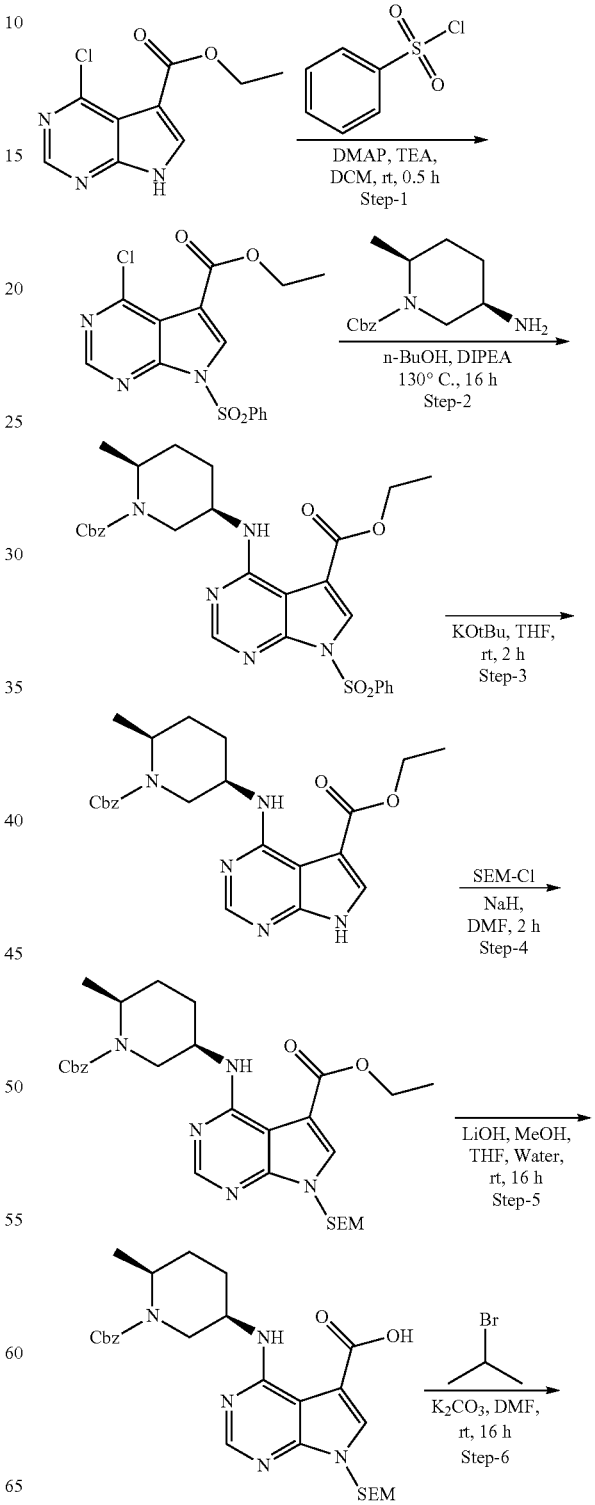

-continued

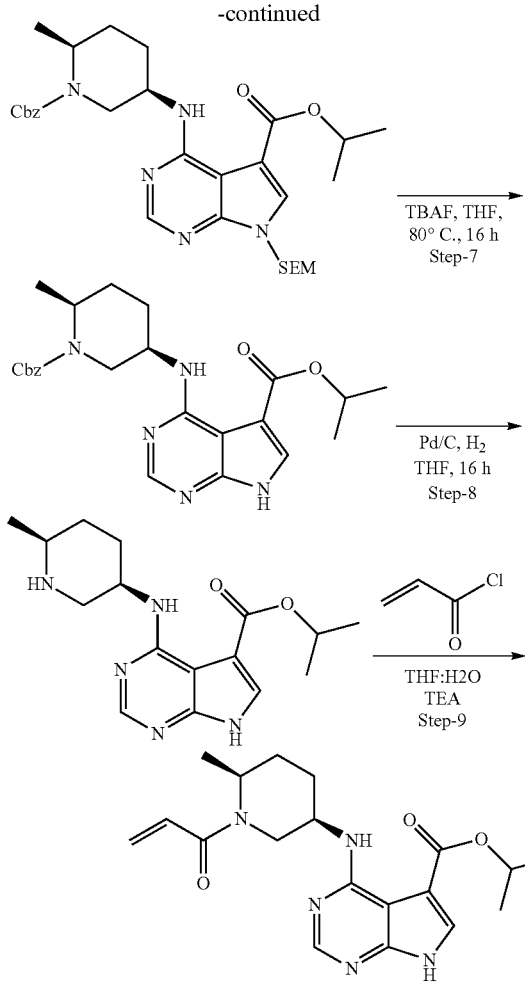

Step 1: Preparation of Ethyl 4-chloro-7-(phenylsulfonyl)-7H-pyrrolo[2,3-d]pyrimidine-5-carboxylate

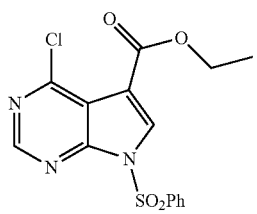

To a stirred solution of ethyl 4-chloro-7H-pyrrolo[2,3-d]pyrimidine-5-carboxylate (4.0 g, 17.7 mmol) in dichloromethane (40 mL) were added triethylamine (7.48 mL, 53.28 mmol), N,N-dimethylaminopyridine (0.21 g, 1.77 mmol) followed by benzenesulfonyl chloride (4 g, 22.88 mmol) dropwise over a period of 10 minutes and the mixture was stirred at ambient temperature for 0.5 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (20% ethyl acetate/hexane) to provide ethyl 4-chloro-7-(phenylsulfonyl)-7H-pyrrolo[2,3-d]pyrimidine-5-carboxylate as a light yellow solid (5.3 g, 82% yield): MS (ES) m/z 366.3 (M+H).

Step 2: Preparation of Ethyl 4-(((3R,6S)-1-((benzyloxy)carbonyl)-6-methylpiperidin-3-yl)amino)-7-(phenylsulfonyl)-7H-pyrrolo-[2,3-d]pyrimidine-5-carboxylate

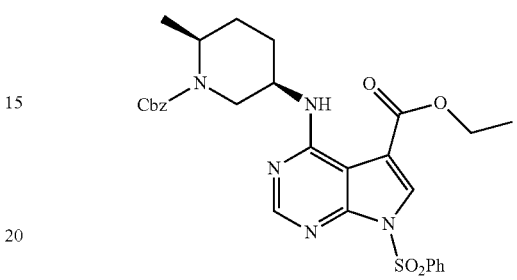

To a stirred solution of ethyl 4-chloro-7-(phenylsulfonyl)-7H-pyrrolo[2,3-d]pyrimidine-5-carboxylate (5.3 g, 14.5 mmol) in n-butanol (50 mL) were added benzyl (2S,5R)-5-amino-2-methylpiperidine-1-carboxylate (4.53 g, 15.9 mmol), N,N-diisopropylethylamine (10.1 mL, 58 mmol) and the mixture was heated in a sealed tube at 130° C. for 16 hours. The mixture was cooled to ambient temperature, poured into water and extracted with ethyl acetate. The combined organic layer was washed with brine, dried over anhydrous sodium sulfate, filtered and concentrated in vacuo. The crude material was purified using flash chromatography (50% ethyl acetate/hexane) to provide benzyl ethyl 4-(((3R,6S)-1-((benzyloxy)carbonyl)6-methyl-piperidin-3-yl)amino)-7-(phenylsulfonyl)-7H-pyrrolo[2,3-d]pyrimidine-5-carboxylate as a pale brown solid (6.5 g, 77.6% yield): MS (ES) m/z 578.1 (M+H).

Step 3: Preparation of Ethyl 4-(((3R,6S)-1-((benzyloxy)carbonyl)-6-methylpiperidin-3-yl)amino)-7H-pyrrolo[2,3-d]pyrimidine-5-carboxylate

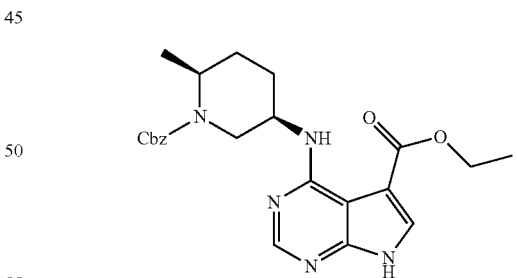

To a stirred solution of benzyl ethyl 4-(((3R,6S)-1-((benzyloxy)carbonyl)-6-methylpiperidin-3-yl)amino)-7-(phenylsulfonyl)-7H-pyrrolo[2,3-d]pyrimidine-5-carboxylate (6.5 g, 11.69 mmol) in tetrahydrofuran (100 mL) was added potassium tert-butoxide (3.9 g, 35 mmol) and the mixture was stirred at ambient temperature for 2 hours. The reaction mixture was poured into water and extracted with ethyl acetate. The combined organic layers were washed with brine, dried over anhydrous sodium sulfate, filtered and concentrated in vacuo to provide ethyl 4-(((3R,6S)-1-((benzyloxy)carbonyl)-6-methylpiperidin-3-yl)amino)-7H-pyrrolo[2,3-d]pyrimidine-5-carboxylate as a light yellow solid (3.4 g, 69% yield): MS (ES) m/z 438.1 (M+H).

Step 4: Preparation of Ethyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate

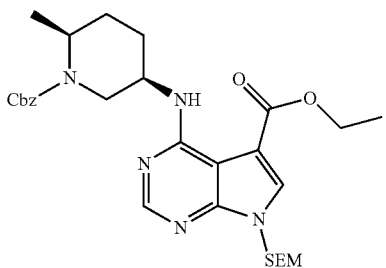 [SMILES: CCOC(=O)c1cn(COCC[Si](C)(C)C)c2ncnc(N[C@@H]3CC[C@H](C)N(C(=O)OCc4ccccc4)C3)c12]

To a suspension of sodium hydride (0.12 g, 3.29 mmol) in N,N-dimethylformamide (30 mL) ethyl 4-(((3R,6S)-1-((benzyloxy)carbonyl)-6-methylpiperidin-3-yl)amino)-7H-pyrrolo[2,3-d]pyrimidine-5-carboxylate (1.2 g, 2.74 mmol) was added at 0° C. The suspension was stirred for 15 minutes and then 2-(trimethylsilyl)ethoxymethyl chloride (0.55 g, 3.29 mmol) was added at 0° C. The reaction mixture was warmed to ambient temperature and stirred for 2 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (20% ethyl acetate/hexane) to provide ethyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate as a white solid (0.9 g, 58% yield): MS (ES) m/z 568.2 (M+H).

Step 5: Preparation of 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylic Acid

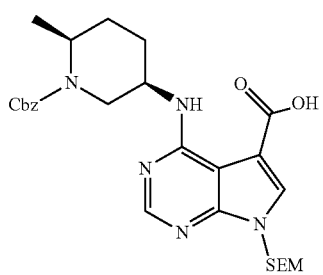 [SMILES: C[C@H]1CC[C@@H](Nc2ncnc3c2c(C(=O)O)cn3COCC[Si](C)(C)C)CN1C(=O)OCc1ccccc1]

To a stirred solution of ethyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate (0.85 g, 1.49 mmol) in tetrahydrofuran:methanol (10:10 mL) was added lithium hydroxide monohydrate (0.63 g, 14.9 mmol) and the mixture was stirred at ambient temperature for 16 hours. The volatiles were removed in vacuo and the residue was diluted with water and acidified with 1N hydrochloric acid (pH=~4). The aqueous layer was extracted with ethyl acetate, washed with brine, dried over anhydrous sodium sulfate, filtered and concentrated in vacuo to provide 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylic acid as a white solid (0.75 g, 93.7% yield): MS (ES) m/z 540.2 (M+H).

Step 6: Preparation of Isopropyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate

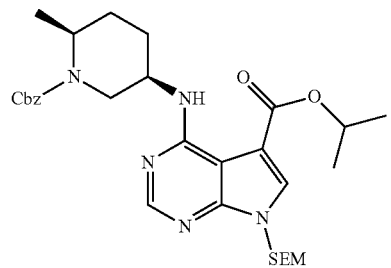 [SMILES: CC(C)OC(=O)c1cn(COCC[Si](C)(C)C)c2ncnc(N[C@@H]3CC[C@H](C)N(C(=O)OCc4ccccc4)C3)c12]

To a suspension of potassium carbonate (0.19 g, 1.39 mmol) in N,N-dimethylformamide (10 mL) 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylic acid (0.25 g, 0.46 mmol) and isopropyl bromide (0.13 mL, 1.39 mmol) were added and the mixture was stirred at ambient temperature for 16 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (30% ethyl acetate/hexane) to provide isopropyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]-pyrimidine-5-carboxylate as a pale yellow solid (0.2 g, 74.3% yield): MS (ES) m/z 582.5 (M+H).

Step 7: Preparation of Isopropyl 4-(((3R,6S)-1-((benzyloxy)carbonyl)-6-methylpiperidin-3-yl)amino)-7H-pyrrolo[2,3-d]pyrimidine-5-carboxylate

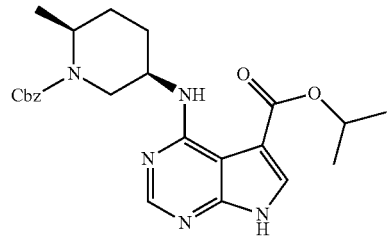 [SMILES: CC(C)OC(=O)c1c[nH]c2ncnc(N[C@@H]3CC[C@H](C)N(C(=O)OCc4ccccc4)C3)c12]

To a solution of isopropyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate (0.2 g, 0.34 mmol) in tetrahydrofuran (5 mL) was added tetrabutylammonium fluoride (5 mL, 1M in tetrahydrofuran) and the solution was heated to 80° C. for 16 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (70% ethyl acetate/hexane) to provide isopropyl 4-(((3R,6S)-1-((benzyloxy)carbonyl)-6-methylpiperidin-3-yl)amino)-7H-pyrrolo[2,3-d]pyrimidine-5-carboxylate as a white solid (0.1 g, 64% yield): MS (ES) m/z 452.2 (M+H).

Step 8: Preparation of Isopropyl 4-(((3R,6S)-6-methylpiperidin-3-yl)amino)-7H-pyrrolo[2,3-d]pyrimidine-5-carboxylate

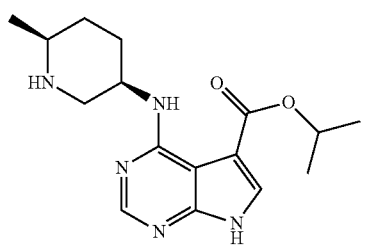 [SMILES: CC(C)OC(=O)c1c[nH]c2ncnc(N[C@@H]3CC[C@H](C)NC3)c12]

To a solution of isopropyl 4-(((3R,6S)-1-((benzyloxy)carbonyl)-6-methylpiperidin-3-yl)amino)-7H-pyrrolo[2,3-d]pyrimidine-5-carboxylate (0.1 g, 0.22 mmol) in tetrahydrofuran (10 mL) was added palladium on carbon (0.05 g, 10 wet w/w) under nitrogen atmosphere. The reaction mixture was stirred under hydrogen atmosphere at room temperature for 16 hours. The reaction mixture was filtered through celite and filtrate was concentrated in vacuo to provide isopropyl 4-(((3R,6S)-6-methylpiperidin-3-yl)amino)-7H-pyrrolo[2,3-d]pyrimidine-5-carboxylate as a white solid (0.08 g, crude): MS (ES) m/z 318.3 (M+H).

Step 9: Preparation of Isopropyl 4-(((3R,6S)-1-acryloyl-6-methylpiperidin-3-yl)amino)-7H-pyrrolo[2,3-d]pyrimidine-5-carboxylate

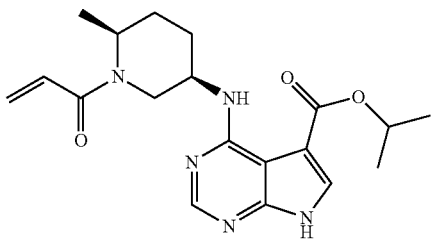 [SMILES: C=CC(=O)N1C[C@H](Nc2ncnc3[nH]cc(C(=O)OC(C)C)c23)CC[C@@H]1C]

To a solution of isopropyl 4-(((3R,6S)-6-methylpiperidin-3-yl)amino)-7H-pyrrolo[2,3-d]pyrimidine-5-carboxylate (0.08 g, 0.25 mmol) in tetrahydrofuran:water (3:2 mL) was added triethylamine (0.1 mL, 0.75 mmol) followed by a solution acryloyl chloride (0.018 mL, 0.22 mmol) in tetrahydrofuran (0.5 mL) at 0° C. and stirred for 20 minutes. The reaction mixture was quenched with a saturated aqueous sodium bicarbonate solution and extracted with ethyl acetate. The organic layer was washed with brine, dried over anhydrous sodium sulfate, filtered and concentrated in vacuo. The crude material was purified using flash chromatography (20% methanol/dichloromethane) to provide isopropyl 4-(((3R,6S)-1-acryloyl-6-methylpiperidin-3-yl)amino)-7H-pyrrolo[2,3-d]pyrimidine-5-carboxylate as a white solid (0.02 g, 19% yield). $^1$H NMR (400 MHz, DMSO-d$_6$): δ 12.41 (s, 1H), 8.43 (d, J=7.2 Hz, 1H), 8.18 (s, 1H), 7.85 (s, 1H), 6.74-6.81 (dd, J$_1$=10.8 Hz, J$_2$=16.8 Hz, 1H), 6.05-6.09 (dd, J$_1$=2 Hz, J$_2$=16.8 Hz, 1H), 5.66 (d, J=10.4 Hz, 1H), 5.10-5.16 (m, 1H), 4.5 (br s, 3H), 3.93 (br s, 1H), 1.92 (br s, 1H), 1.71-1.68 (m, 3H), 1.31 (d, J=6 Hz, 6H), 1.16-1.21 (m, 3H); MS (ES) m/z 372.3 (M+H).

EXAMPLE 5

Preparation of (R)-1-(3-((5-(cyclopropanecarbonyl)-7H-pyrrolo[2,3-d]pyrimidin-4-yl)amino)piperidin-1-yl)prop-2-en-1-one

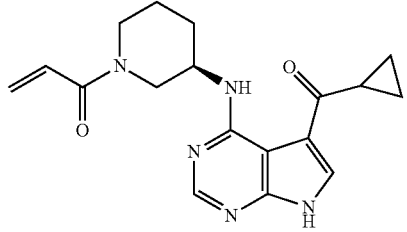 [SMILES: C=CC(=O)N1CCC[C@@H](Nc2ncnc3[nH]cc(C(=O)C4CC4)c23)C1]

The title compound was prepared by the method described in Scheme 34

Scheme 34

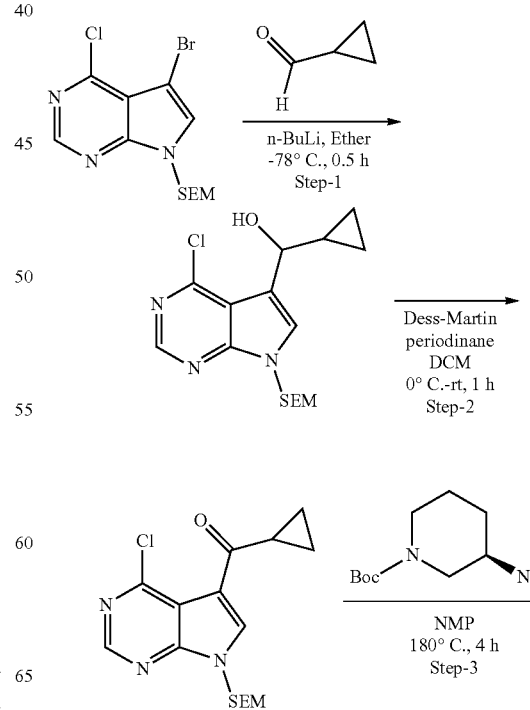

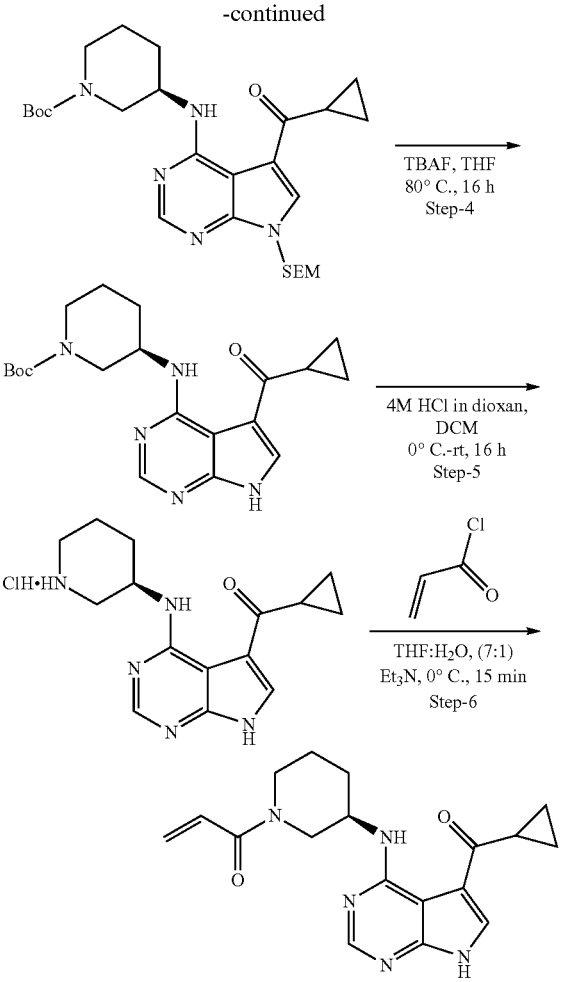

Step 1: Preparation of (4-chloro-7-((2-(trimethylsilyl)ethoxy)methyl)-7H-pyrrolo[2,3-d]pyrimidin-5-yl)(cyclopropyl)methanol

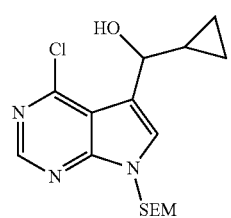 [SMILES: C[Si](C)(C)CCOCn1cc(C(O)C2CC2)c2c(Cl)ncnc21]

To a stirred solution of 5-bromo-4-chloro-7-((2-(trimethylsilyl)ethoxy)methyl)-7H-pyrrolo[2,3-d]pyrimidine (prepared by the method described in example 7, 2 g, 5.52 mmol) in diethyl ether (30 mL) was added n-butyl lithium (5.17 mL, 8.28 mmol, 1 M in hexane) at −78° C. and stirred for 0.5 hours. Then a solution of cyclopropane carbaldehyde (0.64 mL, 8.28 mmol) in diethyl ether (3 mL) was added at −78° C. and the mixture was stirred for 30 minutes. The reaction mixture was quenched with saturated aqueous ammonium chloride and extracted with diethyl ether (2×100 mL). The combined organic layer was washed with water, brine, dried over anhydrous sodium sulfate, filtered and concentrated in vacuo. The crude material was purified using flash chromatography (40% ethyl acetate/hexane) to provide (4-chloro-7-((2-(trimethylsilyl) ethoxy)methyl)-7H-pyrrolo[2,3-d]pyrimidin-5-yl)-(cyclopropyl)methanol as a brown liquid (1.2 g, 53% yield). $^1$H NMR (400 MHz, DMSO-$d_6$): δ 8.61 (s, 1H), 7.76 (s, 1H), 5.61 (s, 2H), 5.11 (s, 1H), 4.76 (s, 1H), 3.50 (t, J=7.6 Hz, 2H), 1.31-1.32 (m, 1H), 0.82 (t, J=8 Hz, 2H), 0.34-0.44 (m, 4H), 0.03 (s, 9H); MS (ES) m/z 354.0 (M+H).

Step 2: Preparation of (4-chloro-7-((2-(trimethylsilyl)ethoxy)methyl)-7H-pyrrolo[2,3-d]pyrimidin-5-yl)(cyclopropyl)methanone

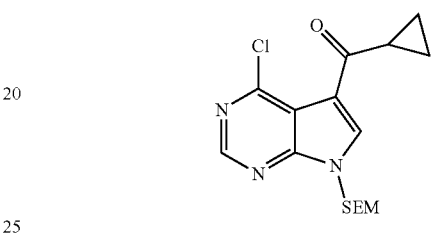

To a stirred solution of (4-chloro-7-((2-(trimethylsilyl) ethoxy)methyl)-7H-pyrrolo[2,3-d]pyrimidin-5-yl)(cyclopropyl)-methanol (1.2 g, 3.39 mmol) in dichloromethane (20 mL) was added Dess-Martin periodinane (2.1 g, 5.09 mmol) at 0° C. and the mixture was stirred at ambient temperature for 1 hour. The reaction mixture was quenched with saturated aqueous sodium bicarbonate and sodium thiosulfate and extracted with dichloromethane (2×100 mL). The combined organic layers were washed with brine, dried over anhydrous sodium sulfate, filtered and concentrated in vacuo. The crude material was purified using flash chromatography (20% ethyl acetate/hexane) to provide (4-chloro-7-((2-(trimethylsilyl)ethoxy)methyl)-7H-pyrrolo[2,3-d]pyrimidin-5-yl)(cyclopropyl)methanone as a brown liquid (0.5 g, 45% yield); $^1$H NMR (400 MHz, DMSO-$d_6$) δ 8.66 (s, 1H), 8.02 (s, 1H), 5.62 (s, 2H), 3.52 (t, J=8 Hz, 2H), 1.50-1.54 (m, 1H), 0.80 (t, J=8 Hz, 2H), 0.48-0.59 (m, 4H), 0.08 (s, 9H); MS (ES) m/z 352.1 (M+H).

Step 3: Preparation of tert-butyl (R)-3-((5-(cyclopropanecarbonyl)-7-((2-(trimethylsilyl)ethoxy)methyl)-7H-pyrrolo[2,3-d]pyrimidin-4-yl)amino)piperidine-1-carboxylate

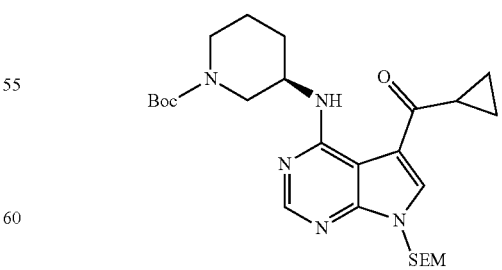

To a stirred solution of (4-chloro-7-((2-(trimethylsilyl) ethoxy)methyl)-7H-pyrrolo[2,3-d]pyrimidin-5-yl)(cyclopropyl)methanone (0.5 g, 1.42 mmol) in N-methyl-2-pyrrolidone (30 mL) was added tert-butyl (R)-3- aminopiperidine-1-carboxylate (0.34 g, 1.70 mmol) and the mixture was heated in a sealed tube at 180° C. for 4 hours. The reaction mixture was cooled to ambient temperature, poured into water and extracted with ethyl acetate (2×100 mL). The combined organic layers were washed with brine, dried over anhydrous sodium sulfate, filtered and concentrated in vacuo. The crude material was purified using flash chromatography (27% ethyl acetate/hexane) to provide tert-butyl (R)-3-((5-(cyclopropanecarbonyl)-7-((2-(trimethylsilyl)ethoxy)methyl)-7H-pyrrolo[2,3-d]pyrimidin-4-yl)amino)piperidine-1-carboxylate (0.6 g, crude) as a brown liquid: MS (ES) m/z 516.2 (M+H).

Step 4: Preparation of tert-butyl (R)-3-((5-(cyclopropanecarbonyl)-7H-pyrrolo[2,3-d]pyrimidin-4-yl)amino)piperidine-1-carboxylate

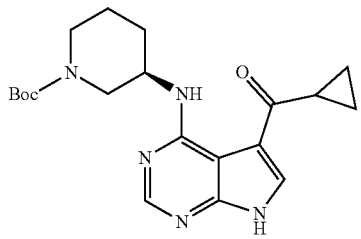 [SMILES: CC(C)(C)OC(=O)N1CCC[C@@H](Nc2ncnc3[nH]cc(C(=O)C4CC4)c23)C1]

To a stirred solution of tert-butyl (R)-3-((5-(cyclopropanecarbonyl)-7-((2-(trimethylsilyl)ethoxy)methyl)-7H-pyrrolo[2,3-d]pyrimidin-4-yl)amino)piperidine-1-carboxylate (0.6 g, 1.16 mmol) in tetrahydrofuran (4 mL) was added tetrabutylammonium fluoride (10 mL, 1 M in tetrahydrofuran) and the solution was heated to 80° C. for 16 hours. The reaction mixture was cooled to ambient temperature, poured into ice water and extracted with ethyl acetate. The organic layer was washed with water, brine, dried over anhydrous sodium sulfate, filtered and concentrated in vacuo. The crude material was purified using flash chromatography (4% methanol/dichloromethane) to provide tert-butyl (R)-3-((5-(cyclopropanecarbonyl)-7H-pyrrolo[2,3-d]pyrimidin-4-yl)amino)piperidine-1-carboxylate as a yellow liquid (0.17 g, 39% yield): MS (ES) m/z 386.2 (M+H).

Step 5: Preparation of (R)-cyclopropyl(4-(piperidin-3-ylamino)-7H-pyrrolo[2,3-d]pyrimidin-5-yl)methanone hydrochloride

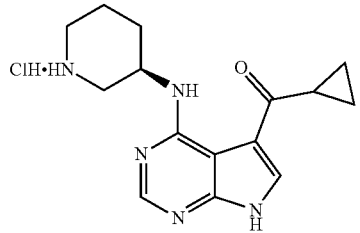

To a stirred solution of tert-butyl (R)-3-((5-(cyclopropanecarbonyl)-7H-pyrrolo[2,3-d]pyrimidin-4-yl)amino)piperidine-1-carboxylate (0.17 g, 0.44 mmol) in dichloromethane (2 mL) was added hydrogen chloride (1.1 mL, 4.41 mmol, 4 M in dioxane) at 0° C. and the mixture was stirred at ambient temperature for 16 hours. The reaction was concentrated in vacuo and the residue was washed with ether to provide (R)-cyclopropyl(4-(piperidin-3-ylamino)-7H-pyrrolo[2,3-d]pyrimidin-5-yl)methanone hydrochloride as an off-white solid (0.17 g, crude): MS (ES) m/z 286.1 (M+H).

Step 6: Preparation of (R)-1-(3-((5-(cyclopropanecarbonyl)-7H-pyrrolo[2,3-d]pyrimidin-4-yl)amino)piperidin-1-yl)prop-2-en-1-one

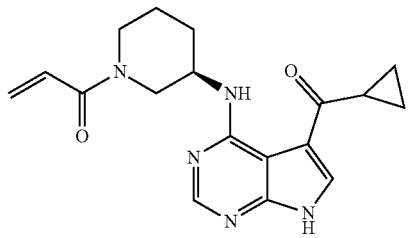 [SMILES: C=CC(=O)N1CCC[C@@H](Nc2ncnc3[nH]cc(C(=O)C4CC4)c23)C1]

To a stirred solution of (R)-cyclopropyl(4-(piperidin-3-ylamino)-7H-pyrrolo[2,3-d]pyrimidin-5-yl)methanone hydrochloride (0.17 g, 0.52 mmol) in tetrahydrofuran:water (10:6 mL) was added triethylamine (0.22 mL, 1.58 mmol) followed by addition of acryloyl chloride (0.04 g, 0.42 mmol) at 0° C. and stirred for 15 minutes. The reaction mixture was quenched with sodium bicarbonate and extracted with ethyl acetate (2×100 mL). The combined organic layers were washed with brine, dried over anhydrous sodium sulfate, filtered and concentrated in vacuo. The crude material was purified using flash chromatography (3% methanol/dichloromethane) to provide (R)-1-(3-((5-(cyclopropanecarbonyl)-7H-pyrrolo[2,3-d]pyrimidin-4-yl)amino)piperidin-1-yl)prop-2-en-1-one as a white solid (0.03 g, 18% yield): $^1$H NMR (400 MHz, DMSO-$d_6$ at 90° C.): δ 12.2 (s, 1H), 9.07-9.09 (m, 1H), 8.34 (s, 1H), 8.17 (s, 1H), 6.59 (br s, 1H), 5.93-5.97 (m, 1H), 5.50-5.53 (m, 1H), 4.15 (b, 1H), 3.91-3.95 (m, 1H), 3.60-3.64 (m, 1H), 3.37-3.47 (m, 2H), 2.75-2.76 (m, 1H), 1.98-2.01 (m, 1H), 1.78-1.79 (m, 1H), 1.66-1.68 (m, 1H), 1.51-1.57 (m, 1H), 1.01-1.02 (m, 2H), 0.92-0.95 (m, 2H); MS (ES) m/z 340.0 (M+H).

EXAMPLE 6

Preparation of (R)-1-(3-((5-(cyclopentanecarbonyl)-7H-pyrrolo[2,3-d]pyrimidin-4-yl)amino)piperidin-1-yl)prop-2-en-1-one

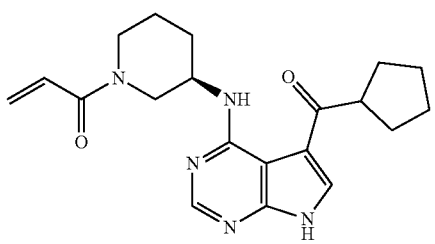 [SMILES: C=CC(=O)N1CCC[C@@H](Nc2ncnc3[nH]cc(C(=O)C4CCCC4)c23)C1]

The title compound was prepared by the method described in Scheme 11.

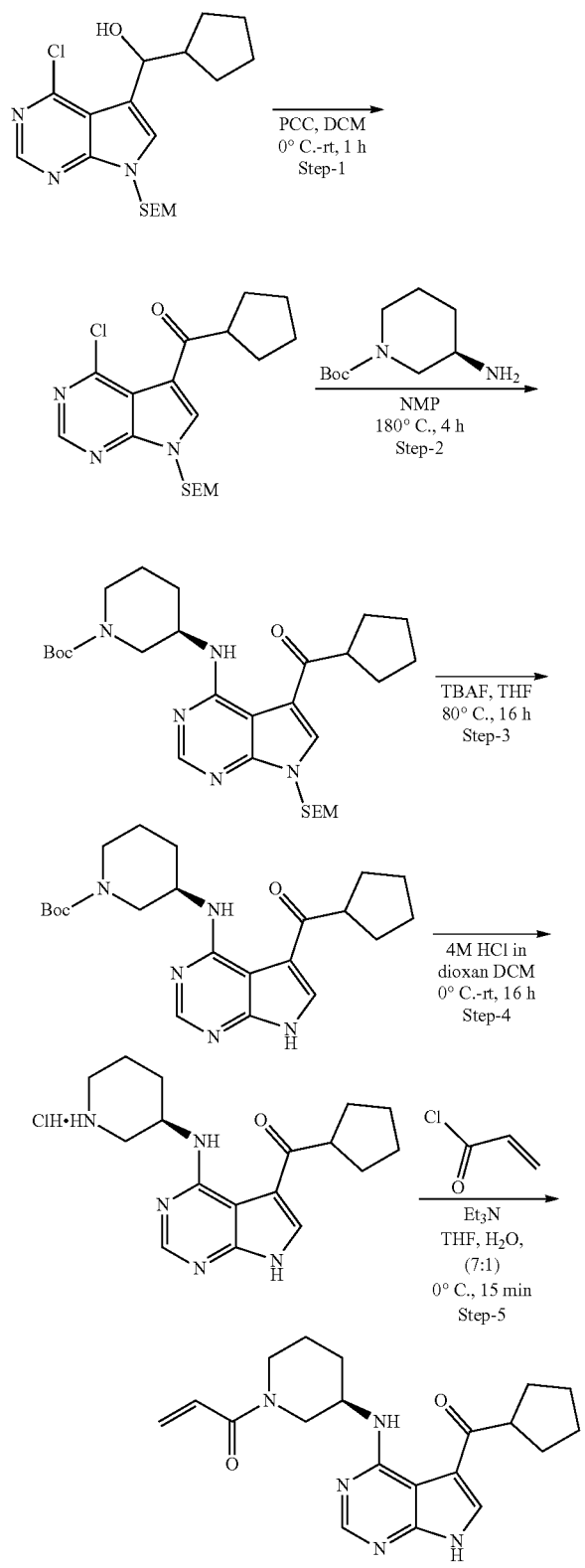

Scheme 11. Preparation of (R)-1-(3-((5-(cyclopentanecarbonyl)-7H-pyrrolo[2,3-d]pyrimidin-4-yl)amino)piperidin-1-yl)prop-2-en-1-one Step 1: Preparation of (4-Chloro-7-((2-(trimethylsilyl)ethoxy)methyl)-7H-pyrrolo[2,3-d]pyrimidin-5-yl)(cyclopentyl)methanone

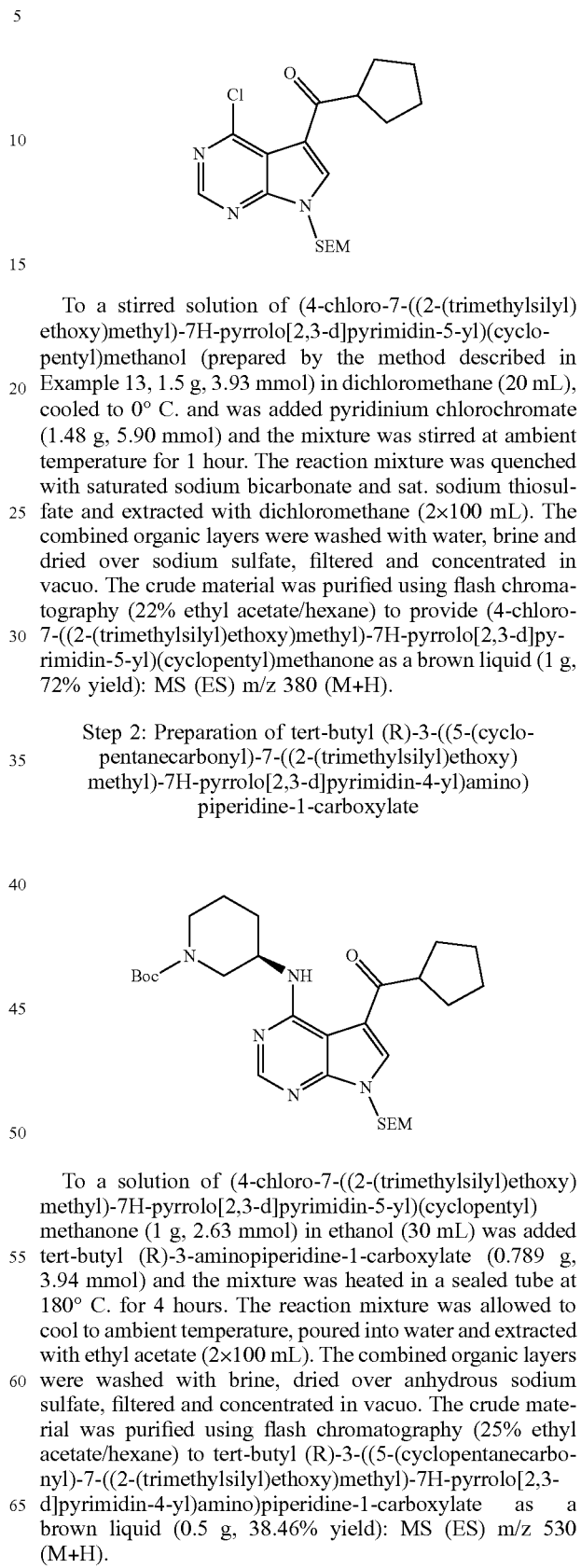

To a stirred solution of (4-chloro-7-((2-(trimethylsilyl)ethoxy)methyl)-7H-pyrrolo[2,3-d]pyrimidin-5-yl)(cyclopentyl)methanol (prepared by the method described in Example 13, 1.5 g, 3.93 mmol) in dichloromethane (20 mL), cooled to 0° C. and was added pyridinium chlorochromate (1.48 g, 5.90 mmol) and the mixture was stirred at ambient temperature for 1 hour. The reaction mixture was quenched with saturated sodium bicarbonate and sat. sodium thiosulfate and extracted with dichloromethane (2×100 mL). The combined organic layers were washed with water, brine and dried over sodium sulfate, filtered and concentrated in vacuo. The crude material was purified using flash chromatography (22% ethyl acetate/hexane) to provide (4-chloro-7-((2-(trimethylsilyl)ethoxy)methyl)-7H-pyrrolo[2,3-d]pyrimidin-5-yl)(cyclopentyl)methanone as a brown liquid (1 g, 72% yield): MS (ES) m/z 380 (M+H).

Step 2: Preparation of tert-butyl (R)-3-((5-(cyclopentanecarbonyl)-7-((2-(trimethylsilyl)ethoxy)methyl)-7H-pyrrolo[2,3-d]pyrimidin-4-yl)amino)piperidine-1-carboxylate To a solution of (4-chloro-7-((2-(trimethylsilyl)ethoxy)methyl)-7H-pyrrolo[2,3-d]pyrimidin-5-yl)(cyclopentyl)methanone (1 g, 2.63 mmol) in ethanol (30 mL) was added tert-butyl (R)-3-aminopiperidine-1-carboxylate (0.789 g, 3.94 mmol) and the mixture was heated in a sealed tube at 180° C. for 4 hours. The reaction mixture was allowed to cool to ambient temperature, poured into water and extracted with ethyl acetate (2×100 mL). The combined organic layers were washed with brine, dried over anhydrous sodium sulfate, filtered and concentrated in vacuo. The crude material was purified using flash chromatography (25% ethyl acetate/hexane) to tert-butyl (R)-3-((5-(cyclopentanecarbonyl)-7-((2-(trimethylsilyl)ethoxy)methyl)-7H-pyrrolo[2,3-d]pyrimidin-4-yl)amino)piperidine-1-carboxylate as a brown liquid (0.5 g, 38.46% yield): MS (ES) m/z 530 (M+H).

Step 3: Preparation of tert-butyl (R)-3-((5-(cyclo-pentanecarbonyl)-7H-pyrrolo[2,3-d]pyrimidin-4-yl)amino)piperidine-1-carboxylate

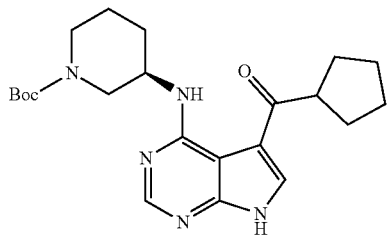 [SMILES: CC(C)(C)OC(=O)N1CCC[C@@H](Nc2ncnc3[nH]cc(C(=O)C4CCCC4)c23)C1]

To a stirred solution of tert-butyl (R)-3-((5-(cyclopentanecarbonyl)-7-((2-(trimethylsilyl)ethoxy)methyl)-7H-pyrrolo[2,3-d]pyrimidin-4-yl)amino)piperidine-1-carboxylate (0.5 g, 0.94 mmol) in tetrahydrofuran (6 mL) was added tetrabutylammonium fluoride (8 mL, 1 M in tetrahydrofuran) and the solution was heated to 80° C. for 16 hours. The reaction mixture was allowed to cool to ambient temperature, poured into ice water and extracted with ethyl acetate. The organic layer was washed with water, brine, dried over anhydrous sodium sulfate, filtered and concentrated in vacuo. The crude material was purified using flash chromatography (4% methanol/dichloromethane) to provide tert-butyl (R)-3-((5-(cyclopentanecarbonyl)-7H-pyrrolo[2,3-d]pyrimidin-4-yl)amino)piperidine-1-carboxylate as a yellow liquid (0.25 g, 63% yield): MS (ES) m/z 414 (M+H).

Step 4: Preparation of (R)-cyclopentyl(4-(piperidin-3-ylamino)-7H-pyrrolo[2,3-d]pyrimidin-5-yl)methanone·hydrochloride

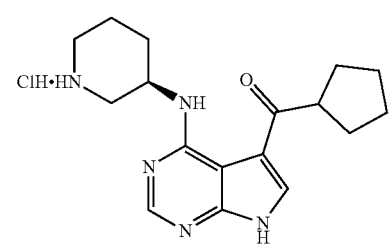

To a stirred solution of tert-butyl (R)-3-((5-(cyclopentanecarbonyl)-7H-pyrrolo[2,3-d]pyrimidin-4-yl)amino)piperidine-1-carboxylate (0.25 g, 0.60 mmol) in dichloromethane (2 mL) was added hydrogen chloride (2.5 mL, 6.05 mmol, 4 M in dioxane) at 0° C. and the mixture was stirred at ambient temperature for 16 hours. The reaction mixture was concentrated in vacuo and the residue was washed with diethyl ether to provide (R)-cyclopentyl(4-(piperidin-3-ylamino)-7H-pyrrolo[2,3-d]pyrimidin-5-yl)methanone hydrochloride as an off-white solid (0.15 g, crude): MS (ES) m/z 314 (M+H).

Step 5: Preparation of (R)-1-(3-((5-(cyclopentanecarbonyl)-7H-pyrrolo[2,3-d]pyrimidin-4-yl)amino)piperidin-1-yl)prop-2-en-1-one

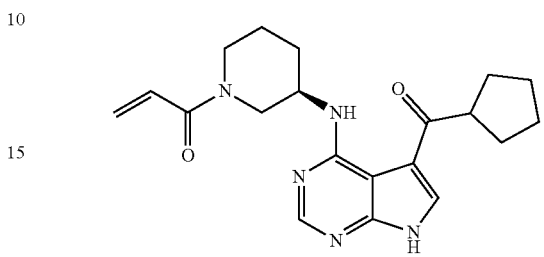

To a solution of (R)-cyclopentyl(4-(piperidin-3-ylamino)-7H-pyrrolo[2,3-d]pyrimidin-5-yl)methanone hydrochloride (0.15 g, 0.47 mmol) in tetrahydrofuran:water (10:6 mL) and cooled to 0° C. was added triethylamine (0.1 mL, 0.96 mmol), a solution of acryloyl chloride (0.07 mL, 0.86 mmol) in tetrahydrofuran (0.5 mL) at 0° C. and stirred for 15 minutes. The reaction mixture was quenched with aqueous sodium bicarbonate and extracted with ethyl acetate. The organic layer was washed with brine, dried over anhydrous sodium sulfate, filtered and concentrated in vacuo. The crude material was purified using flash chromatography (5% methanol/dichloromethane) to provide (R)-1-(3-((5-(cyclopentane-carbonyl)-7H-pyrrolo[2,3-2015]pyrimidin-4-yl)amino)piperidin-1-yl)prop-2-en-1-one as a white solid (0.04 g, 23% yield): $^1$H NMR (400 MHz, DMSO-$d_6$ at 90° C.) δ 12.2 (s, 1H), 9.07 (d, J=7.2 Hz, 1H), 8.16 (d, J=3.2 Hz, 2H), 6.62 (t, J=15.2 Hz, 1H), 5.93-5.98 (m, 1H), 5.51 (d, J=10 Hz, 1H), 4.16 (s, 1H), 3.94 (d, J=13.2 Hz, 1H), 3.61-3.72 (m, 2H), 3.03-3.49 (m, 2H), 2.00-2.05 (m, 1H), 1.81-1.85 (m, 3H), 1.53-1.79 (m, 8H); MS (ES) m/z 368.4 (M+H).

EXAMPLE 7

Preparation of 1-(3-((5-(cyclopropanecarbonyl)-7H-pyrrolo[2,3-d]pyrimidin-4-yl)amino)azetidin-1-yl)prop-2-en-1-one

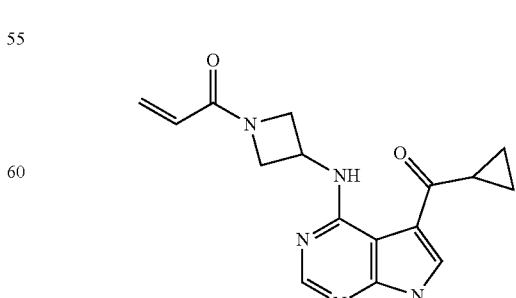

The title compound was prepared by the method described in Scheme 12.

Scheme 12.
Preparation of 1-(3-((5-(cyclopropanecarbonyl)-7H-pyrrolo[2,3-d]pyrimidin-4-yl)amino)azetidin-1-yl)prop-2-en-1-one

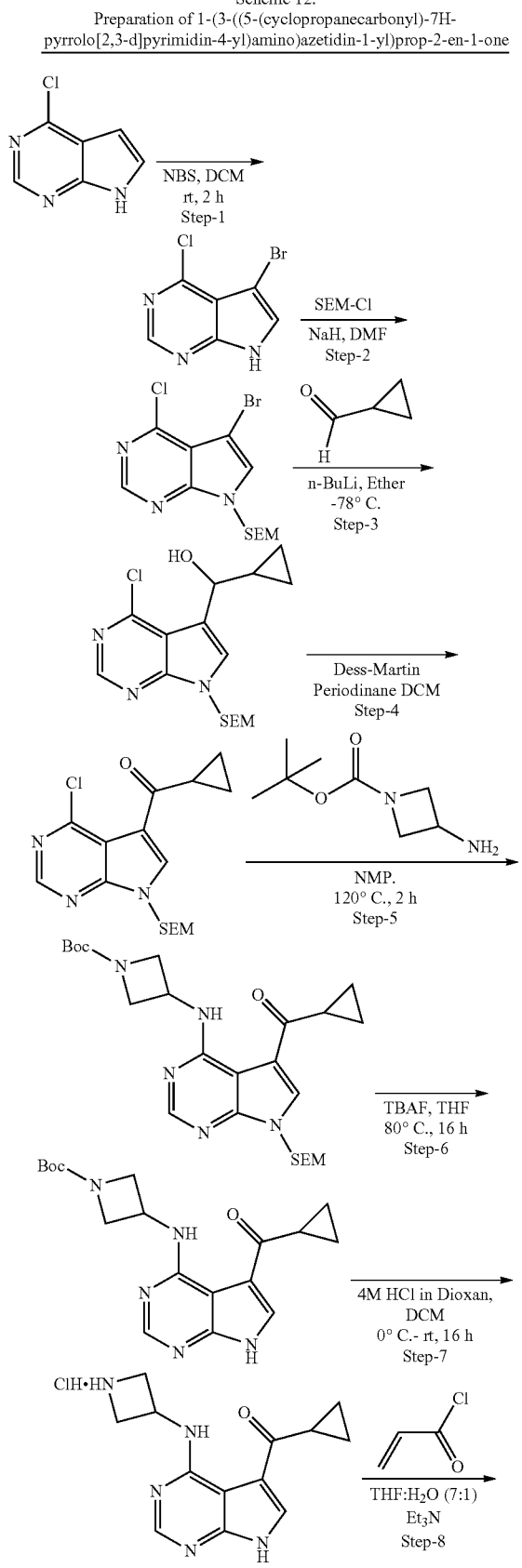

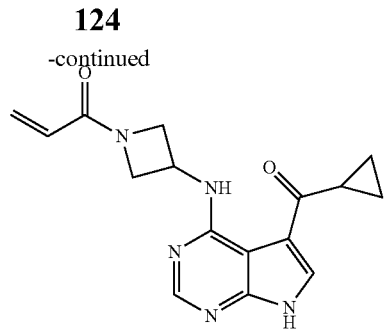

Step 1: Preparation of 5-bromo-4-chloro-7H-pyrrolo[2,3-d]pyrimidine

To a stirred solution of 4-chloro-7H-pyrrolo[2,3-d]pyrimidine (5 g, 32.67 mmol) in dichloromethane (50 mL) was added N-bromosuccinimide (6.9 g 39.21 mmol) and the mixture was stirred at ambient temperature for 2 hours. The reaction was concentrated in vacuo. The resulting solid was filtered, washed with water and dried to provide 5-bromo-4-chloro-7H-pyrrolo[2,3-d]pyrimidine as a brown solid (7.7 g, crude): $^1$H NMR (400 MHz, DMSO-$d_6$) δ 12.93 (s, 1H), 8.60 (s, 1H), 7.92 (s, 1H); MS (ES) m/z 231.9 (M+2H).

Step 2: Preparation of 5-bromo-4-chloro-7-((2-(trimethylsilyl)ethoxy)methyl)-7H-pyrrolo[2,3-d]pyrimidine

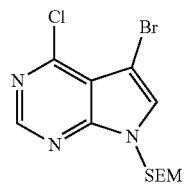 [SMILES: C[Si](C)(C)CCOCn1cc(Br)c2c(Cl)ncnc21]

To a suspension of sodium hydride (5 g, 21.55 mmol) in dimethylformamide (20 mL) was added 5-bromo-4-chloro-7H-pyrrolo[2,3-d]pyrimidine (5 g 21.55 mmol) at 0° C. and stirred at ambient temperature for 30 minutes followed by addition of 2-(trimethylsilyl)ethoxymethyl chloride (4.58 mL, 25.86 mmol) after cooling to 0° C. The reaction mixture was warmed to ambient temperature and stirred for 1 hour. The reaction mixture was quenched with ice water and extracted with ethyl acetate. The organic layer was washed with water, brine, dried over anhydrous sodium sulfate, filtered and concentrated in vacuo. The crude material was purified using flash chromatography (15% ethyl acetate/hexane) to provide 5-bromo-4-chloro-7-((2-(trimethylsilyl)ethoxy)methyl)-7H-pyrrolo[2,3-d]pyrimidine as an off-white solid (4.5 g, 58% yield): $^1$H NMR (400 MHz, DMSO-$d_6$) δ 8.71 (s, 1H), 8.14 (s, 1H), 5.60 (s, 2H), 3.51 (t, J=7.6 Hz, 2H), 0.81 (t, J=8 Hz, 2H), 0.08 (s, 9H); MS (ES) m/z 362.0 (M+H).

Step 3: Preparation of (4-chloro-7-((2-(trimethylsilyl)ethoxy)methyl)-7H-pyrrolo[2,3-d]pyrimidin-5-yl)(cyclopropyl)methanol

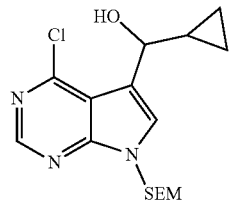 [SMILES: C[Si](C)(C)CCOCn1cc(C(O)C2CC2)c2c(Cl)ncnc21]

To a stirred solution of 5-bromo-4-chloro-7-((2-(trimethylsilyl)ethoxy)methyl)-7H-pyrrolo[2,3-d]pyrimidine (2 g, 5.52 mmol) in diethyl ether (30 mL) was added n-butyllithium (5.17 mL, 8.28 mmol, 1.6 M in hexane) at −78° C. and stirred for 10 minutes. Then a solution of cyclopropanecarbaldehyde (0.64 mL, 8.28 mmol) in diethyl ether (3 mL) was added at −78° C. and the resulting mixture stirred for 0.5 hours. The reaction mixture was quenched with saturated aqueous ammonium chloride and extracted with diethyl ether (2×100 mL). The combined organic layers were washed with brine, dried over anhydrous sodium sulfate, filtered and concentrated in vacuo. The crude material was purified using flash chromatography (32% ethyl acetate/hexane) to provide (4-chloro-7-((2-(trimethylsilyl)ethoxy)methyl)-7H-pyrrolo[2,3-d]pyrimidin-5-yl)(cyclopropyl)methanol as a brown liquid (1.2 g, 61% yield): $^1$H NMR (400 MHz, DMSO-$d_6$) δ 8.61 (s, 1H), 7.76 (s, 1H), 5.61 (s, 2H), 5.11 (s, 1H), 4.76 (s, 1H), 3.50 (t, J=7.6 Hz, 2H), 1.31-1.32 (m, 1H), 0.82 (t, J=8 Hz, 2H), 0.34-0.44 (m, 4H), 0.03 (s, 9H); MS (ES) m/z 354.1 (M+H).

Step 4: Preparation of (4-chloro-7-((2-(trimethylsilyl)ethoxy)methyl)-7H-pyrrolo[2,3-d]pyrimidin-5-yl)(cyclopropyl)methanone

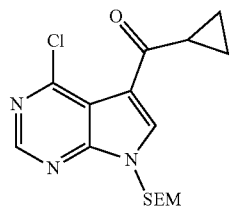 [SMILES: C[Si](C)(C)CCOCn1cc(C(=O)C2CC2)c2c(Cl)ncnc21]

To a stirred solution of (4-chloro-7-((2-(trimethylsilyl)ethoxy)methyl)-7H-pyrrolo[2,3-d]pyrimidin-5-yl)(cyclopropyl)methanol (1.2 g, 3.39 mmol) in dichloromethane (20 mL) was added Dess-Martin periodinane (2.1 g, 5.09 mmol) at 0° C. and the mixture was stirred at ambient temperature for 1 hour. The reaction mixture was quenched with saturated aqueous sodium bicarbonate, sodium thiosulfate and extracted with dichloromethane (2×100 mL). The combined organic layers were washed with brine, dried over anhydrous sodium sulfate, filtered and concentrated in vacuo. The crude material was purified using flash chromatography (20% ethyl acetate/hexane) to provide (4-chloro-7-((2-(trimethylsilyl)ethoxy)methyl)-7H-pyrrolo[2,3-d]pyrimidin-5-yl)(cyclopropyl)methanone as a brown liquid (0.5 g, 45% yield): $^1$H NMR (400 MHz, DMSO-$d_6$) δ 8.66 (s, 1H), 8.02 (s, 1H), 5.62 (s, 2H), 3.52 (t, J=8 Hz, 2H), 1.50-1.54 (m, 1H), 0.80 (t, J=8 Hz, 2H), 0.48-0.59 (m, 4H), 0.08 (s, 9H); MS (ES) m/z 352.1 (M+H).

Step 5: Preparation of tert-butyl 3-((5-(cyclopropanecarbonyl)-7-((2-(trimethylsilyl)ethoxy)methyl)-7H-pyrrolo[2,3-d]pyrimidin-4-yl)amino)azetidine-1-carboxylate

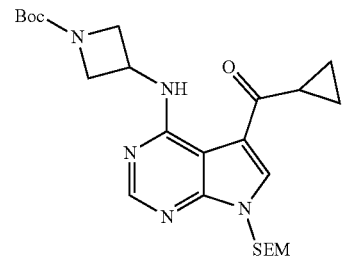 [SMILES: CC(C)(C)OC(=O)N1CC(Nc2ncnc3c2c(C(=O)C2CC2)cn3COCC[Si](C)(C)C)C1]

To a stirred solution of (4-chloro-7-((2-(trimethylsilyl)ethoxy)methyl)-7H-pyrrolo[2,3-d]pyrimidin-5-yl)(cyclopropyl)methanone (0.45 g, 1.28 mmol) in N-methyl-2-pyrrolidone (30 mL) was added tert-butyl 3-aminoazetidine-1-carboxylate (0.33 g, 1.92 mmol) and the mixture was heated in a sealed tube at 120° C. for 2 hours. The reaction mixture was cooled to ambient temperature and then poured into water and extracted with ethyl acetate (2×100 mL). The combined organic layer was washed with brine, dried over anhydrous sodium sulfate, filtered and concentrated in vacuo. The crude material was purified using flash chromatography (50% ethyl acetate/hexane) to provide tert-butyl 3-((5-(cyclopropanecarbonyl)-7-((2-(trimethylsilyl)ethoxy)methyl)-7H-pyrrolo[2,3-d]pyrimidin-4-yl)amino)azetidine-1-carboxylate as a brown liquid (0.4 g, 65% yield): $^1$H NMR (400 MHz, DMSO-$d_6$) δ 9.46 (s, 1H), 8.74 (s, 1H), 8.25 (s, 1H), 5.56 (s, 2H), 4.72-4.76 (m, 1H), 4.22-4.24 (m, 2H), 3.70-3.71 (m, 2H), 3.56 (t, J=7.2 Hz, 2H), 2.78-2.82 (m, 1H), 1.44 (s, 9H), 1.14-1.17 (m, 2H), 1.01-1.09 (m, 2H), 0.83 (t, J=7.6 Hz, 2H), 0.08 (s, 9H); MS (ES) m/z 488.2 (M+H).

Step 6: Preparation of tert-butyl 3-((5-(cyclopropanecarbonyl)-7H-pyrrolo[2,3-d]pyrimidin-4-yl)amino)azetidine-1-carboxylate

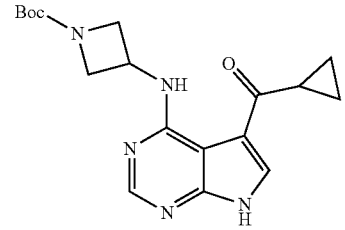 [SMILES: CC(C)(C)OC(=O)N1CC(Nc2ncnc3[nH]cc(C(=O)C4CC4)c23)C1]

To a stirred solution of tert-butyl 3-((5-(cyclopropanecarbonyl)-7-((2-(trimethylsilyl)ethoxy)methyl)-7H-pyrrolo[2,3-d]pyrimidin-4-yl)amino)azetidine-1-carboxylate (0.4 g, 0.82 mmol) in tetrahydrofuran (2 mL) was added tetrabutylammonium fluoride (8 mL, 1 M solution in tetrahydrofuran) and the solution was heated to 80° C. for 16 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (4% methanol/dichloromethane) to provide tert-butyl 3-((5-(cyclopropanecarbonyl)-7H-pyrrolo[2,3-d]pyrimidin-4-yl)amino)azetidine-1-carboxylate as an off-white solid (0.2 g, 69% yield): $^1$H NMR (400 MHz, DMSO-$d_6$) δ 12.60 (s, 1H), 9.47 (s, 1H), 8.52 (s, 1H), 8.17 (s, 1H), 4.70 (br s, 1H), 4.21-4.22 (m, 2H), 3.68-3.70 (m, 2H), 1.56-157 (m, 1H), 1.37 (s, 9H), 1.06-1.08 (m, 2H), 0.90-0.96 (m, 2H); MS (ES) m/z 358.1 (M+H).

Step 7: Preparation of (4-(azetidin-3-ylamino)-7H-pyrrolo[2,3-d]pyrimidin-5-yl)(cyclopropyl)methanone Hydrochloride

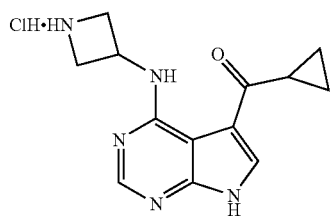

To a stirred solution of tert-butyl 3-((5-(cyclopropanecarbonyl)-7H-pyrrolo[2,3-d]pyrimidin-4-yl)amino)azetidine-1-carboxylate (0.2 g, 0.56 mmol) in dichloromethane (2 mL) was added hydrogen chloride (1.4 mL, 56.02 mmol, 4 M in dioxane) at 0° C. and the mixture was stirred at ambient temperature for 16 hours. The reaction mixture was concentrated in vacuo and the residue was washed with ether to provide (4-(azetidin-3-ylamino)-7H-pyrrolo[2,3-d]pyrimidin-5-yl)(cyclopropyl)methanone hydrochloride as an off-white solid (0.15 g, 94% yield): MS (ES) m/z 258.1 (M+H).

Step 8: Preparation of 1-(3-((5-(cyclopropanecarbonyl)-7H-pyrrolo[2,3-d]pyrimidin-4-yl)amino)azetidin-1-yl)prop-2-en-1-one

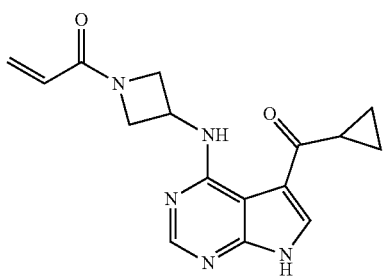 [SMILES: C=CC(=O)N1CC(Nc2ncnc3[nH]cc(C(=O)C4CC4)c23)C1]

To a stirred solution of (4-(azetidin-3-ylamino)-7H-pyrrolo[2,3-d]pyrimidin-5-yl)(cyclopropyl)methanone hydrochloride (0.15 g, 0.51 mmol) in tetrahydrofuran:water (10:6 mL) was added triethylamine (0.22 mL, 1.53 mmol) followed by addition of acryloyl chloride (0.04 g, 0.40 mmol) at 0° C. and stirred for 15 minutes. The reaction mixture was quenched with saturated aqueous sodium bicarbonate and extracted with ethyl acetate (2×100 mL). The combined organic layers were washed with brine, dried over anhydrous sodium sulfate, filtered and concentrated in vacuo. The crude material was purified using flash chromatography (3% methanol/dichloromethane) and further purified by using prep HPLC to provide 1-(3-((5-(cyclo-propanecarbonyl)-7H-pyrrolo[2,3-d]pyrimidin-4-yl)amino)azetidin-1-yl)prop-2-en-1-one as a white solid (0.04 g, 27%): $^1$H NMR (400 MHz, DMSO-$d_6$) δ 12.60 (s, 1H), 9.51 (d, J=5.6 Hz, 1H), 8.52 (s, 1H), 8.18 (s, 1H), 6.33-6.36 (m, 1H), 6.29-6.31 (m, 1H), 5.64-5.66 (m, 1H), 4.76-4.83 (m, 1H), 4.59 (t, J=8.4 Hz, 1H) 4.31 (t, J=10 Hz, 1H), 4.04-4.07 (m, 1H), 3.74-3.78 (m, 1H), 2.81-2.86 (m, 1H), 1.01-1.06 (m, 2H), 0.94-0.97 (m, 2H); MS (ES) m/z 312.1 (M+H).

Prep HPLC method:

Column: ZORBAX XDB C-18 (150 mm×4.6 mm×5 m)

Mobile phase (A): 0.1% Ammonia in water

Mobile phase (B): ACN

Flow rate: 1.0 mL/min

Retention time: 3.129 minutes.

EXAMPLE 8

Preparation of (R)-1-(3-((3-(3-methoxypropanoyl)-1H-pyrrolo[2,3-b]pyridin-4-yl)amino)piperidin-1-yl)prop-2-en-1-one

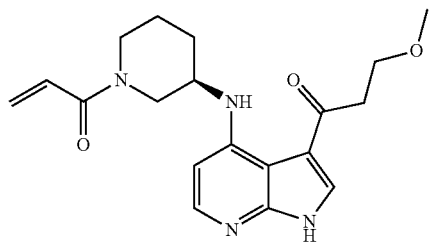 [SMILES: C=CC(=O)N1CCC[C@@H](Nc2ccnc3[nH]cc(C(=O)CCOC)c23)C1]

The title compound was prepared by the method described in Scheme 13.

Scheme 13.
Preparation of (R)-1-(3-((3-(3-methoxypropanoyl)-1H-pyrrolo[2,3-d]pyridin-4-yl)amino)piperidin-1-yl)prop-2-en-1-one

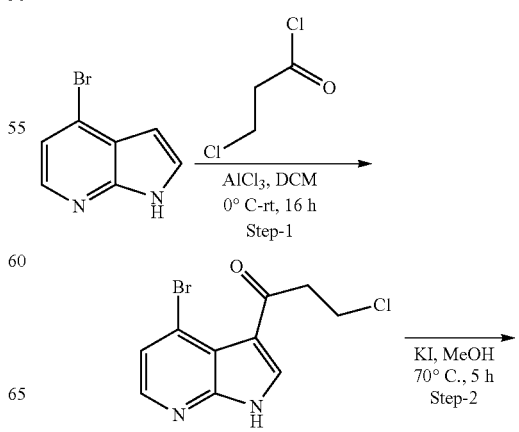

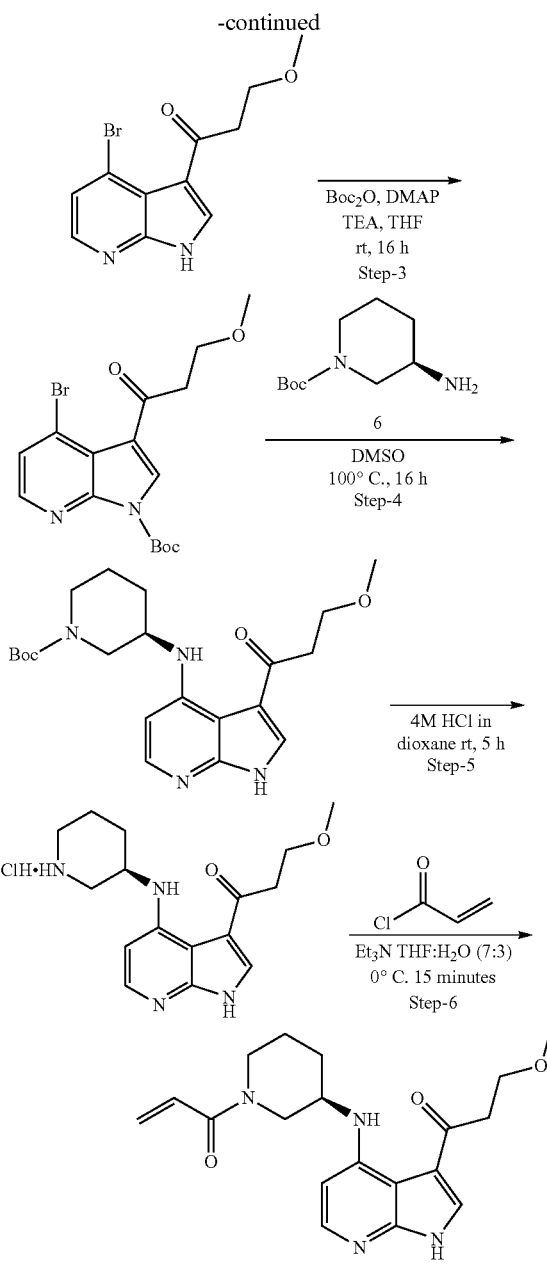

Step 1: Preparation of 1-(4-bromo-1H-pyrrolo[2,3-b]pyridin-3-yl)-3-chloropropan-1-one

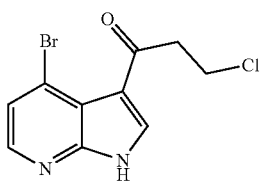 [SMILES: O=C(CCCl)c1c[nH]c2nccc(Br)c12]

To a solution of 4-bromo-1H-pyrrolo[2,3-b]pyridine (5.0 g, 25.37 mmol) in dichloromethane (100 mL) was added aluminum chloride (10.12 g, 50.74 mmol) portion-wise at 0° C. for 50 minutes at same temperature. Then 3-chloropropanoyl chloride (4.8 mL, 76.11 mmol) was added by drop-wise at 0° C., warmed to ambient temperature and the mixture was stirred for 16 hours. The reaction mixture was quenched with ice water and extracted with dichloromethane. The organic layer was washed with brine and dried over anhydrous sodium sulfate. The solution was filtered and concentrated in vacuo. The obtained solid was dissolved in methanol and was added triethylamine (30 mL) and the solution was stirred at 65° C. for 16 hours. The reaction was concentrated in vacuo the white solid was washed with saturated aqueous sodium bicarbonate, water and dried to provide 1-(4-bromo-1H-pyrrolo[2,3-b]pyridin-3-yl)-3-chloropropan-1-one as a brown solid (4.5 g, 61.8%): MS (ES) m/z 286.9 (M+H).

Step 2: Preparation of 1-(4-bromo-1H-pyrrolo[2,3-b]pyridin-3-yl)-3-methoxypropan-1-one

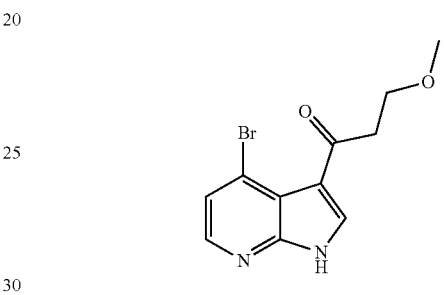

A suspension of 1-(4-bromo-1H-pyrrolo[2,3-b]pyridin-3-yl)-3-chloropropan-1-one (3.0 g, 10.43 mmol) in methanol (50 mL) was added potassium iodide (2.6 g, 15.64 mmol) and stirred at 70° C. for 5 hours. The reaction mixture was concentrated in vacuo and the residue was dissolved in 10% methanol in dichloromethane. The organic layer was washed with brine, dried over anhydrous sodium sulfate, filtered and concentrated in vacuo. The crude product was washed with diethyl ether and n-pentane to provide 1-(4-bromo-1H-pyrrolo[2,3-b]pyridin-3-yl)-3-methoxypropan-1-one as a yellow solid (1.4 g, 47% yield): MS (ES) m/z 285.0 (M+H).

Step 3: Preparation of tert-butyl 4-bromo-3-(3-methoxypropanoyl)-1H-pyrrolo[2,3-b]pyridine-1-carboxylate

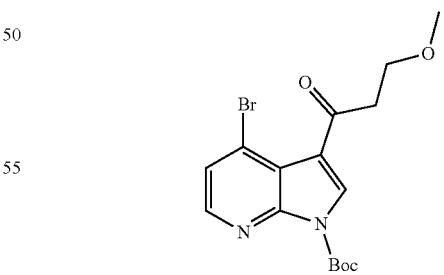

To a suspension of 1-(4-bromo-1H-pyrrolo[2,3-b]pyridin-3-yl)-3-methoxypropan-1-one (1.4 g, 4.94 mmol) in tetrahydrofuran (30 mL) was added triethylamine (2.0 mL, 14.83 mmol), 4-dimethylaminopyridine (0.06 g, 0.49 mmol) and di-tert-butyldicarbonate (1.7 mL, 7.41 mmol) at 0° C. and the mixture was stirred at ambient temperature for 16 hours. The reaction mixture was quenched with ice and extracted with ethyl acetate. The organic layer was washed with water, brine, dried over anhydrous sodium sulfate, filtered and concentrated in vacuo. The crude material was purified using flash chromatography (20% ethyl acetate/hexane) to provide tert-butyl 4-bromo-3-(3-methoxypropanoyl)-1H-pyrrolo[2,3-b]pyridine-1-carboxylate as a brown viscous oil (0.8 g, 42% yield): MS (ES) m/z 385.0 (M+H).

Step 4: Preparation of tert-butyl (R)-4-((1-(tert-butoxycarbonyl)piperidin-3-yl)amino)-3-(3-methoxypropanoyl)-1H-pyrrolo[2,3-b]pyridine-1-carboxylate

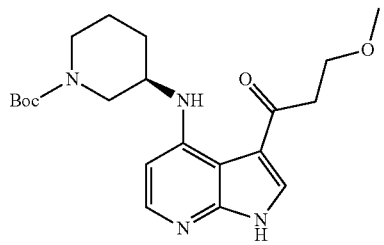 [SMILES: COCCC(=O)c1c[nH]c2nccc(N[C@@H]3CCCN(C(=O)OC(C)(C)C)C3)c12]

To a stirred solution of tert-butyl 4-bromo-3-(3-methoxypropanoyl)-1H-pyrrolo[2,3-b]pyridine-1-carboxylate (0.3 g, 0.78 mmol) in N,N-dimethylsulfoxide (3 mL) was added tert-butyl (R)-3-aminopiperidine-1-carboxylate (0.62 g, 3.14 mmol) and the mixture was heated in a sealed tube at 100° C. for 16 hours. The reaction mixture was poured into water and extracted with ethyl acetate. The combined organic layer was washed with brine, dried over anhydrous sodium sulfate, filtered and concentrated in vacuo. The crude material was purified using flash chromatography (5% methanol/dichloromethane) to provide tert-butyl (R)-4-((1-(tert-butoxycarbonyl)piperidin-3-yl)amino)-3-(3-methoxy-propanoyl)-1H-pyrrolo[2,3-b]pyridine-1-carboxylate as a pale brown sticky mass (0.2 g, 50% yield): MS (ES) m/z 403.2 (M+H).

Step 5: Preparation of (R)-3-methoxy-1-(4-(piperidin-3-ylamino)-1H-pyrrolo[2,3-b]pyridin-3-yl)propan-1-one Hydrochloride

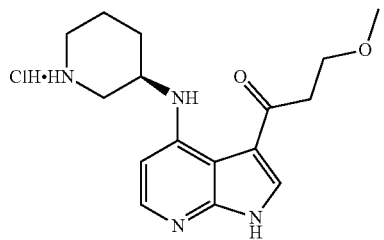

To a stirred solution of tert-butyl (R)-4-((1-(tert-butoxycarbonyl)piperidin-3-yl)amino)-3-(3-methoxypropanoyl)-1H-pyrrolo[2,3-b]pyridine-1-carboxylate (0.4 g, 0.795 mmol) in dichloromethane (5 mL) was added hydrogen chloride (10 mL, 4 M in dioxane) at 0° C. and the mixture was warmed to ambient temperature and stirred for 5 hours. The reaction mixture was concentrated in vacuo and the residue was washed with diethyl ether to provide (R)-3-methoxy-1-(4-(piperidin-3-ylamino)-1H-pyrrolo[2,3-b]pyridin-3-yl)propan-1-one hydrochloride (0.35 g, crude): MS (ES) m/z 303.1 (M+H).

Step 6: Preparation of (R)-1-(3-((3-(3-methoxypropanoyl)-1H-pyrrolo[2,3-b]pyridin-4-yl)amino)piperidin-1-yl)prop-2-en-1-one

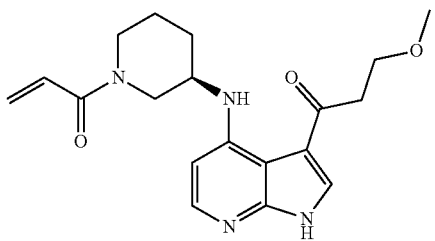 [SMILES: C=CC(=O)N1CCC[C@@H](Nc2ccnc3[nH]cc(C(=O)CCOC)c23)C1]

To a solution of (R)-3-methoxy-1-(4-(piperidin-3-ylamino)-1H-pyrrolo[2,3-b]pyridin-3-yl)propan-1-one hydrochloride (0.12 g, 0.32 mmol) in tetrahydrofuran:water (7:3 mL) was added triethylamine (0.13 mL, 0.96 mmol) and followed by a solution of acryloyl chloride (0.02 mL, 0.24 mmol) in tetrahydrofuran (0.4 mL) at 0° C. and stirred for 15 minutes. Then reaction mixture was quenched with aqueous sodium bicarbonate and extracted with ethyl acetate. The organic layer was washed with brine, dried over anhydrous sodium sulfate, filtered and concentrated in vacuo. The crude material was purified using flash chromatography (5% methanol/dichloromethane) and further purified by using prep HPLC to provide (R)-1-(3-((3-(3-methoxypropanoyl)-1H-pyrrolo[2,3-b]pyridin-4-yl)amino)piperidin-1-yl)prop-2-en-1-one as a white solid (0.06 g, 5.5% yield): $^1$H NMR (400 MHz, DMSO-d$_6$, at 80° C.) δ 12.0 (br s, 1H), 8.73 (d, J=7.6 Hz, 1H), 8.18 (s, 1H), 7.87 (d, J=5.6 Hz, 1H), 6.55-6.75 (m, 1H), 6.28 (d, J=5.6 Hz, 1H), 5.99 (d, J=16.4 Hz, 1H), 5.48-5.62 (m, 1H), 3.95-4.15 (m, 1H), 3.65-3.80 (m, 4H), 3.50-3.62 (m, 2H), 3.36-3.45 (m, 2H), 3.34 (s, 3H), 2.00-2.10 (m, 1H), 1.79-1.90 (m, 1H), 1.62-1.73 (m, 1H), 1.50-1.69 (m, 1H); MS (ES) m/z 357.4 (M+H).

Prep HPLC method:
Column: Inertsil ODS 3V (250 mm×4.6 mm×5 mic)
Mobile phase (A): 0.1% Ammonia in water
Mobile phase (B): Methanol
Flow rate: 1.0 mL/min (45:55)
Retention time: 3.186 minutes.

EXAMPLE 9

Preparation of (R)-1-(3-((3-(cyclopropanecarbonyl)-1H-pyrrolo[2,3-b]pyridin-4-yl)amino)piperidin-1-yl)prop-2-en-1-one

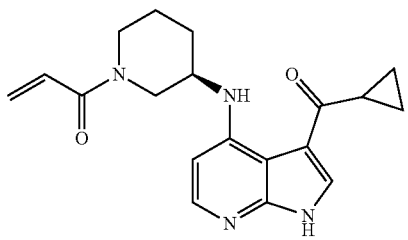 [SMILES: C=CC(=O)N1CCC[C@@H](Nc2ccnc3[nH]cc(C(=O)C4CC4)c23)C1]

133

Step 1: Preparation of 4-chloro-3-cyclopropanecarbonyl-1H-pyrrolo[2,3-b]pyridine

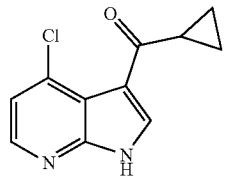 [SMILES: O=C(c1c[nH]c2nccc(Cl)c12)C1CC1]

To a solution of 4-chloro-1H-pyrrolo[2,3-b]pyridine (400 mg, 2.62 mmol) in 1.5 mL of dichloromethane was added aluminium chloride (2.43 g, 18.3 mmol). After one hour of stirring at ambient temperature, cyclopropanecarbonyl chloride (236 μL, 2.62 mmol) was added. The reaction was stirred overnight at ambient temperature. The reaction was quenched with a saturated solution of Rochelle salts. The solution was stirred rapidly for one hour. The resulting yellow solid was collected by vacuum filtration to provide 4-chloro-3-cyclopropanecarbonyl-1H-pyrrolo[2,3-b]pyridine (580 mg, 2.62 mmol): MS (ES) m/z 221 (M+H).

Step 2: Preparation of tert-butyl (3R)-3-({3-cyclopropanecarbonyl-1H-pyrrolo[2,3-b]pyridin-4-yl}amino)piperidine-1-carboxylate

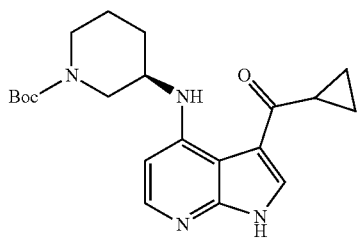

To a solution of 4-chloro-3-cyclopropanecarbonyl-1H-pyrrolo[2,3-b]pyridine from step 1 (95 mg, 0.430 mmol) in N-methylpyrrolidine (2 mL) was added tert-butyl (3R)-3-aminopiperidine-1-carboxylate (258 mg, 1.29 mmol) and triethylamine (59.9 μL, 0.431 mmol). The solution was treated with microwave radiation at 130° C. for a total of 13 hours. After cooling the solution was partitioned between ethyl acetate and water. The organic layer was concentrated and the residue purified using normal phase chromatography (ethyl acetate/heptane). The desired material was collected and concentrated to provide tert-butyl (3R)-3-({3-cyclopropanecarbonyl-1H-pyrrolo[2,3-b]pyridin-4-yl}amino)piperidine-1-carboxylate (20.0 mg, 0.052 mmol) as a light yellow oil: MS (ES) m/z 385 (M+H).

134

Step 3: Preparation of 1-[(3R)-3-({3-cyclopropanecarbonyl-1H-pyrrolo[2,3-b]pyridin-4-yl}amino)piperidin-1-yl]prop-2-en-1-one

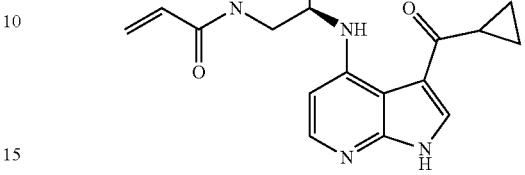

To a solution of tert-butyl (3R)-3-({3-cyclopropanecarbonyl-1H-pyrrolo[2,3-b]pyridin-4-yl}amino)piperidine-1-carboxylate from step 2 (20 mg, 0.0520 mmol) in dichloromethane (2 mL) was added trifluoroacetic acid (1 mL) and the solution was stirred for two hours and concentrated in vacuo. The residue was dissolved into tetrahydrofuran (1 mL) and triethylamine (18.0 μL, 0.130 mmol) was added. To this solution was added a solution of N-[3-(dimethylamino)propyl]propanimidamide hydrochloride (12.0 mg, 0.0624 mmol), prop-2-enoic acid (3.55 μL, 0.0520 mmol) and triethylamine (18.0 μL, 0.130 mmol) in tetrahydrofuran (0.5 mL). The mixture was stirred at ambient temperature for 4 hours. The solution was partitioned between ethyl acetate and water. The organic layer was separated and concentrated. The crude material was purified using normal phase chromatography (dichloromethane/methanol) to provide 1-[(3R)-3-({3-cyclopropanecarbonyl-1H-pyrrolo[2,3-b]pyridin-4-yl}amino)piperidin-1-yl]prop-2-en-1-one (4.5 mg, 0.013 mmol): $^1$H NMR (400 MHz, DMSO-$d_6$) δ 12.26 (br s, 1H), 8.85-9.02 (m, 1H), 8.43-8.52 (m, 1H), 7.84-7.93 (m, 1H), 6.48-6.89 (m, 1H), 5.86-6.16 (m, 1H), 5.40-5.72 (m, 1H), 4.38-4.64 (m, 1H), 4.08-4.34 (m, 1H), 3.52-3.91 (m, 2H), 3.38-3.51 (m, 1H), 2.96-3.12 (m, 1H), 1.91-2.10 (m, 1H), 1.36-1.91 (m, 3H), 0.86-1.05 (m, 4H); MS (ES) m/z 339 (M+H).

EXAMPLE 10

Preparation of 1-(4-((3-(cyclopropanecarbonyl)-1H-pyrrolo[2,3-b]pyridin-4-yl)amino)piperidin-1-yl)prop-2-en-1-one

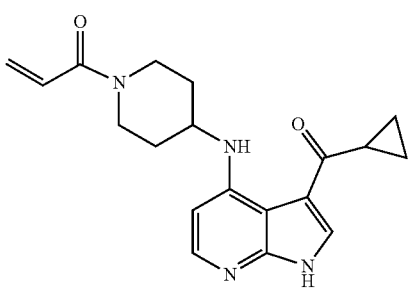 [SMILES: C=CC(=O)N1CCC(Nc2ccnc3[nH]cc(C(=O)C4CC4)c23)CC1]

Step 1: Preparation of 4-chloro-3-cyclopropanecarbonyl-1H-pyrrolo[2,3-b]pyridine

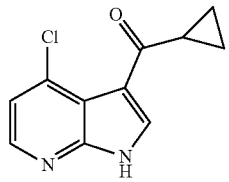 [SMILES: O=C(c1c[nH]c2nccc(Cl)c12)C1CC1]

To a solution of 4-chloro-1H-pyrrolo[2,3-b]pyridine (400 mg, 2.62 mmol) in 1.5 mL dichloromethane was added aluminium chloride (2.43 g, 18.3 mmol). After one hour of stirring at ambient temperature, cyclopropanecarbonyl chloride (236 µL, 2.62 mmol) was added. The reaction was stirred overnight at ambient temperature. The reaction was quenched with a saturated solution of Rochelle salts. The solution was stirred rapidly for one hour. The resulting yellow solid was collected by vacuum filtration to provide 4-chloro-3-cyclopropanecarbonyl-1H-pyrrolo[2,3-b]pyridine (580 mg, 2.62 mmol): MS (ES) m/z 221 (M+H).

Step 2: Preparation of tert-butyl 4-({3-cyclopropanecarbonyl-1H-pyrrolo[2,3-b]pyridin-4-yl}amino)piperidine-1-carboxylate

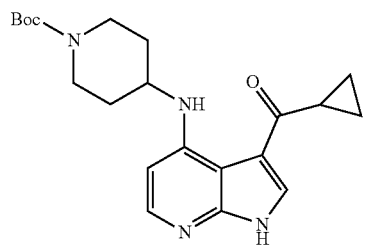 [SMILES: CC(C)(C)OC(=O)N1CCC(Nc2ccnc3[nH]cc(C(=O)C4CC4)c23)CC1]

To a solution of 4-chloro-3-cyclopropanecarbonyl-1H-pyrrolo[2,3-b]pyridine from step 1 (50 mg, 0.2265 mmol) in N-methylpyrrolidine (2 mL) was added tert-butyl 4-aminopiperidine-1-carboxylate (136 mg, 0.680 mmol) and triethylamine (31.5 µL, 0.227 mmol). The solution was treated with microwave radiation at 130° C. for 19 hours. After cooling the resulting solution was partitioned between ethyl acetate and water. The organic layer was washed with brine, dried over magnesium sulfate, filtered and concentrated. The crude material was purified using normal phase chromatography (dichloromethane/methanol). The desired material was collected and concentrated to provide tert-butyl 4-({3-cyclopropanecarbonyl-1H-pyrrolo[2,3-b]pyridin-4-yl}amino)piperidine-1-carboxylate (36.0 mg, 0.0936 mmol) as a light yellow oil: MS (ES) m/z 385 (M+H).

Step 3: Preparation of 1-[4-({3-cyclopropanecarbonyl-1H-pyrrolo[2,3-b]pyridin-4-yl}amino)piperidin-1-yl]prop-2-en-1-one

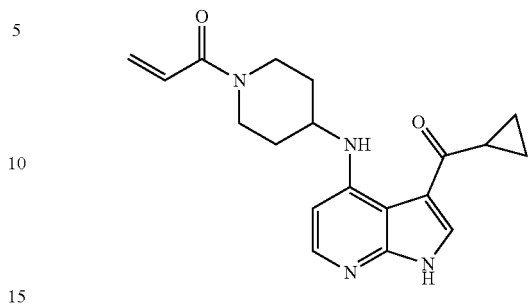

To a solution of tert-butyl 4-({3-cyclopropanecarbonyl-1H-pyrrolo[2,3-b]pyridin-4-yl}amino)piperidine-1-carboxylate from step 2 (36 mg, 0.0936 mmol) in dichloromethane (2 mL) was added trifluoroacetic acid (1 mL) and the solution was stirred for two hours and concentrated in vacuo. The residue was dissolved into tetrahydrofuran (1 mL) and triethylamine (32.5 µL, 0.234 mmol) was added. To this solution was added a solution of N-[3-(dimethylamino)propyl]propanimidamide hydrochloride (21.7 mg, 0.112 mmol), prop-2-enoic acid (6.41 µL, 0.0936 mmol) and triethylamine (32.5 µL, 0.234 mmol) in tetrahydrofuran (0.5 mL). The mixture was stirred at ambient temperature for 4 hours. The solution was partitioned between ethyl acetate and water. The organic layer was separated and concentrated. The crude material was purified using normal phase chromatography (dichloromethane/methanol) to provide 1-[4-({3-cyclopropanecarbonyl-1H-pyrrolo[2,3-b]pyridin-4-yl}amino)piperidin-1-yl]prop-2-en-1-one (7.50 mg, 0.0222 mmol): $^1$H NMR (400 MHz, DMSO-$d_6$) δ ppm 12.16-12.33 (m, 1H), 8.88-8.99 (m, 1H), 8.48 (s, 1H), 8.24-8.32 (m, 1H), 7.82-7.90 (m, 1H), 6.78-6.89 (m, 1H), 6.04-6.17 (m, 1H), 5.59-5.73 (m, 1H), 4.40-4.64 (m, 1H), 4.07-4.22 (m, 1H), 3.64-4.01 (m, 2H), 3.35-3.42 (m, 1H), 2.93-3.16 (m, 1H), 2.70-2.88 (m, 1H), 1.91-2.07 (m, 1H), 1.23-1.49 (m, 2H), 0.78-1.05 (m, 4H); MS (ES) m/z 339 (M+H).

EXAMPLES 11 AND 12

Preparation of 1-((R)-3-((5-((S)-tetrahydrofuran-3-carbonyl)-7H-pyrrolo[2,3-d]pyrimidin-4-yl)amino)piperidin-1-yl)prop-2-en-1-one The title compounds were prepared by the methods described in Scheme 14.

Scheme 14.
Preparation of 1-((R)-3-((5-((S)-tetrahydrofuran-3-carbonyl)-7H-pyrrolo[2,3-d]pyrimidin-4-yl)amino)piperidin-1-yl)prop-2-en-1-one

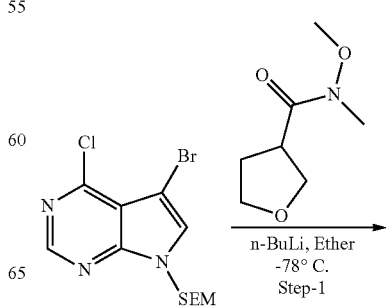

n-BuLi, Ether
-78° C.
Step-1

138

Synthesis of N-methoxy-N-methyltetrahydrofuran 3-carboxamide

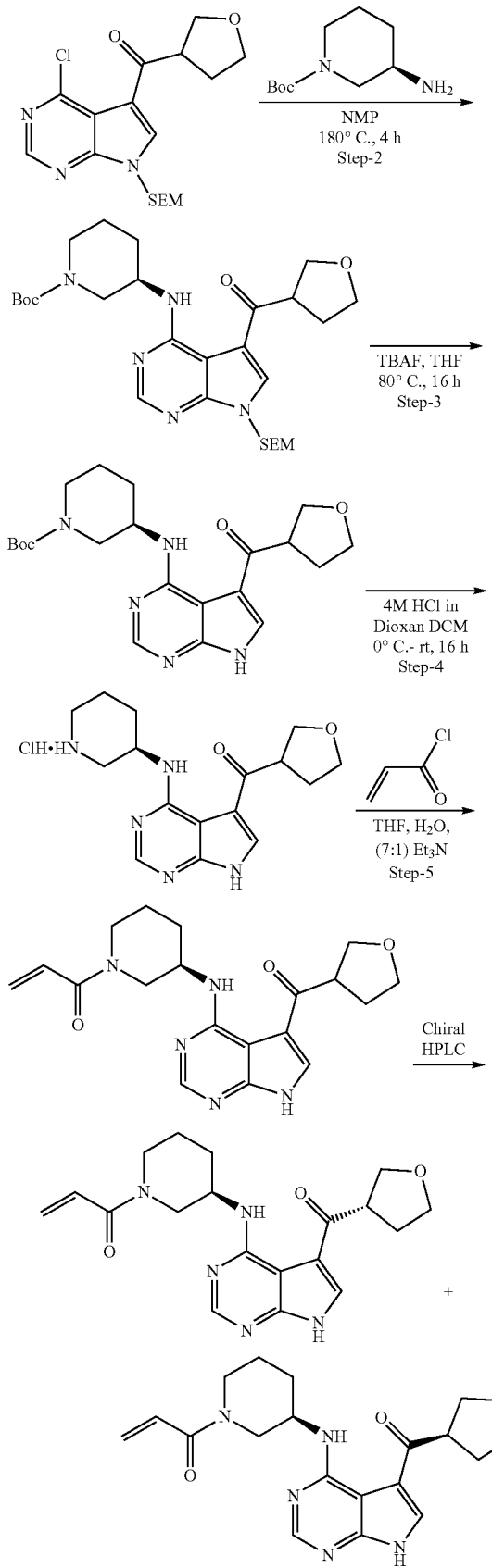

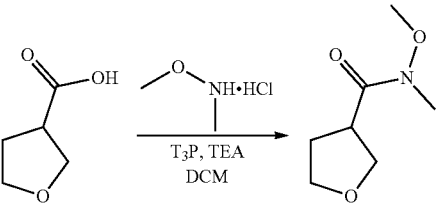

Preparation of N-Methoxy-N-methyltetrahydrofuran-3-carboxamide

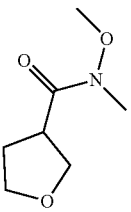

To a stirred solution of tetrahydrofuran-3-carboxylic acid (1 g, 8.61 mmol) in dichloromethane (10 mL), was added N,O-dimethylhydroxylamine hydrochloride (2 g, 21.52 mmol) and triethylamine (3 mL, 30.14 mmol) at 0° C. The reaction mixture was stirred 10 minutes and then propylphosphonic anhydride solution (50% in ethyl acetate) (10 mL, 34.44 mmol) was added and stirred at ambient temperature for 12 hours. The reaction mixture was poured into water and extracted with dichloromethane (2×50 mL). The combined organic extracts were washed with brine, dried over anhydrous sodium sulfate, filtered and concentrated in vacuo to provide N-methoxy-N-methyltetrahydrofuran-3-carboxamide as a brown liquid (1.2 g, 92% yield): MS (ES) m/z 160 (M+H).

Step 1: Preparation of (4-chloro-7-((2-(trimethylsilyl)ethoxy)methyl)-7H-pyrrolo[2,3-d]pyrimidin-5-yl)(tetrahydrofuran-3-yl)methanone

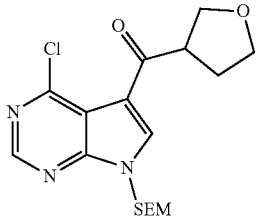 [SMILES: C[Si](C)(C)CCOCn1cc(C(=O)C2CCOC2)c2c(Cl)ncnc21]

To a stirred solution of 5-bromo-4-chloro-7-((2-(trimethylsilyl)ethoxy)methyl)-7H-pyrrolo[2,3-d]pyrimidine (prepared by the method described in Example 7, 1.4 g, 3.86 mmol) in diethyl ether (20 mL) was added n-butyl lithium (3.6 mL, 5.80 mmol, 1.6 M in hexane) at −78° C. The mixture was stirred for 0.5 hours and then a solution of N-methoxy-N-methyl-tetrahydrofuran-3-carboxamide (0.84 mL, 5.80 mmol) in diethyl ether (2 mL) was added. The mixture was stirred for 1 hour at that temperature. The reaction mixture was quenched with saturated aqueous ammonium chloride solution and extracted with ethyl acetate (2×40 mL). The combined organic extracts were washed with brine, dried over anhydrous sodium sulfate, filtered and concentrated in vacuo. The crude material was purified using flash chromatography (40% ethyl acetate/hexane) to provide (4-chloro-7-((2-(trimethylsilyl)ethoxy)methyl)-7H-pyrrolo[2,3-d]pyrimidin-5-yl)(tetrahydrofuran-3-yl)methanone as a brown liquid (1.0 g, 68% yield): MS (ES) m/z 381.0 (M+H).

Step 2: Preparation of tert-butyl (3R)-3-((5-(tetrahydrofuran-3-carbonyl)-7-((2-(trimethylsilyl)ethoxy)methyl)-7H-pyrrolo[2,3-d]pyrimidin-4-yl)amino)piperidine-1-carboxylate

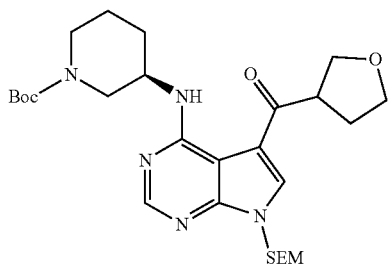 [SMILES: CC(C)(C)OC(=O)N1CCC[C@@H](Nc2ncnc3c2c(C(=O)C2CCOC2)cn3COCC[Si](C)(C)C)C1]

To a stirred solution of (4-chloro-7-((2-(trimethylsilyl)ethoxy)methyl)-7H-pyrrolo[2,3-d]pyrimidin-5-yl)(tetrahydrofuran-3-yl)methanone (0.85 g, 2.23 mmol) in N-methyl-2-pyrrolidone (15 mL) was added tert-butyl (R)-3-aminopiperidine-1-carboxylate (0.67 g, 3.34 mmol) and the mixture was heated in a sealed tube at 180° C. for 4 hours. The reaction mixture was poured into water and extracted with ethyl acetate (2×100 mL). The combined organic layer was washed with brine, dried over anhydrous sodium sulfate and concentrated in vacuo. The crude material was purified using flash chromatography (15% ethyl acetate/hexane) to provide tert-butyl (3R)-3-((5-(tetrahydrofuran-3-carbonyl)-7-((2-(trimethylsilyl)ethoxy)-methyl)-7H-pyrrolo[2,3-d]pyrimidin-4-yl)amino)piperidine-1-carboxylate as a brown liquid (0.75 g, 62% yield): MS (ES) m/z 546 (M+H).

Step-3: Preparation of tert-butyl (3R)-3-((5-(tetrahydrofuran-3-carbonyl)-7H-pyrrolo[2,3-d]pyrimidin-4-yl)amino)piperidine-1-carboxylate

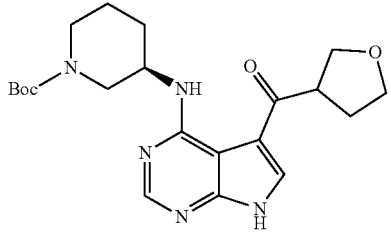 [SMILES: CC(C)(C)OC(=O)N1CCC[C@@H](Nc2ncnc3[nH]cc(C(=O)C4CCOC4)c23)C1]

To a stirred solution of tert-butyl (3R)-3-((5-(tetrahydrofuran-3-carbonyl)-7-((2-(trimethylsilyl)ethoxy)methyl)-7H-pyrrolo[2,3-d]pyrimidin-4-yl)amino)piperidine-1-carboxylate (0.75 g, 1.37 mmol) in tetrahydrofuran (6 mL) was added tetrabutylammonium fluoride (8 mL, 1 M in tetrahydrofuran) and the solution was heated to 80° C. for 16 hours. The reaction was allowed to cool to ambient temperature, poured into ice water and extracted with ethyl acetate. The organic layer was washed with water, brine, dried over anhydrous sodium sulfate, filtered and concentrated in vacuo. The crude material was purified using flash chromatography (4% methanol/dichloromethane) to provide tert-butyl (3R)-3-((5-(tetrahydrofuran-3-carbonyl)-7H-pyrrolo[2,3-d]pyrimidin-4-yl)amino)piperidine-1-carboxylate as a yellow liquid (0.6 g, 79% yield): MS (ES) m/z 416 (M+H).

Step 4: Preparation of (4-(((R)-piperidin-3-yl)amino)-7H-pyrrolo[2,3-d]pyrimidin-5-yl)(tetrahydrofuran-3-yl)methanone hydrochloride

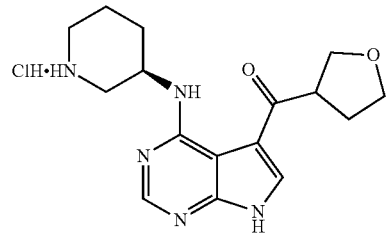

To a stirred solution of tert-butyl (3R)-3-((5-(tetrahydrofuran-3-carbonyl)-7H-pyrrolo[2,3-d]pyrimidin-4-yl)amino)-piperidine-1-carboxylate (0.60 g, 1.44 mmol) in dichloromethane (2 mL) was added hydrogen chloride (2.5 mL, 6.05 mmol, 4 M in dioxane) at 0° C. and the mixture was stirred at ambient temperature for 16 hours. The reaction was concentrated in vacuo and the residue was washed with diethyl ether to provide (4-(((R)-piperidin-3-yl)amino)-7H-pyrrolo[2,3-d]pyrimidin-5-yl)(tetrahydrofuran-3-yl)methanone hydrogen chloride as an off-white solid (1.0 g, crude): MS (ES) m/z 316 (M+H). The crude product was progressed for next step.

Step 5: Preparation of 1-((3R)-3-((5-(tetrahydrofuran-3-carbonyl)-7H-pyrrolo[2,3-d]pyrimidin-4-yl)amino)piperidin-1-yl)prop-2-en-1-one

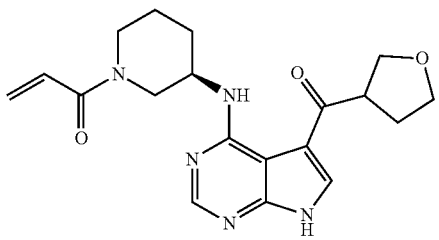 [SMILES: C=CC(=O)N1CCC[C@@H](Nc2ncnc3[nH]cc(C(=O)C4CCOC4)c23)C1]

To a stirred solution of (4-(((R)-piperidin-3-yl)amino)-7H-pyrrolo[2,3-d]pyrimidin-5-yl)(tetrahydrofuran-3-yl)methanone hydrogen chloride (0.5 g, 1.58 mmol) in tetrahydrofuran:water (7.0:3.0 mL) was added triethylamine (0.48 mL, 0.4.75 mmol) followed by a solution of acryloyl chloride (0.25 mL, 2.85 mmol) in tetrahydrofuran (0.5 mL) at 0° C. and the mixture stirred for 15 minutes. The reaction mixture was quenched with saturated aqueous sodium bicarbonate and extracted with ethyl acetate. The organic layer was washed with brine, dried over anhydrous sodium sulfate, filtered and concentrated in vacuo. The crude material was purified using flash chromatography (5% methanol/dichloromethane) and further purified by using prep HPLC to provide 1-((3R)-3-((5-(tetrahydrofuran-3-carbonyl)-7H-pyrrolo[2,3-d]pyrimidin-4-yl)amino)piperidin-1-yl)prop-2-en-1-one as an off-white solid (0.1 g, 23% yield).

Prep HPLC method:
Column: X-Bridge $C_{18}$ (100 mm×4.6 mm×3.5 mic)
Mobile phase (A): 0.1% Ammonia in water
Mobile phase (B): Methanol
Flow rate: 1.0 mL/min
T/% B: 0/20, 8/50, 12/80, 14/20, 15/20

EXAMPLE 11

1-((R)-3-((5-(tetrahydrofuran-3-carbonyl)-7H-pyrrolo[2,3-d]pyrimidin-4-yl)amino)piperidin-1-yl)prop-2-en-1-one

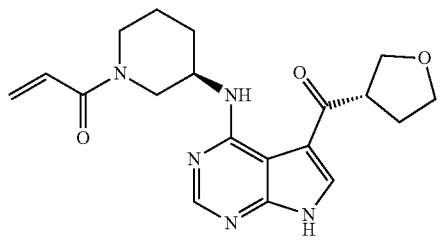 [SMILES: C=CC(=O)N1CCC[C@@H](Nc2ncnc3[nH]cc(C(=O)[C@H]4CCOC4)c23)C1]

Absolute configuration of tetrahydrofuran stereogenic center unknown, but opposite to Example 12.

The title compound was isolated as an off-white solid (0.02 g, 3.4%): $^1$H NMR (400 MHz, DMSO-$d_6$) δ 12.6 (br s, 1H), 9.02 (d, J=6.8 Hz, 1H), 8.32 (s, 1H), 8.17 (s, 1H), 6.78 (m, 2H), 5.94 (t, J=14.8 Hz, 1H), 5.47-5.60 (m, 1H), 4.09-4.16 (m, 1H), 4.0-4.07 (m, 2H), 3.90-3.98 (m, 1H), 3.64-3.87 (m, 3H), 3.45-3.27 (br s, 2H), 2.14-1.99 (m, 3H), 1.78 (m, 1H), 1.52-1.54 (m, 1H), 1.21 (br s, 1H); MS (ES) m/z 370.0 (M+H). Retention time: 9.46 minutes.

EXAMPLE 12

1-((R)-3-((5-(tetrahydrofuran-3-carbonyl)-7H-pyrrolo[2,3-d]pyrimidin-4-yl)amino)piperidin-1-yl)prop-2-en-1-one

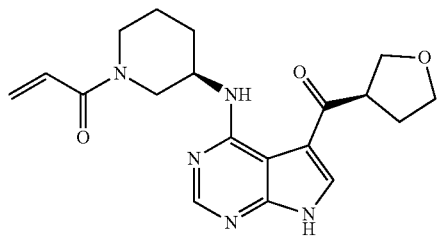 [SMILES: C=CC(=O)N1CCC[C@@H](Nc2ncnc3[nH]cc(C(=O)[C@@H]4CCOC4)c23)C1]

Absolute configuration of tetrahydrofuran stereogenic center unknown, but opposite to Example 11.

The title compound was isolated as an off-white solid (0.01 g, 2% yield): $^1$H NMR (400 MHz, DMSO-$d_6$ at 90° C.) δ 8.95 (d, J=6.8 Hz, 1H), 8.24 (s, 1H), 8.18 (s, 1H), 6.62 (m, 1H), 6.13 (s, 1H), 5.95 (d, J=16.8 Hz, 1H), 5.51-5.52 (m, 1H), 4.16-4.18 (m, 1H), 3.93-4.04 (m, 3H), 3.63-3.80 (m, 4H), 3.05-3.48 (m, 2H), 2.10-2.14 (m, 2H), 2.02 (m, 1H), 1.56-1.81 (m, 3H); MS (ES) m/z 370.0 (M+H). Retention time: 9.905 minutes.

EXAMPLE 13

Preparation of (R)-1-(3-((3-(cyclopentanecarbonyl)-1H-pyrrolo[2,3-b]pyridin-4-yl)amino)piperidin-1-yl)prop-2-en-1-one

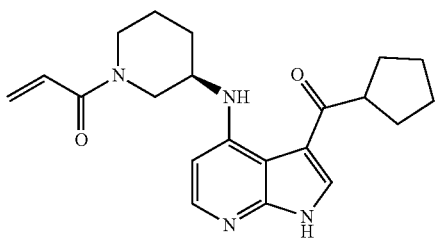 [SMILES: C=CC(=O)N1CCC[C@@H](Nc2ccnc3[nH]cc(C(=O)C4CCCC4)c23)C1]

The title compound was prepared by the method described in Scheme 15.

Scheme 15. Preparation of (R)-1-(3-((3-(cyclopentanecarbonyl)-1H-pyrrolo[2,3-b]pyridin-4-yl)amino)piperidin-1-yl)prop-2-en-1-one

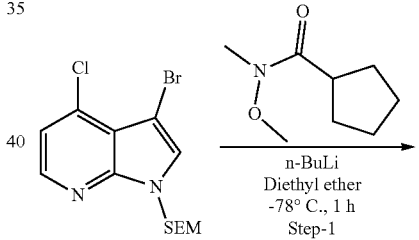

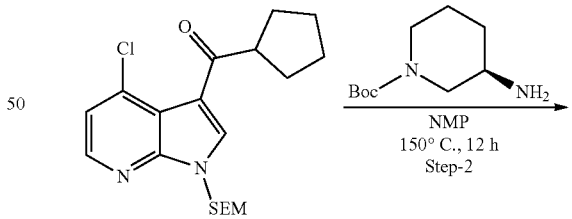

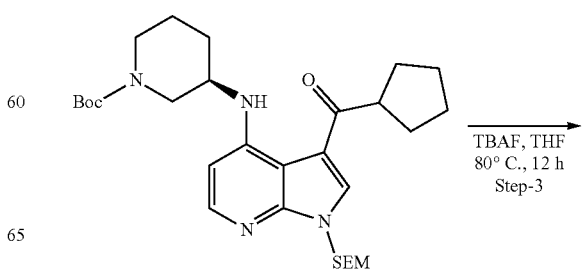

-continued

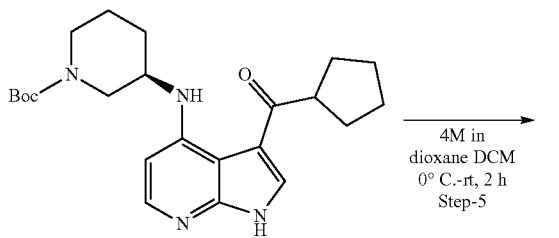

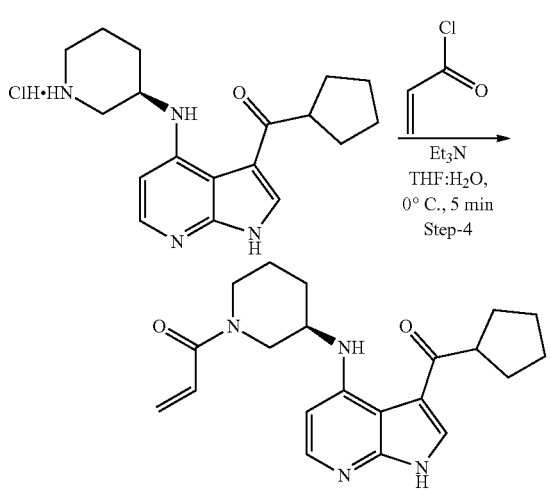

Step 1: Preparation of (4-chloro-1-((2-(trimethylsilyl)ethoxy)methyl)-1H-pyrrolo[2,3-b]pyridin-3-yl)(cyclopentyl)methanone

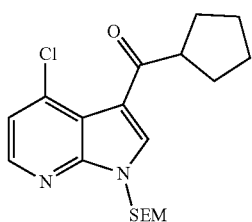 [SMILES: C[Si](C)(C)CCOCn1cc(C(=O)C2CCCC2)c2c(Cl)ccnc21]

To a stirred solution of 3-bromo-4-chloro-1H-pyrrolo[2,3-b]pyridine (prepared by the method described in Example 7, 4 g, 8.28 mmol) in diethyl ether (50 mL) was added n-butyllithium (8.28 mL, 66.5 mmol, 1.6 M in hexane) at −78° C. followed by addition of N-methoxy-N-methylcyclopentanecarboxamide (2.59 g, 16.56 mmol) in diethyl ether (4 mL) and stirred for 1 hour at same temperature. The reaction mixture was quenched with saturated aqueous ammonium chloride and extracted with ethyl acetate. The organic layer was washed with water, brine, dried over sodium sulfate, filtered and concentrated in vacuo. The crude material was purified using flash chromatography (15% ethyl acetate/hexane) to provide (4-chloro-1-((2-(trimethylsilyl)-ethoxy)methyl)-1H-pyrrolo[2,3-b]pyridin-3-yl)(cyclopentyl)methanone as a yellow liquid (2.3 g, 55% yield): MS (ES) m/z 379.1 (M+H).

Step 2: Preparation of tert-butyl (R)-3-((3-(cyclopentanecarbonyl)-1-((2-(trimethylsilyl)ethoxy)methyl)-1H-pyrrolo[2,3-b]pyridin-4-yl)amino)piperidine-1-carboxylate

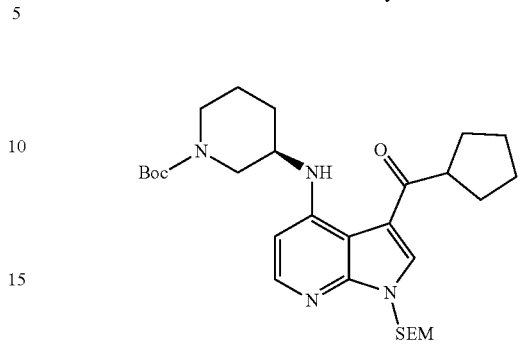

To a solution of (4-chloro-1-((2-(trimethylsilyl)ethoxy)methyl)-1H-pyrrolo[2,3-b]pyridin-3-yl)(cyclopentyl)methanone (1.5 g, 3.96 mmol) in N-methylpyrrolidone (10 mL) was added tert-butyl (R)-3-aminopiperidine-1-carboxylate (0.95 g, 4.76 mmol), the mixture was heated in a sealed tube at 150° C. for 12 hours. After cooling to ambient temperature, the reaction mixture was poured into ice water and extracted with ethyl acetate. The organic layer was washed with water, brine, dried over anhydrous sodium sulfate, filtered and concentrated in vacuo. The crude material was purified using flash chromatography (10% ethyl acetate/hexane) to provide tert-butyl (R)-3-((3-(cyclopentanecarbonyl)-1-((2-(trimethylsilyl)ethoxy)methyl)-1H-pyrrolo[2,3-b]pyridin-4-yl)amino)piperidine-1-carboxylate as a pale yellow solid (1.2 g, crude): MS (ES) m/z 543.3 (M+H).

Step 3: Preparation of tert-butyl (R)-3-((3-(cyclopentanecarbonyl)-1H-pyrrolo[2,3-b]pyridin-4-yl)amino)piperidine-1-carboxylate

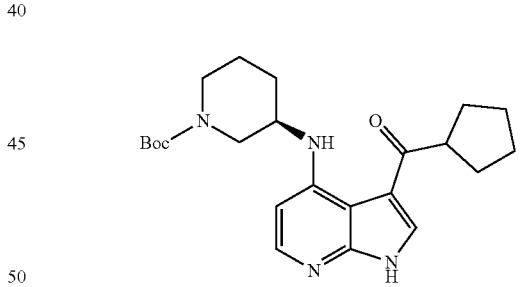

To a solution of tert-butyl (R)-3-((3-(cyclopentanecarbonyl)-1-((2-(trimethylsilyl)ethoxy)methyl)-1H-pyrrolo[2,3-b]pyridin-4-yl)amino)piperidine-1-carboxylate (0.7 g, 1.29 mmol) in tetrahydrofuran (5 mL) was added tetrabutylammonium fluoride (13 mL, 1 M in tetrahydrofuran) and the solution was heated to 80° C. for 12 hours. After cooling to ambient temperature, the reaction mixture was poured into ice water and extracted with ethyl acetate. The organic layer was washed with water, brine, dried over anhydrous sodium sulfate, filtered and concentrated in vacuo. The crude material was purified using flash chromatography (50% ethyl acetate/hexane) to provide tert-butyl (R)-3-((3-(cyclopentanecarbonyl)-1H-pyrrolo[2,3-b]pyridin-4-yl)amino)piperidine-1-carboxylate as a brown color solid (0.28 g, crude yield): MS (ES) m/z 413.2 [M+H].

Step 4: Preparation of (R)-cyclopentyl(4-(piperidin-3-ylamino)-1H-pyrrolo[2,3-b]pyridin-3-yl)methanone hydrochloride

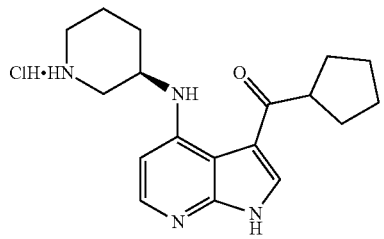

To a solution of tert-butyl (R)-3-((3-(cyclopentanecarbonyl)-1H-pyrrolo[2,3-b]pyridin-4-yl)amino)piperidine-1-carboxylate (0.28 g) in dichloromethane (4 mL) was added hydrogen chloride (4 mL, 4 M in dioxane) at 0° C. and the mixture was stirred at ambient temperature for 2 hours. The reaction mixture was concentrated in vacuo and the residue was washed with diethyl ether to provide (R)-cyclopentyl (4-(piperidin-3-ylamino)-1H-pyrrolo[2,3-b]pyridin-3-yl) methanone hydrochloride as a pale yellow solid (0.26 g, crude): MS (ES) m/z 313.1 [M+H].

Step 5: Preparation of (R)-(4-((1-(buta-1,3-dienyl)piperidine-3-yl)amino-1H-pyrrolo[2,3-b]pyridine-3-yl) cyclopentyl) methanone

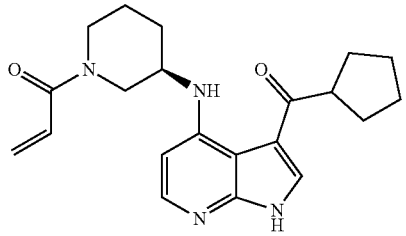 [SMILES: C=CC(=O)N1CCC[C@@H](Nc2ccnc3[nH]cc(C(=O)C4CCCC4)c23)C1]

To a stirred solution of (R)-cyclopentyl(4-(piperidin-3-ylamino)-1H-pyrrolo[2,3-b]pyridine-3-yl) methanone hydrochloride (0.1 g, 0.28 mmol) in tetrahydrofuran:water (8:2 mL) was added triethylamine (0.08 mL, 0.57 mmol) followed by a solution of acryloyl chloride (0.01 g, 0.14 mmol) in tetrahydrofuran (0.2 mL) at 0° C. and stirred for 5 minutes. The reaction mixture was quenched with aqueous sodium bicarbonate and extracted with ethyl acetate. The organic layer was washed with brine, dried over anhydrous sodium sulfate, filtered and concentrated in vacuo. The crude material was purified using flash chromatography (5% methanol/dichloromethane) to provide (R)-(4-((1-(buta-1,3-dienyl)piperidine-3-yl)amino-1H-pyrrolo[2,3-b]pyridine-3-yl)cyclopentyl)methanone as a white solid (0.02 g, 17%): $^1$H NMR (400 MHz, DMSO-$d_6$) δ 12.16 (s, 1H), 8.92 (d, J=7.6 Hz, 1H), 8.26 (s, 1H), 7.85 (d, J=6.0 Hz, 1H), 6.72-6.82 (m, 1H), 6.48-6.60 (m, 1H), 6.24-6.29 (m, 1H), 5.90-6.09 (m, 2H), 5.63-5.66 (m, 1H), 5.49-5.50 (m, 1H), 4.21-4.32 (m, 1H), 3.68-3.79 (m, 2H), 3.46-3.60 (m, 2H), 2.86-2.99 (s, 1H), 1.96-2.09 (m, 1H), 1.59-1.83 (m, 8H); MS (ES) m/z 367.1 (M+H).

EXAMPLE 14

Preparation of (R)-1-(3-((3-(1-methylcyclopropane-1-carbonyl)-1H-pyrrolo[2,3-b]pyridin-4-yl)amino)piperidin-1-yl)prop-2-en-1-one

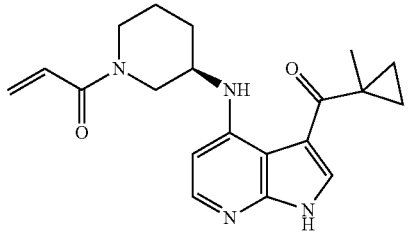 [SMILES: C=CC(=O)N1CCC[C@@H](Nc2ccnc3[nH]cc(C(=O)C4(C)CC4)c23)C1]

The title compound was prepared by the method described in Scheme 16.

Scheme 16. Preparation of (R)-1-(3-((3-(1-methylcyclopropane-1-carbonyl)-1H-pyrrolo[2,3-b]pyridin-4-yl)amino)piperidin-1-yl)prop-2-en-1-one

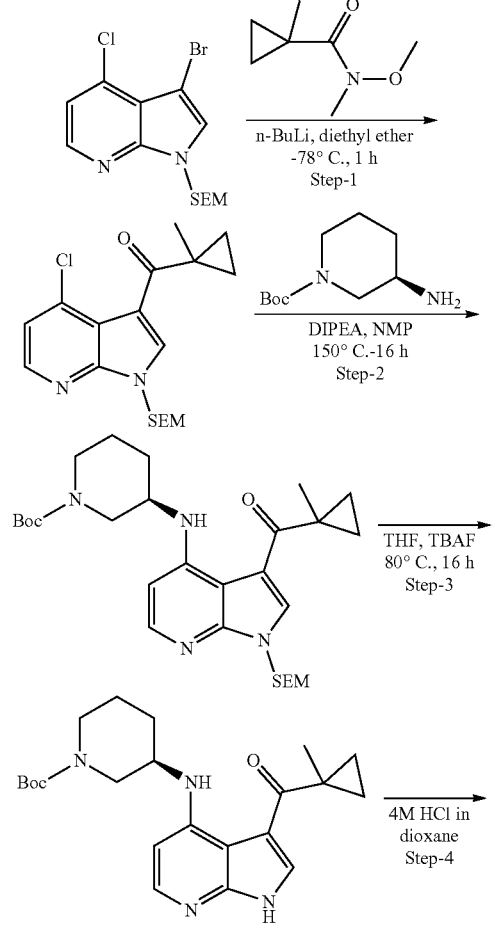

-continued

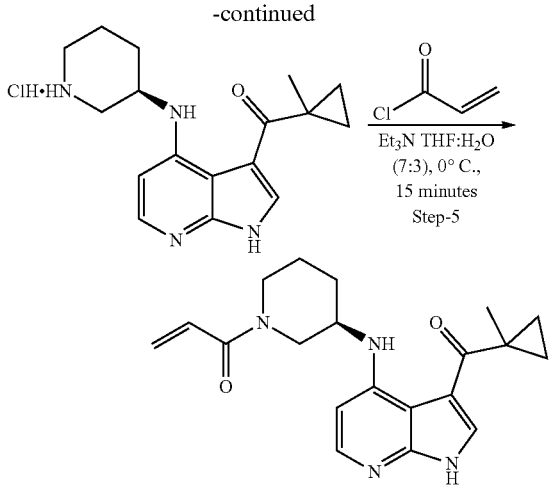

Preparation of
N-methoxy-N,1-dimethylcyclopropane-1-carboxamide

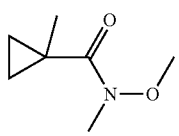

A solution of 1-methylcyclopropane-1-carboxylic acid (2.0 g, 19.99 mmol) and carbonyldiimidazole (3.55 g, 21.92 mmol) in dichloromethane (70 mL) was stirred at ambient temperature for 1 hour, then N,O-dimethylhydroxylamine (2.14 g, 21.99 mmol) was added and stirred at ambient temperature for 16 hours. The reaction mixture was poured into water and extracted with dichloromethane (2×50 mL). The combined organic layers were washed with brine, dried over anhydrous sodium sulfate, filtered and concentrated in vacuo. The crude material was purified using flash chromatography (21% ethyl acetate/hexane) to provide N-methoxy-N,1-dimethylcyclopropane-1-carboxamide as a colorless liquid (1.55 g, 52% yield): MS (ES) m/z 144.1 (M+H).

Step 1: Preparation of (4-chloro-1-((2-(trimethylsilyl)ethoxy)methyl)-1H-pyrrolo[2,3-b]pyridin-3-yl)(1-methylcyclopropyl)methanone

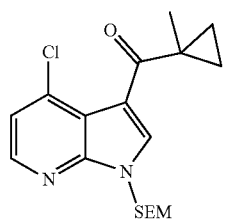 [SMILES: CC1(C(=O)c2cn(COCC[Si](C)(C)C)c3nccc(Cl)c23)CC1]

To a solution of 3-bromo-4-chloro-1-((2-(trimethylsilyl)ethoxy)methyl)-1H-pyrrolo[2,3-b]pyridine (prepared by the method described in Example 7, 1.5 g, 4.16 mmol) in diethyl ether (40 mL) was added n-butyl lithium (3.87 mL, 6.24 mmol, 1.6 M in hexane) at −78° C. and stirred for 0.5 hours.

Then a solution of N-methoxy-N,O-dimethylcyclopropane-1-carboxamide (0.89 g, 6.24 mmol) in diethyl ether (40 mL) was added at −78° C. and stirred for 1 hour. The reaction mixture was quenched with saturated ammonium chloride solution and extracted with ethyl acetate (2×40 mL). The combined organic layers were washed with brine, dried over anhydrous sodium sulfate, filtered and concentrated in vacuo. The crude material was purified using flash chromatography (25% ethyl acetate/hexane) to provide (4-chloro-1-((2-(trimethylsilyl)-ethoxy)methyl)-1H-pyrrolo[2,3-b]pyridin-3-yl)(1-methylcyclopropyl)methanone as a yellow sticky solid (1.0 g, 66% yield): MS (ES) m/z 365.1 (M+H).

Step 2: Preparation of tert-butyl (R)-3-((3-(1-methylcyclopropane-1-carbonyl)-1-((2-(trimethylsilyl)ethoxy)methyl)-1H-pyrrolo-[2,3-b]pyridin-4-yl)amino)piperidine-1-carboxylate

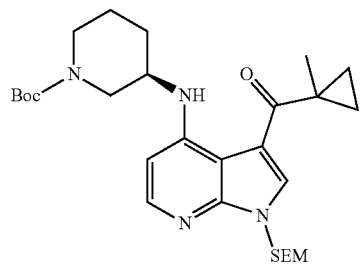 [SMILES: CC(C)(C)OC(=O)N1CCC[C@@H](Nc2ccnc3c2c(C(=O)C2(C)CC2)cn3COCC[Si](C)(C)C)C1]

To a stirred solution of (4-chloro-1-((2-(trimethylsilyl)ethoxy)methyl)-1H-pyrrolo[2,3-b]pyridin-3-yl)(1-methyl-cyclo-propyl)methanone (1.1 g, 3.02 mmol) in N-methyl-2-pyrrolidone (20 mL) was added tert-butyl (R)-3-aminopiperidine-1-carboxylate (1.5 g, 7.55 mmol), N,N-diisopropylethylamine (1.57 mL, 9.06 mmol) and the mixture was heated in a sealed tube at 150° C. for 16 hours. The reaction mixture was diluted with water and extracted with ethyl acetate (2×50 mL). The combined organic layers were washed with brine, dried over anhydrous sodium sulfate, filtered and concentrated in vacuo. The crude material was purified using flash chromatography (20% ethyl acetate/hexane) to provide tert-butyl (R)-3-((3-(1-methylcyclopropane-1-carbonyl)-1-((2-(trimethylsilyl)ethoxy)methyl)-1H-pyrrolo[2,3-b]pyridin-4-yl)amino)piperidine-1-carboxylate as a yellow sticky solid (0.52 g, 33% yield): MS (ES) m/z 529.3 (M+H).

Step 3: Preparation of tert-butyl (R)-3-((3-(1-methylcyclopropane-1-carbonyl)-1H-pyrrolo[2,3-b]pyridin-4-yl)amino)piperidine-1-carboxylate

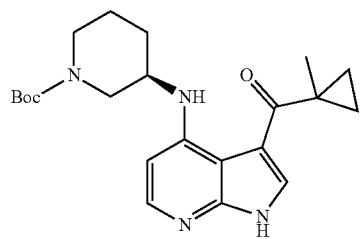 [SMILES: CC(C)(C)OC(=O)N1CCC[C@@H](Nc2ccnc3[nH]cc(C(=O)C4(C)CC4)c23)C1]

To a stirred solution of tert-butyl (R)-3-((3-(1-methylcyclopropane-1-carbonyl)-1-((2-(trimethylsilyl)ethoxy)methyl)-1H-pyrrolo[2,3-b]pyridin-4-yl)amino)piperidine-1-carboxylate (0.52 g, 0.98 mmol) in tetrahydrofuran (8 mL) was added tetrabutylammonium fluoride (8 mL, 1 M in tetrahydrofuran) and the solution heated to 80° C. for 16 hours. The mixture was cooled to ambient temperature, poured into ice water and extracted with ethyl acetate. The organic layer was washed with water, brine, dried over anhydrous sodium sulfate, filtered and concentrated in vacuo. The crude material was purified using flash chromatography (50% ethyl acetate/hexane) to provide tert-butyl (R)-3-((3-(1-methylcyclopropane-1-carbonyl)-1H-pyrrolo[2,3-b]pyridin-4-yl)amino)piperidine-1-carboxylate as a yellow solid (0.26 g, 67% yield): MS (ES) m/z 399.2 (M+H).

Step 4: Preparation of (R)-(1-methylcyclopropyl)(4-(piperidin-3-ylamino)-1H-pyrrolo[2,3-b]pyridin-3-yl)methanone

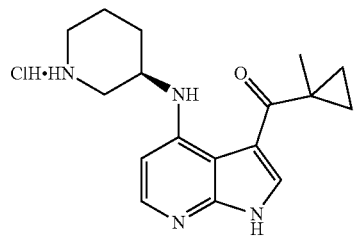

To a solution of tert-butyl (R)-3-((3-(1-methylcyclopropane-1-carbonyl)-1H-pyrrolo[2,3-b]pyridin-4-yl)amino)piperidine-1-carboxylate (0.26 g, 0.65 mmol) in dichloromethane (5 mL) was added hydrogen chloride (6.0 mL, 4 M in dioxane) at 0° C. and the mixture stirred at ambient temperature for 16 hours. The reaction mixture was concentrated in vacuo and the residue was washed with diethyl ether to provide (R)-(1-methylcyclopropyl)(4-(piperidin-3-ylamino)-1H-pyrrolo[2,3-b]pyridin-3-yl)methanone hydrochloride as a light brown solid (0.22 g, crude). The crude product was progressed for next stage without further purification.

Step 5: (R)-1-(3-((3-(1-methylcyclopropane-1-carbonyl)-1H-pyrrolo[2,3-b]pyridin-4-yl)amino)piperidin-1-yl)prop-2-en-1-one

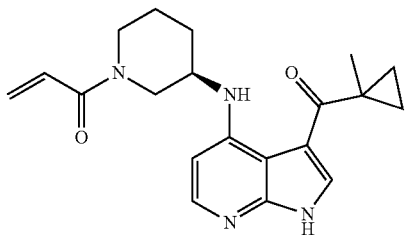 [SMILES: C=CC(=O)N1CCC[C@@H](Nc2ccnc3[nH]cc(C(=O)C4(C)CC4)c23)C1]

To a stirred solution of (R)-(1-methylcyclopropyl)(4-(piperidin-3-ylamino)-1H-pyrrolo[2,3-b]pyridin-3-yl)methanone hydrochloride (0.11 g, 0.29 mmol) in tetrahydrofuran:water (7.0:3.0 mL) was added triethylamine (0.11 mL, 0.87 mmol) followed by a solution of acryloyl chloride (0.02 mL, 0.22 mmol) in tetrahydrofuran (0.5 mL) at 0° C. and stirred for 15 minutes. The reaction mixture was quenched with saturated aqueous sodium bicarbonate solution and extracted with ethyl acetate. The organic layer was washed with brine, dried over anhydrous sodium sulfate, filtered and concentrated in vacuo. The crude material was purified using flash chromatography (5% methanol/dichloromethane) followed by prep HPLC to provide (R)-1-(3-((3-(1-methylcyclopropane-1-carbonyl)-1H-pyrrolo[2,3-b]pyridin-4-yl)amino)piperidin-1-yl)prop-2-en-1-one as a white solid (0.02 g, 6% yield): $^1$H NMR (400 MHz, DMSO-$d_6$ at 80° C.) δ 11.99 (s, 1H), 8.49 (d, J=7.2 Hz, 1H), 8.13 (s, 1H) 7.87 (d, J=5.6 Hz, 1H), 6.61 (br s, 1H), 6.28 (d, J=5.6 Hz, 1H), 5.98 (d, J=15.2 Hz, 1H), 5.53 (br s, 1H), 3.7 (s, 1H), 3.55 (s, 1H), 3.38 (s, 1H), 2.04 (s, 1H), 1.81 (s, 1H), 1.65 (d, J=9.2 Hz, 1H), 1.52-1.58 (m, 3H), 1.48 (s, 2H), 1.2 (s, 1H) 1.0 (s, 2H), 0.71 (s, 2H); MS (ES) m/z 353.1 (M+H).

Prep HPLC method:
Column: Inertsil ODS 3V (250 mm×4.6 mm×5 mic)
Mobile phase (A): 0.1% Ammonia in water
Mobile phase (B): ACN
Flow rate: 1.0 mL/min

EXAMPLE 15

Preparation of (R)-1-(3-((3-(cyclopropanecarbonyl)-1H-pyrrolo[2,3-b]pyridin-4-yl)amino)pyrrolidin-1-yl)prop-2-en-1-one

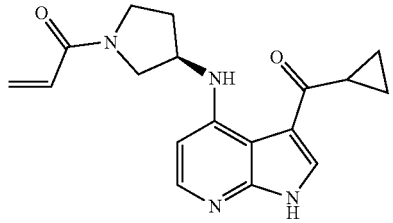 [SMILES: C=CC(=O)N1CC[C@@H](Nc2ccnc3[nH]cc(C(=O)C4CC4)c23)C1]

Step 1: Preparation of 4-chloro-3-cyclopropanecarbonyl-1H-pyrrolo[2,3-b]pyridine

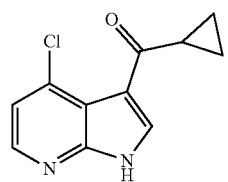 [SMILES: O=C(c1c[nH]c2nccc(Cl)c12)C1CC1]

To a solution of 4-chloro-1H-pyrrolo[2,3-b]pyridine (400 mg, 2.62 mmol) in 1.5 mL dichloromethane was added aluminium chloride (2.43 g, 18.3 mmol). After one hour of stirring at ambient temperature, cyclopropanecarbonyl chloride (236 µL, 2.62 mmol) was added. The reaction was stirred overnight at ambient temperature. The reaction was quenched with a saturated solution of Rochelle salts. The solution was stirred rapidly for one hour. The resulting yellow solid was collected by vacuum filtration to provide 4-chloro-3-cyclopropanecarbonyl-1H-pyrrolo[2,3-b]pyridine (580 mg, 2.62 mmol): MS (ES) m/z 221 (M+H).

Step 2: Preparation of 4-chloro-3-cyclopropanecarbonyl-1-{[2-(trimethylsilyl)ethoxy]methyl}-1H-pyrrolo[2,3-b]pyridine

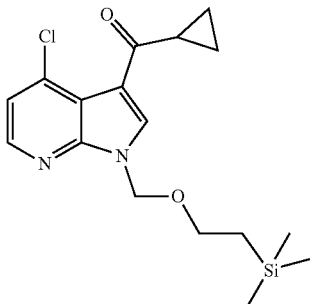 [SMILES: C[Si](C)(C)CCOCn1cc(C(=O)C2CC2)c2c(Cl)ccnc21]

To a solution of 4-chloro-3-cyclopropanecarbonyl-1H-pyrrolo[2,3-b]pyridine from step 1 (238 mg, 1.07 mmol) in tetrahydrofuran (2 mL) was added sodium hydride (60% mineral oil dispersion, 25.6 mg, 1.07 mmol). After 15 min, [2-(chloromethoxy)ethyl]trimethylsilane (207 µL, 1.17 mmol) was added. The reaction was complete within 2 hours. The solution was quenched with the addition of water. The solution was extracted with ethyl acetate and concentrated. The crude material was purified using normal phase chromatography (ethyl acetate/heptane) to provide 4-chloro-3-cyclopropanecarbonyl-1-{[2-(trimethylsilyl)ethoxy]methyl}-1H-pyrrolo[2,3-b]pyridine (195 mg, 0.556 mmol) as a yellow oil: MS (ES) m/z 351 (M+H).

Step 3: Preparation of tert-butyl (3R)-3-[(3-cyclopropanecarbonyl-1-{[2-(trimethylsilyl)ethoxy]methyl}-1H-pyrrolo[2,3-b]pyridin-4-yl)amino]pyrrolidine-1-carboxylate

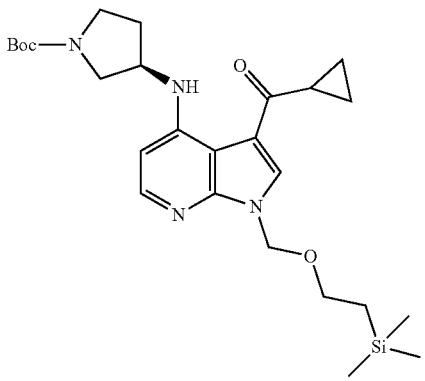 [SMILES: CC(C)(C)OC(=O)N1CC[C@@H](Nc2ccnc3c2c(C(=O)C2CC2)cn3COCC[Si](C)(C)C)C1]

A mixture of 4-chloro-3-cyclopropanecarbonyl-1-{[2-(trimethylsilyl)ethoxy]methyl}-1H-pyrrolo[2,3-b]pyridine from step 2 (45 mg, 0.13 mmol), tert-butyl (3R)-3-amino-pyrrolidine-1-carboxylate (23.8 mg, 0.128 mmol), cesium carbonate (125 mg, 0.385 mmol), bis(dibenzylideneacetone)palladium (3.68 mg, 0.00641 mmol) and Xantphos (7.41 mg, 0.0128 mmol) in 1,4-dioxane (1 mL) was treated with microwave radiation at 120° C. for 4 hours. After cooling the solution was partitioned between ethyl acetate and water and the organic layer was concentrated. The crude material was purified using normal phase chromatography (ethyl acetate/heptane) to provide tert-butyl (3R)-3-[(3-cyclopropanecarbonyl-1-{[2-(trimethylsilyl)ethoxy]methyl}-1H-pyrrolo[2,3-b]pyridin-4-yl)amino]pyrrolidine-1-carboxylate (66.0 mg, 0.132 mmol): MS (ES) m/z 500 (M+H).

Step 4: Preparation of 1-[(3R)-3-({3-cyclopropanecarbonyl-1H-pyrrolo[2,3-b]pyridin-4-yl}amino)pyrrolidin-1-yl]prop-2-en-1-one

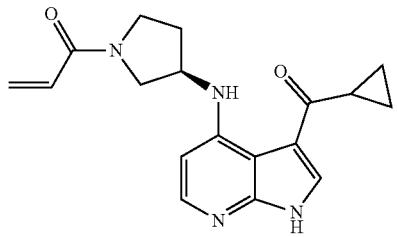 [SMILES: C=CC(=O)N1CC[C@@H](Nc2ccnc3[nH]cc(C(=O)C4CC4)c23)C1]

To a solution of tert-butyl (3R)-3-[(3-cyclopropanecarbonyl-1-{[2-(trimethylsilyl)ethoxy]methyl}-1H-pyrrolo[2,3-b]pyridin-4-yl)amino]pyrrolidine-1-carboxylate from step 3 (66 mg, 0.132 mmol) in 2 mL of dichloromethane was added 1 mL of trifluoroacetic acid. The solution was stirred at ambient temperature for 3 hours. The solution was concentrated in vacuo. The reside was dissolved into dichloromethane (1 mL) and triethylamine (36.6 µL, 0.2636 mmol) was added. To this solution was added a solution of prop-2-enoic acid (9.49 mg, 0.1318 mmol), N-[3-(dimethylamino)propyl]propanimidamide hydrochloride (76.5 mg, 0.395 mmol) and triethylamine (36.6 µL, 0.264 mmol) and the mixture was stirred at ambient temperature for 2 hours. The solution was partitioned between ethyl acetate and water and the organic layer was concentrated. The crude material was purified using normal phase chromatography (dichloromethane/methanol) to provide 1-[(3R)-3-({3-cyclopropanecarbonyl-1H-pyrrolo[2,3-b]pyridin-4-yl}amino)pyrrolidin-1-yl]prop-2-en-1-one (6.00 mg, 0.0185 mmol) as a yellow oil: $^1$H NMR (400 MHz, DMSO-$d_6$) δ ppm 12.23-12.36 (m, 1H), 8.97-9.13 (m, 1H), 8.47-8.52 (m, 1H), 8.25-8.34 (m, 1H), 7.83-7.98 (m, 1H), 6.45-6.69 (m, 1H), 6.03-6.17 (m, 1H), 5.52-5.74 (m, 1H), 4.36-4.68 (m, 1H), 3.91-4.33 (m, 2H), 3.60-3.83 (m, 1H), 3.42-3.60 (m, 1H), 2.77-3.09 (m, 1H), 2.18-2.40 (m, 1H), 1.78-2.07 (m, 1H), 0.75-1.06 (m, 4H); MS (ES) m/z 325 (M+H).

EXAMPLE 16

Preparation of isobutyl 4-(((3R,6S)-1-acryloyl-6-methylpiperidin-3-yl)amino)-7H-pyrrolo[2,3-d]pyrimidine-5-carboxylate

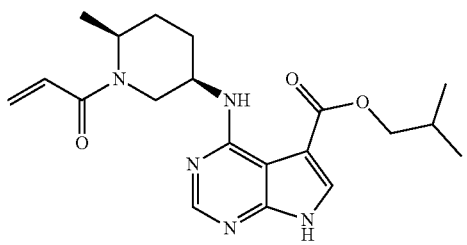 [SMILES: C=CC(=O)N1C[C@H](Nc2ncnc3[nH]cc(C(=O)OCC(C)C)c23)CC[C@@H]1C]

The title compound was made by the method described in Scheme 17.

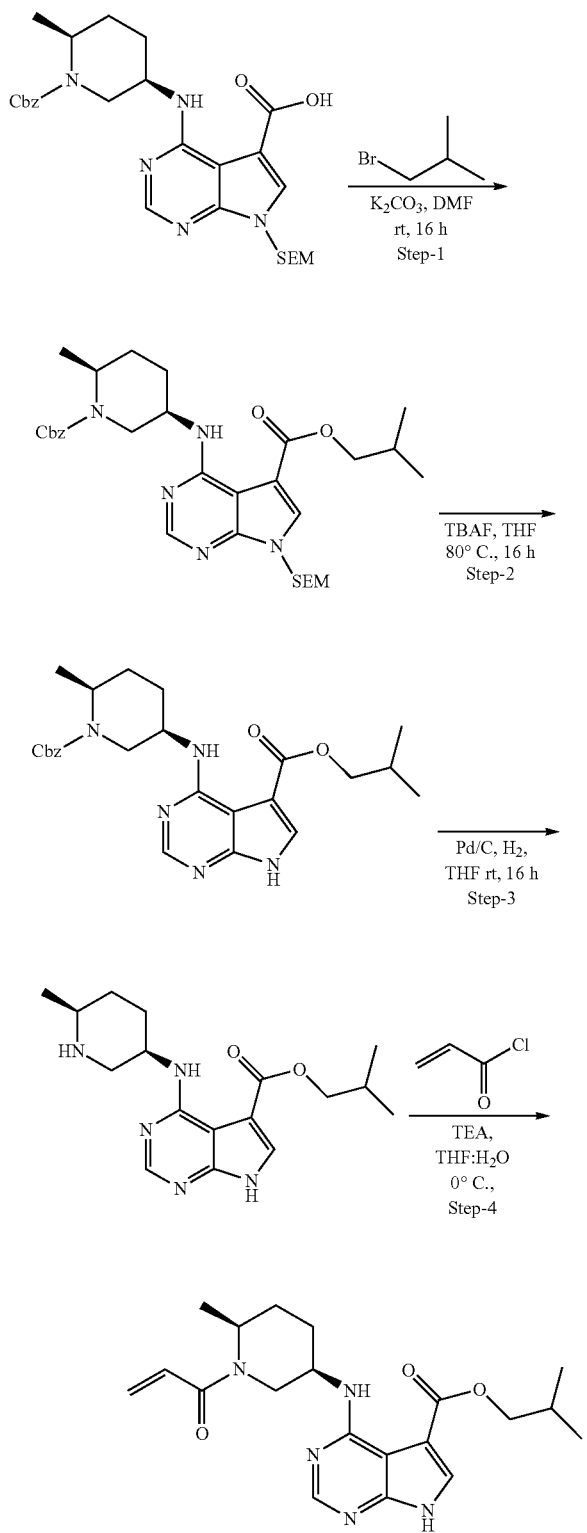

Scheme 17.
Preparation of isobutyl 4-(((3R,6S)-1-acryloyl-6-methylpiperidin-3-yl)amino)-7H-pyrrolo[2,3-d]pyrimidine-5-carboxylate Step 1: Preparation of isobutyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate To a stirred solution of potassium carbonate (0.15 g, $^F$1.1 mmol) in N,N-dimethylformamide (10 mL) was added benzyl ethyl-4-(((3R,6S)-1-((benzyloxy)carbonyl)-6-methylpiperidin-3-yl)amino)-7-((2-(trimethylsilyl) ethoxy)methyl)-7H-pyrrolo[2,3-d]-pyrimidine-5-carboxylic acid (prepared by the method described in Example 4, 0.2 g, 0.37 mmol) and isobutyl bromide (0.25 g, 1.85 mmol). The reaction mixture was stirred at ambient temperature for 16 hours and the reaction mixture was poured into ice water and extracted with ethyl acetate. The organic layer was washed with water, brine, dried over anhydrous sodium sulfate, filtered and concentrated in vacuo. The crude material was purified using flash chromatography (30% ethyl acetate/hexane) to provide isobutyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate as a yellow solid (0.18 g, 82% yield): MS (ES) m/z 596.5 (M+H).

Step 2: Preparation of isobutyl 4-(((3R,6S)-1-((benzyloxy)carbonyl)-6-methylpiperidin-3-yl)amino)-7H-pyrrolo[2,3-d]pyrimidine-5-carboxylate To a stirred solution of isobutyl 4-(((3R,6S)-1-((benzyloxy)carbonyl)-6-methylpiperidin-3-yl)amino)-7-((2-(trimethylsilyl)ethoxy)methyl)-7H-pyrrolo[2,3-d]pyrimidine-5-carboxylate (0.18 g, 0.3 mmol) in tetrahydrofuran (5 mL) was added tetrabutylammonium fluoride (5 mL, 1M in tetrahydrofuran) and the solution was heated to 80° C. for 16 hours. After allowing the reaction mixture to cool to ambient temperature, the reaction mixture was poured into ice water and extracted with ethyl acetate. The organic layer was washed with water, brine, dried over anhydrous sodium sulfate, filtered and concentrated in vacuo. The crude material was purified using flash chromatography (70% ethyl acetate/hexane) to provide isobutyl 4-(((3R,6S)-1-((benzyloxy)carbonyl)-6-methylpiperidin-3-yl)amino)-7H-pyrrolo[2,3-d]pyrimidine-5-carboxylate as a white solid (0.1 g, 71% yield): MS (ES) m/z 466.4 (M+H).

Step 3: Preparation of isobutyl 4-(((3R,6S)-6-methylpiperidin-3-yl)amino)-7H-pyrrolo[2,3-d]pyrimidine-5-carboxylate

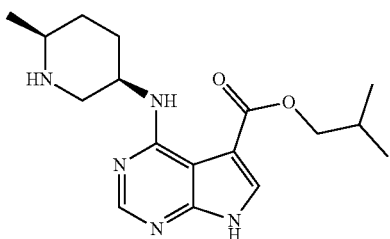 [SMILES: CC(C)COC(=O)c1c[nH]c2ncnc(N[C@@H]3CC[C@H](C)NC3)c12]

To a stirred solution of isobutyl 4-(((3R,6S)-1-((benzyloxy)carbonyl)-6-methylpiperidin-3-yl)amino)-7H-pyrrolo[2,3-d]pyrimidine-5-carboxylate (0.1 g, 0.21 mmol) in tetrahydrofuran (10 mL) was added palladium on carbon (0.05 g, 10 wet w/w) under a nitrogen atmosphere. The mixture was stirred under a hydrogen atmosphere at room temperature for 16 hours. The reaction mixture was filtered through celite and the filtrate was concentrated in vacuo to provide isobutyl 4-(((3R,6S)-6-methylpiperidin-3-yl)amino)-7H-pyrrolo[2,3-d]pyrimidine-5-carboxylate as a white solid (0.06 g, crude): MS (ES) m/z 332.2 (M+H).

Step 4: Preparation of isobutyl 4-(((3R,6S)-1-acryloyl-6-methylpiperidin-3-yl)amino)-7H-pyrrolo[2,3-d]pyrimidine-5-carboxylate

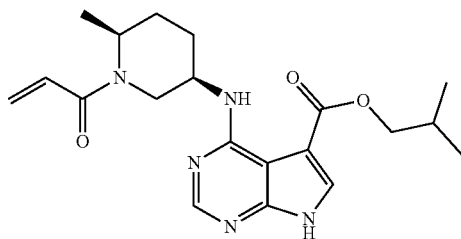 [SMILES: C=CC(=O)N1C[C@H](Nc2ncnc3[nH]cc(C(=O)OCC(C)C)c23)CC[C@@H]1C]

To a stirred solution of isobutyl 4-(((3R,6S)-6-methylpiperidin-3-yl)amino)-7H-pyrrolo[2,3-d]pyrimidine-5-carboxylate (0.06 g, 0.18 mmol) in tetrahydrofuran:water (3:2 mL) was added triethylamine (0.12 mL, 0.9 mmol) followed by a solution of acryloyl chloride (0.019 mL, 0.21 mmol) in tetrahydrofuran (0.5 mL) at 0° C. and stirred for 20 minutes. The reaction mixture was quenched with aqueous sodium bicarbonate and extracted with ethyl acetate. The organic layer was washed with brine, dried over anhydrous sodium sulfate, filtered and concentrated in vacuo. The crude material was purified using flash chromatography (20% methanol/dichloromethane) to provide isobutyl 4-(((3R,6S)-1-acryloyl-6-methylpiperidin-3-yl)amino)-7H-pyrrolo[2,3-d]pyrimidine-5-carboxylate as a white solid (0.013 g, 18.6% yield): $^1$H NMR (400 MHz, DMSO-$d_6$) δ 12.45 (s, 1H), 8.42 (d, J=6.8 Hz, 1H), 8.19 (s, 1H), 7.92 (s, 1H), 6.77 (dd, $J_1$=10.4, $J_2$=16.8 Hz, 1H), 6.07 (dd, $J_1$=1.6, $J_2$=16.8 Hz, 1H), 5.66 (dd, $J_1$=2.4 Hz, $J_2$=10.8 Hz, 1H), 4.50 (br s, 2H), 4.03 (d, J=6.4 Hz, 2H), 3.93 (br s, 1H), 2.03-1.91 (m, 2H), 1.73-1.63 (m, 3H), 1.31-1.12 (m, 4H), 0.95 (d, J=6.8 Hz, 6H); MS (ES) m/z 386.2 (M+H).

EXAMPLE 17

Preparation of 1-((2S,5R)-5-((5-(cyclobutanecarbonyl)-7H-pyrrolo[2,3-d]pyrimidin-4-yl)amino)-2-methylpiperidin-1-yl)prop-2-en-1-one

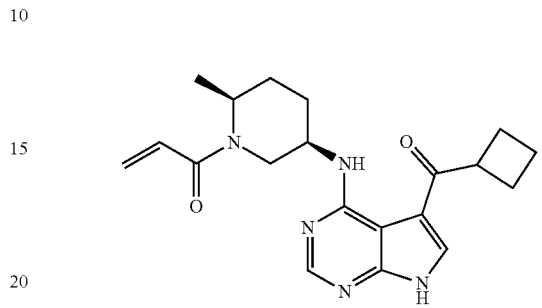

The title compound was made by the method described in Scheme 18.

Scheme 18.
Preparation of 1-((2S,5R)-5-((5-(cyclobutanecarbonyl)-7H-pyrrolo[2,3-d]pyrimidin-4-yl)amino)-2-methylpiperidin-1-yl)prop-2-en-1-one

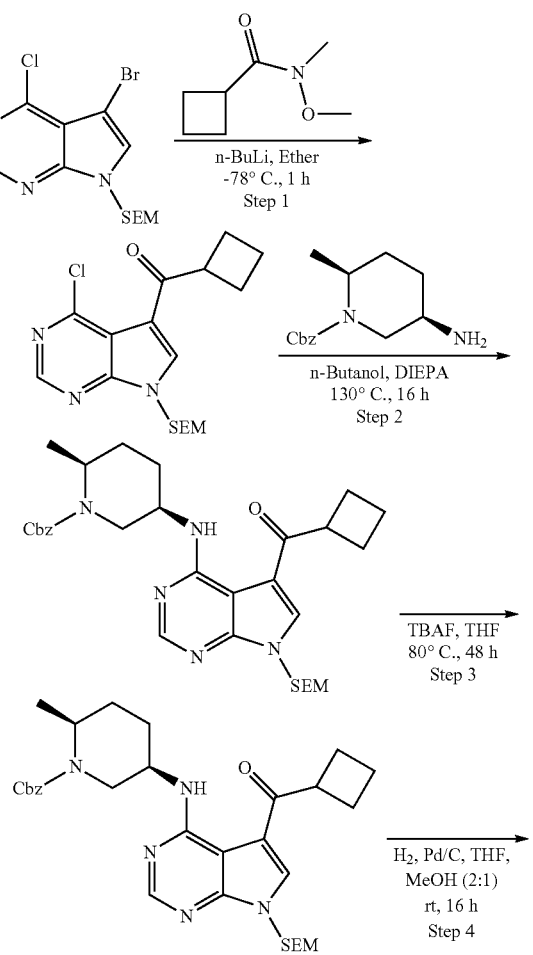

-continued

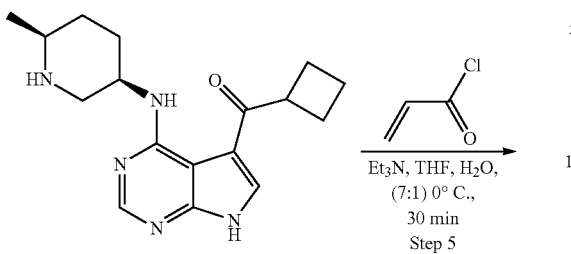

Step 1: Preparation of (4-chloro-7-((2-(trimethylsilyl)ethoxy)methyl)-7H-pyrrolo[2,3-d]pyrimidin-5-yl)(cyclobutyl)methanone

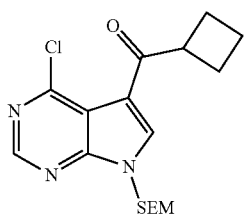 [SMILES: C[Si](C)(C)CCOCn1cc(C(=O)C2CCC2)c2c(Cl)ncnc21]

To a stirred solution of 5-bromo-4-chloro-7-((2-(trimethylsilyl)ethoxy)methyl)-7H-pyrrolo[2,3-d]pyrimidine (prepared by the method described in Example 7, 2 g, 5.52 mmol) in diethyl ether (30 mL) was added n-butyl lithium (6.9 mL, 11.04 mmol, 1.6 M in hexane) at −78° C. and stirred for 10 minutes. This was followed by addition of N-methoxy-N-methyl-cyclobutanecarboxamide (1.58 g, 11.04 mmol) in diethyl ether (5 mL) and the mixture stirred at same temperature for 1 hour. The reaction mixture was quenched with saturated aqueous ammonium chloride and extracted with diethyl ether (2×100 mL). The combined organic layers were washed with water, brine, dried over anhydrous sodium sulfate, filtered and concentrated in vacuo. The crude material was purified using flash chromatography (15% ethyl acetate/hexane) to provide (4-chloro-7-((2-(trimethylsilyl)ethoxy)methyl)-7H-pyrrolo[2,3-d]pyrimidin-5-yl)(cyclobutyl)methanone as a brown liquid (1.2 g, 60% yield): MS (ES) m/z 366.1 (M+H).

Step 2: Preparation of Benzyl (2S,5R)-5-((5-(cyclobutanecarbonyl)-7-((2-(trimethylsilyl)ethoxy)methyl)-7H-pyrrolo[2,3-d]pyrimidin-4-yl)amino)-2-methylpiperidine-1-carboxylate

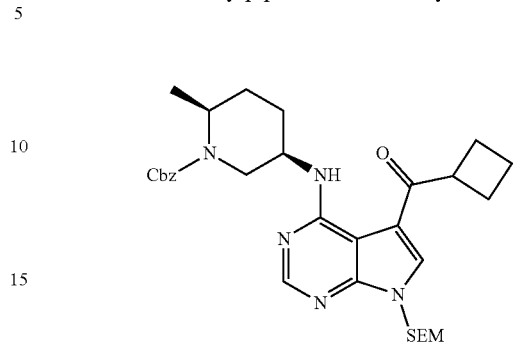

To a stirred solution of (4-chloro-7-((2-(trimethylsilyl)ethoxy)methyl)-7H-pyrrolo[2,3-d]pyrimidin-5-yl)(cyclobutyl)methanone (0.8 g, 2.19 mmol) in n-butanol (50 mL) was added diisopropylethylamine (1.2 mL, 6.57 mmol) followed by benzyl (2S,5R)-5-amino-2-methylpiperidine-1-carboxylate (0.65 g, 2.63 mmol) and the mixture was heated in a sealed tube at 130° C. for 16 hours. The reaction mixture was cooled to ambient temperature, concentrated in vacuo and the residue poured in water and extracted with ethyl acetate (2×100 mL). The combined organic layers were washed with brine, dried over sodium sulfate, filtered and concentrated in vacuo. The crude material was purified using flash chromatography (25% ethyl acetate/hexane) to provide benzyl (2S,5R)-5-((5-(cyclobutanecarbonyl)-7-((2-(trimethylsilyl) ethoxy)methyl)-7H-pyrrolo[2,3-d]pyrimidin-4-yl)amino)-2-methylpiperidine-1-carboxylate as a brown liquid (1.2 g, 95% yield): MS (ES) m/z 578.3 (M+H).

Step 3: Preparation of Benzyl (2S,5R)-5-((5-(cyclobutanecarbonyl)-7H-pyrrolo[2,3-d]pyrimidin-4-yl)amino)-2-methylpiperidine-1-carboxylate

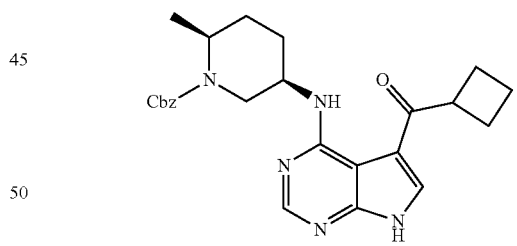

To a stirred solution of benzyl (2S,5R)-5-((5-(cyclobutanecarbonyl)-7-((2-(trimethylsilyl)ethoxy)methyl)-7H-pyrrolo[2,3-d]pyrimidin-4-yl)amino)-2-methylpiperidine-1-carboxylate (1.2 g, 2.07 mmol) in tetrahydrofuran (10 mL) was added tetrabutylammonium fluoride (21 mL, in 1 M in tetrahydrofuran) and the mixture was heated to 80° C. for 48 hours. The reaction mixture was cooled to ambient temperature and then concentrated in vacuo. The obtained residue was diluted with water and extracted with ethyl acetate (2×100 mL). The combined organic layers were washed with brine, dried over sodium sulfate, filtered and concentrated in vacuo. The crude material was purified by flash column chromatography (4% methanol/dichloromethane) to provide benzyl (2S,5R)-5-((5-(cyclobutanecarbonyl)-7H- pyrrolo[2,3-d]pyrimidin-4-yl)amino)-2-methylpiperidine-1-carboxylate as a yellow liquid (0.4 g, 43% yield): MS (ES) m/z 448.2 (M+H).

Step 4: Preparation of cyclobutyl(4-(((3R,6S)-6-methylpiperidin-3-yl)amino)-7H-pyrrolo[2,3-d]pyrimidin-5-yl)methanone

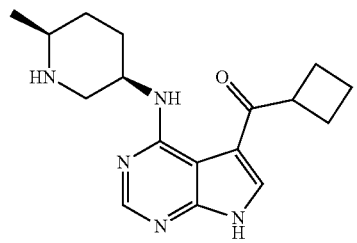 [SMILES: C[C@H]1CC[C@@H](Nc2ncnc3[nH]cc(C(=O)C4CCC4)c23)CN1]

To a stirred solution of benzyl (2S,5R)-5-((5-(cyclobutanecarbonyl)-7H-pyrrolo[2,3-d]pyrimidin-4-yl)amino)-2-methylpiperidine-1-carboxylate (0.35 g, 0.78 mmol) in tetrahydrofuran:methanol (10:5 mL) was added palladium on carbon (0.3 g, 10% wet w/w) under a nitrogen atmosphere. The mixture was stirred under a hydrogen atmosphere at ambient temperature for 16 hours. The reaction was filtered through celite and the filtrate was concentrated in vacuo to provide cyclobutyl(4-(((3R,6S)-6-methylpiperidin-3-yl)amino)-7H-pyrrolo[2,3-d]pyrimidin-5-yl)methanone as a pink liquid (0.18 g, 75% yield): MS (ES) m/z 314.2 (M+H).

Step 5: 1-((2S,5R)-5-((5-(cyclobutanecarbonyl)-7H-pyrrolo[2,3-d]pyrimidin-4-yl)amino)-2-methylpiperidin-1-yl)prop-2-en-1-one

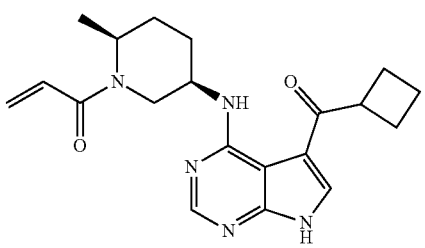 [SMILES: C=CC(=O)N1C[C@H](Nc2ncnc3[nH]cc(C(=O)C4CCC4)c23)CC[C@@H]1C]

To a stirred solution of cyclobutyl(4-(((3R,6S)-6-methylpiperidin-3-yl)amino)-7H-pyrrolo[2,3-d]pyrimidin-5-yl)methanone (0.18 g, 0.57 mmol) in tetrahydrofuran:water (10:4 mL) cooled to 0° C. was added triethylamine (0.24 mL, 1.72 mmol) followed by acryloyl chloride (0.05 g, 0.57 mmol) and stirred at 0° C. for 30 minutes. The reaction mixture was quenched with aqueous sodium bicarbonate and extracted with ethyl acetate (2×100 mL). The combined organic layers were washed with brine, dried over sodium sulfate, filtered and concentrated in vacuo. The crude material was purified using flash chromatography (3% methanol/dichloromethane) to provide 1-((2S,5R)-5-((5-(cyclobutanecarbonyl)-7H-pyrrolo[2,3-d]pyrimidin-4-yl)amino)-2-methylpiperidin-1-yl)prop-2-en-1-one as a pink solid (0.07 g, 33% yield): $^1$H NMR (400 MHz, DMSO-$d_6$) δ 12.47 (s, 1H), 9.05 (d, J=6.8 Hz, 1H), 8.13-8.17 (m, 2H), 6.75-6.81 (m, 1H), 6.05-6.09 (m, 1H), 5.64-5.67 (m, 1H), 4.51 (br s, 1H), 4.02-4.10 (m, 1H), 3.87-3.90 (m, 1H), 2.98-3.03 (m, 1H), 2.17-2.27 (m, 4H), 1.93-2.05 (m, 2H), 1.67-1.79 (m, 4H), 1.52-1.59 (m, 1H), 1.19 (d, J=6.4 Hz, 3H); MS (ES) m/z 368.3 (M+H).

EXAMPLE 18

Preparation of (R)-1-(3-((5-(cyclopropylmethyl)-7H-pyrrolo[2,3-d]pyrimidin-4-yl)amino)piperidin-1-yl)prop-2-en-1-one

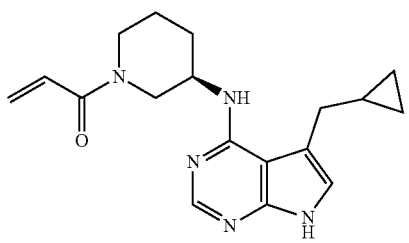 [SMILES: C=CC(=O)N1CCC[C@@H](Nc2ncnc3[nH]cc(CC4CC4)c23)C1]

The title compound was made by the method described in Scheme 19.

Scheme 19. Preparation of (R)-1-(3-((5-(cyclopropylmethyl)-7H-pyrrolo[2,3-d]pyrimidin-4-yl)amino)piperidin-1-yl)prop-2-en-1-one

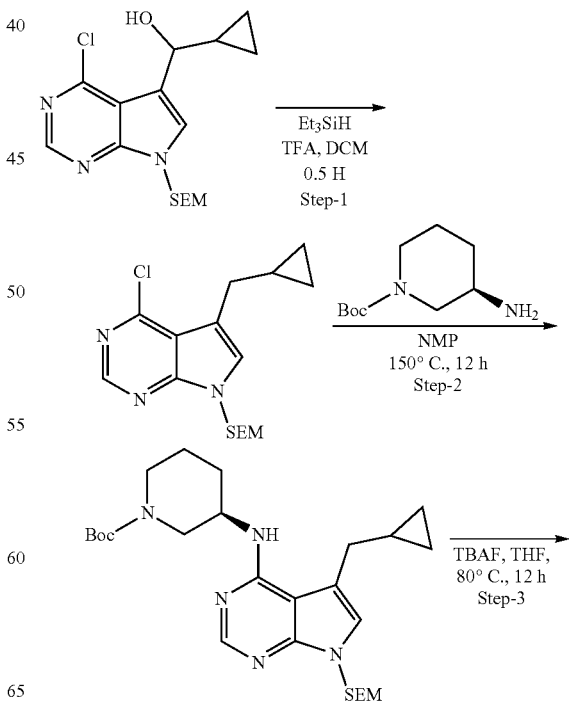

161

-continued

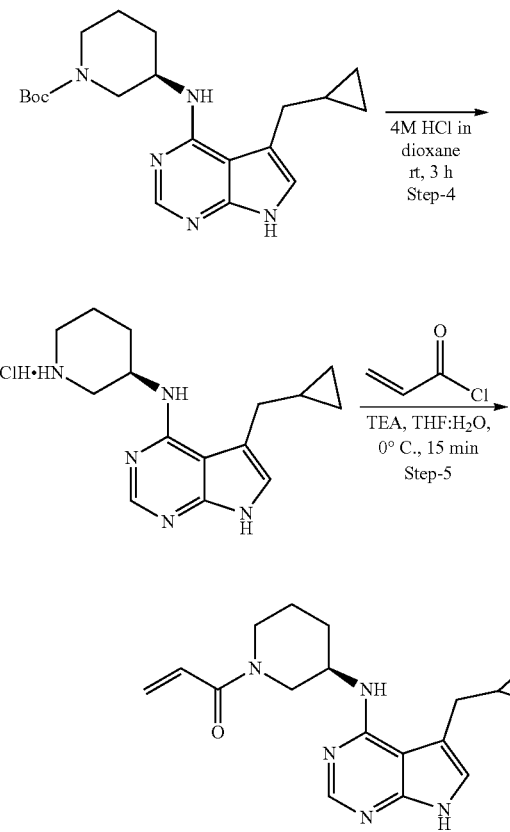

Step 1: Preparation of 4-chloro-5-(cyclopropylmethyl)-7-((2-(trimethylsilyl)ethoxy)methyl)-7H-pyrrolo[2,3-d]pyrimidine

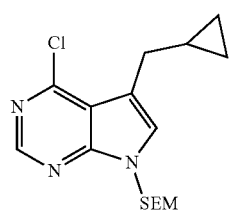 [SMILES: C[Si](C)(C)CCOCn1cc(CC2CC2)c2c(Cl)ncnc21]

To a stirred solution of 4-chloro-7-((2-(trimethylsilyl)ethoxy)methyl)-7H-pyrrolo[2,3-d]pyrimidin-5-yl)(cyclopropyl)methanol (prepared by the method described in Example 7, 3.1 g, 8.80 mmol) in dichloromethane (30 mL) was added trifluroacetic acid (3.39 mL, 44.04 mmol) and triethylsilane (4.22 mL, 26.42 mmol) at 0° C. The mixture was stirred at ambient temperature for 0.5 hours. The reaction mixture was quenched with saturated aqueous sodium bicarbonate and extracted with dichloromethane. The organic layer was washed with brine, dried over anhydrous sodium sulfate, filtered and concentrated in vacuo. The crude material was purified using flash chromatography (9% ethyl acetate/hexane) to provide 4-chloro-5-(cyclopropylmethyl)-7-((2-(trimethylsilyl)ethoxy)methyl)-7H-pyrrolo[2,3-d]pyrimidine as a pale yellow liquid (2.89 g, 88% yield): MS (ES) m/z 338.1 (M+H).

162

Step 2: Preparation of tert-butyl (R)-3-((5-(cyclopropylmethyl)-7-((2-(trimethylsilyl)ethoxy)methyl)-7H-pyrrolo[2,3-d]pyrimidin-4-yl)amino)piperidine-1-carboxylate

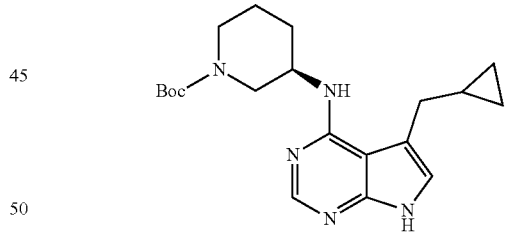

To a stirred solution of 4-chloro-5-(cyclopropylmethyl)-7-((2-(trimethylsilyl)ethoxy)methyl)-7H-pyrrolo[2,3-d]pyrimidine (2.89 g, 8.57 mmol) in N-methyl-2-pyrrolidone (10 mL) was added tert-butyl (R)-3-aminopiperidine-1-carboxylate (3.43 g, 1.71 mmol) and the mixture was heated in a sealed tube at 150° C. for 12 hours. The reaction mixture was cooled to room temperature, poured into water and extracted with ethyl acetate (2×100 mL). The combined organic layers were washed with brine, dried over anhydrous sodium sulfate, filtered and concentrated in vacuo. The crude material was purified using flash chromatography (30% ethyl acetate/hexane) to provide tert-butyl (R)-3-((5-(cyclopropylmethyl)-7-((2-(trimethylsilyl)ethoxy)methyl)-7H-pyrrolo[2,3-d]pyrimidin-4-yl)amino)piperidine-1-carboxylate as a pale yellow liquid (2.0 g, 62% yield): MS (ES) m/z 502.3 (M+H).

Step 3: Preparation of tert-butyl (R)-3-((5-(cyclopropylmethyl)-7H-pyrrolo[2,3-d]pyrimidin-4-yl)amino)piperidine-1-carboxylate To a stirred solution of tert-butyl (R)-3-((5-(cyclopropylmethyl)-7-((2-(trimethylsilyl)ethoxy)methyl)-7H-pyrrolo[2,3-d]pyrimidin-4-yl)amino)piperidine-1-carboxylate (2.0 g, 3.99 mmol) in tetrahydrofuran (5 mL) was added tetrabutylammonium fluoride (25 mL, 1 M in tetrahydrofuran) and the solution was heated to 80° C. for 12 hours. The reaction mixture was cooled to ambient temperature, poured into ice water and extracted with ethyl acetate. The organic layer was washed with water, brine, dried over anhydrous sodium sulfate, filtered and concentrated in vacuo. The crude material was purified using flash chromatography (66% ethyl acetate/hexane) to provide tert-butyl (R)-3-((5-(cyclopropylmethyl)-7H-pyrrolo[2,3-d]pyrimidin-4-yl)amino)piperidine-1-carboxylate as a pale yellow liquid (1.02 g, 68% yield): MS (ES) m/z 372.2 (M+H).

Step 4: Preparation of (R)-5-(cyclopropylmethyl)-N-(piperidin-3-yl)-7H-pyrrolo[2,3-d]pyrimidin-4-amine Hydrogen Chloride

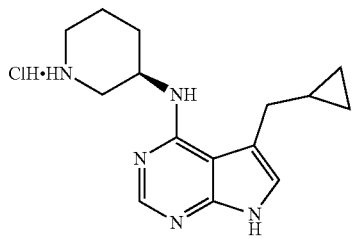

To a stirred solution of tert-butyl (R)-3-((5-(cyclopropylmethyl)-7H-pyrrolo[2,3-d]pyrimidin-4-yl)amino)piperidine-1-carboxylate (1 g, 2.69 mmol) in dichloromethane (10 mL) was added hydrogen chloride (5 mL, 4 M in dioxane) at 0° C. and the mixture was stirred at ambient temperature for 3 hours. The reaction mixture was concentrated in vacuo and the residue was washed with diethyl ether to provide (R)-5-(cyclopropylmethyl)-N-(piperidin-3-yl)-7H-pyrrolo[2,3-d]pyrimidin-4-amine hydrogen chloride as a white solid (1 g, crude): MS (ES) m/z 272.4 (M+H).

Step 5: Preparation of (R)-1-(3-((5-(cyclopropylmethyl)-7H-pyrrolo[2,3-d]pyrimidin-4-yl)amino)piperidin-1-yl)prop-2-en-1-one

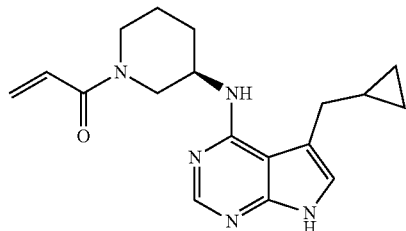

To a solution of ((R)-5-(cyclopropylmethyl)-N-(piperidin-3-yl)-7H-pyrrolo[2,3-d]pyrimidin-4-amine hydrogen chloride (0.35 g, 1.15 mmol) in tetrahydrofuran:water (7:3 mL) was added triethylamine (0.485 mL, 3.45 mmol) followed by addition of acryloyl chloride (0.114 g, 1.26 mmol) at 0° C. and the solution was for 15 minutes. The reaction mixture was quenched with saturated aqueous sodium bicarbonate and extracted with ethyl acetate (2×100 mL). The combined organic layers were washed with brine, dried over anhydrous sodium sulfate, filtered and concentrated in vacuo. The crude material was purified using flash chromatography (6% methanol/dichloromethane) and further purified by using prep HPLC to provide (R)-1-(3-((5-(cyclopropylmethyl)-7H-pyrrolo[2,3-d]pyrimidin-4-yl)amino)piperidin-1-yl)prop-2-en-1-one as a colorless semisolid (0.030 g, 8% yield): $^1$H NMR (400 MHz, DMSO-$d_6$, at 80° C.) δ 11.07 (br s, 1H), 8.07 (s, 1H), 6.87 (s, 1H), 6.60-6.80 (m, 1H), 6.38 (d, J=16.3 Hz, 1H), 5.62 (d, J=11.18 Hz, 1H), 5.45-5.55 (m, 1H), 4.17-4.32 (m, 1H), 3.40-3.94 (m, 1H), 3.15-3.82 (m, 1H), 3.40-3.47 (m, 1H), 3.28-3.38 (m, 1H), 2.71 (d, J=5.99 Hz, 2H), 1.92-2.05 (m, 1H), 1.82-1.90 (m, 1H), 1.67-1.80 (m, 1H), 1.48-1.60 (m, 1H), 0.95-1.05 (m, 1H), 0.46 (d, J=7.59 Hz, 2H), 0.13 (d, J=3.99 Hz, 2H); MS (ES) m/z 326.1 (M+H).

Prep HPLC method:
Column: Inertsil ODS 3V (250 mm×4.6 mm×5 mic)
Mobile phase (A): 0.1% Ammonia in water
Mobile phase (B): ACN
Flow rate: 1.0 mL/min

EXAMPLE 19

Preparation of (R)-1-(3-((3-(cyclopropylmethyl)-1H-pyrrolo[2,3-b]pyridin-4-yl)amino)piperidin-1-yl)prop-2-en-1-one

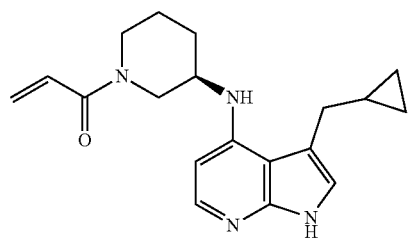 [SMILES: C=CC(=O)N1CCC[C@@H](Nc2ccnc3[nH]cc(CC4CC4)c23)C1]

The title compound was prepared by the method described in Scheme 20.

Scheme 20. Preparation of (R)-1-(3-((3-(cyclopropylmethyl)-1H-pyrrolo[2,3-b]pyridin-4-yl)amino)piperidin-1-yl)prop-2-en-1-one

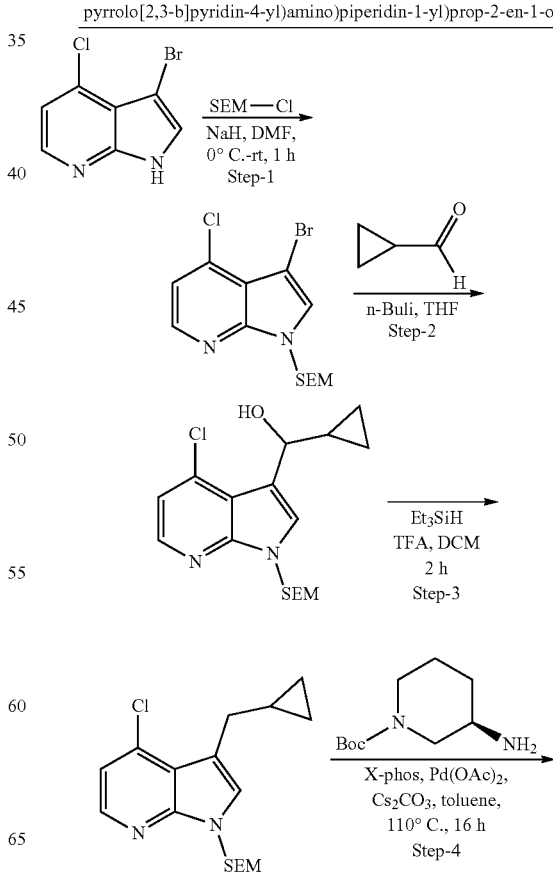

-continued

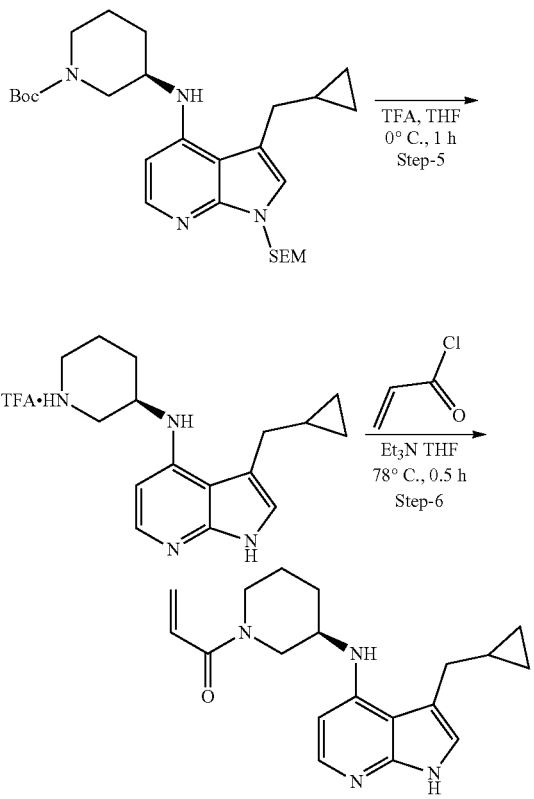

Step 1: Preparation of 3-bromo-4-chloro-1-((2-(trimethylsilyl)ethoxy)methyl)-1H-pyrrolo[2,3-b]pyridine

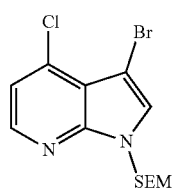

To a suspension of sodium hydride (0.22 g, 5.19 mmol) in N,N-dimethylformamide (15 mL) was added 3-bromo-4-chloro-1H-pyrrolo[2,3-b]pyridine (1.0 g, 4.32 mmol) at 0° C. and the suspension was stirred at ambient temperature for 0.5 hours. The mixture was cooled to 0° C. and (2-chloromethoxyethyl)trimethylsilane (0.92 mL, 5.19 mmol) was added. The reaction mixture was allowed to warm to ambient temperature and stir for 1 hour. The reaction mixture was quenched with ice and extracted with ethyl acetate. The organic layer was washed with water, brine, dried over anhydrous sodium sulfate, filtered and concentrated in vacuo. The crude material was purified using flash chromatography (5% ethyl acetate/hexane) to provide 3-bromo-4-chloro-1-((2-(trimethylsilyl)ethoxy)methyl)-1H-pyrrolo[2,3-b]pyridine as a viscous oil (1.5 g, 95% yield): MS (ES) m/z 362.0 (M+H).

Step 2: Preparation of (4-chloro-1-((2-(trimethylsilyl)ethoxy)methyl)-1H-pyrrolo[2,3-b]pyridin-3-yl)(cyclopropyl)methanol To a stirred solution of 3-bromo-4-chloro-1-((2-(trimethylsilyl)ethoxy)methyl)-1H-pyrrolo[2,3-b]pyridine (prepared by the method described in example 5, 1.6 g, 4.4 mmol) in tetrahedrafuran (50 mL) was added n-butyllithium (0.37 g, 5.2 mmol, 1.6 M in hexane) at −78° C. and stirred for 30 minutes. Then a solution of cyclopropanecarbaldehyde (0.34 g, 5.3 mmol) in tetrahedrafuran (3 mL) was added at −78° C. and stirred for 2 hours. The reaction mixture was quenched with saturated aqueous ammonium chloride and extracted with diethyl ether (2×100 mL). The combined organic layers were washed with water, brine, dried over anhydrous sodium sulfate, filtered and concentrated in vacuo. The crude material was purified using flash chromatography (20% ethyl acetate/hexane) to provide (4-chloro-1-((2-(trimethylsilyl)-ethoxy)methyl)-1H-pyrrolo[2,3-b]pyridin-3-yl)(cyclopropyl)-methanol as a colorless liquid (0.35 g, 23% yield). MS (ES) m/z 353.1 (M+H).

Step 3: Preparation of 4-chloro-3-(cyclopropylmethyl)-1-((2-(trimethylsilyl)ethoxy)methyl)-1H-pyrrolo[2,3-b]pyridine To a stirred solution of (4-chloro-1-((2-(trimethylsilyl)ethoxy)methyl)-1H-pyrrolo[2,3-b]pyridin-3-yl)(cyclopropyl)methanol (0.3 g, 0.85 mmol) in dichloromethane (4 mL) was added trifluoroacetic acid (0.6 mL, 5.6 mmol) followed by the addition of triethylsilane (0.4 mL, 3.4 mmol) and the mixture was stirred at ambient temperature for 2 hours. The reaction mixture was quenched with ice cold water and extracted with ethyl acetate. The organic layer was washed with water, brine, dried over anhydrous sodium sulfate, filtered and concentrated in vacuo. The crude material was purified using flash chromatography (30% ethyl acetate/hexane) to provide 4-chloro-3-(cyclopropylmethyl)-1-((2-(trimethylsilyl)ethoxy)methyl)-1H-pyrrolo[2,3-b]pyridine as a colorless liquid (0.21 g, 75% yield): MS (ES) m/z 337 (M+H).

Step 4: Preparation of tert-butyl (R)-3-((3-(cyclopropylmethyl)-1-((2-(trimethylsilyl)ethoxy)methyl)-1H-pyrrolo[2,3-b]pyridin-4-yl)amino)piperidine-1-carboxylate

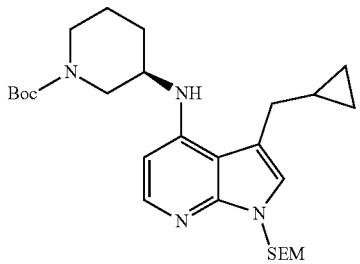 [SMILES: CC(C)(C)OC(=O)N1CCC[C@@H](Nc2ccnc3c2c(CC2CC2)cn3COCC[Si](C)(C)C)C1]

To a stirred solution of 4-chloro-3-(cyclopropylmethyl)-1-((2-(trimethylsilyl)ethoxy)methyl)-1H-pyrrolo[2,3-b]pyridine (0.2 g, 0.59 mmol) in toluene (5 mL) was added tert-butyl (R)-3-aminopiperidine-1-carboxylate (0.178 g, 0.89 mmol), 2-dicyclohexylphosphino-2',4',6'-triisopropylbiphenyl (0.028 g, 0.89 mmol), cesium carbonate (0.582 g, 1.78 mmol) and palladium(II) acetate (0.013 g, 0.057 mmol) under an argon atmosphere and the resulting mixture was heated to 110° C. for 16 hours. The reaction mixture was cooled to ambient temperature, filtered through celite and the filtrate was concentrated in vacuo. The crude material was purified using flash chromatography (40% ethyl acetate/hexane) to provide tert-butyl (R)-3-((5-(cyclopropylmethyl)-7-((2-(trimethylsilyl)ethoxy)methyl)-7H-pyrrolo[2,3-d]pyrimidin-4-yl)amino)piperidine-1-carboxylate as a colorless liquid (0.2 g, 90% yield): MS (ES) m/z 501.3 (M+H).

Step 5: Preparation of tert-butyl (R)-3-((3-(cyclopropylmethyl)-1H-pyrrolo[2,3-b]pyridin-4-yl)amino)piperidine-1-carboxylate

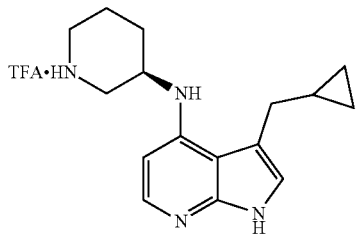

To a stirred solution of tert-butyl (R)-3-((5-(cyclopropylmethyl)-7-((2-(trimethylsilyl)ethoxy)methyl)-7H-pyrrolo[2,3-d]-pyrimidin-4-yl)amino)piperidine-1-carboxylate (0.2 g, 0.4 mmol) in tetrahydrofuran (5 mL) was added trifluoroacetic acid (0.3 mL) at 0° C. and the mixture was stirred at ambient temperature for 1 hour. The reaction mixture was concentrated in vacuo and the residue was dissolved in water and basified with saturated sodium bicarbonate whereupon the oil was separated which was extracted with ethyl acetate. The organic layer was washed with water, brine, dried over anhydrous sodium sulfate, filtered and concentrated in vacuo. The crude material was purified by flash chromatography (40% ethyl acetate/hexane) to provide (R)-3-(cyclopropylmethyl)-N-(piperidin-3-yl)-1H-pyrrolo[2,3-b]pyridin-4-amine as a colorless liquid (0.16 g, 68% yield): MS (ES) m/z 271.2 (M+H).

Step 6: Preparation of (R)-1-(3-((3-(cyclopropylmethyl)-1H-pyrrolo[2,3-b]pyridin-4-yl)amino)piperidin-1-yl)prop-2-en-1-one

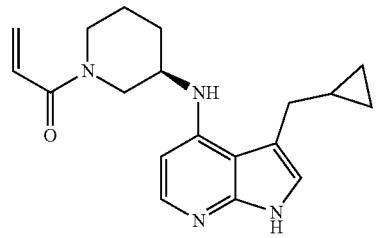 [SMILES: C=CC(=O)N1CCC[C@@H](Nc2ccnc3[nH]cc(CC4CC4)c23)C1]

To a stirred solution of (R)-3-(cyclopropylmethyl)-N-(piperidin-3-yl)-1H-pyrrolo[2,3-b]pyridin-4-amine (0.1 g, 0.37 mmol) in tetrahydrofuran:water (8:2 mL) was added triethylamine (0.1 ml, 0.33 mmol) followed by a solution of acryloyl chloride (0.03 ml, 0.33 mmol) in tetrahydrofuran (0.2 mL) at 0° C. and stirred for 0.5 hours. The reaction mixture was quenched with saturated aqueous sodium bicarbonate and extracted with ethyl acetate. The organic layer was washed with water, brine, dried over anhydrous sodium sulfate, filtered and concentrated in vacuo. The crude material was purified using flash chromatography (50% ethyl acetate/hexane) to provide (R)-1-(3-((3-(cyclopropylmethyl)-1H-pyrrolo[2,3-b]pyridin-4-yl)amino)piperidin-1-yl)prop-2-en-1-one as a white solid (0.03 g, 22% yield): $^1$H NMR (400 MHz, DMSO-$d_6$, at 90° C.) δ 10.67 (br s, 1H), 7.72-7.74 (d, J=8 Hz, 1H), 6.68-6.72 (m, 1H), 6.29 (s, 1H), 6.16-6.17 (m, 1H), 6.03-6.16 (m, 2H), 5.79-5.81 (m, 1H), 5.59-5.62 (d, J=12 Hz, 1H), 4.01 (br s, 1H), 3.49-3.56 (m, 1H), 2.56-2.65 (m, 1H), 2.53-2.56 (m, 3H) 2.05 (m, 1H), 1.64-1.78 (m, 1H), 1.55-1.59 (m, 2H), 1.50 (s, 1H), 1.25 (s, 1H), 1.07-1.08 (d, 1H), 0.47-0.49 (d, J=8 Hz, 1H), 0.20-0.21 (d, J=4 Hz, 1H); MS (ES) m/z 325.1 (M+H).

EXAMPLE 20

Preparation of (R)-1-(3-((5-(cyclobutylmethyl)-7H-pyrrolo[2,3-d]pyrimidin-4-yl)amino)piperidin-1-yl)prop-2-en-1-one

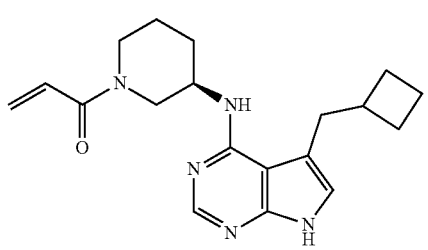 [SMILES: C=CC(=O)N1CCC[C@@H](Nc2ncnc3[nH]cc(CC4CCC4)c23)C1]

The title compound was prepared by the method described in Scheme 21.

Scheme 21. Preparation of (R)-1-(3-((5-cyclobutylmethyl)-7H-pyrrolo[2,3-d]pyrimidin-4-yl)amino)piperidin-1-yl)prop-2-en-1-one

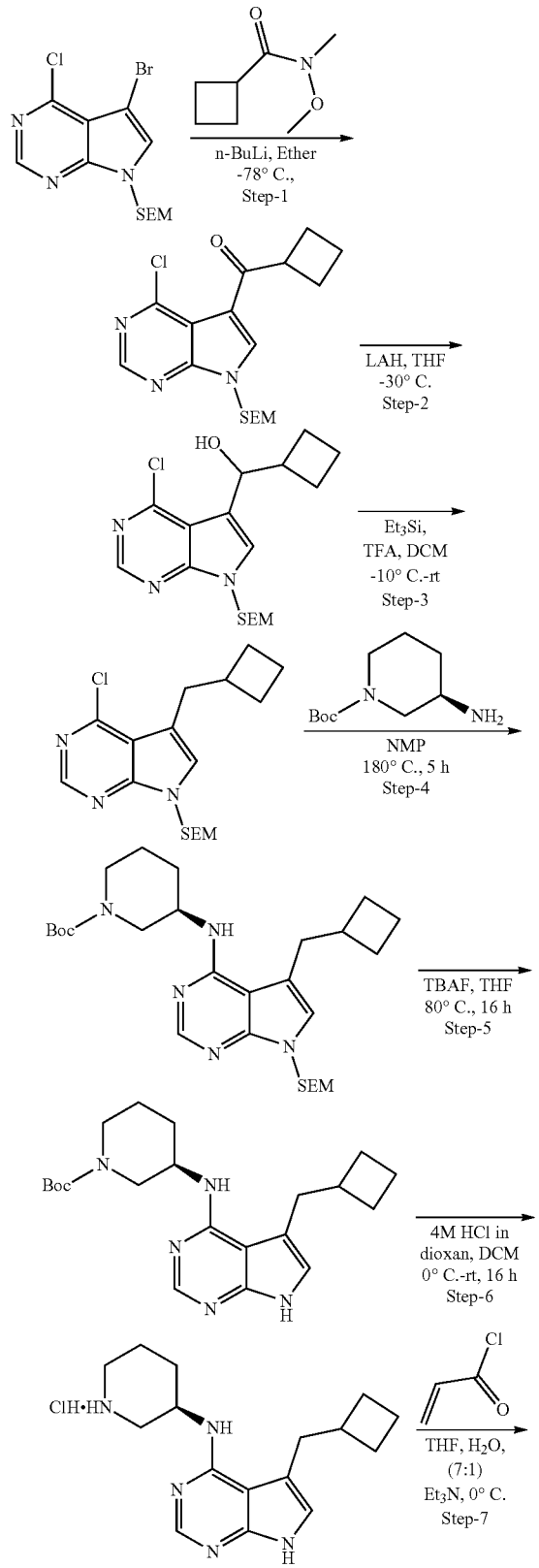

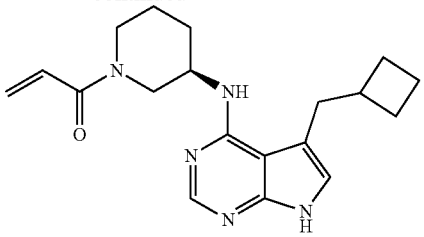

Step 1: Preparation of (4-chloro-7-((2-(trimethylsilyl)ethoxy)methyl)-7H-pyrrolo[2,3-d]pyrimidin-5-yl)(cyclobutyl)methanone

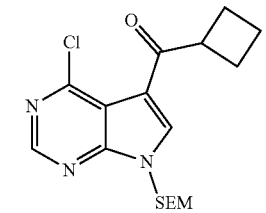 [SMILES: C[Si](C)(C)CCOCn1cc(C(=O)C2CCC2)c2c(Cl)ncnc21]

To a stirred solution of 5-bromo-4-chloro-7-((2-(trimethylsilyl)ethoxy)methyl)-7H-pyrrolo[2,3-d]pyrimidine (prepared by the method described in Example 7, 2 g, 5.52 mmol) in diethyl ether (30 mL) was added n-butyl lithium (6.9 mL, 11.04 mmol, 1.6 M in hexane) at −78° C. and stirred for 10 minutes. Then a solution of N-methoxy-N-methylcyclobutanecarboxamide (1.58 g, 11.04 mmol, prepared by the method described in Example 101) in diethyl ether (5 mL) was added and the reaction mixture was stirred for 1 hour at −78° C. The reaction was quenched with saturated aqueous ammonium chloride and extracted with diethyl ether (2×100 mL). The combined organic layers were washed with water, brine, dried over anhydrous sodium sulfate, filtered and concentrated in vacuo. The crude material was purified using flash chromatography (15% ethyl acetate/hexane) to provide (4-chloro-7-((2-(trimethylsilyl)ethoxy)methyl)-7H-pyrrolo[2,3-d]pyrimidin-5-yl)(cyclobutyl)methanone as a brown liquid (1.2 g, 60% yield): MS (ES) m/z 366.1 (M+H).

Step 2: Preparation of (4-chloro-7-((2-(trimethylsilyl)ethoxy)methyl)-7H-pyrrolo[2,3-d]pyrimidin-5-yl)(cyclobutyl)methanol

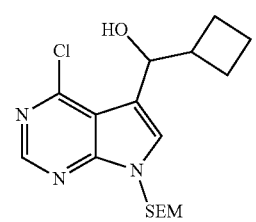 [SMILES: C[Si](C)(C)CCOCn1cc(C(O)C2CCC2)c2c(Cl)ncnc21]

To a stirred solution of (4-chloro-7-((2-(trimethylsilyl)ethoxy)methyl)-7H-pyrrolo[2,3-d]pyrimidin-5-yl)(cyclobutyl)methanone (1.1 g, 3.00 mmol) in tetrahydrofuran (30 mL) was added lithium aluminium hydride (3.97 mL, 3.90 mmol, 1 M in tetrahydrofuran) at −30° C. and the mixture stirred for 1 hour. The reaction mixture was quenched with ice cold water and extracted with ethyl acetate. The organic layer was washed with water, brine, dried over sodium sulfate, filtered and concentrated in vacuo. The crude material was purified using flash chromatography (25% ethyl acetate/hexane) to provide (4-chloro-7-((2-(trimethylsilyl)ethoxy)methyl)-7H-pyrrolo[2,3-d]pyrimidin-5-yl)(cyclobutyl)methanol as a brown liquid (0.9 g, 82% yield): $^1$H NMR (400 MHz, DMSO-d$_6$) δ 8.60 (s, 1H), 7.65 (s, 1H), 5.55-5.67 (m, 2H), 5.13-5.14 (m, 1H), 5.02-5.05 (m, 1H), 3.48 (t, J=7.6 Hz, 2H), 2.71-2.78 (m, 1H), 1.95-2.01 (m, 1H), 1.71-1.82 (m, 5H), 0.76-0.83 (m, 2H), 0.10 (s, 9H); MS (ES) m/z 368.1 (M+H).

Step 3: Preparation of 4-chloro-5-(cyclobutylmethyl)-7-((2-(trimethylsilyl)ethoxy)methyl)-7H-pyrrolo[2,3-d]pyrimidine

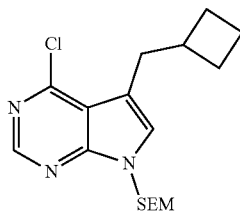

To a stirred solution (4-chloro-7-((2-(trimethylsilyl)ethoxy)methyl)-7H-pyrrolo[2,3-d]pyrimidin-5-yl)(cyclobutyl)methanol (0.85 g, 2.31 mmol) in dichloromethane (10 mL) was added triethylsilane (1.5 mL, 9.26 mmol) followed by trifluoroacetic acid (1.4 mL, 18.52 mmol) at −30° C. and the mixture was stirred at −10° C. for 1 hour. The reaction mixture was quenched with saturated aqueous sodium bicarbonate and extracted with dichloromethane (3×100 mL). The combined organic layers were washed with brine, dried over anhydrous sodium sulfate, filtered and concentrated in vacuo. The crude material was purified using flash chromatography (12% ethyl acetate/hexane) to provide 4-chloro-5-(cyclobutylmethyl)-7-((2-(trimethylsilyl)ethoxy)methyl)-7H-pyrrolo[2,3-d]pyrimidine as a brown liquid (0.7 g, 86% yield): $^1$H NMR (400 MHz, DMSO-d$_6$) δ 8.58 (s, 1H), 7.56 (s, 1H), 5.57 (s, 2H), 3.47 (t, J=8 Hz, 2H), 2.61-2.68 (m, 1H), 1.99-2.05 (m, 2H), 1.76-1.88 (m, 2H), 1.64-1.72 (m, 2H), 0.87 (t, J=8 Hz, 2H), 0.77 (t, J=8 Hz, 2H), 0.10 (s, 9H); MS (ES) m/z 352.1 (M+H).

Step 4: Preparation of tert-butyl (R)-3-((5-(cyclobutylmethyl)-7-((2-(trimethylsilyl)ethoxy)methyl)-7H-pyrrolo[2,3-d]pyrimidin-4-yl)amino)piperidine-1-carboxylate

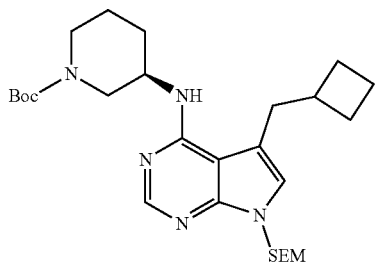 [SMILES: CC(C)(C)OC(=O)N1CCC[C@@H](Nc2ncnc3c2c(CC2CCC2)cn3COCC[Si](C)(C)C)C1]

To a stirred solution of 4-chloro-5-(cyclobutylmethyl)-7-((2-(trimethylsilyl)ethoxy)methyl)-7H-pyrrolo[2,3-d]pyrimidine (0.7 g, 1.99 mmol) in N-methyl-2-pyrrolidone (8 mL) was added tert-butyl (R)-3-aminopiperidine-1-carboxylate (0.47 g, 2.39 mmol) and the mixture was heated in a sealed tube at 180° C. for 5 hours. The reaction mixture was cooled to room temperature, poured into water and extracted with ethyl acetate (2×100 mL). The combined organic layers were washed with brine, dried over sodium sulfate, filtered and concentrated in vacuo. The crude material was purified using flash chromatography (20% ethyl acetate/hexane) to provide tert-butyl (R)-3-((5-(cyclobutylmethyl)-7-((2-(trimethylsilyl)ethoxy)methyl)-7H-pyrrolo[2,3-d]pyrimidin-4-yl)amino)piperidine-1-carboxylate as a yellow liquid (0.6 g, 60% yield): MS (ES) m/z 516.3 (M+H).

Step 5: Preparation of tert-butyl (R)-3-((5-(cyclobutylmethyl)-7H-pyrrolo[2,3-d]pyrimidin-4-yl)amino)piperidine-1-carboxylate

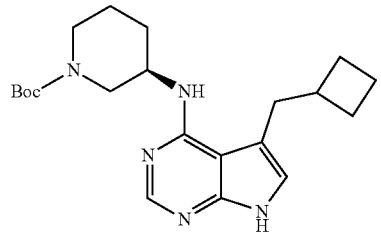 [SMILES: CC(C)(C)OC(=O)N1CCC[C@@H](Nc2ncnc3[nH]cc(CC4CCC4)c23)C1]

To a stirred solution of tert-butyl (R)-3-((5-(cyclobutylmethyl)-7-((2-(trimethylsilyl)ethoxy)methyl)-7H-pyrrolo[2,3-d]pyrimidin-4-yl)amino)piperidine-1-carboxylate (0.6 g, 0.82 mmol) in tetrahydrofuran (2 mL) was added tetrabutylammonium fluoride (11.6 mL, 1 M in tetrahydrofuran) and the solution was heated to 80° C. for 16 hours. The reaction was poured into ice water and extracted with ethyl acetate. The organic layer was washed with water, brine, dried over anhydrous sodium sulfate, filtered and concentrated in vacuo. The crude material was purified using flash chromatography (4% methanol/dichloromethane) to provide tert-butyl (R)-3-((5-(cyclobutylmethyl)-7H-pyrrolo[2,3-d]pyrimidin-4-yl)-amino)piperidine-1-carboxylate as a yellow liquid (0.32 g, 73% yield): MS (ES) m/z 386.2 (M+H).

Step 6: Preparation of (R)-5-(cyclobutylmethyl)-N-(piperidin-3-yl)-7H-pyrrolo[2,3-d]pyrimidin-4-amine Hydrochloride

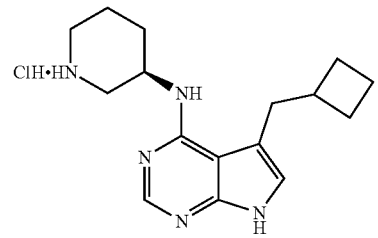

To a stirred solution of tert-butyl (R)-3-((5-(cyclobutylmethyl)-7H-pyrrolo[2,3-d]pyrimidin-4-yl)amino)piperidine-1-carboxylate (0.32 g, 0.83 mmol) in dichloromethane (3 mL) was added a hydrogen chloride solution (2 mL, 8.31 mmol, 4 M in dioxane) at 0° C. and the mixture was stirred at ambient temperature for 16 hours. The reaction was concentrated in vacuo to dryness to provide (R)-5-(cyclobutylmethyl)-N-(piperidin-3-yl)-7H-pyrrolo[2,3-d]pyrimidin-4-amine hydrochloride as a yellow solid (0.2 g, 77% yield): MS (ES) m/z 286.2 (M+H).

Step-7: Preparation of (R)-1-(3-((5-(cyclobutylmethyl)-7H-pyrrolo[2,3-d]pyrimidin-4-yl)amino)piperidin-1-yl)prop-2-en-1-one

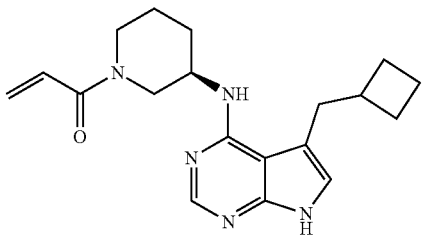 [SMILES: C=CC(=O)N1CCC[C@@H](Nc2ncnc3[nH]cc(CC4CCC4)c23)C1]

To a stirred solution of (R)-5-(cyclobutylmethyl)-N-(piperidin-3-yl)-7H-pyrrolo[2,3-d]pyrimidin-4-amine hydrochloride (0.2 g, 0.62 mmol) in tetrahydrofuran:water (7:3 mL) was added triethylamine (0.26 mL, 1.86 mmol) followed by a solution of acryloyl chloride (0.05 g, 0.49 mmol) in tetrahydrofuran (0.5 mL) at 0° C. and the mixture stirred for 15 minutes. The reaction was quenched with sodium bicarbonate and extracted with ethyl acetate (2×100 mL). The combined organic layers were washed with brine, dried over anhydrous sodium sulfate, filtered and concentrated in vacuo. The crude material was purified using flash chromatography (3% methanol/dichloromethane) followed by purification using prep HPLC to provide (R)-1-(3-((5-(cyclobutylmethyl)-7H-pyrrolo[2,3-d]pyrimidin-4-yl)amino)piperidin-1-yl)prop-2-en-1-one as a white solid (0.02 g, 7% yield): $^1$H NMR (400 MHz, DMSO-d$_6$, at 90° C.) δ 11.06 (s, 1H), 8.07 (s, 1H), 6.68-6.74 (m, 2H), 6.04-6.08 (m, 1H), 5.59-5.61 (m, 1H), 5.44 (br s, 1H), 4.24 (br s, 1H), 3.89-3.93 (m, 1H), 3.67-3.69 (m, 1H), 3.40-3.48 (m, 1H), 3.49-3.51 (m, 1H), 2.80-2.84 (m, 2H), 2.52-2.59 (m, 1H), 1.95-2.05 (m, 3H), 1.78-1.86 (m, 3H), 1.63-1.71 (m, 3H), 1.51-1.57 (m, 1H); MS (ES) m/z 340.1 (M+H).

Prep HPLC method:
Column: Inertsil ODS 3V (250 mm×4.6 mm×5 mic)
Mobile phase (A): 0.1% Ammonia in water
Mobile phase (B): Methanol
Flow rate: 1.0 mL/min(30:70)
Retention time 3.22 min.

EXAMPLE 21

Preparation of 1-((3R)-3-((5-(1-cyclopropylethyl)-7H-pyrrolo[2,3-d]pyrimidin-4-yl)amino)piperidin-1-yl)prop-2-en-1-one

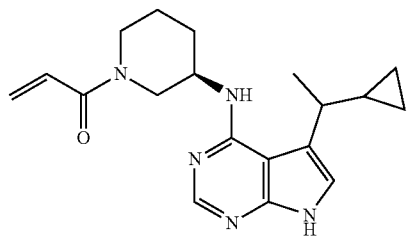 [SMILES: C=CC(=O)N1CCC[C@@H](Nc2ncnc3[nH]cc(C(C)C4CC4)c23)C1]

The title compound was prepared by the method described in Scheme 22.

Scheme 22. Preparation of 1-((3R)-3-((5-(1-cyclopropylethyl)-7H-pyrrolo[2,3-d]pyrimidin-4-yl)amino)piperidin-1-yl)prop-2-en-1-one

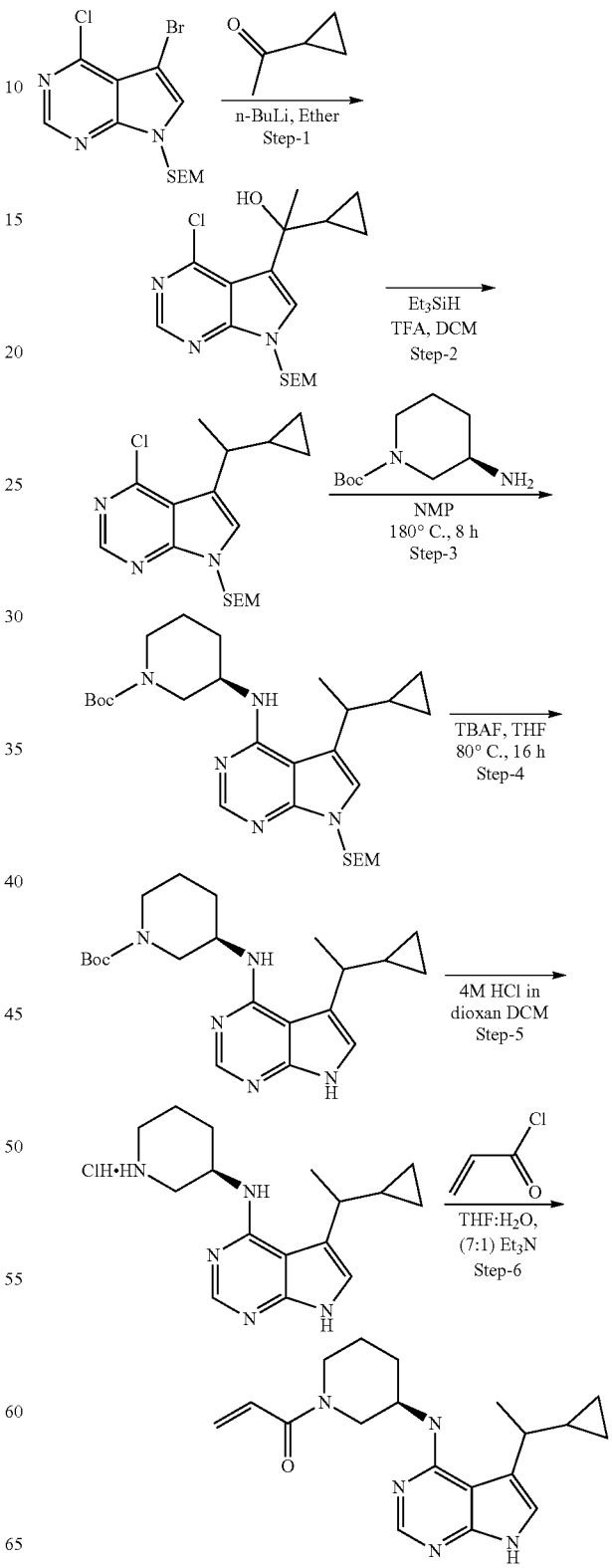

Step 1: Preparation of 1-(4-chloro-7-((2-(trimethylsilyl)ethoxy)methyl)-7H-pyrrolo[2,3-d]pyrimidin-5-yl)-1-cyclopropylethan-1-ol

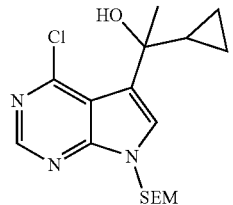 [SMILES: CC(O)(c1cn(COCC[Si](C)(C)C)c2ncnc(Cl)c12)C1CC1]

To a stirred solution of 5-bromo-4-chloro-7-((2-(trimethylsilyl)ethoxy)methyl)-7H-pyrrolo[2,3-d]pyrimidine (prepared by the method described in Example 7, 3 g, 8.287 mmol) in diethyl ether (100 mL) was added n-butyllithium (10.3 mL, 16.57 mmol, 1.6 M in hexane) at −78° C. and the solution was stirred for 10 minutes. Then a solution of 1-cyclopropylethan-1-one (1.3 g, 16.57 mmol) in diethyl ether (10 mL) was added and the resulting mixture stirred at −78° C. for 1 hour. The reaction mixture was quenched with saturated aqueous ammonium chloride and extracted with diethyl ether (2×100 mL). The combined organic layers were washed with water, brine, dried over anhydrous sodium sulfate, filtered and concentrated in vacuo. The crude material was purified using flash chromatography (18% ethyl acetate/hexane) to provide 1-(4-chloro-7-((2-(trimethylsilyl)ethoxy)methyl)-7H-pyrrolo[2,3-d]pyrimidin-5-yl)-1-cyclopropylethan-1-ol as a yellow liquid (2.2 g, 73% yield): $^1$H NMR (400 MHz, DMSO-$d_6$) δ 8.60 (s, 1H), 7.70 (s, 1H), 5.60 (s, 2H), 4.63 (s, 1H), 3.50 (t, J=8 Hz, 2H), 1.66 (s, 3H), 1.58-1.62 (m, 1H), 0.79 (t, J=7.68 Hz, 2H), 0.23-0.49 (m, 4H), 0.11 (s, 9H); MS (ES) m/z 368.1 (M+H).

Step 2: Preparation of 4-chloro-5-(1-cyclopropylethyl)-7-((2-(trimethylsilyl)ethoxy)methyl)-7H-pyrrolo[2,3-d]pyrimidine

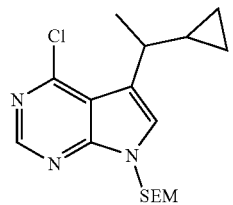 [SMILES: CC(c1cn(COCC[Si](C)(C)C)c2ncnc(Cl)c12)C1CC1]

To a stirred solution 1-(4-chloro-7-((2-(trimethylsilyl)ethoxy)methyl)-7H-pyrrolo[2,3-d]pyrimidin-5-yl)-1-cyclopropylethan-1-ol (2.2 g, 5.99 mmol) in dichloromethane (50 mL) was added triethylsilane (3.8 mL, 2.97 mmol) at −30° C., followed by an addition of trifluoroacetic acid (3.6 mL, 47.95 mmol) and the resulting mixture was stirred at −20° C. for 1 hour. The reaction mixture was quenched with saturated aqueous sodium bicarbonate and extracted with dichloromethane (3×100 mL). The combined organic layers were washed with water, brine, dried over anhydrous sodium sulfate, filtered and concentrated in vacuo. The crude material was purified using flash chromatography (8% ethyl acetate/hexane) to provide 4-chloro-5-(1-cyclopropylethyl)-7-((2-(trimethylsilyl)ethoxy)methyl)-7H-pyrrolo[2,3-d]pyrimidine as a colorless liquid (2 g, 95% yield): $^1$H NMR (400 MHz, DMSO-$d_6$) δ 8.59 (s, 1H), 7.72 (s, 1H), 5.60 (s, 2H), 3.50 (t, J=8 Hz, 2H), 2.74-2.79 (m, 1H), 1.32 (d, J=6.4 Hz, 3H), 1.01-1.14 (m, 1H), 0.87 (t, J=8 Hz, 2H), 0.37-0.58 (m, 4H), 0.10 (s, 9H); MS (ES) m/z 352.1 (M+H).

Step 3: Preparation of tert-butyl (3R)-3-((5-(1-cyclopropylethyl)-7-((2-(trimethylsilyl)ethoxy)methyl)-7H-pyrrolo[2,3-d]pyrimidin-4-yl)amino)piperidine-1-carboxylate

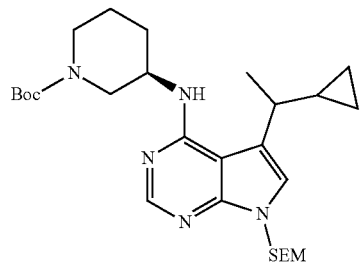 [SMILES: CC(c1cn(COCC[Si](C)(C)C)c2ncnc(N[C@@H]3CCCN(C(=O)OC(C)(C)C)C3)c12)C1CC1]

To a stirred solution of 4-chloro-5-(1-cyclopropylethyl)-7-((2-(trimethylsilyl)ethoxy)methyl)-7H-pyrrolo[2,3-d]pyrimidine (2 g, 5.69 mmol) in N-methyl-2-pyrrolidone (30 mL) was added tert-butyl (R)-3-aminopiperidine-1-carboxylate (1.36 g, 6.83 mmol), the mixture was then heated in a sealed tube at 180° C. for 8 hours. The reaction mixture was cooled to room temperature and then poured into ice water and extracted with ethyl acetate. The organic layer was washed with water, brine, dried over anhydrous sodium sulfate, filtered and concentrated in vacuo. The crude material was purified using flash chromatography (30% ethyl acetate/hexane) to provide tert-butyl (3R)-3-((5-(1-cyclopropylethyl)-7-((2-(trimethylsilyl)ethoxy)methyl)-7H-pyrrolo[2,3-d]pyrimidin-4-yl)amino)piperidine-1-carboxylate as a yellow liquid (2 g, 69% yield): MS (ES) m/z 516.2 (M+H).

Step 4: Preparation of tert-butyl (3R)-3-((5-(1-cyclopropylethyl)-7H-pyrrolo[2,3-d]pyrimidin-4-yl)amino)piperidine-1-carboxylate

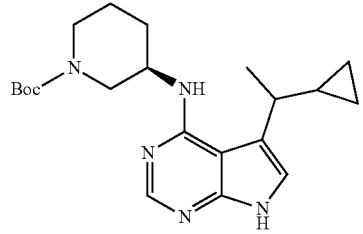 [SMILES: CC(c1c[nH]c2ncnc(N[C@@H]3CCCN(C(=O)OC(C)(C)C)C3)c12)C1CC1]

To a stirred solution of tert-butyl (3R)-3-((5-(1-cyclopropylethyl)-7-((2-(trimethylsilyl)ethoxy)methyl)-7H-pyrrolo[2,3-d]pyrimidin-4-yl)amino)piperidine-1-carboxylate (2 g, 3.88 mmol) in tetrahydrofuran (10 mL) was added tetrabutylammonium fluoride (38 mL, 1 M solution in tetrahydrofuran) and mixture was heated to 80° C. for 16 hours. After cooling the reaction mixture was poured into ice water and extracted with ethyl acetate. The organic layer was washed with water, brine, dried over anhydrous sodium sulfate, filtered and concentrated in vacuo. The crude material was purified using flash chromatography (3% methanol/dichloromethane) to provide tert-butyl (3R)-3-((5-(1-cyclopropylethyl)-7H-pyrrolo[2,3-d]pyrimidin-4-yl)amino)piperidine-1-carboxylate as a yellow liquid (0.95 g, 64% yield): MS (ES) m/z 386.2 (M+H).

Step 5: Preparation of 5-(1-cyclopropylethyl)-N—((R)-piperidin-3-yl)-7H-pyrrolo[2,3-d]pyrimidin-4-amine Hydrochloride

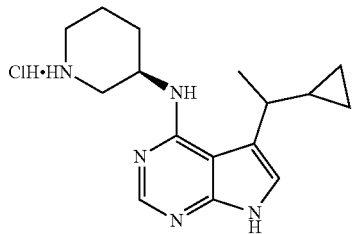

To a stirred solution of tert-butyl (3R)-3-((5-(1-cyclopropylethyl)-7H-pyrrolo[2,3-d]pyrimidin-4-yl)amino)piperidine-1-carboxylate (0.95 g, 2.46 mmol) in dichloromethane (10 mL) at 0° C. was added a solution of hydrogen chloride (6.1 mL, 24.67 mmol, 4M in 1,4-dioxane) and the mixture was stirred at ambient temperature for 16 hours. The reaction was concentrated in vacuo and the residue was washed with ether to provide 5-(1-cyclopropylethyl)-N—((R)-piperidin-3-yl)-7H-pyrrolo[2,3-d]pyrimidin-4-amine hydrochloride as a yellow liquid (0.65 g, 82% yield): MS (ES) m/z 286.2 (M+H).

Step 6: Preparation of 1-((3R)-3-((5-(1-cyclopropylethyl)-7H-pyrrolo[2,3-d]pyrimidin-4-yl)amino)piperidin-1-yl)prop-2-en-1-one

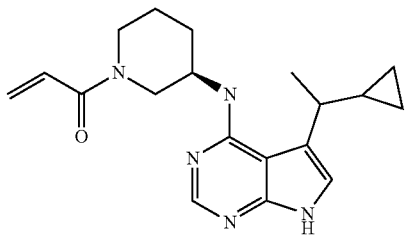 [SMILES: C=CC(=O)N1CCC[C@@H](Nc2ncnc3[nH]cc(C(C)C4CC4)c23)C1]

To a stirred solution of 5-(1-cyclopropylethyl)-N—(R)-piperidin-3-yl)-7H-pyrrolo[2,3-d]pyrimidin-4-amine hydrochloride (0.65 g, 2.02 mmol) in tetrahydrofuran:water (10 mL:3 mL) was added triethylamine (0.87 mL, 6.07 mmol) followed by a solution of acryloyl chloride (0.14 g, 1.61 mmol) in tetrahydrofuran (1 mL) at 0° C. and stirred for 15 minutes. The reaction mixture was quenched with saturated aqueous sodium bicarbonate and extracted with ethyl acetate. The organic layer was washed with water, brine, dried over anhydrous sodium sulfate, filtered and concentrated in vacuo. The crude material was purified using flash chromatography (4% methanol/dichloromethane) and further purified by using prep HPLC to provide 1-((3R)-3-((5-(1-cyclopropylethyl)-7H-pyrrolo[2,3-d]pyrimidin-4-yl)amino)-piperidin-1-yl)prop-2-en-1-one as a white solid (0.02 g, 3% yield): $^1$H NMR (400 MHz, DMSO-$d_6$, at 90° C.) δ 11.62 (s, 1H), 8.23 (s, 1H), 8.03-8.09 (m, 1H), 7.19 (s, 1H), 6.15-6.23 (m, 1H), 6.03-6.08 (m, 1H), 5.54-5.57 (m, 1H), 3.84-3.92 (m, 1H), 3.72-3.75 (m, 1H), 3.60-3.67 (m, 1H), 2.71-2.78 (m, 1H), 2.59-2.68 (m, 1H), 2.30-2.40 (m, 1H), 1.93-1.98 (m, 1H), 1.78-1.90 (m, 1H), 1.53-1.65 (m, 1H), 1.31-1.41 (m, 1H), 1.28 (d, J=7.6 Hz, 3H), 0.83-0.93 (m, 1H), 0.35-0.45 (m, 2H), 0.16-0.28 (m, 2H); MS (ES) m/z 340.4 (M+H).

Prep HPLC method:
Column: Inertsil ODS 3V (250 mm×4.6 mm×5 mic)
Mobile phase (A): 0.1% Ammonia in water
Mobile phase (B): ACN
Flow rate: 1.0 mL/min
Isocratic (A:B): (55:45)

EXAMPLE 22

Preparation of 1-((3R)-3-((5-(1-cyclopropylethyl)-7H-pyrrolo[2,3-d]pyrimidin-4-yl)amino)piperidin-1-yl)prop-2-en-1-one

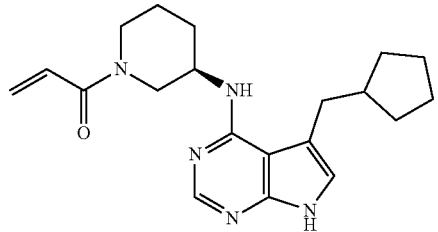 [SMILES: C=CC(=O)N1CCC[C@@H](Nc2ncnc3[nH]cc(CC4CCCC4)c23)C1]

The title compound was prepared the method described in Scheme 23.

Scheme 23. Preparation of 1-((3R)-3-((5-(1-cyclopropylethyl)-7H-pyrrolo[2,3-d]pyrimidin-4-yl)amino)piperidin-1-yl)prop-2-en-1-one

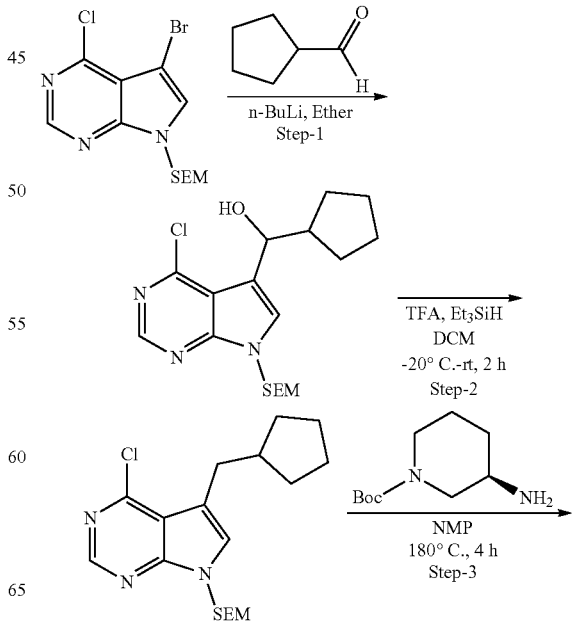

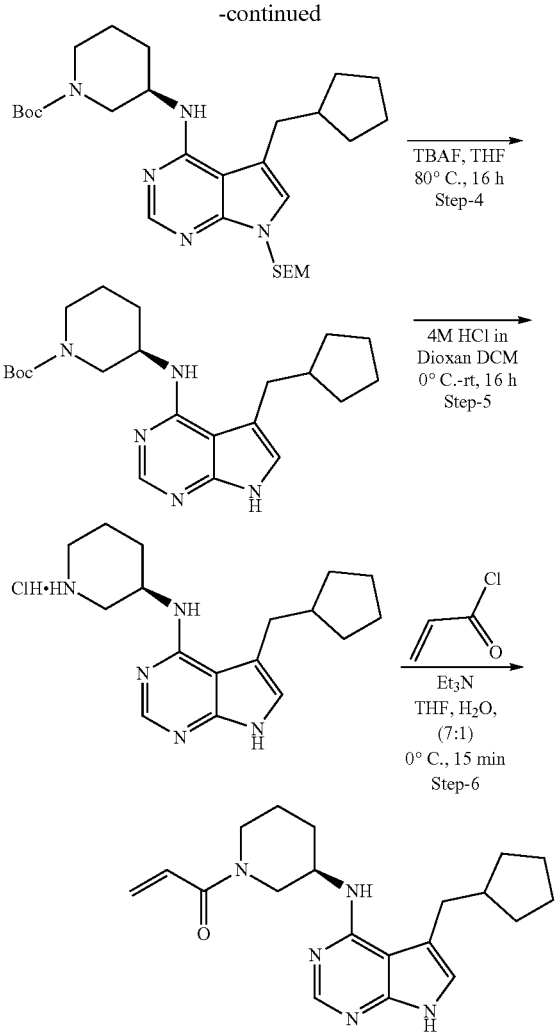

Step 1: Preparation of (4-chloro-7-((2-(trimethylsilyl)ethoxy)methyl)-7H-pyrrolo[2,3-d]pyrimidin-5-yl)(cyclopentyl)methanol

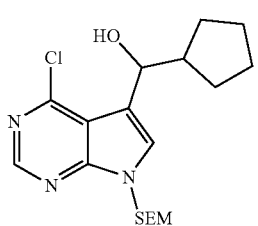 [SMILES: C[Si](C)(C)CCOCn1cc(C(O)C2CCCC2)c2c(Cl)ncnc21]

To a stirred solution of 5-bromo-4-chloro-7-((2-(trimethylsilyl)ethoxy)methyl)-7H-pyrrolo[2,3-d]pyrimidine (prepared by the method described in Example 7, 2.3 g, 6.35 mmol) in diethyl ether (30 mL) was added n-butyllithium (6 mL, 9.53 mmol, 1.6 M in hexane) at −78° C. The solution was stirred for 0.5 hours followed by addition of cyclopentanecarbaldehyde (0.93 mL, 9.53 mmol) at same temperature. The mixture was stirred for 0.5 hours. The reaction mixture was quenched with saturated aqueous ammonium chloride solution and extracted with diethyl ether (3×50 mL). The combined organic extracts were washed with brine, dried over anhydrous sodium sulfate, filtered and concentrated in vacuo. The crude material was purified using flash chromatography (40% ethyl acetate/hexane) to provide (4-chloro-7-((2-(trimethylsilyl)ethoxy)methyl)-7H-pyrrolo[2,3-d]pyrimidin-5-yl)(cyclopentyl)methanol as a brown liquid (1.2 g, 50% yield): MS (ES) m/z 382.0 (M+H).

Step 2: Preparation of 4-chloro-5-(cyclopentylmethyl)-7-((2-(trimethylsilyl)ethoxy)methyl)-7H-pyrrolo[2,3-d]pyrimidine

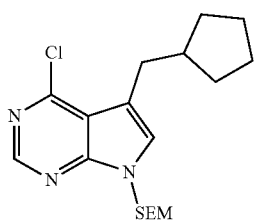 [SMILES: C[Si](C)(C)CCOCn1cc(CC2CCCC2)c2c(Cl)ncnc21]

To a stirred solution of (4-chloro-7-((2-(trimethylsilyl)ethoxy)methyl)-7H-pyrrolo[2,3-d]pyrimidin-5-yl)(cyclopentyl)methanol (1.2 g, 3.32 mmol) in dichloromethane (20 mL) at −20° C. was added trifluoroacetic acid (1.3 g, 16.62 mmol) and triethylsilane (1.5 mL, 9.97 mmol). The mixture was stirred at ambient temperature for 2 hours. The reaction mixture was quenched with saturated sodium bicarbonate and extracted with dichloromethane (3×100 mL). The combined organic extracts were washed with water, brine, dried over anhydrous sodium sulfate, filtered and concentrated in vacuo. The crude material was purified using flash chromatography (22% ethyl acetate/hexane) to provide 4-chloro-5-(cyclopentylmethyl)-7-((2-(trimethylsilyl)ethoxy)methyl)-7H-pyrrolo[2,3-d]pyrimidine as a brown liquid (1.1 g, 66% yield): MS (ES) m/z 367 (M+H).

Step 3: Preparation of tert-butyl (R)-3-((5-(cyclopentylmethyl)-7-((2-(trimethylsilyl)ethoxy)methyl)-7H-pyrrolo[2,3-d]pyrimidin-4-yl)amino)piperidine-1-carboxylate

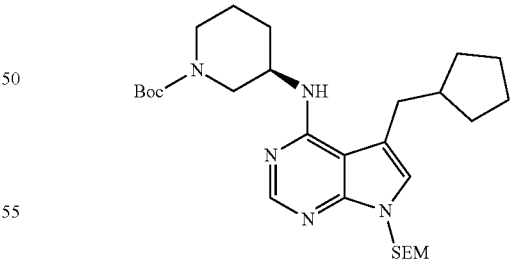

To a stirred solution of 4-chloro-5-(cyclopentylmethyl)-7-((2-(trimethylsilyl)ethoxy)methyl)-7H-pyrrolo[2,3-d]pyrimidine (1.1 g, 3.0 mmol) in N-methyl-2-pyrrolidone (20 mL) was added tert-butyl (R)-3-aminopiperidine-1-carboxylate (0.90 g, 4.51 mmol) and the mixture was heated in a sealed tube at 180° C. for 4 hours. After cooling to ambient temperature, the reaction mixture was poured into water and extracted with ethyl acetate (2×100 mL). The combined organic extracts were washed with brine, dried over anhydrous sodium sulfate, filtered and concentrated in vacuo. The crude material was purified using flash chromatography (25% ethyl acetate/hexane) to provide tert-butyl (R)-3-((5-(cyclopentylmethyl)-7-((2-(trimethylsilyl)ethoxy)methyl)-7H-pyrrolo[2,3-d]pyrimidin-4-yl)amino)piperidine-1-carboxylate as a brown liquid (0.65 g, 40% yield): MS (ES) m/z 530 (M+H).

Step 4: Preparation of tert-butyl (R)-3-((5-(cyclopentylmethyl)-7H-pyrrolo[2,3-d]pyrimidin-4-yl)amino)piperidine-1-carboxylate

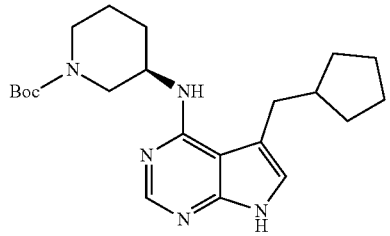 [SMILES: CC(C)(C)OC(=O)N1CCC[C@@H](Nc2ncnc3[nH]cc(CC4CCCC4)c23)C1]

To a stirred solution of tert-butyl (R)-3-((5-(cyclopentylmethyl)-7-((2-(trimethylsilyl)ethoxy)methyl)-7H-pyrrolo[2,3-d]pyrimidin-4-yl)amino)piperidine-1-carboxylate (0.65 g, 1.22 mmol) in tetrahydrofuran (10 mL) was added tetrabutylammonium fluoride (8 mL, 1 M in tetrahydrofuran) and the solution was heated to 80° C. for 16 hours. After cooling to ambient temperature, the reaction mixture was poured into ice water and extracted with ethyl acetate. The organic layer was washed with water, brine, dried over anhydrous sodium sulfate, filtered and concentrated in vacuo. The crude material was purified using flash chromatography (4% methanol/dichloromethane) to provide tert-butyl (R)-3-((5-(cyclopentylmethyl)-7H-pyrrolo[2,3-d]pyrimidin-4-yl)amino)piperidine-1-carboxylate as a yellow liquid (0.25 g, 51% yield): MS (ES) m/z 400 (M+H).

Step 5: Preparation of (R)-5-(cyclopentylmethyl)-N-(piperidin-3-yl)-7H-pyrrolo[2,3-d]pyrimidin-4-amine Hydrochloride

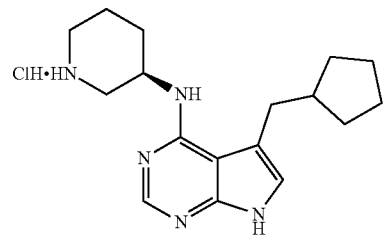

To a stirred solution of tert-butyl (R)-3-((5-(cyclopentylmethyl)-7H-pyrrolo[2,3-d]pyrimidin-4-yl)amino)piperidine-1-carboxylate (0.25 g, 0.62 mmol) in dichloromethane (2 mL) was added a solution of hydrogen chloride (5 mL, 6.26 mmol, 4 M in dioxane) at 0° C. The mixture was stirred at ambient temperature for 16 hours. The reaction mixture was concentrated in vacuo and the residue was washed with diethyl ether to provide (R)-5-(cyclopentylmethyl)-N-(piperidin-3-yl)-7H-pyrrolo[2,3-d]pyrimidin-4-amine hydrochloride as an off-white solid (0.15 g, crude): MS (ES) m/z 300 (M+H).

Step 6: Preparation of (R)-1-(3-((5-(cyclopentylmethyl)-7H-pyrrolo[2,3-d]pyrimidin-4-yl)amino)piperidin-1-yl)prop-2-en-1-one

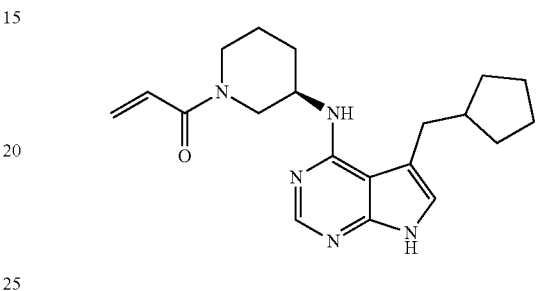

To a stirred solution of (R)-5-(cyclopentylmethyl)-N-(piperidin-3-yl)-7H-pyrrolo[2,3-d]pyrimidin-4-amine hydrochloride (0.15 g, 0.50 mmol) in tetrahydrofuran:water (10:6 mL) was added triethylamine (0.15 mL, 1.50 mmol) followed by a solution of acryloyl chloride (0.08 mL, 0.90 mmol) in tetrahydrofuran (0.5 mL) at 0° C. After stirring for 15 minutes, the reaction mixture was quenched with saturated aqueous sodium bicarbonate solution and extracted with ethyl acetate. The organic layer was washed with brine, dried over anhydrous sodium sulfate, filtered and concentrated in vacuo. The crude material was purified using flash chromatography (5% methanol/dichloromethane) to provide (R)-1-(3-((5-(cyclopentylmethyl)-7H-pyrrolo[2,3-d]pyrimidin-4-yl)amino)piperidin-1-yl)prop-2-en-1-one as a white solid (0.07 g, 40% yield): $^1$H NMR (400 MHz, DMSO-d$_6$ at 90° C.) δ 11.07 (s, 1H), 8.07 (s, 1H), 6.80 (s, 1H), 6.66 (br s, 1H), 6.04 (d, J=16.4 Hz, 1H), 5.59 (br s, 1H), 5.43 (d, J=5.6 Hz, 1H), 4.24 (s, 1H), 3.21-3.88 (m, 1H), 3.54-3.62 (m, 1H), 3.44-3.52 (m, 2H), 2.65-2.72 (m, 2H), 2.05-2.12 (m, 1H), 1.95 (br s, 1H), 1.68-1.84 (m, 3H), 1.37-1.63 (m, 8H); MS (ES) m/z 354.0 (M+H).

EXAMPLE 23

Preparation of (R)-1-(3-((5-(1-methylcyclopropyl)-7H-pyrrolo[2,3-d]pyrimidin-4-yl)amino)piperidin-1-yl)prop-2-en-1-one

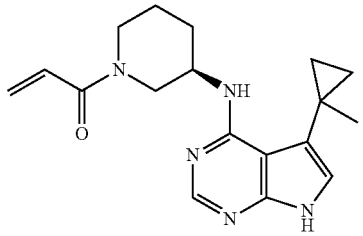 [SMILES: C=CC(=O)N1CCC[C@@H](Nc2ncnc3[nH]cc(C4(C)CC4)c23)C1]

The title compound was prepared by the method described in Scheme 24.

Scheme 24. Preparation of (R)-1-(3-((5-(1-methylcyclopropyl)-7H-pyrrolo[2,3-d]pyrimidin-4-yl)amino)piperidin-1-yl)prop-2-en-1-one

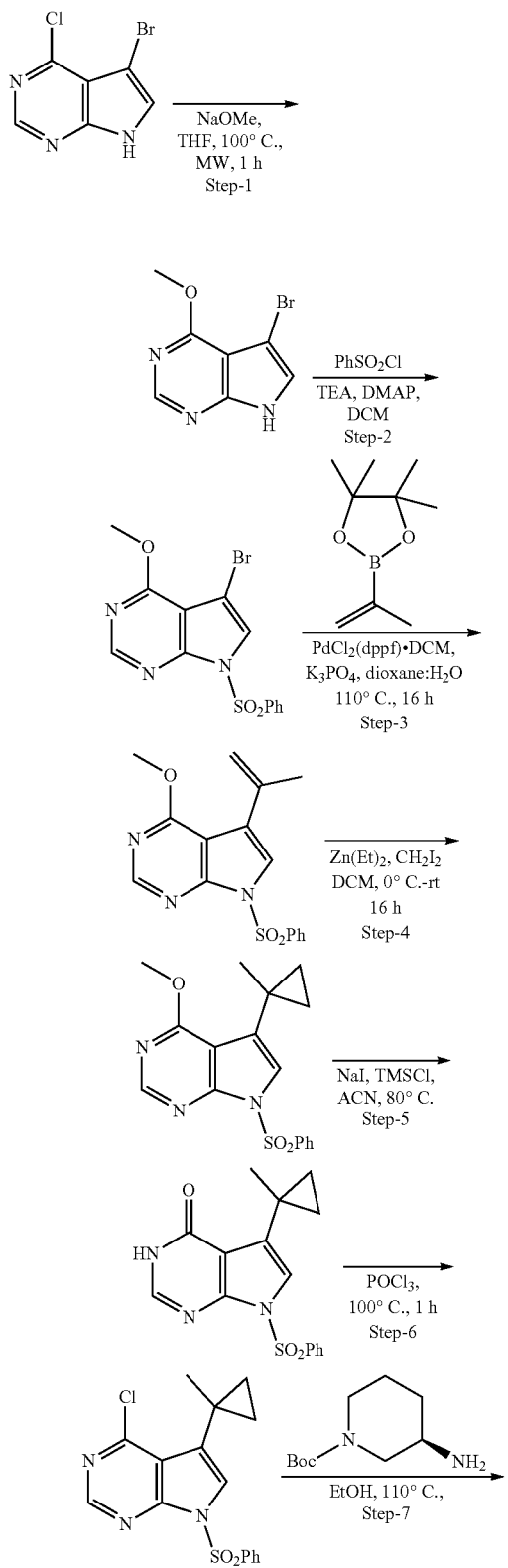
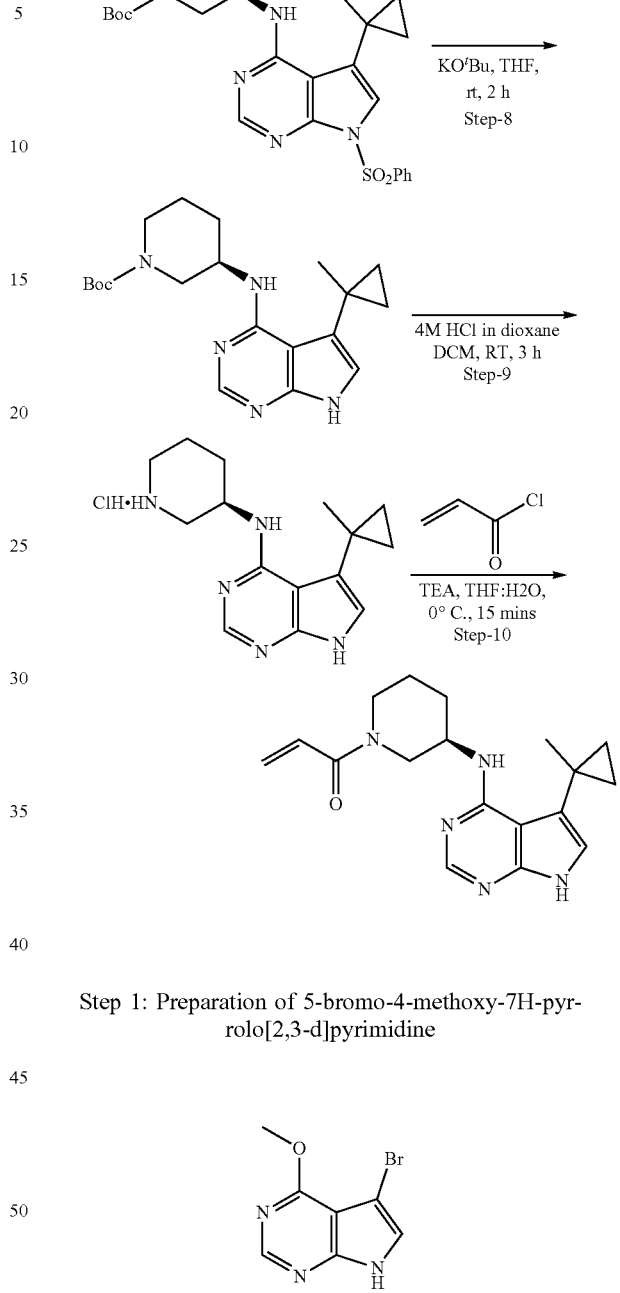

Step 1: Preparation of 5-bromo-4-methoxy-7H-pyrrolo[2,3-d]pyrimidine

To a solution of 5-bromo-4-chloro-7H-pyrrolo[2,3-d]pyrimidine (1 g, 4.31 mmol) in tetrahydrofuran (5 mL) was added sodium methoxide (5 mL, 25% in methanol) and the mixture was subjected to microwave irradiation at 100° C. for 1 hour. After cooling to ambient temperature, the reaction mixture was poured into water and extracted with ethyl acetate. The organic layer was washed with brine, dried over anhydrous sodium sulfate, filtered and concentrated in vacuo. The crude product was triturated with hexane to provide 5-bromo-4-methoxy-7H-pyrrolo[2,3-d]pyrimidine as an off-white solid (0.6 g, 60% yield): MS (ES) m/z 230.0 (M+H).

Step 2: Preparation of 5-bromo-4-methoxy-7-(phenylsulfonyl)-7H-pyrrolo[2,3-d]pyrimidine

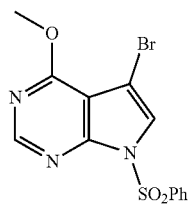

To a solution of 5-bromo-4-methoxy-7H-pyrrolo[2,3-d]pyrimidine (0.6 g, 2.63 mmol) in dichloromethane (40 mL) were added triethylamine (0.73 mL, 5.2 mmol), N,N-(dimethylamino)pyridine (0.03 g, 0.02 mmol) followed by benzenesulfonyl chloride (0.69 g, 3.9 mmol) dropwise over 5 minutes. The mixture was stirred at ambient temperature for 2 hours. The reaction mixture was poured into ice water and extracted with dichloromethane. The organic layer was washed with water, brine, dried over anhydrous sodium sulfate, filtered and concentrated in vacuo. The crude material was purified using flash chromatography (15% ethyl acetate/hexane) to provide 5-bromo-4-methoxy-7-(phenylsulfonyl)-7H-pyrrolo[2,3-d]pyrimidine as an off-white solid. (0.54 g, 56% yield): MS (ES) m/z 367.9 (M+H).

Step 3: Preparation of 4-methoxy-7-(phenylsulfonyl)-5-(prop-1-en-2-yl)-7H-pyrrolo[2,3-d]pyrimidine

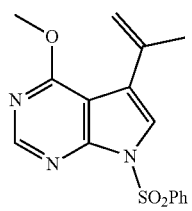

To a solution of 5-bromo-4-methoxy-7-(phenylsulfonyl)-7H-pyrrolo[2,3-d]pyrimidine (2.0 g, 5.46 mmol), 4,4,5,5-tetramethyl-2-(prop-1-en-2-yl)-1,3,2-dioxaborolane (1.83 g, 10.9 mmol), potassium carbonate (2.26 g, 16.3 mmol) in toluene:water (16:4 mL) was added [1,1'-bis(diphenylphosphino)ferrocene]palladium(II) dichloride (0.44 g, 0.05 mmol) under an argon atmosphere, then heated to 110° C. for 16 hours. After cooling to ambient temperature, the reaction mixture was filtered through celite and washed with ethyl acetate. The filtrate was washed with water, brine, dried over anhydrous sodium sulfate, filtered and concentrated in vacuo. The crude material was purified using flash chromatography (12% ethyl acetate/hexane) to provide 4-methoxy-7-(phenylsulfonyl)-5-(prop-1-en-2-yl)-7H-pyrrolo[2,3-d]pyrimidine as an off-white solid (1.2 g, 67% yield): MS (ES) m/z 330.0 (M+H).

Step 4: Preparation of 4-methoxy-5-(1-methylcyclopropyl)-7-(phenylsulfonyl)-7H-pyrrolo[2,3-d]pyrimidine

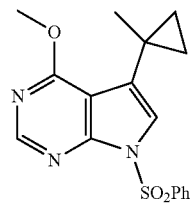

To a solution of 4-methoxy-7-(phenylsulfonyl)-5-(prop-1-en-2-yl)-7H-pyrrolo[2,3-d]pyrimidine (1.2 g, 3.64 mmol) in dichloromethane (25 mL) was added a solution of diethyl zinc (18.29 mL, 18.2 mmol, 1 M in tetrahydrofuran) at 0° C. over a period of 10 minutes followed by addition of diiodomethane (2.94 mL, 36.4 mmol) at 0° C. The resulting mixture was stirred at ambient temperature for 16 hours. The reaction mixture was quenched with saturated aqueous ammonium chloride and extracted with dichloromethane. The organic layer was washed with water, saturated sodium bicarbonate solution, brine, dried over anhydrous sodium sulfate, filtered and concentrated in vacuo. The crude material was purified using flash chromatography (10% ethyl acetate/hexane) to provide 4-methoxy-5-(1-methylcyclopropyl)-7-(phenylsulfonyl)-7H-pyrrolo[2,3-d]pyrimidine as an off-white solid (0.78 g, 62%): MS (ES) m/z 344.1 (M+H).

Step 5: Preparation of 5-(1-methylcyclopropyl)-7-(phenylsulfonyl)-3,7-dihydro-4H-pyrrolo[2,3-d]pyrimidin-4-one

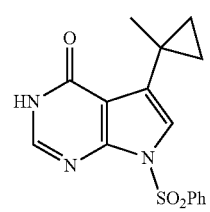

To a solution of 4-methoxy-5-(1-methylcyclopropyl)-7-(phenylsulfonyl)-7H-pyrrolo[2,3-d]pyrimidine (0.55 g, 1.6 mmol) in acetonitrile (8 mL) were added sodium iodide (0.24 g, 1.6 mmol) and chlorotrimethylsilane (0.2 mL, 1.6 mmol) in a sealed tube and the mixture was heated at 80° C. for 1 hour. After cooling the reaction mixture was poured into water and extracted with ethyl acetate. The organic layer was washed with brine, dried over anhydrous sodium sulfate, filtered and concentrated in vacuo. The crude product was triturated with hexane to provide 5-(1-methylcyclopropyl)-7-(phenylsulfonyl)-3,7-dihydro-4H-pyrrolo[2,3-d]pyrimidin-4-one as a light yellow solid (0.54 g, crude): MS (ES) m/z 330.0 (M+H). The crude product was progressed next step without further purification.

Step 6: Preparation of 4-chloro-5-(1-methylcyclopropyl)-7-(phenylsulfonyl)-7H-pyrrolo[2,3-d]pyrimidine

A solution of 5-(1-methylcyclopropyl)-7-(phenylsulfonyl)-3,7-dihydro-4H-pyrrolo[2,3-d]pyrimidin-4-one (0.54 g, 1.64 mmol) in phosphoryl chloride (4 mL) was stirred at 100° C. for 1 hour. After cooling to ambient temperature, the reaction mixture was concentrated in vacuo to remove excess of phosphoryl chloride and the residue was dissolved in ethyl acetate. The organic layer was washed with water, saturated aqueous sodium bicarbonate and brine. The solution was filtered and concentrated in vacuo. The crude product was triturated with hexane to provide 4-chloro-5-(1-methylcyclopropyl)-7-(phenylsulfonyl)-7H-pyrrolo[2,3-d]pyrimidine as an off-white solid (0.45 g, crude): MS (ES) m/z 348.0 (M+H). The crude product was progressed next step without further purification.

Step 7: Preparation of tert-butyl (R)-3-((5-(1-methylcyclopropyl)-7-(phenylsulfonyl)-7H-pyrrolo[2,3-d]pyrimidin-4-yl)amino)piperidine-1-carboxylate

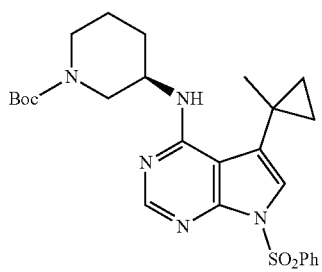

To a solution of 4-chloro-5-(1-methylcyclopropyl)-7-(phenylsulfonyl)-7H-pyrrolo[2,3-d]pyrimidine (0.45 g, 1.29 mmol) in n-butanol (5 mL) was added tert-butyl (R)-3-aminopiperidine-1-carboxylate (0.38 g, 1.94 mmol) followed by addition of N,N-diisopropylethylamine (0.44 mL, 2.59 mmol) and the mixture was heated in a sealed tube at 110° C. for 24 hours. After cooling to ambient temperature, the reaction mixture was concentrated in vacuo and residue was dissolved in ethyl acetate. The organic layer was washed with water, brine, dried over anhydrous sodium sulfate, filtered and concentrated in vacuo. The crude material was purified using flash chromatography (20% ethyl acetate/hexane) to provide tert-butyl (R)-3-((5-(1-methylcyclopropyl)-7-(phenylsulfonyl)-7H-pyrrolo[2,3-d]pyrimidin-4-yl)amino)piperidine-1-carboxylate as an off-white solid (0.4 g, 60% yield): MS (ES) m/z 512.5 (M+H).

Step 8: Preparation of tert-butyl (R)-3-((5-(1-methylcyclopropyl)-7H-pyrrolo[2,3-d]pyrimidin-4-yl)amino)piperidine-1-carboxylate

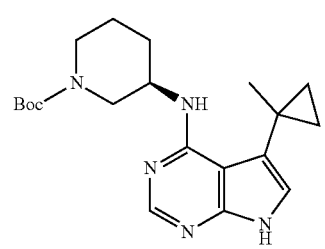 [SMILES: CC(C)(C)OC(=O)N1CCC[C@@H](Nc2ncnc3[nH]cc(C4(C)CC4)c23)C1]

To a solution tert-butyl (R)-3-((5-(1-methylcyclopropyl)-7-(phenylsulfonyl)-7H-pyrrolo[2,3-d]pyrimidin-4-yl)amino)piperidine-1-carboxylate in tetrahydrofuran (5 mL) was added potassium tert-butoxide (0.26 g, 2.34 mmol) at ambient temperature and the mixture was stirred for 2 hours. The reaction mixture was poured into ice water and extracted with ethyl acetate. The organic layer was washed with water, brine, dried over anhydrous sodium sulfate, filtered and concentrated in vacuo to provide tert-butyl (R)-3-((5-(1-methylcyclopropyl)-7H-pyrrolo[2,3-d]pyrimidin-4-yl)-amino)-piperidine-1-carboxylate as a viscous liquid (0.2 g, crude): MS (ES) m/z 372.2 (M+H). The crude product was progressed next step without further purification.

Step 9: Preparation of (R)-5-(1-Methylcyclopropyl)-N-(piperidin-3-yl)-7H-pyrrolo[2,3-d]pyrimidin-4-amine hydrochloride (11)

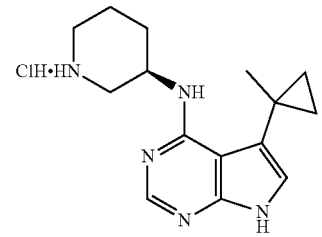

To a stirred solution of tert-butyl (R)-3-((5-(1-methylcyclopropyl)-7H-pyrrolo[2,3-d]pyrimidin-4-yl)amino)piperidine-1-carboxylate (0.2 g, 0.53 mmol) in dichloromethane (3 mL) was added a solution of hydrogen chloride (3 mL, 4 M in dioxane) at 0° C. and the mixture was stirred at ambient temperature for 3 hours. The reaction mixture was concentrated in vacuo and the residue was washed with diethyl ether to provide (R)-5-(1-methylcyclopropyl)-N-(piperidin-3-yl)-7H-pyrrolo[2,3-d]pyrimidin-4-amine-HCl as an off-white solid (0.22 g, crude): MS (ES) m/z 272.1 (M+H).

Step 10: Preparation of (R)-1-(3-((5-(1-methylcyclopropyl)-7H-pyrrolo[2,3-d]pyrimidin-4-yl)amino)piperidin-1-yl)prop-2-en-1-one

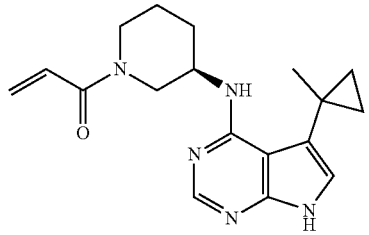 [SMILES: C=CC(=O)N1CCC[C@@H](Nc2ncnc3[nH]cc(C4(C)CC4)c23)C1]

To a solution of (R)-5-(1-methylcyclopropyl)-N-(piperidin-3-yl)-7H-pyrrolo[2,3-d]pyrimidin-4-amine hydrochloride (0.22 g, 0.81 mmol) in tetrahydrofuran:water (8.0:2.0 mL) was added triethylamine (0.16 mL, 2.43 mmol) followed by a solution of acryloyl chloride (0.058 g, 0.64 mmol) in tetrahydrofuran (1 mL) at 0° C. and stirred for 15 minutes. The reaction mixture was quenched with aqueous sodium bicarbonate and extracted with ethyl acetate. The organic layer was washed with brine, dried over anhydrous sodium sulfate, filtered and concentrated in vacuo. The crude material was purified using flash chromatography (6% methanol/dichloromethane) and then further purified by using prep HPLC to provide (R)-1-(3-((5-(1-methylcyclopropyl)-7H-pyrrolo[2,3-d]pyrimidin-4-yl)amino)piperidin-1-yl)prop-2-en-1-one as a white solid (0.06 g, 26%): $^1$H NMR (400 MHz, DMSO-$d_6$) δ 11.06 (s, 1H), 8.10 (s, 1H), 6.85 (d, J=1.6 Hz, 1H), 6.45 (bs, 1H), 6.01 (d, J=16.4 Hz, 1H), 5.72 (d, J=7.2 Hz, 1H), 5.56 (br s, 1H), 4.34 (br s, 1H), 3.72-3.75 (m, 3H), 3.40-3.44 (m, 1H), 1.95-1.98 (m, 1H), 1.83-1.85 (m, 1H), 1.59-1.75 (m, 2H), 1.34 (s, 3H), 0.75-0.78 (m, 2H), 0.66-0.69 (m, 2H); MS (ES) m/z 326.1 (M+H).

EXAMPLE 24

Preparation of 1-((2S,5R)-5-((5-(cyclopropylmethyl)-7H-pyrrolo[2,3-d]pyrimidin-4-yl)amino)-2-methylpiperidin-1-yl)prop-2-en-1-one

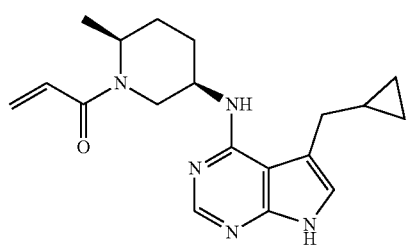 [SMILES: C=CC(=O)N1C[C@H](Nc2ncnc3[nH]cc(CC4CC4)c23)CC[C@@H]1C]

Step 1: Preparation of (4-chloro-7-((2-(trimethylsilyl)ethoxy)methyl-7H-pyrrolo[2,3-d]pyrimidin-5-yl)(cyclopropyl)methanol

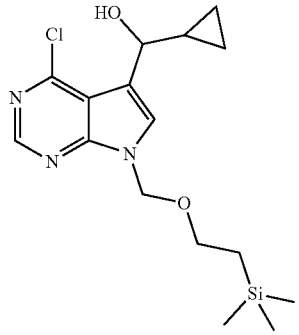 [SMILES: C[Si](C)(C)CCOCn1cc(C(O)C2CC2)c2c(Cl)ncnc21]

A solution of n-butyllithium (2.3 mL of a 2 M solution in cyclohexane, 4.63 mmol) was slowly added to a solution of 4-chloro-5-iodo-7-((2-(trimethylsilyl)ethoxy)methyl-7H-pyrrolo[2,3-d]pyrimidine (2.00 g, 4.88 mmol) in diethyl ether (60 mL) at −78° C. Cyclopropanecarbaldehyde (0.911 mL, 12.2 mmol) was then added and the reaction was stirred for 1 hour at −78° C. The reaction was allowed to warm to ambient temperature, quenched with saturated ammonium chloride (40 mL) and partitioned between ethyl acetate and water. The ethyl acetate layer was washed with brine, dried over sodium sulfate, filtered and concentrated in vacuo. The resulting oil was chromatographed on silica gel, eluting with ethyl acetate and heptane. Pure fractions were pooled and concentrated to give (4-chloro-7-((2-(trimethylsilyl)ethoxy)methyl-7H-pyrrolo[2,3-d]pyrimidin-5-yl)(cyclopropyl)methanol as a dark oil (1.1 g, 64% yield): MS (ES) m/z 354.2 (M+H).

Step 2: Preparation of 4-chloro-5-(cyclopropylmethyl)-7-((2-(trimethylsilyl)ethoxy)methyl-7H-pyrrolo[2,3-d]pyrimidine

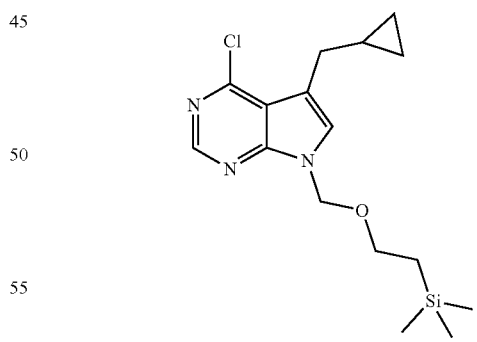

Triethylsilane (3.95 mL, 24.8 mmol) and trifluoroacetic acid (0.711 mL, 9.30 mmol) were added to a solution of (4-chloro-7-((2-(trimethylsilyl)ethoxy)methyl-7H-pyrrolo[2,3-d]pyrimidin-5-yl)(cyclopropyl)methanol (1.10 g, 3.11 mmol) in dichloromethane (30 mL) at 0° C. After 15 minutes at 0° C. the reaction was allowed to warm to ambient temperature and was stirred for 3 hours. At this time the reaction was cooled to 0° C. and excess saturated sodium bicarbonate was added. The reaction was extracted with dichloromethane. The dichloromethane layer was washed with brine, dried over sodium sulfate, filtered and concentrated in vacuo. The resulting oil was chromatographed on silica gel, eluting with ethyl acetate and heptane. Pure fractions were pooled and concentrated to give the product, 4-chloro-5-(cyclopropylmethyl)-7-((2-(trimethylsilyl)ethoxy)methyl-7H-pyrrolo[2,3-d]pyrimidine as a white solid (0.952 g, 91% yield): MS (ES) m/z 338.2 (M+H).

Step 3: Preparation of 4-chloro-5-(cyclopropylmethyl)-7H-pyrrolo[2,3-d]pyrimidine

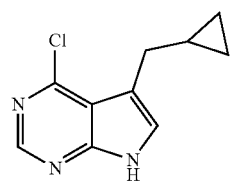 [SMILES: Clc1ncnc2[nH]cc(CC3CC3)c12]

A solution of 4-chloro-5-(cyclopropylmethyl)-7-((2-(trimethylsilyl)ethoxy)methyl-7H-pyrrolo[2,3-d]pyrimidine (0.848 g, 2.50 mmol) and tetrabutylammonium fluoride (25 mL of a 1M solution in tetrahydrofuran, 25 mmol) was heated at 60° C. for 5 hours. The reaction was cooled to ambient temperature and partitioned between ethyl acetate and water. The ethyl acetate layer was washed with brine, dried over sodium sulfate, filtered and concentrated in vacuo. The resulting oil was chromatographed on silica gel, eluting with ethyl acetate and heptane. Pure fractions were pooled and concentrated to give 4-chloro-5-(cyclopropylmethyl)-7H-pyrrolo[2,3-d]pyrimidine as an off-white solid (0.245 g, 47% yield): MS (ES) m/z 208.1 (M+H).

Step 4: Preparation of Benzyl (2S,5R)-5-((-5-(cyclopropylmethyl)-7H-pyrrolo[2,3-d]pyrimidin-4-yl)amino)-2-methylpiperidine-1-carboxylate

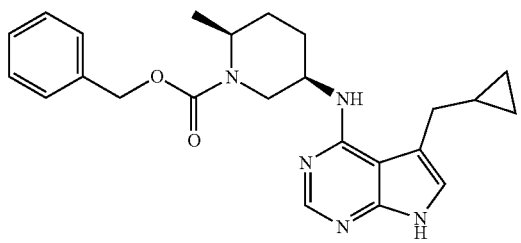 [SMILES: C[C@H]1CC[C@@H](Nc2ncnc3[nH]cc(CC4CC4)c23)CN1C(=O)OCc1ccccc1]

A mixture of 4-chloro-5-(cyclopropylmethyl)-7H-pyrrolo[2,3-d]pyrimidine (0.245 g, 1.17 mmol), benzyl (2S,5R)-5-amino-2-methylpiperidine-1-carboxylate (0.347 g, 1.40 mmol), and N,N-diisopropylethylamine (0.6 mL, 3.5 mmol) in N-methylpyrrolidone (4 mL) was irradiated in a sealed vessel using a microwave at 180° C. for 4 hours. At this time, the reaction was cooled and partitioned between ethyl acetate and water. The ethyl acetate layer was washed with brine, dried over sodium sulfate, filtered and concentrated in vacuo. The resulting oil was chromatographed on silica gel, eluting with ethyl acetate and heptane. Pure fractions were pooled and concentrated to give the desired product, benzyl (2S,5R)-5-((-5-(cyclopropylmethyl)-7H-pyrrolo[2,3-d]pyrimidin-4-yl)amino)-2-methylpiperidine-1-carboxylate as an oil (0.341 g, 69% yield): MS (ES) m/z 420.2 (M+H).

Step 5: Preparation of 5-(cyclopropylmethyl)-N-((3R,6S)-6-methylpiperidin-3-yl)-7H-pyrrolo[2,3-d]pyrimidin-4-amine

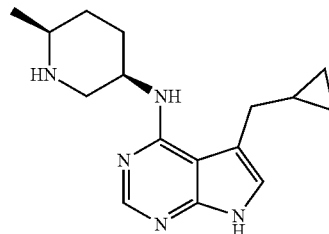

A mixture of benzyl (2S,5R)-5-((-5-(cyclopropylmethyl)-7H-pyrrolo[2,3-d]pyrimidin-4-yl)amino)-2-methylpiperidine-1-carboxylate (0.341 g, 0.813 mmol) and 5% palladium on carbon (0.086 g, 0.040 mmol) in methanol (5 mL) was stirred overnight under a hydrogen atmosphere at ambient temperature. The reaction was filtered through Celite® and concentrated in vacuo to give 5-(cyclopropylmethyl)-N-((3R,6S)-6-methylpiperidin-3-yl)-7H-pyrrolo[2,3-d]pyrimidin-4-amine as an oil (0.223 g, 96% yield): MS (ES) m/z 286.2 (M+H).

Step 6: Preparation of 1-((2S,5R)-5-((5-(cyclopropylmethyl)-7H-pyrrolo[2,3-d]pyrimidin-4-yl)amino)-2-methylpiperidin-1-yl)prop-2-en-1-one

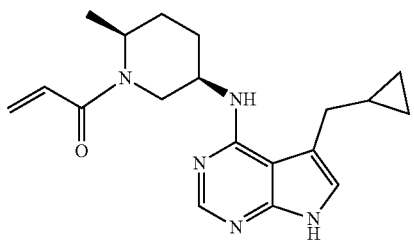 [SMILES: C=CC(=O)N1C[C@H](Nc2ncnc3[nH]cc(CC4CC4)c23)CC[C@@H]1C]

A solution of prop-2-enoic acid (0.079 mg, 1.09 mmol) in dichloromethane (2 mL) was treated with 1-ethyl-3-(3-dimethylaminopropyl)carbodiimide hydrochloride (0.239 g, 1.25 mmol) and triethylamine (0.325 mL, 2.34 mmol). After 15 minutes at ambient temperature, the solution of the activated acid was added to a solution of 5-(cyclopropylmethyl)-N-((3R,6S)-6-methylpiperidin-3-yl)-7H-pyrrolo[2,3-d]pyrimidin-4-amine (0.223 g, 0.781 mmol) in dichloromethane (2 mL) and stirred at ambient temperature for 2 hours. The reaction was then taken up in ethyl acetate and washed with water then brine. The ethyl acetate layer was dried over sodium sulfate, filtered and concentrated in vacuo. The resulting material was chromatographed on a $C_{18}$ column, eluting with acetonitrile and water (with 0.05% formic acid modifier). Pure fractions were pooled and concentrated to give the desired product, 1-((2S,5R)-5-((5-(cyclopropylmethyl)-7H-pyrrolo[2,3-d]pyrimidin-4-yl)amino)-2-methylpiperidin-1-yl)prop-2-en-1-one (28 mg, 10% yield): $^1$H-NMR (400 MHz, DMSO-$d_6$) δ 11.31 (br s, 1H), 8.08 (s, 1H), 6.93 (s, 1H), 6.60-6.88 (m, 1H), 6.08 (dd, J=16.63, 2.15 Hz, 1H), 5.89 (br d, J=8.22 Hz, 1H), 5.67 (dd, J=10.56, 1.96 Hz, 1H), 4.78 (br s, 1H), 4.46 (br s, 1H), 4.35 (br s, 1H), 4.12 (br s, 1H), 2.66-2.92 (m, 2H), 1.94 (br d, J=11.74 Hz, 1H), 1.78 (br d, J=12.13 Hz, 1H), 1.66 (br s, 2H), 1.22 (br s, 3H), 0.89-1.16 (m, 1H), 0.51 (br d, J=7.83 Hz, 2H), 0.02-0.25 (m, 2H); MS (ES) m/z 340.2 (M+H).

EXAMPLES 25 AND 26

Preparation of 1-((R)-3-((5-(2-(methoxymethyl)cyclopropyl)-7H-pyrrolo[2,3-d]pyrimidin-4-yl)amino)piperidin-1-yl)prop-2-en-1-one

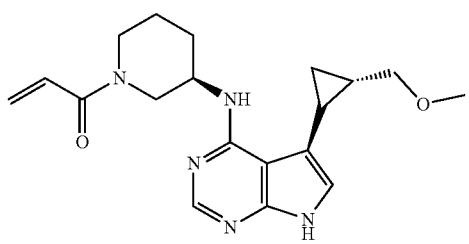

Relative Configuration for Cyclopropyl Substituents

The title compounds were prepared by the method described in Scheme 25.

Scheme 24. Preparation of 1-((R)-3-((5-(2-(methoxymethyl)cyclopropyl)-7H-pyrrolo[2,3-d]pyrimidin-4-yl)amino)piperidin-1-yl)prop-2-en-1-one

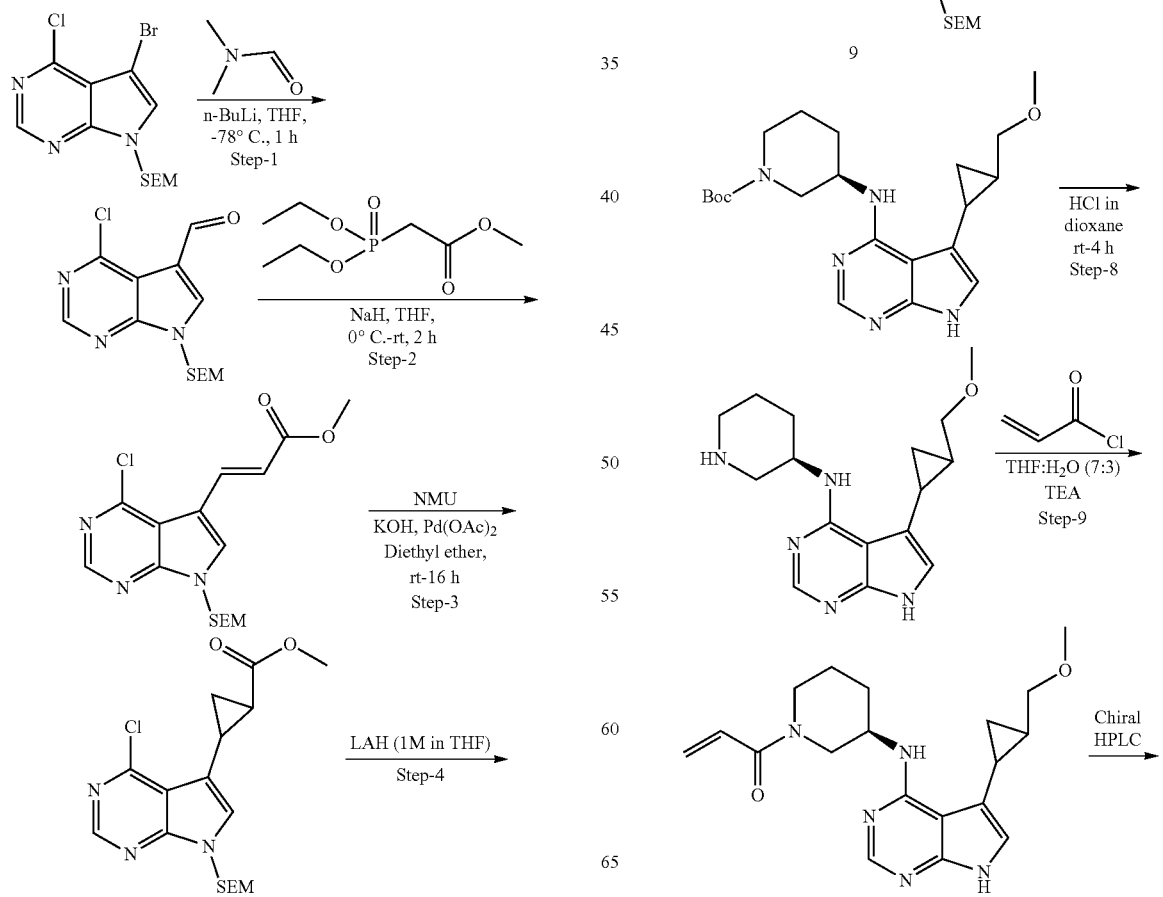
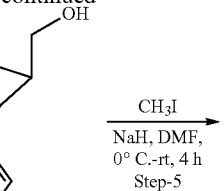
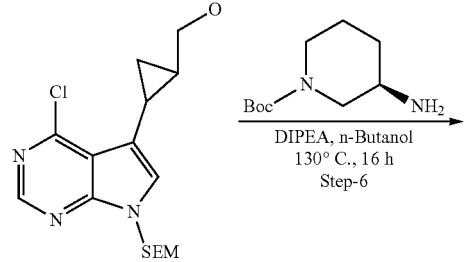
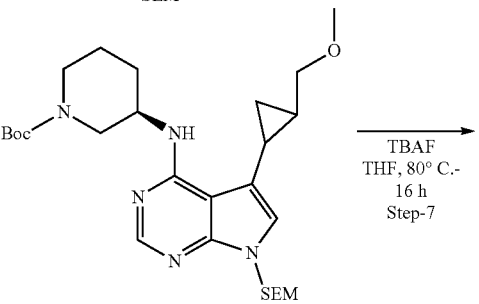
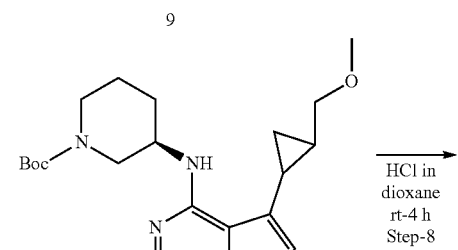
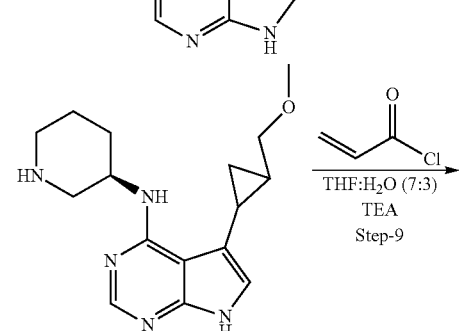
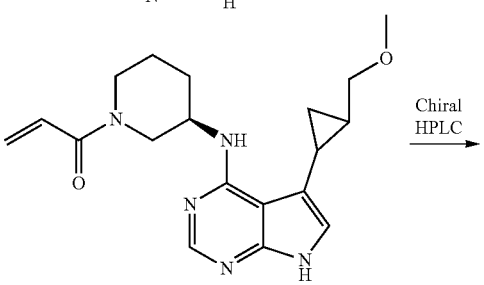

195
-continued

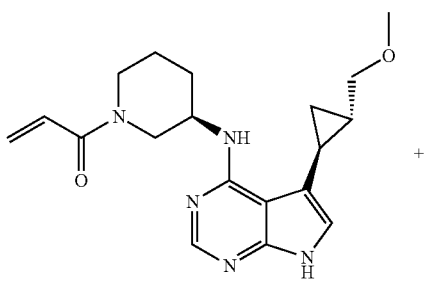

Relative configuration
of cyclopropyl substituents

+

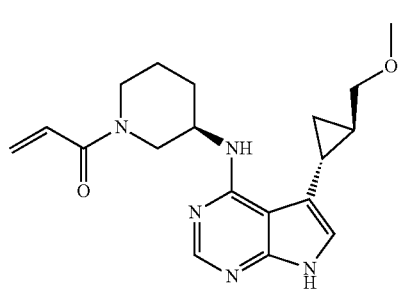

Relative configuration
of cyclopropyl substituents

Step 1: Preparation of 4-chloro-7-((2-(trimethylsilyl)ethoxy)methyl)-7H-pyrrolo[2,3-d]pyrimidine-5-carbaldehyde

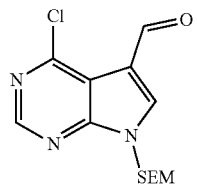

To a stirred solution of 5-bromo-4-chloro-7-((2-(trimethylsilyl)ethoxy)methyl)-7H-pyrrolo[2,3-d]pyrimidine (prepared by the method described in Example 7, 5.0 g, 13.85 mmol) in diethyl ether (70 mL) was added n-butyl lithium (12.93 mL, 20.77 mmol, 1.6 M in hexane) at −78° C. and stirred for 0.5 hours. Then was added N,N-dimethylformamide (2.69 mL, 34.62 mmol) at −78° C. and the solution stirred for 1 hour. The reaction mixture was quenched with saturated aqueous ammonium chloride solution and extracted with ethyl acetate (2×40 mL). The combined organic layers were washed with brine, dried over anhydrous sodium sulfate, filtered and concentrated in vacuo. The crude material was purified using flash chromatography (20% ethyl acetate/hexane) to provide 4-chloro-7-((2-(trimethylsilyl)ethoxy)methyl)-7H-pyrrolo[2,3-d]pyrimidine-5-carbaldehyde as a light brown solid (2.8 g, 60% yield): MS (ES) m/z 312.1 (M+H).

196

Step 2: Preparation of methyl (E)-3-(4-chloro-7-((2-(trimethylsilyl)ethoxy)methyl)-7H-pyrrolo[2,3-d]pyrimidin-5-yl)acrylate

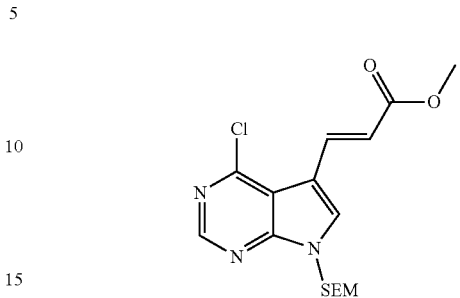

To a suspension of sodium hydride (0.29 g, 12.04 mmol) in tetrahydrofuran (70 mL) was added methyl 2-(diethoxyphosphoryl)acetate (2.28 mL, 12.04 mmol) at 0° C. The resulting suspension was stirred for 2 hours and then 4-chloro-7-((2-(trimethylsilyl)ethoxy)methyl)-7H-pyrrolo[2,3-d]pyrimidine-5-carbaldehyde (2.5 g, 8.02 mmol) was added at 0° C. The reaction mixture was stirred at ambient temperature for 2 hours. The reaction mixture was then quenched with ice water and extracted into ethyl acetate (2×50 mL). The combined organic layers were washed with brine, dried over anhydrous sodium sulfate, filtered and concentrated in vacuo. The crude material was purified using flash chromatography (15% ethyl acetate/hexane) to provide methyl (E)-3-(4-chloro-7-((2-(trimethylsilyl)ethoxy)methyl)-7H-pyrrolo[2,3-d]pyrimidin-5-yl)acrylate as a yellow solid (2.4 g, 82% yield): MS (ES) m/z 368.1 (M+H).

Step 3: Preparation of methyl 2-(4-chloro-7-((2-(trimethylsilyl)ethoxy)methyl)-7H-pyrrolo[2,3-d]pyrimidin-5-yl)cyclopropane-1-carboxylate

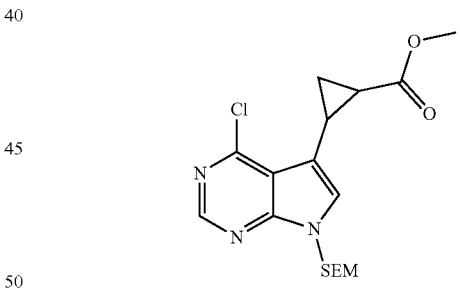

To a stirred solution of methyl (E)-3-(4-chloro-7-((2-(trimethylsilyl)ethoxy)methyl)-7H-pyrrolo[2,3-d]pyrimidin-5-yl)acrylate (2.2 g, 5.99 mmol) in diethyl ether (200 mL) was added palladium(II) acetate (0.26 g, 1.19 mmol) at 0° C. and stirred for 0.5 hours. Freshly prepared diazomethane in diethyl ether (15.44 g, 149.75 mmol) was added at 0° C. and the mixture was stirred at ambient temperature for 16 hours. The reaction was filtered through celite and the filtrate was washed with water, brine and dried over anhydrous sodium sulfate. The solution was filtered and concentrated in vacuo. The crude material was purified using flash chromatography (12% ethyl acetate/hexane) to provide methyl 2-(4-chloro-7-((2-(trimethylsilyl)ethoxy)methyl)-7H-pyrrolo[2,3-d]pyrimidin-5-yl)cyclopropane-1-carboxylate as a yellow sticky solid (1.8 g, 79% yield): MS (ES) m/z 382.1 (M+H).

Step 4: Preparation of (2-(4-chloro-7-((2-(trimethyl-silyl)ethoxy)methyl)-7H-pyrrolo[2,3-d]pyrimidin-5-yl)cyclopropyl)methanol

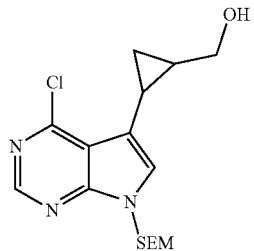

To a stirred solution of methyl 2-(4-chloro-7-((2-(trimethylsilyl)ethoxy)methyl)-7H-pyrrolo[2,3-d]pyrimidin-5-yl)cyclopropane-1-carboxylate (1.0 g, 2.62 mmol) in tetrahydrofuran (60 mL) at 0° C. was added lithium aluminum hydride solution (5.2 mL, 5.24 mmol, 1 M in tetrahydrofuran) dropwise. The mixture was stirred at 0° C. for 45 minutes and the reaction was quenched with ice water and extracted with ethyl acetate (2×50 mL). The combined organic layers were washed with brine, dried over anhydrous sodium sulfate, filtered and concentrated in vacuo. The crude material was purified using flash chromatography (20% ethyl acetate/hexane) to provide (2-(4-chloro-7-((2-(trimethylsilyl)ethoxy)methyl)-7H-pyrrolo[2,3-d]pyrimidin-5-yl)cyclopropyl)methanol as a yellow solid (0.9 g, 98% yield): MS (ES) m/z 354.1 (M+H).

Step 5: Preparation of 4-chloro-5-(2-(methoxymethyl)cyclopropyl)-7-((2-(trimethylsilyl)ethoxy)methyl)-7H-pyrrolo[2,3-d]pyrimidine

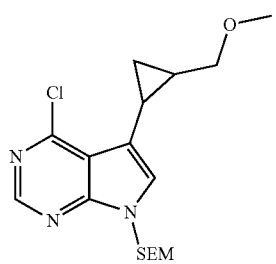 [SMILES: COCC1CC1c1cn(COCC[Si](C)(C)C)c2ncnc(Cl)c12]

A suspension of sodium hydride (0.12 g, 4.81 mmol) in N,N-dimethylformamide (40 mL), was cooled to 0° C. and (2-(4-chloro-7-((2-(trimethylsilyl)ethoxy)methyl)-7H-pyrrolo[2,3-d]pyrimidin-5-yl)cyclopropyl)methanol (0.85 g, 2.40 mmol) was added. The suspension was stirred for 15 minutes and then methyl iodide (0.75 mL, 12.01 mmol) was added at 0° C. and the mixture stirred at ambient temperature for 4 hours. The reaction mixture was quenched with ice water and extracted with ethyl acetate (2×50 mL). The combined organic layers were washed with brine, dried over anhydrous sodium sulfate, filtered and concentrated in vacuo. The crude material was purified using flash chromatography (20% ethyl acetate/hexane) to provide 4-chloro-5-(2-(methoxymethyl)cyclopropyl)-7-((2-(trimethylsilyl)ethoxy)methyl)-7H-pyrrolo[2,3-d]pyrimidine as a yellow liquid (0.45 g, 51% yield): MS (ES) m/z 368.1 (M+H).

Step 6: Preparation of tert-butyl (3R)-3-((5-(2-(methoxymethyl)cyclopropyl)-7-((2-(trimethylsilyl)ethoxy)methyl)-7H-pyrrolo[2,3-d]pyrimidin-4-yl)amino)piperidine-1-carboxylate

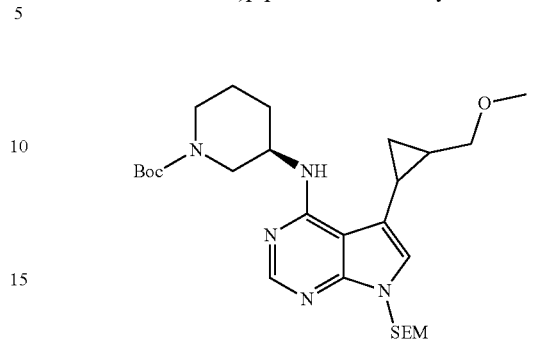

To a stirred solution of 4-chloro-5-(2-(methoxymethyl)cyclopropyl)-7-((2-(trimethylsilyl)ethoxy)methyl)-7H-pyrrolo[2,3-d]pyrimidine (0.45 g, 1.22 mmol) in n-butanol (5 mL) was added tert-butyl (R)-3-aminopiperidine-1-carboxylate (0.36 g, 1.83 mmol) and N,N-diisopropylethylamine (0.41 mL, 2.41 mmol) and the mixture was heated in a sealed tube at 130° C. for 16 hours. The reaction mixture was allowed to cool to ambient temperature, concentrated to remove n-butanol and the crude material was purified using flash chromatography (25% ethyl acetate/hexane) to provide tert-butyl (3R)-3-((5-(2-(methoxymethyl)cyclopropyl)-7-((2-(trimethylsilyl)ethoxy)methyl)-7H-pyrrolo[2,3-d]pyrimidin-4-yl)amino)piperidine-1-carboxylate as a brown liquid (0.4 g, 62.50% yield): MS (ES) m/z 532.3 (M+H).

Step 7: Preparation of tert-butyl (3R)-3-((5-(2-(methoxymethyl)cyclopropyl)-7H-pyrrolo[2,3-d]pyrimidin-4-yl)amino)piperidine-1-carboxylate

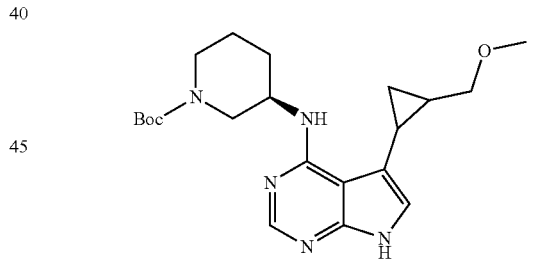

To a solution of tert-butyl (3R)-3-((5-(2-(methoxymethyl)cyclopropyl)-7-((2-(trimethylsilyl)ethoxy)methyl)-7H-pyrrolo[2,3-d]pyrimidin-4-yl)amino)piperidine-1-carboxylate (0.4 g, 0.75 mmol) in tetrahydrofuran (6 mL) was added tetrabutylammonium fluoride (6 mL, 1 M in tetrahydrofuran) and the solution was heated to 80° C. for 16 hours. The reaction mixture was cooled to ambient temperature and then poured into ice water and extracted with ethyl acetate. The organic layer was washed with water, brine, dried over anhydrous sodium sulfate, filtered and concentrated in vacuo. The crude material was purified using flash chromatography (40% ethyl acetate/hexane) to provide tert-butyl (3R)-3-((5-(2-(methoxymethyl)cyclopropyl)-7H-pyrrolo[2,3-d]pyrimidin-4-yl)amino)piperidine-1-carboxylate as a yellow liquid (0.22 g, 73% yield): MS (ES) m/z 402.2 (M+H).

Step 8: Preparation of 5-(2-(methoxymethyl)cyclopropyl)-N—((R)-piperidin-3-yl)-7H-pyrrolo[2,3-d]pyrimidin-4-amine

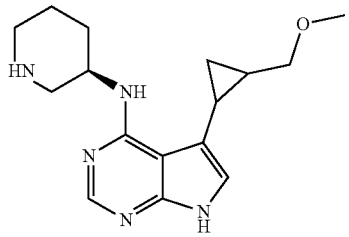 [SMILES: COCC1CC1c1c[nH]c2ncnc(N[C@@H]3CCCNC3)c12]

To a solution of tert-butyl (3R)-3-((5-(2-(methoxymethyl)cyclopropyl)-7H-pyrrolo[2,3-d]pyrimidin-4-yl)amino)piperidine-1-carboxylate (0.22 g, 0.54 mmol) in dichloromethane (6 mL) was added a solution of hydrogen chloride (6.0 mL, 4 M in 1,4-dioxane) at 0° C. and the resulting mixture was stirred at ambient temperature for 4 hours. The reaction mixture was concentrated in vacuo and the residue was washed with diethyl ether to provide 5-(2-(methoxymethyl)cyclopropyl)-N—((R)-piperidin-3-yl)-7H-pyrrolo[2,3-d]pyrimidin-4-amine as a light brown solid (0.22 g, crude). The crude product was progressed for next stage without further purification.

Step 9: Preparation of 1-((R)-3-((5-(2-(methoxymethyl)cyclopropyl)-7H-pyrrolo[2,3-d]pyrimidin-4-yl)amino)piperidin-1-yl)prop-2-en-1-one

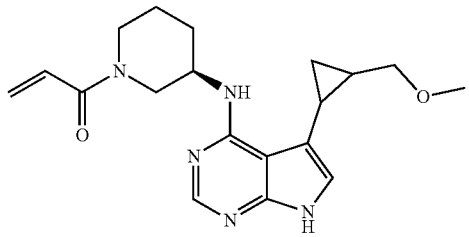 [SMILES: C=CC(=O)N1CCC[C@@H](Nc2ncnc3[nH]cc(C4CC4COC)c23)C1]

To a stirred solution of 5-(2-(methoxymethyl)cyclopropyl)-N—((R)-piperidin-3-yl)-7H-pyrrolo[2,3-d]pyrimidin-4-amine (0.22 g, 0.58 mmol) in tetrahydrofuran:water (7.0:3.0 mL) was added triethylamine (0.23 mL, 1.76 mmol) followed by a solution of acryloyl chloride (0.05 mL, 0.44 mmol) in tetrahydrofuran (0.5 mL) at 0° C. and stirred for 15 minutes. The reaction mixture was quenched with sat. sodium bicarbonate solution and extracted with ethyl acetate. The organic layer was washed with brine, dried over anhydrous sodium sulfate, filtered and concentrated in vacuo. The crude material was purified using flash chromatography (5% methanol/dichloromethane) and further purified by using prep HPLC to provide 1-((3R)-3-((5-(2-(methoxymethyl)cyclopropyl)-7H-pyrrolo[2,3-d]pyrimidin-4-yl)amino)piperidin-1-yl)prop-2-en-1-one as an off-white solid (0.07 g, 33% yield): MS (ES) m/z 356.2 (M+H).
Prep HPLC method:
Column: Inertsil ODS 3V (250 mm×4.6 mm×5 mic)
Mobile phase (A): 0.1% Ammonia in water
Mobile phase (B): Methanol
Flow rate: 1.0 mL/min (45:55).

EXAMPLE 25

1-((R)-3-((5-((1S,2S)-2-(methoxymethyl)cyclopropyl)-7H-pyrrolo[2,3-d]pyrimidin-4-yl)amino)piperidin-1-yl)prop-2-en-1-one

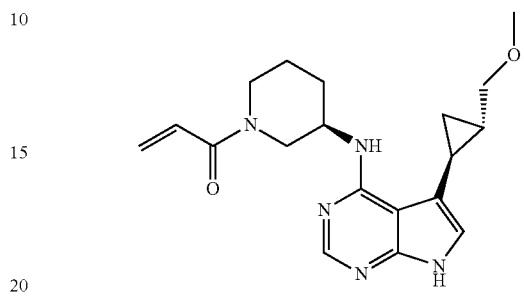

Trans relative configuration with respect to cyclopropyl substituents absolute configurations of cyclopropyl stereogenic centers is unknown Off-white solid (0.02 g, 10% yield): $^1$H NMR (400 MHz, DMSO-$d_6$ at 80° C.) δ 11.08 (s, 1H), 8.07 (s, 1H), 6.67-6.76 (m, 2H), 6.02 (t, J=7.2 Hz, 2H), 5.57 (d, J=9.2 Hz, 1H), 4.14-4.23 (m, 2H), 3.87 (br s, 1H), 3.60-3.64 (m, 1H), 3.32 (s, 3H), 3.03-3.17 (m, 2H), 2.02-2.03 (m, 1H), 1.84-1.86 (m, 1H), 1.67-1.78 (m, 2H), 1.52-154 (m, 1H), 1.18-1.24 (m, 2H), 0.91-0.95 (m, 1H), 0.75-0.77 (m, 1H); MS (ES) m/z 356.2 (M+H). Retention time 15.165 minutes.

EXAMPLE 26

1-((R)-3-((5-((1R,2R)-2-(methoxymethyl)cyclopropyl)-7H-pyrrolo[2,3-d]pyrimidin-4-yl)amino)piperidin-1-yl)prop-2-en-1-one

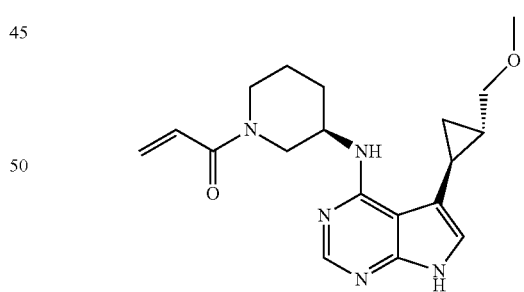

Opposite configuration to Example 26 with respect to trans cyclopropyl substituents Off-white solid (0.02 g, 10% yield): $^1$H NMR (400 MHz, DMSO-$d_6$ at 80° C.) δ 11.10 (s, 1H), 8.07 (s, 1H), 6.71-6.77 (m, 2H), 6.09 (t, J=14.4 Hz, 2H), 5.63 (d, J=10.4 Hz, 1H), 4.23 (br s, 2H), 3.99 (br s, 1H), 3.62-3.65 (m, 1H), 3.34 (s, 3H), 3.09 (s, 2H), 2.01-2.03 (m, 1H), 1.67-1.85 (m, 3H), 1.51-154 (m, 1H), 1.23 (s, 2H), 0.89-0.93 (m, 1H), 0.74-0.75 (m, 1H); MS (ES) m/z 356.2 (M+H). Retention time: 18.162 minutes.

EXAMPLE 27

Preparation of 1-((3R)-3-((5-(2,2-difluorocyclopropyl)-7H-pyrrolo[2,3-d]pyrimidin-4-yl)amino)piperidin-1-yl)prop-2-en-1-one

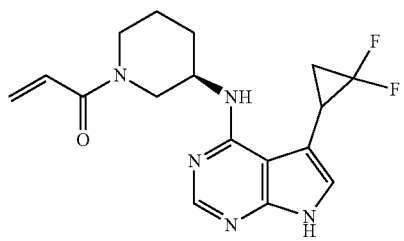 [SMILES: C=CC(=O)N1CCC[C@@H](Nc2ncnc3[nH]cc(C4CC4(F)F)c23)C1]

The title compound was prepared by the method described in Scheme 26.

Scheme 26.
Preparation of 1-((3R)-3-((5-(2,2-difluorocyclopropyl)-7H-pyrrolo[2,3-d]pyrimidin-4-yl)amino)piperidin-1-yl)prop-2-en-1-one

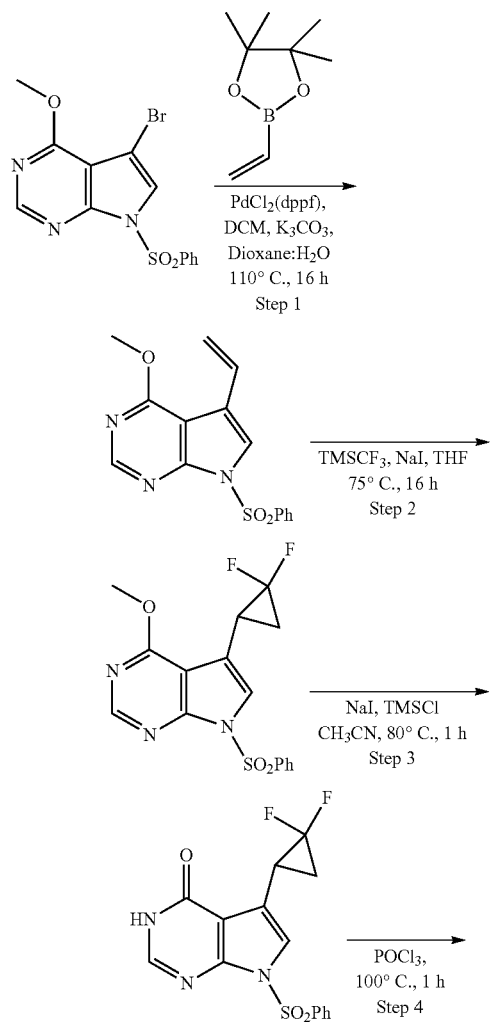

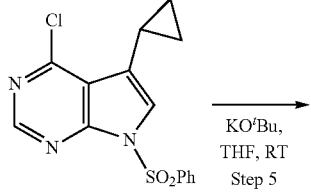
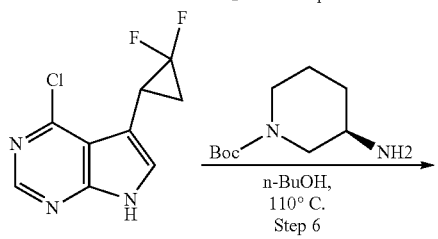
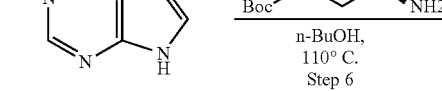
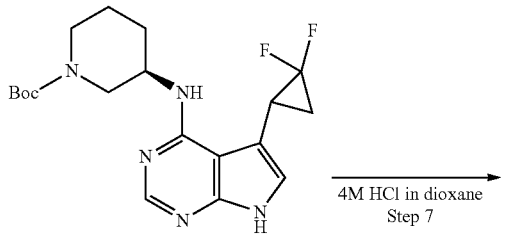
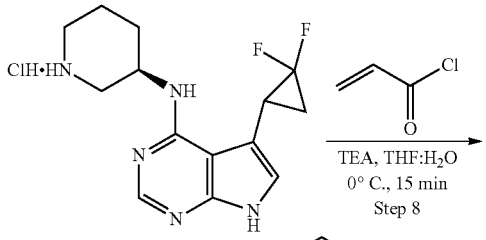
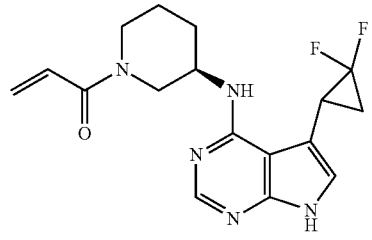

Step 1: Preparation of 4-methoxy-7-(phenylsulfonyl)-5-vinyl-7H-pyrrolo[2,3-d]pyrimidine

To a solution of 5-bromo-4-methoxy-7-(phenylsulfonyl)-7H-pyrrolo[2,3-d]pyrimidine (prepared by the method described in Example 24, 5.0 g, 13.66 mmol) in toluene:water (50:10 mL) was added 4,4,5,5-tetramethyl-2-vinyl-1,3,2-dioxaborolane (4.18 g, 27.32 mmol), potassium carbonate (5.62 g, 40.98 mmol) and [1,1'-bis(diphenylphosphino)ferrocene]palladium(II) dichloride (1.1 g, 1.36 mmol) under an argon atmosphere and then heated to 110° C. for 16 hours. After cooling, the reaction mixture was filtered through celite and the celite washed with ethyl acetate. The filtrate was washed with water, brine, dried over anhydrous sodium sulfate, filtered and concentrated in vacuo. The crude material was purified using flash chromatography (12% ethyl acetate/hexane) to provide 4-methoxy-7-(phenylsulfonyl)-5-vinyl-7H-pyrrolo[2,3-d]pyrimidine as an off-white solid (1.82 g, 42% yield): MS (ES) m/z 316.3 (M+H).

Step 2: Preparation of 5-(2,2-difluorocyclopropyl)-4-methoxy-7-(phenylsulfonyl)-7H-pyrrolo[2,3-d]pyrimidine

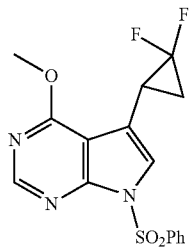

To a suspension of 4-methoxy-7-(phenylsulfonyl)-5-vinyl-7H-pyrrolo[2,3-d]pyrimidine (1.0 g, 3.17 mmol) and sodium iodide (0.19 g, 1.26 mmol) in tetrahydrofuran (10 mL) was added trimethyl(trifluoromethyl)silane (2.34 mL, 15.87 mmol) and the mixture was heated in a sealed tube at 75° C. for 16 hours. After cooling to ambient temperature, the reaction mixture was poured into water and extracted with ethyl acetate. The organic layer was washed with brine, dried over anhydrous sodium sulfate, filtered and concentrated in vacuo. The crude product was triturated with hexane to provide 5-(2,2-difluorocyclopropyl)-4-methoxy-7-(phenylsulfonyl)-7H-pyrrolo[2,3-d]pyrimidine as an off-white solid (1.1 g, crude): MS (ES) m/z 366.0 (M+H).

Step 3: Preparation of 5-(2,2-difluorocyclopropyl)-7-(phenylsulfonyl)-3,7-dihydro-4H-pyrrolo[2,3-d]pyrimidin-4-one

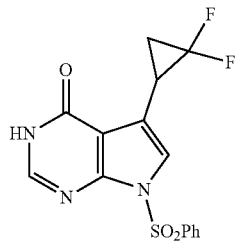

To a solution of 5-(2,2-difluorocyclopropyl)-4-methoxy-7-(phenylsulfonyl)-7H-pyrrolo[2,3-d]pyrimidine (2.5 g, 6.84 mmol) in acetonitrile (25 mL) was added sodium iodide (1.05 g, 6.84 mmol) and chlorotrimethylsilane (0.9 mL, 6.84 mmol) and the mixture heated in a sealed tube at 80° C. for 1 hour. After cooling the reaction mixture was poured into water and extracted with ethyl acetate. The organic layer was washed with brine, dried over anhydrous sodium sulfate, filtered and concentrated in vacuo. The crude product was triturated with hexane to provide 5-(2,2-difluorocyclopropyl)-7-(phenylsulfonyl)-3,7-dihydro-4H-pyrrolo[2,3-d]pyrimidin-4-one as a light yellow solid (2.4 g, crude): MS (ES) m/z 352.0 (M+H).

Step 4: Preparation of 4-chloro-5-(2,2-difluorocyclopropyl)-7-(phenylsulfonyl)-7H-pyrrolo[2,3-d]pyrimidine

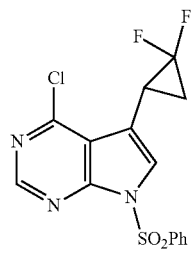

A solution of 5-(2,2-difluorocyclopropyl)-7-(phenylsulfonyl)-3,7-dihydro-4H-pyrrolo[2,3-d]pyrimidin-4-one (2.4 g, 6.8 mmol) in phosphoryl chloride (10 mL) was stirred at 100° C. for 1 hour. After cooling, the reaction mixture was concentrated in vacuo to remove excess of phosphoryl chloride and the residue was dissolved in ethyl acetate. The organic layer was washed with water, sat. sodium bicarbonate, and brine. The solution was filtered and concentrated in vacuo. The crude product was triturated with hexane to provide 4-chloro-5-(2,2-difluorocyclopropyl)-7-(phenylsulfonyl)-7H-pyrrolo[2,3-d]pyrimidine as an off-white solid (1.7 g, crude): MS (ES) m/z 370.0 (M+H).

Step 5: Preparation of 4-chloro-5-(2,2-difluorocyclopropyl)-7H-pyrrolo[2,3-d]pyrimidine

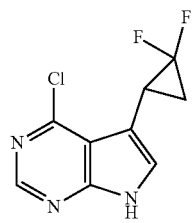

To a solution 4-chloro-5-(2,2-difluorocyclopropyl)-7-(phenylsulfonyl)-7H-pyrrolo[2,3-d]pyrimidine (0.4 g, 0.10 mmol) in tetrahydrofuran (5 mL) was added potassium tert-butoxide (0.24 g, 2.16 mmol) at ambient temperature and the mixture was stirred for 2 hours. The reaction mixture was poured into ice water and extracted with ethyl acetate. The organic layer was washed with water, brine, dried over anhydrous sodium sulfate, filtered and concentrated in vacuo to provide 4-chloro-5-(2,2-difluorocyclopropyl)-7H-pyrrolo[2,3-d]pyrimidine as a viscous liquid (0.2 g, crude): MS (ES) m/z 230.0 (M+H).

Step 6: Preparation of tert-butyl (3R)-3-((5-(2,2-difluorocyclopropyl)-7H-pyrrolo[2,3-d]pyrimidin-4-yl)amino)piperidine-1-carboxylate

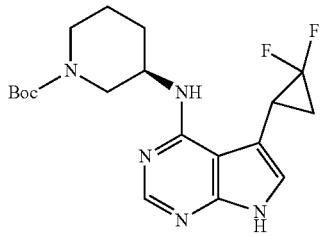 [SMILES: CC(C)(C)OC(=O)N1CCC[C@@H](Nc2ncnc3[nH]cc(C4CC4(F)F)c23)C1]

To a solution of 4-chloro-5-(2,2-difluorocyclopropyl)-7H-pyrrolo[2,3-d]pyrimidine (0.20 g, 0.87 mmol) in n-butanol (4 mL) was added tert-butyl (R)-3-aminopiperidine-1-carboxylate (0.34 g, 1.70 mmol) and N,N-diisopropylethylamine (0.40 mL, 2.62 mmol). The mixture was heated in a sealed tube at 110° C. for 24 hours. After cooling to ambient temperature, the reaction mixture was concentrated in vacuo and the residue was dissolved in ethyl acetate. The organic layer was washed with water, brine, dried over anhydrous sodium sulfate, filtered and concentrated in vacuo. The crude material was purified using flash chromatography (2% methanol/dichloromethane) to provide tert-butyl (3R)-3-((5-(2,2-difluorocyclopropyl)-7H-pyrrolo[2,3-d]pyrimidin-4-yl)amino)piperidine-1-carboxylate as a viscous liquid (0.2 g, 60% yield): MS (ES) m/z 394.1 (M+H).

Step 7: Preparation of 5-(2,2-difluorocyclopropyl)-N—((R)-piperidin-3-yl)-7H-pyrrolo[2,3-d]pyrimidin-4-amine hydrochloride

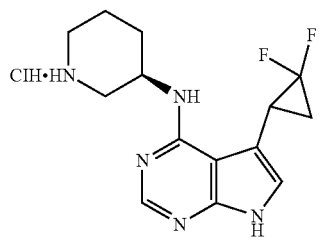

To a stirred solution of tert-butyl (3R)-3-((5-(2,2-difluorocyclopropyl)-7H-pyrrolo[2,3-d]pyrimidin-4-yl)amino)piperidine-1-carboxylate (0.2 g, 0.50 mmol) in dichloromethane (3 mL) was added a solution of hydrogen chloride (3 mL, 4 M in dioxane) at 0° C. and the mixture was stirred at ambient temperature for 4 hours. The reaction mixture was concentrated in vacuo and the residue was washed with diethyl ether to provide 5-(2,2-difluorocyclopropyl)-N—((R)-piperidin-3-yl)-7H-pyrrolo[2,3-d]pyrimidin-4-amine hydrochloride as an off-white solid (0.23 g, crude): MS (ES) m/z: 294.1 (M+H).

Step 8: Preparation of 1-((3R)-3-((5-(2,2-difluorocyclopropyl)-7H-pyrrolo[2,3-d]pyrimidin-4-yl)amino)piperidin-1-yl)prop-2-en-1-one

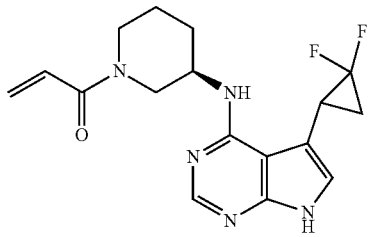 [SMILES: C=CC(=O)N1CCC[C@@H](Nc2ncnc3[nH]cc(C4CC4(F)F)c23)C1]

To a solution of 5-(2,2-difluorocyclopropyl)-N—((R)-piperidin-3-yl)-7H-pyrrolo[2,3-d]pyrimidin-4-amine hydrochloride (0.23 g, 0.69 mmol) in tetrahydrofuran:water (8.0:2.0 mL) was added triethylamine (0.38 mL, 2.79 mmol) followed by a solution of acryloyl chloride (0.05 g, 0.55 mmol) in tetrahydrofuran (1 mL) at 0° C. and stirred for 15 minutes. The reaction mixture was quenched with saturated aqueous sodium bicarbonate solution and extracted with ethyl acetate. The organic layer was washed with brine, dried over anhydrous sodium sulfate, filtered and concentrated in vacuo. The crude material was purified using flash chromatography (20% methanol/dichloromethane) to provide 1-((3R)-3-((5-(2,2-difluorocyclopropyl)-7H-pyrrolo[2,3-d]pyrimidin-4-yl)amino)piperidin-1-yl)prop-2-en-1-one as a white solid (0.07 g, 29% yield): $^1$H NMR (400 MHz, DMSO-$d_6$ at 80° C.) δ 11.34 (s, 1H), 8.12 (s, 1H), 6.96 (s, 1H), 6.66-6.68 (m, 1H), 6.01-6.05 (m, 1H), 5.58-5.64 (m, 2H), 4.21 (br s, 1H), 3.99-4.09 (m, 1H), 3.78 (br s, 1H), 3.37-3.43 (m, 2H), 3.12-3.18 (m, 1H), 1.88-2.01 (m, 2H), 1.73-1.76 (m, 2H), 1.51-1.65 (m, 2H); MS (ES) m/z: 348.1 (M+H).

EXAMPLE 28

Preparation of (R)-1-(3-((5-cyclopentyl-7H-pyrrolo[2,3-d]pyrimidin-4-yl)amino)piperidin-1-yl)prop-2-en-1-one

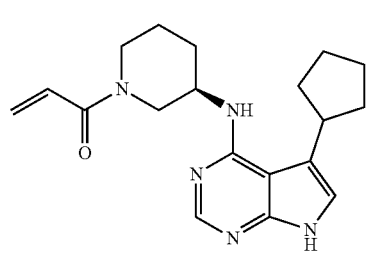 [SMILES: C=CC(=O)N1CCC[C@@H](Nc2ncnc3[nH]cc(C4CCCC4)c23)C1]

Step 1: Preparation of 4-chloro-5-iodo-7-(phenylsulfonyl)-7H-pyrrolo[2,3-d]pyrimidine

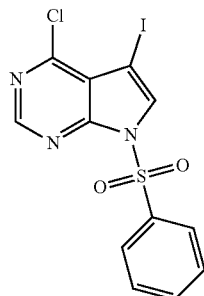

A 60% dispersion of sodium hydride in mineral oil (0.341 g, 8.57 mmol) was added to a solution of 4-chloro-5-iodo-1H-pyrrolo[2,3-d]pyrimidine (2.00 g, 7.15 mmol) in N,N-dimethylformamide (40 mL). Benzenesulfonyl chloride (1.38 g, 7.50 mmol) was added and the reaction was stirred at ambient temperature for 1 hour. The N,N-dimethylformamide was removed in vacuo and the remaining solid was partitioned between ethyl acetate and water. The ethyl acetate layer was washed with brine, dried over sodium sulfate, filtered and concentrated in vacuo to give 4-chloro-5-iodo-7-(phenylsulfonyl)-7H-pyrrolo[2,3-d]pyrimidine as a white solid (3.35 g, quant. yield): MS (ES) m/z 420.0 (M+H).

Step 2: Preparation of 4-chloro-5-(cyclopent-1-en-1-yl)-7-(phenylsulfonyl)-7H-pyrrolo[2,3-d]pyrimidine

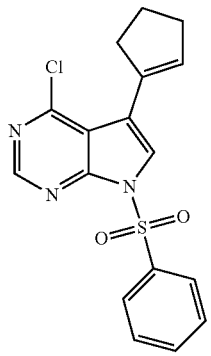 [SMILES: O=S(=O)(c1ccccc1)n1cc(C2=CCCC2)c2c(Cl)ncnc21]

A mixture of 4-chloro-5-iodo-7-(phenylsulfonyl)-7H-pyrrolo[2,3-d]pyrimidine (3.35 g, 7.98 mmol), 2-(cyclopent-1-en-1-yl)-4,4,5,5-tetramethyl-1,3,2-dioxaborolane (1.70 g, 8.77 mmol), potassium carbonate (3.30 g, 23.9 mmol), palladium bis(cyclopenta-1,3-dien-1-yldiphenylphosphane) methylene chloride iron dichloride (Pd(dppf)Cl$_2$-DCM, 0.325 g, 0.399 mmol), dioxane (50 mL) and water (15 mL) was purged with nitrogen for 10 minutes and then heated at 100° C. for 5 hours. The reaction was cooled to ambient temperature and partitioned between ethyl acetate and water. The ethyl acetate layer was washed with brine, dried over sodium sulfate, filtered and concentrated in vacuo. The resulting oil was chromatographed on silica gel (40 g), eluting with ethyl acetate and heptane. Pure fractions were pooled and concentrated to give the desired product, 4-chloro-5-(cyclopent-1-en-1-yl)-7-(phenylsulfonyl)-7H-pyrrolo[2,3-d]pyrimidine as an off-white solid (2.04 g, 71% yield): MS (ES) m/z 360.1 (M+H).

Step 3: Preparation of tert-butyl (R)-3-((5-(cyclopent-1-en-1-yl)-7-(phenylsulfonyl)-7H-pyrrolo[2,3-d]pyrimidin-4-yl)amino)piperidine-1-carboxylate

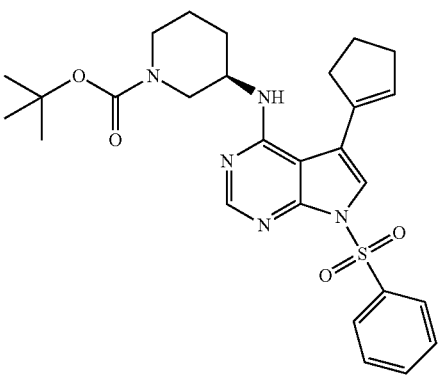 [SMILES: CC(C)(C)OC(=O)N1CCC[C@@H](Nc2ncnc3c2c(C2=CCCC2)cn3S(=O)(=O)c2ccccc2)C1]

A mixture of 4-chloro-5-(cyclopent-1-en-1-yl)-7-(phenylsulfonyl)-7H-pyrrolo[2,3-d]pyrimidine (1.94 g, 5.39 mmol), tert-butyl (3R)-3-aminopiperidine-1-carboxylate (1.18 g, 5.92 mmol), and N,N-diisopropylethylamine (2.8 mL, 16 mmol) in n-butanol (35 mL) was heated overnight at 140° C. in a sealed vessel. The reaction was cooled and partitioned between ethyl acetate and water. The ethyl acetate layer was washed with brine, dried over sodium sulfate, filtered and concentrated in vacuo. The resulting oil was chromatographed on silica gel, eluting with ethyl acetate and heptane. Pure fractions were pooled and concentrated to give product tert-butyl (R)-3-((5-(cyclopent-1-en-1-yl)-7-(phenylsulfonyl)-7H-pyrrolo[2,3-d]pyrimidin-4-yl)amino)piperidine-1-carboxylate as a white foam (2.14 g, 76% yield): MS (ES) m/z 524.3 (M+H).

Step 4: Preparation of tert-butyl (R)-3-((5-(cyclopent-1-en-1-yl)-7H-pyrrolo[2,3-d]pyrimidin-4-yl)amino)piperidine-1-carboxylate

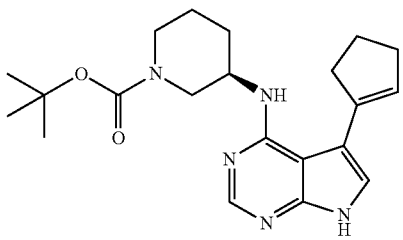 [SMILES: CC(C)(C)OC(=O)N1CCC[C@@H](Nc2ncnc3[nH]cc(C4=CCCC4)c23)C1]

A solution of tert-butyl (R)-3-((5-(cyclopent-1-en-1-yl)-7-(phenylsulfonyl)-7H-pyrrolo[2,3-d]pyrimidin-4-yl)amino)piperidine-1-carboxylate (1.0 g, 1.9 mmol) in a solution of tetrabutylammonium fluoride (13.2 mL of a 1M solution in tetrahydrofuran, 13.2 mmol) was heated overnight in a sealed tube at 40° C. At this time, the reaction mixture was cooled and partitioned between ethyl acetate and saturated sodium bicarbonate. The ethyl acetate layer was washed with brine, dried over sodium sulfate, filtered and concentrated in vacuo. The resulting oil was chromatographed on silica gel, eluting with ethyl acetate and heptane. Pure fractions were pooled and concentrated to give tert-butyl (R)-3-((5-(cyclopent-1-en-1-yl)-7H-pyrrolo[2,3-d]pyrimidin-4-yl)amino)piperidine-1-carboxylate as a yellow oil (0.66 g, 91% yield): MS (ES) m/z 384.3 (M+H).

Step 5: Preparation of tert-butyl (R)-3-((5-cyclopentyl-7H-pyrrolo[2,3-d]pyrimidin-4-yl)amino)piperidine-1-carboxylate

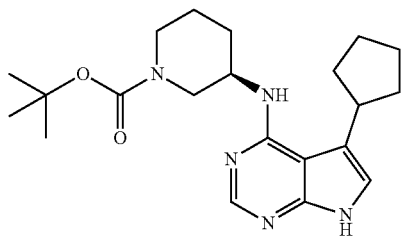 [SMILES: CC(C)(C)OC(=O)N1CCC[C@@H](Nc2ncnc3[nH]cc(C4CCCC4)c23)C1]

A mixture of tert-butyl (R)-3-((5-(cyclopent-1-en-1-yl)-7H-pyrrolo[2,3-d]pyrimidin-4-yl)amino)piperidine-1-carboxylate (0.311 g, 0.811 mmol) and palladium hydroxide (0.028 g, 0.04 mmol) in methanol (5 mL) was stirred overnight under a hydrogen atmosphere at ambient temperature. The reaction was filtered through a plug of Celite® and concentrated in vacuo. The resulting oil was chromatographed on silica gel, eluting with ethyl acetate and heptane. Pure fractions were pooled and concentrated to give product tert-butyl (R)-3-((5-cyclopentyl-7H-pyrrolo[2,3-d]pyrimidin-4-yl)amino)piperidine-1-carboxylate as a clear oil (0.198 g, 63% yield): MS (ES) m/z 386.3 (M+H).

Step 6: Preparation of (R)-5-cyclopentyl-N-(piperidin-3-yl)-7H-pyrrolo[2,3-d]pyrimidin-4-amine

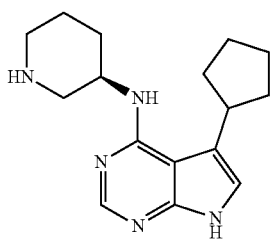 [SMILES: c1nc(N[C@@H]2CCCNC2)c2c(C3CCCC3)c[nH]c2n1]

Trifluoroacetic acid (0.97 mL, 12.8 mmol) was added to a solution of tert-butyl (R)-3-((5-cyclopentyl-7H-pyrrolo[2,3-d]pyrimidin-4-yl)amino)piperidine-1-carboxylate (0.198 g, 0.514 mmol) in dichloromethane (3 mL) at 0° C. and stirred overnight at room temperature. The reaction was concentrated in vacuo to give (R)-5-cyclopentyl-N-(piperidin-3-yl)-7H-pyrrolo[2,3-d]pyrimidin-4-amine as an oil (0.146 g, quantitative yield). The material was carried forward without further purification: MS (ES) m/z 286.3 (M+H).

Step 7: Preparation of (R)-1-(3-((5-cyclopentyl-7H-pyrrolo[2,3-d]pyrimidin-4-yl)amino)piperidin-1-yl)prop-2-en-1-one

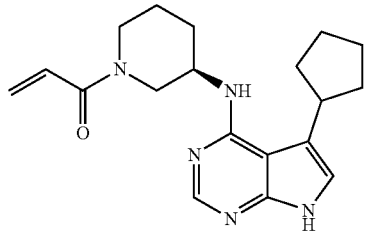 [SMILES: C=CC(=O)N1CCC[C@@H](Nc2ncnc3[nH]cc(C4CCCC4)c23)C1]

To a solution of (R)-5-cyclopentyl-N-(piperidin-3-yl)-7H-pyrrolo[2,3-d]pyrimidin-4-amine (0.146 g, 0.512 mmol) in tetrahydrofuran (2 mL) was added triethylamine (0.212 mL, 1.53 mmol). Separately, a solution of prop-2-enoic acid (0.052 mg, 0.716 mmol) in tetrahydrofuran (2 mL) was treated with 1-ethyl-3-(3-dimethylaminopropyl)carbodiimide hydrochloride (0.156 g, 0.818 mmol) and triethylamine (0.212 mL, 1.53 mmol). After 15 minutes at ambient temperature, the solution of activated acid was added to the amine solution which was stirred at ambient temperature for 4 hours. The reaction mixture was then taken up in ethyl acetate and washed with water then brine. The ethyl acetate layer was then dried over sodium sulfate, filtered and concentrated in vacuo. The resulting material was chromatographed on silica gel, eluting with methanol and ethyl acetate. Pure fractions were pooled and concentrated to give the desired product, (R)-1-(3-((5-cyclopentyl-7H-pyrrolo[2,3-d]pyrimidin-4-yl)amino)piperidin-1-yl)prop-2-en-1-one as an off-white foam (43.6 mg, 25% yield): $^1$H NMR (400 MHz, DMSO-$d_6$) δ ppm 11.29 (br s, 1H), 8.09 (br d, J=11.74 Hz, 1H), 6.87 (br s, 1H), 6.56-6.79 (m, 1H), 6.01-6.22 (m, 1H), 5.53-5.76 (m, 2H), 4.13-4.41 (m, 1H), 3.81-4.07 (m, 1H), 3.45-3.67 (m, 2H), 3.26-3.38 (m, 2H), 1.97 (br s, 2H), 1.90 (br d, J=5.48 Hz, 2H), 1.68 (br s, 4H), 1.42-1.64 (m, 4H); MS (ES) m/z 340.3 (M+H).

EXAMPLE 29

Preparation of (R)-1-(3-((5-(cyclopent-1-en-1-yl)-7H-pyrrolo[2,3-d]pyrimidin-4-yl)amino)piperidin-1-yl)prop-2-en-1-one

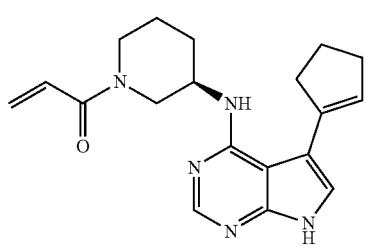 [SMILES: C=CC(=O)N1CCC[C@@H](Nc2ncnc3[nH]cc(C4=CCCC4)c23)C1]

Step 1: Preparation of (R)-5-(cyclopent-1-en-1-yl)-N-(piperidin-3-yl)-7H-pyrrolo[2,3-d]pyrimidin-4-amine

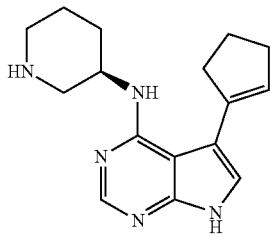 [SMILES: C1=C(c2c[nH]c3ncnc(N[C@@H]4CCCNC4)c23)CCC1]

Trifluoroacetic acid (1.23 mL, 16.2 mmol) was added to a solution of tert-butyl (R)-3-((5-(cyclopent-1-en-1-yl)-7H-pyrrolo[2,3-d]pyrimidin-4-yl)amino)piperidine-1-carboxylate (Example 28 step 4, 0.311 g, 0.811 mmol) in dichloromethane (3 mL) at 0° C. and the mixture stirred overnight at room temperature. The reaction was concentrated in vacuo to give (R)-5-(cyclopent-1-en-1-yl)-N-(piperidin-3-yl)-7H-pyrrolo[2,3-d]pyrimidin-4-amine as an oil (0.229 g, quantitative yield). The material was carried forward without further purification: MS (ES) m/z 284.3 (M+H).

Step 2: Preparation of (R)-1-(3-((5-(cyclopent-1-en-1-yl)-7H-pyrrolo[2,3-d]pyrimidin-4-yl)amino)piperidin-1-yl)prop-2-en-1-one

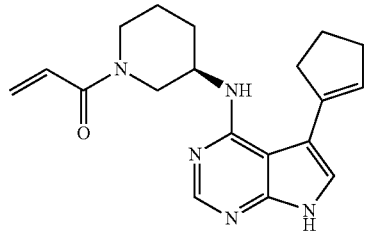 [SMILES: C=CC(=O)N1CCC[C@@H](Nc2ncnc3[nH]cc(C4=CCCC4)c23)C1]

To a solution of (R)-5-(cyclopent-1-en-1-yl)-N-(piperidin-3-yl)-7H-pyrrolo[2,3-d]pyrimidin-4-amine (0.229 g, 0.808 mmol) in tetrahydrofuran (2 mL) was added triethylamine (0.336 mL, 2.42 mmol). Separately, a solution of prop-2-enoic acid (0.082 mg, 1.13 mmol) in tetrahydrofuran (2 mL) was treated with 1-ethyl-3-(3-dimethylaminopropyl)carbodiimide hydrochloride (0.247 g, 1.29 mmol) and triethylamine (0.336 mL, 2.42 mmol). After 15 minutes at ambient temperature, the solution of activated acid was added to the amine solution and stirred at ambient temperature for 4 hours. The reaction was then taken up in ethyl acetate and washed with water then brine. The ethyl acetate layer was then dried over sodium sulfate, filtered and concentrated in vacuo. The resulting material was chromatographed on silica gel, eluting with methanol and ethyl acetate. Pure fractions were pooled and concentrated to give the desired product (R)-1-(3-((5-(cyclopent-1-en-1-yl)-7H-pyrrolo[2,3-d]pyrimidin-4-yl)amino)piperidin-1-yl)prop-2-en-1-one as a pale yellow foam (48 mg, 18% yield): $^1$H NMR (400 MHz, DMSO-$d_6$) δ 11.69 (br s, 1H), 8.17 (br d, J=6.26 Hz, 1H), 7.16 (s, 1H), 6.85 (br dd, J=15.85, 10.37 Hz, 1H), 6.60 (br dd, J=16.63, 10.37 Hz, 1H), 5.89-6.14 (m, 1H), 5.76 (br d, J=7.43 Hz, 1H), 5.60-5.73 (m, 1H), 5.51 (br d, J=10.56 Hz, 1H), 4.22-4.44 (m, 1H), 3.43-3.82 (m, 4H), 3.32 (m, 1H), 2.54-2.74 (m, 2H), 1.83-2.10 (m, 3H), 1.77 (br s, 1H), 1.58 (br s, 2H); MS (ES) m/z 338.3 (M+H).

EXAMPLE 30

Preparation of 1-((2S,5R)-5-((5-cyclopentyl-7H-pyrrolo[2,3-d]pyrimidin-4-yl)amino)-2-methylpiperidin-1-yl)prop-2-en-1-one

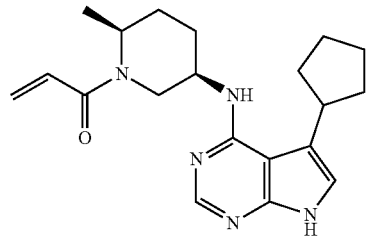 [SMILES: C=CC(=O)N1C[C@H](Nc2ncnc3[nH]cc(C4CCCC4)c23)CC[C@@H]1C]

The title compound was prepared by the method described in Scheme 27.

Scheme 27.
Preparation of 1-((2S,5R)-5-((5-cyclopentyl-7H-pyrrolo[2,3-d]pyrimidin-4-yl)amino)-2-methylpiperidin-1-yl)prop-2-en-1-one

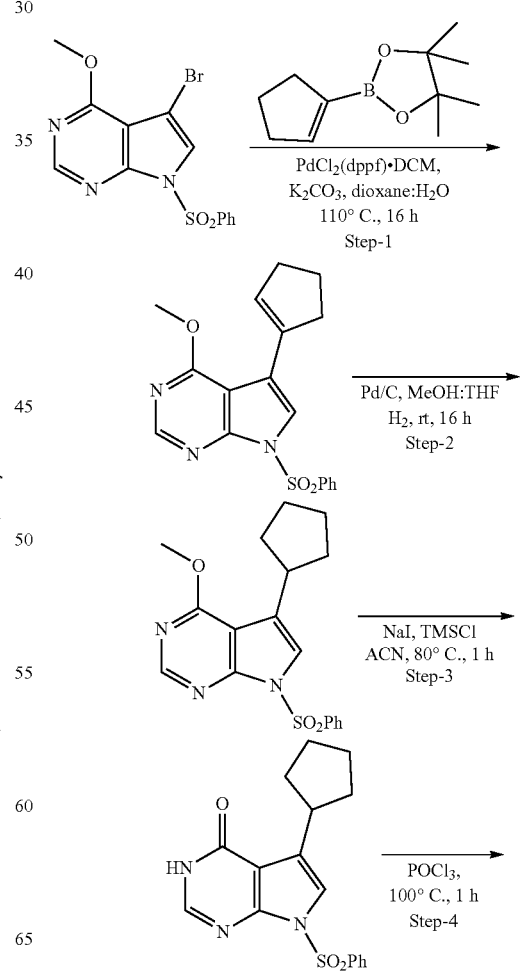

-continued

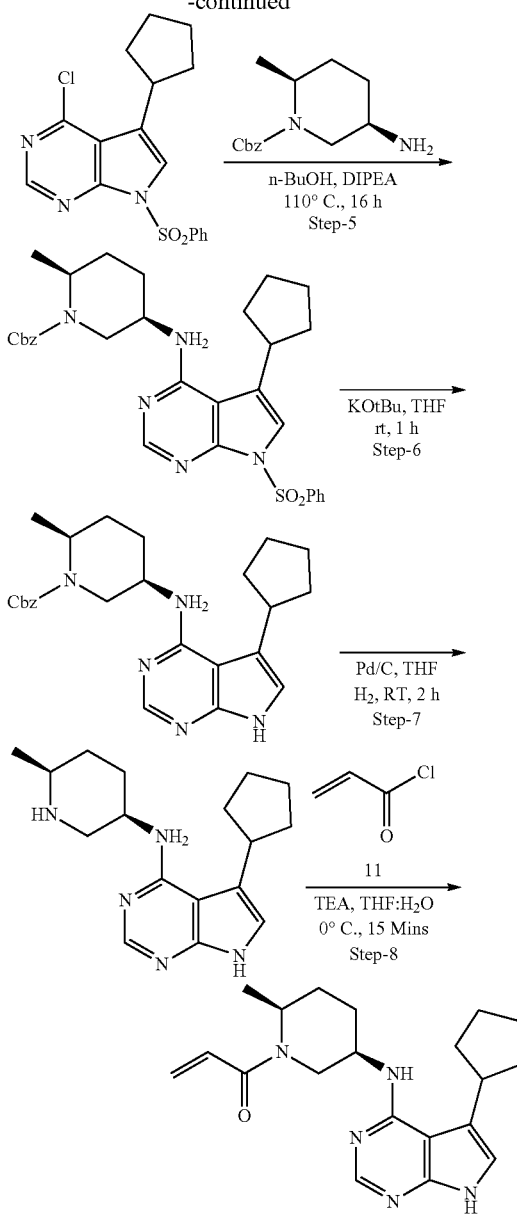

Step 1: Preparation of 5-(cyclopent-1-en-1-yl)-4-methoxy-7-(phenylsulfonyl)-7H-pyrrolo[2,3-d]pyrimidine

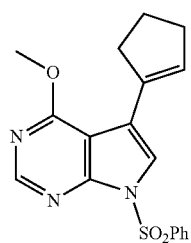

To a stirred solution of 5-bromo-4-methoxy-7-(phenylsulfonyl)-7H-pyrrolo[2,3-d]pyrimidine (prepared by the method described in Example 28, 1.5 g, 4.07 mmol), 2-(cyclopent-1-en-1-yl)-4,4,5,5-tetramethyl-1,3,2-dioxaborolane (1.18 g, 6.10 mmol) and potassium carbonate (1.12 g, 8.14 mmol) in dioxane:water (16:4 mL) was added [1,1'-bis(diphenylphosphino)ferrocene]palladium(II) dichloride-DCM (1:1) (0.33 g, 0.40 mmol) under an argon atmosphere. The reaction mixture was heated to 110° C. for 16 hours and after cooling to ambient temperature, the reaction mixture was filtered through celite and washed with ethyl acetate. The organic layer was washed with water and brine, dried over anhydrous sodium sulfate, filtered and concentrated in vacuo. The crude material was purified using flash chromatography (15% ethyl acetate/hexane) to provide 5-(cyclopent-1-en-1-yl)-4-methoxy-7-(phenylsulfonyl)-7H-pyrrolo[2,3-d]pyrimidine as an off-white solid (1.02 g, 69% yield): MS (ES) m/z 356.1 (M+H).

Step 2: Preparation of 5-cyclopentyl-4-methoxy-7-(phenylsulfonyl)-7H-pyrrolo[2,3-d]pyrimidine

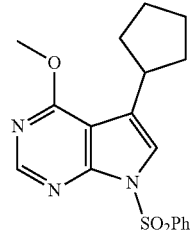

To a stirred solution of 5-(cyclopent-1-en-1-yl)-4-methoxy-7-(phenylsulfonyl)-7H-pyrrolo[2,3-d]pyrimidine (1.0 g, 2.81 mmol) in methanol:tetrahydrofuran (10:10 mL) was added palladium on carbon (0.5 g, 10 wet w/w) under a nitrogen atmosphere. The mixture was stirred under a hydrogen atmosphere at ambient temperature for 16 hours. The reaction mixture was filtered through celite and filtrate was concentrated in vacuo to provide 5-cyclopentyl-4-methoxy-7-(phenylsulfonyl)-7H-pyrrolo[2,3-d]pyrimidine as a white solid (1.0 g, 100% yield): MS (ES) m/z 358.1 (M+H).

Step 3: Preparation of 5-cyclopentyl-7-(phenylsulfonyl)-3,7-dihydro-4H-pyrrolo[2,3-d]pyrimidin-4-one

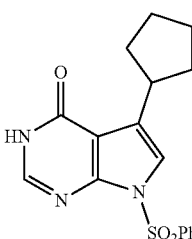

To a stirred solution of 5-cyclopentyl-4-methoxy-7-(phenylsulfonyl)-7H-pyrrolo[2,3-d]pyrimidine (1.0 g, 2.80 mmol) in acetonitrile (15 mL) was added sodium iodide (0.42 g, 2.80 mmol) and chlorotrimethylsilane (0.35 g, 2.80 mmol). The reaction mixture was heated to 80° C. for 1 hour in a sealed tube. After cooling to ambient temperature, the reaction mixture was poured into water and extracted with ethyl acetate. The organic layer was washed with brine, dried over anhydrous sodium sulfate, filtered and concentrated in vacuo. The crude product was triturated with hexane to provide 5-cyclopentyl-7-(phenylsulfonyl)-3,7-dihydro-4H-pyrrolo[2,3-d]pyrimidin-4-one as a light yellow solid (0.94 g, 97% yield): MS (ES) m/z 344.1 (M+H).

Step 4: Preparation of 4-chloro-5-cyclopentyl-7-(phenylsulfonyl)-7H-pyrrolo[2,3-d]pyrimidine

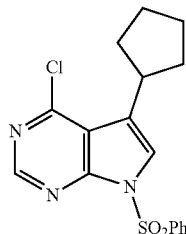

A solution of 5-cyclopentyl-7-(phenylsulfonyl)-3,7-dihydro-4H-pyrrolo[2,3-d]pyrimidin-4-one (0.94 g, 2.73 mmol) in phosphoryl chloride (15 mL) was stirred at 100° C. for 1 hour. The reaction mixture was concentrated in vacuo to remove excess of phosphoryl chloride and the residue was dissolved in ethyl acetate. The organic layer was washed with water and saturated aqueous sodium bicarbonate and brine. The solution was dried over anhydrous sodium sulfate, filtered and concentrated in vacuo. The crude product was triturated with hexane to provide 4-chloro-5-cyclopentyl-7-(phenylsulfonyl)-7H-pyrrolo[2,3-d]pyrimidine as a brown solid (0.85 g, 85% yield): MS (ES) m/z 362.0 (M+H).

Step 5: Preparation of Benzyl (2S,5R)-5-((5-cyclopentyl-7-(phenylsulfonyl)-7H-pyrrolo[2,3-d]pyrimidin-4-yl)amino)-2-methylpiperidine-1-carboxylate

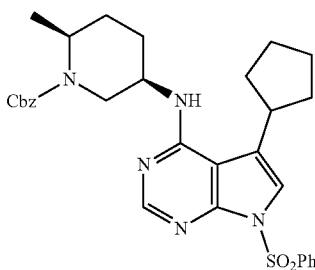

To a stirred solution of 4-chloro-5-cyclopentyl-7-(phenylsulfonyl)-7H-pyrrolo[2,3-d]pyrimidine (0.48 g, 1.33 mmol) in n-butanol (15 mL) was added benzyl (2S,5R)-5-amino-2-methylpiperidine-1-carboxylate (0.3 g, 1.20 mmol) and N,N-diisopropylethylamine (0.62 mL, 3.63 mmol). The reaction mixture was heated in a sealed tube at 110° C. for 16 hours. After cooling to ambient temperature, the reaction mixture was concentrated in vacuo and the residue was dissolved in ethyl acetate. The organic layer was washed with water, brine, dried over anhydrous sodium sulfate, filtered and concentrated in vacuo. The crude material was purified using flash chromatography (35% ethyl acetate/hexane) to provide benzyl (2S,5R)-5-((5-cyclopentyl-7-(phenylsulfonyl)-7H-pyrrolo[2,3-d]pyrimidin-4-yl)amino)-2-methylpiperidine-1-carboxylate as a viscous liquid (0.39 g, 57% yield): MS (ES) m/z 574.2 (M+H).

Step 6: Preparation of Benzyl (2S,5R)-5-((5-cyclopentyl-7H-pyrrolo[2,3-d]pyrimidin-4-yl)amino)-2-methylpiperidine-1-carboxylate

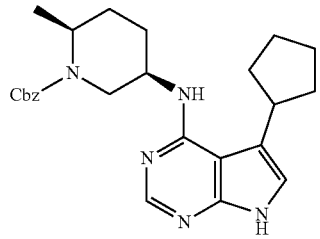 [SMILES: C[C@H]1CC[C@@H](Nc2ncnc3[nH]cc(C4CCCC4)c23)CN1C(=O)OCc1ccccc1]

To a solution benzyl (2S,5R)-5-((5-cyclopentyl-7-(phenylsulfonyl)-7H-pyrrolo[2,3-d]pyrimidin-4-yl)amino)-2-methylpiperidine-1-carboxylate (0.39 g, 0.69 mmol) in tetrahydrofuran (10 mL) was added potassium tert-butoxide (0.15 g, 1.39 mmol) at ambient temperature and the mixture was stirred for 1 hour. The reaction mixture was poured into ice water and extracted with ethyl acetate. The organic layer was washed with water, brine, dried over anhydrous sodium sulfate, filtered and concentrated in vacuo. The crude material was purified using flash chromatography (3% methanol/dichloromethane) to provide benzyl (2S,5R)-5-((5-cyclopentyl-7H-pyrrolo[2,3-d]pyrimidin-4-yl)amino)-2-methylpiperidine-1-carboxylate as a viscous liquid (0.16 g, 67% yield): MS (ES) m/z 434.2 (M+H).

Step 7: Preparation of 5-cyclopentyl-N-((3R,6S)-6-methylpiperidin-3-yl)-7H-pyrrolo[2,3-d]pyrimidin-4-amine

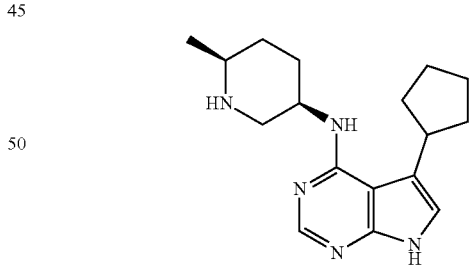

To a stirred solution of benzyl (2S,5R)-5-((5-cyclopentyl-7H-pyrrolo[2,3-d]pyrimidin-4-yl)amino)-2-methyl-piperidine-1-carboxylate (0.16 g, 0.369 mmol) in tetrahydrofuran (25 mL) was added palladium on carbon (0.1 g, 10 wet w/w) under a nitrogen atmosphere. The mixture was stirred under a hydrogen atmosphere at ambient temperature for 2 hours. The reaction mixture was filtered through celite and filtrate was concentrated in vacuo to provide 5-cyclopentyl-N-((3R, 6S)-6-methylpiperidin-3-yl)-7H-pyrrolo[2,3-d]pyrimidin-4-amine as a viscous liquid (0.09 g, 81% yield): MS (ES) m/z 300.2 (M+H).

Step 8: Preparation of 1-((2S,5R)-5-((5-cyclopentyl-7H-pyrrolo[2,3-d]pyrimidin-4-yl)amino)-2-methylpiperidin-1-yl)prop-2-en-1-one

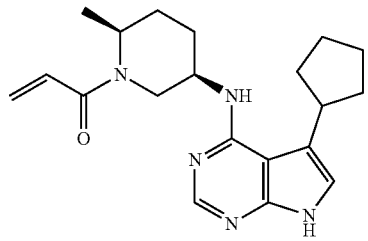 [SMILES: C=CC(=O)N1C[C@H](Nc2ncnc3[nH]cc(C4CCCC4)c23)CC[C@@H]1C]

To a stirred solution of 5-cyclopentyl-N-((3R,6S)-6-methylpiperidin-3-yl)-7H-pyrrolo[2,3-d]pyrimidin-4-amine (0.09 g, 0.30 mmol) in tetrahydrofuran:water (8:2 mL) was added triethylamine (0.04 mL, 0.45 mmol) followed by a solution of acryloyl chloride (0.03 g, 0.27 mmol) in tetrahydrofuran (1 mL) at 0° C. and the mixture was stirred for 15 minutes. The reaction mixture was quenched with saturated aqueous sodium bicarbonate and extracted with ethyl acetate. The organic layer was washed with brine, dried over anhydrous sodium sulfate, filtered and concentrated in vacuo. The crude material was purified using flash chromatography (4% methanol/dichloromethane) to provide 1-((2S,5R)-5-((5-cyclopentyl-7H-pyrrolo[2,3-d]pyrimidin-4-yl)amino)-2-methylpiperidin-1-yl)prop-2-en-1-one as a white solid (0.03 g, 29% yield): $^1$H NMR (400 MHz, DMSO-d$_6$ at 80° C.) δ 11.22 (s, 1H), 8.05 (s, 1H), 6.85 (s, 1H), 6.73-6.79 (m, 1H), 6.06 (dd, J$_1$=2.0 Hz, J$_2$=15.2 Hz, 1H), 5.78 (d, J=8.0 Hz, 1H), 5.64 (dd, J$_1$=1.6 Hz, J$_2$=10.4 Hz, 1H), 4.71 (br s, 1H), 4.42 (br s, 1H), 4.01-4.09 (m, 1H), 3.43-3.49 (m, 1H), 2.95 (br s, 2H), 1.90-2.00 (m, 3H), 1.66-1.88 (m, 7H), 1.50-1.48 (m, 1H), 1.13-1.21 (m, 3H); MS (ES) m/z: 354.2 (M+H).

EXAMPLE 31

Preparation of tert-butyl 4-(((3R,6S)-1-acryloyl-6-methylpiperidin-3-yl)amino)-7H-pyrrolo[2,3-d]pyrimidine-5-carboxylate

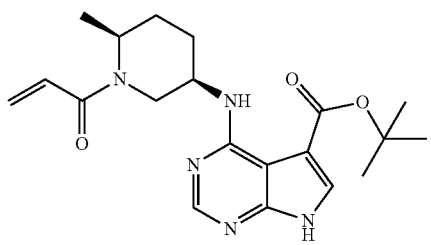 [SMILES: C=CC(=O)N1C[C@H](Nc2ncnc3[nH]cc(C(=O)OC(C)(C)C)c23)CC[C@@H]1C]

Following Example 2 the title compound was prepared starting with tert-butyl 4-chloro-7H-pyrrolo[2,3-d]pyrimidine-5-carboxylate in step 1 to give tert-butyl 4-(((3R,6S)-1-acryloyl-6-methylpiperidin-3-yl)amino)-7H-pyrrolo[2,3-d]pyrimidine-5-carboxylate as a white solid: $^1$H NMR (400 MHz, DMSO-d$_6$) δ 12.34 (s, 1H), 8.42 (s, 1H) 8.17 (s, 1H) 7.76 (s, 1H) 6.74-6.81 (m, 1H), 6.05-6.09 (m, 1H), 5.66 (d, J=10.0 Hz, 1H), 4.52 (br s, 2H), 3.90 (s, 1H), 2.64-2.71 (m, 1H), 1.92 (br s, 1H), 1.68-1.71 (m, 3H) 1.39 (s, 9H), 1.16-1.18 (m, 3H); MS (ES) m/z 386.2 (M+H).

EXAMPLE 32

Preparation of 1-((2S,5R)-5-((5-(cyclopropanecarbonyl)-7H-pyrrolo[2,3-d]pyrimidin-4-yl)amino)-2-methylpiperidin-1-yl)prop-2-en-1-one

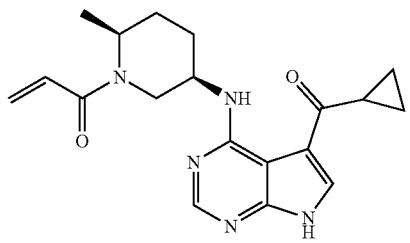 [SMILES: C=CC(=O)N1C[C@H](Nc2ncnc3[nH]cc(C(=O)C4CC4)c23)CC[C@@H]1C]

Following Example 5 the title compound was prepared using benzyl (2S,5R)-5-amino-2-methylpiperidine-1-carboxylate in step 3 and using hydrogenation conditions in step 5 to remove the benzyl protecting group to give 1-((2S,5R)-5-((5-(cyclopropanecarbonyl)-7H-pyrrolo[2,3-d]pyrimidin-4-yl)amino)-2-methylpiperidin-1-yl)prop-2-en-1-one as a white solid: $^1$H NMR (400 MHz, DMSO-d$_6$) δ 12.47 (s, 1H), 9.08 (d, J=6.8 Hz, 1H), 8.50 (s, 1H), 8.17 (s, 1H), 6.74-6.81 (m, 1H), 6.07 (d, J=16.8 Hz, 1H), 5.66 (d, J=10.8 Hz, 1H), 4.41-4.64 (m, 3H), 3.88 (br s, 1H), 2.83 (br s, 1H), 1.89 (br s, 1H), 1.66-1.69 (m, 3H), 1.15-1.30 (m, 4H), 0.99-1.03 (m, 2H), 0.94-0.96 (m, 1H); MS (ES) m/z 354.4 [M+H]*. HPLC purity 98.60% at 280 nM. Chiral HPLC purity 99.79% at 264 nM.

EXAMPLE 33

Preparation of 1-((2S,5R)-2-methyl-5-((5-(2,2,2-trifluoroacetyl)-7H-pyrrolo[2,3-d]pyrimidin-4-yl)amino)piperidin-1-yl)prop-2-en-1-one

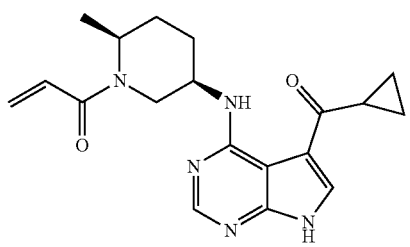 [SMILES: C=CC(=O)N1C[C@H](Nc2ncnc3[nH]cc(C(=O)C4CC4)c23)CC[C@@H]1C]

Following Example 5 the title compound was prepared using benzyl (2S,5R)-5-amino-2-methylpiperidine-1-carboxylate in step 3 and using hydrogenation conditions in step 5 to remove the benzyl protecting group to give 1-((2S,5R)-2-methyl-5-((5-(2,2,2-trifluoroacetyl)-7H-pyrrolo[2,3-d]pyrimidin-4-yl)amino)piperidin-1-yl)prop-2-en-1-one as an off-white solid: $^1$H NMR (400 MHz, DMSO-d$_6$) δ 13.41 (br s, 1H), 8.42 (s, 1H) 8.02-8.28 (m, 2H) 6.74-6.81 (m, 1H), 6.07 (d, J=16.8 Hz, 1H), 5.66 (d, J=10.68 Hz, 1H), 4.5 (br s, 2H), 3.94 (s, 1H), 1.66-1.96 (m, 5H), 1.17-1.21 (m, 3H); MS (ES) m/z 381.9 (M+H).

EXAMPLE 34

Preparation of 1-((2S,5R)-5-((3-(cyclopropanecarbonyl)-1H-pyrrolo[2,3-b]pyridin-4-yl)amino)-2-methylpiperidin-1-yl)prop-2-en-1-one

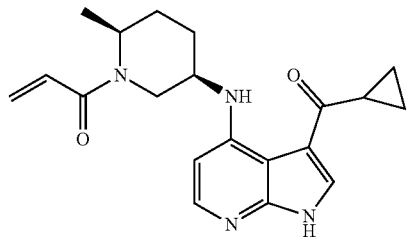 [SMILES: C=CC(=O)N1C[C@H](Nc2ccnc3[nH]cc(C(=O)C4CC4)c23)CC[C@@H]1C]

Following Example 15 the title compound was prepared using benzyl (2S,5R)-5-amino-2-methylpiperidine-1-carboxylate in step 3 and using hydrogenation conditions in step 4 to remove the benzyl protecting group to give 1-((2S,5R)-5-((3-(cyclopropanecarbonyl)-1H-pyrrolo[2,3-b]pyridin-4-yl)amino)-2-methylpiperidin-1-yl)prop-2-en-1-one as a white solid: $^1$H NMR (400 MHz, DMSO-$d_6$) δ 12.27 (s, 1H), 8.12 (d, J=6.65 Hz, 1H), 8.50 (s, 1H), 7.89 (d, J=5.48 Hz, 1H), 6.84-6.74 (m, 1H), 6.29 (d, J=5.09 Hz, 1H), 6.10 (d, J=14.47 Hz, 1H), 5.69 (d, J=11.34 Hz, 1H), 4.81-4.32 (m, 3H), 3.26-3.07 (m, 1H), 2.89-2.80 (m, 1H), 1.99-1.91 (m, 1H), 1.81-1.52 (m, 3H), 1.23-1.12 (m, 3H), 1.06-0.98 (m, 2H), 0.97-0.90 (m, 2H); MS (ES) m/z 353 (M+H).

EXAMPLE 35

Preparation of 1-((2S,5R)-5-((3-(cyclopropylmethyl)-1H-pyrrolo[2,3-b]pyridin-4-yl)amino)-2-methylpiperidin-1-yl)prop-2-en-1-one

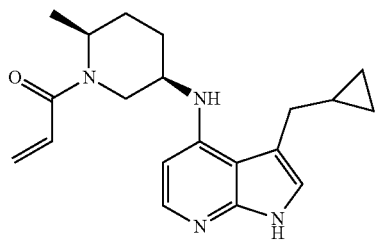 [SMILES: C=CC(=O)N1C[C@H](Nc2ccnc3[nH]cc(CC4CC4)c23)CC[C@@H]1C]

Following Example 19 the title compound was prepared using benzyl (2S,5R)-5-amino-2-methylpiperidine-1-carboxylate in step 4 and using hydrogenation conditions in step 5 to remove the benzyl protecting group to give 1-((2S,5R)-5-((3-(cyclopropylmethyl)-1H-pyrrolo[2,3-b]pyridin-4-yl)amino)-2-methylpiperidin-1-yl)prop-2-en-1-one as a white solid: $^1$H NMR (400 MHz, DMSO-$d_6$) δ 10.88 (s, 1H), 7.76 (d, J=4.0 Hz, 1H), 6.87 (s, 1H), 6.75-6.80 (m, 1H), 6.16 (s, 1H), 6.08 (d, J=16.0 Hz, 1H), 5.64 (d, J=12 Hz, 1H), 5.11 (d, J=8 Hz, 1H), 4.36-4.55 (m, 2H), 2.77-2.81 (m, 2H), 1.95 (s, 2H), 1.63-1.70 (m, 2H), 1.18-1.20 (m, 4H), 1.03-1.08 (m, 1H), 0.7 (s, 1H), 0.46-0.48 (d, J=8.0 Hz, 2H), 0.14-0.16 (m, 2H); MS (ES) m/z 339.2 (M+H).

EXAMPLE 36

Preparation of 1-((2S,5R)-5-((5-((3-ethylcyclopentyl)methyl)-7H-pyrrolo[2,3-d]pyrimidin-4-yl)amino)-2-methylpiperidin-1-yl)prop-2-en-1-one (Mixture of Stereoisomers)

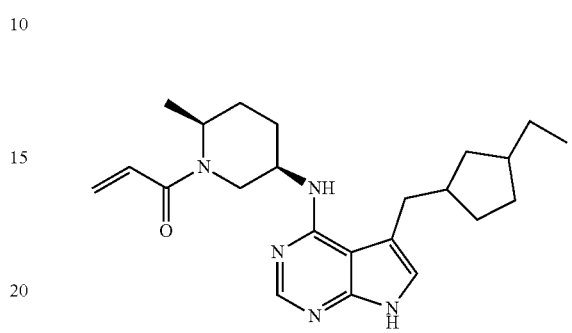

Following Example 22 the title compound was prepared using 3-ethyl cyclopentanecarbaldehyde in step 1 to give 1-((2S,5R)-5-((5-((3-ethylcyclopentyl)methyl)-7H-pyrrolo[2,3-d]pyrimidin-4-yl)amino)-2-methylpiperidin-1-yl)prop-2-en-1-one as a white solid: $^1$H NMR (400 MHz, DMSO-$d_6$ at 70° C.) δ 10.72 (s, 1H), 7.61 (s, 1H), 6.27-6.37 (m, 2H), 5.62 (d, J=16.8 Hz, 1H), 5.25-5.35 (m, 1H), 5.20 (d, J=10.4 Hz, 1H), 3.85-4.15 (m, 2H), 3.55-3.70 (m, 1H), 2.30-2.55 (m, 4H), 1.65-1.79 (m, 2H), 1.15-1.40 (m, 8H), 0.99-1.10 (m, 1H), 0.75-0.95 (m, 8H); MS (ES) m/z 396.2 (M+H).

EXAMPLE 37

Preparation of (E)-1-((2S,5R)-5-((5-(cyclopropylmethyl)-7H-pyrrolo[2,3-d]pyrimidin-4-yl)amino)-2-methylpiperidin-1-yl)-4-(dimethylamino)but-2-en-1-one

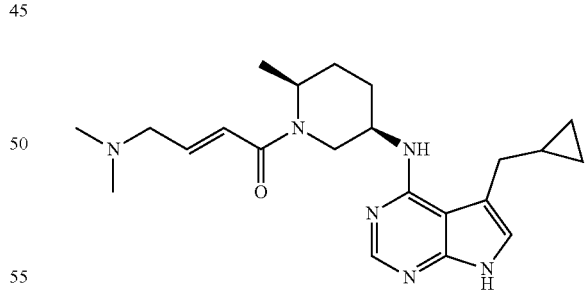

Following Example 24 the title compound was prepared using 4-(dimethylamino)but-2-enoic acid in step 6 to give (E)-1-((2S,5R)-5-((5-(cyclopropylmethyl)-7H-pyrrolo[2,3-d]pyrimidin-4-yl)amino)-2-methylpiperidin-1-yl)-4-(dimethylamino)but-2-en-1-one as an off-white solid: $^1$H NMR (400 MHz, DMSO-$d_6$ at 60° C.) δ 11.15 (s, 1H), 8.05 (s, 1H), 6.89 (s, 1H), 6.54 (s, 2H), 5.73 (s, 1H), 4.27-4.56 (m, 2H), 4.08 (br s, 1H), 2.90-3.01 (m, 7H), 2.14 (s, 3H), 1.64-1.89 (m, 5H), 1.10-1.40 (m, 3H), 1.02 (br s, 1H), 0.49-0.60 (m, 2H), 0.17 (s, 2H); MS (ES) m/z 397.2 (M+H).

EXAMPLE 38

Preparation of 1-(5-((5-(cyclopropylmethyl)-7H-pyrrolo[2,3-d]pyrimidin-4-yl)amino)-2-ethylpiperidin-1-yl)prop-2-en-1-one (Mixture of Stereoisomers)

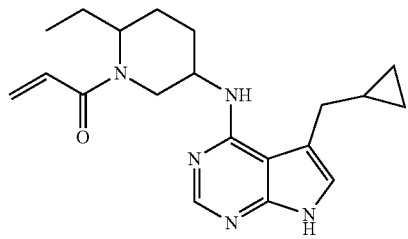 [SMILES: C=CC(=O)N1C[C@@H](Nc2ncnc3[nH]cc(CC4CC4)c23)CC[C@H]1CC]

Following Example 24 the title compound was prepared using benzyl 5-amino-2-ethylpiperidine-1-carboxylate in step 4 to give 1-(5-((5-(cyclopropylmethyl)-7H-pyrrolo[2,3-d]pyrimidin-4-yl)amino)-2-ethylpiperidin-1-yl)prop-2-en-1-one as a white solid: $^1$H NMR (400 MHz, DMSO-$d_6$) δ 11.29 (s, 1H), 8.04 (d, J=11.6 Hz, 1H), 6.90 (s, 1H), 6.80 (t, J=8.2 Hz, 1H), 6.07 (dd, J=2.4 Hz, J=2.0 Hz, 1H), 5.87 (d, J=8.0 Hz, 1H), 5.64 (s, 1H), 4.47-4.55 (m, 1H), 4.03-4.14 (m, 2H), 2.65-3.02 (m, 3H), 1.85-1.88 (m, 1H), 1.68-1.76 (m, 3H), 1.51-1.59 (m, 2H), 0.99-1.01 (m, 1H), 0.78 (t, J=7.2 Hz, 3H), 0.47 (d, J=8.0 Hz, 2H), 0.15 (s, 2H); MS (ES) m/z: 354.4 (M+H).

EXAMPLE 39

Preparation of 1-((2R,5S)-5-((5-(cyclopropylmethyl)-7H-pyrrolo[2,3-d]pyrimidin-4-yl)amino)-2-ethylpiperidin-1-yl)prop-2-en-1-one (Stereoisomer 1, Absolute Configuration Assigned Provisionally)

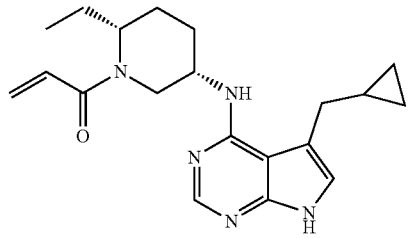

Purified by chiral HPLC (stereoisomer 1) isolated as a white solid (0.046 g, 23% yield): $^1$H NMR (400 MHz, DMSO-$d_6$) δ 11.29 (s, 1H), 8.04 (d, J=10.4 Hz, 1H), 6.90 (s, 1H), 6.77-6.79 (m, 1H), 6.07 (dd, J=2.0 Hz, J=2.0 Hz, 1H), 5.87 (d, J=8.4 Hz, 1H), 5.64 (s, 1H), 4.47-4.54 (m, 1H), 4.03-4.13 (m, 2H), 3.05 (t, J=10.8 Hz, 1H), 2.65-2.75 (m, 2H), 1.68-1.88 (m, 4H), 1.51-1.59 (m, 2H), 0.99-1.02 (m, 1H), 0.77 (t, J=7.2 Hz, 3H), 0.47 (d, J=8.0 Hz, 2H), 0.15 (s, 2H); MS (ES) m/z 354.3 (M+H).
HPLC Conditions:
Column: CHIRALPAK IC (100 mm×4.6 mm×3 mic)
Mobile phase: n-Hexane: IPA with 0.1% DEA (50:50)
Flow rate: 1.0 mL/min
Retention time 9.627 min.

EXAMPLE 40

Preparation of 1-((2S,5R)-5-((5-(cyclopropylmethyl)-7H-pyrrolo[2,3-d]pyrimidin-4-yl)amino)-2-ethylpiperidin-1-yl)prop-2-en-1-one (Stereoisomer 2, Absolute Configuration Assigned Provisionally)

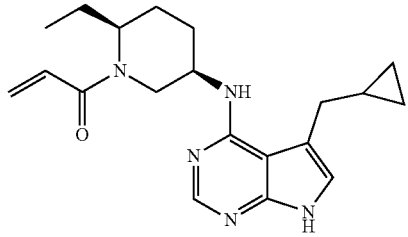 [SMILES: C=CC(=O)N1C[C@H](Nc2ncnc3[nH]cc(CC4CC4)c23)CC[C@@H]1CC]

Purified by chiral HPLC (stereoisomer 2) isolated as a white solid (0.045 g, 22% yield): $^1$H NMR (400 MHz, DMSO-$d_6$) δ 11.28 (s, 1H), 8.04 (d, J=13.2 Hz, 1H), 6.90 (s, 1H), 6.79 (br s, 1H), 6.06 (d, J=16.0 Hz, 1H), 5.86 (d, J=8.0 Hz, 1H), 5.64 (s, 1H), 4.46-4.54 (m, 1H), 4.03-4.12 (m, 2H), 3.05 (t, J=11.6 Hz, 1H), 2.65-2.73 (m, 2H), 1.52-1.87 (m, 6H), 0.99-1.02 (m, 1H), 0.77 (t, J=6.6 Hz, 3H), 0.47 (d, J=7.2 Hz, 2H), 0.15 (s, 2H); MS (ES) m/z 354.3 (M+H).
HPLC Conditions:
Column: CHIRALPAK IC (100 mm×4.6 mm×3 mic)
Mobile phase: n-hexane:IPA with 0.1% DEA (50:50)
Flow rate: 1.0 mL/min
Retention time 3.89 min.

EXAMPLE 41

Preparation of 1-(5-((5-(cyclopropylmethyl)-7H-pyrrolo[2,3-d]pyrimidin-4-yl)amino)-2-isopropylpiperidin-1-yl)prop-2-en-1-one (Mixture of Stereoisomers)

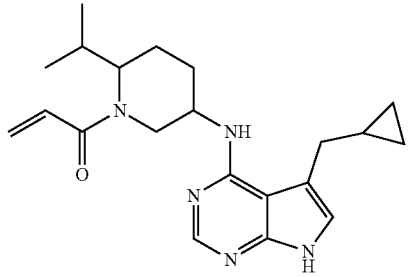 [SMILES: C=CC(=O)N1CC(Nc2ncnc3[nH]cc(CC4CC4)c23)CCC1C(C)C]

Following Example 24 the title compound was prepared using benzyl 5-amino-2-isopropylpiperidine-1-carboxylate in step 4 to give 1-(5-((5-(cyclopropylmethyl)-7H-pyrrolo[2,3-d]pyrimidin-4-yl)amino)-2-isopropylpiperidin-1-yl)prop-2-en-1-one as a white solid: $^1$H NMR (400 MHz, DMSO-$d_6$) δ 11.28 (s, 1H), 8.04 (d, J=16.0 Hz, 1H), 6.90 (s, 1H), 6.76-6.82 (m, 1H), 6.07 (d, J=16.8 Hz, 1H), 5.88 (d, J=8.0 Hz, 1H), 5.64-5.67 (m, 1H), 4.40-4.62 (m, 1H), 4.12-4.30 (m, 1H), 3.89-4.01 (m, 2H), 3.22-3.30 (m, 1H), 2.90-3.09 (m, 2H), 2.73 (d, J=4.0 Hz, 2H), 1.88 (d, J=12.0 Hz, 2H), 1.75 (s, 2H), 1.21 (s, 1H), 0.94 (d, J=8 Hz, 2H), 0.73 (d, J=6.4 Hz, 2H), 0.47 (d, J=7.2 Hz, 2H), 0.15 (s, 2H); MS (ES) m/z 368.3 (M+H).

EXAMPLE 42

Preparation of 1-((2S,5S)-5-((5-(cyclopropylmethyl)-7H-pyrrolo[2,3-d]pyrimidin-4-yl)amino)-2-isopropylpiperidin-1-yl)prop-2-en-1-one (Stereoisomer 1, Absolute Configuration Assigned Provisionally)

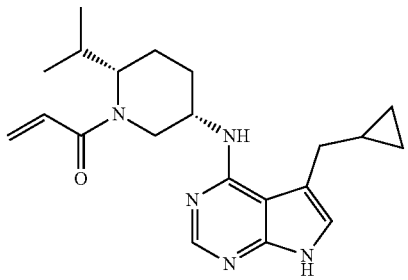 [SMILES: C=CC(=O)N1C[C@@H](Nc2ncnc3[nH]cc(CC4CC4)c23)CC[C@H]1C(C)C]

Purified by chiral HPLC (stereoisomer 1) isolated as a white solid (0.031 g, 12% yield): $^1$H NMR (400 MHz, DMSO-$d_6$) δ 11.28 (s, 1H), 8.05 (d, J=16 Hz, 1H), 6.90 (s, 1H), 6.76-6.85 (m, 1H), 6.07 (d, J=12 Hz, 1H), 5.88 (d, J=8 Hz, 1H), 5.61-5.67 (m, 1H), 4.50 (d, J=12 Hz, 1H), 4.18 (s, 1H), 4.03 (d, J=12 Hz, 1H), 3.63 (s, 1H), 2.97-3.03 (m, 1H), 2.75 (d, J=12.0 Hz, 2H), 2.24 (s, 1H), 1.81-1.94 (m, 2H), 1.75 (s, 1H), 1.40-1.60 (m, 2H), 0.93-1.00 (m, 3H), 0.73 (d, J=8.0 Hz, 2H), 0.47 (d, J=8 Hz, 2H), 0.15 (s, 2H); MS (ES) m/z 368.01 (M+H).

HPLC Conditions:
Column: CHIRALPAK IA (100 mm×4.6 mm×3 mic)
Mobile phase: n-hexane:IPA with 0.1% DEA (80:20)
Flow rate: 1.0 mL/min
Retention time 3.86 min.

EXAMPLE 43

Preparation of 1-((2R,5R)-5-((5-(cyclopropylmethyl)-7H-pyrrolo[2,3-d]pyrimidin-4-yl)amino)-2-isopropylpiperidin-1-yl)prop-2-en-1-one (Stereoisomer 2, Absolute Configuration Assigned Provisionally)

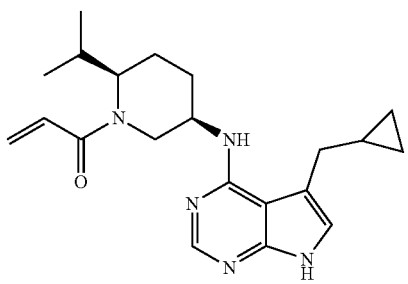 [SMILES: C=CC(=O)N1C[C@H](Nc2ncnc3[nH]cc(CC4CC4)c23)CC[C@@H]1C(C)C]

Purified by chiral HPLC (stereoisomer 2) isolated as a white solid (0.032 g, 13% yield): $^1$H NMR (400 MHz, DMSO-$d_6$) δ 11.28 (s, 1H), 8.05 (d, J=16 Hz, 1H), 6.90 (s, 1H), 6.76-6.85 (m, 1H), 6.07 (d, J=12 Hz, 1H), 5.88 (d, J=8.0 Hz, 1H), 5.61-5.67 (m, 1H), 4.50 (d, J=12.0 Hz, 1H), 4.18 (s, 1H), 4.03 (d, J=12.0 Hz, 1H), 3.63 (s, 1H), 2.97-3.03 (m, 1H), 2.75 (d, J=12.0 Hz, 2H), 2.2 (s, 1H), 1.81-1.90 (m, 2H), 1.75 (s, 1H), 1.50 (d, J=12 Hz, 2H), 1.21 (s, 1H), 1.00-1.12 (m, 1H), 0.94 (d, J=8 Hz, 2H), 0.73 (d, J=8.0 Hz, 2H), 0.47 (d, J=8.0 Hz, 2H), 0.15 (s, 1H); MS (ES) m/z 368.01 (M+H).

HPLC Conditions:
Column: CHIRALPAK IA (100 mm×4.6 mm×3 mic)
Mobile phase: n-hexane:IPA with 0.1% DEA (80:20)
Flow rate: 1.0 mL/min
Retention time 2.89 min.

EXAMPLE 44

Preparation of 1-((2S,5R)-5-((5-(2-(methoxymethyl)cyclopropyl)-7H-pyrrolo[2,3-d]pyrimidin-4-yl)amino)-2-methylpiperidin-1-yl)prop-2-en-1-one (Mixture of Stereoisomers)

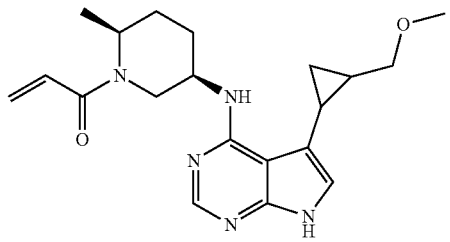 [SMILES: C=CC(=O)N1C[C@H](Nc2ncnc3[nH]cc(C4CC4COC)c23)CC[C@@H]1C]

Following Example 25 the title compound was prepared benzyl (2S,5R)-5-amino-2-methylpiperidine-1-carboxylate in step 6 and using hydrogenation conditions in step 8 to remove the benzyl protecting group to give 1-((2S,5R)-5-((5-(2-(methoxymethyl)cyclopropyl)-7H-pyrrolo[2,3-d]pyrimidin-4-yl)amino)-2-methylpiperidin-1-yl)prop-2-en-1-one as an off-white solid: $^1$H NMR (400 MHz, DMSO-$d_6$) δ 11.28 (s, 1H), 8.06 (s, 1H), 6.75-6.80 (m, 2H), 6.18 (t, J 7.6 Hz, 1H), 6.07 (d, J=16.8 Hz, 1H), 5.65 (d, J=10.4 Hz, 1H), 4.78 (br s, 1H), 4.56 (br s, 1H), 4.36 (br s, 1H), 4.11 (br s, 2H), 3.66-3.73 (m, 1H), 3.33 (d, J=11.2 Hz, 3H), 2.97-3.05 (m, 2H), 1.67-1.91 (m, 4H), 1.20 (d, J=9.6 Hz, 3H), 0.98 (br s, 1H), 0.75 (s, 1H); MS (ES) m/z 370.4 (M+H).

EXAMPLE 45

Preparation of 1-((2S,5R)-5-((5-((1R,2R)-2-(methoxymethyl)cyclopropyl)-7H-pyrrolo[2,3-d]pyrimidin-4-yl)amino)-2-methylpiperidin-1-yl)prop-2-en-1-one (Stereoisomer 1, Absolute Configuration of Cyclopropyl Group Assigned Provisionally)

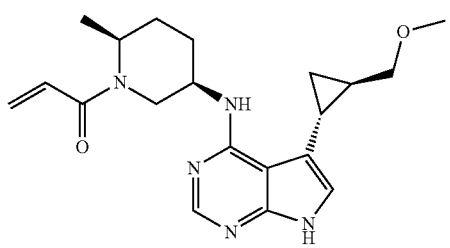 [SMILES: C=CC(=O)N1C[C@H](Nc2ncnc3[nH]cc([C@@H]4C[C@H]4COC)c23)CC[C@@H]1C]

Purified by chiral HPLC (stereoisomer 1) isolated as a white solid (0.028 g, 13% yield): ¹H NMR (400 MHz, DMSO-d₆) δ 11.27 (s, 1H), 8.06 (s, 1H), 6.80 (s, 2H), 6.18 (d, J=8.0 Hz, 1H), 6.07 (d, J=12.8 Hz, 1H), 5.65 (d, J=10.4 Hz, 1H), 4.78 (br s, 1H), 4.56 (br s, 1H), 4.36 (br s, 1H), 4.10 (br s, 2H), 3.35-3.73 (m, 1H), 3.30 (d, J=10.8 Hz, 3H), 2.92-3.05 (m, 1H), 1.67-1.96 (m, 5H), 1.17-1.27 (m, 3H), 0.83-1.00 (m, 1H), 0.72-0.77 (m, 1H); MS (ES) m/z 370.1 (M+H).

HPLC conditions:

Column: CHIRALPAK IC (100 mm×4.6 mm×3 mic)

Mobile phase: n-hexane:IPA with 0.1% DEA (50:50)

Flow rate: 1.0 mL/min

Retention time: 2.27 min.

EXAMPLE 46

Preparation of 1-((2S,5R)-5-((5-((1S,2S)-2-(methoxymethyl)cyclopropyl)-7H-pyrrolo[2,3-d]pyrimidin-4-yl)amino)-2-methylpiperidin-1-yl)prop-2-en-1-one (Stereoisomer 2, Absolute Configuration of Cyclopropyl Group Assigned Provisionally)

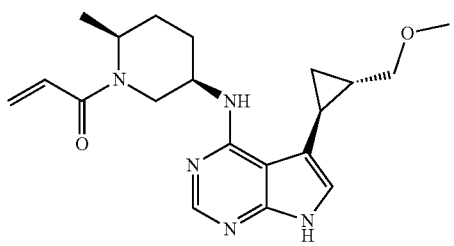 [SMILES: C=CC(=O)N1C[C@H](Nc2ncnc3[nH]cc([C@H]4C[C@@H]4COC)c23)CC[C@@H]1C]

Purified by chiral HPLC (stereoisomer 2) isolated as a white solid (0.029 g, 13% yield): ¹H NMR (400 MHz, DMSO-d₆) δ 11.26 (s, 1H), 8.06 (s, 1H), 6.77-6.90 (m, 2H), 6.16 (d, J 8.0 Hz, 1H), 6.07 (d, J=14.4 Hz, 1H), 5.65 (d, J=8.4 Hz, 1H), 4.78 (br s, 1H), 4.57 (br s, 1H), 4.36 (br s, 1H), 4.10 (br s, 2H), 3.65-3.68 (m, 1H), 3.32 (d, J=11.2 Hz, 3H), 3.00-3.05 (m, 2H), 1.67-1.95 (m, 4H), 1.18 (d, J=9.6 Hz, 3H), 1.01 (d, J=6.4 Hz 1H), 0.74-0.76 (s, 1H); MS (ES) m/z 370.2 (M+H).

HPLC conditions:

Column: CHIRALPAK IC (100 mm×4.6 mm×3 mic)

Mobile phase: n-hexane:IPA with 0.1% DEA (50:50)

Flow rate: 1.0 mL/min

Retention time: 2.01 min.

EXAMPLES 47, 48 AND 49

Preparation of 1-((2S,5R)-5-((5-(2,2-difluorocyclopropyl)-7H-pyrrolo[2,3-d]pyrimidin-4-yl)amino)-2-methylpiperidin-1-yl)prop-2-en-1-one, 1-((2S,5R)-5-((5-((S)-2,2-difluorocyclopropyl)-7H-pyrrolo[2,3-d]pyrimidin-4-yl)amino)-2-methylpiperidin-1-yl)prop-2-en-1-one, 1-((2S,5R)-5-((5-((R)-2,2-difluorocyclopropyl)-7H-pyrrolo[2,3-d]pyrimidin-4-yl)amino)-2-methylpiperidin-1-yl)prop-2-en-1-one Example 47

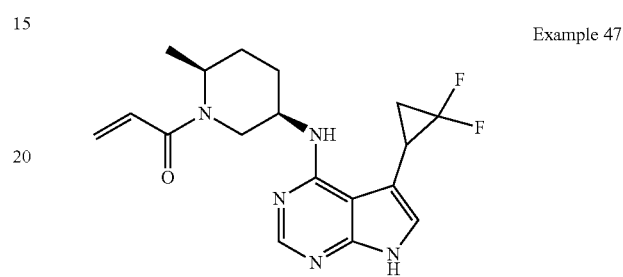

Example 48

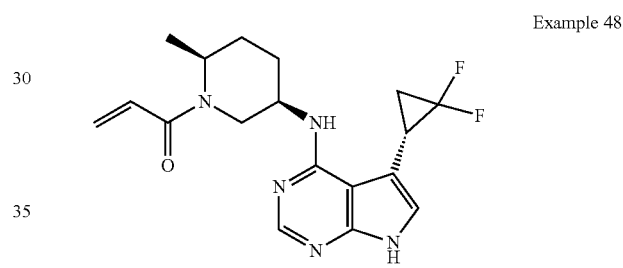

Example 49

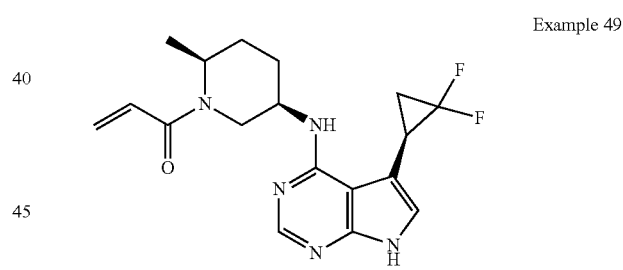

The title compounds were prepared by the methods described in Scheme 28.

Scheme 28.
Synthesis of 1-((2S,5R)-5-((5-((S)-2,2-difluorocyclopropyl)-7H-pyrrolo[2,3-d]pyrimidin-4-yl)amino)-2-methylpiperidin-1-yl)prop-2-en-1-one and 1-((2S,5R)-5-((5-((R)-2,2-difluorocyclopropyl)-7H-pyrrolo[2,3-d]pyrimidin-4-yl)amino)-2-methylpiperidin-1-yl)prop-2-en-1-one.

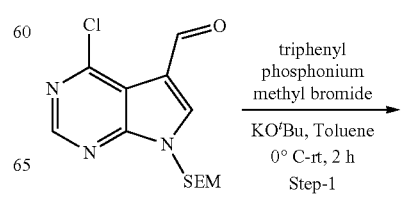

227
-continued

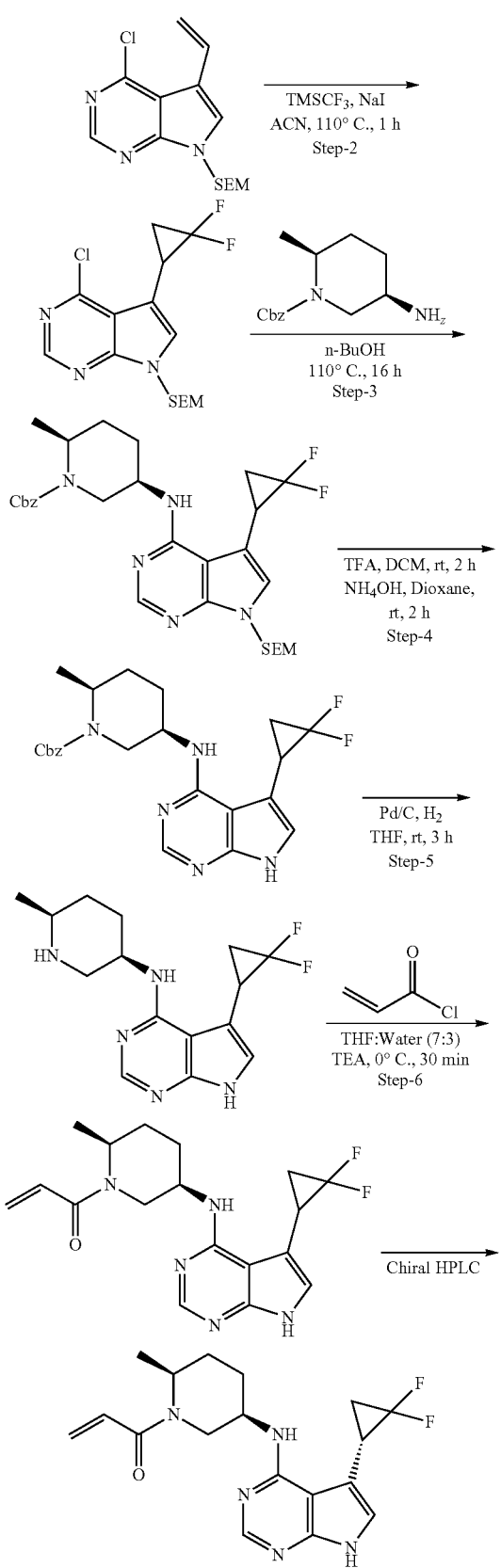

228
-continued

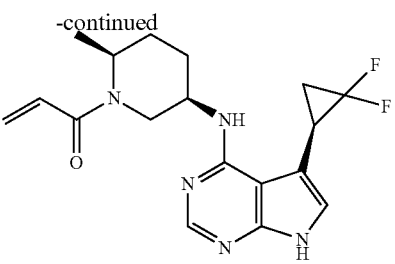

Step 1: Preparation of 4-chloro-7-((2-(trimethylsilyl)ethoxy)methyl)-5-vinyl-7H-pyrrolo[2,3-d]pyrimidine

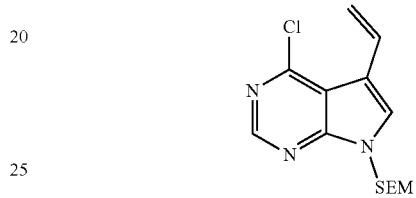

To a stirred suspension of methyl triphenylphosphonium bromide (22.97 g, 64.3 mmol) in toluene (30 mL) was added potassium tert-butoxide (7.2 g, 64.3 mmol) at 0° C. under a nitrogen atmosphere and the resulting mixture was stirred at 0° C. for 30 minutes. A solution of 4-chloro-7-((2-(trimethylsilyl)ethoxy)methyl)-7H-pyrrolo[2,3-d]pyrimidine-5-carbaldehyde (10 g, 32.15 mmol) in toluene (25 mL) was added slowly at 0° C. over period of 10 minutes. After complete addition, the resulting mixture was stirred at ambient temperature for 2 h. The reaction mixture was quenched with water, extracted with ethyl acetate, washed with brine, dried over anhydrous sodium sulfate, filtered and concentrated in vacuo. The crude material was purified by flash column chromatography (8% ethyl acetate:hexane) to provide 4-chloro-7-((2-(trimethylsilyl) ethoxy)methyl)-5-vinyl-7H-pyrrolo[2,3-d]pyrimidine as a yellow solid (5.7 g, 57% yield): MS (ES) m/z: 310.1 (M+H).

Step 2: Preparation of 4-chloro-5-(2,2-difluorocyclopropyl)-7-((2-(trimethylsilyl)ethoxy)methyl)-7H-pyrrolo[2,3-d]pyrimidine

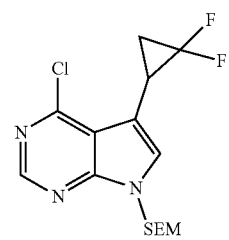 [SMILES: C[Si](C)(C)CCOCn1cc(C2CC2(F)F)c2c(Cl)ncnc21]

A suspension of 4-chloro-7-((2-(trimethylsilyl)ethoxy)methyl)-5-vinyl-7H-pyrrolo[2,3-d]pyrimidine (5.6 g, 18.12 mmol) and sodium iodide (0.19 g, 7.24 mmol) in acetonitrile (60 mL) was treated with trimethyl(trifluoromethyl)silane (13.42 mL, 90.61 mmol) in a sealed vessel and the mixture was heated at 110° C. for 2 hours. After cooling to ambient temperature, the reaction mixture was quenched with water, extracted with ethyl acetate, washed with brine, dried over anhydrous sodium sulfate, filtered and concentrated in vacuo. The crude product was triturated with hexane to provide 4-chloro-5-(2,2-difluorocyclopropyl)-7-((2-(trimethylsilyl)ethoxy)methyl)-7H-pyrrolo[2,3-d]pyrimidine as an off-white solid (5.7 g, crude): MS (ES) m/z 360.1 (M+H).

Step 3: Preparation of Benzyl (2S,5R)-5-((5-(2,2-difluorocyclopropyl)-7-((2-(trimethylsilyl)ethoxy)methyl)-7H-pyrrolo[2,3-d]pyrimidin-4-yl)amino)-2-methylpiperidine-1-carboxylate

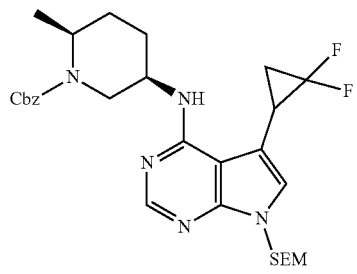 [SMILES: C[C@H]1CC[C@@H](Nc2ncnc3c2c(C2CC2(F)F)cn3COCC[Si](C)(C)C)CN1C(=O)OCc1ccccc1]

To a stirred solution of 4-chloro-5-(2,2-difluorocyclopropyl)-7-((2-(trimethylsilyl)ethoxy)methyl)-7H-pyrrolo[2,3-d]pyrimidine (5.7 g, 15.87 mmol) and triethylamine (4.41 mL, 31.75 mmol) in NMP (25 mL) was added benzyl (2S,5R)-5-amino-2-methylpiperidine-1-carboxylate (3.97 g, 16.03 mmol) and mixture was heated to 130° C. for 16 hours. After cooling, the reaction mixture was concentrated in vacuo and the residue was dissolved in ethyl acetate. The organic layer was washed with water, brine, dried over anhydrous sodium sulfate, filtered and concentrated in vacuo. The crude material was purified by flash column chromatography (25% ethyl aceate:hexane) to provide benzyl (2S,5R)-5-((5-(2,2-difluorocyclopropyl)-7-((2-(trimethylsilyl)ethoxy)methyl)-7H-pyrrolo[2,3-d]pyrimidin-4-yl)amino)-2-methylpiperidine-1-carboxylate as a viscous liquid (7.3 g, 80% yield): MS (ES) m/z 572.3 (M+H).

Step 4: Preparation of Benzyl (2S,5R)-5-((5-(2,2-difluorocyclopropyl)-7H-pyrrolo[2,3-d]pyrimidin-4-yl)amino)-2-methylpiperidine-1-carboxylate

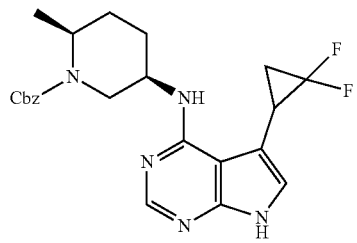 [SMILES: C[C@H]1CC[C@@H](Nc2ncnc3[nH]cc(C4CC4(F)F)c23)CN1C(=O)OCc1ccccc1]

A solution of benzyl (2S,5R)-5-((5-(2,2-difluorocyclopropyl)-7-((2-(trimethylsilyl)ethoxy)methyl)-7H-pyrrolo[2,3-d]pyrimidin-4-yl)amino)-2-methylpiperidine-1-carboxylate (7.3 g, 12.78 mmol) in dichloromethane: trifluoroacetic acid (40 mL: 40 mL) was stirred at ambient temperature. After 2 hours, the reaction mixture was evaporated in vacuo. The residue was dissolved in 1,4-dioxane:aqueous ammonia solution (5 mL: 25 mL) and the mixture stirred at ambient temperature for 2 hours. The reaction mixture was poured into ice water and extracted with ethyl acetate. The organic layer was washed with water, brine, dried over anhydrous sodium sulfate, filtered and concentrated in vacuo. The crude material was purified by flash column chromatography (45% ethyl acetate:hexane) to provide benzyl (2S,5R)-5-((5-(2,2-difluorocyclopropyl)-7H-pyrrolo[2,3-d]pyrimidin-4-yl)amino)-2-methylpiperidine-1-carboxylate as a viscous liquid (4.4 g, 78% yield): MS (ES) m/z 442.1 (M+H).

Step 5: Preparation of 5-(2,2-difluorocyclopropyl)-N-((3R,6S)-6-methylpiperidin-3-yl)-7H-pyrrolo[2,3-d]pyrimidin-4-amine

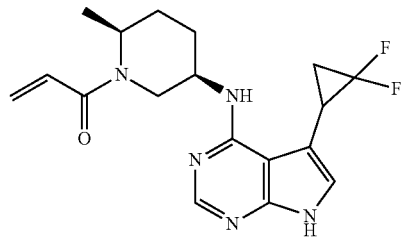 [SMILES: C=CC(=O)N1C[C@H](Nc2ncnc3[nH]cc(C4CC4(F)F)c23)CC[C@@H]1C]

To a suspension of benzyl (2S,5R)-5-((5-(2,2-difluorocyclopropyl)-7H-pyrrolo[2,3-d]pyrimidin-4-yl)amino)-2-methylpiperidine-1-carboxylate (4.4 g, 9.97 mmol) in tetrahydrofuran (100 mL) was added palladium on carbon (2.5 g, 10 wet w/w) under a nitrogen atmosphere. The mixture was stirred under a hydrogen atmosphere at room temperature for 4 hours. The reaction mixture was filtered through celite and the filtrate was concentrated in vacuo to provide 5-(2,2-difluorocyclopropyl)-N-((3R,6S)-6-methylpiperidin-3-yl)-7H-pyrrolo[2,3-d]pyrimidin-4-amine as a viscous liquid (3.2 g, crude): MS (ES) m/z 308.2 (M+H).

EXAMPLE 47

Step 6: Preparation of 1-((2S,5R)-5-((5-(2,2-difluorocyclopropyl)-7H-pyrrolo[2,3-d]pyrimidin-4-yl)amino)-2-methylpiperidin-1-yl)prop-2-en-1-one To a stirred solution of 5-(2,2-difluorocyclopropyl)-N-((3R,6S)-6-methylpiperidin-3-yl)-7H-pyrrolo[2,3-d]pyrimidin-4-amine (3.05 g, 9.93 mmol) in tetrahydrofuran:water (75:25 mL) was added triethylamine (5.52 mL, 39.73 mmol) and acryloyl chloride (0.87 mL, 10.92 mmol) at 0° C. and the mixture was stirred for 30 minutes. The reaction mixture was quenched with saturated sodium bicarbonate solution and extracted with ethyl acetate. The organic layer was washed with brine, dried over anhydrous sodium sulfate, filtered and concentrated in vacuo. The crude material was purified using flash column chromatography (7% of 20% methanol/dichloromethane:dichloromethane) to provide 1-((2S,5R)-5-((5-(2,2-difluorocyclopropyl)-7H-pyrrolo[2,3-d]pyrimidin-4-yl)amino)-2-methylpiperidin-1-yl)prop-2-en-1-one as an off-white solid (1.3 g, 36% yield): $^1$H NMR (400 MHz, DMSO-d$_6$ at 80° C.) δ 11.33 (s, 1H), 8.11 (s, 1H), 6.96 (s, 1H), 6.70-6.77 (m, 1H), 6.05 (d, J=16.8 Hz, 1H), 5.72-5.80 (m, 1H), 5.63 (d, J=12.4 Hz, 1H) 4.56 (br s, 1H), 4.39 (br s, 1H), 4.08 (br s, 1H), 3.26 (br s, 1H), 2.87 (br s, 1H), 1.85-1.98 (m, 3H), 1.63-1.73 (m, 3H), 1.21 (d, J=6.8 Hz, 3H); MS (ES) m/z: 362.0 (M+H).

The stereoisomers of 1-((2S,5R)-5-((5-(2,2-difluorocyclopropyl)-7H-pyrrolo[2,3-d]pyrimidin-4-yl)amino)-2-methylpiperidin-1-yl)prop-2-en-1-one were separated by chiral preparative HPLC.

EXAMPLE 48

Preparation of 1-((2S,5R)-5-((5-((S)-2,2-difluorocyclopropyl)-7H-pyrrolo[2,3-d]pyrimidin-4-yl)amino)-2-methylpiperidin-1-yl)prop-2-en-1-one (Stereoisomer 1, Absolute Configuration of Cyclopropyl Group Assigned Provisionally)

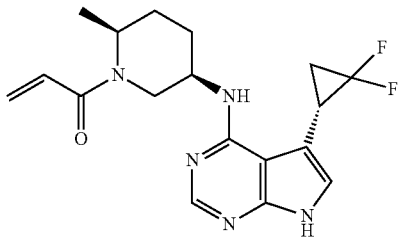 [SMILES: C=CC(=O)N1C[C@H](Nc2ncnc3[nH]cc([C@@H]4CC4(F)F)c23)CC[C@@H]1C]

Purified by chiral HPLC (stereoisomer 1) isolated as a white solid (0.42 g, 12% yield): $^1$H NMR (400 MHz, DMSO-d$_6$) δ 11.54 (s, 1H), 8.11 (s, 1H), 7.01 (s, 1H), 6.77 (br s, 1H), 6.07 (d, J=16.8 Hz, 1H), 5.95 (d, J=8.0 Hz, 1H), 5.65 (d, J=10.4 Hz, 1H), 4.77 (br s, 1H), 4.55 (br s, 1H), 4.32 (br s, 1H), 4.05 (br s, 1H), 3.36 (br s, 1H), 3.02 (br s, 1H), 1.92-2.13 (m, 1H), 1.65-1.98 (m, 4H), 1.19 (br s, 3H); MS (ES) m/z: 362.0 (M+H). Retention time: 3.351.

HPLC Conditions:
Column: CHIRALPAK IA (100 mm×4.6 mm×3 mic)
Mobile phase: n-hexane:IPA with 0.1% DEA (50:50)
Flow rate: 1.0 mL/min.

EXAMPLE 49

Preparation of 1-((2S,5R)-5-((5-((R)-2,2-difluorocyclopropyl)-7H-pyrrolo[2,3-d]pyrimidin-4-yl)amino)-2-methylpiperidin-1-yl)prop-2-en-1-one (Stereoisomer 2, Absolute Configuration of Cyclopropyl Assigned Provisionally)

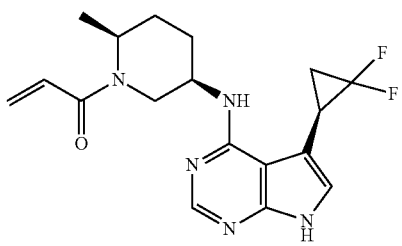 [SMILES: C=CC(=O)N1C[C@H](Nc2ncnc3[nH]cc([C@H]4CC4(F)F)c23)CC[C@@H]1C]

Purified by chiral HPLC (stereoisomer 2) isolated as a white solid (0.1 g, 8% yield): $^1$H NMR (400 MHz, DMSO-d$_6$) δ 11.52 (s, 1H), 8.10 (s, 1H), 6.98 (s, 1H), 6.77 (br s, 1H), 6.06 (d, J=17.2 Hz, 1H), 5.96 (br s, 1H), 5.65 (d, J=9.6 Hz, 1H), 4.77 (br s, 1H), 4.55 (br s, 2H), 4.05 (br s, 2H), 1.64-1.96 (m, 5H), 1.21 (br s, 3H), 1.02 (br s, 1H); MS (ES) m/z: 362.0 (M+H). Retention time: 5.406.

HPLC Conditions:
Column: CHIRALPAK IA (100 mm×4.6 mm×3 mic)
Mobile phase: n-hexane:IPA with 0.1% DEA (50:50)
Flow rate: 1.0 mL/min.

The compounds of Table 3 were prepared as described in Example 45.

TABLE 3

| Example Number | Structure | Compound Name | Spectroscopic Data |
|---|---|---|---|
| Example 50 | 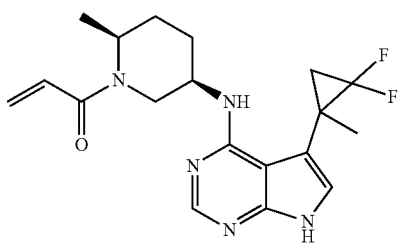 [SMILES: C=CC(=O)N1C[C@H](Nc2ncnc3[nH]cc(C4(C)CC4(F)F)c23)CC[C@@H]1C] | 1-((2S,5R)-5-((5-(2,2-difluoro-1-methylcyclopropyl)-7H-pyrrolo[2,3-d]pyrimidin-4-yl)amino)-2-methylpiperidin-1-yl)prop-2-en-1-one | White solid (0.01 g): $^1$H NMR (400 MHz, DMSO-d$_6$) δ 11.90 (s, 1H), 8.23 (s, 1H), 7.16 (s, 1H), 6.75-6.82 (m, 1H), 6.08 (d, J = 16.8 Hz, 1H), 5.66 (d, J = 10.4 Hz, 1H)), 5.31 (br s, 1H), 4.49 (br s, 3H), 4.03 (br s, 1H), 2.83 (br s, 1H), 1.67-1.91(m, 5H), 1.50 (s, 3H), 1.20-1.18 (m, 3H); MS (ES) m/z 376.0 (M + H). |

TABLE 3-continued

| Example Number | Structure | Compound Name | Spectroscopic Data |
|---|---|---|---|
| Example 51 | 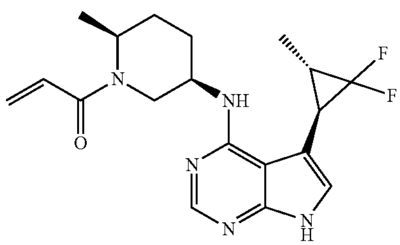 [SMILES: C=CC(=O)N1C[C@H](Nc2ncnc3[nH]cc([C@H]4[C@H](C)C4(F)F)c23)CC[C@@H]1C] | 1-((2S,5R)-5-((5-((1R,3S)-2,2-difluoro-3-methylcyclopropyl)-7H-pyrrolo[2,3-d]pyrimidin-4-yl)amino)-2-methylpiperidin-1-yl)prop-2-en-1-one (Stereoisomer 4, absolute configuration assigned provisionally) | White solid (0.02 g): $^1$H NMR (400 MHz, DMSO-$d_6$) δ 11.52 (s, 1H), 8.11 (s, 1H), 7.0 (s, 1H), 6.77 (br s, 1H), 6.07 (d, J = 14.8 Hz, 1H), 5.86 (d, J = 8.0 Hz, 1H), 5.66 (d, J = 10.4 Hz, 1H), 4.62-4.79 (m, 2H), 4.01-4.35 (m, 4H), 2.97-3.01 (m, 1H), 1.66-1.98 (m, 4H), 1.19-1.33 (m, 5H), 0.83 (br s, 1H); MS (ES) m/z: 376.0 (M + H). HPLC Conditions: Column: CHIRALPAK IA (100 mm × 4.6 mm × 3 mic) Mobile phase: n-Hexane: IPA with 0.1% DEA (50:50) Flow rate: 1.0 mL/min Retention time: 11.165 min. |
| Example 52 | 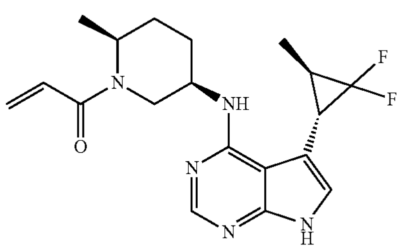 [SMILES: C=CC(=O)N1C[C@H](Nc2ncnc3[nH]cc([C@@H]4[C@@H](C)C4(F)F)c23)CC[C@@H]1C] | 1-((2S,5R)-5-((5-((1S,3R)-2,2-difluoro-3-methylcyclopropyl)-7H-pyrrolo[2,3-d]pyrimidin-4-yl)amino)-2-methylpiperidin-1-yl)prop-2-en-1-one (Stereoisomer 3, absolute configuration assigned provisionally) | White solid (0.02 g): $^1$H NMR (400 MHz, DMSO-$d_6$) δ 11.51 (s, 1H), 8.11 (s, 1H), 6.96 (s, 1H), 6.77 (br s, 1H), 6.07 (d, J = 15.2 Hz, 1H), 5.89 (br s, 1H), 5.66 (d, J = 12.0 Hz, 1H) 4.6-4.79 (m, 2H), 4.14-4.36 (m, 2H), 4.0 (br s, 1H), 2.96-3.02 (m, 2H), 1.66-1.87 (m, 5H), 1.18-1.32 (m, 5H); MS (ES) m/z: 376.0 (M + H). HPLC Conditions: Column: CHIRALPAK IA (100 mm × 4.6 mm × 3 mic) Mobile phase: n-Hexane: IPA with 0.1% DEA (50:50) Flow rate: 1.0 mL/min Retention time: 16.759 min. |
| Example 53 | 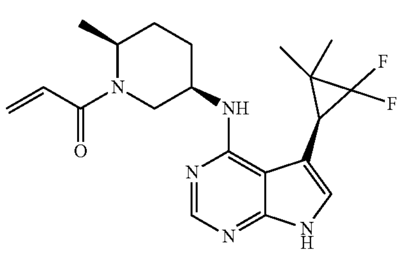 [SMILES: C=CC(=O)N1C[C@H](Nc2ncnc3[nH]cc([C@H]4C(C)(C)C4(F)F)c23)CC[C@@H]1C] | 1-((2S,5R)-5-((5-((S)-2,2-difluoro-3,3-dimethylcyclopropyl)-7H-pyrrolo[2,3-d]pyrimidin-4-yl)amino)-2-methylpiperidin-1-yl)prop-2-en-1-one (Stereoisomer 2, absolute configuration of difluoro-cyclopropyl group assigned provisionally) | White solid (0.01 g): $^1$H NMR (400 MHz, DMSO-$d_6$) δ 11.55 (s, 1H), 8.11 (s, 1H), 6.91 (s, 1H), 6.75-6.82 (m, 1H), 6.07 (d, J = 16.8 Hz, 1H), 5.64-5.67 (m, 2H), 4.36-4.57 (m, 2H), 4.19-4.25 (m, 2H), 3.99 (br s, 1H), 3.05 (d, J = 16.4 Hz, 2H), 1.96 (br s, 1H), 1.64-1.71 (m, 1H), 1.39 (s, 3H), 1.21 (s, 3H), 0.79 (m, 3H); MS (ES) m/z: 389.9. HPLC conditions: Column: CHIRALPAK IA (100 mm × 4.6 mm × 3 mic) Mobile phase: n-hexane: IPA with 0.1% DEA (50:50) Flow rate: 1.0 mL/min Retention time: 2.47 min. |

TABLE 3-continued

| Example Number | Structure | Compound Name | Spectroscopic Data |
|---|---|---|---|
| Example 54 | 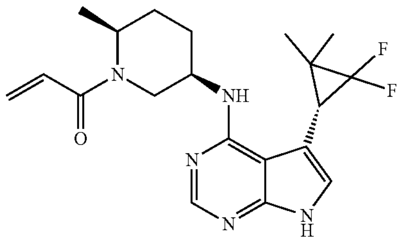 [SMILES: C=CC(=O)N1C[C@H](Nc2ncnc3[nH]cc([C@@H]4C(C)(C)C4(F)F)c23)CC[C@@H]1C] | 1-((2S,5R)-5-((5-((R)-2,2-difluoro-3,3-dimethylcyclopropyl)-7H-pyrrolo[2,3-d]pyrimidin-4-yl)amino)-2-methylpiperidin-1-yl)prop-2-en-1-one (Stereoisomer 1, absolute configuration of difluoro-cyclopropyl group assigned provisionally) | White solid (0.01 g): $^1$H NMR (400 MHz, DMSO-$d_6$) δ 11.53 (s, 1H), 8.12 (s, 1H), 6.89 (s, 1H), 6.75 (br s, 1H), 6.07 (d, J = 17.6 Hz, 1H), 5.49-5.72 (m, 2H), 4.67-4.79 (m, 1H), 4.18-4.35 (m, 2H), 3.99 (br s, 2H), 2.95-3.07 (m, 2H), 1.67-1.96 (m, 2H), 1.38 (s, 3H), 1.18-1.21 (m, 3H), 0.83 (s, 3H); MS (ES) m/z: 390.1 (M + H). HPLC conditions: Column: CHIRALPAK IA (100 mm × 4.6 mm × 3 mic) Mobile phase: n-hexane: IPA with 0.1% DEA (50:50) Flow rate: 1.0 mL/min Retention time: 3.32 min. |
| Example 55 | 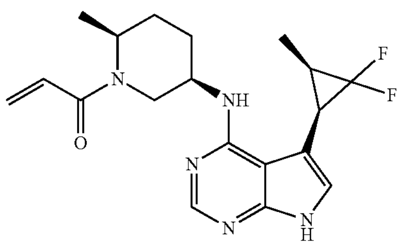 [SMILES: C=CC(=O)N1C[C@H](Nc2ncnc3[nH]cc([C@H]4[C@@H](C)C4(F)F)c23)CC[C@@H]1C] | 1-((2S,5R)-5-((5-((1R,3R)-2,2-difluoro-3-methylcyclopropyl)-7H-pyrrolo[2,3-d]pyrimidin-4-yl)amino)-2-methylpiperidin-1-yl)prop-2-en-1-one (Stereoisomer 2 absolute configuration of difluoro-cyclopropyl group assigned provisionally) | White solid (0.021 g): $^1$H NMR (400 MHz, DMSO-$d_6$) δ 11.56 (s, 1H), 8.09 (s, 1H), 6.92 (s, 1H), 6.78 (br s, 1H), 6.06 (d, J = 16.8 Hz, 1H), 5.90 (br s, 1H), 5.65 (d, J = 10.4 Hz, 1H), 4.78 (br s, 1H), 4.34-4.45 (m, 2H), 4.12 (br s, 2H), 3.15-3.22 (m, 2H), 2.77 (br s, 1H), 2.20 (br s, 1H), 1.84 (br s, 1H), 1.65 (br s, 1H), 1.33 (s, 3H), 0.83 (br s, 3H); MS (ES) m/z: 376.0 (M + H). HPLC Conditions: Column: CHIRALPAK IC (100 mm × 4.6 mm × 3 mic) Mobile phase: n-Hexane: IPA with 0.1% DEA (50:50) Flow rate: 1.0 mL/min Retention time: 7.158 min. |
| Example 56 | 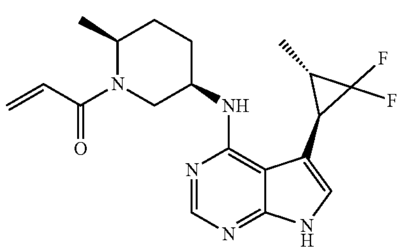 [SMILES: C=CC(=O)N1C[C@H](Nc2ncnc3[nH]cc([C@H]4[C@H](C)C4(F)F)c23)CC[C@@H]1C] | 1-((2S,5R)-5-((5-((1R,3S)-2,2-difluoro-3-methylcyclopropyl)-7H-pyrrolo[2,3-d]pyrimidin-4-yl)amino)-2-methylpiperidin-1-yl)prop-2-en-1-one (Stereoisomer 1 absolute configuration of difluoro-cyclopropyl group assigned provisionally) | White solid (0.03 g): $^1$H NMR (400 MHz, DMSO-$d_6$) δ 11.56 (s, 1H), 8.09 (s, 1H), 6.92 (s, 1H), 6.77 (br s, 1H), 6.07 (d, J = 16.8 Hz, 1H), 5.96 (br s, 1H), 5.66 (d, J = 10.0 Hz, 1H), 4.79 (br s, 1H), 4.52 (br s, 1H), 4.35 (br s, 1H), 3.96-4.08 (m, 2H), 3.17-3.25 (m, 1H), 3.03 (br s, 1H), 2.15-2.17 (m, 1H), 1.95-1.96 (m, 1H), 1.65-1.77 (m, 1H), 1.23 (s, 3H), 0.73 (br s, 3H); MS (ES) m/z: 376.0 (M + H). HPLC Conditions: Column: CHIRALPAK IC (100 mm × 4.6 mm × 3 mic) Mobile phase: n-hexane: IPA with 0.1% DEA (50:50) Flow rate: 1.0 mL/min Retention time: 9.369 min. |

TABLE 3-continued

| Example Number | Structure | Compound Name | Spectroscopic Data |
|---|---|---|---|
| Example 57 | 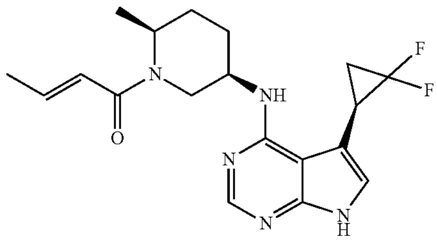 [SMILES: C/C=C/C(=O)N1C[C@H](Nc2ncnc3[nH]cc([C@H]4CC4(F)F)c23)CC[C@@H]1C] | (E)-1-((2S,5R)-5-((5-((R)-2,2-difluorocyclopropyl)-7H-pyrrolo[2,3-d]pyrimidin-4-yl)amino)-2-methylpiperidin-1-yl)but-2-en-1-one (Stereoisomer 2 absolute configuration of difluoro-cyclopropyl group assigned provisionally) | White solid (0.01 g): $^1$H NMR (400 MHz, DMSO-$d_6$) δ 11.54 (s, 1H), 8.10 (s, 1H), 6.98 (s, 1H), 6.61-6.67 (m, 1H), 6.48 (d, J = 15.2 Hz, 1H), 5.97 (d, J = 8.8 Hz, 1H), 4.03-4.80 (m, 5H), 3.31-3.33 (m, 3H), 1.96 (s, 1H), 1.63-1.82 (m, 5H), 1.01 (d, J = 6 Hz, 3H); MS (ES) m/z: 376.1 (M + H)$^+$. HPLC Conditions: Column: CHIRALPAK IC (100 mm × 4.6 mm × 3 mic) Mobile phase: n-hexane: IPA with 0.1% DEA (60:40) Flow rate: 1.0 mL/min Retention time 9.73 min. |
| Example 58 | 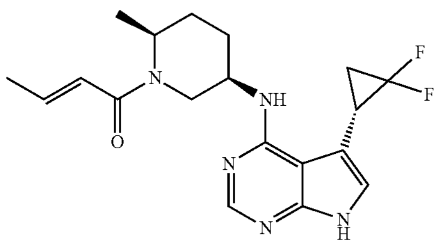 [SMILES: C/C=C/C(=O)N1C[C@H](Nc2ncnc3[nH]cc([C@@H]4CC4(F)F)c23)CC[C@@H]1C] | (E)-1-((2S,5R)-5-((5-((S)-2,2-difluorocyclopropyl)-7H-pyrrolo[2,3-d]pyrimidin-4-yl)amino)-2-methylpiperidin-1-yl)but-2-en-1-one (Stereoisomer 1, absolute configuration of difluoro-cyclopropyl group assigned provisionally) | White solid (0.01 g): $^1$H NMR (400 MHz, DMSO-$d_6$) δ 11.54 (s, 1H), 8.10 (s, 1H), 7.00 (s, 1H), 6.61-6.67 (m, 1H), 6.47 (d, J = 14.4 Hz, 1H), 5.95 (d, J = 8 Hz, 1H), 4.03-4.80 (m, 3H), 3.31-3.33 (m, 2H), 1.96-2.01 (m, 1H), 1.81-1.82 (m, 6H), 1.61-1.64 (m, 2H), 1.17 (br s, 3H); MS (ES) m/z: 376.1 (M + H)$^+$. HPLC Conditions: Column: CHIRALPAK IC (100 mm × 4.6 mm × 3 mic) Mobile phase: n-hexane: IPA with 0.1% DEA (60:40) Flow rate: 1.0 mL/min Retention time 15.25 min. |
| Example 59 | 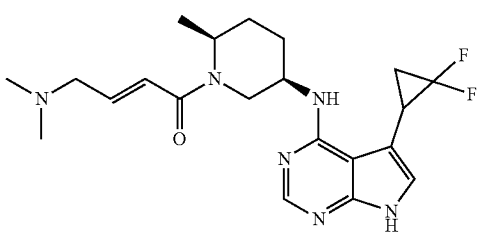 | (E)-1-((2S,5R)-5-((5-(2,2-difluorocyclopropyl)-7H-pyrrolo[2,3-d]pyrimidin-4-yl)amino)-2-methylpiperidin-1-yl)-4-(dimethylamino)but-2-en-1-one (mixture of stereoisomers) | Off-white solid (0.09 g): $^1$H NMR (400 MHz, DMSO-$d_6$) δ 11.54 (s, 1H), 8.09 (s, 1H), 6.98-7.00 (d, J = 8 Hz, 1H), 6.57 (t, J = 8 Hz, 2H), 5.96 (s, 1H), 4.03-4.90 (m, 2H), 2.99 (d, J = 3.2 Hz, 4H), 2.12 (s, 6H), 1.95-2.05 (m, 1H), 1.64-1.84 (m, 6H), 1.18-1.21 (m, 3H); MS (ES) m/z: 419.4 (M + H)$^+$. |
| Example 60 | 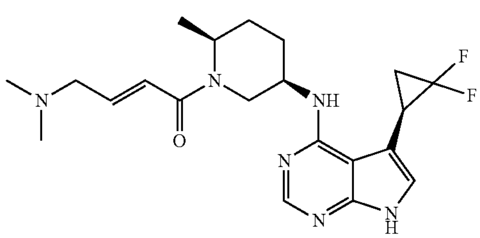 [SMILES: C[C@H]1CC[C@@H](Nc2ncnc3[nH]cc([C@H]4CC4(F)F)c23)CN1C(=O)/C=C/CN(C)C] | (E)-1-((2S,5R)-5-((5-((R)-2,2-difluorocyclopropyl)-7H-pyrrolo[2,3-d]pyrimidin-4-yl)amino)-2-methylpiperidin-1-yl)-4-(dimethylamino)but-2-en-1-one (Stereoisomer 2, absolute configuration of difluoro-cyclopropyl group assigned provisionally) | Off-white solid (0.03 g): $^1$H NMR (400 MHz, DMSO-$d_6$) δ 11.54 (s, 1H), 8.09 (s, 1H), 7.01 (s, 1H), 6.55-6.63 (m, 2H), 5.96 (d, J = 6.8 Hz, 1H), 4.32-4.80 (m, 4H), 4.03 (br s, 1H), 3.30-3.32 (m, 3H), 3.06-3.31 (m, 2H), 2.17 (s, 4H), 1.65-1.98 (m, 5H) 1.18-1.21 (m, 3H); MS (ES) m/z: 419.2 (M + H)$^+$. HPLC Conditions: Column: CHIRALPAK IA (100 mm × 4.6 mm × 3 mic) Mobile phase: n-hexane IPA with 0.1% DEA (70:30) Flow rate: 1.0 mL/min Retention time: 2.10 min. |

TABLE 3-continued

| Example Number | Structure | Compound Name | Spectroscopic Data |
|---|---|---|---|
| Example 61 | 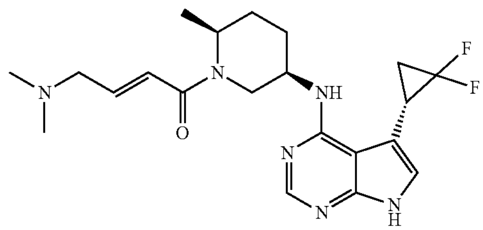 [SMILES: C[C@H]1CC[C@@H](Nc2ncnc3[nH]cc([C@@H]4CC4(F)F)c23)CN1C(=O)/C=C/CN(C)C] | (E)-1-((2S,5R)-5-((5-((S)-2,2-difluorocyclopropyl)-7H-pyrrolo[2,3-d]pyrimidin-4-yl)amino)-2-methylpiperidin-1-yl)-4-(dimethylamino)but-2-en-1-one (Stereoisomer 1, absolute configuration of difluorocyclopropyl group assigned provisionally) | Off-white solid (0.04 g): $^1$H NMR (400 MHz, DMSO-$d_6$) δ 11.54 (s, 1H), 8.09 (s, 1H), 6.99 (s, 1H), 6.52-6.62 (m, 2H), 5.97 (s, 1H), 4.04-4.80 (m, 5H), 3.25-3.27 (m, 3H), 3.04 (br s, 2H), 2.16 (s, 4H), 1.96-1.99 (m, 1H), 1.64-1.84 (m, 4H), 1.20-1.31 (m, 3H); MS (ES) m/z: 419.2 (M + H)$^+$.<br>HPLC Conditions:<br><br>Column: CHIRALPAK IA (100 mm × 4.6 mm × 3 mic)<br>Mobile phase: n-hexane: IPA with 0.1% DEA (70:30)<br>Flow rate: 1.0 mL/min<br>Retention time 2.65 min. |
| Example 62 | 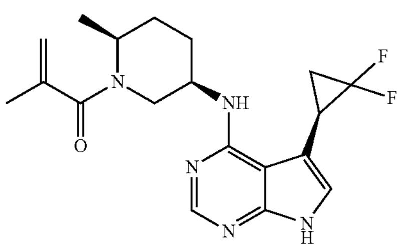 [SMILES: C=C(C)C(=O)N1C[C@H](Nc2ncnc3[nH]cc([C@H]4CC4(F)F)c23)CC[C@@H]1C] | 1-((2S,5R)-5-((5-((R)-2,2-difluorocyclopropyl)-7H-pyrrolo[2,3-d]pyrimidin-4-yl)amino)-2-methylpiperidin-1-yl)-2-methylprop-2-en-1-one (Stereoisomer 1, absolute configuration of difluorocyclopropyl group assigned provisionally) | White solid (0.04 g): $^1$H NMR (400 MHz, DMSO-$d_6$) δ 11.54 (s, 1H), 8.08 (s, 1H), 7.00 (s, 1H), 5.94 (d, J = 8.4 Hz, 1H), 5.10 (s, 1H), 4.97 (s, 1H), 4.06-4.09 (m, 1H), 3.25-3.33 (m, 3H), 2.83 (br s, 2H), 1.85-1.97 (m, 4H), 1.61-1.85 (m, 4H) 1.19 (d, J = 6.4 Hz, 3H); MS (ES) m/z: 376.2 (M + H)$^+$.<br>HPLC Conditions:<br>Column: CHIRALPAK IA (100 mm × 4.6 mm × 3 mic)<br>Mobile phase: n-hexane: IPA with 0.1% DEA (70:30)<br>Flow rate: 1.0 mL/min<br>Retention time: 2.56 min. |
| Example 63 | 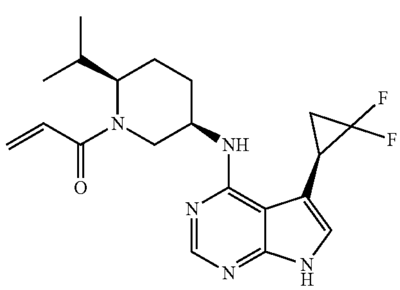 [SMILES: C=CC(=O)N1C[C@H](Nc2ncnc3[nH]cc([C@H]4CC4(F)F)c23)CC[C@@H]1C(C)C] | 1-((2R,5R)-5-((5-((R)-2,2-difluorocyclopropyl)-7H-pyrrolo[2,3-d]pyrimidin-4-yl)amino)-2-isopropylpiperidin-1-yl)prop-2-en-1-one (Stereoisomer 4, absolute configuration assigned provisionally) | White solid (0.034 g): $^1$H NMR (400 MHz, DMSO-$d_6$) δ 11.53 (s, 1H), 8.09 (d, J = 12 Hz, 1H), 6.98 (s, 1H), 6.77-6.86 (m, 1H), 5.97-6.09 (m, 2H), 5.62-5.68 (m, 1H), 4.55-4.62 (m, 1H), 4.08-4.25 (m, 2H), 3.60-3.80 (m, 1H), 2.91-2.97 (m, 1H), 2.55-2.58 (m, 1H), 2.10-2.30 (m, 1H), 1.81-1.96 (m, 4H), 1.50-1.63 (m, 1H), 0.94 (d, J = 4 Hz, 3H), 0.74 (d, J = 8.0 Hz, 3H); MS (ES) m/z 390.2 (M + H).<br>HPLC conditions:<br>Column: CHIRALPAK IA (100 mm × 4.6 mm × 3 mic)<br>Mobile phase: n-hexane: IPA with 0.1% DEA (90:10)<br>Flow rate: 1.0 mL/min<br>Retention time 3.66 min. |

TABLE 3-continued

| Example Number | Structure | Compound Name | Spectroscopic Data |
|---|---|---|---|
| Example 64 | 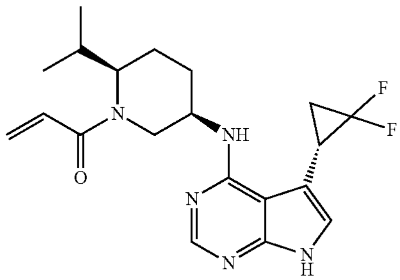 [SMILES: C=CC(=O)N1C[C@H](Nc2ncnc3[nH]cc([C@@H]4CC4(F)F)c23)CC[C@@H]1C(C)C] | 1-((2R,5R)-5-((5-((S)-2,2-difluorocyclopropyl)-7H-pyrrolo[2,3-d]pyrimidin-4-yl)amino)-2-isopropylpiperidin-1-yl)prop-2-en-1-one (Stereoisomer 3, absolute configuration assigned provisionally) | White solid (0.042 g): $^1$H NMR (400 MHz, DMSO-$d_6$) δ 11.53 (s, 1H), 8.09 (d, J = 12 Hz, 1H), 7.01 (s, 1H), 6.77-6.88 (m, 1H), 6.08 (d, J = 16 Hz, 1H), 5.94-5.97 (m, 1H), 5.62-5.70 (m, 1H), 4.59-4.63 (m, 1H), 4.04-4.21 (m, 2H), 3.66 (d, J = 8 Hz, 1H), 2.90-2.96 (m, 1H), 2.57-2.65 (m, 1H), 2.19-2.30 (m, 1H), 1.89-1.96 (m, 2H), 1.78-1.89 (m, 2H), 1.49-1.56 (m, 1H), 0.95 (d, J = 8 Hz, 3H), 0.73 (d, J = 8 Hz, 3H); MS (ES) m/z 390.2 (M + H). HPLC conditions: Column: CHIRALPAK IA (100 mm × 4.6 mm × 3 mic) Mobile phase: n-hexane:IPA with 0.1% DEA (90:10) Flow rate: 1.0 mL/min Retention time 5.36 min. |
| Example 65 | 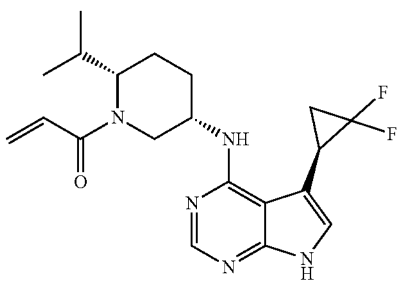 [SMILES: C=CC(=O)N1C[C@@H](Nc2ncnc3[nH]cc([C@H]4CC4(F)F)c23)CC[C@H]1C(C)C] | 1-((2S,5S)-5-((5-((R)-2,2-difluorocyclopropyl)-7H-pyrrolo[2,3-d]pyrimidin-4-yl)amino)-2-isopropylpiperidin-1-yl)prop-2-en-1-one (Stereoisomer 2, absolute configuration assigned provisionally) | White solid (0.044 g): $^1$H NMR (400 MHz, DMSO-$d_6$) δ 11.53 (s, 1H), 8.09 (d, J = 12 Hz, 1H), 7.01 (s, 1H), 6.77-6.86 (m, 1H), 6.08 (d, J = 16 Hz, 1H), 5.94-5.96 (m, 1H), 5.62-5.70 (m, 1H), 4.62-4.68 (m, 1H), 4.05-4.25 (m, 2H), 3.66 (d, J = 8 Hz, 1H), 2.90-2.96 (m, 1H), 2.57-2.65 (m, 1H), 2.30-2.19 (m, 1H), 1.89-1.96 (m, 2H), 1.70-1.85 (m, 2H), 1.49-1.56 (m, 1H), 0.95 (d, J = 8 Hz, 3H), 0.73 (d, J = 8 Hz, 3H); MS (ES) m/z 390.3 (M + H). HPLC conditions: Column: CHIRALPAK IA (100 mm × 4.6 mm × 3 mic) Mobile phase: n-hexane:IPA with 0.1% DEA (90:10) Flow rate: 1.0 mL/min Retention time 5.80 min. |
| Example 66 | 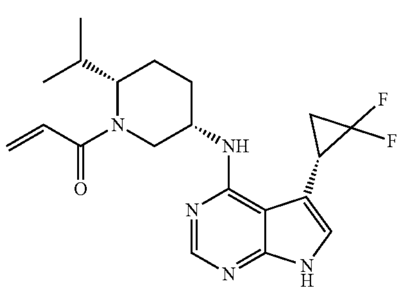 [SMILES: C=CC(=O)N1C[C@@H](Nc2ncnc3[nH]cc([C@@H]4CC4(F)F)c23)CC[C@H]1C(C)C] | 1-((2S,5S)-5-((5-((S)-2,2-difluorocyclopropyl)-7H-pyrrolo[2,3-d]pyrimidin-4-yl)amino)-2-isopropylpiperidin-1-yl)prop-2-en-1-one (Stereoisomer 1, absolute configuration assigned provisionally) | White solid (0.032 g): $^1$H NMR (400 MHz, DMSO-$d_6$) δ 11.53 (s, 1H), 8.09 (d, J = 12 Hz, 1H), 7.01(s, 1H), 6.77-6.99 (m, 1H), 6.08 (d, J = 16 Hz, 1H), 5.94-6.06 (m, 1H), 5.62-5.70 (m, 1H), 4.53-4.70 (m, 1H), 4.00-4.11 (m, 2H), 4.04-4.21 (m, 1H), 3.66 (d, J = 8 Hz, 1H), 2.90-2.96 (m, 1H), 2.57-2.65 (m, 1H), 2.19-2.30 (m, 1H), 1.89-1.96 (m, 2H), 1.78-1.89 (m, 2H), 1.49-1.56 (m, 1H), 1.21 (s, 1H), 0.95 (d, J = 8 Hz, 3H), 0.73 (d, J = 8 Hz, 3H); MS (ES) m/z 390.2(M + H). |

TABLE 3-continued

| Example Number | Structure | Compound Name | Spectroscopic Data |
|---|---|---|---|
| | | | HPLC conditions: Column: CHIRALPAK IA (100 mm × 4.6 mm × 3 mic) Mobile phase: n-hexane: IPA with 0.1% DEA (90:10) Flow rate: 1.0 mL/min Retention time 7.674 min. |
| Example 67 | 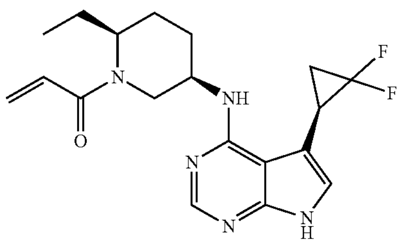 [SMILES: C=CC(=O)N1C[C@H](Nc2ncnc3[nH]cc([C@H]4CC4(F)F)c23)CC[C@@H]1CC] | 1-((2S,5R)-5-((5-((R)-2,2-difluorocyclopropyl)-7H-pyrrolo[2,3-d]pyrimidin-4-yl)amino)-2-ethylpiperidin-1-yl)prop-2-en-1-one (Stereoisomer 4, absolute configuration assigned provisionally) | White solid (0.03 g): $^1$H NMR (400 MHz, DMSO-$d_6$) δ 11.54 (s, 1H), 8.10 (d, J = 12.0 Hz, 1H), 6.98 (s, 1H), 6.78-6.80 (m, 1H), 6.08 (d, J = 16.4 Hz, 1H), 5.98 (s, 1H), 5.65 (t, J = 11.8 Hz, 1H), 4.55 (br s, 1H), 4.07 (br s, 2H), 3.31 (br s, 1H), 2.58-2.95 (m, 1H), 1.83-1.96 (m, 2H), 1.58-1.70 (m, 5H), 1.51-1.56 (m, 1H), 0.78 (t, J = 7.4 Hz, 3H); MS (ES) m/z: 376.4 (M + H). HPLC Conditions: Column: CHIRALPAK IA (100 mm × 4.6 mm × 3 mic) Mobile phase: n-hexane: IPA with 0.1% DEA (90:10) Flow rate: 1.0 mL/min Retention time: 5.540 min. |
| Example 68 | 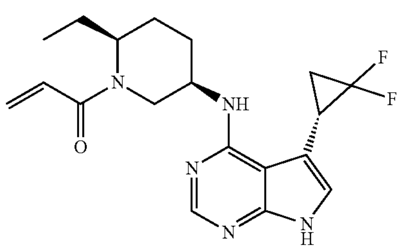 [SMILES: C=CC(=O)N1C[C@H](Nc2ncnc3[nH]cc([C@@H]4CC4(F)F)c23)CC[C@@H]1CC] | 1-((2S,5R)-5-((5-((S)-2,2-difluorocyclopropyl)-7H-pyrrolo[2,3-d]pyrimidin-4-yl)amino)-2-ethylpiperidin-1-yl)prop-2-en-1-one (Stereoisomer 3, absolute configuration assigned provisionally) | White solid (0.04 g): $^1$H NMR (400 MHz, DMSO-$d_6$) δ 11.54 (s, 1H), 8.10 (d, J = 12.8 Hz, 1H), 7.00 (s, 1H), 6.78-6.82 (m, 1H), 6.08 (d, J = 16.8 Hz, 1H), 5.95 (s, 1H), 5.65 (t, J = 11.8 Hz, 1H), 4.57 (br s, 1H), 4.03 (br s, 2H), 3.26 (br s, 1H), 2.58-2.95 (m, 1H), 1.95-1.98 (m, 1H), 1.72-1.79 (m, 5H), 1.51-1.56 (m, 2H), 0.78 (t, J = 7.2 Hz, 3H); MS (ES) m/z: 376.4 (M + H). HPLC Conditions: Column: CHIRALPAK IA (100 mm × 4.6 mm × 3 mic) Mobile phase: n-hexane: IPA with 0.1% DEA (90:10) Flow rate: 1.0 mL/min Retention time: 3.54 min. |
| Example 69 | 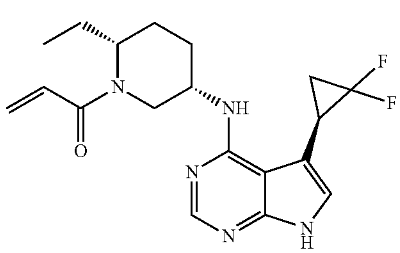 [SMILES: C=CC(=O)N1C[C@@H](Nc2ncnc3[nH]cc([C@H]4CC4(F)F)c23)CC[C@H]1CC] | 1-((2R,5S)-5-((5-((R)-2,2-difluorocyclopropyl)-7H-pyrrolo[2,3-d]pyrimidin-4-yl)amino)-2-ethylpiperidin-1-yl)prop-2-en-1-one (Stereoisomer 2, absolute configuration assigned provisionally) | White solid (0.04 g): $^1$H NMR (400 MHz, DMSO-$d_6$) δ 11.54 (s, 1H), 8.10 (d, J = 12.8 Hz, 1H), 7.00 (s, 1H), 6.78-6.82 (m, 1H), 6.08 (d, J = 16.8 Hz, 1H), 5.95 (s, 1H), 5.65 (t, J = 11.8 Hz, 1H), 4.57 (br s, 1H), 4.06 (br s, 2H), 3.31 (br s, 1H), 2.60-2.95 (m, 1H), 1.95-1.98 (m, 1H), 1.58-1.79 (m, 5H), 1.51-1.56 (m, 2H), 0.78 (t, J = 7.2 Hz, 3H); MS (ES) m/z: 376.1 (M + H). |

TABLE 3-continued

| Example Number | Structure | Compound Name | Spectroscopic Data |
|---|---|---|---|
| | | | HPLC Conditions: Column: CHIRALPAK IA (100 mm × 4.6 mm × 3 mic) Mobile phase: n-hexane: IPA with 0.1% DEA (90:10) Flow rate: 1.0 mL/min Retention time: 4.72 min |
| Example 70 | 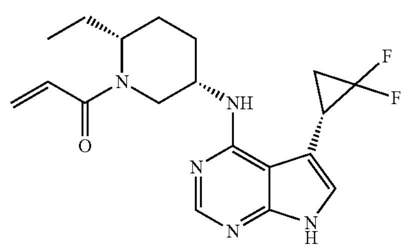 [SMILES: C=CC(=O)N1C[C@@H](Nc2ncnc3[nH]cc([C@@H]4CC4(F)F)c23)CC[C@H]1CC] | 1-((2R,5S)-5-((5-((S)-2,2-difluorocyclopropyl)-7H-pyrrolo[2,3-d]pyrimidin-4-yl)amino)-2-ethylpiperidin-1-yl)prop-2-en-1-one (Stereoisomer 1, absolute configuration assigned provisionally) | White solid (0.03 g): $^1$H NMR (400 MHz, DMSO-$d_6$) δ 11.54 (s, 1H), 8.10 (d, J = 12.4 Hz, 1H), 6.98 (s, 1H), 6.78-6.80 (m, 1H), 6.08 (d, J = 16.0 Hz, 1H), 5.98 (s, 1H), 5.65 (t, J = 11.8 Hz, 1H), 4.56 (br s, 1H), 4.07 (br s, 2H), 3.31 (br s, 1H), 2.61-2.95 (m, 1H), 1.83-1.96 (m, 1H), 1.56-1.70 (m, 6H), 1.51-1.56 (m, 1H), 0.78 (t, J = 7.2 Hz, 3H); MS (ES) m/z: 376.4 (M + H). HPLC Conditions: Column: CHIRALPAK IA (100 mm × 4.6 mm × 3 mic) Mobile phase: n-hexane: IPA with 0.1% DEA (90:10) Flow rate: 1.0 mL/min Retention time: 5.54 min. |
| Example 71 | 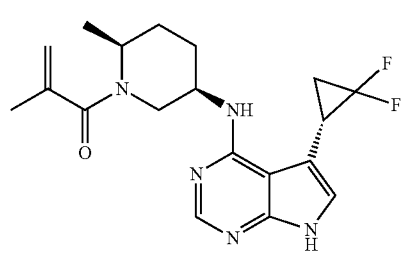 [SMILES: C=C(C)C(=O)N1C[C@H](Nc2ncnc3[nH]cc([C@@H]4CC4(F)F)c23)CC[C@@H]1C] | 1-((2S,5R)-5-((5-((S)-2,2-difluorocyclopropyl)-7H-pyrrolo[2,3-d]pyrimidin-4-yl)amino)-2-methylpiperidin-1-yl)-2-methylprop-2-en-1-one (Stereoisomer 2, absolute configuration of difluoro-cyclopropyl group assigned provisionally) | White solid (0.04 g): $^1$H NMR (400 MHz, DMSO-$d_6$) δ 11.54 (s, 1H), 8.08 (s, 1H), 6.98 (s, 1H), 5.97 (d, 1H), 5.10 (s, 1H), 4.97 (s, 1H), 4.06 (br s, 2H), 3.46-3.49 (m, 3H), 2.85 (m, 2H), 1.85-1.98 (m, 5H), 1.63-1.82 (m, 3H), 1.19-1.21 (d, J = 7.2 Hz, 3H); MS (ES) m/z: 376.2 (M + H). HPLC Conditions: Column: CHIRALPAK IA (100 mm × 4.6 mm × 3 mic) Mobile phase: n-hexane: IPA with 0.1% DEA (70:30) Flow rate: 1.0 mL/min Retention time: 4.007 min. |

EXAMPLE 72, 73 and 74

Preparation of 1-((2S,5R)-5-((3-(2,2-difluorocyclopropyl)-1H-pyrrolo[2,3-b]pyridin-4-yl)amino)-2-methylpiperidin-1-yl)prop-2-en-1-one, 1-((2S,5R)-5-((3-((R)-2,2-difluorocyclopropyl)-1H-pyrrolo[2,3-b]pyridin-4-yl)amino)-2-methylpiperidin-1-yl)prop-2-en-1-one, and 1-((2S,5R)-5-((3-((S)-2,2-difluorocyclopropyl)-1H-pyrrolo[2,3-b]pyridin-4-yl)amino)-2-methylpiperidin-1-yl)prop-2-en-1-one

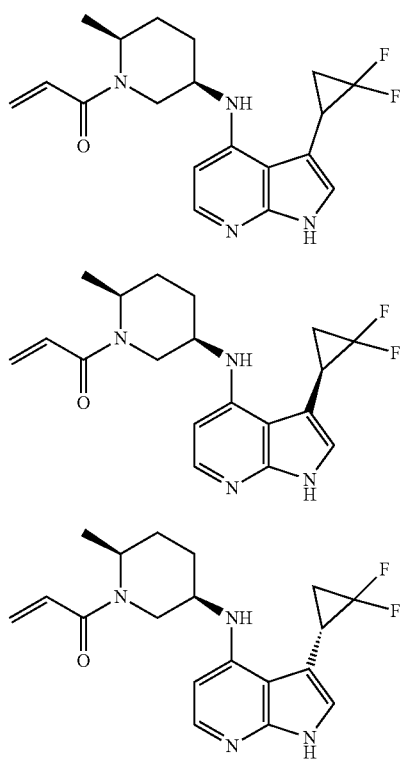

Example 72

Example 73

Example 74

The title compounds were prepared by the methods described in Scheme 29.

Scheme 29. Synthesis of 1-((2S,5R)-5-((3-((R)-2,2-difluorocyclopropyl)-1H-pyrrolo[2,3-b]pyridin-4-yl)amino)-2-methylpiperidin-1-yl)prop-2-en-1-one and 1-((2S,5R)-5-((3-((S)-2,2-difluorocyclopropyl)-1H-pyrrolo[2,3-b]pyridin-4-yl)amino)-2-methylpiperidin-1-yl)prop-2-en-1-one.

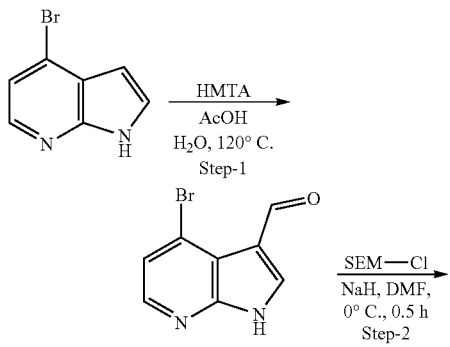

-continued

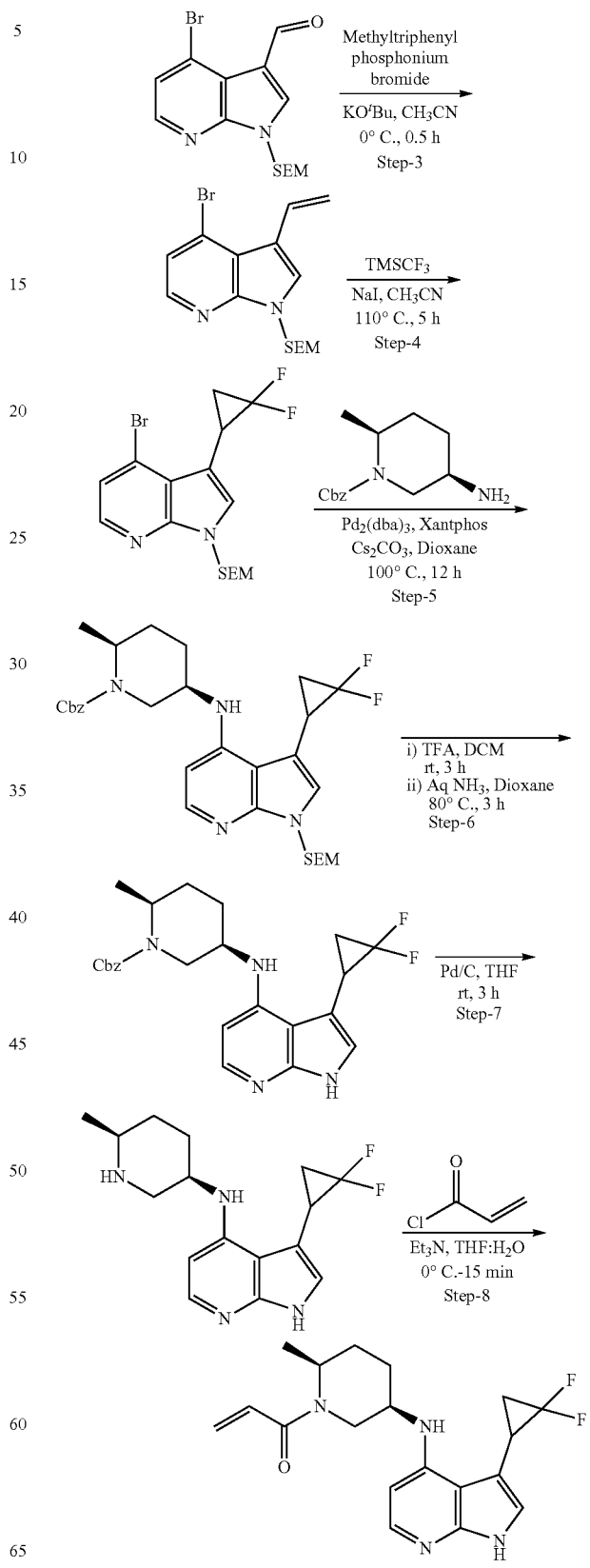

Step 1: Preparation of 4-bromo-1H-pyrrolo[2,3-b]pyridine-3-carbaldehyde

To a stirred solution of 4-bromo-1H-pyrrolo[2,3-b]pyridine (10 g, 15.02 mmol) in water (80 mL), was added hexamethylenetetramine (10.7 g, 76.53 mmol) and acetic acid (20 mL). The reaction mixture was heated at 100° C. for 16 hours. The reaction mixture was cooled to ambient temperature and poured into water. The precipitated solid was filtered, washed with water and dried in vacuum to provide 4-bromo-1H-pyrrolo[2,3-b]pyridine-3-carbaldehyde as a pale yellow solid (9.8 g, 86% yield): MS (ES) m/z 225.0 (M+H).

Step 2: Preparation of 4-bromo-1-((2-(trimethylsilyl)ethoxy)methyl)-1H-pyrrolo[2,3-b]pyridine-3-carbaldehyde

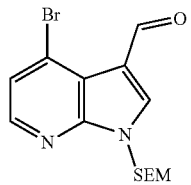 [SMILES: C[Si](C)(C)CCOCn1cc(C=O)c2c(Br)ccnc21]

A suspension of sodium hydride (2.16 g, 45.19 mmol) in N,N-dimethylformamide (80 mL) was treated with 4-bromo-1H-pyrrolo[2,3-b]pyridine-3-carbaldehyde (8 g, 22.59 mmol) at 0° C. The suspension was stirred at ambient temperature for 0.5 hours and then (2-chloromethoxyethyl)trimethylsilane (6 mL, 33.88 mmol) was added at 0° C. The mixture was stirred at ambient temperature for another 2 hours. The reaction mixture was quenched with ice and extracted with ethyl acetate. The organic layer was washed with water, brine, dried over anhydrous sodium sulfate, filtered and concentrated in vacuo. The crude material was purified using flash chromatography (5% ethyl acetate/hexane) to provide 4-bromo-1-((2-(trimethylsilyl)ethoxy)methyl)-1H-pyrrolo[2,3-b]pyridine-3-carbaldehyde as a viscous oil (7 g, 55% yield): MS (ES) m/z 355.0 (M+H).

Step 3: Preparation of 4-bromo-1-((2-(trimethylsilyl)ethoxy)methyl)-3-vinyl-1H-pyrrolo[2,3-b]pyridine

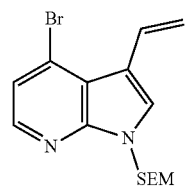 [SMILES: C=Cc1cn(COCC[Si](C)(C)C)c2nccc(Br)c12]

Potassium tert-butoxide (1.89 g, 16.94 mmol) was added to a stirred suspension of methyltriphenylphosphoniumbromide (6 g, 16.94 mmol) in toluene (10 mL) at 0° C. and the resulting mixture was stirred at 0° C. for 0.5 hours. Then 4-bromo-1-((2-(trimethylsilyl)ethoxy)methyl)-1H-pyrrolo[2,3-b]pyridine-3-carbaldehyde (2 g, 5.64 mmol) was added at 0° C. and the resulting mixture was stirred at 0° C. for 0.5 hours. The reaction mixture was quenched with ice and extracted with ethyl acetate. The organic layer was washed with water, brine, dried over anhydrous sodium sulfate, filtered and concentrated in vacuo. The crude material was purified using flash chromatography (10% ethyl acetate/hexane) to provide 4-bromo-1-((2-(trimethylsilyl)ethoxy)methyl)-3-vinyl-1H-pyrrolo[2,3-b]pyridine as a viscous oil (0.68 g, 34% yield): MS (ES) m/z 353.1 (M+H).

Step 4: Preparation of 4-bromo-3-(2,2-difluorocyclopropyl)-1-((2-(trimethylsilyl)ethoxy)methyl)-1H-pyrrolo[2,3-b]pyridine

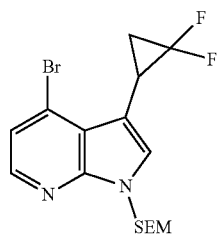 [SMILES: C[Si](C)(C)CCOCn1cc(C2CC2(F)F)c2c(Br)ccnc21]

To a stirred suspension of 5-bromo-1-((2-(trimethylsilyl)ethoxy)methyl)-3-vinyl-1H-pyrrolo[2,3-b]pyridine (0.68 g, 1.93 mmol) and sodium iodide (0.14 g, 0.96 mmol) in acetonitrile (10 mL) was added trimethyl(trifluoromethyl)silane (1.47 mL, 9.65 mmol) and the mixture was heated at 110° C. for 4 hours in a sealed tube. The reaction mixture was cooled to ambient temperature, poured into water and extracted with ethyl acetate. The organic layer was washed with brine, dried over anhydrous sodium sulfate, filtered and concentrated in vacuo. The crude material was purified using flash chromatography (15% ethyl acetate/hexane) to provide 4-bromo-3-(2,2-difluorocyclopropyl)-1-((2-(trimethylsilyl)ethoxy)methyl)-1H-pyrrolo[2,3-b]pyridine as a viscous oil (1.07 g, 80% yield): MS (ES) m/z 403.1 (M+H).

Step 5: Preparation of Benzyl (2S,5R)-5-((3-(2,2-difluorocyclopropyl)-1-((2-(trimethylsilyl)ethoxy)methyl)-1H-pyrrolo[2,3-b]pyridin-4-yl)amino)-2-methylpiperidine-1-carboxylate

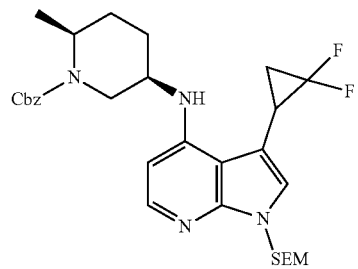

A stirred suspension of 4-bromo-3-(2,2-difluorocyclopropyl)-1-((2-(trimethylsilyl) ethoxy)methyl)-1H-pyrrolo[2,3-b]pyridine (1.07 g, 2.66 mmol), benzyl (2S,5R)-5-amino-2-methylpiperidine-1-carboxylate (0.65 g, 2.66 mmol), cesium carbonate (1.7 g, 5.32 mmol), tris(dibenzylideneacetone)dipalladium (0.24 g, 0.26 mmol) and xantphos (0.3 g, 0.532 mmol) in dioxane (20 mL) was heated at 100° C. for 12 hours. After cooling to ambient temperature, the reaction mixture was filtered through celite, the filtrate was washed with water, brine, dried over anhydrous sodium sulfate, filtered and concentrated in vacuo. The crude material was purified using flash chromatography (50% ethyl acetate/hexane) to provide benzyl (2S,5R)-5-((3-(2,2-difluorocyclopropyl)-1-((2-(trimethylsilyl)ethoxy)methyl)-1H-pyrrolo[2,3-b]pyridin-4-yl)-amino)-2-methylpiperidine-1-carboxylate as colorless oil (0.88 g, 56% yield): MS (ES) m/z 571.3 (M+H).

Step 6: Preparation of Benzyl (2S,5R)-5-((3-(2,2-difluorocyclopropyl)-1H-pyrrolo[2,3-b]pyridin-4-yl)amino)-2-methylpiperidine-1-carboxylate

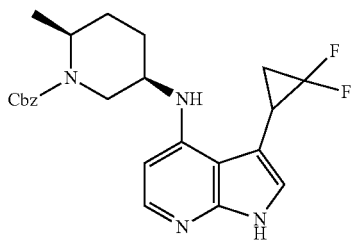

A solution of benzyl (2S,5R)-5-((3-(2,2-difluorocyclopropyl)-1-((2-(trimethylsilyl) ethoxy)methyl)-1H-pyrrolo[2,3-b]pyridin-4-yl)amino)-2-methylpiperidine-1-carboxylate (0.88 g, 1.54 mmol) in dichloromethane:trifluoroacetic acid (5 mL:2 mL) was stirred at ambient temperature for 3 hours. The reaction mixture was concentrated to dryness to provide a gummy compound which was dissolved in dioxane:ammonium hydroxide (5 mL: 10 mL) and stirred at ambient temperature for 3 hours. The reaction mixture was poured into water and extracted with ethyl acetate. The organic layer was washed with brine, dried over anhydrous sodium sulfate, filtered and concentrated in vacuo. The crude material was purified using flash chromatography (75% ethyl acetate/hexane) to provide benzyl (2S,5R)-5-((3-(2,2-difluorocyclopropyl)-1H-pyrrolo[2,3-b]pyridin-4-yl)amino)-2-methylpiperidine-1-carboxylate as a colorless oil (0.61 g, 91% yield): MS (ES) m/z 441.2 (M+H).

Step 7: Preparation of 3-(2,2-difluorocyclopropyl)-N-((3R,6S)-6-methylpiperidin-3-yl)-1H-pyrrolo[2,3-b]pyridin-4-amine

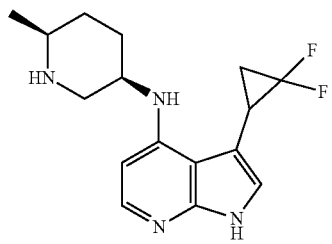

Palladium on carbon (1 g, 10% wet w/w) was added to a stirred solution of benzyl (2S,5R)-5-((3-(2,2-difluorocyclopropyl)-1H-pyrrolo[2,3-b]pyridin-4-yl)amino)-2-methylpiperidine-1-carboxylate (0.61 g, 1.38 mmol) in tetrahydrofuran (20 mL) and the suspension was stirred at ambient temperature for 3 hours under a hydrogen atmosphere. The reaction mixture was filtered through celite and the filtrate was concentrated in vacuo to provide 3-(2,2-difluorocyclopropyl)-N-((3R,6S)-6-methylpiperidin-3-yl)-1H-pyrrolo[2,3-b]pyridin-4-amine as a colorless oil (0.35 g, crude): MS (ES) m/z 307.2 (M+H).

EXAMPLE 72

Step 8: Preparation of 1-((2S,5R)-5-((3-(2,2-difluorocyclopropyl)-1H-pyrrolo[2,3-b]pyridin-4-yl)amino)-2-methylpiperidin-1-yl)prop-2-en-1-one

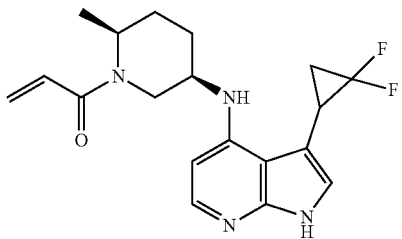

Triethylamine (0.47 mL, 3.43 mmol) was added to a stirred solution of 3-(2,2-difluorocyclopropyl)-N-((3R,6S)-6-methylpiperidin-3-yl)-1H-pyrrolo[2,3-b]pyridin-4-amine (0.35 g, 1.14 mmol) in tetrahydrofuran:water (8.0:2.0 mL) at 0° C. followed by a solution of acryloyl chloride (0.15 g, 1.71 mmol) in tetrahydrofuran (0.5 mL). The solution was stirred for 15 minutes. The reaction mixture was quenched with saturated sodium bicarbonate solution and extracted with ethyl acetate. The organic layer was washed with brine, dried over anhydrous sodium sulfate, filtered and concentrated in vacuo. The crude material was purified using flash chromatography (4% methanol/dichloromethane) to provide 1-((2S,5R)-5-((3-(2,2-difluorocyclopropyl)-1H-pyrrolo[2,3-b]pyridin-4-yl)amino)-2-methylpiperidin-1-yl)prop-2-en-1-one as a white solid (0.08 g, 20% yield).

The stereoisomers of 1-((2S,5R)-5-((3-(2,2-difluorocyclopropyl)-1H-pyrrolo[2,3-b]pyridin-4-yl)amino)-2-methylpiperidin-1-yl)prop-2-en-1-one were separated by chiral Prep HPLC.

Column: CHIRALPAK IA (100 mm×4.6 mm×3 mic)
Mobile phase: n-hexane:IPA with 0.1% DEA (50:50)
Flow rate: 1.0 mL/min.

EXAMPLE 73

1-((2S,5R)-5-((3-((R)-2,2-difluorocyclopropyl)-1H-pyrrolo[2,3-b]pyridin-4-yl)amino)-2-methylpiperidin-1-yl)prop-2-en-1-one (Stereoisomer 1, Absolute Configuration of Difluorocyclopropyl Group Assigned Provisionally)

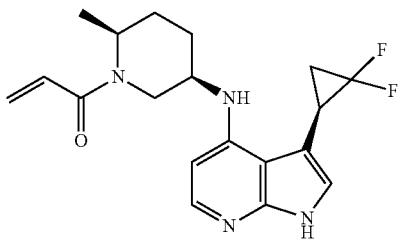 [SMILES: C=CC(=O)N1C[C@H](Nc2ccnc3[nH]cc([C@H]4CC4(F)F)c23)CC[C@@H]1C]

Purified by chiral HPLC (stereoisomer 1), isolated as a white solid (0.03 g, 7% yield): $^1$H NMR (400 MHz, DMSO-d$_6$) δ 11.15 (s, 1H), 7.83 (s, 1H), 6.98 (s, 1H), 6.77 (br s, 1H), 6.24 (s, 1H), 6.08 (d, J=16.0 Hz, 1H), 5.67 (d, J=10.0 Hz, 1H), 5.23 (br s, 1H), 4.50-4.65 (m, 2H), 4.36 (br s, 1H), 4.01 (br s, 1H), 1.65-1.94 (m, 6H), 1.21 (br s, 4H); MS (ES) m/z 361.1 (M+H)$^+$. Retention time: 2.659 min.

EXAMPLE 74

1-((2S,5R)-5-((3-((S)-2,2-difluorocyclopropyl)-1H-pyrrolo[2,3-b]pyridin-4-yl)amino)-2-methylpiperidin-1-yl)prop-2-en-1-one (Stereoisomer 2 Absolute Configuration of difluoro-cyclopropyl Group Assigned Provisionally)

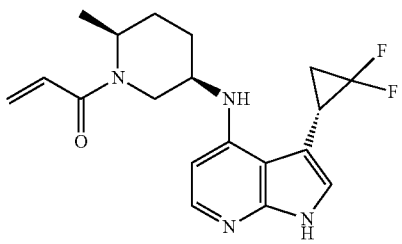 [SMILES: C=CC(=O)N1C[C@H](Nc2ccnc3[nH]cc([C@@H]4CC4(F)F)c23)CC[C@@H]1C]

Purified by chiral HPLC (stereoisomer 2), isolated as a white solid (0.01 g, 3.0% yield): $^1$H NMR (400 MHz, DMSO-d$_6$) δ 11.16 (s, 1H), 7.82 (d, J=6.0 Hz, 1H), 6.97 (s, 1H), 6.77 (br s, 1H), 6.24 (d, J=5.6 Hz, 1H), 6.09 (br s, 1H), 5.66 (d, J=10.4 Hz, 1H), 5.26 (d, J=8.4 Hz, 1H), 4.50-4.65 (m, 3H), 4.36 (br s, 2H), 1.93-1.96 (m, 2H), 1.64-1.74 (m, 4H), 1.21 (br s, 4H); MS (ES) m/z 361.1 (M+H)$^+$. Retention time: 4.054 min.

EXAMPLE 75, 76 AND 77

Preparation of 1-((2S,5R)-5-((3-(2-(methoxymethyl)cyclopropyl)-1H-pyrrolo[2,3-b]pyridin-4-yl)amino)-2-methylpiperidin-1-yl)prop-2-en-1-one, 1-((2S,5R)-5-((3-((1S,2S)-2-(methoxymethyl)cyclopropyl)-1H-pyrrolo[2,3-b]pyridin-4-yl)amino)-2-methylpiperidin-1-yl)prop-2-en-1-one, and 1-((2S,5R)-5-((3-((1R,2R)-2-(methoxymethyl)cyclopropyl)-1H-pyrrolo[2,3-b]pyridin-4-yl)amino)-2-methylpiperidin-1-yl)prop-2-en-1-one

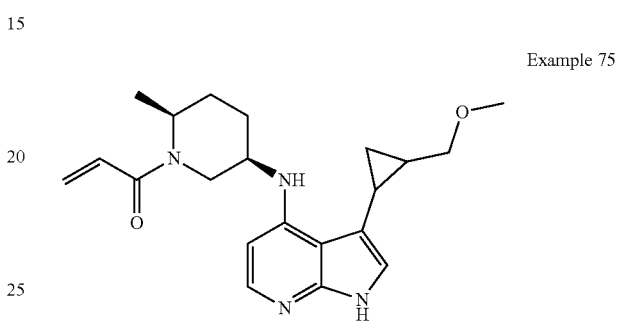

Example 75

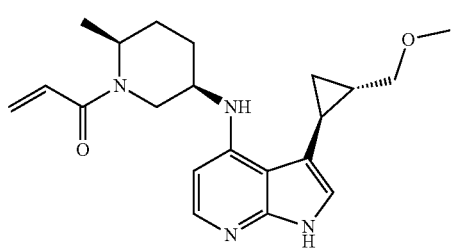

Example 76

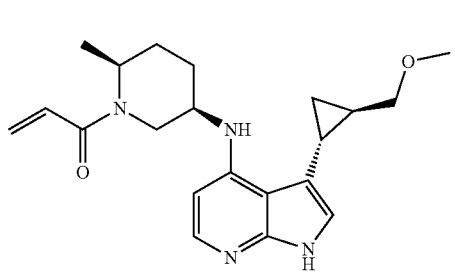

Example 77

The title compounds were prepared by the methods described in Scheme 30.

Scheme 30.
Synthesis of 1-((2S,5R)-5-((3-((1S,2S)-2-(methoxymethyl)cyclopropyl)-1H-pyrrolo[2,3-b]pyridin-4-yl)amino)-2-methylpiperidin-1-yl)prop-2-en-1-one and 1-((2S,5R)-5-((3-((1R,2R)-2-(methoxymethyl)cyclopropyl)-1H-pyrrolo[2,3-b]pyridin-4-yl)amino)-2-methylpiperidin-1-yl)prop-2-en-1-one.

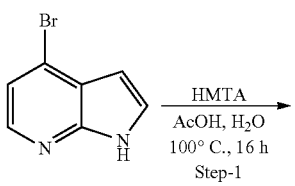

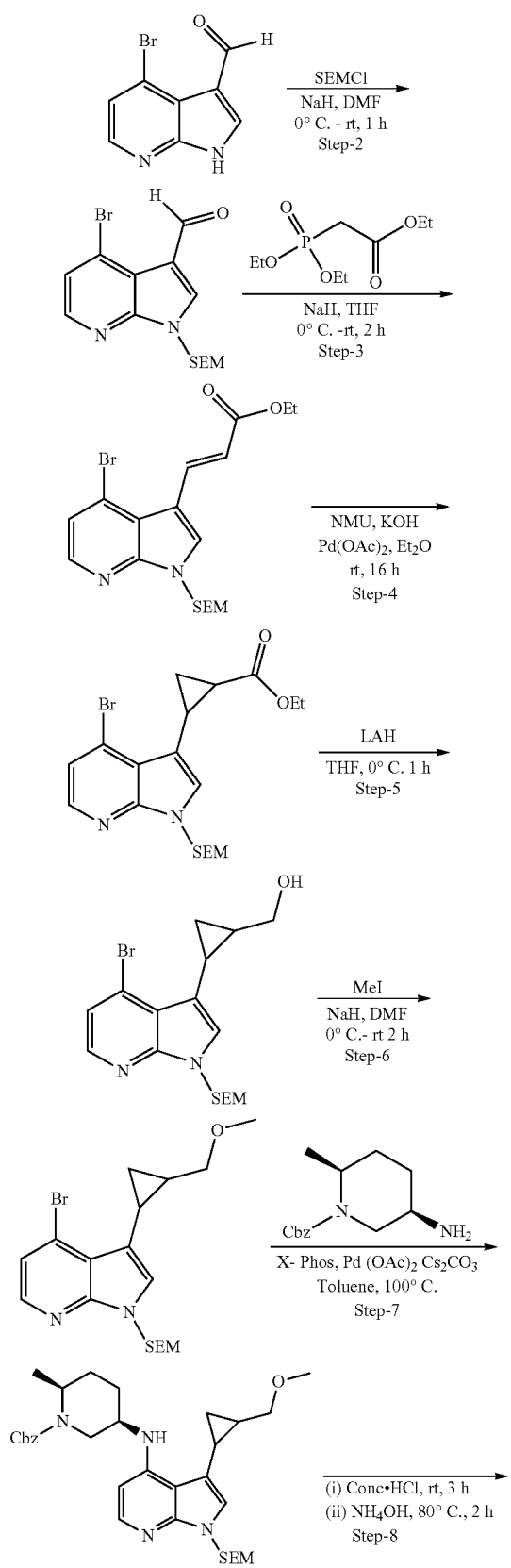
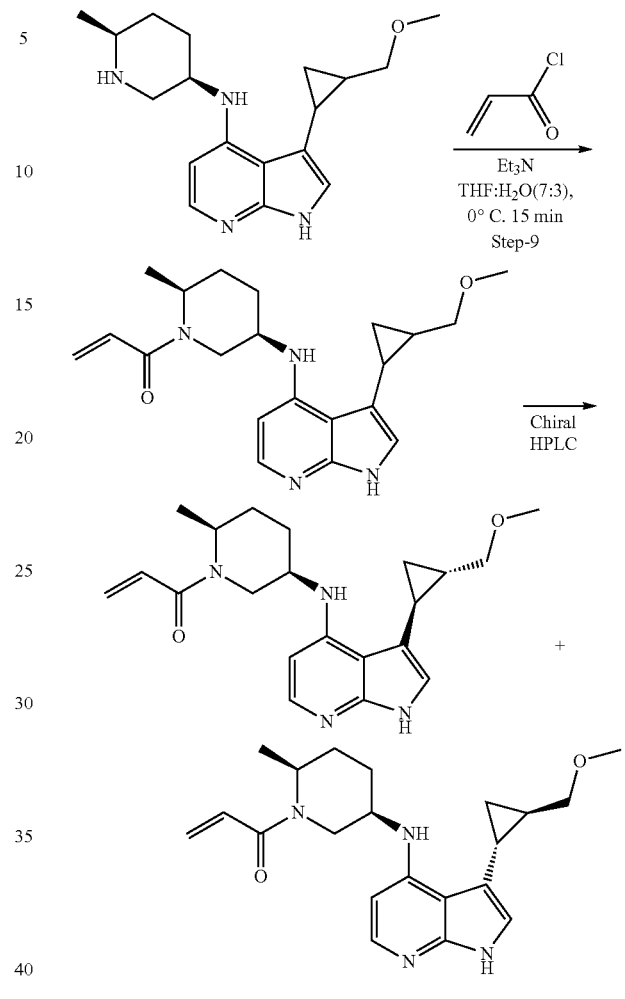

Step 1: Preparation of 4-bromo-1H-pyrrolo[2,3-b]pyridine-3-carbaldehyde

A solution of 4-bromo-1H-pyrrolo[2,3-b]pyridine (10 g, 50.75 mmol) in acetic acid:water (25 mL:50 mL) was treated with hexamethylenetetramine (10.6 g, 76.12 mmol) at 0° C. and then the reaction mixture was heated at 100° C. for 16 hours. The reaction was cooled to ambient temperature and poured in ice water. The resulting solid was filtered, washed with water, n-hexane, diethyl ether and dried in vacuo to provide 4-bromo-1H-pyrrolo[2,3-b]pyridine-3-carbaldehyde as an off-white solid (7.5 g, 65% yield): MS (ES) m/z 226.9 (M+H).

Step-2: Preparation of 4-bromo-1-((2-(trimethylsilyl)ethoxy)methyl)-1H-pyrrolo[2,3-b]pyridine-3-carbaldehyde

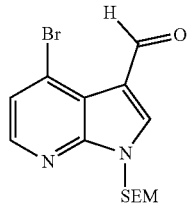 [SMILES: C[Si](C)(C)CCOCn1cc(C=O)c2c(Br)ccnc21]

A solution of 4-bromo-1H-pyrrolo[2,3-b]pyridine-3-carbaldehyde (7.0 g, 31.10 mmol) in N,N-dimethylformamide (70 mL) was added dropwise to a stirred suspension of sodium hydride (60%, 1.62 g, 40.43 mmol) in N,N-dimethylformamide (35.0 mL) at 0° C. After stirring the mixture for 0.5 hours, (2-chloromethoxyethyl)trimethylsilane (7.2 mL, 40.43 mmol) was added at 0° C. and the resulting mixture was stirred at ambient temperature for 1 hour. The reaction mixture was quenched with ice and then extracted into ethyl acetate. The organic layer was washed with water, brine, dried over anhydrous sodium sulfate, filtered and concentrated in vacuo. The crude material was washed with n-pentane to provide 4-bromo-1-((2-(trimethylsilyl)ethoxy)methyl)-1H-pyrrolo[2,3-b]pyridine-3-carbaldehyde as an off-white solid (8.0 g, 73% yield): MS (ES) m/z 355.0 (M+H).

Step 3: Preparation of Ethyl (E)-3-(4-bromo-1-((2-(trimethylsilyl)ethoxy)methyl)-1H-pyrrolo[2,3-b]pyridin-3-yl)acrylate

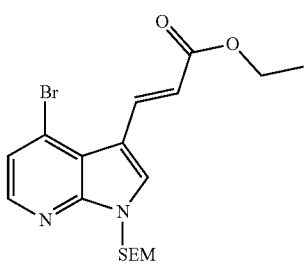 [SMILES: CCOC(=O)/C=C/c1cn(COCC[Si](C)(C)C)c2nccc(Br)c12]

Ethyl 2-(diethoxyphosphoryl)acetate (3.76 mL, 18.99 mmol) was added to a stirred suspension of sodium hydride (0.76 g, 18.99 mmol) in tetrahydrofuran (20 mL) at 0° C. and the mixture stirred for 1 hour at that temperature. A solution of 4-bromo-1-((2-(trimethylsilyl)ethoxy)methyl)-1H-pyrrolo[2,3-b]pyridine-3-carbaldehyde (4.5 g, 12.66 mmol) in tetrahydrofuran (20 mL) was then added at 0° C. and the mixture was stirred at ambient temperature for 2 hours. The reaction was quenched with ice water and extracted into ethyl acetate. The combined organic layers were washed with brine, dried over anhydrous sodium sulfate, filtered and concentrated in vacuo. The crude material was purified using flash chromatography (15% ethyl acetate/hexane) to provide ethyl (E)-3-(4-bromo-1-((2-(trimethylsilyl)ethoxy)methyl)-1H-pyrrolo[2,3-b]pyridin-3-yl)acrylate as a white solid (4.6 g, 85% yield): MS (ES) m/z 425.0 (M+H).

Step 4: Preparation of Ethyl 2-(4-bromo-1-((2-(trimethylsilyl)ethoxy)methyl)-1H-pyrrolo[2,3-b]pyridin-3-yl)cyclopropane-1-carboxylate

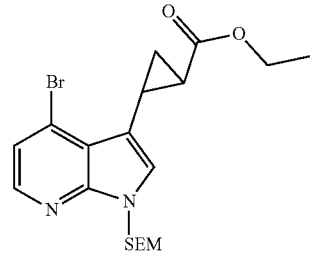 [SMILES: CCOC(=O)C1CC1c1cn(COCC[Si](C)(C)C)c2nccc(Br)c12]

A solution of ethyl (E)-3-(4-bromo-1-((2-(trimethylsilyl)ethoxy)methyl)-1H-pyrrolo[2,3-b]pyridin-3-yl)acrylate (10.0 g, 23.47 mmol) in dichloromethane (150 mL) was treated with palladium(II) acetate (1.0 g, 4.69 mmol) at 0° C. and the mixture stirred for 0.5 hour. Freshly prepared diazomethane in diethyl ether (24.6 g, 586.7 mmol) was added at 0° C. and the mixture was stirred at ambient temperature for 16 hours. The reaction was filtered through celite and the filtrate was washed with water and brine. The solution was dried over anhydrous sodium sulfate, filtered and concentrated in vacuo. The crude material was purified using flash chromatography (5% ethyl acetate/hexane) to provide ethyl 2-(4-bromo-1-((2-(trimethylsilyl)ethoxy)methyl)-1H-pyrrolo[2,3-b]pyridin-3-yl)cyclopropane-1-carboxylate as a pale yellow oil (5.2 g, 50% yield): MS (ES) m/z 439.0 (M+H).

Step 5: Preparation of (2-(4-bromo-1-((2-(trimethylsilyl)ethoxy)methyl)-1H-pyrrolo[2,3-b]pyridin-3-yl)cyclopropyl)methanol

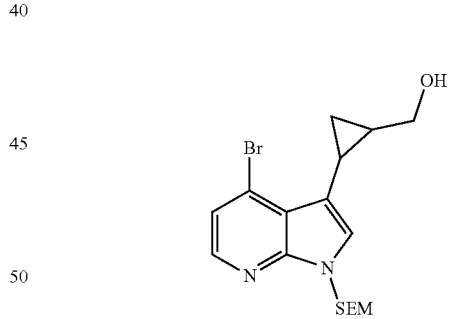

Lithium aluminum hydride (17.0 mL, 17.06 mmol, 1M in tetrahydrofuran) was added to a stirred solution of ethyl 2-(4-bromo-1-((2-(trimethylsilyl)ethoxy)methyl)-1H-pyrrolo[2,3-b]pyridin-3-yl)cyclopropane-1-carboxylate (3.0 g, 6.82 mmol) in tetrahydrofuran (170 mL) at 0° C. After 1 hour the reaction was quenched with saturated ammonium chloride and extracted with ethyl acetate. The organic layer was washed with brine, dried over anhydrous sodium sulfate, filtered and concentrated in vacuo. The crude material was purified using flash chromatography (15% ethyl acetate/hexane) to provide (2-(4-bromo-1-((2-(trimethylsilyl)ethoxy)methyl)-1H-pyrrolo[2,3-b]pyridin-3-yl)cyclopropyl)methanol as a thick yellow mass (1.5 g, 55% yield): MS (ES) m/z 443.1 (M+HCO$_2$H).

Step 6: Preparation of 4-bromo-3-(2-(methoxymethyl)cyclopropyl)-1-((2-(trimethylsilyl)ethoxy)methyl)-1H-pyrrolo[2,3-b]pyridine

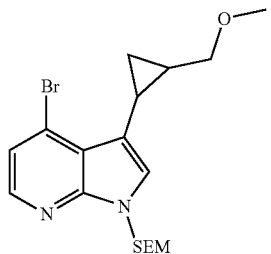 [SMILES: COCC1CC1c1cn(COCC[Si](C)(C)C)c2nccc(Br)c12]

A suspension of sodium hydride (0.23 g, 5.66 mmol) in N,N-dimethylformamide (15 mL) was treated with (2-(4-bromo-1-((2-(trimethylsilyl)ethoxy)methyl)-1H-pyrrolo[2,3-b]pyridin-3-yl)cyclopropyl)methanol (1.5 g, 3.77 mmol) at 0° C. and the mixture stirred for 30 minutes. Methyl iodide (1.17 mL, 18.87 mmol) was added at 0° C. and the mixture was stirred at ambient temperature for 2 hours. The reaction was quenched with ice water and extracted with ethyl acetate. The organic layer was washed with brine, dried over anhydrous sodium sulfate, filtered and concentrated in vacuo to provide 4-bromo-3-(2-(methoxymethyl)cyclopropyl)-1-((2-(trimethylsilyl)ethoxy)methyl)-1H-pyrrolo[2,3-b]pyridine as a thick yellow syrup (1.4 g, 90% yield): MS (ES) m/z 411.1 (M+H).

Step 7: Preparation of Benzyl (2S,5R)-5-((3-(2-(methoxymethyl)cyclopropyl)-1-((2-(trimethylsilyl)ethoxy)methyl)-1H-pyrrolo[2,3-b]pyridin-4-yl)amino)-2-methylpiperidine-1-carboxylate

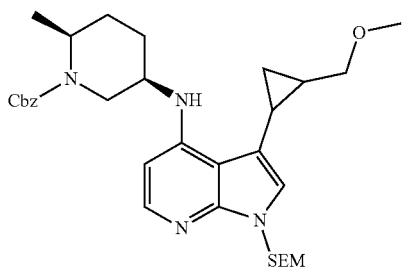

Benzyl (2S,5R)-5-amino-2-methylpiperidine-1-carboxylate (0.45 g, 1.82 mmol) and cesium carbonate (1.18 g, 3.64 mmol) were added to a mixture of 4-bromo-3-(2-(methoxymethyl)cyclopropyl)-1-((2-(trimethylsilyl)ethoxy)methyl)-1H-pyrrolo[2,3-b]pyridine (0.50 g, 1.21 mmol) in toluene (15 mL) and the mixture was degassed by bubbling argon for 5 minutes. Then 4,5-bis(diphenylphosphino)-9,9-dimethylxanthene (0.11 g, 0.24 mmol) and palladium(II) acetate (0.054 g, 0.24 mmol) were added and the mixture was heated at 110° C. for 16 hours in a sealed tube. After cooling to ambient temperature, the reaction mixture was filtered through celite and washed with ethyl acetate. The organic layer was washed with water, saturated sodium bicarbonate solution and brine, dried over anhydrous sodium sulphate, filtered and concentrated in vacuo. The crude material was purified using flash chromatography (20% ethyl acetate/hexane) to provide benzyl (2S,5R)-5-((3-(2-(methoxymethyl)cyclopropyl)-1-((2-(trimethylsilyl)ethoxy)methyl)-1H-pyrrolo[2,3-b]pyridin-4-yl)amino)-2-methylpiperidine-1-carboxylate as a thick yellow syrup (0.32 g, 45% yield): MS (ES) m/z 579.5 (M+H).

Step 8: Preparation of 3-(2-(methoxymethyl)cyclopropyl)-N-((3R,6S)-6-methylpiperidin-3-yl)-1H-pyrrolo[2,3-b]pyridin-4-amine

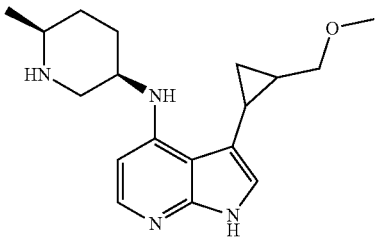

A solution of benzyl (2S,5R)-5-((3-(2-(methoxymethyl)cyclopropyl)-1-((2-(trimethylsilyl)ethoxy)methyl)-1H-pyrrolo[2,3-b]pyridin-4-yl)amino)-2-methylpiperidine-1-carboxylate (0.5 g, 0.86 mmol) in concentrated hydrochloric acid (5 mL) was stirred at room temperature for 3 hours. The reaction mixture was concentrated in vacuo and residue was treated with aqueous ammonia (10 mL). The mixture was then stirred at 80° C. for 2 hours. The reaction mixture was cooled to ambient temperature and the resulting solid isolated by filtration. The solid was washed with water, diethyl ether and n-pentane to obtain 3-(2-(methoxymethyl)-cyclopropyl)-N-((3R,6S)-6-methylpiperidin-3-yl)-1H-pyrrolo[2,3-b]pyridin-4-amine (0.17 g, 62% yield) as a brown solid: MS (ES) m/z 315.2 (M+H).

EXAMPLE 75

Step 9: Preparation of 1-((2S,5R)-5-((3-(2-(methoxymethyl)cyclopropyl)-1H-pyrrolo[2,3-b]pyridin-4-yl)amino)-2-methylpiperidin-1-yl)prop-2-en-1-one

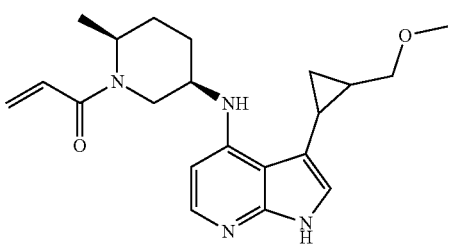 [SMILES: C=CC(=O)N1C[C@H](Nc2ccnc3[nH]cc(C4CC4COC)c23)CC[C@@H]1C]

A solution of triethylamine (0.13 mL, 0.95 mmol) and acryloyl chloride (0.82 mL, 0.41 mmol) in tetrahydrofuran (5 mL) was added to a stirred solution of 3-(2-(methoxymethyl)cyclopropyl)-N-((3R,6S)-6-methylpiperidin-3-yl)-1H-pyrrolo[2,3-b]pyridin-4-amine (0.10 g, 0.31 mmol) in a mixture of tetrahydrofuran:water (7 mL: 3 mL) at 0° C. and the resulting mixture was stirred at same temperature for 15 minutes. The reaction mixture was quenched with saturated sodium bicarbonate, diluted with water, extracted with ethyl acetate and washed with brine. The organic layer was dried over anhydrous sodium sulphate, filtered and concentrated in vacuo. The crude material was purified using flash chromatography (4% methanol/dichloromethane) followed by purification using prep HPLC to provide 1-((2S,5R)-5-((3-(2-(methoxymethyl)cyclopropyl)-1H-pyrrolo[2,3-b]pyridin-4-yl)amino)-2-methylpiperidin-1-yl)prop-2-en-1-one as a white solid (0.03 g, 21% yield): MS (ES) m/z 369.3 (M+H).

The stereoisomers of 1-((2S,5R)-5-((3-(2-(methoxymethyl)cyclopropyl)-1H-pyrrolo[2,3-b]pyridin-4-yl)amino)-2-methylpiperidin-1-yl)prop-2-en-1-one were separated by chiral chromatography.

HPLC Conditions:
Column: Inertsil ODS 3V (250 mm×4.6 mm×5 mic)
Mobile phase (A): 0.1% Ammonia in water
Mobile phase (B): ACN
Flow rate: 1.0 mL/min
T/% B: 0/10, 12/80, 25/90, 27/10, 30/10

EXAMPLE 76

1-((2S,5R)-5-((3-((1S,2S)-2-(methoxymethyl)cyclopropyl)-1H-pyrrolo[2,3-b]pyridin-4-yl)amino)-2-methylpiperidin-1-yl)prop-2-en-1-one (Stereoisomer 1, Absolute Configuration of Cyclopropyl Group Assigned Provisionally)

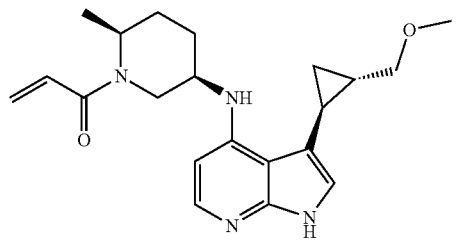 [SMILES: C=CC(=O)N1C[C@H](Nc2ccnc3[nH]cc([C@H]4C[C@@H]4COC)c23)CC[C@@H]1C]

Purified by chiral HPLC (stereoisomer 1), isolated as a white solid (0.002 g, 4% yield): $^1$H NMR (400 MHz, DMSO-$d_6$ at 80° C.) δ 10.66 (s, 1H), 7.78 (s, 1H), 6.58-6.82 (m, 1H), 6.20 (s, 1H), 6.00-6.15 (m, 1H), 5.60-5.71 (m, 1H), 5.45-5.58 (m, 1H), 5.25-5.41 (s, 1H), 4.32-4.62 (m, 2H), 3.80-3.92 (m, 1H), 3.39-3.65 (m, 3H), 1.95-2.10 (m, 3H), 1.65-1.90 (m, 3H), 1.18-1.35 (m, 6H), 0.95-1.05 (m, 1H), 0.75-0.90 (m, 1H); MS (ES) m/z 369.2 (M+H). Retention time: 3.482 min.

EXAMPLE 77

1-((2S,5R)-5-((3-((1R,2R)-2-(methoxymethyl)cyclopropyl)-1H-pyrrolo[2,3-b]pyridin-4-yl)amino)-2-methylpiperidin-1-yl)prop-2-en-1-one (Stereoisomer 2 Absolute Configuration of Cyclopropyl Group Assigned Provisionally)

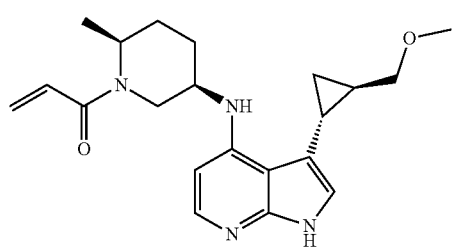 [SMILES: C=CC(=O)N1C[C@H](Nc2ccnc3[nH]cc([C@@H]4C[C@H]4COC)c23)CC[C@@H]1C]

Purified by chiral HPLC (stereoisomer 2), isolated as a white solid (0.008 g, 7% yield): $^1$H NMR (400 MHz, DMSO-$d_6$ at 80° C.) δ 10.72 (s, 1H), 7.78 (s, 1H), 6.74 (s, 2H), 6.15-6.25 (m, 1H), 6.00-6.15 (m, 1H), 5.60-5.75 (m, 1H), 5.50-5.60 (s, 1H), 4.32-4.62 (m, 2H), 3.65-3.70 (m, 1H), 3.31-3.45 (m, 3H), 1.95-2.10 (m, 3H), 1.62-1.85 (m, 3H), 1.15-1.35 (m, 6H), 0.95-1.05 (m, 1H), 0.60-0.75 (m, 1H); MS (ES) m/z 369.2 (M+H). Retention time 3.969 min.

EXAMPLE 78, 79 AND 80

Preparation of 1-((3R)-3-((5-(6,6-difluorobicyclo[3.1.0]hexan-1-yl)-7H-pyrrolo[2,3-d]pyrimidin-4-yl)amino)piperidin-1-yl)prop-2-en-1-one, 1-((R)-3-((5-((1R,5S)-6,6-difluorobicyclo[3.1.0]hexan-1-yl)-7H-pyrrolo[2,3-d]pyrimidin-4-yl)amino)piperidin-1-yl)prop-2-en-1-one, and 1-((R)-3-((5-((1S,5R)-6,6-difluorobicyclo[3.1.0]hexan-1-yl)-7H-pyrrolo[2,3-d]pyrimidin-4-yl)amino)piperidin-1-yl)prop-2-en-1-one

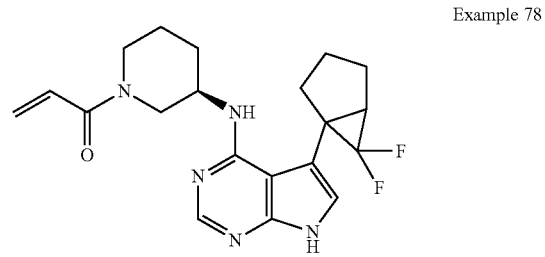

Example 78

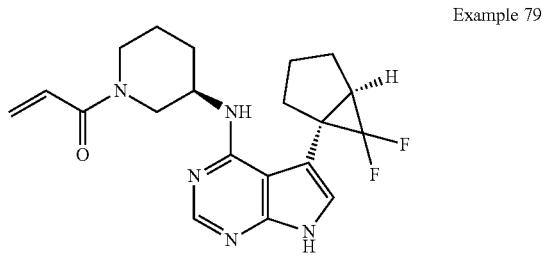

Example 79

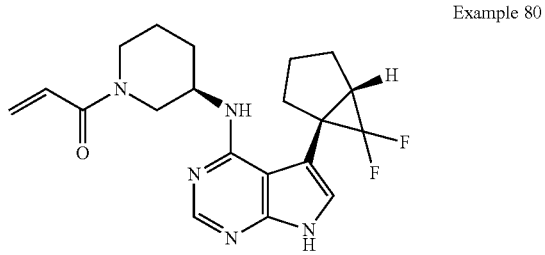

Example 80

The title compounds were prepared by the methods described in Scheme 31.
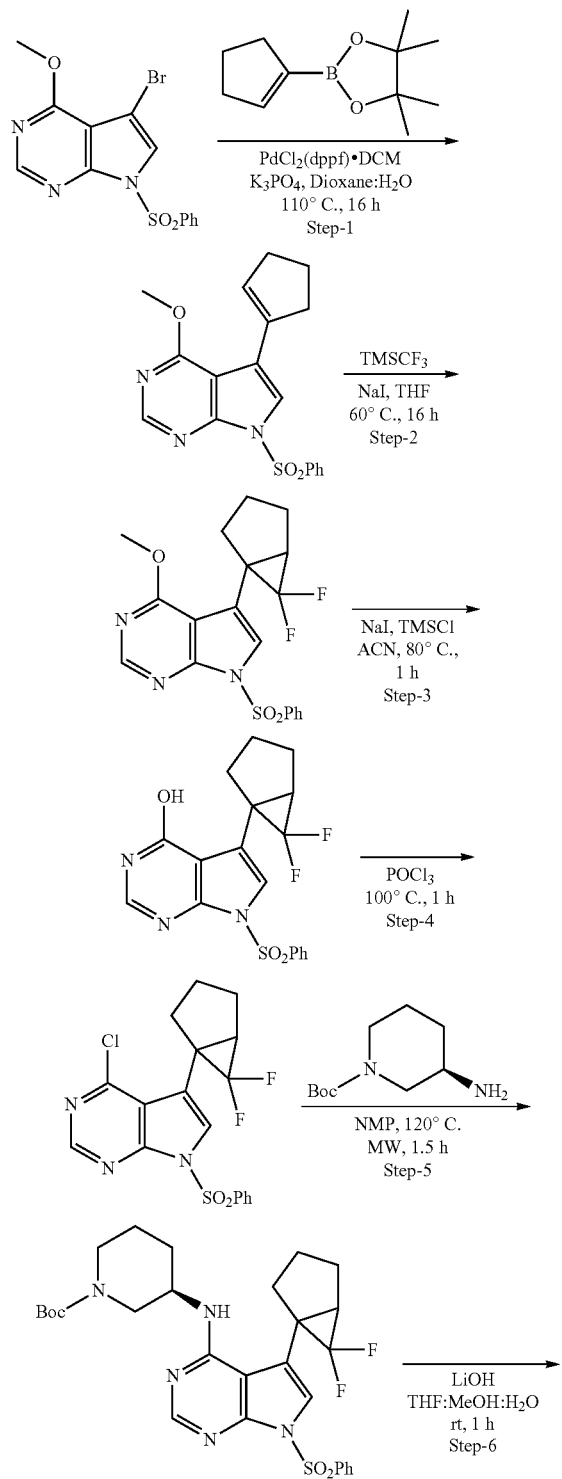
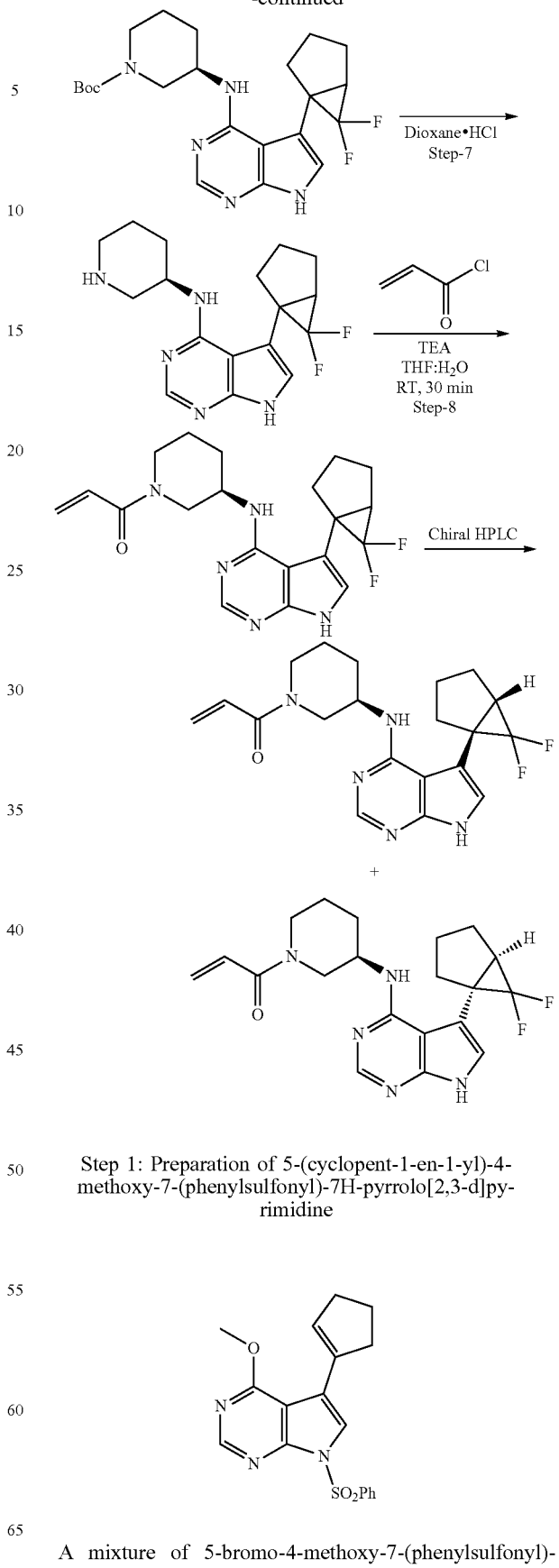
Step 1: Preparation of 5-(cyclopent-1-en-1-yl)-4-methoxy-7-(phenylsulfonyl)-7H-pyrrolo[2,3-d]pyrimidine
A mixture of 5-bromo-4-methoxy-7-(phenylsulfonyl)-7H-pyrrolo[2,3-d]pyrimidine (2.0 g, 5.47 mmol), 4,4,5,5- tetramethyl-2-(2-methylprop-1-en-1-yl)-1,3,2-dioxaborolane (2.12 g, 10.92 mmol), [1,1'-bis(diphenylphosphino)ferrocene]palladium(II) dichloride·dichloromethane complex (0.44 g, 0.05 mmol), and potassium carbonate (1.5 g, 16.39 mmol) in dioxane:water (20 mL:5 mL) was heated at 110° C. for 16 hours. The reaction mixture was cooled to ambient temperature, diluted with ethyl acetate and washed with water. The organic layer was washed with brine, dried over anhydrous sodium sulfate, filtered and concentrated in vacuo. The crude material was purified by flash chromatography (12% ethyl acetate/hexane) to provide 5-(cyclopent-1-en-1-yl)-4-methoxy-7-(phenylsulfonyl)-7H-pyrrolo[2,3-d]pyrimidine as an off-white solid (1.54 g, 46.8% yield): MS (ES) m/z 356.0 (M+H).

Step 2: Preparation of 5-(6,6-difluorobicyclo[3.1.0]hexan-1-yl)-4-methoxy-7-(phenylsulfonyl)-7H-pyrrolo[2,3-d]pyrimidine

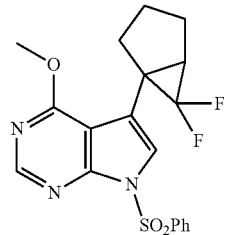

Trimethyl(trifluoromethyl)silane (2 mL, 14.05 mmol) was added to a stirred suspension of 5-(cyclopent-1-en-1-yl)-4-methoxy-7-(phenylsulfonyl)-7H-pyrrolo[2,3-d]pyrimidine (1.0 g, 2.81 mmol) and sodium iodide (0.28 g, 1.40 mmol) in tetrahydrofuran (10 mL) and the mixture was heated at 80° C. for 6 hours in a sealed tube. The reaction mixture was cooled to ambient temperature, the reaction mixture was poured into water and extracted with ethyl acetate. The organic layer was washed with brine, dried over anhydrous sodium sulfate, filtered and concentrated in vacuo. The crude material was purified using flash chromatography (18% ethyl acetate/hexane) to provide 5-(6,6-difluorobicyclo[3.1.0]hexan-1-yl)-4-methoxy-7-(phenyl sulfonyl)-7H-pyrrolo[2,3-d]pyrimidine as an off-white solid (1.05 g, 92%): MS (ES) m/z 406.0 (M+H).

Step 3: Preparation of 5-(6,6-difluorobicyclo[3.1.0]hexan-1-yl)-7-(phenylsulfonyl)-7H-pyrrolo[2,3-d]pyrimidin-4-ol

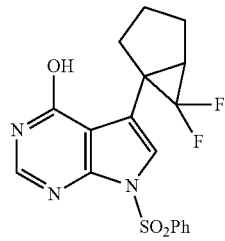

Sodium iodide (0.39 g, 2.58 mmol) and chlorotrimethylsilane (0.33 mL, 2.58 mmol) were added to a solution of 5-(6,6-difluorobicyclo[3.1.0]hexan-1-yl)-4-methoxy-7-(phenylsulfonyl)-7H-pyrrolo[2,3-d]pyrimidine (1.05 g, 2.58 mmol) in acetonitrile (14 mL) and the mixture was heated at 80° C. for 1 hour in a sealed tube. The reaction mixture was cooled to ambient temperature and then poured into water and extracted with ethyl acetate. The organic layer was washed with brine, dried over anhydrous sodium sulfate, filtered and concentrated in vacuo. The crude product was triturated with n-hexane to provide 5-(6,6-difluorobicyclo[3.1.0]hexan-1-yl)-7-(phenylsulfonyl)-7H-pyrrolo[2,3-d]pyrimidin-4-ol as an off-white solid (1 g, crude): MS (ES) m/z 392.0 (M+H).

Step 4: Preparation of 4-chloro-5-(6,6-difluorobicyclo[3.1.0]hexan-1-yl)-7-(phenylsulfonyl)-7H-pyrrolo[2,3-d]pyrimidine

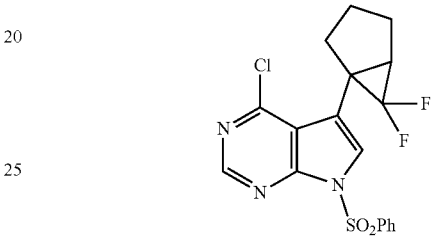

A solution of 5-(6,6-difluorobicyclo[3.1.0]hexan-1-yl)-7-(phenylsulfonyl)-7H-pyrrolo[2,3-d]pyrimidin-4-ol (1.0 g, 2.55 mmol) in phosphoryl chloride (8 mL) was stirred at 100° C. for 1 hour. After cooling, the reaction mixture was concentrated in vacuo to remove excess phosphoryl chloride and the residue was dissolved in ethyl acetate. The organic layer was washed with water, saturated sodium bicarbonate and brine. The solution was filtered and concentrated in vacuo. The crude product was triturated with n-hexane to provide 4-chloro-5-(6,6-difluorobicyclo[3.1.0]hexan-1-yl)-7-(phenylsulfonyl)-7H-pyrrolo[2,3-d]pyrimidine as a light brown solid (0.93 g, crude): MS (ES) m/z 410.0 (M+H).

Step 5: Preparation of tert-butyl (3R)-3-((5-(6,6-difluorobicyclo[3.1.0]hexan-1-yl)-7-(phenylsulfonyl)-7H-pyrrolo[2,3-d]pyrimidin-4-yl)amino)piperidine-1-carboxylate

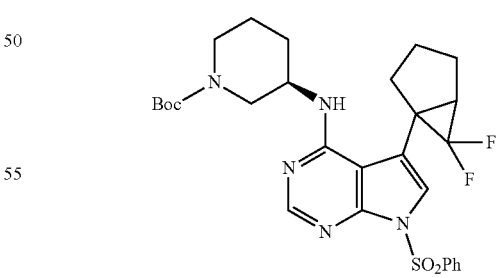

A solution of 4-chloro-5-(6,6-difluorobicyclo[3.1.0]hexan-1-yl)-7-(phenylsulfonyl)-7H-pyrrolo[2,3-d]pyrimidine (0.05 g, 0.12 mmol) in NMP (1 mL) was treated with tert-butyl (R)-3-aminopiperidine-1-carboxylate (0.03 g, 0.15 mmol) and the mixture was subjected to microwave irradiation at 120° C. for 1 hour. The reaction mixture was cooled to ambient temperature, concentrated in vacuo and the

267 residue was dissolved in ethyl acetate. The organic layer was washed with water, brine, dried over anhydrous sodium sulfate, filtered and concentrated in vacuo to provide tert-butyl (3R)-3-((5-(6,6-difluorobicyclo[3.1.0]hexan-1-yl)-7-(phenylsulfonyl)-7H-pyrrolo[2,3-d]pyrimidin-4-yl)amino) piperidine-1-carboxylate as a viscous liquid (0.07 g, crude): MS (ES) m/z 574.2 (M+H).

Step 6: Preparation of tert-butyl (3R)-3-((5-(6,6-difluorobicyclo[3.1.0]hexan-1-yl)-7H-pyrrolo[2,3-d]pyrimidin-4-yl)amino)piperidine-1-carboxylate

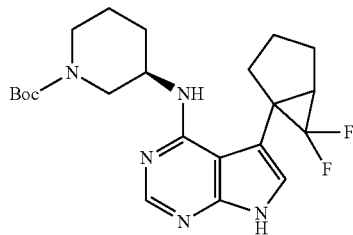 [SMILES: CC(C)(C)OC(=O)N1CCC[C@@H](Nc2ncnc3[nH]cc(C45CCCC4C5(F)F)c23)C1]

Lithium hydroxide monohydrate (0.12 g, 5.08 mmol) was added to a solution tert-butyl (3R)-3-((5-(6,6-difluorobicyclo[3.1.0]hexan-1-yl)-7-(phenylsulfonyl)-7H-pyrrolo[2,3-d]pyrimidin-4-yl)amino)piperidine-1-carboxylate (0.2 g, 2.54 mmol) in tetrahydrofuran:methanol:water (3:1:1 mL) and the mixture was stirred at ambient temperature for 1 hour. The reaction was poured into ice water and extracted with ethyl acetate. The organic layer was washed with water, brine, dried over anhydrous sodium sulfate, filtered and concentrated in vacuo to provide tert-butyl (3R)-3-((5-(6,6-difluorobicyclo[3.1.0]hexan-1-yl)-7H-pyrrolo[2,3-d]pyrimidin-4-yl)amino)piperidine-1-carboxylate as a viscous liquid (0.1 g, crude): MS (ES) m/z 434.2 (M+H).

Step 7: Preparation of 5-(6,6-difluorobicyclo[3.1.0] hexan-1-yl)-N—((R)-piperidin-3-yl)-7H-pyrrolo[2,3-d]pyrimidin-4-amine

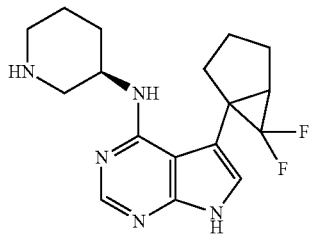 [SMILES: FC1(F)C2CCCC21c1c[nH]c2ncnc(N[C@@H]3CCCNC3)c12]

A solution of hydrogen chloride (1 mL, 4 M in dioxane) was added to a solution of tert-butyl (3R)-3-((5-(6,6-difluorobicyclo[3.1.0]hexan-1-yl)-7H-pyrrolo[2,3-d]pyrimidin-4-yl)amino)piperidine-1-carboxylate (0.1 g, 0.23 mmol) in dichloromethane (1 mL) and the mixture was stirred at ambient temperature for 2 hours. The reaction mixture was concentrated in vacuo and the residue was triturated with diethyl ether to provide 5-(6,6-difluorobicyclo[3.1.0]hexan-1-yl)-N—((R)-piperidin-3-yl)-7H-pyrrolo[2,3-d]pyrimidin-4-amine as an off-white solid (0.12 g, crude): MS (ES) m/z 334.1 (M+H).

268

EXAMPLE 78

Step 8: Preparation of 1-((3R)-3-((5-(6,6-difluorobicyclo[3.1.0]hexan-1-yl)-7H-pyrrolo[2,3-d]pyrimidin-4-yl)amino)piperidin-1-yl)prop-2-en-1-one

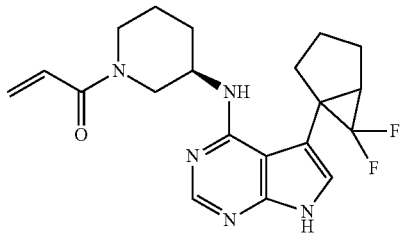 [SMILES: C=CC(=O)N1CCC[C@@H](Nc2ncnc3[nH]cc(C45CCCC4C5(F)F)c23)C1]

Triethylamine (0.23 mL, 1.60 mmol) and acryloyl chloride (0.03 g, 0.33 mmol) were added to a stirred solution of 5-(6,6-difluorobicyclo[3.1.0]hexan-1-yl)-N—((R)-piperidin-3-yl)-7H-pyrrolo[2,3-d]pyrimidin-4-amine (0.14 g, 0.42 mmol) in tetrahydrofuran:water (4 mL:4 mL) at 0° C. and the mixture was stirred for 30 minutes. The reaction mixture was quenched with saturated sodium bicarbonate solution and extracted with ethyl acetate. The organic layer was washed with brine, dried over anhydrous sodium sulfate, filtered and concentrated in vacuo. The crude material was purified using flash column chromatography (4% methanol/dichloromethane) to provide 1-((3R)-3-((5-(6,6-difluorobicyclo[3.1.0]hexan-1-yl)-7H-pyrrolo[2,3-d]pyrimidin-4-yl)amino)piperidin-1-yl)prop-2-en-1-one as an off-white solid (0.025 g, 15% yield).

The stereoisomers of 1-((3R)-3-((5-(6,6-difluorobicyclo[3.1.0]hexan-1-yl)-7H-pyrrolo[2,3-d]pyrimidin-4-yl)amino)piperidin-1-yl)prop-2-en-1-one were separated by chiral preparative HPLC.

HPLC conditions:
Column: CHIRALPAK IA (100 mm×4.6 mm×3 mic)
Mobile phase: n-hexane:IPA with 0.1% DEA (50:50)
Flow rate: 1.0 mL/min
Peak-1: RT 2.103
Peak-2: RT 4.832

EXAMPLE 79

1-((R)-3-((5-((1R,5S)-6,6-difluorobicyclo[3.1.0] hexan-1-yl)-7H-pyrrolo[2,3-d]pyrimidin-4-yl)amino) piperidin-1-yl)prop-2-en-1-one (Stereoisomer 1, Absolute Configuration of Cyclopropyl Group Assigned Provisionally)

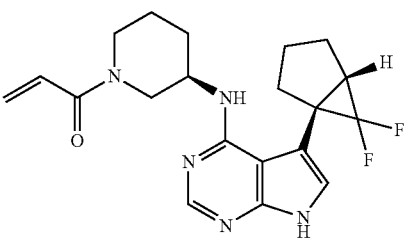 [SMILES: C=CC(=O)N1CCC[C@@H](Nc2ncnc3[nH]cc([C@@]45CCC[C@@H]4C5(F)F)c23)C1]

Purified by chiral HPLC (stereoisomer 1), isolated as a white solid (0.01 g, 5% yield): $^1$H NMR (400 MHz, DMSO-d$_6$) δ 11.58 (s, 1H), 8.14 (d, J=10.0 Hz, 1H), 7.09 (s, 1H), 6.76-6.83 (m, 1H), 6.54-6.61 (m, 1H), 5.96-6.08 (m, 1H), 5.45-5.66 (m, 1H), 5.00-5.08 (m, 1H), 4.23-4.42 (m, 2H), 3.67-3.80 (m, 3H), 3.42 (br s, 1H), 2.25-2.40 (m, 2H), 1.87-2.05 (m, 4H), 1.58-1.69 (m, 3H); MS (ES) m/z 388.3 (M+H). Retention time 2.10 min.

EXAMPLE 80

1-((R)-3-((5-((1S,5R)-6,6-difluorobicyclo[3.1.0]hexan-1-yl)-7H-pyrrolo[2,3-d]pyrimidin-4-yl)amino)piperidin-1-yl)prop-2-en-1-one (Stereoisomer 2, Absolute Configuration of Cyclopropyl Group Assigned Provisionally)

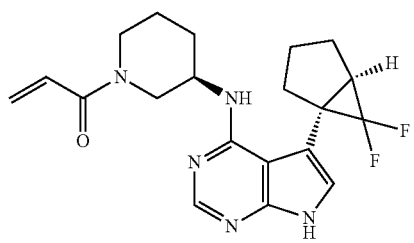 [SMILES: C=CC(=O)N1CCC[C@@H](Nc2ncnc3[nH]cc([C@]45CCC[C@H]4C5(F)F)c23)C1]

Purified by chiral HPLC (stereoisomer 2), isolated as a white solid (0.01 g, 6% yield): $^1$H NMR (400 MHz, DMSO-d$_6$) δ 11.60 (s, 1H), 8.16 (br s, 1H), 7.09 (s, 1H), 6.72-6.78 (m, 1H), 6.55-6.60 (m, 1H), 6.01 (t, J=17.2 Hz, 1H) 5.51-5.64 (m, 1H), 4.90-4.92 (m, 1H), 3.97-4.22 (m, 3H), 3.61-3.66 (m, 1H), 3.31-3.39 (m, 2H), 2.37-2.42 (m, 1H), 2.06-2.30 (m, 4H), 1.89-1.98 (m, 1H), 1.56-1.66 (m, 3H); MS (ES) m/z 388.0 (M+H). Retention time 4.83 min.

EXAMPLE 96

Preparation of Ethyl 5-((1-acryloylpiperidin-4-yl)amino)-1H-pyrrolo[2,3-b]pyridine-3-carboxylate

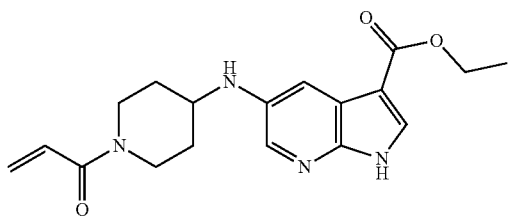 [SMILES: C=CC(=O)N1CCC(Nc2cnc3[nH]cc(C(=O)OCC)c3c2)CC1]

The title compound was prepared by the method described in Scheme 32.

Scheme 32. Preparation of ethyl 5-((1-acryloylpiperidin-4-yl)amino)-1H-pyrrolo[2,3-b]pyridine-3-carboxylate

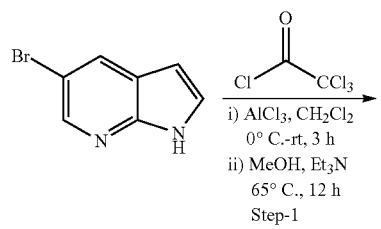

-continued

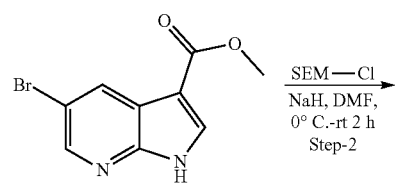

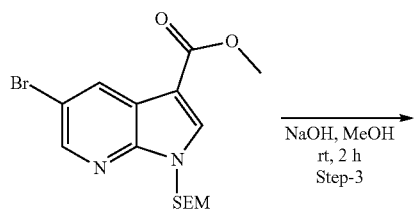

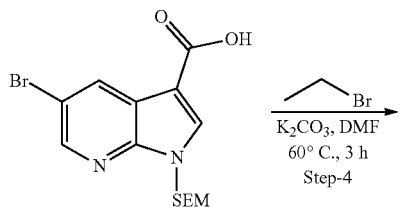

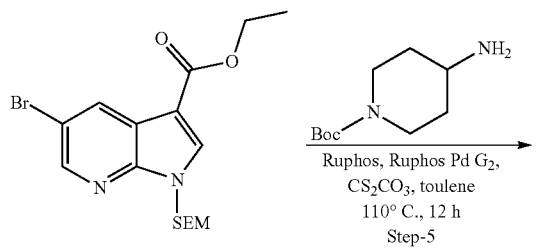

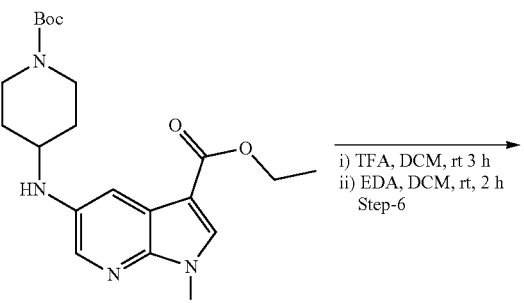

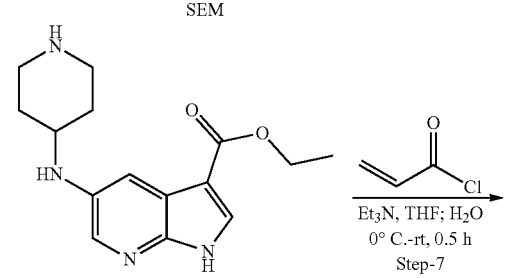

-continued

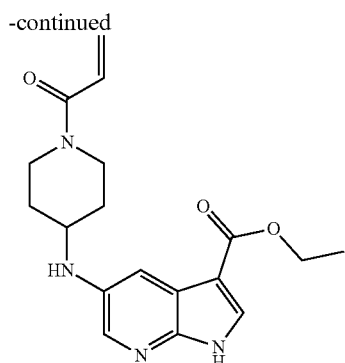

Step 1: Preparation of methyl 5-bromo-1H-pyrrolo[2,3-b]pyridine-3-carboxylate

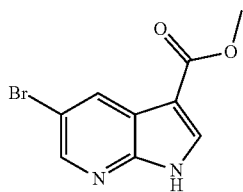

To a stirred solution of 5-bromo-1H-pyrrolo[2,3-b]pyridine (5.0 g, 25.51 mmol) in dichloromethane (100 mL) was added aluminum chloride (10.19 g, 76.54 mmol) portionwise at 0° C. followed by 2,2,2-trichloroacetyl chloride (4.21 mL, 38.27 mmol) dropwise at the same temperature. The mixture was stirred at ambient temperature for 3 hours. The reaction mixture was quenched with ice water and extracted with 5% methanol in dichloromethane. The organic layer was washed with brine, dried over anhydrous sodium sulfate, filtered and concentrated in vacuo. The obtained solid was dissolved in methanol (100 mL) and triethylamine (30 mL) was added and the mixture stirred at 65° C. for 12 hours. The reaction mixture was concentrated in vacuo to obtain a white solid which was washed with saturated aqueous sodium bicarbonate, water and dried to provide methyl 5-bromo-1H-pyrrolo[2,3-b]pyridine-3-carboxylate as an off-white solid (4.51 g, 69.2%): MS (ES) m/z 351.2 (M+H).

Step 2: Preparation of methyl 5-bromo-1-((2-(trimethylsilyl)ethoxy)methyl)-1H-pyrrolo[2,3-b]pyridine-3-carboxylate

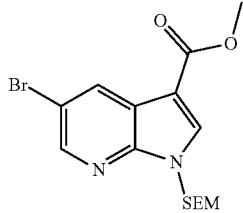 [SMILES: COC(=O)c1cn(COCC[Si](C)(C)C)c2ncc(Br)cc12]

To a suspension of sodium hydride (0.63 g, 26.56 mmol) in N,N-dimethylformamide (20 mL) was added methyl 5-bromo-1H-pyrrolo[2,3-b]pyridine-3-carboxylate (4.5 g, 17.70 mmol) slowly at 0° C. followed by addition of (2-chloromethoxyethyl)trimethylsilane (4.71 mL, 26.56 mmol) at the same temperature and the mixture stirred for 30 minutes. The reaction mixture was warmed to ambient temperature and stirred for 2 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (8% ethyl acetate/hexane) to provide methyl 5-bromo-1-((2-(trimethylsilyl)ethoxy)methyl)-1H-pyrrolo[2,3-b]pyridine-3-carboxylate as an off-white solid (4.01 g, 59% yield): MS (ES) m/z 351.2 (M+H).

Step 3: Preparation of 5-bromo-1-((2-(trimethylsilyl)ethoxy)methyl)-1H-pyrrolo[2,3-b]pyridine-3-carboxylic Acid

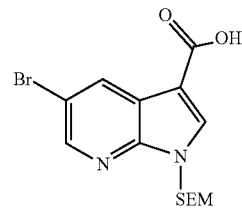 [SMILES: C[Si](C)(C)CCOCn1cc(C(=O)O)c2cc(Br)cnc21]

To a solution of methyl 5-bromo-1-((2-(trimethylsilyl)ethoxy)methyl)-1H-pyrrolo[2,3-b]pyridine-3-carboxylate (4.01 g, 10.44 mmol) in methanol:water (16:4 mL) was added sodium hydroxide (1.67 g, 41.76 mmol) and the mixture stirred at ambient temperature for 2 hours. The reaction was concentrated to remove volatiles in vacuo. The obtained residue was dissolved in water and acidified using (3 M) hydrochloric acid, whereupon an oil separated which was extracted with ethyl acetate. The organic layer was washed with brine, dried over anhydrous sodium sulfate, filtered and concentrated in vacuo to provide 5-bromo-1-((2-(trimethylsilyl)ethoxy)methyl)-1H-pyrrolo[2,3-b]pyridine-3-carboxylic acid as a white solid (3.71 g, 97%): MS (ES) m/z 351.2 (M+H).

Step 4: Preparation of Ethyl 5-bromo-1-((2-(trimethylsilyl)ethoxy)methyl)-1H-pyrrolo[2,3-b]pyridine-3-carboxylate

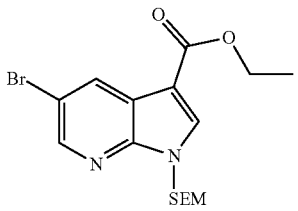 [SMILES: CCOC(=O)c1cn(COCC[Si](C)(C)C)c2ncc(Br)cc12]

To a solution of 5-bromo-1-((2-(trimethylsilyl)-ethoxy)methyl)-1H-pyrrolo[2,3-b]pyridine-3-carboxylic acid (1.0 g, 2.70 mmol) in N,N-dimethylformamide (10 mL) was added potassium carbonate (1.12 g, 8.10 mmol) followed by addition of iodoethane (0.43 mL, 5.40 mmol) and the mixture stirred at 60° C. for 3 hours. After cooling the reaction mixture was quenched with ice water and extracted with ethyl acetate. The organic layer was washed with water, saturated aqueous sodium bicarbonate, brine, dried over anhydrous sodium sulfate, filtered and concentrated in vacuo. The crude material was purified by flash chromatography (10% ethyl acetate/hexane) to provide ethyl 5-bromo-1-((2-(trimethylsilyl)ethoxy)methyl)-1H-pyrrolo[2,3-b]pyridine-3-carboxylate as an off-white solid (0.9 g, 84% yield): $^1$H NMR (400 MHz, DMSO-$d_6$) δ 8.49 (s, 1H), 8.48 (s, 1H), 8.43 (s, 1H), 5.65 (s, 2H), 4.31 (q, J=7.2 Hz, 2H), 3.53 (t, J=8.0 Hz, 2H), 1.33 (t, J=7.2 Hz, 3H), 0.80 (t, J=8.0 Hz, 2H), 0.09 (s, 9H).

Step 5: Preparation of Ethyl 5-((1-(tert-butoxycarbonyl)piperidine-4-yl)amino)-1-((2-(trimethylsilyl)ethoxy)methyl)-1H-pyrrolo[2,3-b]pyridine-3-carboxylate

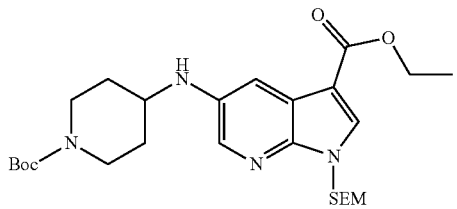 [SMILES: CCOC(=O)c1cn(COCC[Si](C)(C)C)c2ncc(NC3CCN(C(=O)OC(C)(C)C)CC3)cc12]

To a solution of ethyl 5-bromo-1-((2-(trimethylsilyl)ethoxy)methyl)-1H-pyrrolo[2,3-b]pyridine-3-carboxylate (0.5 g, 1.25 mmol) in toluene (10 mL) was added tert-butyl 4-aminopiperidine-1-carboxylate (0.50 g, 2.51 mmol), sodium tert-butoxide (0.24 g, 2.51 mmol), RuPhos (0.03 g, 0.06 mmol) followed by RuPhos PdG2 (0.02 g, 0.02 mmol) under an argon atmosphere and the resulting mixture was stirred at 110° C. for 12 hours. The reaction mixture was filtered through celite and the filtrate was concentrated in vacuo. The crude material was purified by flash chromatography (30% ethyl acetate/hexane) to provide ethyl 5-((1-(tert-butoxycarbonyl)piperidine-4-yl)amino)-1-((2-(trimethylsilyl)ethoxy)methyl)-1H-pyrrolo[2,3-b]pyridine-3-carboxylate as a brown oil (0.18 g, 28% yield): MS (ES) m/z 519.2 (M+H).

Step 6: Preparation of Ethyl 5-(piperidin-4-yl)amino)-1H-pyrrolo[2,3-b]pyridine-3-carboxylate

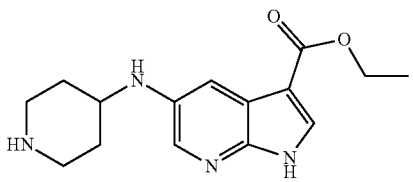 [SMILES: CCOC(=O)c1c[nH]c2ncc(NC3CCNCC3)cc12]

To a solution of ethyl 5-((1-(tert-butoxidecabonyl)piperidine-4-yl)amino)-1-((2-(trimethylsilyl)ethoxy)methyl)-1H-pyrrolo[2,3-b]pyridine-3-carboxylate (0.18 g, 0.35 mmol) in dichloromethane (5 mL) was added trifluoroacetic acid (6 mL) and the mixture stirred at ambient temperature for 3 hours. The reaction mixture was concentrated in vacuo to provide a gummy like solid, which was dissolved in dichloromethane (2 mL). Ethylenediamine (12 mL) was added and the mixture stirred at ambient temperature for 2 hours. The reaction mixture was quenched with water and extracted with dichloromethane. The organic layer was washed with water, saturated aqueous sodium bicarbonate, brine, dried over anhydrous sodium sulfate, filtered and concentrated in vacuo. The crude material was purified using flash chromatography (5% methanol/dichloromethane) to provide ethyl 5-(piperidin-4-yl)amino)-1H-pyrrolo[2,3-b]pyridine-3-carboxylate as an off-white solid (0.12 g, crude): MS (ES) m/z 289.1 (M+H).

Step 7: Preparation of Ethyl 5-((1-acryloylpiperidine-4-yl)amino)-1H-pyrrolo[2,3-b]pyridine-3-carboxylate

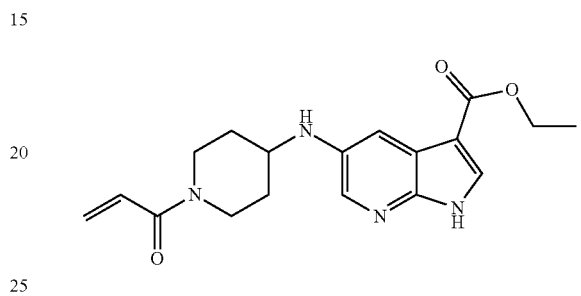

To a stirred solution of ethyl 5-(piperidin-4-yl)amino)-1H-pyrrolo[2,3-b]pyridine-3-carboxylate (0.06 g, 0.20 mmol) in tetrahydrofuran:water (8:2 mL) was added triethylamine (0.06 mL, 0.42 mmol) followed by a solution of acryloyl chloride (0.02 mL, 0.21 mmol) in tetrahydrofuran (0.3 mL) at 0° C. and the mixture stirred for 0.5 hours. The reaction mixture was quenched with saturated aqueous sodium bicarbonate solution and extracted with ethyl acetate. The organic layer was washed with brine, dried over anhydrous sodium sulfate, filtered and concentrated in vacuo. The crude material was purified using flash chromatography (5% methanol/dichloromethane) to provide ethyl 5-((1-acryloylpiperidine-4-yl)amino)-1H-pyrrolo[2,3-b]pyridine-3-carboxylate as a white solid (0.03 g, 22.8%): $^1$H NMR (400 MHz, DMSO-$d_6$) δ 12.02 (s, 1H), 7.93 (s, 1H), 7.83 (s, 1H), 7.46 (s, 1H), 6.78-6.85 (m, 1H), 6.08 (d, J=15.6 Hz, 1H), 5.64 (d, J=10 Hz, 1H), 5.46 (s, 1H), 4.22-4.23 (m, 3H), 4.01 (d, J=8.0 Hz, 1H), 3.51 (br s, 1H), 3.24-3.29 (m, 3H), 2.91-2.92 (m, 1H), 1.96 (m, 2H), 1.28-1.31 (m, 3H); MS (ES) m/z 343.1 (M+H).

EXAMPLE 97

Preparation of Ethyl 2-((1-acryloylpiperidin-4-yl)amino)-5H-pyrrolo[2,3-b]pyrazine-7-carboxylate

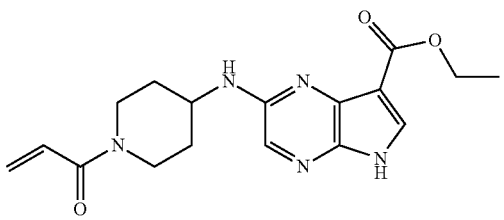 [SMILES: C=CC(=O)N1CCC(Nc2cnc3[nH]cc(C(=O)OCC)c3n2)CC1]

The title compound was prepared by the method described in Scheme 33.

Scheme 33. Preparation of ethyl 2-((1-acryloylpiperidin-4-yl)amino)-5H-pyrrolo[2,3-b]pyrazine-7-carboxylate

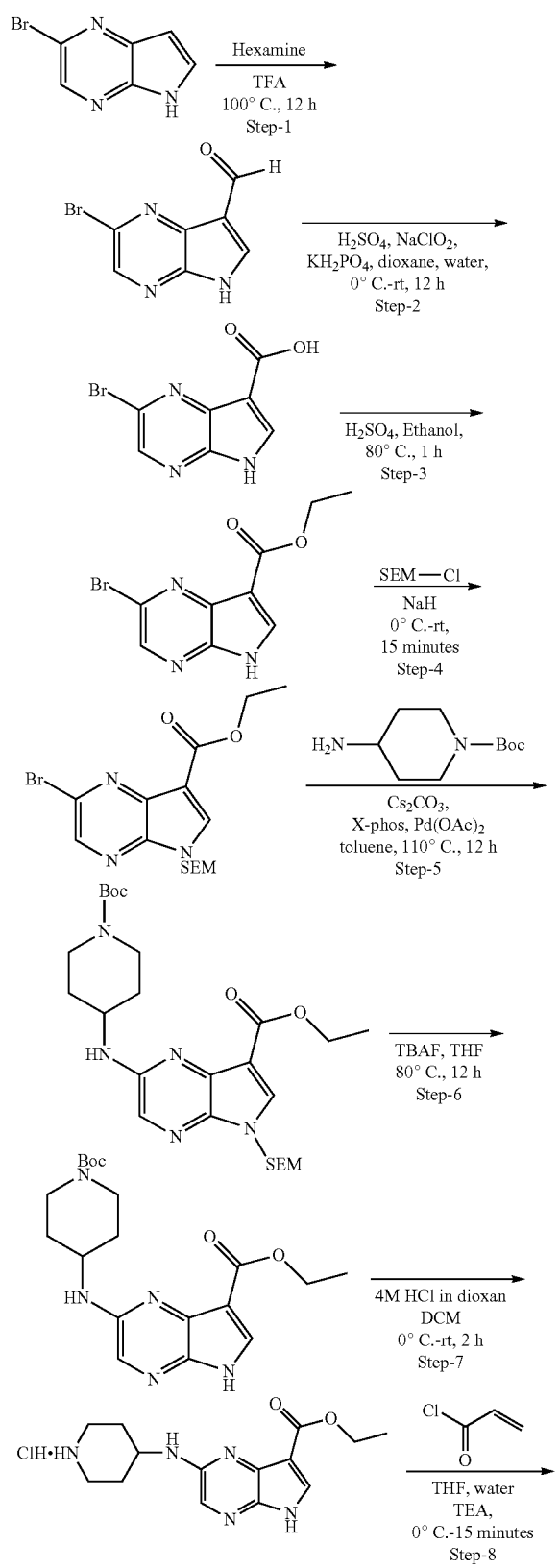

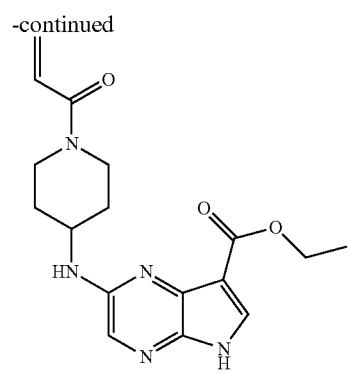

Step 1: Preparation of 2-bromo-5H-pyrrolo[2,3-b]pyrazine-7-carbaldehyde

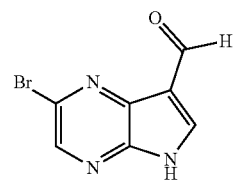 [SMILES: O=Cc1c[nH]c2ncc(Br)nc12]

To a solution of 2-bromo-5H-pyrrolo[2,3-b]pyrazine (5 g, 25.2 mmol) in trifluroacetic acid (50 mL) was added hexamine (5.34 g, 37.8 mmol) at 0° C. and the reaction mixture was stirred at 110° C. for 12 hours. The reaction mixture was concentrated in vacuo to remove excess trifluroacetic acid and the residue was quenched with aqueous sodium bicarbonate and extracted with ethyl acetate. The organic layer was washed with water, brine, dried over anhydrous sodium sulfate, filtered and concentrated in vacuo. The crude material was purified using flash chromatography (10% ethyl acetate/hexane) to provide 2-bromo-5H-pyrrolo[2,3-b]pyrazine-7-carbaldehyde as a pale brown color solid (2.7 g, 40% yield): MS (ES) m/z 227.9 (M+H).

Step 2: Preparation of 2-bromo-5H-pyrrolo[2,3-b]pyrazine-7-carboxylic Acid

To a solution of 2-bromo-5H-pyrrolo[2,3-b]pyrazine-7-carbaldehyde (2.7 g, 11.94 mmol) in dioxane:water (90:18 mL), was added sulfuric acid (6.95 g, 71.68 mmol), sodium chlorite (1.4 g, 15.53 mmol) at 0° C. followed by a solution of potassium dihydrogenphospate (19.4 g, 143.3 mmol) in water (20 mL) dropwise. The reaction mixture was stirred at ambient temperature for 12 hours and the mixture was quenched with ice and extracted with ethyl acetate. The organic layer was washed with water, brine, dried over anhydrous sodium sulfate, filtered and concentrated in vacuo. The crude material was purified using flash chromatography (6% methanol/dichloromethane) to provide 2-bromo-5H-pyrrolo[2,3-b]pyrazine-7-carboxylic acid as an off-white solid (1.5 g, 60% yield): MS (ES) m/z 241.9 (M+H).

Step 3: Preparation of Ethyl 2-bromo-5H-pyrrolo[2,3-b]pyrazine-7-carboxylate

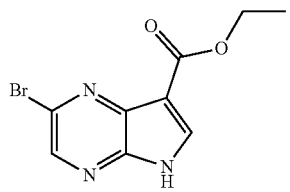

To a solution of 2-bromo-5H-pyrrolo[2,3-b]pyrazine-7-carboxylic acid (1.4 g, 5.22 mmol) in ethanol (20 mL) was added sulfuric acid (0.5 mL) at 0° C. and the mixture was stirred at 80° C. for 1 hour. After cooling the reaction mixture was quenched with ice and extracted with ethyl acetate. The organic layer was washed with water, brine, dried over anhydrous sodium sulfate, filtered and concentrated in vacuo. The crude material was purified using flash chromatography (10% ethyl acetate/hexane) to provide ethyl 2-bromo-5H-pyrrolo[2,3-b]pyrazine-7-carboxylate as a brown liquid (1.4 g, 80% yield): MS (ES) m/z 272 (M+H).

Step 4: Preparation of Ethyl 2-bromo-5-((2-(trimethylsilyl)ethoxy)methyl)-5H-pyrrolo[2,3-b]pyrazine-7-carboxylate

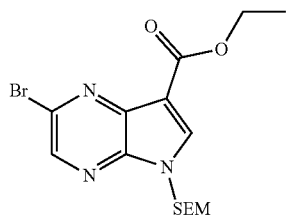 [SMILES: CCOC(=O)c1cn(COCC[Si](C)(C)C)c2ncc(Br)nc12]

To a suspension of sodium hydride (0.31 g, 7.77 mmol, 60% mineral oil dispersion) in N,N-dimethylformamide (20 mL) was added 2-bromo-5H-pyrrolo[2,3-b]pyrazine-7-carboxylate (1.4 g, 5.18 mmol) at 0° C. followed by the addition of (2-chloromethoxyethyl)trimethylsilane (1.1 mL, 6.22 mmol) at the same temperature. The resulting mixture was stirred at ambient temperature for 15 minutes. The reaction mixture was quenched with ice and extracted with acetate. The organic layer was washed with water, brine, dried over anhydrous sodium sulfate, filtered and concentrated in vacuo. The crude material was purified using flash chromatography (10% ethyl acetate/hexane) to provide ethyl 2-bromo-5-((2-(trimethylsilyl)ethoxy)methyl)-5H-pyrrolo[2,3-b]pyrazine-7-carboxylate as a pale yellow liquid (1.4 g, 60% yield): MS (ES) m/z 400.0 (M+H).

Step 5: Preparation of Ethyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate

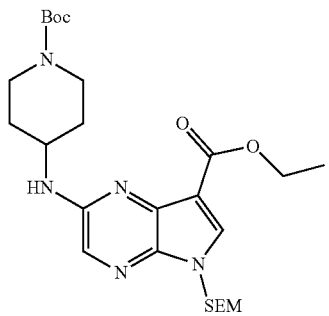 [SMILES: CCOC(=O)c1cn(COCC[Si](C)(C)C)c2ncc(NC3CCN(C(=O)OC(C)(C)C)CC3)nc12]

To a solution of ethyl 2-bromo-5-((2-(trimethylsilyl)ethoxy)methyl)-5H-pyrrolo[2,3-b]pyrazine-7-carboxylate (1.2 g, 3 mmol) in toluene (20 mL) was added tert-butyl 4-aminopiperidine-1-carboxylate (0.9 g, 4.5 mmol), cesium carbonate (2.94 g, 9 mmol), X-phos (0.29 g, 0.6 mmol) and palladium(II) acetate (0.068 g, 0.3 mmol) under an argon atmosphere and the resulting mixture was heated to 110° C. for 12 hours. After cooling, the reaction mixture was filtered through celite and the filtrate was concentrated in vacuo. The crude material was purified using flash chromatography (40% ethyl acetate/hexane) to provide ethyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate as a pale brown solid (1 g, 60% yield): MS (ES) m/z 520.2 (M+H).

Step 6: Preparation of Ethyl 2-((1-(tert-butoxycarbonyl)piperidin-4-yl)amino)-5H-pyrrolo[2,3-b]pyrazine-7-carboxylate

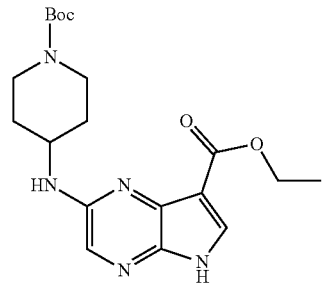 [SMILES: CCOC(=O)c1c[nH]c2ncc(NC3CCN(C(=O)OC(C)(C)C)CC3)nc12]

To a stirred solution of ethyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate (0.6 g, 0.96 mmol) in tetrahydrofuran (6 mL) was added tetrabutylammonium fluoride (4.8 mL, 1 M in tetrahydrofuran) and the solution was heated to 80° C. for 12 hours. After cooling the reaction mixture was quenched with saturated aqueous ammonium chloride solution and extracted into ethyl acetate. The organic layer was washed with water, brine, dried over anhydrous sodium sulfate, filtered and concentrated in vacuo. The crude material was purified using flash chromatography (3% methanol/dichloromethane) to provide ethyl 2-((1-(tert-butoxycarbonyl)piperidin-4-yl)amino)-5H- pyrrolo[2,3-b]pyrazine-7-carboxylate as a pale brown solid (0.4 g, 70% yield): MS (ES) m/z 390.1 (M+H).

Step 7: Preparation of Ethyl 2-(piperidin-4-ylamino)-5H-pyrrolo[2,3-b]pyrazine-7-carboxylate

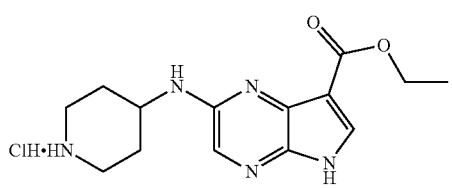

To a stirred solution of ethyl 2-((1-(tert-butoxycarbonyl)piperidin-4-yl)amino)-5H-pyrrolo[2,3-b]pyrazine-7-carboxylate (0.4 g, 1.1 mmol) in dichloromethane (5 mL) was added a solution of hydrogen chloride (10 mL, 4 M in dioxane) at 0° C. and the mixture was warmed to ambient temperature and stirred for 2 hours. The reaction mixture was concentrated in vacuo and the residue was washed with diethyl ether to provide ethyl 2-(piperidin-4-ylamino)-5H-pyrrolo[2,3-b]pyrazine-7-carboxylate as a pale yellow solid (0.25 g crude): MS (ES) m/z 290.1 (M+H). The crude product was progressed for the next step.

Step 8: Preparation of Ethyl 2-((1-acryloylpiperidin-4-yl)amino)-5H-pyrrolo[2,3-b]pyrazine-7-carboxylate

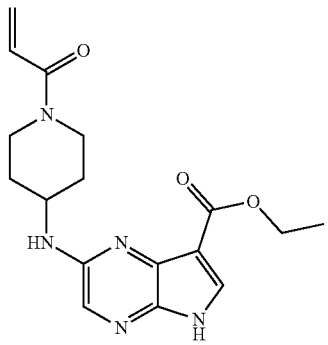 [SMILES: C=CC(=O)N1CCC(Nc2cnc3[nH]cc(C(=O)OCC)c3n2)CC1]

To a solution of ethyl 2-(piperidin-4-ylamino)-5H-pyrrolo[2,3-b]pyrazine-7-carboxylate (0.2 g, 0.6 mmol) in tetrahydrofuran:water (4:1 mL) was added triethylamine (0.48 mL, 3.44 mmol) followed by a solution of acryloyl chloride (0.05 mL g, 0.6 mmol) in tetrahydrofuran (1 mL) at 0° C. and the mixture stirred for 15 minutes. The reaction mixture was quenched with saturated aqueous sodium bicarbonate and extracted with ethyl acetate. The organic layer was washed with water, brine, dried over anhydrous sodium sulfate, filtered and concentrated in vacuo. The crude material was purified using flash chromatography (4% methanol/dichloromethane) and further purified by using prep HPLC to provide ethyl 2-((1-acryloylpiperidin-4-yl)amino)-5H-pyrrolo[2,3-b]pyrazine-7-carboxylate as a white solid (0.03 g, 13% yield): $^1$H NMR (400 MHz, DMSO-$d_6$) δ 12.18 (s, 1H), 8.00 (s, 1H), 7.64 (s, 1H), 6.79-6.85 (m, 2H), 6.69 (d, J=6.4 Hz, 1H), 6.05-6.10 (m, 1H), 5.63-5.66 (m, 1H), 4.30 (m, 1H), 4.17-4.26 (m, 2H), 3.99 (m, 2H), 3.22 (m, 1H), 2.88-2.94 (m, 1H), 2.05 (m, 2H), 1.35 (m, 2H), 1.25-1.30 (m, 2H); MS (ES) m/z 344.2 (M+H).

EXAMPLE 98

Preparation of 1-(4-((3-(cyclopropanecarbonyl)-1H-pyrrolo[2,3-b]pyridin-5-yl)amino)piperidin-1-yl)prop-2-en-1-one

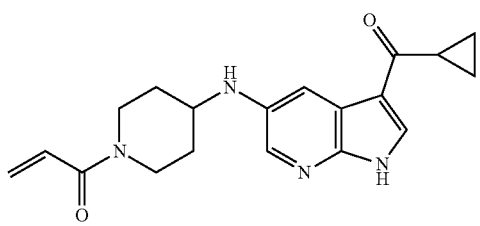 [SMILES: C=CC(=O)N1CCC(Nc2cnc3[nH]cc(C(=O)C4CC4)c3c2)CC1]

The title compound was prepared by the method described in Scheme 34.

Scheme 34. Preparation of 1-(4-((3-(cyclopropanecarbonyl)-1H-pyrrolo[2,3-b]pyridin-5-yl)amino)piperidin-1-yl)prop-2-en-1-one

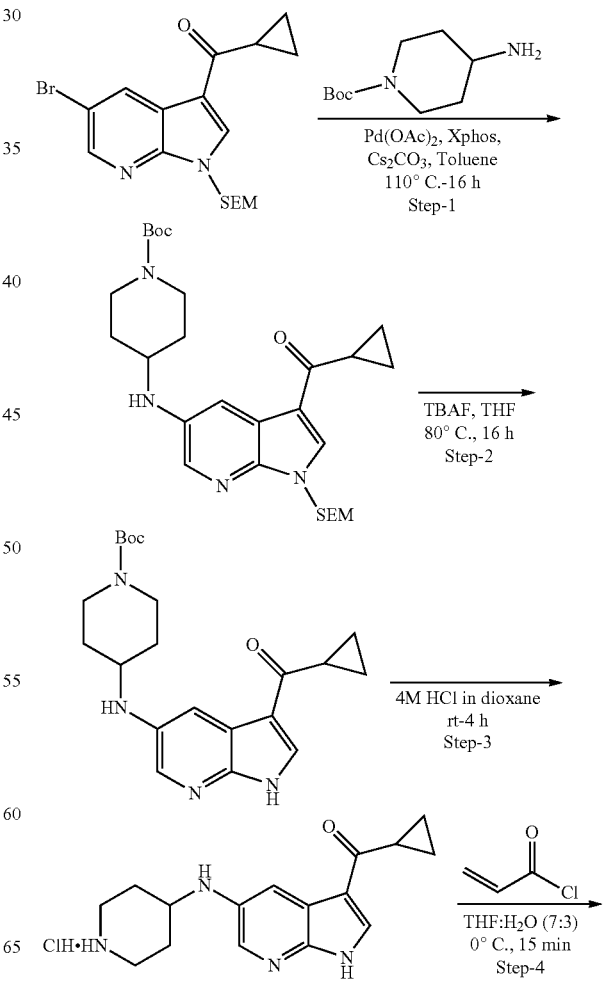

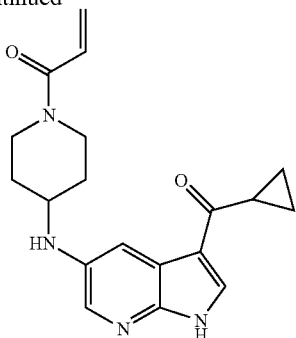

Step 1: Preparation of tert-butyl 4-((3-(cyclopropanecarbonyl)-1-((2-(trimethylsilyl)ethoxy)methyl)-1H-pyrrolo[2,3-b]pyridin-5-yl)amino)piperidine-1-carboxylate

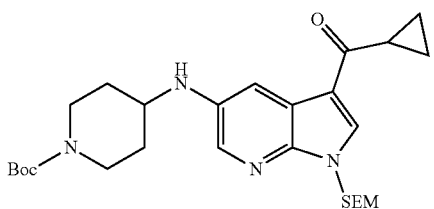 [SMILES: CC(C)(C)OC(=O)N1CCC(Nc2cnc3c(c2)c(C(=O)C2CC2)cn3COCC[Si](C)(C)C)CC1]

To a solution of (5-bromo-1-((2-(trimethylsilyl)ethoxy)methyl)-1H-pyrrolo[2,3-b]pyridin-3-yl)(cyclopropyl)methanone (1.0 g, 2.53 mmol) in toluene (25 mL) was added tert-butyl 4-aminopiperidine-1-carboxylate (0.76 g, 3.80 mmol), cesium carbonate (1.24 g, 3.80 mmol), 2-dicyclohexylphosphino-2',4',6'-triisopropylbiphenyl (0.12 g, 0.12 mmol) and palladium(II) acetate (0.02 g, 0.12 mmol) under an argon atmosphere and resulting mixture was heated to 110° C. for 16 hours. After cooling to ambient temperature, the reaction was filtered through celite and the filtrate was concentrated in vacuo. The crude material was purified using flash chromatography (45% ethyl acetate/hexane) to provide tert-butyl 4-((3-(cyclopropanecarbonyl)-1-((2-(trimethylsilyl)ethoxy)methyl)-1H-pyrrolo[2,3-b]pyridin-5-yl)amino)piperidine-1-carboxylate as a yellow gummy solid (0.9 g, 69% yield): MS (ES) m/z 515.2 (M+H).

Step 2: Preparation of tert-butyl 4-((3-(cyclopropanecarbonyl)-1H-pyrrolo[2,3-b]pyridin-5-yl)amino)piperidine-1-carboxylate

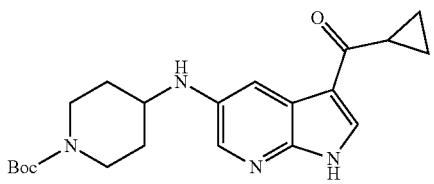 [SMILES: CC(C)(C)OC(=O)N1CCC(Nc2cnc3[nH]cc(C(=O)C4CC4)c3c2)CC1]

To a stirred solution of tert-butyl 4-((3-(cyclopropanecarbonyl)-1-((2-(trimethylsilyl)ethoxy)methyl)-1H-pyrrolo[2,3-b]pyridin-5-yl)amino)piperidine-1-carboxylate (0.9 g, 1.75 mmol) in tetrahydrofuran (10 mL) was added tetrabutylammonium fluoride (10 mL, 1 M in tetrahydrofuran) and the solution was heated to 80° C. for 16 hours. After cooling the reaction mixture was quenched with saturated aqueous ammonium chloride solution and extracted into ethyl acetate. The organic layer was washed with water, brine, dried over sodium sulfate, filtered and concentrated in vacuo. The crude material was purified using flash chromatography (50% ethyl acetate/hexane) to provide tert-butyl 4-((3-(cyclopropanecarbonyl)-1H-pyrrolo[2,3-b]pyridin-5-yl)amino)piperidine-1-carboxylate as a yellow gummy solid (0.52 g, 77% yield): MS (ES) m/z 385.2 (M+H).

Step 3: Preparation of cyclopropyl(5-(piperidin-4-ylamino)-1H-pyrrolo[2,3-b]pyridin-3-yl)methanone Hydrochloride

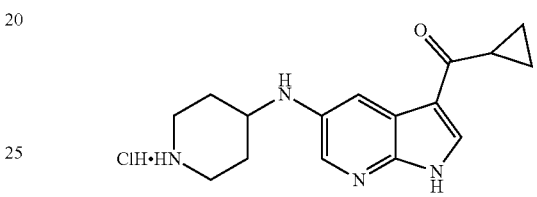

To a stirred solution of tert-butyl 4-((3-(cyclopropanecarbonyl)-1H-pyrrolo[2,3-b]pyridin-5-yl)amino)piperidine-1-carboxylate (0.52 g, 4.97 mmol) in dichloromethane (5 mL) was added a solution of hydrogen chloride (10 mL, 4 M in dioxane) at 0° C. and the mixture was warmed to ambient temperature and stirred for 4 hours. The reaction mixture was concentrated in vacuo and the residue was washed with diethyl ether to provide cyclopropyl(5-(piperidin-4-ylamino)-1H-pyrrolo[2,3-b]pyridin-3-yl)methanone hydrochloride (0.36 g, crude): MS (ES) m/z 285.1 (M+H). The crude product was progressed for the next step.

Step 4: Preparation of 1-(4-((3-(cyclopropanecarbonyl)-1H-pyrrolo[2,3-b]pyridin-5-yl)amino)piperidin-1-yl)prop-2-en-1-one

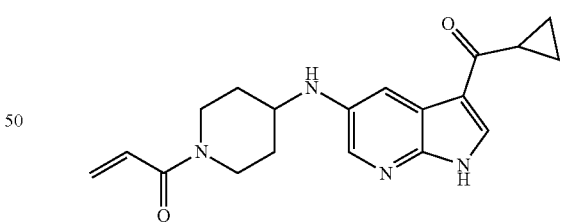

To a stirred solution of cyclopropyl(5-(piperidin-4-ylamino)-1H-pyrrolo[2,3-b]pyridin-3-yl)methanone hydrochloride (0.2 g, 0.31 mmol) in tetrahydrofuran:water (14:6 mL) was added triethylamine (0.16 mL, 0.93 mmol) followed by a solution of acryloyl chloride (0.02 mL, 0.25 mmol) in tetrahydrofuran (1 mL) at 0° C. and the mixture stirred at 0° C. for 15 minutes. The reaction mixture was quenched with saturated sodium bicarbonate and extracted with ethyl acetate. The organic layer was washed with water, brine, dried over anhydrous sodium sulfate, filtered and concentrated in vacuo. The crude material was purified using flash chromatography (4% methanol/dichloromethane) and further purified using prep HPLC to provide 1-(4-((3-(cyclopropanecarbonyl)-1H-pyrrolo[2,3-b]pyridin-5-yl)amino)piperidin-1-yl)prop-2-en-1-one as a white solid (0.01 g, 6% yield): ¹H NMR (400 MHz, DMSO-d₆) δ 12.03 (s, 1H), 8.41 (d, J=2.4 Hz, 1H), 7.82 (d, J=2.4 Hz, 1H), 7.67 (d, J=2.8 Hz, 1H), 6.77-6.84 (m, 1H), 6.05-6.10 (m, 1H), 5.62-5.66 (m, 1H), 5.42 (d, J=7.6 Hz, 1H), 4.25 (d, J=10 Hz, 1H), 4.0 (d, J=13.2 Hz, 1H), 3.48-3.51 (m, 1H), 3.28-3.33 (m, 1H), 2.92 (d, J=12.0 Hz, 1H), 2.65-2.68 (m, 1H), 1.93 (br s, 2H), 1.21-1.26 (m, 2H), 0.61-0.82 (m, 2H), 0.83-0.92 (m, 2H); MS (ES) m/z 339.1 (M+H).

Prep HPLC method:
Column: Inertsil ODS 3V (250 mm×4.6 mm×5 mic)
Mobile phase (A): 0.1% Ammonia in water
Mobile phase (B): ACN
Flow rate: 1.0 mL/min
Retention time: 15.935 minutes.

EXAMPLE 99

Preparation of 1-(4-((7-(cyclopropanecarbonyl)-5H-pyrrolo[2,3-b]pyrazin-2-yl)amino)piperidin-1-yl)prop-2-en-1-one

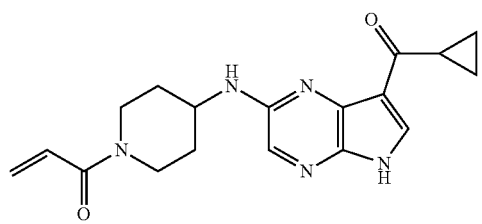 [SMILES: C=CC(=O)N1CCC(Nc2cnc3[nH]cc(C(=O)C4CC4)c3n2)CC1]

The title compound was prepared by the method described in Scheme 35.

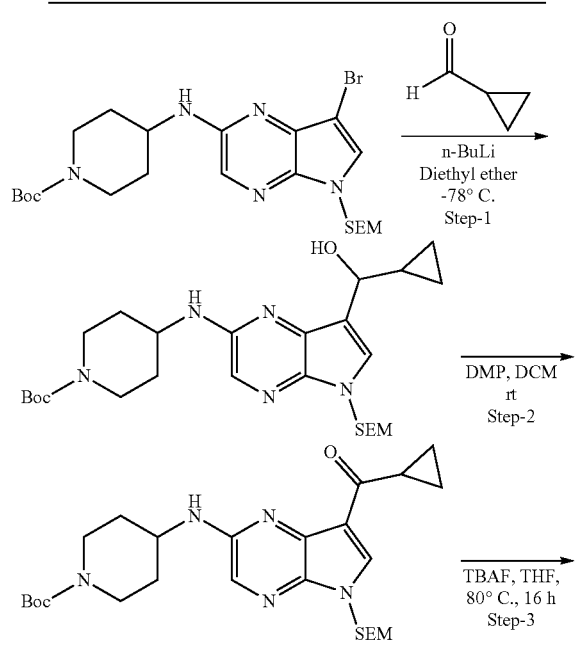

Scheme 35. Preparation of 1-(4-((7-(cyclopropanecarbonyl)-5H-pyrrolo[2,3-b]pyrazin-2-yl)amino)piperidin-1-yl)prop-2-en-1-one

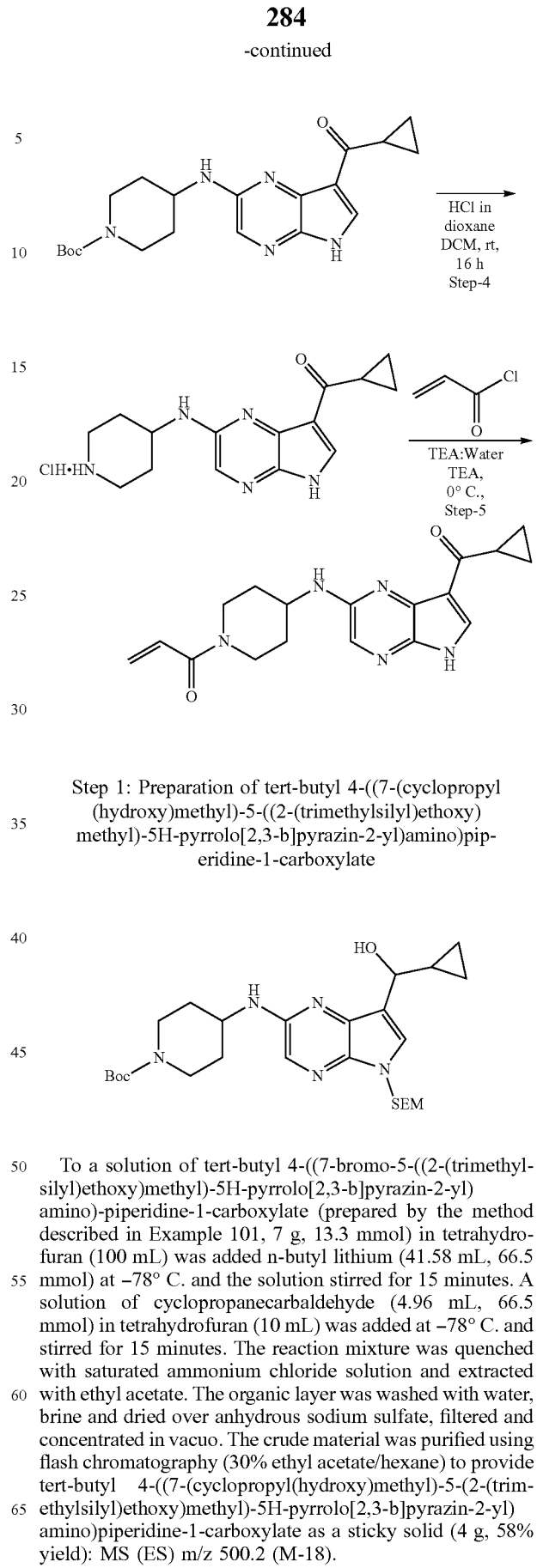

Step 1: Preparation of tert-butyl 4-((7-(cyclopropyl(hydroxy)methyl)-5-((2-(trimethylsilyl)ethoxy)methyl)-5H-pyrrolo[2,3-b]pyrazin-2-yl)amino)piperidine-1-carboxylate To a solution of tert-butyl 4-((7-bromo-5-((2-(trimethylsilyl)ethoxy)methyl)-5H-pyrrolo[2,3-b]pyrazin-2-yl)amino)-piperidine-1-carboxylate (prepared by the method described in Example 101, 7 g, 13.3 mmol) in tetrahydrofuran (100 mL) was added n-butyl lithium (41.58 mL, 66.5 mmol) at −78° C. and the solution stirred for 15 minutes. A solution of cyclopropanecarbaldehyde (4.96 mL, 66.5 mmol) in tetrahydrofuran (10 mL) was added at −78° C. and stirred for 15 minutes. The reaction mixture was quenched with saturated ammonium chloride solution and extracted with ethyl acetate. The organic layer was washed with water, brine and dried over anhydrous sodium sulfate, filtered and concentrated in vacuo. The crude material was purified using flash chromatography (30% ethyl acetate/hexane) to provide tert-butyl 4-((7-(cyclopropyl(hydroxy)methyl)-5-(2-(trimethylsilyl)ethoxy)methyl)-5H-pyrrolo[2,3-b]pyrazin-2-yl)amino)piperidine-1-carboxylate as a sticky solid (4 g, 58% yield): MS (ES) m/z 500.2 (M-18).

Step 2: Preparation of tert-butyl 4-((7-(cyclopropanecarbonyl)-5-((2-(trimethylsilyl)ethoxy)methyl)-5H-pyrrolo[2,3-b]pyrazin-2-yl)amino)piperidine-1-carboxylate

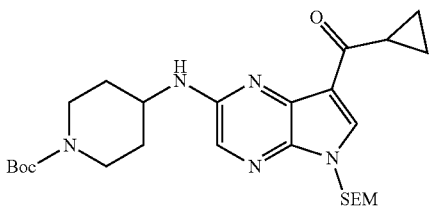 [SMILES: CC(C)(C)OC(=O)N1CCC(Nc2cnc3c(n2)c(C(=O)C2CC2)cn3COCC[Si](C)(C)C)CC1]

To a solution of tert-butyl 4-((7-(cyclopropyl(hydroxy)methyl)-5-((2-(trimethylsilyl)ethoxy)methyl)-5H-pyrrolo[2,3-b]pyrazin-2-yl)amino)piperidine-1-carboxylate (6 g, 11.6 mmol) in dichloromethane (60 mL) was added Dess-Martin periodinane (4.92 g, 11.6 mmol) at ambient temperature and the mixture was stirred for 1 hour. The reaction mixture was quenched with water and extracted with ethyl acetate. The organic layer was washed with water, brine and dried over anhydrous sodium sulfate, filtered and concentrated in vacuo. The crude material was purified using flash chromatography (30% ethyl acetate/hexane) to provide tert-butyl 4-((7-(cyclopropanecarbonyl)-5-((2-(trimethylsilyl)ethoxy)methyl)-5H-pyrrolo[2,3-b]pyrazin-2-yl)amino)piperidine-1-carboxylate (3.7 g, 62% yield): MS (ES) m/z 516.2 (M+H).

Step 3: Preparation of tert-butyl 4-((7-(cyclopropanecarbonyl)-5H-pyrrolo[2,3-b]pyrazin-2-yl)amino)piperidine-1-carboxylate

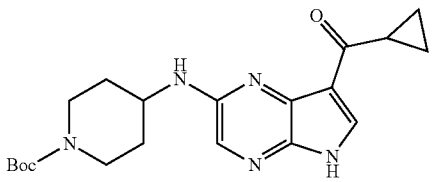 [SMILES: CC(C)(C)OC(=O)N1CCC(Nc2cnc3[nH]cc(C(=O)C4CC4)c3n2)CC1]

To a stirred solution of tert-butyl 4-((7-(cyclopropanecarbonyl)-5-((2-(trimethylsilyl)ethoxy)methyl)-5H-pyrrolo[2,3-b]pyrazin-2-yl)amino)piperidine-1-carboxylate (4 g, 7.76 mmol) in tetrahydrofuran (40 mL) was added tetrabutylammonium fluoride (80 mL, 1 M in tetrahydrofuran) and the solution was heated to 80° C. for 16 hours. After cooling the reaction mixture was quenched with saturated aqueous ammonium chloride solution and extracted with ethyl acetate. The organic layer was washed with water, brine and dried over anhydrous sodium sulfate, filtered and concentrated in vacuo. The crude material was purified using flash chromatography (30% ethyl acetate/hexane) to provide tert-butyl 4-((7-(cyclopropanecarbonyl)-5H-pyrrolo[2,3-b]pyrazin-2-yl)amino)piperidine-1-carboxylate as a pale yellow solid (1.8 g, 60% yield): MS (ES) m/z 386.2 (M+H).

Step 4: Preparation of cyclopropyl(2-(piperidin-4-ylamino)-5H-pyrrolo[2,3-b]pyrazin-7-yl)methanone Hydrochloride

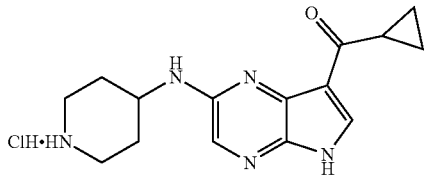

To a stirred solution of tert-butyl 4-((7-(cyclopropanecarbonyl)-5H-pyrrolo[2,3-b]pyrazin-2-yl)amino)piperidine-1-carboxylate (1.8 g, 4.97 mmol) in dichloromethane (18 mL) was added a solution of hydrogen chloride (18 mL, 4 M in dioxane) at 0° C. and the mixture was warmed to ambient temperature and stirred for 16 hours. The reaction was concentrated in vacuo and the residue was triturated with diethyl ether to provide cyclopropyl(2-(piperidin-4-ylamino)-5H-pyrrolo[2,3-b]pyrazin-7-yl)methanone hydrochloride (1.8 g, crude): MS (ES) m/z 286.1 (M+H).

Step 5: Preparation of 1-(4-((7-(cyclopropanecarbonyl)-5H-pyrrolo[2,3-b]pyrazin-2-yl)amino)piperidin-1-yl)prop-2-en-1-one

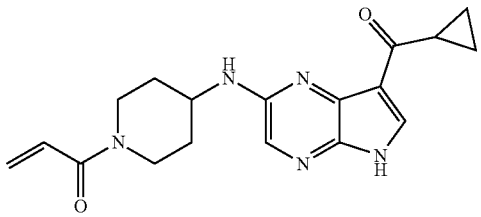 [SMILES: C=CC(=O)N1CCC(Nc2cnc3[nH]cc(C(=O)C4CC4)c3n2)CC1]

To a stirred solution of cyclopropyl(2-(piperidin-4-ylamino)-5H-pyrrolo[2,3-b]pyrazin-7-yl)methanone hydrochloride (1.8 g, 5.6 mmol) in tetrahydrofuran:water (30:30 mL) was added triethylamine (2.35 mL, 16.8 mmol) followed by a solution acryloyl chloride (0.40 g, 4.48 mmol) in tetrahydrofuran (1 mL) at 0° C. and stirred for 15 minutes. The reaction mixture was quenched with saturated sodium bicarbonate and extracted with ethyl acetate. The organic layer was washed with water, brine and dried over anhydrous sodium sulfate, filtered and concentrated in vacuo. The crude material was purified using flash chromatography (4% methanol/dichloromethane) followed by purification using prep HPLC to provide 1-(4-((7-(cyclopropanecarbonyl)-5H-pyrrolo[2,3-b]pyrazin-2-yl)amino)piperidin-1-yl)prop-2-en-1-one as a white solid (0.52 g, 29% yield): $^1$H NMR (400 MHz, DMSO-$d_6$ at 90° C.) δ 12.32 (s, 1H), 7.98 (s, 1H), 7.68 (s, 1H), 6.77-6.84 (m, 2H), 6.04-6.09 (m, 1H), 5.62-5.65 (m, 1H), 4.22-4.25 (m, 1H), 3.90-3.99 (m, 2H), 3.54-3.61 (m, 1H), 3.18-3.27 (m, 1H), 2.92-3.02 (m, 1H), 2.01-2.04 (m, 2H), 1.37-1.40 (m, 2H), 0.83-0.98 (m, 4H); MS (ES) m/z 340.1 (M+H).

Prep HPLC method:
Column: Inertsil ODS 3V (250 mm×4.6 mm×5 mic)
Mobile phase (A): 0.1% Ammonia in water
Mobile phase (B): ACN
Flow rate: 1.0 mL/min.

EXAMPLE 100
Preparation of 1-(4-((7-(cyclobutanecarbonyl)-5H-pyrrolo[2,3-b]pyrazin-2-yl)amino)piperidin-1-yl)prop-2-en-1-one
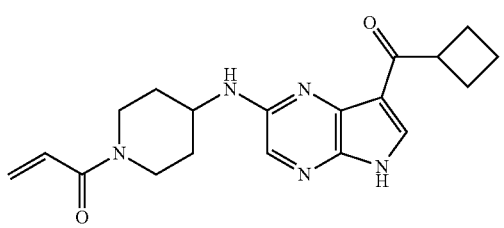 [SMILES: C=CC(=O)N1CCC(Nc2cnc3[nH]cc(C(=O)C4CCC4)c3n2)CC1]
The title compound was prepared by the method described in Scheme 36.
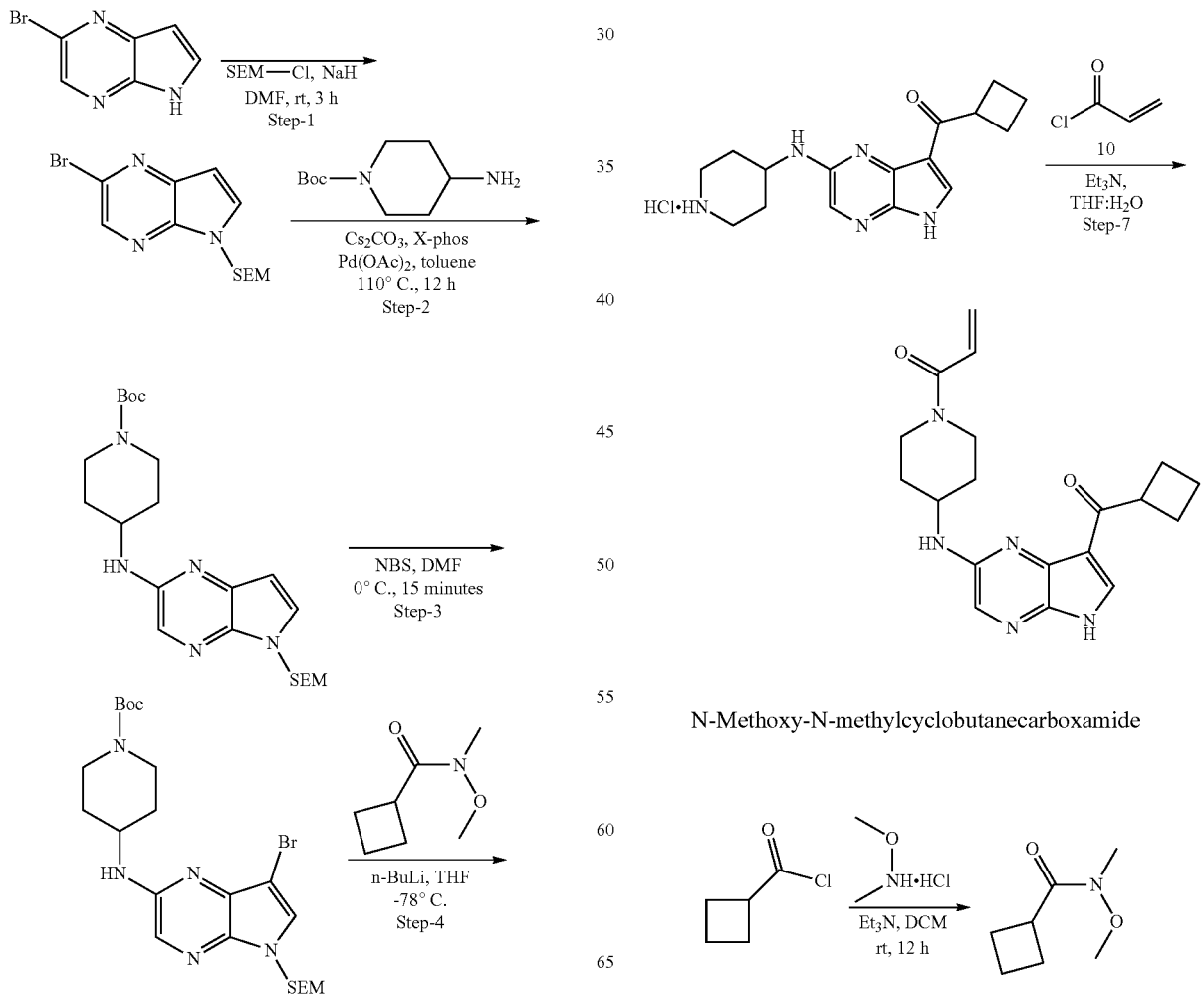
N-Methoxy-N-methylcyclobutanecarboxamide Preparation of
N-methoxy-N-methylcyclobutanecarboxamide

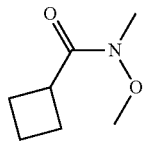

To a stirred solution of cyclobutanecarbonyl chloride (2.5 g, 21.18 mmol) in tetrahydrofuran (25 mL) was added triethylamine (3.2 mL, 31.7 mmol) and N,O-dimethyl hydroxylamine (2.28 g, 23.30 mmol) at 0° C. The reaction mixture was allowed to warm to ambient temperature and stir for 12 hours. The reaction was quenched with ice and extracted with ethyl acetate. The organic layer was washed with water, brine, dried over sodium sulfate, filtered and concentrated in vacuo. The crude material was purified using flash chromatography (12% ethyl acetate/hexane) to provide N-methoxy-N-methylcyclobutanecarboxamide as a viscous liquid (1.5 g, 50% yield): MS (ES) m/z 144.1 (M+H).

Step 1: Preparation of 2-bromo-5-((2-(trimethylsilyl) ethoxy) methyl)-5H-pyrrolo[2,3-b]pyrazine

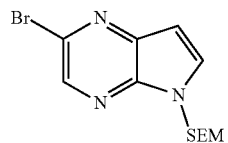 [SMILES: C[Si](C)(C)CCOCn1ccc2nc(Br)cnc21]

To a suspension of sodium hydride (1.25 g, 30.6 mmol, 60% mineral oil dispersion) in N,N-dimethylformamide (40 mL) was added 2-bromo-5H-pyrrolo[2,3-b]pyrazine (5.0 g, 25.5 mmol) at 0° C. The suspension was stirred for 0.5 hours and (2-chloromethoxyethyl)trimethylsilane (5.5 mL, 30.65 mmol) was slowly added at 0° C. The mixture was allowed to warm to ambient temperature and stir for an additional 3 hours. The reaction mixture was poured into ice water and extracted with ethyl acetate. The organic layer was washed with water, brine, dried over anhydrous sodium sulfate, filtered and concentrated in vacuo. The crude material was purified using flash chromatography (5% ethyl acetate/hexane) to provide 2-bromo-5-((2-(trimethylsilyl)ethoxy) methyl)-5H-pyrrolo[2,3-b]pyrazine as an off-white solid (7.5 g, 90% yield): MS (ES) m/z 328.0 (M+2H).

Step 2: Preparation of tert-butyl 4-((5-((2-(trimethylsilyl)ethoxy)methyl)-5H-pyrrolo[2,3-b]pyrazin-2-yl)amino)piperidine-1-carbo-xylate

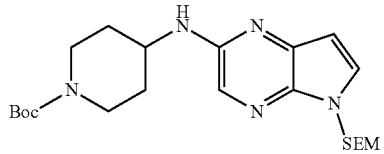 [SMILES: CC(C)(C)OC(=O)N1CCC(Nc2cnc3c(ccn3COCC[Si](C)(C)C)n2)CC1]

To a solution of 2-bromo-5-((2-(trimethylsilyl)ethoxy)methyl)-5H-pyrrolo[2,3-b]pyrazine (7.0 g, 21.47 mmol) in toluene (80 mL) was added tert-butyl 4-aminopiperidine-1-carboxylate (6.5 g, 32.20 mmol), cesium carbonate (10.56 g, 32.20 mmol), 2-dicyclohexylphosphino-2',4',6'-triisopropylbiphenyl (1.02 g, 2.14 mmol) and palladium(II) acetate (0.49 g, 2.14 mmol) under an argon atmosphere. The mixture was heated at 110° C. for 12 hours. After cooling the reaction mixture was filtered through celite and washed with ethyl acetate. The organic layer was washed with saturated sodium bicarbonate solution, brine, dried over anhydrous sodium sulfate, filtered and concentrated in vacuo. The crude material was purified using flash chromatography (50% ethyl acetate/hexane) to provide tert-butyl 4-((5-((2-(trimethylsilyl)ethoxy)methyl)-5H-pyrrolo[2,3-b]pyrazin-2-yl)amino)piperidine-1-carboxylate as a yellow oil (4.6 g, 48% yield): MS (ES) m/z 448.1 (M+H).

Step 3: Preparation of tert-butyl 4-((7-bromo-5-((2-(trimethylsilyl)ethoxy)methyl)-5H-pyrrolo[2,3-b] pyrazin-2-yl)amino)piperidine-1-carboxylate

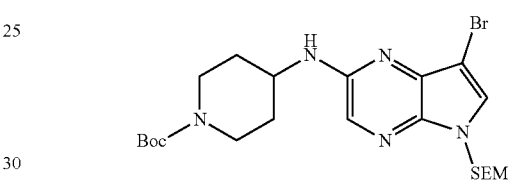

To a stirred solution of tert-butyl 4-((5-((2-(trimethylsilyl) ethoxy)methyl)-5H-pyrrolo[2,3-b]pyrazin-2-yl)amino)piperidine-1-carboxylate (4.5 g, 10.06 mmol) in N,N-dimethylformamide (50 mL) was added N-bromosuccinimide (1.6 g, 9.06 mmol) portion-wise and the mixture was stirred at 0° C. for 15 minutes. The reaction mixture was poured into ice water and extracted with ethyl acetate. The organic layer was washed with saturated sodium bicarbonate solution, brine, dried over sodium sulfate, filtered and concentrated in vacuo. The crude material was purified using flash chromatography (30% ethyl acetate/hexane) to provide tert-butyl 4-((7-bromo-5-((2-(trimethylsilyl)ethoxy)methyl)-5H-pyrrolo[2,3-b]pyrazin-2-yl)amino)piperidine-1-carboxylate as a brown solid (2.8 g, 52% yield): MS (ES) m/z 526.1 (M+H).

Step 4: Preparation of tert-butyl 4-((7-(cyclobutanecarbonyl)-5-((2-(trimethylsilyl)ethoxy)methyl)-5H-pyrrolo[2,3-b]pyrazin-2-yl)amino)piperidine-1-carboxylate

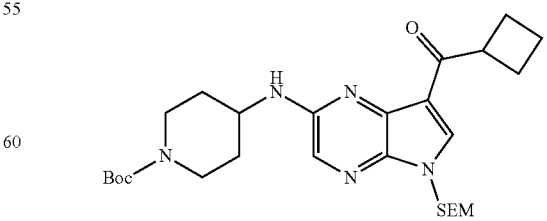

To a stirred solution of tert-butyl 4-((7-bromo-5-((2-(trimethylsilyl)ethoxy)methyl)-5H-pyrrolo[2,3-b]pyrazin-2-yl)amino)piperidine-1-carboxylate (1.5 g, 2.84 mmol) in tetrahydrofuran (40 mL) was added n-butyllithium (7.1 mL, 14.28 mmol, 1.6 M in hexane) at −78° C. The reaction mixture was stirred for 20 minutes and then a solution of N-methoxy-N-methylcyclobutane carboxamide (2.03 mL, 14.28 mmol) in tetrahydrofuran (5 mL) was added at −78° C. and stirred for 2 hours. The reaction mixture was quenched with saturated ammonium chloride solution and extracted with ethyl acetate. The organic layer was washed with water, brine, dried over anhydrous sodium sulfate, filtered and concentrated in vacuo. The crude material was purified using flash chromatography (30% ethyl acetate/hexane) to provide tert-butyl 4-((7-(cyclobutane-carbonyl)-5-((2-(trimethylsilyl)ethoxy)methyl)-5H-pyrrolo[2,3-b]pyrazin-2-yl)amino)piperidine-1-carboxylate as a brown solid (0.75 g, crude): MS (ES) m/z 530.2 (M+H).

Step 5: Preparation of tert-butyl 4-((7-(cyclobutanecarbonyl)-5H-pyrrolo[2,3-b]pyrazin-2-yl)amino)piperidine-1-carboxylate

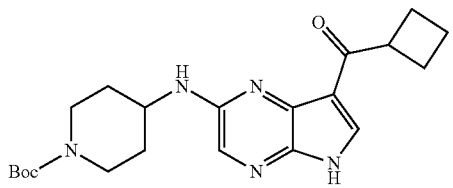 [SMILES: CC(C)(C)OC(=O)N1CCC(Nc2cnc3[nH]cc(C(=O)C4CCC4)c3n2)CC1]

To a stirred solution of tert-butyl 4-((7-(cyclobutanecarbonyl)-5-((2-(trimethylsilyl)ethoxy)methyl)-5H-pyrrolo[2,3-b]pyrazin-2-yl)amino)piperidine-1-carboxylate (0.8 g, 1.51 mmol) in tetrahydrofuran (10 mL) was added tetrabutylammonium fluoride (20 mL, 1M solution in tetrahydrofuran) and the mixture heated to 80° C. for 12 hours. After cooling the reaction mixture was quenched with saturated ammonium chloride solution and extracted with ethyl acetate. The organic layer was washed with water, brine and dried over anhydrous sodium sulfate. The solution was filtered and concentrated in vacuo. The crude material was purified using flash chromatography (30% ethyl acetate/hexane) to provide tert-butyl 4-((7-(cyclobutanecarbonyl)-5H-pyrrolo[2,3-b]pyrazin-2-yl)amino)piperidine-1-carboxylate as a viscous liquid (0.28 g, 49% yield): MS (ES) m/z 400.2 (M+H).

Step 6: Preparation of cyclobutyl(2-(piperidin-4-ylamino)-5H-pyrrolo[2,3-b]pyrazin-7-yl)methanone hydrogen chloride

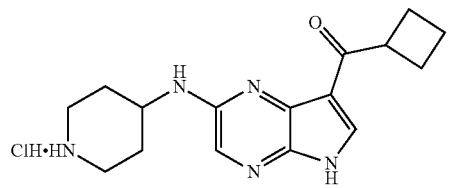

To a solution of tert-butyl 4-((7-(cyclobutanecarbonyl)-5H-pyrrolo[2,3-b]pyrazin-2-yl)amino)piperidine-1-carboxylate (0.28 g, 0.70 mmol) in dichloromethane (5 mL) was added a solution of hydrogen chloride (5.0 mL, 4 M in dioxane) at 0° C. and the mixture was warmed to ambient temperature and stirred for 3 hours. The reaction was concentrated in vacuo to provide cyclobutyl(2-(piperidin-4-ylamino)-5H-pyrrolo[2,3-b] pyrazin-7-yl)methanone hydrochloride as a viscous liquid (0.16 g, crude): MS (ES) m/z 300.1 (M+H).

Step 7: Preparation of 1-(4-((7-(cyclobutanecarbonyl)-5H-pyrrolo[2,3-b]pyrazin-2-yl)amino)piperidin-1-yl)prop-2-en-1-one

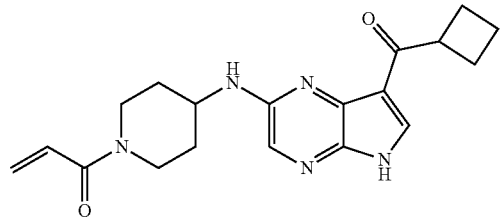 [SMILES: C=CC(=O)N1CCC(Nc2cnc3[nH]cc(C(=O)C4CCC4)c3n2)CC1]

To a stirred solution of cyclobutyl(2-(piperidin-4-ylamino)-5H-pyrrolo[2,3-b]pyrazin-7-yl)methanone hydrogen chloride (0.16 g, 0.47 mmol) in tetrahydrofuran:water (8:2 mL) was added triethylamine (0.07 mL, 0.71 mmol) and a solution of acryloyl chloride (0.03 mL, 0.36 mmol) in tetrahydrofuran (0.5 mL) at 0° C. and the mixture stirred for 10 minutes. The reaction mixture was quenched with saturated sodium bicarbonate solution and extracted into ethyl acetate. The organic layer was washed with water, saturated sodium bicarbonate solution, brine, filtered and concentrated in vacuo. The crude material was purified using flash chromatography (10% methanol/dichloromethane) to provide 1-(4-((7-(cyclobutanecarbonyl)-5H-pyrrolo[2,3-b]pyrazin-2-yl)amino)piperidin-1-yl)prop-2-en-1-one as an off-white solid (0.04 g, 25% yield): $^1$H NMR (400 MHz, DMSO-d$_6$) δ 12.72 (d, J=15.2 Hz, 1H), 7.99 (s, 1H), 7.65 (s, 1H), 6.80-6.87 (m, 2H), 6.09 (dd, J=2.4 Hz, J=14.4 Hz, 1H), 5.65 (dd, J=2.4 Hz, J=8.4 Hz, 1H), 4.29-4.42 (m, 2H), 4.02-4.03 (m, 2H), 2.95-3.01 (m, 1H), 2.46-2.48 (m, 2H), 2.20 (q, J=8.0 Hz, 2H), 2.00-2.08 (m, 3H), 1.91-1.98 (m, 1H), 1.74-1.79 (m, 1H), 1.38-1.40 (m, 2H); MS (ES) m/z 354.1 (M+H).

EXAMPLE 101

Preparation of 1-(4-((3-(1-cyclopropyl-2-methoxyethyl)-1H-pyrrolo[2,3-b]pyridin-5-yl)amino)piperidin-1-yl)prop-2-en-1-one

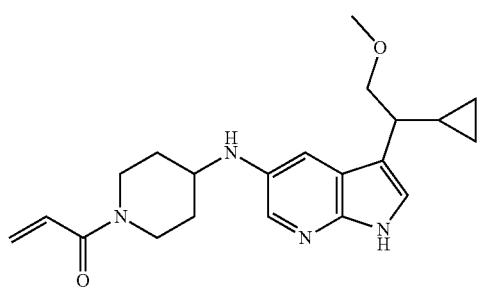 [SMILES: C=CC(=O)N1CCC(Nc2cnc3[nH]cc(C(COC)C4CC4)c3c2)CC1]

The title compound was prepared by the method described in Scheme 37.

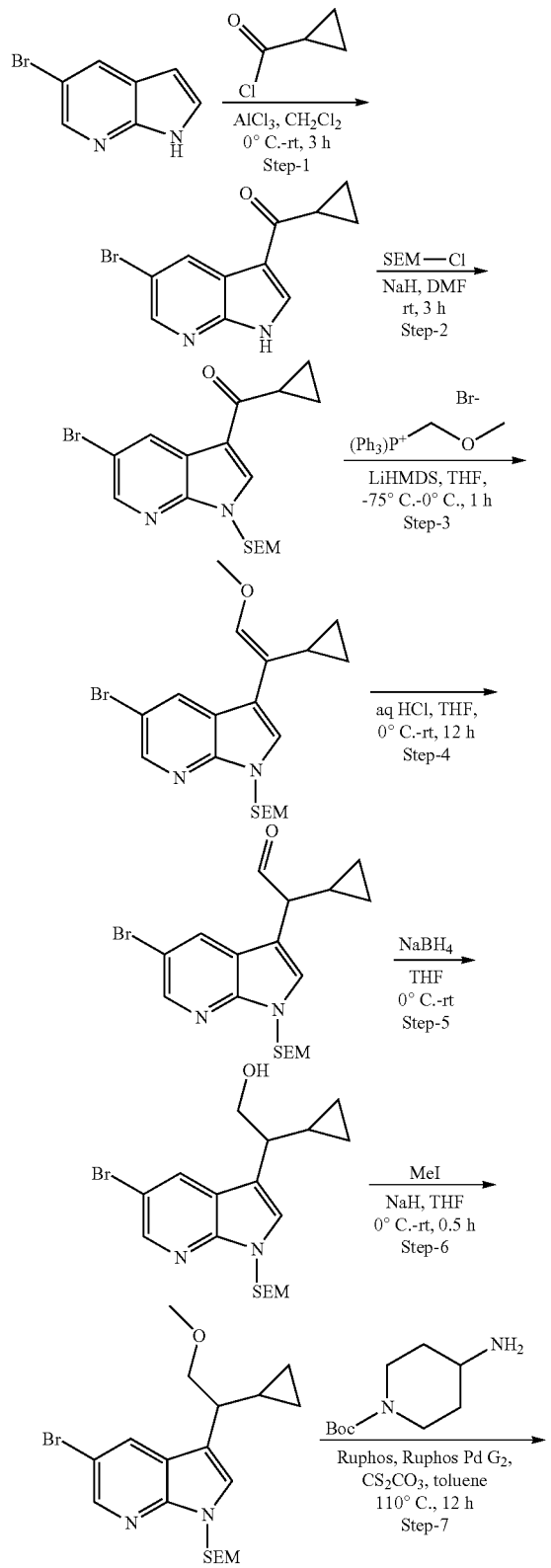

Scheme 37. Preparation of 1-(4-((3-(1-cyclopropyl-2-methoxyethyl)-1H-pyrrolo[2,3-b]pyridin-5-yl)amino)piperidin-1-yl)prop-2-en-1-one

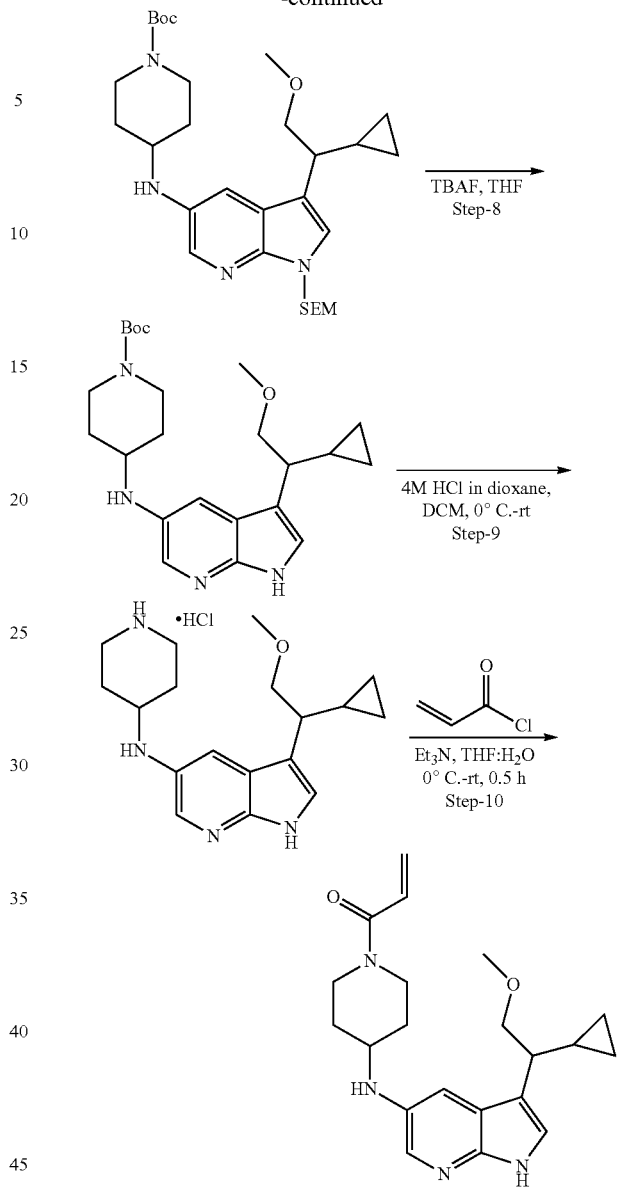

Step 1: Preparation of (5-bromo-1H-pyrrolo[2,3-b]pyridine-3-yl)(cyclopropyl)methanone To a solution of 5-bromo-1H-pyrrolo[2,3-b]pyridine (5.0 g, 25.51 mmol) in dichloromethane (100 mL) was added aluminum chloride (10.20 g, 76.53 mmol) portion-wise at 0° C. followed by cyclopropane carbonyl chloride (5.02 mL, 76.53 mmol) dropwise at the same temperature. The reaction mixture was warmed to ambient temperature and was stirred for 3 hours. The reaction mixture was quenched with ice water and extracted with 500 methanol in dichloromethane. The organic layer was washed with brine, dried over anhydrous sodium sulfate, filtered and concentrated in vacuo to provide 5-bromo-1H-pyrrolo[2,3-b]pyridine-3-yl) cyclopropyl)methanone as an off-brown solid (4.2 g, 62%): MS (ES) m/z 265.1 (M+H).

Step 2: Preparation of (5-bromo-1-((2-(trimethylsilyl)ethoxy)methyl)-1H-pyrrolo[2,3-b]pyridin-3-yl)(cyclopropyl)methanone

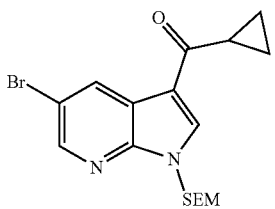 [SMILES: C[Si](C)(C)CCOCn1cc(C(=O)C2CC2)c2cc(Br)cnc21]

To a suspension of sodium hydride (0.90 g, 22.71 mmol, 60% mineral oil dispersion) in N,N-dimethylformamide (30 mL) was added (5-bromo-1H-pyrrolo[2,3-b]pyridin-3-yl)(cyclopropyl)methanone (5 g, 18.93 mmol) at 0° C. followed by 2-(trimethylsilyl)-ethoxymethylchloride (4.09 mL, 22.71 mmol). The reaction mixture was warmed to ambient temperature and stirred for 3 hours. The reaction mixture was quenched into ice water and extracted with ethyl acetate. The organic layer was washed with water, brine, dried over anhydrous sodium sulfate, filtered and concentrated in vacuo. The crude material was purified using flash chromatography (7% ethyl acetate/hexane) to provide (5-bromo-1-((2-(trimethylsilyl)ethoxy)methyl)-1H-pyrrolo[2,3-b]pyridin-3-yl)(cyclopropyl)methanone as an off-white solid (5 g, 67% yield): MS (ES) m/z 395.1 (M+H).

Step 3: Preparation of (E)-5-bromo-3-(1-cyclopropyl-2-methoxyvinyl)-1-((2-(trimethylsilyl)ethoxy)methyl)-1H-pyrrolo[2,3-b]pyridine

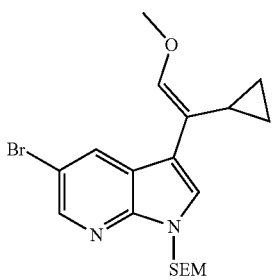 [SMILES: CO/C=C(/c1cn(COCC[Si](C)(C)C)c2ncc(Br)cc12)C1CC1]

To a solution of (5-bromo-1-((2-(trimethylsilyl)ethoxy)methyl)-1H-pyrrolo[2,3-b]pyridine-3-yl)(cyclopropyl)methanone (15.0 g, 3.04 mmol) in tetrahydrofuran (20 mL) was added lithium bis(trimethylsilyl)amide (9.13 mL, 9.91 mmol 1M in tetrahydrofuran) at −78° C. and the mixture stirred for 1 hour. A solution of (methoxymethyl)triphenylphosphonium bromide (3.53 g, 9.13 mmol) in tetrahydrofuran (15 mL) was added at the same temperature and the mixture stirred at ambient temperature for 12 hours. The reaction mixture was quenched with saturated aqueous ammonium chloride and extracted with ethyl acetate. The organic layer was washed with brine, dried over anhydrous sodium sulfate and concentrated in vacuo. The crude material was purified by flash chromatography (8% ethyl acetate/hexane) to provide (E)-5-bromo-3-(1-cyclopropyl-2-methoxyvinyl)-1-((2-(trimethylsilyl)ethoxy)methyl-1H-pyrrolo[2,3-b]pyridine as a pale yellow oil (1.2 g, 75% yield): MS (ES) m/z 423.1 (M+H).

Step 4: Preparation of 2-(5-bromo-1-((2-(trimethylsilyl)ethoxy)methyl)-1H-pyrrolo[2,3-b]pyridine-3-yl)-2-cyclopropyl Acetaldehyde

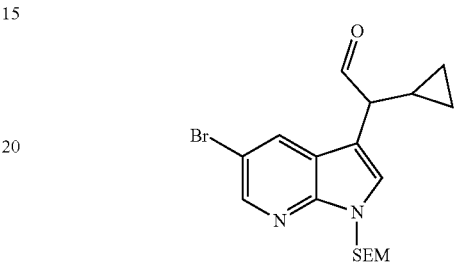

To a solution of (E)-5-bromo-3-(1-cyclopropyl-2-methoxyvinyl)-1-((2-(trimethylsilyl)ethoxy)methyl-1H-pyrrolo[2,3-b]pyridine (1.2 g, 2.84 mmol) in tetrahydrofuran (10 mL) was added hydrochloric acid (10 mL) at 0° C. and the mixture stirred at ambient temperature for 12 hours. The reaction mixture was quenched with ice and extracted with ethyl acetate. The organic layer was washed with water, saturated aqueous sodium bicarbonate, brine, dried over anhydrous sodium sulfate, filtered and concentrated in vacuo. The crude material was purified by flash chromatography (10% ethyl acetate/hexane) to provide 2-(5-bromo-1-((2-(trimethylsilyl)ethoxy)methyl)-1H-pyrrolo[2,3-b]pyridine-3-yl)-2-cyclopropyl acetaldehyde as a pale brown oil (0.51 g, 44% yield): MS (ES) m/z 411.1 (M+3H).

Step 5: Preparation of 2-(5-bromo-1-((2-(trimethylsilyl)ethoxy)methyl)-1H-pyrrolo[2,3-b]pyridine-3-yl)-2-cyclopropylethan-1-ol

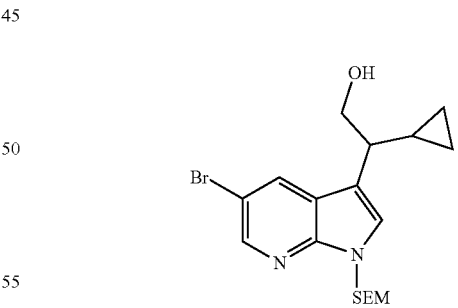

To a solution of 2-(5-bromo-1-((2-(trimethylsilyl)ethoxy)methyl)-1H-pyrrolo-[2,3-b]pyridine-3-yl)-2-cyclopropyl acetaldehyde (0.52 g, 1.27 mmol) in tetrahydrofuran: methanol ((8:0.5 mL) was added sodium borohydride (0.1 g, 2.54 mmol) at 0° C. and the mixture was stirred at ambient temperature for 2 hours. The reaction mixture was quenched with ice water and extracted with ethyl acetate. The combined organic layers were washed with water, brine, dried over anhydrous sodium sulfate, filtered and concentrated in vacuo to provide 2-(5-bromo-1-((2-(trimethylsilyl)ethoxy)

methyl)-1H-pyrrolo[2,3-b]pyridine-3-yl)-2-cyclopropyl-ethan-1-ol as a colorless oil (0.37 g, 71% yield): MS (ES) m/z 413.1 (M+3H).

Step 6: Preparation of 5-bromo-3-(1-cyclopropyl-2-methoxyethyl)-1-((2-(trimethylsilyl)ethoxy)methyl)-1H-pyrrolo[2,3-b]pyridine

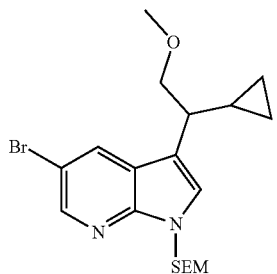 [SMILES: COCC(c1cn(COCC[Si](C)(C)C)c2ncc(Br)cc12)C1CC1]

A suspension of sodium hydride (0.04 g, 1.80 mmol, 60% mineral oil dispersion) in tetrahydrofuran (10 mL) was cooled to 0° C. and 2-(5-bromo-1-((2-(trimethylsilyl)ethoxy)methyl)-1H-pyrrolo[2,3-b]pyridine-3-yl)-2-cyclopropylethan-1-ol (0.37 g, 0.9 mmol) was added followed by addition of iodomethane (0.11 mL, 1.80 mmol). The resulting mixture was stirred for 0.5 hours at 0° C. The reaction mixture was warmed to ambient temperature and stirred for another 2 hours. The reaction mixture was quenched with ice water and extracted with ethyl acetate. The organic layer was washed with water, brine, dried over anhydrous sodium sulfate, filtered and concentrated in vacuo. The crude material was purified by flash chromatography (10% ethyl acetate/hexane) to provide 5-bromo-3-(1-cyclopropyl-2-methoxyethyl)-1-((2-(trimethylsilyl)ethoxy)methyl)-1H-pyrrolo[2,3-b]pyridine as a colorless oil (0.3 g, 79% yield): MS (ES) m/z 425.1 (M+H).

Step 7: Preparation of tert-butyl 4-((3-(1-cyclopropyl-2-methoxyethyl)-1-((2-(trimethylsilyl)ethoxy)methyl)-1H-pyrrolo [2,3-b] pyridine-5-yl) amino) piperidine-1-carboxylate

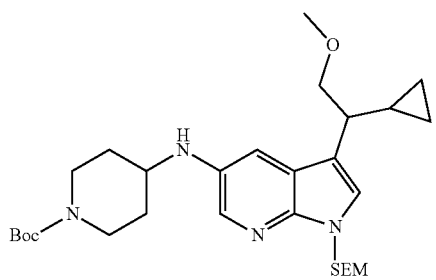 [SMILES: COCC(c1cn(COCC[Si](C)(C)C)c2ncc(NC3CCN(C(=O)OC(C)(C)C)CC3)cc12)C1CC1]

To a solution of 5-bromo-3-(1-cyclopropyl-2-methoxyethyl)-1-((2-(trimethylsilyl)ethoxy)methyl)-1H-pyrrolo[2,3-b]pyridine (0.25 g, 0.59 mmol) in toluene (10 mL) was added tert-butyl 4-aminopiperidine-1-carboxylate (0.23 g, 1.17 mmol), cesium carbonate (0.38 g, 1.17 mmol), Ruphos (0.01 g, 0.03 mmol) followed by Ruphos PdG$_2$ (0.01 g, 0.001 mmol) under an argon atmosphere and the resulting mixture was heated in a sealed to 110° C. for 12 hours. After cooling the reaction mixture was filtered through celite and the filtrate was concentrated in vacuo. The crude material was purified by flash chromatography (30% ethyl acetate/hexane) to provide tert-butyl 4-((3-(1-cyclopropyl-2-methoxyethyl)-1-((2-(trimethylsilyl)ethoxy)methyl)-1H-pyrrolo[2,3-b]pyridine-5-yl)amino)piperidine-1-carboxylate as a brown oil (0.19 g, 59% yield): MS (ES) m/z 545.3 (M+H).

Step 8: Preparation of tert-butyl 4-((3-(1-cyclopropyl-2-methoxyethyl)-1H-pyrrolo[2,3-b]pyridine-5-yl)amino)piperidine-1-carboxylate

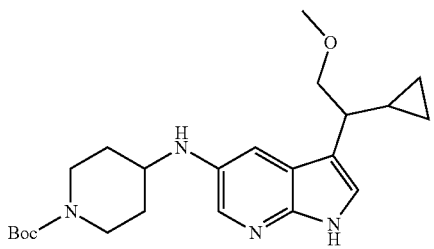 [SMILES: COCC(c1c[nH]c2ncc(NC3CCN(C(=O)OC(C)(C)C)CC3)cc12)C1CC1]

To a solution of tert-butyl 4-((3-(1-cyclopropyl-2-methoxyethyl)-1-((2-(trimethylsilyl) ethoxy)methyl)-1H-pyrrolo[2,3-b]pyridine-5-yl)amino)piperidine-1-carboxylate (0.19 g, 0.35 mmol) in tetrahydrofuran (5 mL) was added tetrabutylammonium fluoride (1.7 mL, 1.74 mmol, 1 M in tetrahydrofuran) and the solution was heated to 80° C. for 16 hours. After cooling the reaction mixture was poured into ice water and extracted with ethyl acetate. The organic layer was washed with water, brine, dried over anhydrous sodium sulfate, filtered and concentrated in vacuo. The crude material was purified using flash chromatography (5% methanol/dichloromethane) to provide tert-butyl 4-((3-(1-cyclopropyl-2-methoxyethyl)-1H-pyrrolo[2,3-b]pyridine-5-yl)amino)piperidine-1-carboxylate as light brown oil (0.09 g, 66% yield): MS (ES) m/z 415.2 (M+H).

Step 9: Preparation of 3-(1-cyclopropyl-2-methoxyethyl)-N-(piperidine-4-yl)-1H-pyrrolo[2,3-b]pyridine-5-amine Hydrochloride

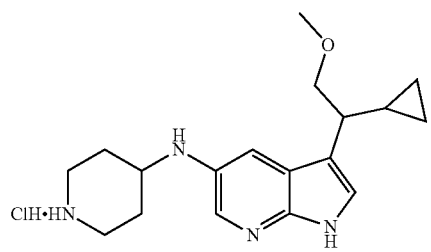

To a solution of tert-butyl 4-((3-(1-cyclopropyl-2-methoxyethyl)-1H-pyrrolo[2,3-b]pyridine-5-yl)amino)piperidine-1-carboxylate (0.09 g, 0.23 mmol) in dichloromethane (5 mL) was added was added a solution of hydrogen chloride (2 mL, 4 M in dioxane) at 0° C. and the mixture was stirred at ambient temperature for 3 hours. The reaction mixture was concentrated in vacuo and the residue was washed with diethyl ether to provide 3-(1-cyclopropyl-2-methoxyethyl)-N-(piperidine-4-yl)-1H-pyrrolo[2,3-b]pyridine-5-amine hydrochloride as an off-white solid (0.06 g, crude). The crude product was progressed for next stage.

Step 10: Preparation of 1-(4-((3-(1-cyclopropyl-2-methoxyethyl)-1H-pyrrolo[2,3-b]pyridine-5-yl) amino)piperidine-1-yl)prop-2-en-1-one

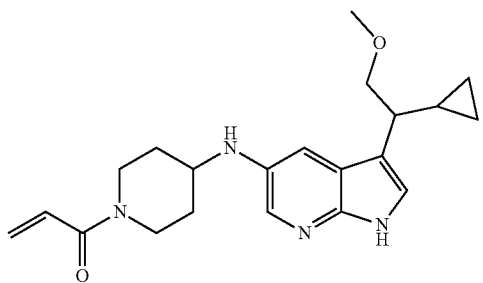 [SMILES: C=CC(=O)N1CCC(Nc2cnc3[nH]cc(C(COC)C4CC4)c3c2)CC1]

To a solution of 3-(1-cyclopropyl-2-methoxyethyl)-N-(piperidine-4-yl)-1H-pyrrolo[2,3-b]pyridine-5-amine hydrochloride (0.06 g, 0.19 mmol) in tetrahydrofuran:water (10:2 mL) was added triethylamine (0.05 mL, 0.38 mmol) and a solution of acryloyl chloride (0.02 mL, 0.19 mmol) in tetrahydrofuran (0.3 mL). The mixture was stirred at 0° C. for 0.5 hours and then quenched with aqueous sodium bicarbonate and extracted with ethyl acetate. The organic layer was washed with brine, dried over anhydrous sodium sulfate, filtered and concentrated in vacuo. The crude material was purified using flash chromatography (5% methanol/dichloromethane) to provide 1-(4-((3-(1-cyclopropyl-2-methoxyethyl)-1H-pyrrolo[2,3-b]pyridine-5-yl)amino) piperidine-1-yl)prop-2-en-1-one as a white solid (0.01 g, 13% yield): $^1$H NMR (400 MHz, DMSO-$d_6$) δ 10.79 (s, 1H), 7.71 (d, J=2.4 Hz, 1H), 7.12 (d, J=2.4 Hz, 1H), 7.04 (d, J=2.0 Hz, 1H), 6.77-6.84 (m, 1H), 6.06 (dd, J=16.8, 2.4 Hz, 1H), 5.63 (dd, J=10.4, 2.4 Hz, 1H), 4.95 (d, J=8.4 Hz, 1H), 4.25 (d, J=11.6 Hz, 1H), 3.98 (d, J=12.0 Hz, 1H), 3.61 (d, J=6.8 Hz, 2H), 3.44-3.55 (m, 1H), 3.21 (s, 4H), 2.89-2.97 (m, 1H), 1.95-2.01 (m, 3H), 1.03-1.12 (m, 1H), 0.84-0.89 (m, 2H), 0.29-0.49 (m, 2H), 0.06-0.20 (m, 2H); MS (ES) m/z 369.2 (M+H).

Biological Activity Assay
ITK Inhibitor Binding Potency

The ability of candidate compounds to interact with ITK is quantitated by a competitive binding assay using the LanthaScreen technology developed by Life Technologies. This assay is based on the binding of a proprietary, Alexa Fluor® 647-labeled, ATP-competitive kinase inhibitor (kinase tracer-236) to the ITK expression construct in the presence of a Europium-conjugated antibody, resulting in a FRET (fluorescence resonance energy transfer) signal. Displacement of the kinase tracer by compound results in a lower emission ratio upon excitation of the Europium chelate. Candidate compounds are designed as potential irreversible inhibitors of ITK, capable of ligating to an active site cysteine residue resulting in time dependent covalent binding. The time dependent nature of irreversible inhibition is investigated by performing the binding assay with and without a pre-incubation of compound and ITK. An increase in potency in the pre-incubated assay suggests the candidate compound could be irreversibly modifying ITK or having a slowly reversible mechanism. The inhibitory potency of candidate compounds is measured in 20 mM HEPES pH 7.5, 10 mM $MgCl_2$, 0.01% BSA, 0.0005% Tween-20, and 2% DMSO in the presence of 10 nM ITK, 2 nM Eu-anti-GST antibody, and 50 nM kinase tracer-236 using a 384-well plate format. Background signal is defined in the absence of ITK and uninhibited signal is defined in the presence of vehicle (2% DMSO) alone. Compounds were evaluated in an 11 point dose-response ranging from 20 uM to 0.34 nM. The binding assays are performed under two preincubation conditions to evaluate time dependence of inhibition. For the pre-incubation assay, ITK and Eu-anti-GST antibody are pre-incubated with compound or vehicle for two hours prior to the addition of kinase tracer. The non-preincubated assay is run under conditions where ITK and Eu-anti-GST antibody are added to a mixture of compound and kinase tracer. $IC_{50}$ values of compounds are determined using a 4 parameter logistical fit of emission ratio as a function of the concentration of compound.

ITK Inhibitor Binding Kinetics

To obtain a better understanding of the kinetics of binding by inhibitor compounds to ITK, association and dissociation experiments were performed. Using the same TR-FRET buffer and conditions as described above, the kinetic rate constants for the binding of KT-236 to ITK were initially determined. Once knowing the association (kon) and dissociation (koff) rates of KT-236 binding, the binding kinetics for these candidate compounds could be further elucidated. The dissociation rates were determined by pre-incubating ITK for two hours with various concentrations of the candidate compounds. After this period of time, excess (200 nM final) KT-236 was added to the incubation and the resulting increase in fluorescence followed for approximately four hours. For the association rates, ITK was pre-incubated with KT-236 (50 nM) for 90-120 minutes and then various concentrations of candidate compound added. The resulting decrease in signal was then evaluated for the next two hours. Data from both sets of time course experiments was then analyzed using Dynafit software to obtain the kinetic rate constants (kon, koff, kinact, Ki) utilizing multiple reaction models.

ITK Target Modulation Assay

Target modulation was based upon the ability of a compound to inhibit ITK phosphorylation of its substrate, PLCγ1, at Y783. Human Jurkat T cells (ATCC TIB-152) were plated in V-bottom 96 well plates at 400,000 cells/well in 80 μL medium (RPMI1640 with 10% heat inactivated serum and 55 μM 2-mercaptoethanol and supplemented with glutamine/penicillin/streptomycin). Compounds were added as 10 μL of 10× working stock solutions in medium with 1% DMSO (or medium with 1% DMSO for controls) and placed in a 37° C. incubator with gentle shaking for 1 hour. Stimulation was carried out using anti-CD3 Dynabeads (Invitrogen catalog #11151D) to activate the T cell receptor and mimic antigen presenting cells. Beads were washed and resuspended in medium at 1.84×10^8 beads/ml. Beads were added rapidly to all compound containing and stimulation only wells at 10 μL/well (bead:cell=2:1) with gentle mixing of the bead source between each addition. Wells designated 'unstimulated' received 10 μL of media only. The plate was immediately sealed with a plate seal and cells pelleted at 400×g for 4 minutes. Media was removed using a multichannel aspirator, 25 μL of cold hypotonic lysis buffer (VWR M334-100 ml) plus 1× HALT Protease Inhibitor Cocktail (ThermoFisher #78437), 1× Phosphatase Inhibitor Cocktail 2 (Sigma Aldrich #P5726), 1× Phosphatase Inhibitor Cocktail 3 (Sigma Aldrich #P0044) and 2 mM PMSF was added per well. Cells were incubated on ice for 30 minutes to swell the cells then lysed by pipetting 20 times using a multichannel pipet. The plates were then resealed and centrifuged for 5 minutes at 400×g to pellet the cellular debris. Two µL of the soluble component of each sample was spotted onto nitrocellulose and allowed to dry for 30 minutes. Nitrocellulose was wet in 1× Tris Buffer Saline (20 mM Tris pH7.5, 150 mM NaCl) then blocked in LiCOR Odyssey Blocking Buffer (TBS) (LiCOR #927-50000) for 1 hour at room temperature with rocking. Following blocking, nitrocellulose was incubated in LiCOR Odyssey Blocking Buffer (TBS) plus 0.2% Tween20 plus anti-phospho-PLCγ1 (Y783) antibody (CST #2821S) at 1:1000 and anti-PLCγ1 (Abcam #41433) at 1:5000 with gentle rocking overnight at 4° C. Nitrocellulose was then washed four times for 5 minutes each with TBS plus 0.1% Tween20 (TBST) then incubated in LiCOR Odyssey Blocking Buffer (TBS) plus 0.2% Tween20 plus secondary antibodies IRDye 800CW (LiCOR 926-32211) and IRDye 680RD (LiCOR 926-68070) both at 1:15,000 with gentle rocking at room temperature in the dark for 1 hour. Nitrocellulose was then washed four times for 5 minutes each with TBST at room temperature in the dark. A final rinse with TBS was done prior to imaging and quantifying using the LiCOR Odyssey Imager and software respectively.

JAK3 Enzyme Activity Assays

The ability of candidate compounds to interact with JAK3 is quantitated by a mobility shift assay using an LC3000 instrument developed by Caliper Life Sciences. This assay is based on mobility shift electrophoresis, in which fluorescently labelled product and fluorescently labelled substrate peaks are separated and detected independently. JAK3 product/substrate separation is obtained using the following instrument settings: Pressure=−1.4 psi, Downstream voltage=−2550V and Upstream voltage=−800V. The inhibitory potency of candidate compounds of JAK3 is measured in 20 mM HEPES pH 7.5, 10 mM $MgCl_2$, 0.01% BSA, 0.0005% Tween-20, and 2% DMSO in the presence of 2.5 nM JAK3 (Life Technologies Catalog #PV3855), 1 mM SRCtide (Anaspec Catalog #AS-64106) and 16 mM ATP (Km level) using a 384-well plate format. Background signal is defined in the absence of enzyme and uninhibited signal is defined in the presence of vehicle (2% DMSO) alone. Compounds were evaluated in an 11 point dose-response ranging from 20 mM to 0.34 nM. $IC_{50}$ values of compounds are determined using a 4 parameter logistical fit of emission ratio as a function of the concentration of compound. The results are shown in Table 2.

JAK1/3 Target Modulation Assay

Target modulation was based upon the ability of a compound to inhibit JAK1/3 phosphorylation of its substrate, STAT5, at Y694. Primary human peripheral blood mononuclear cells were plated in V-bottom 96 well plates at 200,000 cells/well in 120 µL medium (RPMI-1640 with 10% fetal bovine serum, 10 mM HEPES buffer, 12.2 mM 2-mercaptoethanol, and supplemented with glutamine/penicillin/streptomycin). Compounds were added as 15 µL of 10× working stock solutions in medium with 1% DMSO (or medium with 1% DMSO for controls) and placed in a 37° C. incubator with gentle shaking for 1 hour. Stimulation was carried out using recombinant human IL-2 (R&D Systems #202-IL-050) to activate JAK1/3. IL-2 stock solution was diluted in media to 250 ng/mL and was added rapidly to all compound containing and stimulation only wells at 15 µL/well (final concentration=25 ng/mL). Wells designated 'unstimulated' received 15 µL of media only. The plate was placed back in a 37° C. incubator with gentle shaking for 5 minutes. After stimulation, the plates were immediately sealed with a plate seal, and cells pelleted at 400×g for 5 minutes. Media was removed using a multichannel aspirator, and 75 µL of cold Tris lysis buffer (MSD #$R_{60}$TX-3) plus 1× Protease Inhibitor Solution (MSD #$R_{70}$AA-1), 1× Phosphatase Inhibitor I (MSD #$R_{70}$AA-1), and 1× Phosphatase Inhibitor II (MSD #$R_{70}$AA-1) was added per well. Cells were incubated at 4° C. with gentle shaking for at least 30 minutes to allow for complete lysis. The plates were removed from 4° C., and 25 µL of lysate from each well was added to the corresponding well on the MSD plate. Samples were analyzed by either an MSD multiplex kit for Phospho-STAT5a,b/Total-STAT5a,b (MSD #K15163D) or an MSD single-plex kit for Phospho-STAT5a,b (MSD #K150IGD). The protocols for the respective kits were followed, and the plates were read on the MSD SECTOR S 600.

Dual Stimulation IFNγ Release Assay

This assay is based on the ability of signaling downstream of the T cell receptor (ITK-dependent) and IL-15 receptor (JAK3 dependent) to synergistically induce transcription of the IFNγ gene and release of IFNγ protein from human peripheral blood mononuclear cells (PBMC). $2 \times 10^5$ PBMC are plated in a 96-well plate with compound dilutions (final DMSO—0.1%), soluble αCD3 antibody (BioLegend #300432) at a final concentration of 0.01 µg/ml and human IL-15 (R&D Systems #247-ILB-005) at a final concentration of 100 ng/ml in a final volume of 200 µl/well. Cells were incubated overnight at 37° C. and 150 µl supernatant harvested and analyzed for IFNγ levels using the V-PLEX Human IFNγ Kit (MSD, #K151QOD-2). To the remaining 50 µl of cells, 50 µl of CTG (CellTiterGlo® Luminescent Cell Viability Assay, Promega #G7572) and luminescent signal read in white plate as a measure of cell number.

BTK Target Modulation Assay

Target modulation was based upon the ability of a compound to inhibit BTK phosphorylation of its substrate, PLCγ2, at Y1217. Human Ramos B cells (ATCC CRL-1596) were plated in V-bottom 96 well plates at 250,000 cells/well in 80 µL medium (RPMI1640 with 55 µM 2-mercaptoethanol). Compounds were added as 10 µL of 10× working stock solutions in medium with 1% DMSO (or medium with 1% DMSO for controls) and placed in a 37° C. incubator with gentle shaking for 1 hour. Stimulation was carried out using αIgM (Jackson ImmunoResearch catalog #109-006-129) to activate the B cell receptor and mimic antigen presenting cells. αIgM was added rapidly to all compound containing and stimulation only wells at 10 µL/well. Wells designated 'unstimulated' received 10 µL of media only. The plate was immediately sealed with a plate seal and cells pelleted at 400×g for 4 minutes. Media was removed using a multichannel aspirator, 25 µL of cold hypotonic lysis buffer (VWR M334-100 ml) plus 1× HALT Protease Inhibitor Cocktail (ThermoFisher #78437), 1× Phosphatase Inhibitor Cocktail 2 (Sigma Aldrich #P5726), 1× Phosphatase Inhibitor Cocktail 3 (Sigma Aldrich #P0044) and 2 mM PMSF was added per well. Cells were incubated on ice for 30 minutes to swell the cells then lysed by pipetting 20 times using a multichannel pipet. The plates were then resealed and centrifuged for 5 minutes at 400×g to pellet the cellular debris. Two µL of the soluble component of each sample was spotted onto nitrocellulose and allowed to dry for 30 minutes. Nitrocellulose was wet in 1× Tris Buffer Saline (20 mM Tris pH7.5, 150 mM NaCl) then blocked in LiCOR Odyssey Blocking Buffer (TBS) (LiCOR #927-50000) for 1 hour at room temperature with rocking. Following blocking, nitrocellulose was incubated in LiCOR Odyssey Blocking Buffer (TBS) plus 0.2% Tween20, with anti-phospho-PLCγ2 (Y1217) antibody (CST #3871) at 1:1000 and anti-PLCγ2 (B-10 SC-5283) at 1:1000, overnight at 4° C. while gently rocking. Nitrocellulose was then washed four times for 5 minutes each with TBS plus 0.1% Tween20 (TBST) then incubated in LiCOR Odyssey Blocking Buffer (TBS) plus 0.2% Tween20 plus secondary antibodies IRDye 800CW (LiCOR 926-32211) and IRDye 680RD (LiCOR 926-68070) both at 1:15,000 with gentle rocking at room temperature in the dark for 1 hour. Nitrocellulose was then washed four times for 5 minutes each with TBST at room temperature in the dark. A final rinse with TBS was done prior to imaging and quantifying using the LiCOR Odyssey Imager and software respectively.

TABLE 2

| | Biological Activity | | | |
|---|---|---|---|---|
| Example # | ITK Inh. IC$_{50}$ uM ++ ≤ 0.01 μM + ≤ 0.1 μM − > 0.1 μM | JAK3 Inh. IC$_{50}$ uM ++ ≤ 0.01 μM + ≤ 0.1 μM − > 0.1 μM | PLC-γ Inh. IC$_{50}$ uM ++ ≤ 0.1 μM + ≤ 0.1-1 μM − > 1 μM | IL2-STAT5 Inh. IC$_{50}$ uM ++ ≤ 0.1 μM + ≤ 0.1-1 μM − > 1 μM |
| 1 | ++ | ++ | − | + |
| 2 | ++ | ++ | + | + |
| 3 | ++ | ++ | ++ | + |
| 4 | ++ | ++ | + | + |
| 5 | ++ | + | + | − |
| 6 | ++ | + | + | − |
| 7 | + | − | − | − |
| 8 | + | + | − | − |
| 9 | ++ | ++ | + | + |
| 10 | − | − | − | − |
| 11 | + | − | − | − |
| 12 | ++ | + | − | − |
| 13 | ++ | + | + | + |
| 14 | ++ | ++ | + | + |
| 15 | ++ | + | + | − |
| 16 | + | ++ | − | + |
| 17 | ++ | ++ | ++ | + |
| 18 | ++ | ++ | ++ | + |
| 19 | ++ | ++ | ++ | + |
| 20 | ++ | ++ | + | + |
| 21 | − | − | − | − |
| 22 | ++ | ++ | + | + |
| 23 | ++ | ++ | + | + |
| 24 | ++ | ++ | ++ | + |
| 25 | ++ | + | + | − |
| 26 | ++ | ++ | ++ | + |
| 27 | ++ | ++ | ++ | + |
| 28 | ++ | ++ | ++ | + |
| 29 | ++ | ++ | + | + |
| 30 | ++ | ++ | ++ | ++ |
| 31 | ++ | ++ | + | + |
| 32 | ++ | ++ | + | + |
| 33 | ++ | + | + | ND |
| 34 | ++ | ++ | ++ | + |
| 35 | ++ | ++ | + | + |
| 36 | ++ | ++ | + | + |
| 37 | ++ | + | + | − |
| 38 | ++ | ++ | + | + |
| 39 | ++ | ++ | + | + |
| 40 | − | − | − | − |
| 41 | + | + | + | − |
| 42 | ++ | ++ | + | + |
| 43 | − | − | − | − |
| 44 | ++ | ++ | ++ | + |
| 45 | ++ | ++ | ++ | ++ |
| 46 | ++ | ++ | + | + |
| 47 | ++ | ++ | ++ | ++ |
| 48 | ++ | ++ | ++ | ++ |
| 49 | ++ | ++ | + | + |
| 50 | ++ | ++ | ++ | + |
| 51 | ++ | ++ | ++ | ++ |
| 52 | ++ | ++ | + | + |
| 53 | ++ | ND | + | ++ |
| 54 | ++ | ++ | + | + |
| 55 | ++ | ++ | + | ++ |
| 56 | ++ | ++ | + | + |
| 57 | − | − | − | − |
| 58 | − | − | + | − |
| 59 | ++ | + | ++ | ND |
| 60 | ++ | ++ | ++ | + |
| 61 | ++ | + | + | − |
| 62 | − | − | + | − |
| 63 | − | − | − | − |
| 64 | − | − | − | − |
| 65 | ++ | ++ | ++ | + |

TABLE 2-continued

| | Biological Activity | | | |
|---|---|---|---|---|
| Example # | ITK Inh.<br>$IC_{50}$ uM<br>++ ≤ 0.01 μM<br>+ ≤ 0.1 μM<br>− > 0.1 μM | JAK3 Inh.<br>$IC_{50}$ uM<br>++ ≤ 0.01 μM<br>+ ≤ 0.1 μM<br>− > 0.1 μM | PLC-γ Inh.<br>$IC_{50}$ uM<br>++ ≤ 0.1 μM<br>+ ≤ 0.1-1 μM<br>− > 1 μM | IL2-STAT5 Inh.<br>$IC_{50}$ uM<br>++ ≤ 0.1 μM<br>+ ≤ 0.1-1 μM<br>− > 1 μM |
| 66 | + | + | + | − |
| 67 | − | − | − | − |
| 68 | ++ | ++ | ++ | ++ |
| 69 | + | + | + | − |
| 70 | ++ | ++ | + | + |
| 71 | − | − | − | − |
| 72 | ND | ND | ND | ND |
| 73 | ++ | ++ | ++ | ++ |
| 74 | ++ | ++ | + | + |
| 75 | ND | ND | ND | ND |
| 76 | − | + | − | − |
| 77 | ++ | ++ | + | + |
| 78 | ND | ND | ND | ND |
| 79 | ++ | ++ | + | + |
| 80 | + | ++ | − | − |
| 96 | − | ++ | − | + |
| 97 | − | ++ | − | + |
| 98 | − | + | − | − |
| 99 | + | ++ | − | ++ |
| 100 | + | ++ | + | ++ |
| 101 | − | − | − | − |

Other Anti-Inflammatory Assays

Anti-inflammatory Efficacy—Rat Carrageenan Foot Pad Edema: The compounds of the present disclosure will be evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-inflammatory Efficacy—Rat Carrageenan-Induced Analgesia Test: The compounds of the present disclosure will be evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Efficacy in Collagen-Induced Arthritis: The compounds of the present disclosure will be evaluated in a mouse autoimmune model of rheumatoid arthritis. Methods to determine efficacy in collagen-induced arthritis in the mouse are described by Grimstein, et al. (2011) J. Translational Med. 9, 1-13.

Six week-old male DBA/1J mice are obtained from The Jackson Laboratory. At eight weeks of age, mice are orally administered test compounds daily. Mice are immunized by intradermal injection, at twelve weeks of age, with 0.1 mL of emulsion containing 100 g of bovine type II collagen (bCII). At 21 days following immunization, mice are boosted with 0.1 mL of bCII (100 g) emulsified in equal volume of incomplete Freund's Adjuvant (IFA) (Difco, Detroit, MI). All mice are monitored three times for the incidence of arthritis and evaluation of a clinical score, ranging from 0-4 was used (0: no swelling or redness; 1: detectable arthritis with erythema; 2: significant swelling and redness; 3: severe swelling and redness from joint to digit; 4: joint stiffness or deformity with ankylosis). The score is calculated from the average cumulative value of all four paws. Severe arthritis is defined as a score >3.

For terminal evaluation of arthritis, mice are euthanized 28 days after initial immunization. The two hind limbs are removed, fixed in formalin, decalcified in RDO solution (Apex Engineering, Aurora, IL) for 10-20 min depending on tissue size and examined for pliability. Sections are cut (4 m thick) and stained with hematoxylin and eosin. Histological evaluation is performed by examining for infiltration of immune cells, hyperplasia, pannus formation and bone deformation for each paw, using a scale ranging from 0-3, according to severity of pathological changes (0: normal, 1: mild, 2: moderate, 3: severe).

What is claimed is:

1. A method of treating an ITK and JAK3 mediated disorder in a subject in need thereof, said method comprising:

administering to the subject one or more compounds of Formula (I):

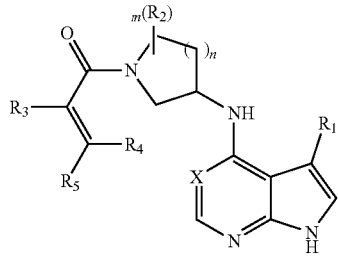

(I)

wherein:

X is N;

n is 1 or 2;

m is 0, 1, or 2;

R₁ is selected from COOR₆, C₁-C₅ alkyl-COOR₆, bicycloalkyl, C₁-C₅-alkyl-heterocyclyl, C₁-alkyl-C₃-C₆-cyclcoalkyl, C₃-C₆ cycloalkyl, C(O)C₁-C₅ alkyl, C(O)C₃-C₆ cycloalkyl, where cycloalkyl, bicycloalkyl, heterocyclyl, and alkyl are optionally substituted with one or more groups selected from C₂-C₅ alkyl, C₁-C₅ alkoxy, C₁-C₅ alkyl-C₁-C₅ alkoxy, CN, halogen, COOR₆, or C₁-C₅-alkyl-COOR₆;

R₂ is selected from H, C₁ alkyl, C₃-C₆ cycloalkyl, C₁-C₅-alkyl-C₃-C₆-cyclcoalkyl, CN, OH, C₁-C₅ alkoxy, and halogen where two R₂ groups on the same carbon may be joined with or without a heteroatom to make a spirocyclic ring system;

R₃ is H;

R₄ is selected from H, C₁-C₆ alkyl;

R₅ is selected from H, C₁-C₆ alkyl-N(C₁-C₆ alkyl)(C₁-C₆ alkyl);

R₆ is selected from H, C₁-C₅ alkyl, C₃-C₆ cycloalkyl, C₁-C₅-alkyl-C₃-C₆-cyclcoalkyl, C₁-C₅ alkyl-C₁-C₅ alkoxy, C₁-C₅ alkyl-OH, C₁-C₅ alkyl-NH₂, C₁-C₅ alkyl-NH—C₁-C₅ alkyl, and C₁-C₅ alkyl-N—(C₁-C₅ alkyl)(C₁-C₅ alkyl); and a derivative thereof, wherein said compound is administered in an amount effective to treat the ITK and JAK3-mediated disorder in the subject; and wherein the ITK and JAK3 mediated disorder is selected from rheumatoid arthritis, psoriatic arthritis, ankylosing spondylitis, inflammatory bowel disease, T-cell lymphoma, cutaneous T-cell lymphoma, Crohn's disease, ulcerative colitis, psoriasis, hidradenitis suppurativa, organ transplant rejection, lupus nephritis, non-alcoholic steatohepatitis, and juvenile idiopathic arthritis.

2. The method of claim 1, wherein the compound, or a derivative thereof, is selected from:

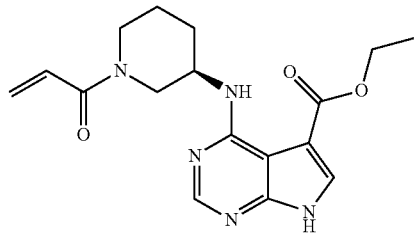

ethyl (R)-4-((1-acryloylpiperidin-3-yl)amino)-7H-pyrrolo[2,3-d]pyrimidine-5-carboxylate ,

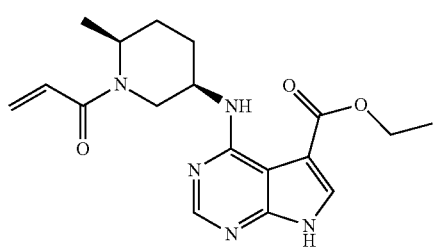

ethyl 4-(((3R,6S)-1-acryloyl-6-methylpiperidin-3-yl)amino)-7H-pyrrolo[2,3-d]pyrimidine-5-carboxylate ,

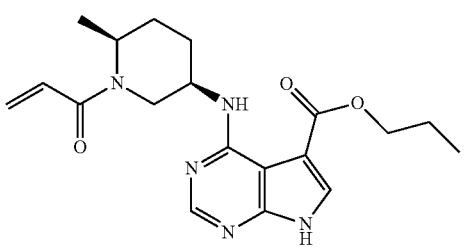

propyl 4-(((3R,6S)-1-acryloyl-6-methylpiperidin-3-yl)amino)-7H-pyrrolo[2,3-d]pyrimidine-5-carboxylate ,

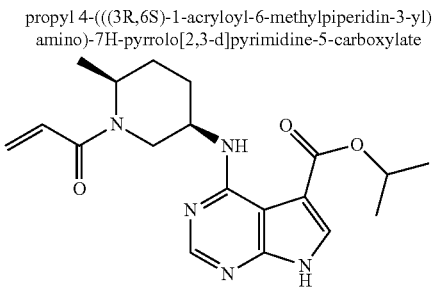

isopropyl 4-(((3R,6S)-1-acryloyl-6-methylpiperidin-3-yl)amino)-7H-pyrrolo[2,3-d]pyrimidine-5-carboxylate ,

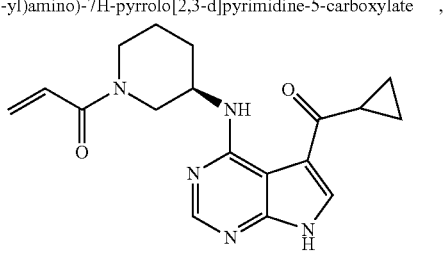
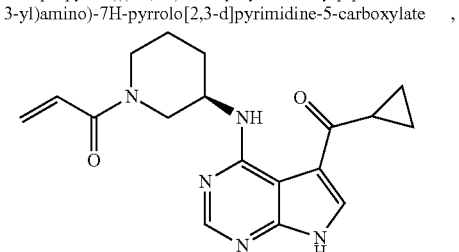

(R)-1-(3-((5-(cyclopropanecarbonyl)-7H-pyrrolo[2,3-d]pyrimidin-4-yl)amino)piperidin-1-yl)prop-2-en-1-one , 309
-continued

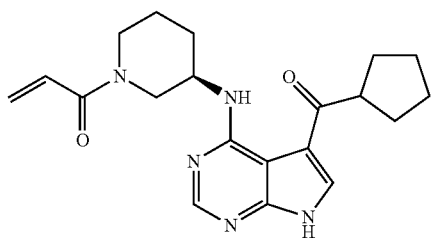

(R)-1-(3-((5-(cyclopentanecarbonyl)-7H-pyrrolo[2,3-d]
pyrimidin-4-yl)amino)piperidin-1-yl)prop-2-en-1-one,

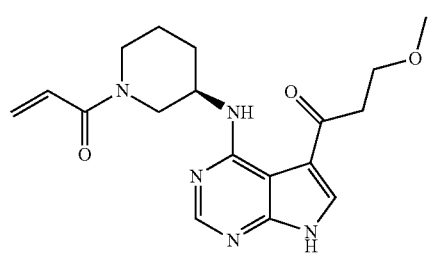

(R)-1-(3-((3-(3-methoxypropanoyl)-1H-pyrrolo[2,3-b]
pyridin-4-yl)amino)piperidin-1-yl)prop-2-en-1-one,

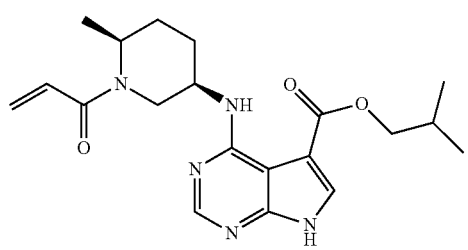

isobutyl 4-(((3R,6S)-1-acryloyl-6-methylpiperidin-3-
yl)amino)-7H-pyrrolo[2,3-d]pyrimidine-5-carboxylate,

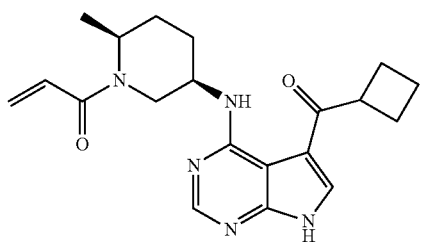

1-((2S,5R)-5-((5-(cyclobutanecarbonyl)-7H-pyrrolo
[2,3-d]pyrimidin-4-yl)amino)-2-methylpiperidin-
1-yl)prop-2-en-1-one,

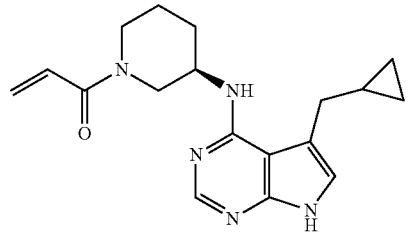

(R)-1-(3-((5-(cyclopropylmethyl)-7H-pyrrolo[2,3-d]
pyrimidin-4-yl)amino)piperidin-1-yl)prop-2-en-1-one, 310
-continued

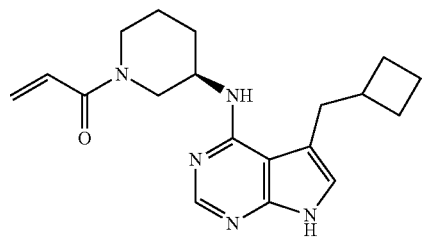

(R)-1-(3-((5-(cyclobutylmethyl)-7H-pyrrolo[2,3-d]
pyrimidin-4-yl)amino)piperidin-1-yl)prop-2-en-1-one,

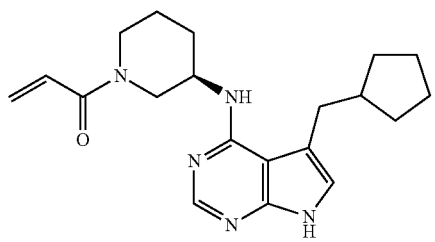

(R)-1-(3-((3-(cyclopentylmethyl)-1H-pyrrolo[2,3-b]
pyridin-4-yl)amino)piperidin-1-yl)prop-2-en-1-one,

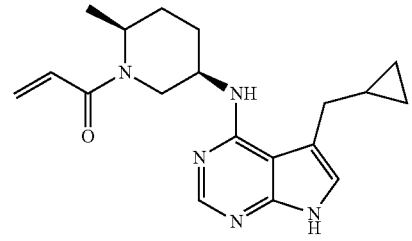

1-((2S,5R)-5-((5-(cyclopropylmethyl)-7H-pyrrolo
[2,3-d]pyrimidin-4-yl)amino)-2-methylpiperidin-1-
yl)prop-2-en-1-one,

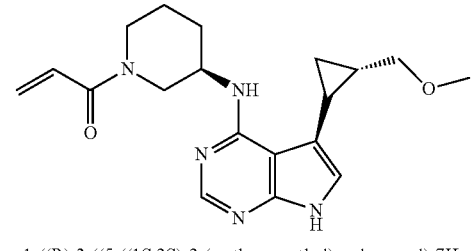

1-((R)-3-((5-((1S,2S)-2-(methoxymethyl)cyclopropyl)-7H-
pyrrolo[2,3-d]pyrimidin-4-yl)amino)piperidin-1-yl)
prop-2-en-1-one,

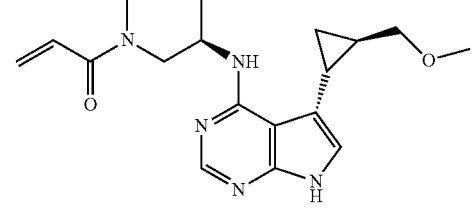

1-((R)-3-((5-((1R,2R)-2-(methoxymethyl)cyclopropyl)-7H-
pyrrolo[2,3-d]pyrimidin-4-yl)amino)piperidin-1-yl)
prop-2-en-1-one,

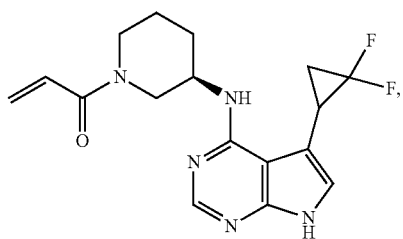

1-((3R)-3-((5-(2,2-difluorocyclopropyl)-7H-pyrrolo
[2,3-d]pyrimidin-4-yl)amino)piperidin-1-yl)
prop-2-en-1-one

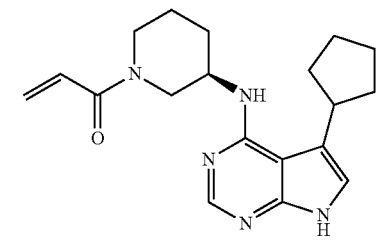

(R)-1-(3-((3-(cyclopentyl-1H-pyrrolo[2,3-b]
pyridin-4-yl)amino)piperidin-1-yl)prop-2-en-1-one,

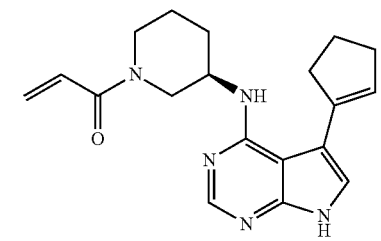

(R)-1-(3-((3-(cyclopent-1-en-1-yl)-1H-pyrrolo[2,3-b]
pyridin-4-yl)amino)piperidin-1-yl)prop-2-en-1-one,

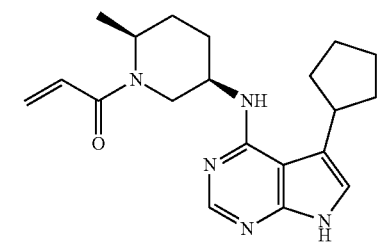

1-((2S,5R)-5-((5-(cyclopentyl-7H-pyrrolo[2,3-d]
pyrimidin-4-yl)amino)-2-methylpiperidin-1-yl)
prop-2-en-1-one,

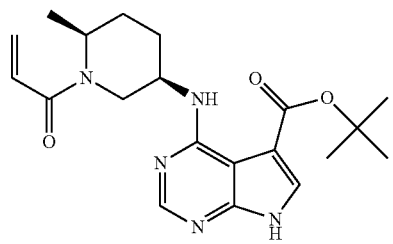

tert-butyl 4-(((3R,6S)-1-acryloyl-6-methylpiperidin-
3-yl)amino)-7H-pyrrolo[2,3-d]pyrimidine-5-carboxylate,

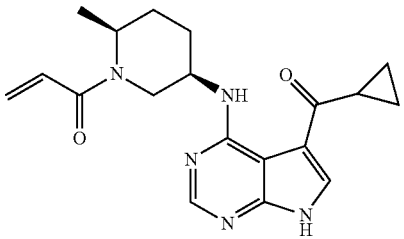

1-((2S,5R)-5-((5-(cyclopropanecarbonyl)-7H-
pyrrolo[2,3-d]pyrimidin-4-yl)amino)-2-
methylpiperidin-1-yl)prop-2-en-1-one,

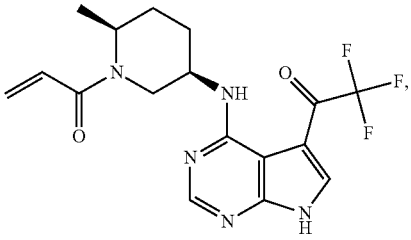

1-((2S,5R)-2-methyl-5-((5-(2,2,2-trifluoroacetyl)-7H-
pyrrolo[2,3-d]pyrimidin-4-yl)amino)piperidin-1-yl)
prop-2-en-1-one

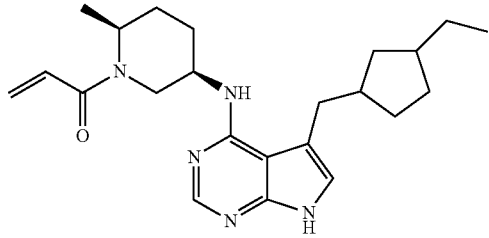

1-((2S,5R)-5-((5-((3-ethylcyclopentyl)methyl)-7H-
pyrrolo[2,3-d]pyrimidin-4-yl)amino)-2-
methylpiperidin-1-yl)prop-2-en-1-one,

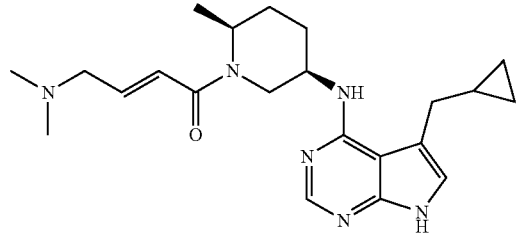

(E)-1-((2S,5R)-5-((5-(cyclopropylmethyl)-7H-
pyrrolo[2,3-d]pyrimidin-4-yl)amino)-2-
methylpiperidin-1-yl)-4-(dimethylamino)
but-2-en-1-one,

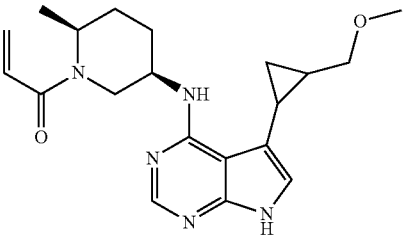

1-((2S,5R)-5-((5-(2-(methoxymethyl)
cyclopropyl)-7H-pyrrolo[2,3-d]pyrimidin-4-yl)
amino)-2-methylpiperidin-1-yl)prop-2-en-1-one,

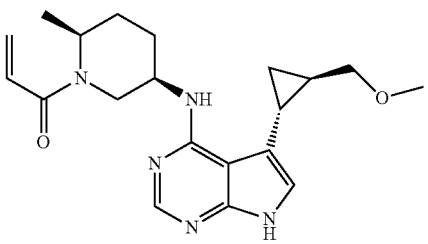

1-((2S,5R)-5-((5-((1R,2R)-2-(methoxymethyl)
cyclopropyl)-7H-pyrrolo[2,3-d]pyrimidin-4-yl)
amino)-2-methylpiperidin-1-yl)prop-2-en-1-one ,

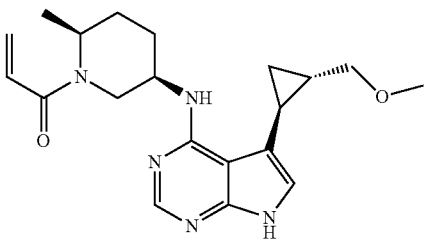

1-((2S,5R)-5-((5-((1S,2S)-2-(methoxymethyl)
cyclopropyl)-7H-pyrrolo[2,3-d]pyrimidin-4-yl)
amino)-2-methylpiperidin-1-yl)prop-2-en-1-one ,

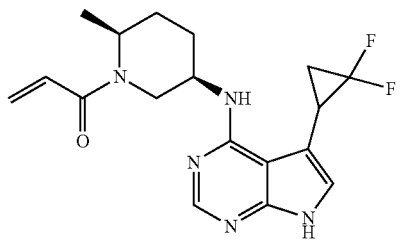

1-((2S,5R)-5-((5-(2,2-difluorocyclopropyl)-7H-pyrrolo
[2,3-d]pyrimidin-4-yl)amino)-2-methylpiperidin-1-yl)
prop-2-en-1-one ,

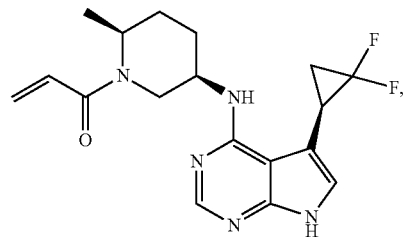

1-((2S,5R)-5-((5-((R)-2,2-difluorocyclopropyl)-7H-
pyrrolo[2,3-d]pyrimidin-4-yl)amino)-2-
methylpiperidin-1-yl)prop-2-en-1-one ,

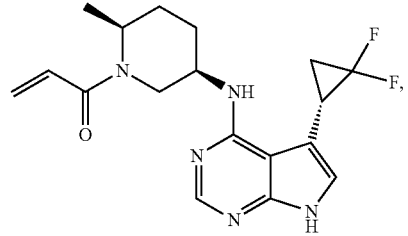

1-((2S,5R)-5-((5-((S)-2,2-difluorocyclopropyl)-7H-
pyrrolo[2,3-d]pyrimidin-4-yl)amino)-2-
methylpiperidin-1-yl)prop-2-en-1-one ,

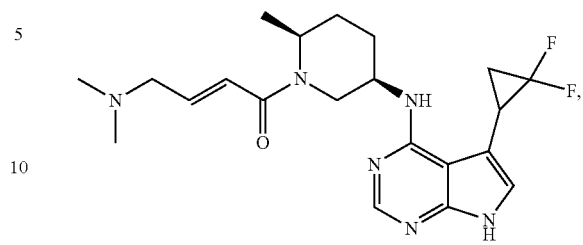

(E)-1-((2S,5R)-5-((5-(2,2-difluorocyclopropyl)-7H-
pyrrolo[2,3-d]pyrimidin-4-yl)amino)-2-
methylpiperidin-1-yl)-4-(dimethylamino)but-2-en-1-one

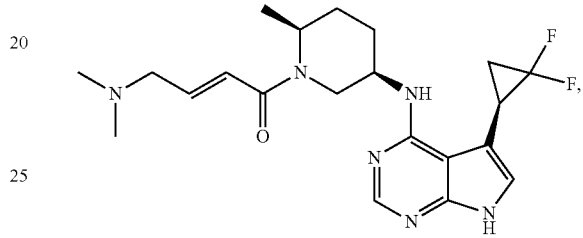

(E)-1-((2S,5R)-5-((5-((R)-2,2-difluorocyclopropyl)-7H-
pyrrolo[2,3-d]pyrimidin-4-yl)amino)-2-
methylpiperidin-1-yl)-4-(dimethylamino)but-2-en-1-one

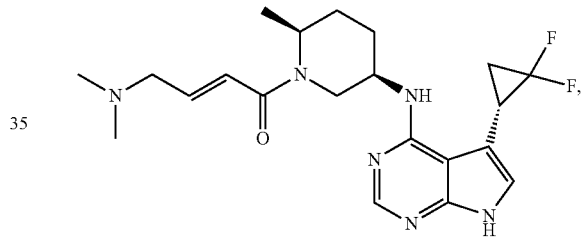

(E)-1-((2S,5R)-5-((5-((S)-2,2-difluorocyclopropyl)-7H-
pyrrolo[2,3-d]pyrimidin-4-yl)amino)-2-
methylpiperidin-1-yl)-4-(dimethylamino)but-2-en-1-one

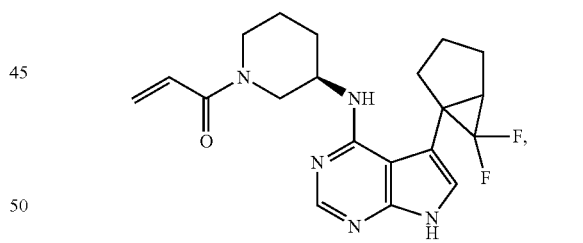

1-((3R)-3-((5-(6,6-difluorobicyclo[3.1.0]hexan-
1-yl)-7H-pyrrolo[2,3-d]pyrimidin-4-yl)amino)
piperidin-1-yl)prop-2-en-1-one ,

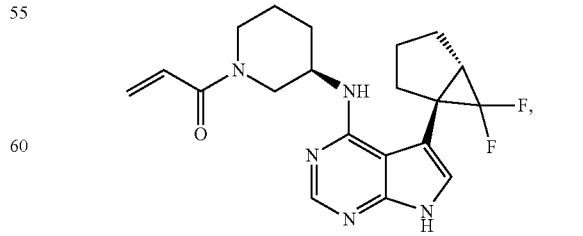

1-((R)-3-((5-((1R,5S)-6,6-difluorobicyclo[3.1.0]
hexan-1-yl)-7H-pyrrolo[2,3-d]pyrimidin-4-yl)
amino)piperidin-1-yl)prop-2-en-1-one ,

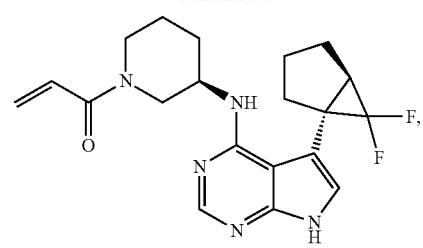

1-((R)-3-((5-((1S,5R)-6,6-difluorobicyclo[3.1.0]
hexan-1-yl)-7H-pyrrolo[2,3-d]pyrimidin-4-yl)
amino)piperidin-1-yl)prop-2-en-1-one

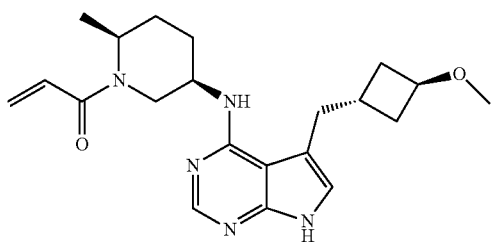

1-((2S,5R)-5-((5-(((1r,3S)-3-methoxycyclobutyl)
methyl)-7H-pyrrolo[2,3-d]pyrimidin-4-yl)
amino)-2-methylpiperidin-1-yl)prop-2-en-1-one,

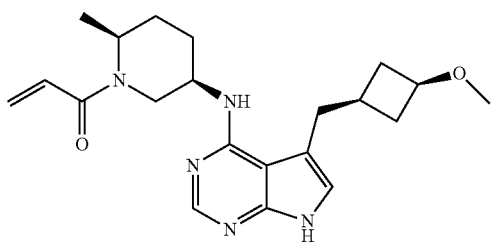

1-((2S,5R)-5-((5-(((1s,3R)-3-methoxycyclobutyl)
methyl)-7H-pyrrolo[2,3-d]pyrimidin-4-yl)
amino)-2-methylpiperidin-1-yl)prop-2-en-1-one,

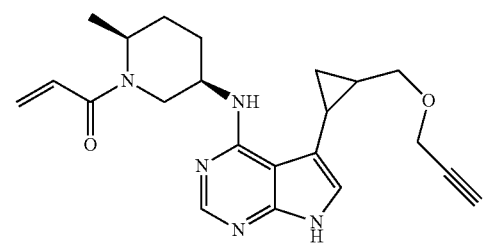

1-((2S,5R)-2-methyl-5-((5-(2-((prop-2-yn-1-
yloxy)methyl)cyclopropyl)-7H-pyrrolo[2,3-d]
pyrimidin-4-yl)amino)piperidin-1-yl)prop-2-en-1-one,

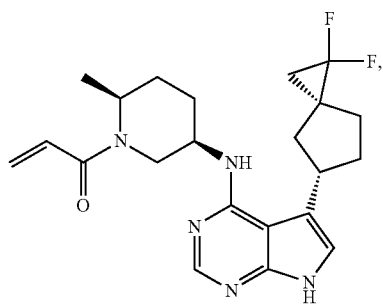

1-((2S,5R)-5-((5-((3S,5S)-1,1-difluorospiro
[2.4]heptan-5-yl)-7H-pyrrolo[2,3-d]pyrimidin-
4-yl)amino)-2-methylpiperidin-1-yl)
prop-2-en-1-one

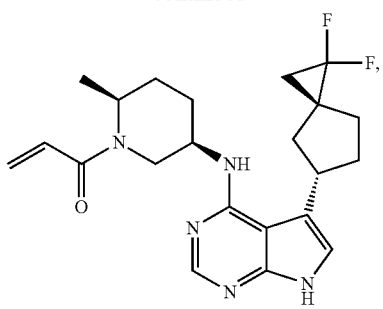

1-((2S,5R)-5-((5-((3R,5S)-1,1-difluorospiro
[2.4]heptan-5-yl)-7H-pyrrolo[2,3-d]pyrimidin-
4-yl)amino)-2-methylpiperidin-1-yl)
prop-2-en-1-one

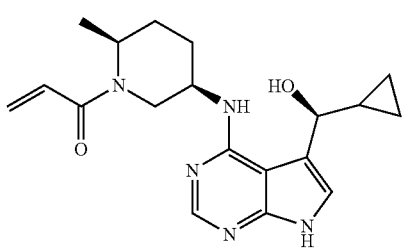

1-((2S,5R)-5-((5-((S)-cyclopropyl(hydroxy)
methyl)-7H-pyrrolo[2,3-d]pyrimidin-4-yl)
amino)-2-methylpiperidin-1-yl)prop-2-en-1-one,

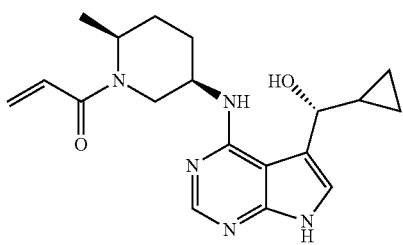

1-((2S,5R)-5-((5-((R)-cyclopropyl(hydroxy)
methyl)-7H-pyrrolo[2,3-d]pyrimidin-4-yl)
amino)-2-methylpiperidin-1-yl)prop-2-en-1-one,

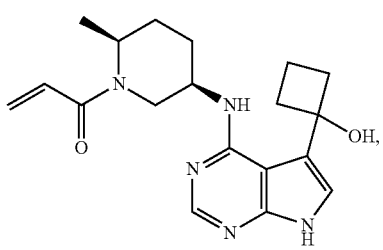

1-((2S,5R)-5-((5-(1-hydroxycyclobutyl)-7H-
pyrrolo[2,3-d]pyrimidin-4-yl)amino)-2-
methylpiperidin-1-yl)prop-2-en-1-one

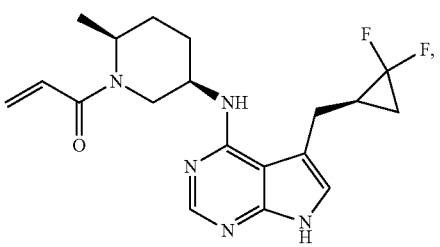

1-((2S,5R)-5-((5-(((R)-2,2-difluorocyclopropyl)
methyl)-7H-pyrrolo[2,3-d]pyrimidin-4-yl)amino)-
2-methylpiperidin-1-yl)prop-2-en-1-one -continued

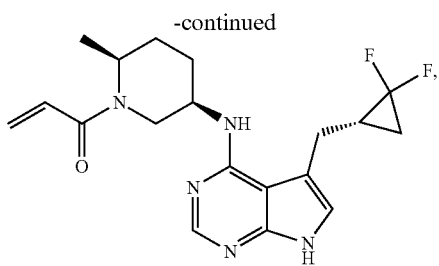

1-((2S,5R)-5-((5-(((S)-2,2-diflurocyclopropyl)methyl)-7H-pyrrolo[2,3-d]pyrimidin-4-yl)amino)-2-methylpiperidin-1-yl)prop-2-en-1-one

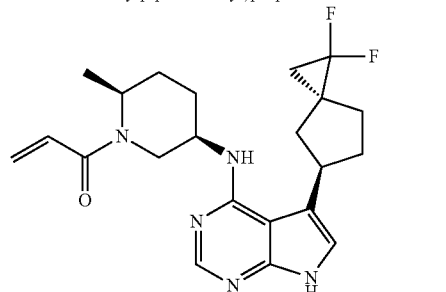

1-((2S,5R)-5-((5-((3S,5R)-1,1-difluorospiro[2.4]heptan-5-yl)-7H-pyrrolo[2,3-d]pyrimidin-4-yl)amino)-2-methylpiperidin-1-yl)prop-2-en-1-one, and

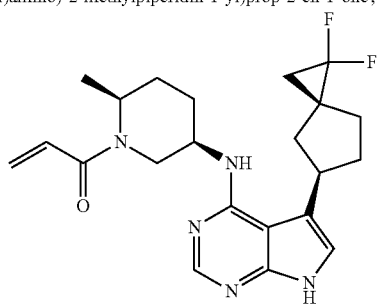

1-((2S,5R)-5-((5-((3R,5R)-1,1-difluorospiro[2.4]heptan-5-yl)-7H-pyrrolo[2,3-d]pyrimidin-4-yl)amino)-2-methylpiperidin-1-yl)prop-2-en-1-one.

3. The method of claim 1 further comprising: administering, sequentially or concurrently to said subject, a second pharmaceutical agent.

4. The method of claim 3, wherein the second pharmaceutical agent is selected from a corticosteroid, a nonsteroidal anti-inflammatory drug (NSAID), a calcineurin inhibitor, an alkylating agent, a CD20 blocker, a Tumor Necrosis factor (TNF) blocker, an inhibitor of inosine monophosphate dehydrogenase (IMPDH), an immunosuppressant, an anti-metabolite, an aminosalicylate, an anti-lymphocyte globulin antibody, an anti-thymocyte globulin antibody, a monoclonal anti-T-cell antibody, an anti-interleukin-12/23 antibody, an anti-interleukin-17 antibody, an anti-interleukin-17 receptor antibody, an anti-α4β7 integrin antibody, an interleukin-1 receptor antagonist, an interleukin-6 inhibitor, an interleukin-17 inhibitor, a Janus kinase inhibitor, and a syk inhibitor.

5. The method of claim 3, wherein the second pharmaceutical agent is an immune checkpoint inhibitor selected from an adenosine A2A receptor (A2AR) inhibitor, a B7-H3 (CD276) inhibitor, a cytotoxic T-lymphocyte associated protein 4 (CTLA4) inhibitor, a programmed cell death ligand 1 (PD-L1) inhibitor, a programmed cell death protein 1 (PD-1) inhibitor, a B7-H4 (VTCN1) inhibitor, a T-cell immunoglobulin and mucin-domain containing-3 (TIM3) inhibitor, a B and T lymphocyte attenuator (BTLA) inhibitor, an indoleamine-pyrrole 2,3-dioxygenase (IDO) inhibitor, a killer-cell immunoglobulin-like receptors (KIRs) inhibitor, a lymphocyte-activation gene 3 (LAG-3) inhibitor, a T-cell immunoreceptor with Ig and ITIM domains (TIGIT) inhibitor, an ILT-3 inhibitor, an ILT-4 inhibitor, and a V-domain Ig suppressor of T cell activation (Vista) inhibitor.

6. The method of claim 3, wherein the second pharmaceutical agent is selected from an alkylating agent, an anti-metabolite, a plant alkaloid, a topoisomerase inhibitor, a cytotoxic antibiotic, an angiogenesis inhibitor, and a tyrosine kinase inhibitor.

7. The method of claim 1, wherein the compound, or a derivative thereof, is

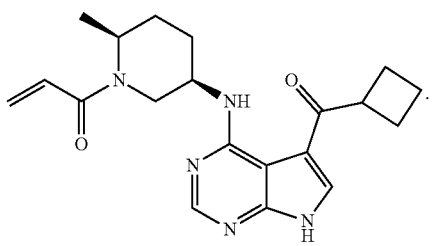

1-((2S,5R)-5-((5-(cyclobutanecarbonyl)-7H-pyrrolo[2,3-d]pyrimidin-4-yl)amino)-2-methylpiperidin-1-yl)prop-2-en-1-one 8. The method of claim 1, wherein the compound, or a derivative thereof, is

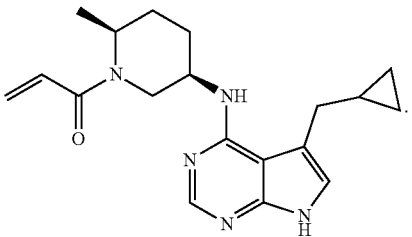

1-((2S,5R)-5-((5-(cyclopropylmethyl)-7H-pyrrolo[2,3-d]pyrimidin-4-yl)amino)-2-methylpiperidin-1-yl)prop-2-en-1-one 9. The method of claim 1, wherein the compound, or a derivative thereof, is

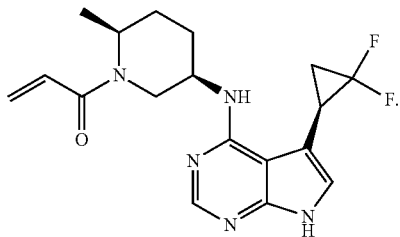

1-((2S,5R)-5-((5-((R)-2,2-difluorocyclopropyl)-7H-pyrrolo[2,3-d]pyrimidin-4-yl)amino)-2-methylpiperidin-1-yl)prop-2-en-1-one

10. The method of claim 1, wherein the compound, or a derivative thereof, is

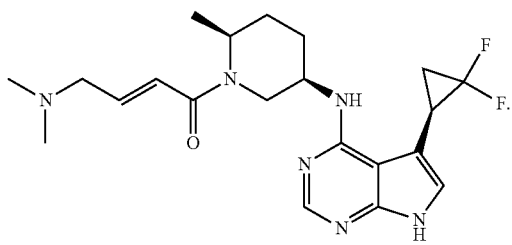

(E)-1-((2S,5R)-5-((5-((R)-2,2-difluorocyclopropyl)-7H-pyrrolo[2,3-d]pyrimidin-4-yl)amino)-2-methylpiperidin-1-yl)-4-(dimethylamino)but-2-en-1-one

11. The method of claim 1, wherein the compound, or a derivative thereof, is

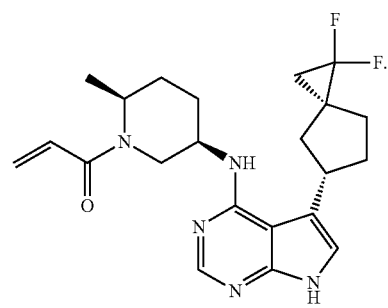

1-((2S,5R)-5-((5-((3S,5S)-1,1-difluorospiro[2.4]heptan-5-yl)-7H-pyrrolo[2,3-d]pyrimidin-4-yl)amino)-2-methylpiperidin-1-yl)prop-2-en-1-one

12. The method of claim 1, wherein the compound, or a derivative thereof, is

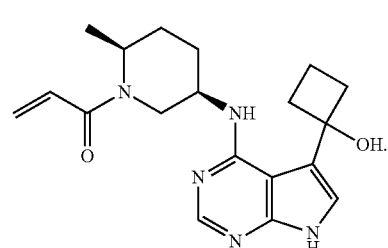

1-((2S,5R)-5-((5-(1-hydroxycyclobutyl)-7H-pyrrolo[2,3-d]pyrimidin-4-yl)amino)-2-methylpiperidin-1-yl)prop-2-en-1-one

13. The method of claim 1, wherein the compound, or a derivative thereof, is

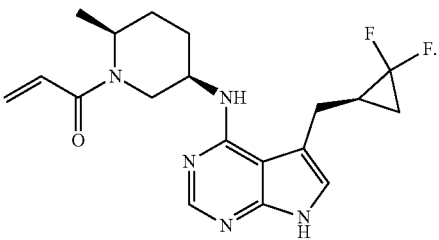

1-((2S,5R)-5-((5-(((R)-2,2-difluorocyclopropyl)methyl)-7H-pyrrolo[2,3-d]pyrimidin-4-yl)amino)-2-methylpiperidin-1-yl)prop-2-en-1-one

14. The method of claim 1, wherein the compound, or a derivative thereof, is

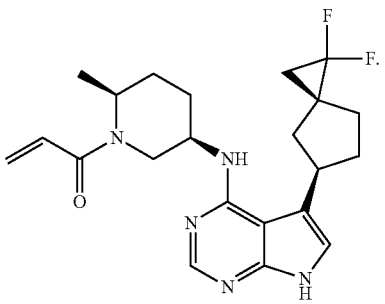

1-((2S,5R)-5-((5-((3R,5R)-1,1-difluorospiro[2.4]heptan-5-yl)-7H-pyrrolo[2,3-d]pyrimidin-4-yl)amino)-2-methylpiperidin-1-yl)prop-2-en-1-one

15. The method of claim 1, wherein the compound, or a derivative thereof, is

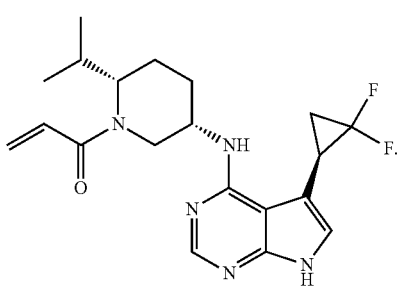

1-((2S,5S)-5-((5-((R)-2,2-difluorocyclopropyl)-7H-pyrrolo[2,3-d]pyrimidin-4-yl)amino)-2-isopropylpiperidin-1-yl)prop-2-en-1-one 16. The method of claim 1, wherein the compound, or a derivative thereof, is

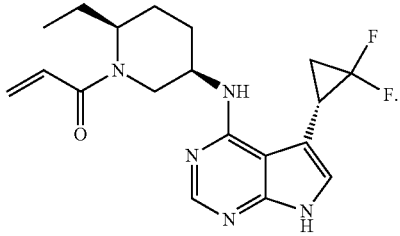

1-((2S,5R)-5-((5-((S)-2,2-difluorocyclopropyl)-
7H-pyrrolo[2,3-d]pyrimidin-4-yl)amino)-2-
ethylpiperidin-1-yl)prop-2-en-1-one 17. The method of claim 1, wherein the compound, or a derivative thereof, is

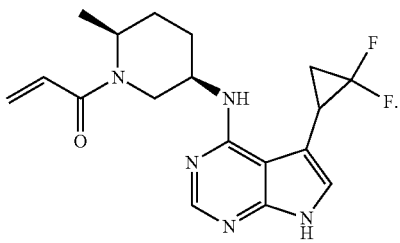

1-((2S,5R)-5-((5-(2,2-difluorocyclopropyl)-7H-
pyrrolo[2,3-d]pyrimidin-4-yl)amino)-2-
methylpiperidin-1-yl)prop-2-en-1-one 18. The method of claim 1, wherein when $R_1$ is cycloalkyl, bicycloalkyl, heterocyclyl, or alkyl, the cycloalkyl, bicycloalkyl, heterocyclyl, and alkyl are substituted with one or more groups selected from $C_2$-$C_5$ alkyl, $C_1$-$C_5$ alkoxy, $C_1$-$C_5$ alkyl-$C_1$-$C_5$ alkoxy, CN, halogen, $COOR_6$, or $C_1$-$C_5$-alkyl-$COOR_6$.

19. A method of treating an ITK and JAK3 mediated disorder in a subject in need thereof, said method comprising:

administering to the subject a compound selected from the group consisting of:

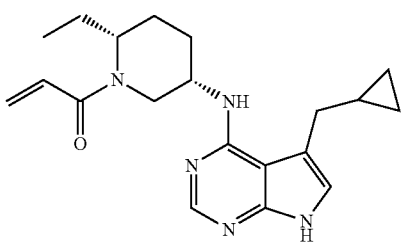

1-((2R,5S)-5-((5-(cyclopropylmethyl)-7H-
pyrrolo[2,3-d]pyrimidin-4-yl)amino)-2-
ethylpiperidin-1-yl)prop-2-en-1-one ,

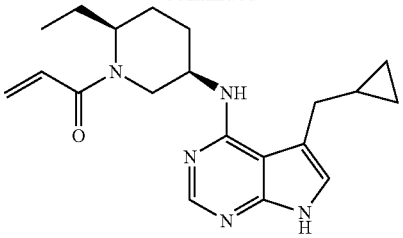

1-((2S,5R)-5-((5-(cyclopropylmethyl)-7H-
pyrrolo[2,3-d]pyrimidin-4-yl)amino)-2-
ethylpiperidin-1-yl)prop-2-en-1-one ,

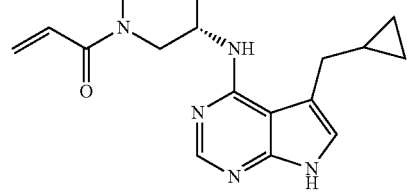

1-((2R,5S)-5-((5-(cyclopropylmethyl)-7H-
pyrrolo[2,3-d]pyrimidin-4-yl)amino)-2-
isopropylpiperidin-1-yl)prop-2-en-1-one , and

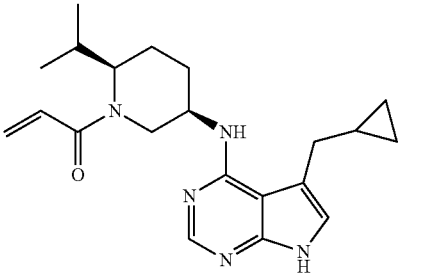

1-((2R,5R)-5-((5-(cyclopropylmethyl)-7H-
pyrrolo[2,3-d]pyrimidin-4-yl)amino)-2-
isopropylpiperidin-1-yl)prop-2-en-1-one , wherein said compound is administered in an amount effective to treat the ITK and JAK3-mediated disorder in the subject; and wherein the ITK and JAK3 mediated disorder is selected from rheumatoid arthritis, psoriatic arthritis, ankylosing spondylitis, inflammatory bowel disease, T-cell lymphoma, cutaneous T-cell lymphoma, Crohn's disease, ulcerative colitis, psoriasis, hidradenitis suppurativa, organ transplant rejection, lupus nephritis, non-alcoholic steatohepatitis, and juvenile idiopathic arthritis.

20. The method of claim 19 further comprising:

administering, sequentially or concurrently to said subject, a second pharmaceutical agent.

21. The method of claim 20, wherein the second pharmaceutical agent is selected from a corticosteroid, a non-steroidal anti-inflammatory drug (NSAID), a calcineurin inhibitor, an alkylating agent, a CD20 blocker, a Tumor Necrosis factor (TNF) blocker, an inhibitor of inosine monophosphate dehydrogenase (IMPDH), an immunosuppressant, an anti-metabolite, an aminosalicylate, an anti-lymphocyte globulin antibody, an anti-thymocyte globulin antibody, a monoclonal anti-T-cell antibody, an anti-interleukin-12/23 antibody, an anti-interleukin-17 antibody, an anti-interleukin-17 receptor antibody, an anti-α4β7 integrin antibody, an interleukin-1 receptor antagonist, an interleukin-6 inhibitor, an interleukin-17 inhibitor, a Janus kinase inhibitor, and a syk inhibitor.

22. The method of claim 20, wherein the second pharmaceutical agent is an immune checkpoint inhibitor selected from an adenosine A2A receptor (A2AR) inhibitor, a B7-H3 (CD276) inhibitor, a cytotoxic T-lymphocyte associated protein 4 (CTLA4) inhibitor, a programmed cell death ligand 1 (PD-L1) inhibitor, a programmed cell death protein 1 (PD-1) inhibitor, a B7-H4 (VTCN1) inhibitor, a T-cell immunoglobulin and mucin-domain containing-3 (TIM3) inhibitor, a B and T lymphocyte attenuator (BTLA) inhibitor, an indoleamine-pyrrole 2,3-dioxygenase (IDO) inhibitor, a killer-cell immunoglobulin-like receptors (KIRs) inhibitor, a lymphocyte-activation gene 3 (LAG-3) inhibitor, a T-cell immunoreceptor with Ig and ITIM domains (TIGIT) inhibitor, an ILT-3 inhibitor, an ILT-4 inhibitor, and a V-domain Ig suppressor of T cell activation (Vista) inhibitor.

23. The method of claim 20, wherein the second pharmaceutical agent is selected from an alkylating agent, an anti-metabolite, a plant alkaloid, a topoisomerase inhibitor, a cytotoxic antibiotic, an angiogenesis inhibitor, and a tyrosine kinase inhibitor.

24. A method of treating an ITK and JAK3 mediated disorder in a subject in need thereof, said method comprising:

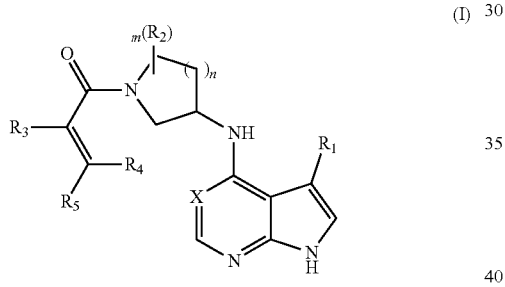

wherein:
X is N;
n is 2;
m is 1;
$R_1$ is $C_3$-$C_6$ cycloalkyl, where the cycloalkyl, is substituted with one or more groups selected from $C_1$-$C_5$ alkyl and halogen;
$R_2$ is $C_1$-$C_5$alkyl;
$R_3$ is H, or $C_1$-$C_6$ alkyl;
$R_4$ is H;
$R_5$ is selected from H, $C_1$-$C_6$ alkyl or $C_1$-$C_6$ alkyl NH($C_1$-$C_6$ alkyl);
and a derivative thereof, wherein said compound is administered in an amount effective to treat the ITK and JAK3-mediated disorder in the subject; and
wherein the ITK and JAK3 mediated disorder is selected from rheumatoid arthritis, psoriatic arthritis, ankylosing spondylitis, inflammatory bowel disease, T-cell lymphoma, cutaneous T-cell lymphoma, Crohn's disease, ulcerative colitis, psoriasis, hidradenitis suppurativa, organ transplant rejection, lupus nephritis, non-alcoholic steatohepatitis, and juvenile idiopathic arthritis.

25. The method of claim 24, wherein the compound, or a derivative thereof, is selected from:

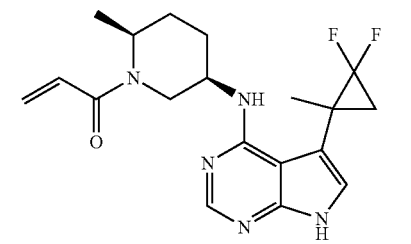

1-((2S,5R)-5-((5-(2,2-difluoro-1-methylcyclopropyl)-7H-pyrrolo[2,3-d]pyrimidin-4-yl)amino)-2-methylpiperidin-1-yl)prop-2-en-1-one ,

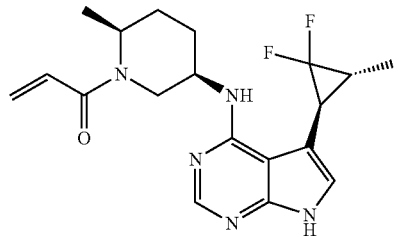

1-((2S,5R)-5-((5-((1S,3R)-2,2-difluoro-3-methylcyclopropyl)-7H-pyrrolo[2,3-d]pyrimidin-4-yl)amino)-2-methylpiperidin-1-yl)prop-2-en-1-one ,

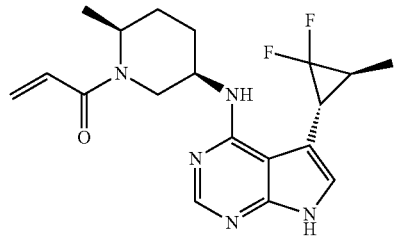

1-((2S,5R)-5-((5-((1R,3S)-2,2-difluoro-3-methylcyclopropyl)-7H-pyrrolo[2,3-d]pyrimidin-4-yl)amino)-2-methylpiperidin-1-yl)prop-2-en-1-one ,

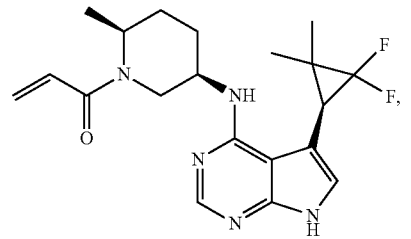

1-((2S,5R)-5-((5-((S)-2,2-difluoro-3,3-dimethylcyclopropyl)-7H-pyrrolo[2,3-d]pyrimidin-4-yl)amino)-2-methylpiperidin-1-yl)prop-2-en-1-one

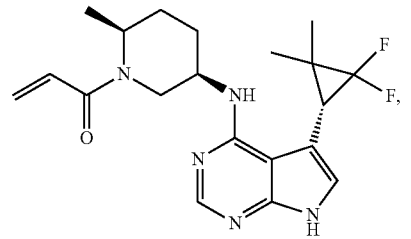

1-((2S,5R)-5-((5-((R)-2,2-difluoro-3,3-dimethylcyclopropyl)-7H-pyrrolo[2,3-d]pyrimidin-4-yl)amino)-2-methylpiperidin-1-yl)prop-2-en-1-one

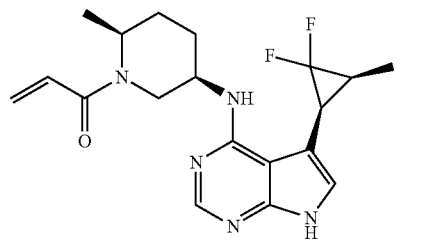

1-((2S,5R)-5-((5-((1S,3S)-2,2-difluoro-3-
methylcyclopropyl)-7H-pyrrolo[2,3-d]
pyrimidin-4-yl)amino)-2-
methylpiperidin-1-yl)prop-2-en-1-one,

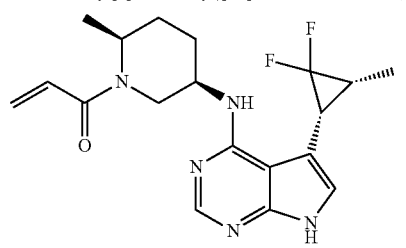

1-((2S,5R)-5-((5-((1R,3R)-2,2-difluoro-3-
methylcyclopropyl)-7H-pyrrolo[2,3-d]
pyrimidin-4-yl)amino)-2-
methylpiperidin-1-yl)prop-2-en-1-one,

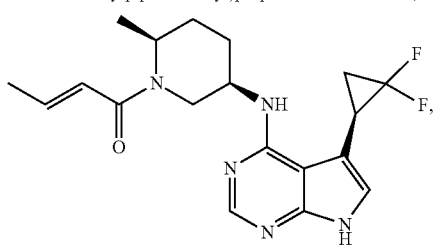

(E)-1-((2S,5R)-5-((5-((R)-2,2-difluorocyclopropyl-
7H-pyrrolo[2,3-d]pyrimidin-4-yl)amino)-2-
methylpiperidin-1-yl)prop-2-en-1-one

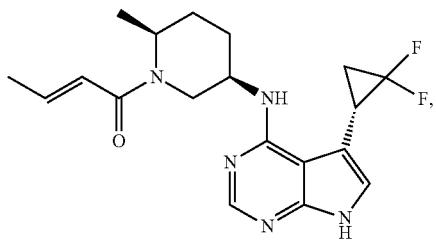

(E)-1-((2S,5R)-5-((5-((S)-2,2-difluorocyclopropyl-
7H-pyrrolo[2,3-d]pyrimidin-4-yl)amino)-2-
methylpiperidin-1-yl)prop-2-en-1-one

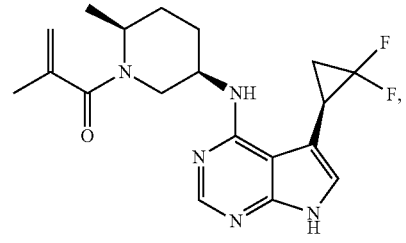

1-((2S,5R)-5-((5-((R)-2,2-difluorocyclopropyl-
7H-pyrrolo[2,3-d]pyrimidin-4-yl)amino)-2-
methylpiperidin-1-yl)prop-2-en-1-one

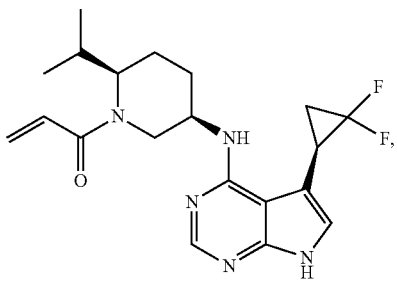

1-((2R,5R)-5-((5-((R)-2,2-difluorocyclopropyl-
7H-pyrrolo[2,3-d]pyrimidin-4-yl)amino)-2-
isopropylpiperidin-1-yl)prop-2-en-1-one

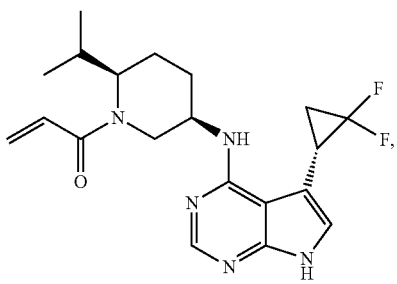

1-((2R,5R)-5-((5-((S)-2,2-difluorocyclopropyl-
7H-pyrrolo[2,3-d]pyrimidin-4-yl)amino)-2-
isopropylpiperidin-1-yl)prop-2-en-1-one

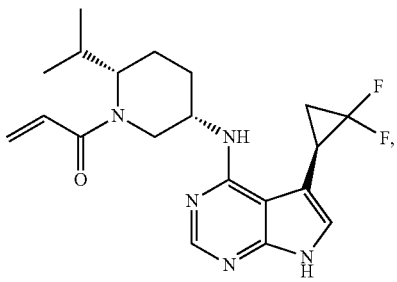

1-((2S,5S)-5-((5-((R)-2,2-difluorocyclopropyl-
7H-pyrrolo[2,3-d]pyrimidin-4-yl)amino)-2-
isopropylpiperidin-1-yl)prop-2-en-1-one

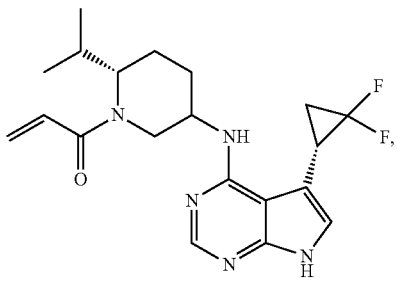

1-((2S)-5-((5-((S)-2,2-difluorocyclopropyl-
7H-pyrrolo[2,3-d]pyrimidin-4-yl)amino)-2-
isopropylpiperidin-1-yl)prop-2-en-1-one

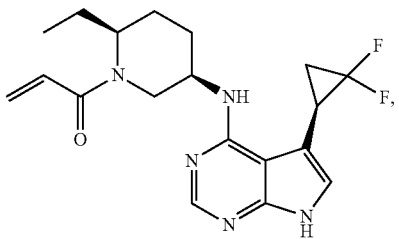

1-((2S,5R)-5-((5-((R)-2,2-difluorocyclopropyl-
7H-pyrrolo[2,3-d]pyrimidin-4-yl)amino)-2-
ethylpiperidin-1-yl)prop-2-en-1-one

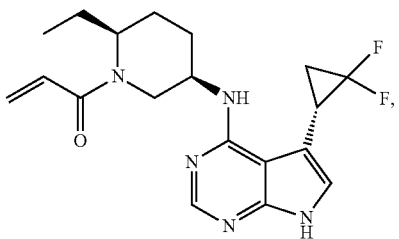

1-((2S,5R)-5-((5-((S)-2,2-difluorocyclopropyl-
7H-pyrrolo[2,3-d]pyrimidin-4-yl)amino)-2-
ethylpiperidin-1-yl)prop-2-en-1-one

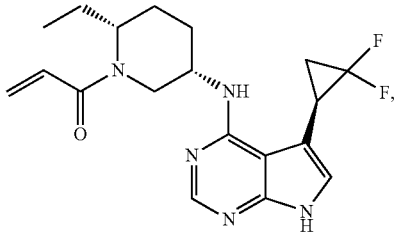

1-((2S,5S)-5-((5-((R)-2,2-difluorocyclopropyl-
7H-pyrrolo[2,3-d]pyrimidin-4-yl)amino)-2-
ethylpiperidin-1-yl)prop-2-en-1-one

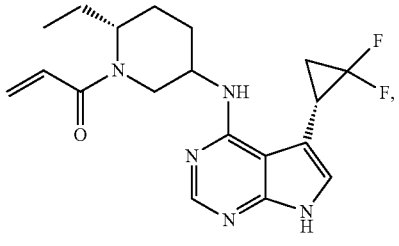

1-((2R)-5-((5-((S)-2,2-difluorocyclopropyl-
7H-pyrrolo[2,3-d]pyrimidin-4-yl)amino)-2-
ethylpiperidin-1-yl)prop-2-en-1-one

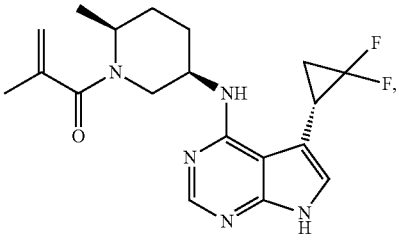

1-((2S,5R)-5-((5-((S)-2,2-difluorocyclopropyl-
7H-pyrrolo[2,3-d]pyrimidin-4-yl)amino)-2-
methylpiperidin-1-yl)-2-methylprop-2-en-1-one

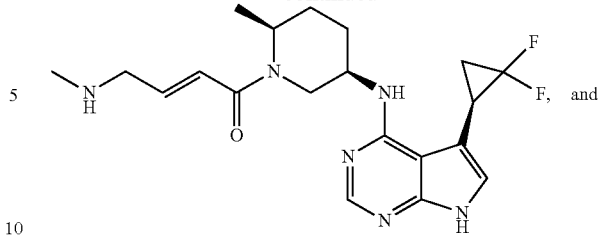

(E)-1-((2S,5R)-5-((5-((R)-2,2-difluorocyclopropyl-
7H-pyrrolo[2,3-d]pyrimidin-4-yl)amino)-2-
methylpiperidin-1-yl)-4-(methylamino)but-2-en-1-one

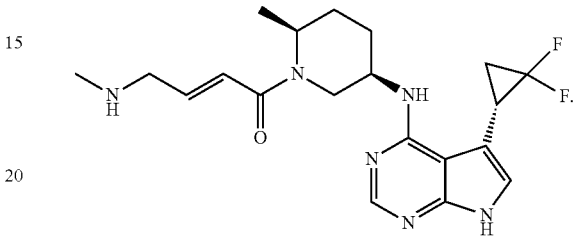

(E)-1-((2S,5R)-5-((5-((S)-2,2-difluorocyclopropyl-
7H-pyrrolo[2,3-d]pyrimidin-4-yl)amino)-2-
methylpiperidin-1-yl)-4-(methylamino)but-2-en-1-one 26. The method of claim 24 further comprising:
administering, sequentially or concurrently to the subject, a second pharmaceutical agent.

27. The method of claim 26, wherein the second pharmaceutical agent is selected from a corticosteroid, a non-steroidal anti-inflammatory drug (NSAID), a calcineurin inhibitor, an alkylating agent, a CD20 blocker, a Tumor Necrosis factor (TNF) blocker, an inhibitor of inosine monophosphate dehydrogenase (IMPDH), an immunosuppressant, an anti-metabolite, an aminosalicylate, an anti-lymphocyte globulin antibody, an anti-thymocyte globulin antibody, a monoclonal anti-T-cell antibody, an anti-interleukin-12/23 antibody, an anti-interleukin-17 antibody, an anti-interleukin-17 receptor antibody, an anti-α4β7 integrin antibody, an interleukin-1 receptor antagonist, an interleukin-6 inhibitor, an interleukin-17 inhibitor, a Janus kinase inhibitor, and a syk inhibitor.

28. The method of claim 26 wherein the second pharmaceutical agent is an immune checkpoint inhibitor selected from an adenosine A2A receptor (A2AR) inhibitor, a B7-H3 (CD276) inhibitor, a cytotoxic T-lymphocyte associated protein 4 (CTLA4) inhibitor, a programmed cell death ligand 1 (PD-L1) inhibitor, a programmed cell death protein 1 (PD-1) inhibitor, a B7-H4 (VTCN1) inhibitor, a T-cell immunoglobulin and mucin-domain containing-3 (TIM3) inhibitor, a B and T lymphocyte attenuator (BTLA) inhibitor, an indoleamine-pyrrole 2,3-dioxygenase (IDO) inhibitor, a killer-cell immunoglobulin-like receptors (KIRs) inhibitor, a lymphocyte-activation gene 3 (LAG-3) inhibitor, a T-cell immunoreceptor with Ig and ITIM domains (TIGIT) inhibitor, an ILT-3 inhibitor, an ILT-4 inhibitor, and a V-domain Ig suppressor of T cell activation (Vista) inhibitor.

29. The method of claim 26, wherein the second pharmaceutical agent is selected from an alkylating agent, an anti-metabolite, a plant alkaloid, a topoisomerase inhibitor, a cytotoxic antibiotic, an angiogenesis inhibitor, and a tyrosine kinase inhibitor.

30. A method of treating an ITK and JAK3 mediated disorder in a subject in need thereof, said method comprising:

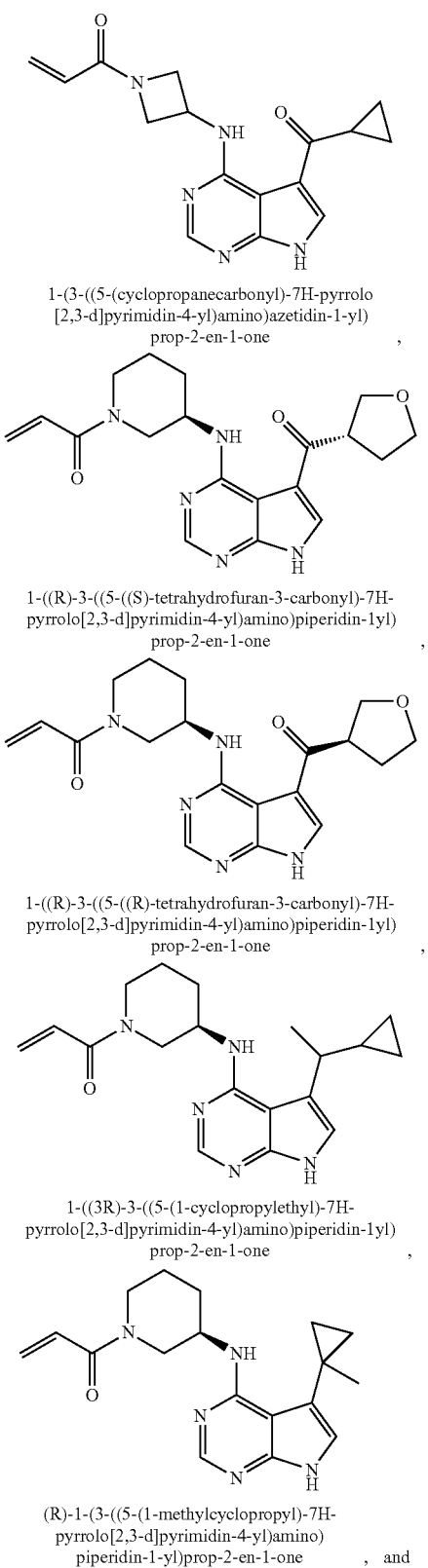 [SMILES: C=CC(=O)N1CC(Nc2ncnc3[nH]cc(C(=O)C4CC4)c23)C1 ; C=CC(=O)N1CCC[C@@H](Nc2ncnc3[nH]cc(C(=O)[C@H]4CCOC4)c23)C1 ; C=CC(=O)N1CCC[C@@H](Nc2ncnc3[nH]cc(C(=O)[C@@H]4CCOC4)c23)C1 ; C=CC(=O)N1CCC[C@@H](Nc2ncnc3[nH]cc(C(C)C4CC4)c23)C1 ; C=CC(=O)N1CCC[C@@H](Nc2ncnc3[nH]cc(C4(C)CC4)c23)C1]

1-(3-((5-(cyclopropanecarbonyl)-7H-pyrrolo[2,3-d]pyrimidin-4-yl)amino)azetidin-1-yl)prop-2-en-1-one, 1-((R)-3-((5-((S)-tetrahydrofuran-3-carbonyl)-7H-pyrrolo[2,3-d]pyrimidin-4-yl)amino)piperidin-1yl)prop-2-en-1-one, 1-((R)-3-((5-((R)-tetrahydrofuran-3-carbonyl)-7H-pyrrolo[2,3-d]pyrimidin-4-yl)amino)piperidin-1yl)prop-2-en-1-one, 1-((3R)-3-((5-(1-cyclopropylethyl)-7H-pyrrolo[2,3-d]pyrimidin-4-yl)amino)piperidin-1yl)prop-2-en-1-one, (R)-1-(3-((5-(1-methylcyclopropyl)-7H-pyrrolo[2,3-d]pyrimidin-4-yl)amino)piperidin-1-yl)prop-2-en-1-one, and

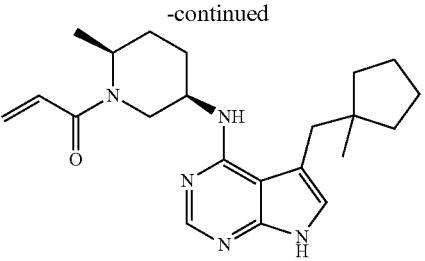

1-((2S,5R)-2-methyl-5-((5-((1-methylcyclopentyl)methyl)-7H-pyrrolo[2,3-d]pyrimidin-4-yl)amino)piperidin-1-yl)prop-2-en-1-one.

wherein the ITK and JAK3 mediated disorder is selected from rheumatoid arthritis, psoriatic arthritis, ankylosing spondylitis, inflammatory bowel disease, T-cell lymphoma, cutaneous T-cell lymphoma, Crohn's disease, ulcerative colitis, psoriasis, hidradenitis suppurativa, organ transplant rejection, lupus nephritis, non-alcoholic steatohepatitis, and juvenile idiopathic arthritis.

31. The method of claim 30 further comprising:
administering, sequentially or concurrently to the subject, a second pharmaceutical agent.

32. The method of claim 31 wherein the second pharmaceutical agent is selected from a corticosteroid, a nonsteroidal anti-inflammatory drug (NSAID), a calcineurin inhibitor, an alkylating agent, a CD20 blocker, a Tumor Necrosis factor (TNF) blocker, an inhibitor of inosine monophosphate dehydrogenase (IMPDH), an immunosuppressant, an antimetabolite, an aminosalicylate, an anti-lymphocyte globulin antibody, an anti-thymocyte globulin antibody, a monoclonal anti-T-cell antibody, an anti-interleukin-12/23 antibody, an anti-interleukin-17 antibody, an anti-interleukin-17 receptor antibody, an anti-α4β7 integrin antibody, an interleukin-1 receptor antagonist, an interleukin-6 inhibitor, an interleukin-17 inhibitor, a Janus kinase inhibitor, and a syk inhibitor.

33. The method of claim 31, wherein the second pharmaceutical agent is an immune checkpoint inhibitor selected from an adenosine A2A receptor (A2AR) inhibitor, a B7-H3 (CD276) inhibitor, a cytotoxic T-lymphocyte associated protein 4 (CTLA4) inhibitor, a programmed cell death ligand 1 (PD-L1) inhibitor, a programmed cell death protein 1 (PD-1) inhibitor, a B7-H4 (VTCN1) inhibitor, a T-cell immunoglobulin and mucin-domain containing-3 (TIM3) inhibitor, a B and T lymphocyte attenuator (BTLA) inhibitor, an indoleamine-pyrrole 2,3-dioxygenase (IDO) inhibitor, a killer-cell immunoglobulin-like receptors (KIRs) inhibitor, a lymphocyte-activation gene 3 (LAG-3) inhibitor, a T-cell immunoreceptor with Ig and ITIM domains (TIGIT) inhibitor, an ILT-3 inhibitor, an ILT-4 inhibitor, and a V-domain Ig suppressor of T cell activation (Vista) inhibitor.

34. The method of claim 31, wherein the second pharmaceutical agent is selected from an alkylating agent, an anti-metabolite, a plant alkaloid, a topoisomerase inhibitor, a cytotoxic antibiotic, an angiogenesis inhibitor, and a tyrosine kinase inhibitor.

* * * * *